(12) United States Patent
Besin et al.

(10) Patent No.: US 10,556,018 B2
(45) Date of Patent: Feb. 11, 2020

(54) COMPOSITIONS AND METHODS FOR DELIVERY OF AGENTS

(71) Applicant: ModernaTX, Inc., Cambridge, MA (US)

(72) Inventors: Gilles Besin, Brookline, MA (US);
Stephen Hoge, Brookline, MA (US);
Joseph Senn, Cambridge, MA (US);
Kerry Benenato, Sudbury, MA (US);
Staci Sabnis, Cambridge, MA (US)

( * ) Notice: Subject to any disclaimer, the term of this patent is extended or adjusted under 35 U.S.C. 154(b) by 0 days.

(21) Appl. No.: 15/674,107

(22) Filed: Aug. 10, 2017

(65) Prior Publication Data
US 2018/0147298 A1    May 31, 2018

Related U.S. Application Data

(63) Continuation of application No. PCT/US2016/000129, filed on Dec. 10, 2016.

(60) Provisional application No. 62/413,050, filed on Oct. 26, 2016, provisional application No. 62/413,027, filed on Oct. 26, 2016, provisional application No. 62/350,172, filed on Jun. 14, 2016, provisional application No. 62/350,165, filed on Jun. 14, 2016, provisional application No. 62/311,386, filed on Mar. 21, 2016, provisional application No. 62/311,388, filed on Mar. 21, 2016, provisional application No. 62/311,380, filed on Mar. 21, 2016, provisional application No. 62/266,581, filed on Dec. 12, 2015, provisional application No. 62/265,973, filed on Dec. 10, 2015.

(51) Int. Cl.
| | |
|---|---|
| *A61K 48/00* | (2006.01) |
| *A61K 9/127* | (2006.01) |
| *C12N 15/88* | (2006.01) |
| *A61K 47/54* | (2017.01) |
| *A61K 47/69* | (2017.01) |
| *A61K 47/60* | (2017.01) |
| *A61K 31/713* | (2006.01) |
| *A61K 39/39* | (2006.01) |
| *A61K 47/10* | (2017.01) |
| *C08G 65/332* | (2006.01) |
| *C08G 65/333* | (2006.01) |
| *C08G 65/334* | (2006.01) |
| *C08G 65/335* | (2006.01) |
| *C12N 15/117* | (2010.01) |
| *A61K 31/7115* | (2006.01) |
| *A61K 47/14* | (2017.01) |
| *A61K 47/18* | (2017.01) |
| *A61K 39/00* | (2006.01) |

(52) U.S. Cl.
CPC .......... *A61K 48/0033* (2013.01); *A61K 9/127* (2013.01); *A61K 9/1271* (2013.01); *A61K 31/713* (2013.01); *A61K 31/7115* (2013.01); *A61K 39/39* (2013.01); *A61K 47/10* (2013.01); *A61K 47/14* (2013.01); *A61K 47/18* (2013.01); *A61K 47/543* (2017.08); *A61K 47/544* (2017.08); *A61K 47/60* (2017.08); *A61K 47/6929* (2017.08); *A61K 48/0066* (2013.01); *C08G 65/3322* (2013.01); *C08G 65/3326* (2013.01); *C08G 65/3331* (2013.01); *C08G 65/3348* (2013.01); *C08G 65/3356* (2013.01); *C08G 65/33306* (2013.01); *C08G 65/33317* (2013.01); *C08G 65/33324* (2013.01); *C12N 15/117* (2013.01); *C12N 15/88* (2013.01); *A61K 2039/55555* (2013.01); *C08G 2650/04* (2013.01); *C12N 2310/141* (2013.01); *C12N 2310/17* (2013.01); *C12N 2320/32* (2013.01)

(58) Field of Classification Search
CPC ............ A61K 2300/00; A61K 31/4188; A61K 47/6929; A61K 47/6935; C12N 15/63
USPC ...... 514/44 R; 424/9.1; 435/6.1, 91.1, 91.31, 435/455, 458; 536/23.1, 24.5
See application file for complete search history.

(56) References Cited

U.S. PATENT DOCUMENTS

| | | |
|---|---|---|
| 6,652,886 B2 | 11/2003 | Ahn et al. |
| 6,696,038 B1 | 2/2004 | Mahala et al. |
| 7,268,120 B1 | 9/2007 | Horton et al. |
| 7,371,404 B2 | 5/2008 | Panzner et al. |
| 7,943,168 B2 | 5/2011 | Schlesinger et al. |
| 8,058,069 B2 | 11/2011 | Yaworski et al. |
| 8,158,601 B2 | 4/2012 | Chen et al. |
| 8,420,123 B2 | 4/2013 | Troiano et al. |
| 8,440,614 B2 | 5/2013 | Castor |
| 8,450,298 B2 | 5/2013 | Mahon et al. |
| 8,460,696 B2 | 6/2013 | Slobodkin et al. |

(Continued)

FOREIGN PATENT DOCUMENTS

| | | |
|---|---|---|
| CN | 102068701 A | 5/2011 |
| CN | 102204920 A | 10/2011 |

(Continued)

OTHER PUBLICATIONS

Delmas et al, J. Colloid Science and Biotechnology, vol. 1, pp. 16-25. (Year: 2012).*

(Continued)

*Primary Examiner* — Jane J Zara
(74) *Attorney, Agent, or Firm* — Wolf, Greenfield & Sacks, P.C.

(57) ABSTRACT

This disclosure provides improved lipid-based compositions, including lipid nanoparticle compositions, and methods of use thereof for delivering agents in vivo including nucleic acids and proteins. These compositions are not subject to accelerated blood clearance and they have an improved toxicity profile in vivo.

28 Claims, 123 Drawing Sheets
Specification includes a Sequence Listing.

(56) References Cited

U.S. PATENT DOCUMENTS

| | | |
|---|---|---|
| 8,460,709 B2 | 6/2013 | Ausborn et al. |
| 8,568,784 B2 | 10/2013 | Lillard et al. |
| 8,569,256 B2 | 10/2013 | Heyes et al. |
| 8,580,297 B2 | 11/2013 | Essler et al. |
| 8,642,076 B2 | 2/2014 | Manoharan et al. |
| 8,652,487 B2 | 2/2014 | Maldonado |
| 8,691,750 B2 | 4/2014 | Constein et al. |
| 8,697,098 B2 | 4/2014 | Perumal et al. |
| 8,709,483 B2 | 4/2014 | Farokhzad et al. |
| 8,710,200 B2 | 4/2014 | Schrum et al. |
| 8,715,736 B2 | 5/2014 | Sachdeva et al. |
| 8,734,832 B2 | 5/2014 | O'Hagan et al. |
| 8,734,846 B2 | 5/2014 | Ali et al. |
| 8,754,062 B2 | 6/2014 | De Fougerolles et al. |
| 8,822,663 B2 | 9/2014 | Schrum et al. |
| 8,999,380 B2 | 4/2015 | Bancel et al. |
| 9,221,891 B2 | 12/2015 | Bancel et al. |
| 9,303,079 B2 | 4/2016 | Bancel et al. |
| 9,512,456 B2 | 6/2016 | Wang et al. |
| 9,464,124 B2 | 11/2016 | Bancel et al. |
| 9,597,380 B2 | 3/2017 | Chakraborty et al. |
| 9,868,691 B2 * | 1/2018 | Benenato ............. A61K 9/5123 |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,273,269 B2 | 4/2019 | Ciaramella |
| 2003/0073619 A1 | 4/2003 | Mahato et al. |
| 2003/0092653 A1 | 5/2003 | Kisich et al. |
| 2004/0142474 A1 | 7/2004 | Mahala et al. |
| 2005/0143336 A1 | 6/2005 | Ramesh et al. |
| 2006/0008910 A1 | 1/2006 | Maclachlan et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2012/0021042 A1 | 1/2012 | Panzner et al. |
| 2012/0065252 A1 | 3/2012 | Schrum et al. |
| 2012/0157500 A1 | 6/2012 | Weikang |
| 2012/0172411 A1 | 7/2012 | Heyes et al. |
| 2012/0177724 A1 | 7/2012 | Irvine et al. |
| 2012/0178702 A1 | 7/2012 | Huang |
| 2012/0251618 A1 | 10/2012 | Schrum et al. |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0102034 A1 | 4/2013 | Schrum et al. |
| 2013/0115273 A1 | 5/2013 | Yang et al. |
| 2013/0115274 A1 | 5/2013 | Knopov et al. |
| 2013/0116307 A1 | 5/2013 | Heyes et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0130348 A1 | 5/2013 | Gu et al. |
| 2013/0142876 A1 | 6/2013 | Howard et al. |
| 2013/0150625 A1 | 6/2013 | Budzik et al. |
| 2013/0156845 A1 | 6/2013 | Manoharan et al. |
| 2013/0164400 A1 | 6/2013 | Knopov et al. |
| 2013/0171241 A1 | 7/2013 | Geall |
| 2013/0178541 A1 | 7/2013 | Stanton et al. |
| 2013/0183355 A1 | 7/2013 | Jain et al. |
| 2013/0189351 A1 | 7/2013 | Geall |
| 2013/0195765 A1 | 8/2013 | Gho et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0236550 A1 | 9/2013 | Ausborn et al. |
| 2013/0243848 A1 | 9/2013 | Lobovkina et al. |
| 2013/0243867 A1 | 9/2013 | Mahapatra et al. |
| 2013/0245104 A1 | 9/2013 | de Fougerolles et al. |
| 2013/0245107 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0274504 A1 | 10/2013 | Colletti et al. |
| 2013/0274523 A1 | 10/2013 | Bawiec, III et al. |
| 2013/0295043 A1 | 11/2013 | Kallen et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0330401 A1 | 12/2013 | Payne et al. |
| 2013/0336998 A1 | 12/2013 | Kallen et al. |
| 2013/0338210 A1 | 12/2013 | Manoharan et al. |
| 2014/0037714 A1 | 2/2014 | Quay et al. |
| 2014/0039032 A1 | 2/2014 | Kumboyama et al. |
| 2014/0044772 A1 | 2/2014 | Maclachlan et al. |
| 2014/0044791 A1 | 2/2014 | Basilion et al. |
| 2014/0045913 A1 | 2/2014 | Kumboyama et al. |
| 2014/0050775 A1 | 2/2014 | Slobodkin et al. |
| 2014/0065172 A1 | 3/2014 | Echeverri et al. |
| 2014/0065204 A1 | 3/2014 | Hayes et al. |
| 2014/0065228 A1 | 3/2014 | Yarowoski et al. |
| 2014/0093579 A1 | 4/2014 | Zale et al. |
| 2014/0113137 A1 | 4/2014 | Podobinski et al. |
| 2014/0121263 A1 | 5/2014 | Fitzgerald et al. |
| 2014/0121393 A1 | 5/2014 | Manoharan et al. |
| 2014/0141070 A1 | 5/2014 | Geall et al. |
| 2014/0141089 A1 | 5/2014 | Liang |
| 2014/0141483 A1 | 5/2014 | Bossard et al. |
| 2014/0142165 A1 | 5/2014 | Grayson et al. |
| 2014/0142254 A1 | 5/2014 | Fonnum et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0378538 A1 | 12/2014 | Bancel |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376115 A1 | 12/2015 | Ansell et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0271272 A1 | 9/2016 | Bancel et al. |
| 2016/0317647 A1 | 11/2016 | Ciaramella et al. |
| 2016/0331828 A1 | 11/2016 | Ciaramella et al. |
| 2017/0065675 A1 | 3/2017 | Bancel et al. |
| 2017/0130255 A1 | 5/2017 | Wang et al. |
| 2017/0202979 A1 | 7/2017 | Chakraborty et al. |
| 2017/0340724 A1 | 11/2017 | Ciaramella et al. |
| 2018/0002393 A1 | 1/2018 | Bancel et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2019/0008938 A1 | 1/2019 | Ciaramella et al. |

(56) References Cited

U.S. PATENT DOCUMENTS

2019/0099481 A1  4/2019  Ciaramella et al.
2019/0192646 A1  6/2019  Cohen et al.

FOREIGN PATENT DOCUMENTS

| | | | |
|---|---|---|---|
| CN | 102813929 A | 12/2012 | |
| CN | 104644555 A | 5/2015 | |
| EP | 1404860 B1 | 5/2002 | |
| EP | 2073848 B1 | 8/2013 | |
| WO | WO 99/14346 A2 | 3/1999 | |
| WO | WO 99/52503 A2 | 10/1999 | |
| WO | WO 2005/034979 A2 | 4/2005 | |
| WO | WO 2008/042973 A2 | 4/2008 | |
| WO | WO 2009/024599 A1 | 2/2009 | |
| WO | WO 2009/127060 A1 | 10/2009 | |
| WO | WO 2010/042877 A1 | 4/2010 | |
| WO | WO 2010/054406 A1 | 5/2010 | |
| WO | WO 2010/088537 A3 | 8/2010 | |
| WO | WO 2010/129709 A1 | 11/2010 | |
| WO | WO 2010/144710 A1 | 12/2010 | |
| WO | WO 2011/017108 A2 | 2/2011 | |
| WO | WO 2011/068810 A1 | 6/2011 | |
| WO | WO 2011/127255 A1 | 10/2011 | |
| WO | WO 2012/006376 A2 | 1/2012 | |
| WO | WO 2012/006378 A1 | 1/2012 | |
| WO | WO 2012/030901 A1 | 3/2012 | |
| WO | WO 2012/031043 A1 | 3/2012 | |
| WO | WO 2012/031046 A2 | 3/2012 | |
| WO | WO 2012/099755 A1 | 7/2012 | |
| WO | WO 2012/129483 A1 | 9/2012 | |
| WO | WO 2012/149252 A2 | 11/2012 | |
| WO | WO 2012/149393 A2 | 11/2012 | |
| WO | WO 2012/153338 A2 | 11/2012 | |
| WO | WO 2012/170889 A1 | 12/2012 | |
| WO | WO 2012/170930 A1 | 12/2012 | |
| WO | WO 2013/006825 A1 | 1/2013 | |
| WO | WO 2013/006834 A1 | 1/2013 | |
| WO | WO 2013/006837 A1 | 1/2013 | |
| WO | WO 2013/006838 A1 | 1/2013 | |
| WO | WO 2013/006842 A2 | 1/2013 | |
| WO | WO 2013/033438 A2 | 3/2013 | |
| WO | WO 2013/033563 A1 | 3/2013 | |
| WO | WO 2013/049328 A1 | 4/2013 | |
| WO | WO 2013/052167 A2 | 4/2013 | |
| WO | WO 2013/056132 A2 | 4/2013 | |
| WO | WO 2013/057715 A1 | 4/2013 | |
| WO | WO 2013/059496 A1 | 4/2013 | |
| WO | WO 2013/059922 A1 | 5/2013 | |
| WO | WO 2013/064911 A2 | 5/2013 | |
| WO | WO 2013/066903 A1 | 5/2013 | |
| WO | WO 2013/067537 A1 | 5/2013 | |
| WO | WO 2013/086322 A1 | 6/2013 | |
| WO | WO 2013/086354 A1 | 6/2013 | |
| WO | WO 2013/086373 A1 | 6/2013 | |
| WO | WO 2013/086526 A1 | 6/2013 | |
| WO | WO 2013/087083 A1 | 6/2013 | |
| WO | WO 2013/090186 A1 | 6/2013 | |
| WO | WO 2013/093648 A2 | 6/2013 | |
| WO | WO 2013/135359 A1 | 9/2013 | |
| WO | WO 2013/143555 A1 | 10/2013 | |
| WO | WO 2013/143683 A1 | 10/2013 | |
| WO | WO 2013/148186 A1 | 10/2013 | |
| WO | WO 2013/148541 A1 | 10/2013 | |
| WO | WO 2013/149141 A1 | 10/2013 | |
| WO | WO 2013/151669 A1 | 10/2013 | |
| WO | WO 2013/151672 A1 | 10/2013 | |
| WO | WO 2013/158127 A1 | 10/2013 | |
| WO | WO 2013/158579 A1 | 10/2013 | |
| WO | WO 2013/166498 A1 | 11/2013 | |
| WO | WO 2013/173693 A1 | 11/2013 | |
| WO | WO 2013/185069 A1 | 12/2013 | |
| WO | WO 2014/008334 A1 | 1/2014 | |
| WO | WO 2014/026284 A1 | 2/2014 | |
| WO | WO 2014/028487 A1 | 2/2014 | |
| WO | WO 2014/054026 A1 | 4/2014 | |
| WO | WO 2014/071072 A2 | 5/2014 | |
| WO | WO 2014/072997 A1 | 5/2014 | |
| WO | WO 2014/081507 A1 | 5/2014 | |
| WO | WO 2014/144196 A1 | 9/2014 | |
| WO | WO 2014/152774 A1 | 9/2014 | |
| WO | WO 2014/160243 A1 | 10/2014 | |
| WO | WO 2014/172045 A1 | 10/2014 | |
| WO | WO-2014172045 A1 * | 10/2014 | ......... A61K 31/7105 |
| WO | WO 2014/182661 A2 | 11/2014 | |
| WO | WO 2014/210356 A1 | 12/2014 | |
| WO | WO 2015/095340 A1 | 6/2015 | |
| WO | WO 2015/130584 A2 | 9/2015 | |
| WO | WO 2015/148247 A1 | 10/2015 | |
| WO | WO 2015/164674 A1 | 10/2015 | |
| WO | WO 2015/164786 A1 | 10/2015 | |
| WO | WO 2016/037053 A1 | 3/2016 | |
| WO | WO 2016/118724 A1 | 7/2016 | |
| WO | WO 2016/118725 A1 | 7/2016 | |
| WO | WO 2016/164762 A1 | 10/2016 | |
| WO | WO 2016/201377 A1 | 12/2016 | |
| WO | WO 2017/015457 A1 | 1/2017 | |
| WO | WO 2017/015463 A1 | 1/2017 | |
| WO | WO 2017/019935 A1 | 2/2017 | |
| WO | WO 2017/020026 A1 | 2/2017 | |
| WO | WO 2017/031232 A1 | 2/2017 | |
| WO | WO 2017/031241 A1 | 2/2017 | |
| WO | WO 2017/049245 A1 | 3/2017 | |
| WO | WO 2017/062513 A1 | 4/2017 | |
| WO | WO 2017/066789 A1 | 4/2017 | |
| WO | WO 2017/070601 A1 | 4/2017 | |
| WO | WO 2017/070613 A1 | 4/2017 | |
| WO | WO 2017/070616 A1 | 4/2017 | |
| WO | WO 2017/070618 A1 | 4/2017 | |
| WO | WO 2017/070620 A1 | 4/2017 | |
| WO | WO 2017/070622 A1 | 4/2017 | |
| WO | WO 2017/070623 A1 | 4/2017 | |
| WO | WO 2017/070624 A1 | 4/2017 | |
| WO | WO 2017/070626 A2 | 4/2017 | |
| WO | WO-2017070624 A1 * | 4/2017 | ............. A61K 48/00 |
| WO | WO 2017/099823 A1 | 6/2017 | |
| WO | WO 2017/201333 A1 | 11/2017 | |
| WO | WO 2017/201340 A1 | 11/2017 | |
| WO | WO 2017/201342 A1 | 11/2017 | |
| WO | WO 2017/201347 A1 | 11/2017 | |
| WO | WO 2018/053209 A1 | 3/2018 | |
| WO | WO 2018/075980 A1 | 4/2018 | |
| WO | WO 2018/081459 A1 | 5/2018 | |
| WO | WO 2018/081462 A1 | 5/2018 | |
| WO | WO 2018/089851 A1 | 5/2018 | |
| WO | WO 2018/107088 A1 | 6/2018 | |
| WO | WO 2018/111967 A1 | 6/2018 | |
| WO | WO 2018/144082 A1 | 8/2018 | |
| WO | WO 2018/144778 A1 | 8/2018 | |
| WO | WO 2018/151816 A1 | 8/2018 | |
| WO | WO 2018/170245 A1 | 9/2018 | |
| WO | WO 2018/170256 A1 | 9/2018 | |
| WO | WO 2018/170260 A1 | 9/2018 | |
| WO | WO 2018/170270 A1 | 9/2018 | |
| WO | WO 2018/170347 A1 | 9/2018 | |
| WO | WO-2018/175783 A1 | 9/2018 | |
| WO | WO 2018/187590 A2 | 10/2018 | |
| WO | WO 2018/200737 A1 | 11/2018 | |
| WO | WO 2018/232355 A1 | 12/2018 | |
| WO | WO 2018/232357 A1 | 12/2018 | |
| WO | WO 2019/036670 A1 | 2/2019 | |
| WO | WO 2019/036682 A1 | 2/2019 | |
| WO | WO 2019/036683 A1 | 2/2019 | |
| WO | WO 2019/036685 A1 | 2/2019 | |
| WO | WO 2019/103993 A1 | 5/2019 | |

OTHER PUBLICATIONS

U.S. Appl. No. 15/846,084, filed 2017.*
U.S. Appl. No. 16/005,286, filed 2018.*
U.S. App. No. 90/014,167, filed Aug. 17, 2018, Ciaramella et al.
U.S. Appl. No. 15/905,576, filed Feb. 26, 2018, Bancel et al.
U.S. Appl. No. 16/040,981, filed Jul. 20, 2018, Ciaramella et al.
U.S. Appl. No. 16/031,951, filed Jul. 10, 2018, Ciaramella.

(56) References Cited

OTHER PUBLICATIONS

Invitation to Pay Additional Fees for Application No. PCT/US2016/000129 dated Mar. 6, 2017.
International Search Report and Written Opinion for Application No. PCT/US2016/000129 dated May 22, 2017.
Abu Lila et al., Application of polyglycerol coating to plasmid DNA lipoplex for the evasion of the accelerated blood clearance phenomenon in nucleic acid delivery. J Pharm Sci. Feb. 2014;103(2):557-66. doi: 10.1002/jps.23823. Epub Dec. 17, 2013.
Abu Lila et al., Use of polyglycerol (PG), instead of polyethylene glycol (PEG), prevents induction of the accelerated blood clearance phenomenon against long-circulating liposomes upon repeated administration. Int J Pharm. Nov. 1, 2013;456(1):235-42. doi: 10.1016/j.ijpharm.2013.07.059. Epub Aug. 5, 2013.
Chamberlain et al., Recurrent lymphomatous meningitis treated with intra-CSF rituximab and liposomal ara-C. J Neurooncol. Feb. 2009;91(3):271-7. doi: 10.1007/s11060-008-9707-1. Epub Sep. 27, 2008.
Corazzelli et al., Biweekly rituximab, cyclophosphamide, vincristine, non-pegylated liposome-encapsulated doxorubicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.1111/j.1365-2141.2011.08786.x. Epub Jun. 28, 2011.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull. 2015;38(3):417-24. doi: 10.1248/bpb.b14-00653.
Krause et al., Prevention of the hemodynamic effects of iopromide-carrying liposomes in rats and pigs. Invest Radiol. Aug. 2000;35(8):493-503.
Marina et al., Dose escalation and pharmacokinetics of pegylated liposomal doxorubicin (Doxil) in children with solid tumors: a pediatric oncology group study. Clin Cancer Res. Feb. 2002;8(2):413-8.
Oja et al., Doxorubicin entrapped within liposome-associated antigens results in a selective inhibition of the antibody response to the linked antigen. Biochim Biophys Acta. Sep. 29, 2000;1468(1-2):31-40.
Popov et al., Multivalent rituximab lipid nanoparticles as improved lymphoma therapies: indirect mechanisms of action and in vivo activity. nNanomedicine (Lond). Nov. 2011;6(9):1575-91. doi: 10.2217/nnm.11.50. Epub Oct. 20, 2011.
Shimizu et al., Transport of PEGylated liposomes from the splenic marginal zone to the follicle in the induction phase of the accelerated blood clearance phenomenon. Immunobiology. May 2013;218(5):725-32. doi: 10.1016/j.imbio.2012.08.274. Epub Aug. 23, 2012.
Taguchi et al., Effect of Repeated Injections of Adenosine Diphosphate-Encapsulated Liposomes Coated with a Fibrinogen γ-Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.
Taguchi et al., Hemoglobin vesicles, polyethylene glycol (PEG)ylated liposomes developed as a red blood cell substitute, do not induce the accelerated blood clearance phenomenon in mice. Drug Metab Dispos. Nov. 2009;37(11):2197-203. doi: 10.1124/dmd.109.028852. Epub Aug. 13, 2009.
PCT/US2016/000129, Dec. 11, 2017, International Preliminary Report on Patentability.
International Preliminary Report on Patentability for Application No. PCT/US2016/000129, dated Dec. 11, 2017.
Akinc et al., Targeted Delivery of RNAi Therapeutics With Endogenous and Exogenous Ligand-Based Mechanisms, Mol Ther. 2009 17:872-879.
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andreakos et al., Amphoteric liposomes enable systemic antigen-presenting cell-directed delivery of CD40 antisense and are therapeutically effective in experimental arthritis. Arthritis Rheum. Apr. 2009;60(4):994-1005. doi: 10.1002/art.24434.
Andries, 0., et al., Comparison of the gene transfer efficiency of mRNA/GL67 and pDNA/GL67 complexes in respiratory cells. Mal Pharmaceutics. 2012; 9: 2136-2145.
Bag, J., Recovery of normal protein synthesis in heat-shocked chicken myotubes by liposome-mediated transfer of mRNAs. Can. J. Biochem. Cell Biol. 1985; 63(3): 231-235.
Belliveau, N.M., et al., Microfluidic synthesis of highly potent limit-size lipid nanoparticles for in vivo delivery of siRNA. Mol Ther Nucleic Acids. Aug. 2012; 1(8): e37.
Bettinger, T. et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bolhassani et al. , Improvement of Different Vaccine Delivery Systems for Cancer Therapy, Molecular Cancer, Biomed Central, London, GB, 2011, vol. 10, No. 3, pp. 1-20.
Chen, D., et al., Rapid discovery of potent siRNA-containing lipid nanoparticles enabled by controlled microfluidic formulation. J Am Chem Soc. 2012; 134: 6948-6951.
Cun et al., Preparation and characterization of poly(DL-lactide-co-glycolide) nanoparticles for siRNA delivery. International Journal of Pharmaceutics 390 (2010) 70-75.
Dahlman et al., In vivo endothelial siRNA delivery using polymeric nanoparticles with low molecular weight, Nature Nanotechnology, 2014, No vol.#, pp. 1-8.
Delehanty Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.
Felgner, Cationic lipid/polynucleotide condensates for in vitro and in vivo polynucleotide delivery—the cytofectins. J. of Liposome Research. 1993; 3(1): 3-16.
Felgner, Particulate systems and polymers for in vitro and in vivo delivery of polynucleotides. Adv. Drug Delivery Rev. 1990; 5(3): 163-187.
Felgner, et al., Lipofection: a highly efficient, lipid-mediated DNA-transfection procedure. Proc Natl Acad Sci U SA. Nov. 1987;84(21):7413-7.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
He et al., Synthesis and Separation of Diastereomers of Ribonucleoside 5'-(alpha-P-Borano)triphosphates. J Org Chem. Aug. 21, 1998;63(17):5769-5773.
Hecker et al., Non-Viral DNA and mRNA Gene Delivery to the CNS Pre-Operatively for Neuroprotection and Following Neurotrauma. Molecular Therapy. 2004; 9, S258-S258.
Juliano et al., Cell-targeting and cell-penetrating peptides for delivery of therapeutic and imaging agents. Wiley Interdisciplinary Reviews: Nanomedicine and Nanobiotechnology. May/Jun. 2009; 1( 3): 324-335.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.

(56) References Cited

OTHER PUBLICATIONS

Kanapathipillai et al., Nanoparticle targeting of anti-cancer drugs that alter intracellular signaling or influence the tumor microenvironment, Adv. Drug Deliv. Rev. (2014), , pp. 1-12.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kariko et al., Phosphate-enhanced transfection of cationic lipid-complexed mRNA and plasmid DNA. Biochim Biophys Acta. Mar. 2, 1998;1369(2):320-34.
Kariko et al., Generating the optimal mRNA for therapy: HPLC purification eliminates immune activation and improves translation of nucleoside-modified, protein-encoding mRNA. Nucleic Acids Res. vol. 39, No. 21, Nov. 1, 2011, pp. e142-1, XP002696190.
Kariko et al., In vivo protein expression from mRNA delivered into adult rat brain. J. of Neuroscience Methods. Jan. 2001; 105(1): 77-86.
Kariko et al., Incorporation of pseudouridine into mRNA yields superior nonimmunogenic vector with increased translational capacity and biological stability, Molecular Therapy, Nature Publishing Group, GB, vol. 16, No. 11, Nov. 1, 2008 (Nov. 1, 2008), pp. 1833-1840.
Keown et al., Methods for Introducing DNA into Mammalian Cells. Methods in Enzymology, 1990, 185:527-37.
Kirpotin et al., Antibody targeting of long-circulating lipidic nanoparticles does not increase tumor localization but does increase internalization in animal models. Cancer Res. 2006; 66: 6732-67 40.
Kozielski et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8,'No. 4',pp. 3232-3241.
Lai et al., Mucus-penetrating nanoparticles for drug and gene delivery to mucosal tissues. Adv Drug Deliv Rev. Feb. 27, 2009; 61(2): 158-171.
Lai et al., Rapid transport of large polymeric nanoparticles in fresh undiluted human mucus. PNAS. Jan. 30, 2007; 104(5): 1482-1487.
Lee et al., Lipid Nanoparticle siRNA Systems for Silencing the Androgen Receptor in Human Prostate Cancer in Vivo, International Journal of Cancer, 2012, vol. 131, pp. 781-790.
Lehto et al., Cell-penetrating peptides for the delivery of nucleic acids. Expert Opin. Drug Deliv. Jul. 2012; 9(7): 823-836.
Lewis, Dynamic Polyconjugates (DPC) Technology: An elegant solution to the siRNA delivery problem. Arrowhead Research Corp (NASDAQ: ARWR). Nov. 2011.
Li et al., Overcoming obstacles to develop effective and safe siRNA therapeutics. Expert Opin Biol Ther. May 2009; 9(5): 609-19.
Li et al., Preparation and gene delivery of alkaline amino acids-based cationic liposomes. Arch Pharm Res. Jul. 2008;31(7):924-31. Epub Aug. 14, 2008.
Lian et al., Trends and developments in liposome drug delivery systems. J Pharm Sci. Jun. 2001;90(6):667-80.
Lopez-Berestein et al., Treatment of systemic fungal infections with liposomal amphotericin B. Arch Intern Med. Nov. 1989;149(11):2533-6.
Mackey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Magee et al., Marked stimulation of lymphocyte-mediated attack on tumor cells by target-directed liposomes containing immune RNA, Cancer Res., 1978, 38(4):1173-6.
Malone et al., Cationic liposome-mediated RNA transfection. Proc Natl Acad Sci U SA. Aug. 1989;86 (16):6077-81.
Martinon et al., Induction of virus-specific cytotoxic T lymphocytes in vivo by liposome-entrapped mRNA. EurJ lmmunol. Jul. 1993;23(7):1719-22.
Maurer et al., Spontaneous entrapment of polynucleotides upon electrostatic interaction with ethanol-destabilized cationic liposomes. Biophys J. May 2001; 80(5): 2310-2326.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mishra et al., Improved leishmanicidal effect of phosphorothioate antisense oligonucleotides by LDL-mediated delivery. Biochim Biophys Acta. Nov. 7, 1995;1264(2):229-37.
Nair et al., Soluble proteins delivered to dendritic cells via pH-sensitive liposomes induce primary cytotoxic T lymphocyte responses in vitro. J Exp Med. Feb. 1, 1992;175(2):609-12.
Oster et al. Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface lntegrins as an Efficient, Cytoplasmic Transfection Mechanism, Journal of Bioactive and Compatible Polymers, Jul. 2002, pp. 1-10.
Pollard et al., Type I IFN counteracts the induction of antigen-specific immune responses by lipid-based delivery of mRNA vaccines. Mol Ther. Jan. 2013; 21 (1): 251-259.
Pulford et al., Liposome-siRNA-peptide complexes cross the blood-brain barrier and significantly decrease PrP'C on neuronal cells and PrP'RES in infected cell cultures. PLoS ONE. 2010; 5(6): e11085.
Saito et al., Distribution of liposomes into brain and rat brain tumor models by convection-enhanced delivery monitored with magnetic resonance imaging. Cancer Res. Apr. 2004; 64: 2572-2579.
Sakuma et al., Mucoadhesion of polystyrene nanoparticles having surface hydrophilic polymeric chains in the gastrointestinal tract. Int J Pharm. Jan. 25, 1999;177(2):161-72.
Schott et al., Viral and non-viral approaches for transient delivery of mRNA and proteins. Current Gene Ther. 2011; 11 (5): 382-398.
Shea et al., Synthesis, hybridization properties and antiviral activity of lipid-oligodeoxynucleotide conjugates. Nucleic Acids Res.Jul. 11, 1990;18(13):3777-83.
Strobel et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Tavernier et al., mRNA as gene therapeutic: How to control protein expression. J. of Controlled Release. Mar. 2011; 150(3): 238-247.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Torchilin et al., Multifunctional and Stimuli-Sensitive Pharmaceutical Nanocarriers, Eur J. Pharm Biopharm, 2009, vol. 71, No. 3, pp. 431-444.
Tracy, "Progress in the Development of LNP Delivery for siRNA Advancing LNPs to the Clinic," International Liposome Research Days Meeting, Vancouver, Canada. Aug. 2010, pp. 1-52.
Treat et al., Liposomes in the Therapy of Infectious Disease and Cancer, Lopez-Berestein and Fidler (eds.), Liss, New York, 1989. 353-65.
Uzgun et al., PEGylation improves nanoparticle formation and transfection efficiency of messenger RNA. Pharm Res. Sep. 2011; 28(9); 2223-2232.
Wan et al., Lipid nanoparticle delivery systems for siRNA-based therapeutics. Drug Deliv Transl Res. Feb. 2014;4(1):74-83. doi:10.1007/s13346-013-0161-z.

(56) References Cited

OTHER PUBLICATIONS

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Yamamoto et al., Current prospects for mRNA gene delivery, European Journal of Pharmaceutics and Biopharmaceutics 71 (2009) 484-489.

Zhigaltsev et al., Bottom-Up design and synthesis of limit size lipid nanoparticle systems with aqueous and triglyceride cores using millisecond microfluidic mixing. Langmuir. Feb. 21, 2012; 28(7): 3633-3640.

Zimmermann et al., Electrolyte- and pH-stabilities of aqueous solid lipid nanoparticle (SLN™) dispersions in artificial gastrointestinal media. Eur J Pharm Biopharm. Sep. 2001;52(2):203-10.

Zohra et al., Drastic effect of nanoapatite particles on liposome-mediated mRNA delivery to mammalian cells. Analytical Biochem. Oct. 2005; 345(1): 164-166.

Zohra et al., Effective delivery with enhanced translational activity synergistically accelerates mRNA-based transfection. Biochem Biophys Res Comm. Jun. 2007; 358(1): 373-378.

U.S. Appl. No. 15/239,613, filed Aug. 17, 2016, Laska et al.
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 16/001,751, filed Jun. 6, 2018, Mousavi et al.
U.S. Appl. No. 15/767,587, filed Apr. 11, 2018, Ciaramella.
U.S. Appl. No. 16/006,526, filed Jun. 12, 2018, Ciaramella.
U.S. Appl. No. 16/450,882, filed Jun. 24, 2019, Ciaramella.
U.S. Appl. No. 15/767,600, filed Apr. 11, 2018, Ciaramella et al.
U.S. Appl. No. 16/023,013, filed Jun. 29, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/136,386, filed Sep. 20, 2018, Ciaramella et al.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,811, filed Jun. 15, 2018, Ciaramella et al.
U.S. Appl. No. 16/009,848, filed Jun. 15, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 16/229,509, filed Dec. 21, 2018, Besin et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/389,545, filed Apr. 19, 2019, Ciaramella et al.
U.S. Appl. No. 16/368,099, filed Mar. 28, 2019, Ciaramella et al.
U.S. Appl. No. 16/368,270, filed Mar. 28, 2019, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 15/880,436, filed Jan. 25, 2018, Ciaramella.
U.S. Appl. No. 16/432,541, filed Jun. 5, 2019, Rabideau et al.
U.S. Appl. No. 16/362,366, filed Mar. 22, 2019, Ciaramella.
U.S. Appl. No. 16/302,607, filed Nov. 16, 2018, Benenato et al.
U.S. Appl. No. 16/131,793, filed Sep. 14, 2018, Ciaramella et al.
U.S. Appl. No. 16/180,076, filed Nov. 5, 2018, Cohen et al.
U.S. Appl. No. 15/239,613, filed Jun. 17, 2016, Laska et al.
U.S. Appl. No. 15/089,050, filed Apr. 1, 2016, Ciaramella et al.
U.S. Appl. No. 15/091,123, filed Apr. 5, 2016, Ciaramella et al.
U.S. Appl. No. 15/155,986, filed May 16, 2016, Fritz.
U.S. Appl. No. 15/156,249, filed May 16, 2016, Miracco.
U.S. Appl. No. 15/674,569, filed Aug. 11, 2017, Ciaramella et al.
U.S. Appl. No. 15/674,585, filed Aug. 11, 2017, Ciaramella et al.
U.S. Appl. No. 15/674,591, filed Aug. 11, 2017, Ciaramella et al.
U.S. Appl. No. 15/266,791, filed Sep. 15, 2016, Bancel et al.
U.S. Appl. No. 15/174,594, filed Jun. 6, 2016, Bancel et al.
U.S. Appl. No. 15/387,263, filed Dec. 21, 2016, Chen et al.
U.S. Appl. No. 15/674,872, filed Aug. 11, 2017, Besin et al.
U.S. Appl. No. 14/364,187, filed Jun. 10, 2014, Bancel.
U.S. Appl. No. 15/356,132, filed Nov. 18, 2016, Wang et al.
U.S. Appl. No. 15/674,599, filed Aug. 11, 2017, Ciaramella et al.

* cited by examiner

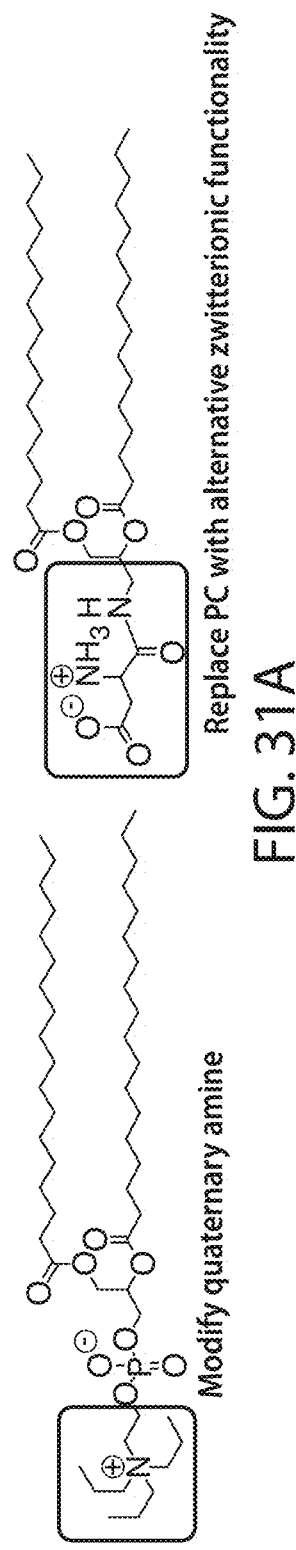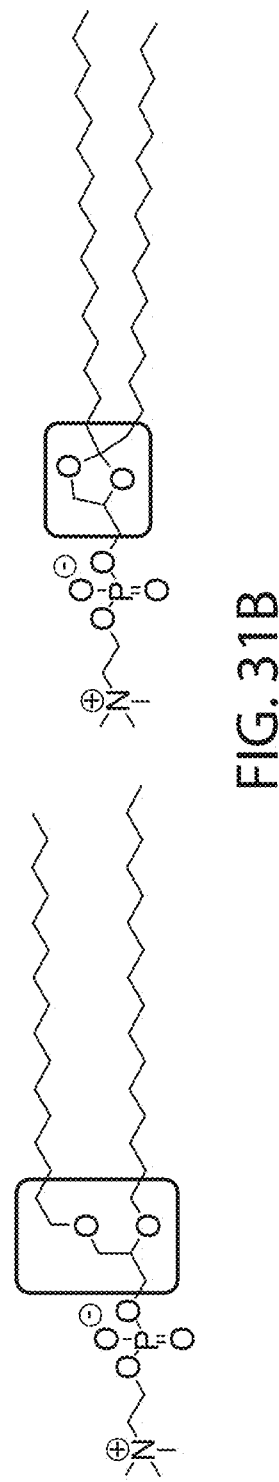
FIG. 31A
FIG. 31B

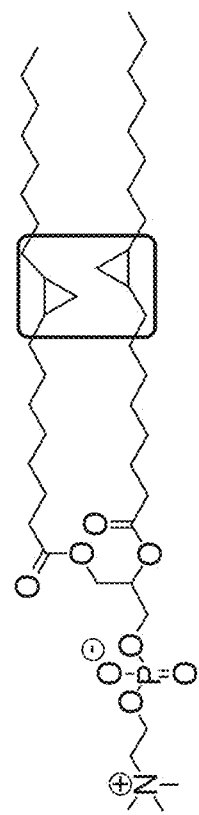
FIG. 31C
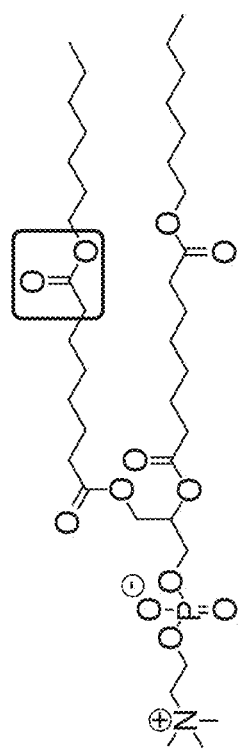
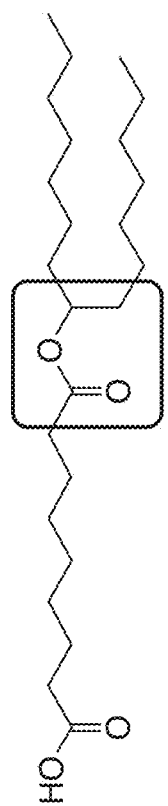
FIG. 31D

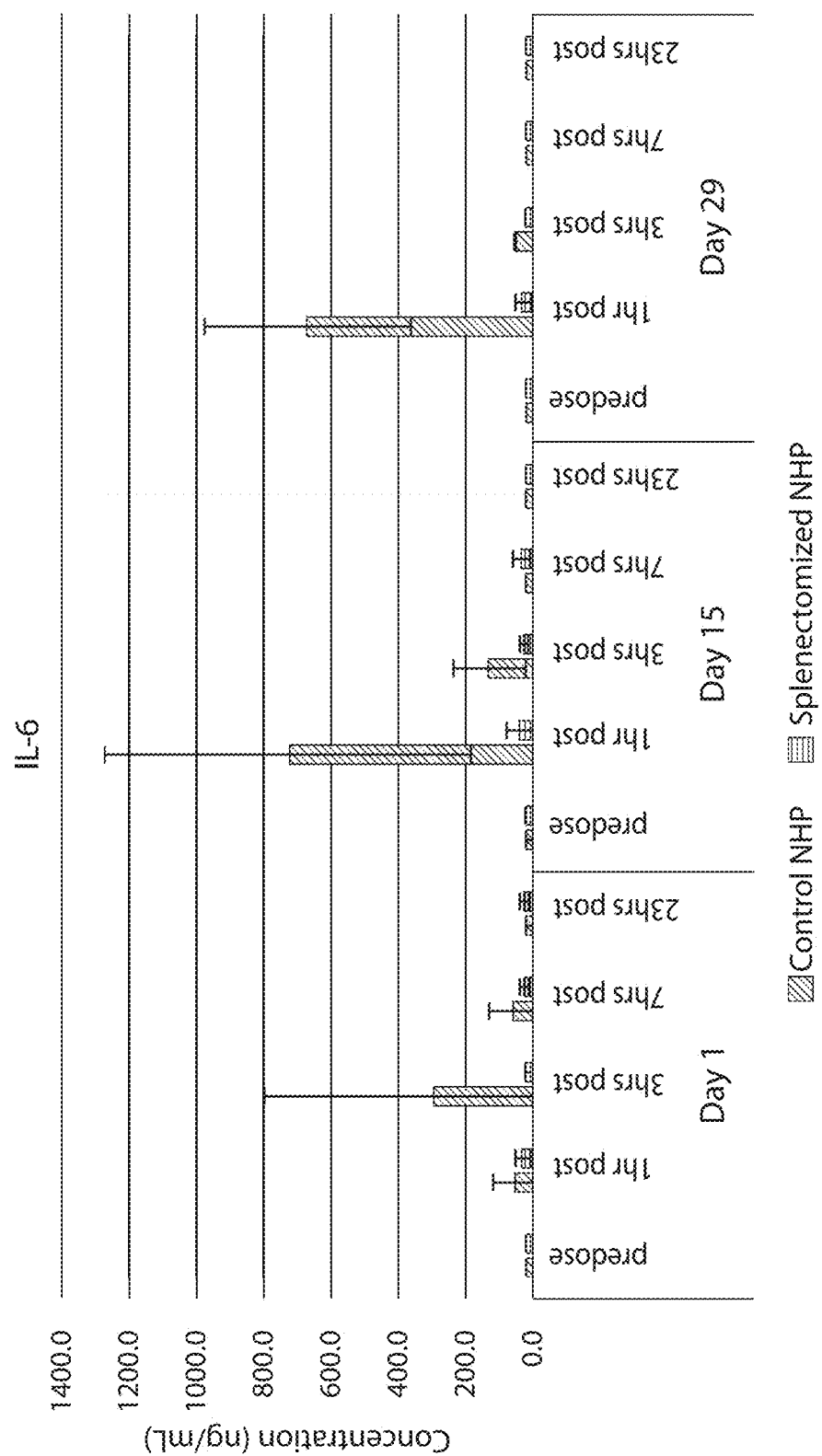

```
                        SEQUENCE LISTING

<160> NUMBER OF SEQ ID NOS: 4

<210> SEQ ID NO 1
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 1

Met Ala Glu Pro Ala Gly Ser Pro Thr Ser Thr Glu Glu Gly Thr Pro
1               5                   10                  15

Gly Ser Gly Thr Ala Ser Ser Ser Pro Gly Ser Ser Thr Pro Ser Gly
            20                  25                  30

Ala Thr Gly Ser Pro Gly Ala Ser Pro Gly Thr Ser Ser Thr Gly Ser
        35                  40                  45

<210> SEQ ID NO 2
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 2

Met Ala Glu Pro Ala Gly Ser Pro Thr Ser Thr Glu Glu Gly Ala Ser
1               5                   10                  15

Pro Gly Thr Ser Ser Thr Gly Ser Pro Gly Ser Ser Thr Pro Ser Gly
            20                  25                  30

Ala Thr Gly Ser Pro Gly Ser Ser Thr Pro Ser Gly Ala Thr Gly Ser
        35                  40                  45

<210> SEQ ID NO 3
<211> LENGTH: 60
<212> TYPE: PRT
<213> ORGANISM: Artificial Sequence
<220> FEATURE:
<223> OTHER INFORMATION: Synthetic Polypeptide

<400> SEQUENCE: 3

Ser Ala Pro Ser Ser Pro Ser Pro Ser Ala Pro Ser Ser Pro Ser Pro
1               5                   10                  15

Ala Ser Pro Ser Ser Ala Pro Ser Ser Pro Ser Pro Ser Ala Pro Ser
            20                  25                  30

Ser Pro Ser Pro Ala Ser Pro Ser Ser Ala Pro Ser Ser Pro Ser Pro
        35                  40                  45

Ser Ala Pro Ser Ser Pro Ser Pro Ala Ser Pro Ser
    50                  55                  60
```

```
<210> SEQ ID NO 4
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 4

Ala Ala Ser Pro Ala Ala Pro Ser Ala Pro Pro Ala Ala Ala Ser Pro
1               5                   10                  15

Ala Ala Pro Ser Ala Pro Pro Ala Ala Ala Ser Pro Ala Ala Pro Ser
                20                  25                  30

Ala Pro Pro Ala Ala Ala Ser Pro Ala Ala Pro Ser Ala Pro Pro Ala
            35                  40                  45
```

COMPOSITIONS AND METHODS FOR DELIVERY OF AGENTS

RELATED APPLICATIONS

This application is a continuation of International Patent Application Serial No. PCT/US2016/000129, filed Dec. 10, 2016, which claims priority under 35 U.S.C. § 119(e) to U.S. Provisional Application Ser. No. 62/413,050, entitled "COMPOSITIONS AND METHODS FOR DELIVERY OF AGENTS" filed on Oct. 26, 2016, to U.S. Provisional Application Ser. No. 62/413,027, filed on Oct. 26, 2016, to U.S. Provisional Application Ser. No. 62/350,172, filed on Jun. 14, 2016, to U.S. Provisional Application Ser. No. 62/350,165, filed on Jun. 14, 2016, to U.S. Provisional Application Ser. No. 62/311,386, entitled "COMPOSITIONS AND METHODS FOR DELIVERY OF THERAPEUTIC AGENTS" filed on Mar. 21, 2016, to U.S. Provisional Application Ser. No. 62/311,388, filed on Mar. 21, 2016, to U.S. Provisional Application Ser. No. 62/311,380, entitled "COMPOSITIONS AND METHODS FOR DELIVERY OF AGENTS" filed on Mar. 21, 2016, to U.S. Provisional Application Ser. No. 62/266,581, entitled "COMPOSITIONS AND METHODS FOR DELIVERY OF THERAPEUTIC AGENTS" filed on Dec. 12, 2015, to U.S. Provisional Application Ser. No. 62/265,973, entitled "COMPOSITIONS AND METHODS FOR DELIVERY OF AGENTS WITH REDUCED CLEARANCE" filed on Dec. 10, 2015. The entire contents of these applications are incorporated herein by reference in their entirety.

BACKGROUND

Effective in vivo delivery of active agents such as small molecule drugs, proteins, peptides, and nucleic acids represents a continuing medical challenge. Some active agents are recognized by the immune system, resulting in decreased efficacy. To address this issue, certain active agent formulations have incorporated polymers such as polyethylene glycol which was thought to cloak or mask the agent, thereby reducing its antigenicity and immunogenicity. However, even these "stealth" formulations have their limitations, including an inability to be repeatedly and frequently dosed, for example, over a period of days without loss of activity.

In addition, some agents or formulations when administered in vivo may interact with one or more cells or factors, potentially interfering with their functions, and ultimately resulting in adverse effects. Such adverse effects may limit the administration frequency and/or administered dose of the agent, or may preclude in vivo use altogether.

SUMMARY

The present disclosure is based, at least in part, on the discoveries that components of lipid nanoparticles (LNPs) may induce an innate immune response. In some embodiments components of the LNPs, such as phosphatidylcholine, may induce the production of natural IgM and/or IgG molecules, which may be mediated by activation of B1 cells, such as B1a and/or B1b cells. These biological mechanisms may contribute to drug responses caused by LNPs, including accelerated blood clearance (ABC) and dose-limiting toxicity such as acute phase response (APR) and complement activation-related pseudoallergy (CARPA). Both B1a cells and platelets express CD36, which can bind phosphatidylcholine.

The activation of B1 cells and platelets by LNPs may be mediated by activation of the CD36 receptor by a component in the LNPs such as phosphatidylcholine. Additionally, the PEG-lipid on the LNPs may contribute to the production of natural IgM and/or anti-PEG IgG and IgM. Accordingly, provided herein are methods and compositions for delivering LNPs to a subject without promoting the same degree of LNP-related drug responses as noted herein by using LNPs that do not trigger an innate immune response characterized by natural IgM production, natural IgG production, anti-PEG IgM, anti-PEG IgG, B1a cell activation, B1b cell activation, pDC cell activation and/or platelet aggregation and/or activation, and/or using secondary agents, in particular, pharmacological agents, that inhibit the production of this innate immune response, as well as suppress the downstream signaling pathways leading to the LNP-related drug responses.

This disclosure provides, in part, novel lipid nanoparticles (LNP) and LNP formulations that are less susceptible to recognition and thus clearance, by the immune system. The LNP provided herein have surprisingly improved clearance and in some instances, toxicity profiles. While not intending to be bound by any particular mechanism or theory, the improved clearance profiles are believed to have reduced recognition by and/or binding to certain immune cells and less overall effect on those and other immune cells and factors. More specifically, certain of the LNPs provided herein have no or low binding to B1a and/or B1b cells, B1a and/or B1b activating activity, pDC activating activity, platelet aggregating activity, and/or platelet activating activity. This activity may be due at least in part to the components of the LNP, or an agent that inhibits immune responses induced by the LNP components. Such an agent may be incorporated within the LNP administered or or formulated separately.

Also provided in this disclosure are compounds and compositions, including formulations, that modulate immune responses to administered nanoparticles such as LNP. Also provided herein are methods of use of such compounds and compositions, particularly relating to immune modulation in vivo. Also provided are methods of use of LNPs together with certain classes of secondary agents, including for example use of LNPs in subjects that have been co-medicated, e.g., pre-medicated with certain secondary agents. Also provided are pre-administration and/or pre-treatment screening methods that identify patients that respond to LNP administration and optionally classify such patients according the degree of their response. Identifying such subjects may lead, in some instances, to a modified treatment regimen.

Certain of the LNPs provided herein comprise a cationic lipid, a helper lipid, a structural lipid, and a stabilizer which may or may not be provided conjugated to another lipid.

The cationic lipid may be but is not limited to DLin-DMA, DLin-D-DMA, DLin-MC3-DMA, DLin-KC2-DMA and DODMA. The cationic lipid may be an ionizable lipid.

The structural lipid may be but is not limited to a sterol such as for example cholesterol.

The helper lipid is an amphiphilic surface active lipid, or surfactant. In some embodiments it is a non-cationic lipid. The helper lipid may comprise at least one non-polar chain and at least one polar headgroup moiety. A helper lipid may also be referred to as a complementary lipid i.e. the lipid functions to "complement" the amino lipid and increase the fusogenicity of the bilayer to help endosomal escape. In some embodiments the non-polar chain is a lipid. In other embodiments it is a fatty acid of at least 8C. In exemplary embodiments, the helper lipid is non-naturally occurring (e.g., not naturally occurring in human subjects) or is exogenous.

Certain of the LNPs lack any phosphatidyl choline (PC) lipids (i.e., are free of phosphatidyl choline (PC)). Certain of the LNPs provided herein lack specific phosphatidyl choline lipids such as but not limiting to DSPC. Certain of the LNPs comprise a phosphatidyl choline analog, such analogs comprising modified head groups (e.g., a modified quaternary amine head group), modified core group, and/or modified lipid tail group. Such analogs may comprise a zwitterionic group that is a non-PC zwitterionic group. The helper lipid may be a lipid of any one or any combination of Formulae I, I-a, I-b, I-b-1, I-b-2, I-b-3, I-b-4, I-c, I-c-1, I-c-2, I-c-3, or II as provided herein.

Certain LNPs comprise other helper non-cationic lipids including for example oleic acid or oleic acid analogs. The helper lipid may be a lipid of Formula IV as provided herein.

The stabilizer may be polyethylene glycol (PEG). PEG may be conjugated to a lipid and thus may be provided as PEG-c-DOMG or PEG-DMG, for example. The stabilizer, whether provided in a conjugated or an unconjugated form, may comprise 1.5 mol % of the LNP, or it may comprise less than 0.5 mol % of the LNP. For example, it may comprise less than 0.4 mol %, less than 0.3 mol %, less than 0.2 mol %, or less than 0.1 mol %. Each possibility represents a separate embodiment of the present invention.

The LNP may comprise a PEGylated lipid of Formula III, including Formulae III-OH, III-a-1, III-a-2, III-b-1, IIII-b-2, III-b-1-OH, III-b-2-OH, V, V-OH. Each possibility represents a separate embodiment of the present invention.

Certain of the LNPs provided herein comprise no or low levels of PEGylated lipids, including no or low levels of alkyl-PEGylated lipids, and may be referred to herein as being free of PEG or PEGylated lipid. Thus, some LNPs comprise less than 0.5 mol % PEGylated lipid. In some instances, PEG may be an alkyl-PEG such as methoxy-PEG. Still other LNPs comprise non-alkyl-PEG such as hydroxy-PEG, and/or non-alkyl-PEGylated lipids such as hydroxy-PEGylated lipids. Each possibility represents a separate embodiment of the present invention.

The PEGylated lipid may be a Cmpd420, a Cmpd396, a Cmpd394, Cmpd397, Cmpd395, Cmpd417, Cmpd418, or Cmpd419. Each possibility represents a separate embodiment of the present invention.

In some instances, the LNP may comprise about 50 mol %, 10 mol % helper lipid, 1.5 mol % PEGylated lipid, and 38.5 mol % structural lipid.

In some instances, the LNP may comprise about 50 mol %, 10 mol % helper lipid, less than 0.5 mol % PEGylated lipid, and 39.5 mol % structural lipid. Each possibility represents a separate embodiment of the present invention.

In some embodiments, the stabilizer is a non-PEG moiety such as an XTEN peptide that may or may not be conjugated to a lipid. The XTEN peptide is capable of forming a hydrated shell around the LNP due to its hydrophilic nature. It further serves to increase the half-life of the LNP, compared to an LNP lacking (or free of) any stabilizer. Unlike PEG, however, it is biodegradable and has been reported to be non-immunogenic. The XTEN peptide may have an amino acid sequence of MAEPAGSPTSTEEGTPGSG-TASSSPGSSTPSGATGSPGASPGTSSTGS (SEQ ID NO:1) or MAEPAGSPTSTEEGASPGTSSTGSPGSSTPS-GATGSPGSSTPSGATGS (SEQ ID NO:2). Other XTEN amino acid sequences are known in the art, including for example those reported in U.S. Pat. No. 9,062,299. Examples of XTEN conjugated lipids include but are not limited to Cmpd431, and Cmpd432 and Cmpd433. Click chemistry may be used to conjugate the XTEN peptide to the lipid.

In some embodiments, the stabilizer is a non-PEG moiety such as a PAS peptide. A PAS peptide is a peptide comprising primarily if not exclusively proline, alanine and serine. Like PEG and XTEN peptides, the PAS peptide is capable of forming a hydrated shell around the LNP. It too serves to increase the half-life of an LNP, compared to an LNP lacking (or free of) a stabilizer. Unlike XTEN peptides, however, PAS peptides tend to be neutral in charge, and thus at least in this respect more similar to PEG. The PAS peptide may have an amino acid sequence of SAPSSPSPSAPSS-PSPASPSSAPSSPSPSAPSSPSPASPSSAPSSPSPSAPSSP-SPASPS (SEQ ID NO:3 or AASPAAPSAPPAAASPAAPS-APPAAASPAAPSAPPAAASPAAPSAPPA (SEQ ID NO: 4). Other PAS amino acid sequences are known in the art, including for example, those reported in WO 2008155134.

The disclosure contemplates LNPs having any combination of the foregoing characteristics. Such LNPs may be further characterized as having reduced binding to B1a cells and/or reduced B1a cell activation activity. Additionally or alternatively, they may be further characterized as having reduced platelet aggregation activity, which may be indicated as reduced platelet activation activity.

This disclosure further contemplates that such LNPs may be used in vivo to deliver an agent, such as a protein or a nucleic acid, without triggering accelerated blood clearance (ABC). Thus, such LNPs can be administered to a subject repeatedly and within short time periods without risk of enhanced clearance by the immune system, as has been previously reported for a variety of administered agents including lipid formulated agents. Thus, the LNPs and more importantly their cargo can be administered more frequently, and effectively at higher doses over these short time periods, than was previously possible.

Even more surprisingly, certain of these LNPs also demonstrate reduced toxicity upon administration. Again, while not intending to be bound by any particular mechanism or theory, this is believed to result from the reduced platelet aggregation activity of these LNPs. This inability or reduced ability to aggregate platelets reduces the likelihood and severity of coagulopathy-related toxicity that has been observed following LNP administration in vivo.

It was wholly unexpected that certain LNPs would have the dual benefit of reduced susceptibility to ABC and reduced toxicity in vivo. As a result, these LNPs allow for higher doses of encapsulated agent to be administered to a subject, due in part to the reduced toxicity profile of their encapsulating LNP. The LNPs also lead to a longer half-life for the LNPs and thus their cargo, due in part to their reduced susceptibility to ABC. This results in higher and more stable levels of cargo between administrations. Moreover, in the case of cargo requires repeated frequent administration, the LNPs provided herein facilitate such administration. This serves to increase the efficacy of certain agents by allowing more frequent dosing than may currently be possible. This also serves to render useful other agents that may have not been used previously in vivo due to these restrictions.

This disclosure further provides other novel formulations and methods of use of LNPs, including LNP formulations. Specifically, provided herein are methods of use of LNPs and LNP formulations together with anti-platelet agents including but not limited to platelet aggregation inhibitors. This disclosure contemplates that such agents may be administered to a subject prior to and/or substantially simultaneously with, and/or even after administration of the LNP. Thus, such agents may be formulated together with the LNP or they may be separately formulated but administered together, via the same route, and/or at the same or substantially the same time. Significantly, pre-medication or co-medication of a subject with these anti-platelet agents results in reduced toxicity, including coagulopathy-related toxicity, and in a lower and less severe incidence of ABC. According to certain embodiments, subjects may be pre-medicated or co-medicated with a combination of secondary agents including platelet aggregation inhibitors, anti-histamines, and NSAIDS or COX enzyme inhibitors. Certain secondary agents that may be used have dual functionality (i.e., they are able to inhibit platelet aggregation, in whole or in part, and also have a general anti-inflammatory effect). One such example is aspirin.

A lipid nanoparticle (LNP) encapsulating an mRNA encoding a protein is provided in some aspects of the invention. The LNP has a cationic lipid, a non-cationic helper lipid comprising at least one fatty acid chain of at least 8C and at least one polar head group moiety, and wherein the helper lipid is not a phosphatidyl choline (PC), a PEG lipid, and a sterol. In some aspects the LNP further comprises an agent that inhibits immune responses by the LNP. In other aspects the non-cationic helper lipid is a zwitterionic non-cationic helper lipid, a DSPC analog, oleic acid, an oleic acid analog, or a 1,2-distearoyl-sn-glycero-3-phosphocholine (DSPC) substitute.

In certain embodiments, non-cationic lipids useful in the present invention are DSPC analogs wherein the phosphocholine moiety is replaced by a different zwitterionic group. In certain embodiments, the different zwitterionic group is not a phosphocholine group. In certain embodiments, a non-cationic lipid useful in the present invention is a compound of Formula (II). Provided herein are compounds of Formula (II):

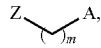
(II)

or a salts thereof, wherein:
Z is a zwitterionic moiety,
wherein the zwitterionic moiety is not of the formula:

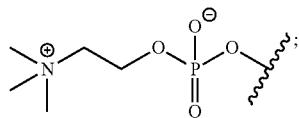 [SMILES: *OP(=O)([O-])OCC[N+](C)(C)C]

m is 0, 1, 2, 3, 4, 5, 6, 7, 8, 9, or 10;
A is of the formula:

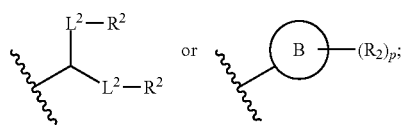

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —N$R^N$C(O)—, —C(O)O—, —OC(O)—, —OC(O)O—, —OC(O)N($R^N$)—, —N$R^N$C(O)O—, or —N$R^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, Z is an amino acid or a derivative thereof. In certain embodiments, Z is of one of the following formulae:

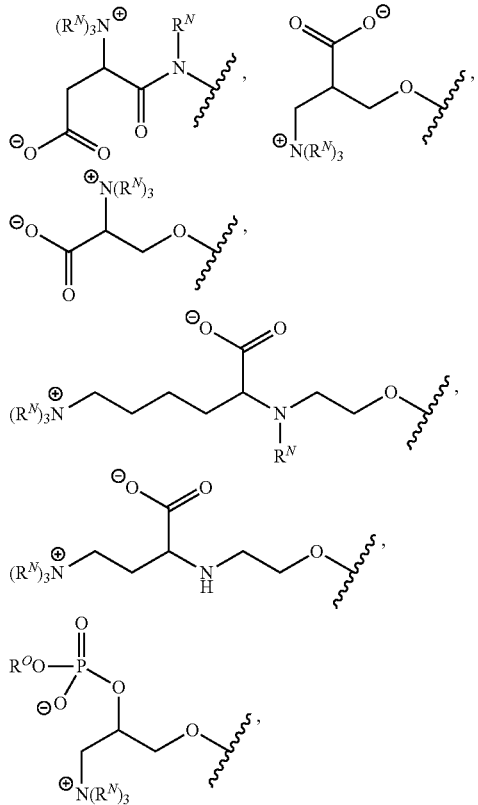

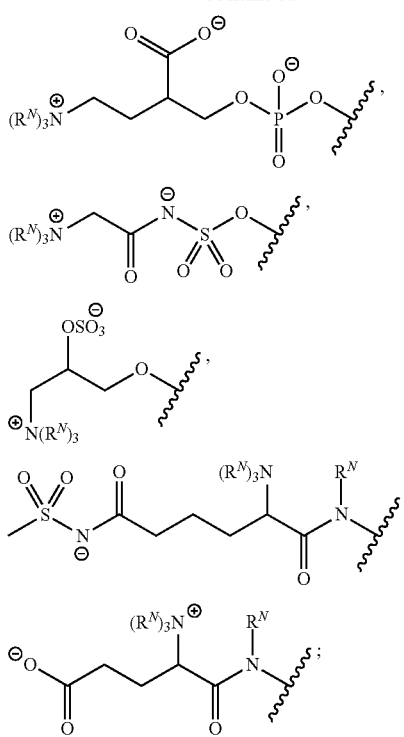
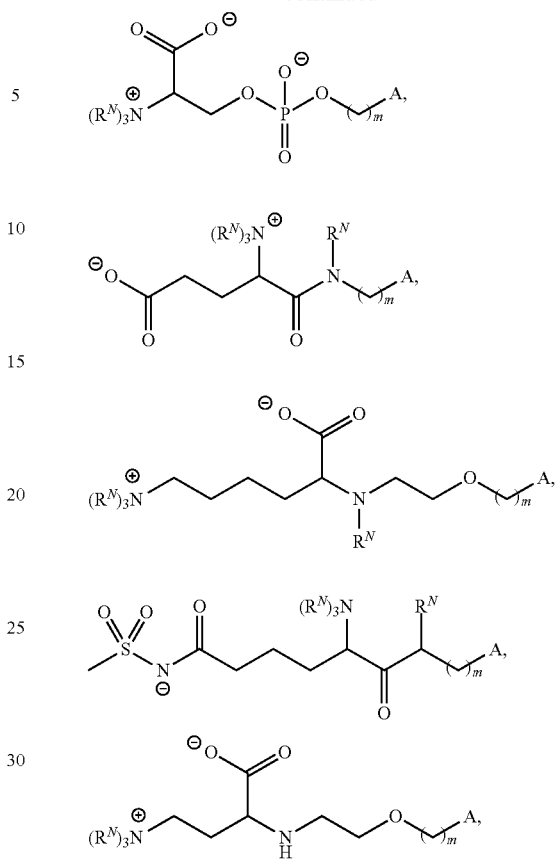
wherein $R^O$ is hydrogen, optionally substituted alkyl or an oxygen protecting group. In certain embodiments, a compound of Formula (II) is of one of the following formulae:
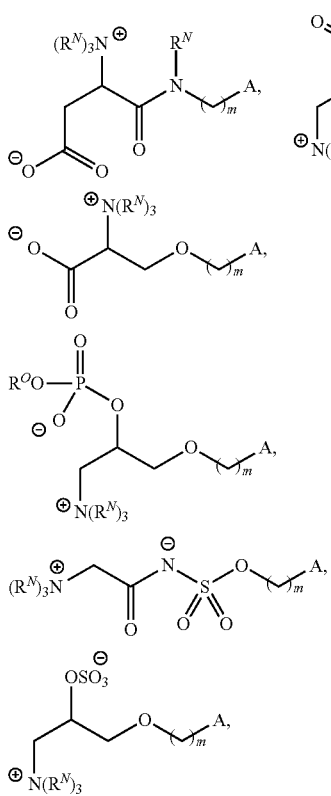
or a salt thereof.
In certain embodiments, a compound of Formula (II) is of one of the following formulae:
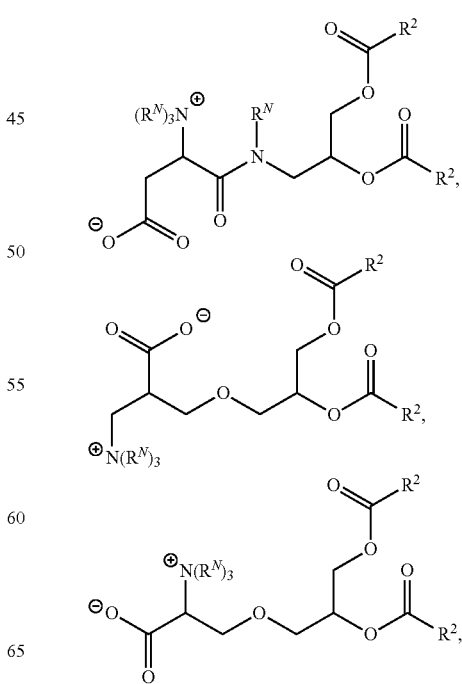

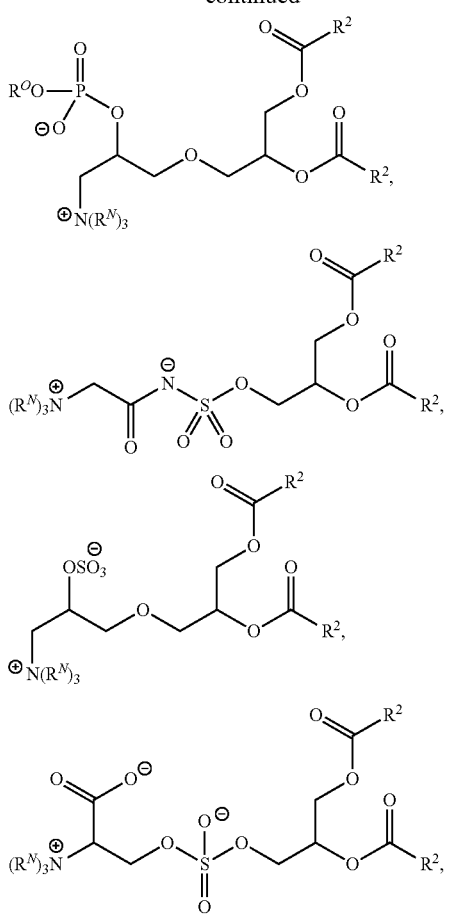
or a salt thereof.
For example, in certain embodiments, a compound of Formula (II) is one of the following:

-continued
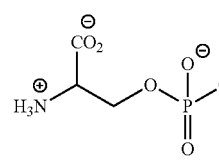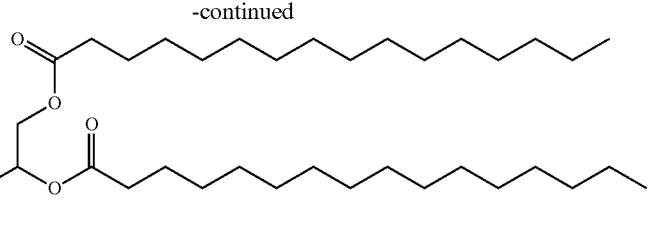
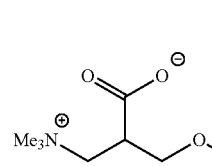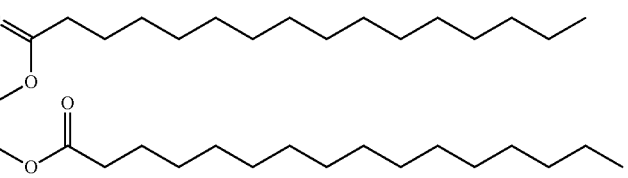
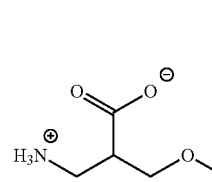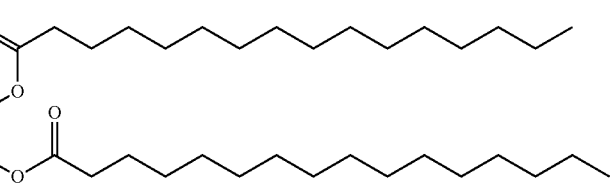
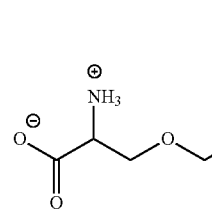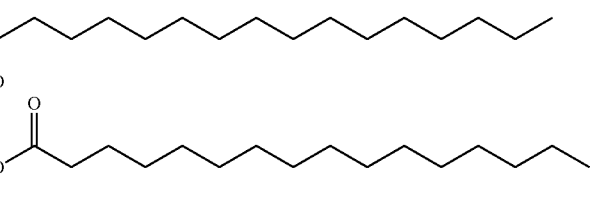
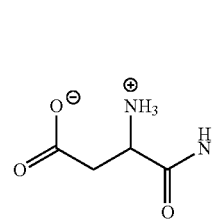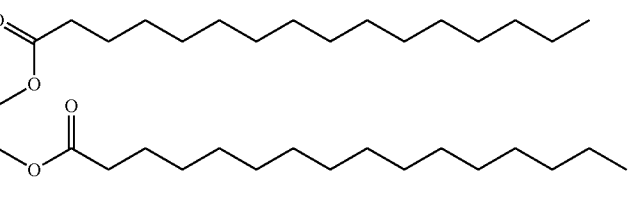
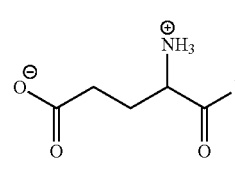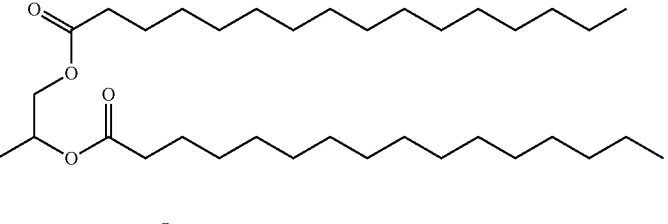
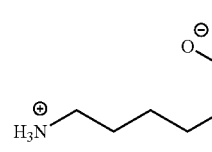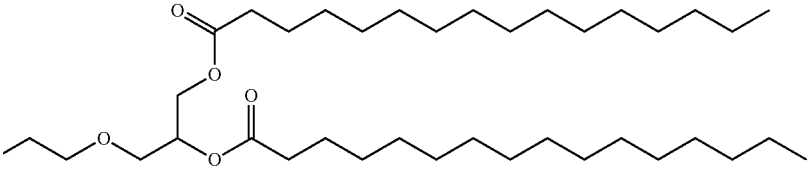
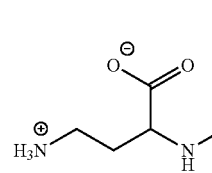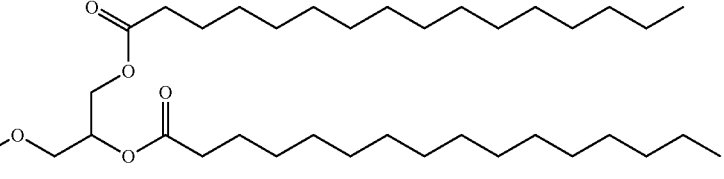

-continued

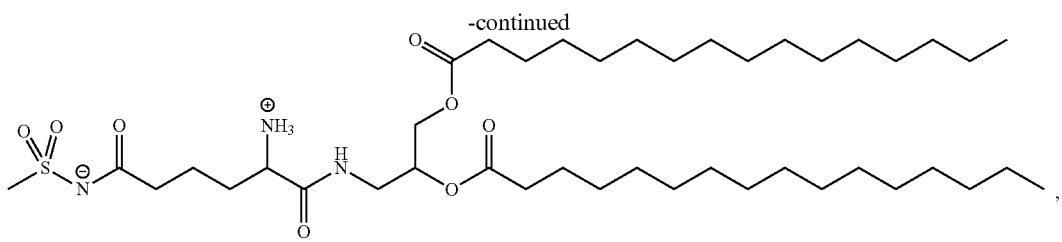

or salts thereof.

Non-cationic lipids useful in the present invention also include analogs of oleic acid. As described herein, an oleic acid analog can comprise a modified oleic acid tail, a modified carboxylic acid moiety, or both. In certain embodiments, an analog of oleic acid is a compound of Formula (IV). Provided herein are compounds of Formula (IV):

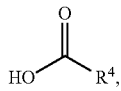
(IV)

or a salt thereof, wherein:

$R^4$ is optionally substituted, $C_{10-40}$ alkyl; optionally substituted, $C_{10-40}$ alkenyl; optionally substituted, $C_{10-40}$ alkynyl; wherein at least one methylene group of $R^4$ is independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)—, —OS(O)—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (IV) is one of the following:

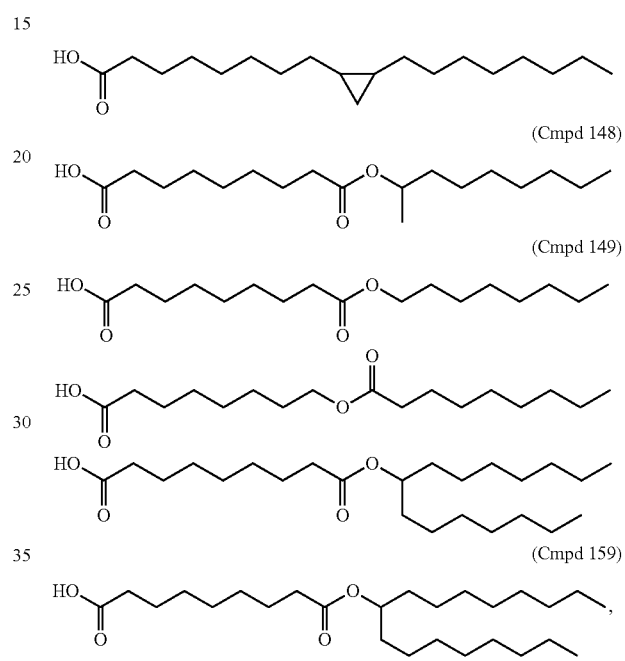

or salts thereof.

In certain embodiments, an oleic acid analog is a compound wherein the carboxylic acid moiety of oleic acid replaced by a different group. In certain embodiments, an oleic acid analog useful in the present invention is one of the following:

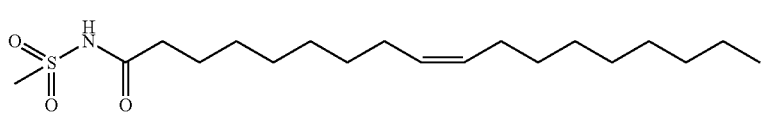
(Cmpd157)

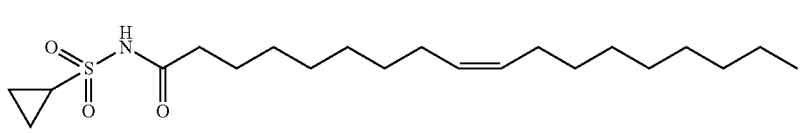
(Cmpd158)

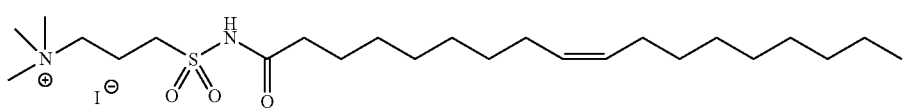

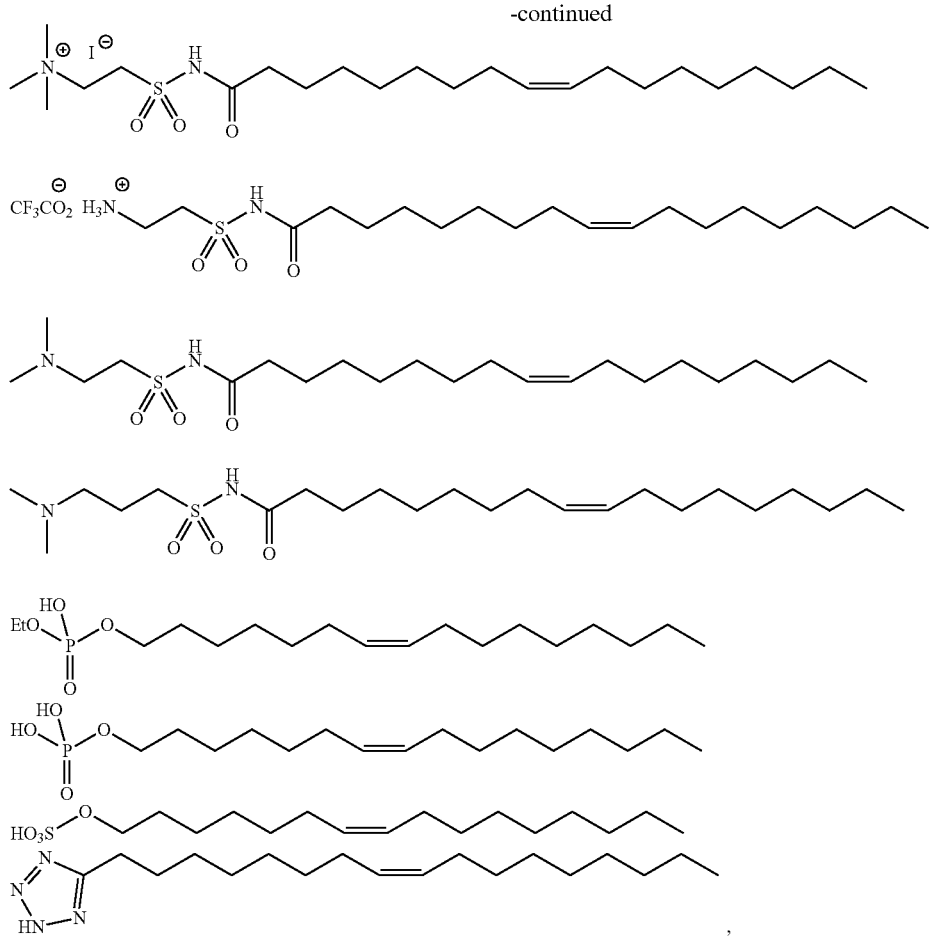
or salts thereof.
Examples of non-cationic lipids include, but are not limited to, the following:
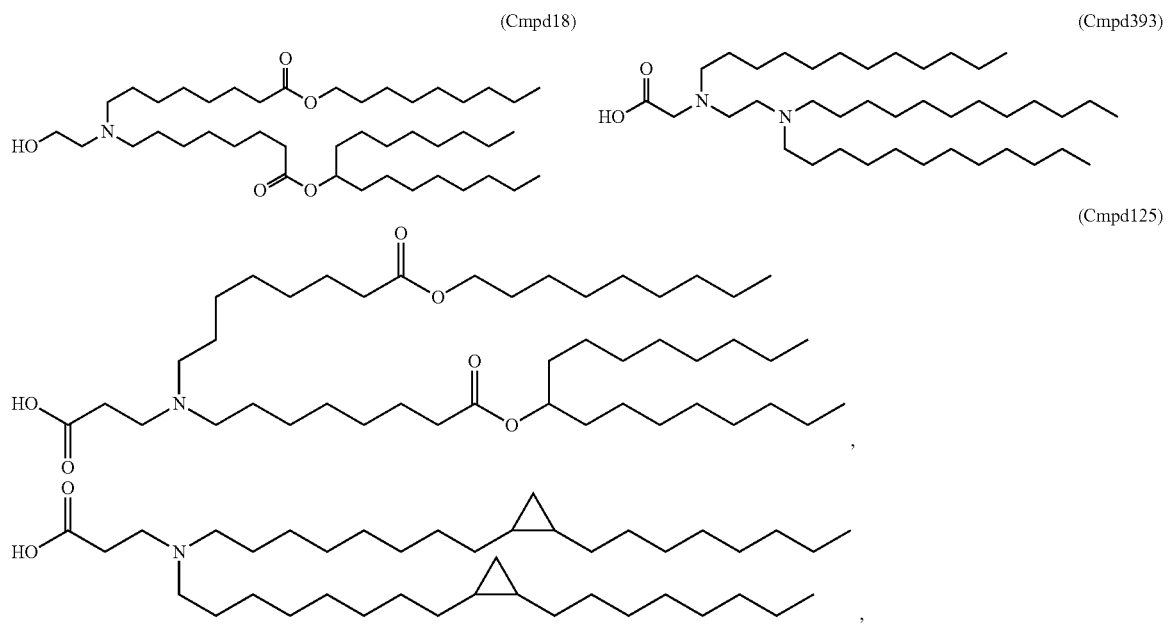

-continued
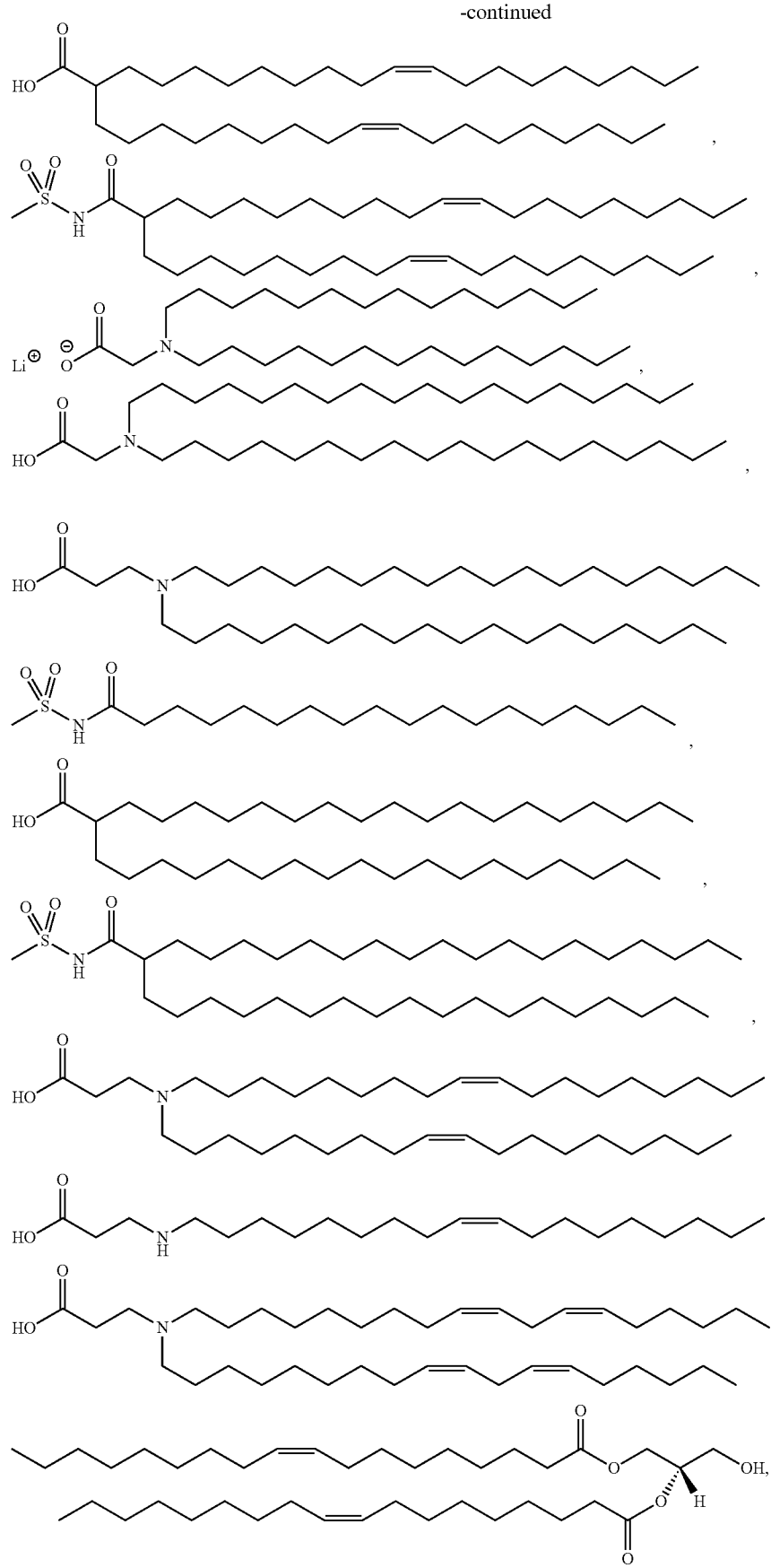

-continued
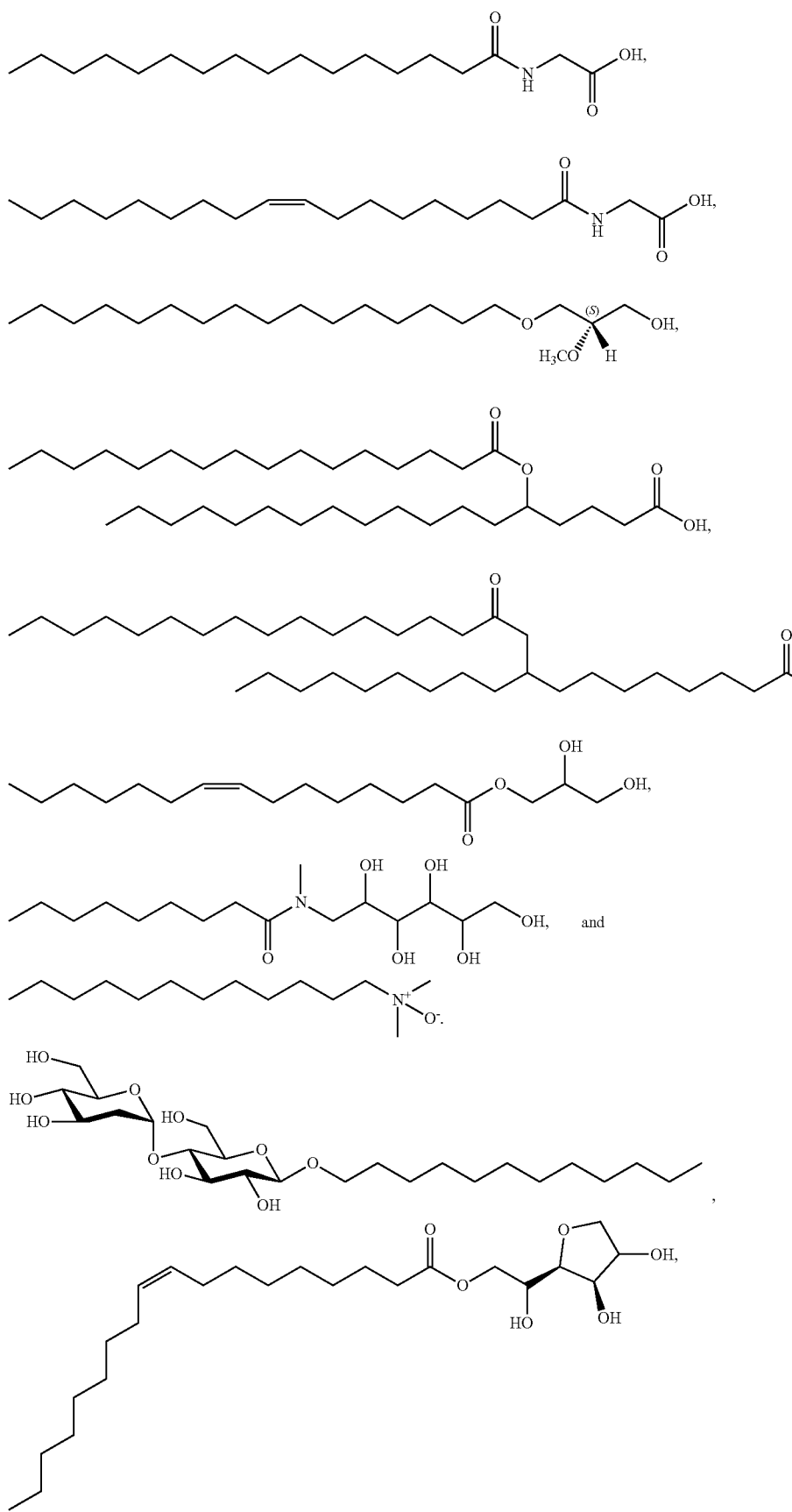

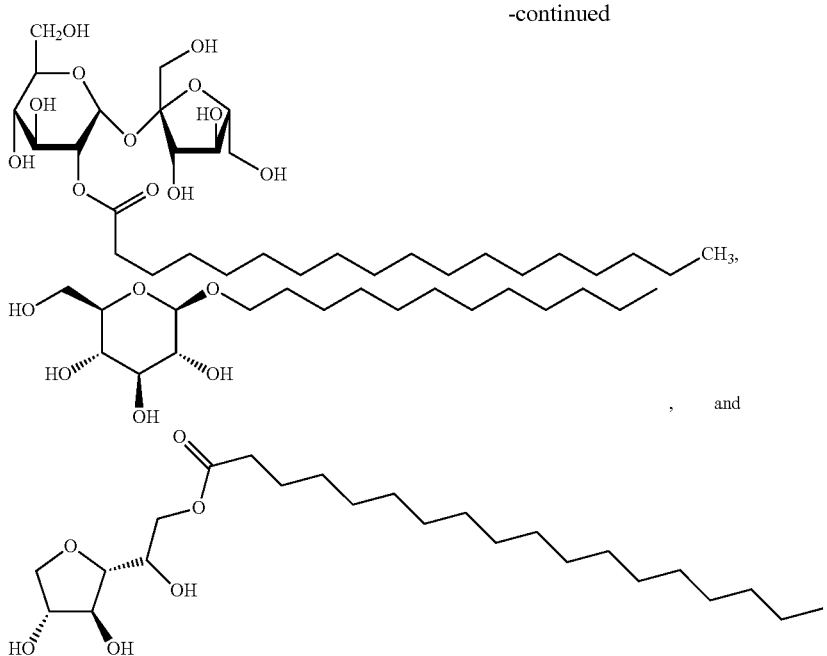
, and

A lipid nanoparticle (LNP) encapsulating an mRNA encoding a protein is provided in some aspects of the invention. The LNP has a cationic lipid, a non-cationic helper lipid comprising at least one fatty acid chain of at least 8C and at least one polar head group moiety, a PEG lipid, and a sterol. In some aspects the LNP further comprises an agent that inhibits immune responses by the LNP. In some embodiments the PEG lipid is an alkyl-PEGylated lipids, non-alkyl-PEG such as hydroxy-PEG, a non-alkyl-PEGylated lipid such as hydroxy-PEGylated lipid, a Cmpd420, a Cmpd396, a Cmpd394, Cmpd397, Cmpd395, Cmpd417, Cmpd418, or Cmpd419, Cmpd421, Cmpd422, or wherein the PEG lipid contains less than 0.5% molar ratio of PEG lipid to the other components.

In certain embodiments, a PEG lipid useful in the present invention is a compound of Formula (III). Provided herein are compounds of Formula (III):

or salts thereof, wherein:
$R^3$ is —$OR^O$;
$R^O$ is hydrogen, optionally substituted alkyl, or an oxygen protecting group;
r is an integer between 1 and 100, inclusive;
$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;
D is a moiety obtained by click chemistry or a moiety cleavable under physiological conditions;
m is 0, 1, 2, 3, 4, 5, 6, 7, 8, 9, or 10;

A is of the formula:

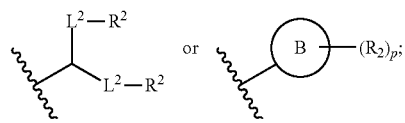

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;
each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;
each instance of $R^N$ is independently hydrogen, optionally substituted alkyl, or a nitrogen protecting group;
Ring B is optionally substituted carbocyclyl, optionally substituted heterocyclyl, optionally substituted aryl, or optionally substituted heteroaryl; and
p is 1 or 2.

In certain embodiments, the compound of Formula (III) is a PEG-OH lipid (i.e., $R^3$ is —$OR^O$, and $R^O$ is hydrogen). In certain embodiments, the compound of Formula (III) is of Formula (III-OH):

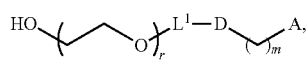

(III-OH)

or a salt thereof.

In certain embodiments, D is a moiety obtained by click chemistry (e.g., triazole). In certain embodiments, the compound of Formula (III) is of Formula (III-a-1) or (III-a-2):

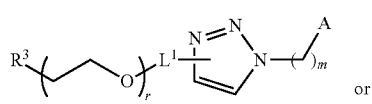

(III-a-1)

or

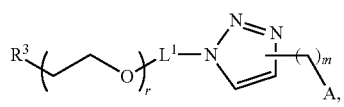

(III-a-2)

or a salt thereof.

In certain embodiments, the compound of Formula (III) is of one of the following formulae:

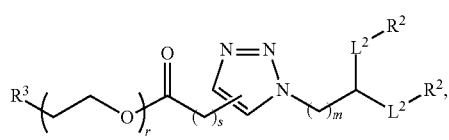

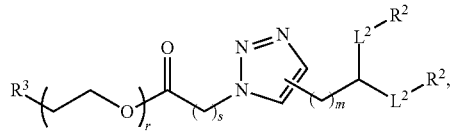

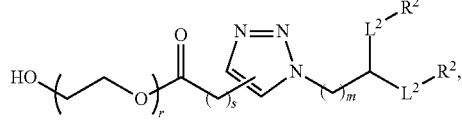

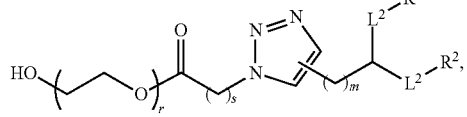

or a salt thereof, wherein
s is 0, 1, 2, 3, 4, 5, 6, 7, 8, 9, or 10.

In certain embodiments, the compound of Formula (III) is of one of the following formulae:

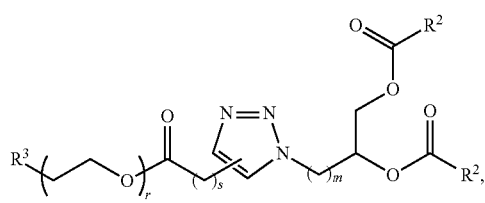

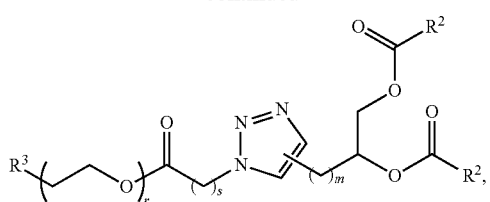

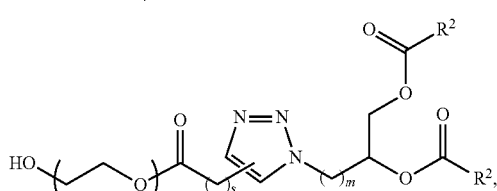

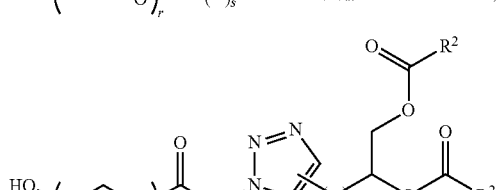

or a salt thereof.

In certain embodiments, a compound of Formula (III) is of one of the following formulae:

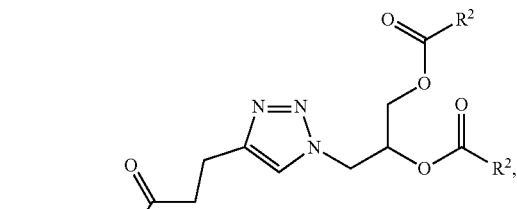

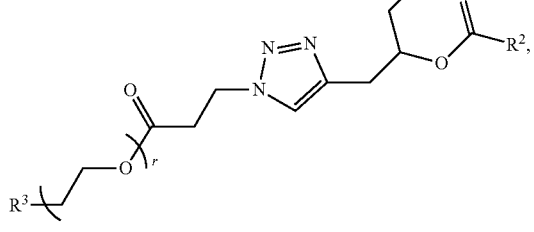

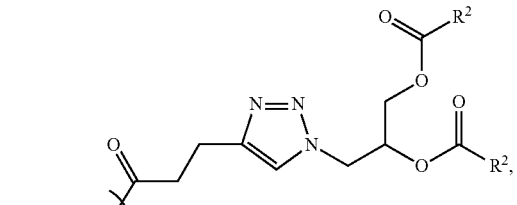

-continued

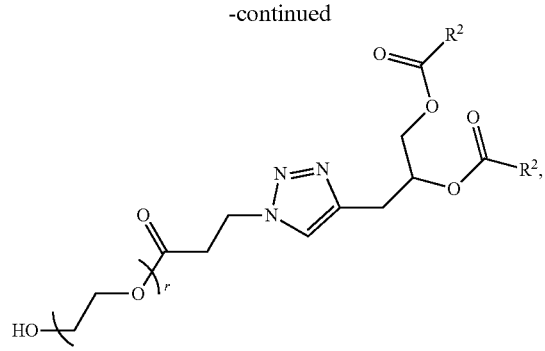

or a salt thereof.

In certain embodiments, a compound of Formula (III) is of one of the following formulae:

(Cmpd394)

(Cmpd396)

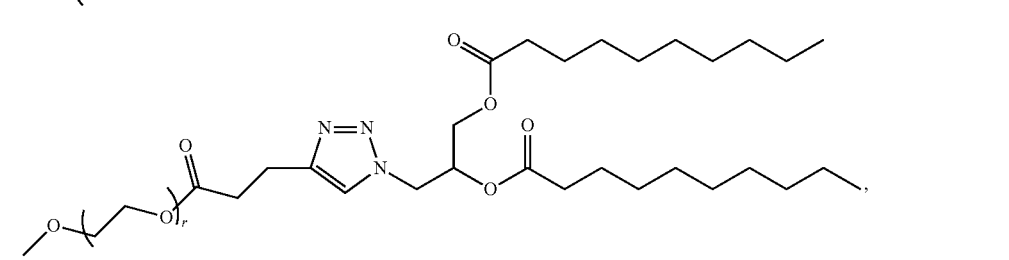
(Cmpd395)

(Cmpd397)

or a salt thereof.

In certain embodiments, D is a moiety cleavable under physiological conditions (e.g., ester, amide, carbonate, carbamate, urea). In certain embodiments, a compound of Formula (III) is of Formula (III-b-1) or (III-b-2):

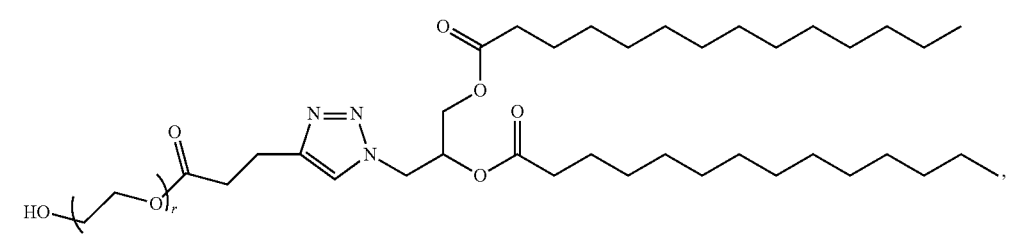
(III-b-1)

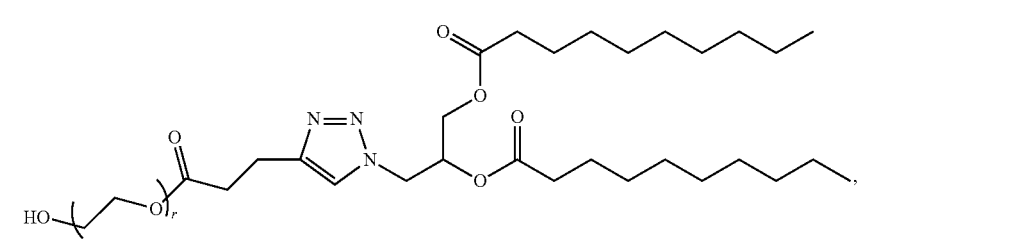
(III-b-2)

or a salt thereof.

In certain embodiments, a compound of Formula (III) is of Formula (III-b-1-OH) or (III-b-2-OH):

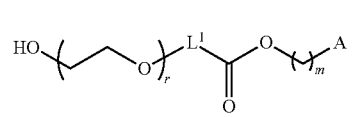
(III-b-1-OH)

(III-b-2-OH)

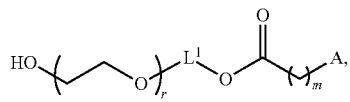

or a salt thereof.

In certain embodiments, the compound of Formula (III) is of one of the following formulae:

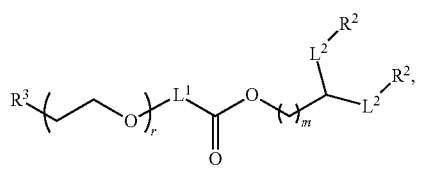

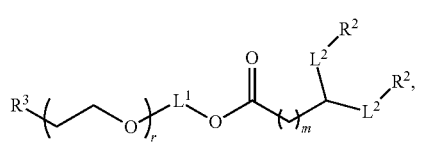

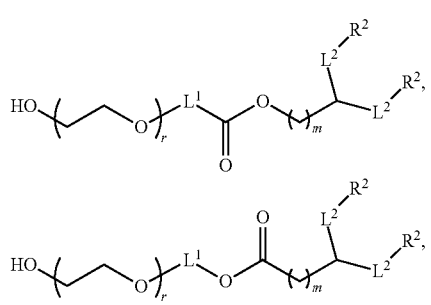

or a salt thereof.

In certain embodiments, a compound of Formula (III) is of one of the following formulae:

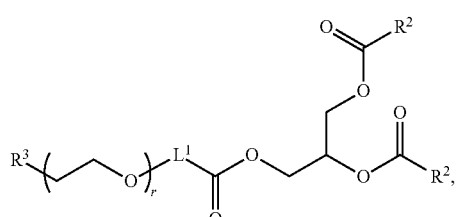

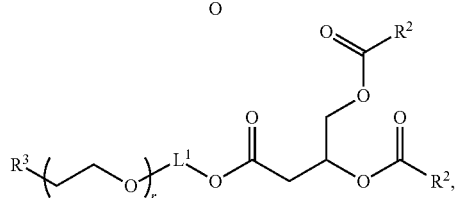

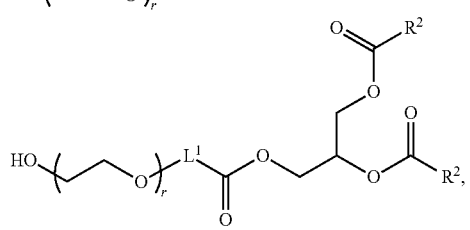

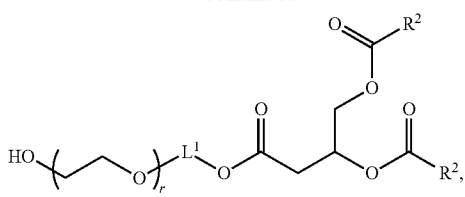

or a salt thereof.

In certain embodiments, a compound of Formula (III) is of one of the following formulae:

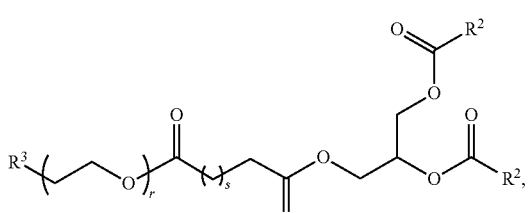
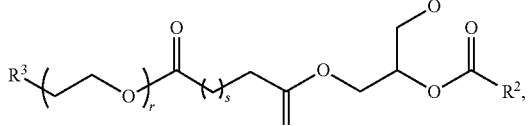

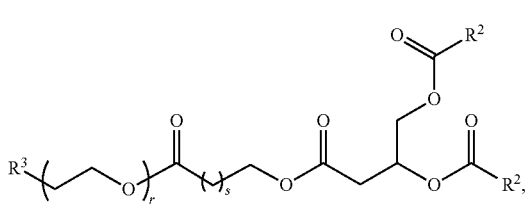
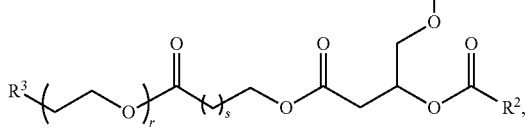

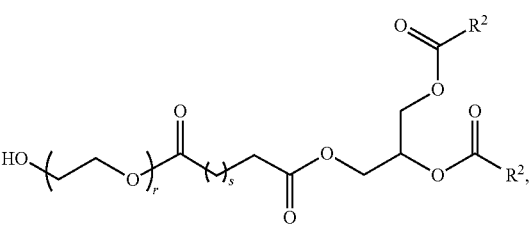

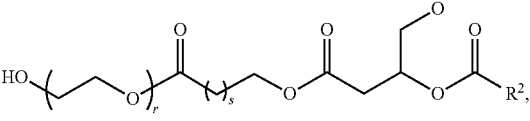

or a salt thereof.

In certain embodiments, a compound of Formula (III) is of one of the following formulae:

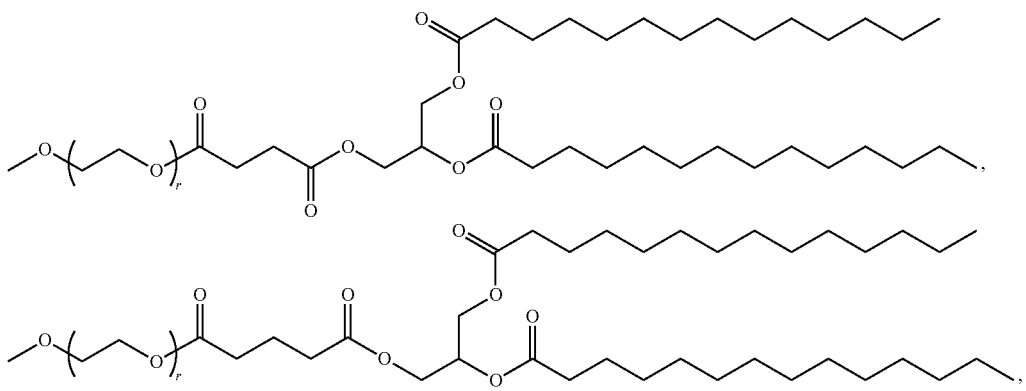

or salts thereof.

In certain embodiments, a PEG lipid useful in the present invention is a PEGylated fatty acid. In certain embodiments, a PEG lipid useful in the present invention is a compound of Formula (V). Provided herein are compounds of Formula (V):

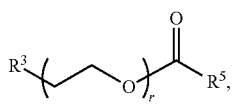
(V)

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)—, —OS(O)—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (V) is of Formula (V-OH):

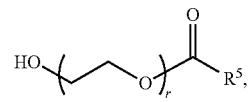
(V-OH)

or a salt thereof.

In certain embodiments, a compound of Formula (V) is of one of the following formulae:

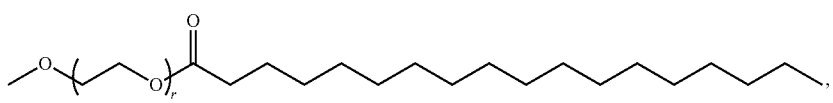
(Cmpd400)

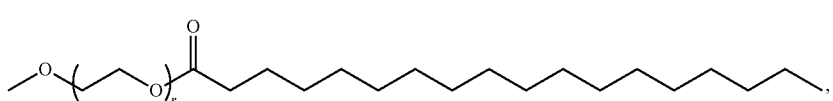
(Cmpd401)

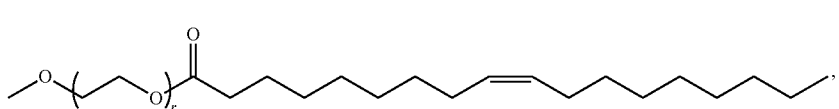
(Cmpd401)

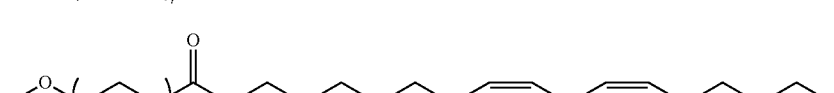
(Cmpd402)

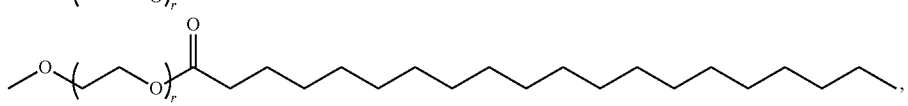

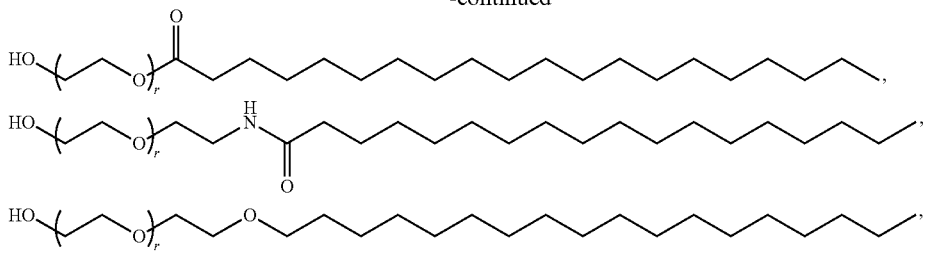

or a salt thereof.

In other aspects the non-cationic helper lipid is a zwitterionic non-cationic helper lipid, a lipid that is not a phosphatidyl choline (PC), a DSPC analog, oleic acid, an oleic acid analog, or a 1,2-distearoyl-sn-glycero-3-phosphocholine (DSPC) substitute.

In some embodiments the agent that inhibits immune responses by the LNP comprises a miR binding site. In other embodiments the miR binding site is selected from miR 126, miR 155, and miR 142 3p. The miR binding site is incorporated into a mRNA in some embodiments. In other embodiments the miR binding site is separate from the mRNA.

In some embodiments the agent that inhibits immune responses by the LNP comprises an mRNA comprising a miR binding site. In various embodiments, the mRNA comprises 1-4, one, two, three or four miR binding sites, wherein at least one of the miR binding sites is a miR-126 binding site. In one embodiment, the mRNA, comprises at least two microRNA binding sites, wherein at least one of the microRNA binding sites is a miR-126 binding site. In one embodiment, the mRNA, e.g., mmRNA, comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27. In another embodiment, the mRNA, comprises a miR-126 (e.g., miR-126-3p) binding site and a miR-142 (e.g., miR-142-3p) binding site. A miR referred to by number herein can refer to either of the two mature microRNAs originating from opposite arms of the same pre-miRNA (e.g., either the 3p or 5p microRNA). All miRs referred to by number herein are intended to include both the 3p and 5p arms/sequences. It has now been discovered that incorporation of at least one microRNA binding site for a microRNA expressed in immune cells (e.g., miR-126, miR-142, miR-155 and combinations thereof) into an mRNA construct can reduce or inhibit ABC when the lipid-comprising compound or composition comprising the mRNA is administered to a subject. In one embodiment, the mechanism of action of the miRNA binding site(s) is a microRNA "sponge", wherein the miRNA binding site(s) in the construct or LNP "soaks up" microRNAs that bind to the binding site(s).

The DSPC analog may have a modified head group that is a modified quaternary amine head group, a modified core group, or a modified lipid tail group. In some embodiments. The PEG lipid in other embodiments contains at least 0.0001%, at least 0.0005%, at least 0.001%, at least 0.005%, at least 0.01%, at least 0.05%, at least 0.1%, at least 0.15%, at least 0.2%, at least 0.25%, at least 0.3%, at least 0.35%, at least 0.4%, at least 0.45%, and less than 0.5% molar ratio of PEG lipid to the other components.

In some embodiments the LNP may have a molar ratio of about 45-65% cationic lipid, about 0.15-15% PEG lipid, about 15-45% cholesterol and about 5-25% non-cationic helper lipid or a molar ratio of about 55% cationic lipid, about 2.5% PEG lipid, about 32.5% cholesterol and about 10% non-cationic lipid.

In other embodiments the cationic lipid is selected from DLin-DMA, DLin-D-DMA, DLin-MC3-DMA, DLin-KC2-DMA or DODMA. In other embodiments the cationic lipid is selected from the lipid Cmpd numbers provided herein.

The invention in some aspects is a method for delivering lipid nanoparticles (LNPs) to a subject without producing an immune response that promotes accelerated blood clearance (ABC) in response to subsequent doses of the LNP. The method involves administering a first dose of LNPs to the subject, wherein the first dose of LNPs does not induce an immune response that promotes ABC upon administration of a second dose of LNP, and administering a second dose of LNPs to the subject, wherein the subject does not have an ABC response to the second dose of LNPs. In some embodiments the LNPs encapsulate a therapeutic agent and wherein the subject receives an effective amount of the therapeutic agent for treating a disease.

In other aspects the invention is a method for delivering lipid nanoparticles (LNPs) to a subject without producing an immune response that promotes accelerated blood clearance (ABC) in response to subsequent doses of the LNP, by administering a first dose of LNPs to the subject, wherein the LNPs are capable of inducing an immune response that promotes ABC upon administration of a second dose of LNP, administering an agent that inhibits immune responses induced by the LNPs and administering a second dose of LNPs to the subject, wherein the subject does not have an ABC response to the second dose of LNPs.

In yet other aspects the invention is a method for reducing dose-limiting toxicity (DLT) in a subject being treated with a therapeutic regimen involving lipid nanoparticle (LNP)-mediated drug delivery, by administering LNPs to the subject, wherein the LNPs do not induce an immune response associated with B1 cell activation or platelet activation, and optionally administering an agent that inhibits immune responses induced by the LNPs, such that DLT is reduced in the subject being treated with the therapeutic regimen.

In yet other aspects the invention is a method in a subject of increasing the therapeutic index of a therapeutic regimen involving lipid nanoparticle (LNP)-mediated drug delivery, by administering LNPs to the subject, wherein the LNPs do not induce an immune response associated with B1 cell activation or platelet activation, and optionally administering an agent that inhibits immune responses induced by the LNPs, such that DLT is reduced in the subject being treated with the therapeutic regimen.

A method for reducing dose-limiting toxicity (DLT) in a subject being treated with therapeutic regimen involving lipid nanoparticle (LNP)-mediated drug delivery is provided in other aspects of the invention. The method involves administering to the subject LNPs and an agent that inhibits platelet activation, such that DLT is reduced in the subject being treated with therapeutic regimen.

A method for delivering a therapeutic level of a protein of interest to a subject is provided in other aspects of the invention. The method involves administering to the subject a first dose of lipid nanoparticles (LNPs), which encapsulate an mRNA coding for the protein of interest, wherein the first dose of LNPs does not induce an immune response that promotes accelerated blood clearance (ABC) upon administration of a second dose of LNP.

According to other aspects the invention is a method for reducing dose-limiting toxicity (DLT) and/or accelerated blood clearance (ABC) in a subject being treated with a therapeutic regimen involving lipid nanoparticle (LNP)-mediated drug delivery, by administering to the subject a first dose of lipid nanoparticles (LNPs), which encapsulates an mRNA coding for the protein of interest, wherein the first dose of LNPs do not activate a CD36-dependent signaling pathway in an immune cell upon administration of a second dose of LNP.

An accelerated blood clearance (ABC) insensitive lipid nanoparticle (LNP) having a cationic lipid, a PEG-lipid, a sterol, and a helper lipid, wherein the helper lipid does not comprise a phosphatidyl choline (PC) is provided in other aspects of the invention.

According to other aspects the invention is a lipid nanoparticle (LNP) having a cationic lipid, a non-cationic, non-PC lipid, less than 0.5% (w/w) of a PEGylated lipid, and a sterol. The LNP is insensitive to accelerated blood clearance upon repeated administration in vivo within 2 days-3 weeks. In some embodiments the LNP is insensitive to accelerated blood clearance upon repeated administration in vivo within 4-12 days.

In some aspects, the invention is a method for reducing accelerated blood clearance (ABC) in a subject being treated with a therapeutic regimen involving repeat dosing of lipid nanoparticles (LNPs), the method comprising administering LNPs to the subject, wherein the LNPs do not activate B1a cells and/or do not induce production of natural IgM molecules capable of binding to the LNPs, such that ABC is reduced upon repeat administration of the LNPs to the subject.

In some aspects, the invention is a method for reducing accelerated blood clearance (ABC) in a subject being treated with a therapeutic regimen involving multiple dosing of lipid nanoparticles (LNPs), the method comprising administering a dose of LNPs to the subject, wherein the LNPs do not activate B1a cells and/or do not induce production of natural IgM molecules capable of binding to the LNPs, such that ABC is reduced upon administration of one or more subsequent doses of the LNPs to the subject.

In some aspects, the invention is a method for reducing accelerated blood clearance (ABC) of lipid nanoparticles (LNPs) in a subject being treated with a multi-dose or repeat dosing therapeutic regimen, the method comprising administering LNPs to the subject, wherein the LNPs do not activate B1a cells and/or do not induce production of natural IgM molecules capable of binding to the LNPs, such that ABC is reduced upon subsequent or repeat dosing of LNPs in the subject.

In some aspects, the invention is a method for decelerating blood clearance of LNPs, the method comprising administering LNPs to a subject, wherein the LNPs do not activate B1a cells and/or do not induce production of natural IgM molecules capable of binding to the LNPs, such that upon administration of a subsequent dose of the LNPs to the subject blood clearance of the LNPs is decelerated. As used herein, "decelerating" or "decelerated" refers to slow, delay or repress blood clearance.

In some aspects, the invention is a method for delivering lipid nanoparticles (LNPs) to a subject without promoting accelerated blood clearance (ABC), the method comprising administering LNPs to the subject, wherein the LNPs do not promote ABC.

In some embodiments, the LNPs do not induce production of natural IgM molecules capable of binding to the LNPs.

In some embodiments, the LNPs do not activate B1a cells.

In some embodiments, the LNPs do not activate CD36 or B1a cells. In some embodiments, the LNPs are free of an epitope that activates B1a cells.

In some embodiments, the LNPs comprise a helper lipid, which comprises at least one fatty acid chain of at least 8C and at least one polar moiety, and wherein the helper lipid does not activate B1a cells.

In some embodiments, the LNPs are free of phosphatidyl choline (PC). In other embodiments, the helper lipid is a phosphatidyl choline analog. In some embodiments, the phosphatidyl choline analog comprises a modified PC head group, a modified PC core group, and/or a modified PC lipid tail. In some embodiments, the helper lipid competitively inhibits phosphatidylcholine from binding to CD36. In some embodiments, the helper lipid does not bind or has low binding activity to CD36. In some embodiments, the LNPs comprise oleic acid or an oleic acid analog. In some embodiments, the LNPs are free of PEG or a PEGylated lipid.

In some embodiments, the LNPs further comprise a PEGylated lipid. In other embodiments, the PEGylated lipid is an alkyl-PEGylated lipid. In some embodiments, the PEGylated lipid is a methoxy-PEGylated lipid. In some embodiments, the PEGylated lipid is DMG-PEG. In some embodiments, the PEGylated lipid is a hydroxy-PEGylated lipid. In some embodiments, the PEGylated lipid is less than 0.5% (w/w). In some embodiments, the PEGylated lipid is less than 0.25% (w/w).

In some embodiments, the LNPs further comprise a cationic lipid. In some embodiments, the cationic lipid is MC3 or DLin-MC3-DMA. In some embodiments, the LNPs further comprise a sterol. In some embodiments, the sterol is cholesterol.

In some embodiments, the LNPs encapsulate a therapeutic agent. In some embodiments, the therapeutic agent is a protein or a nucleic acid. In some embodiments, the therapeutic agent is a mRNA coding for a therapeutic protein. In some embodiments, the LNPs are administered to the subject at multiple doses. In some embodiments, wherein the interval of two consecutive doses is less than 2 weeks. In some embodiments, the interval of two consecutive doses is less than 1 week. In other embodiments the doses are between 2 days-3 weeks; 3-days-3 weeks, 4 days-3 weeks, 5 days-3 weeks, 2 days-2 weeks; 3-days-2 weeks, 4 days-2 weeks, 5 days-2 weeks, 2-15 days; 3-15 days, 3-10 days, or 3-7 day apart.

In some aspects, the invention is a method for reducing accelerated blood clearance (ABC) of lipid nanoparticles (LNPs) encapsulating an mRNA, the method comprising: administering to a subject in need thereof a first dose of the LNPs, and administering to the subject a second dose of the LNPs; wherein the first dose, the second dose, or both are equal to or less than about 0.3 mg/kg.

In some embodiments, the first dose, the second dose, or both are equal to or less than about 0.2 mg/kg. In some embodiments, the first dose, the second dose, or both are equal to or less than about 0.1 mg/kg. In some embodiments, the first dose, the second dose, or both are about 0.1-0.3 mg/kg. In some embodiments, the interval between the first dose and the second dose is less than 2 weeks. In some embodiments, the interval between the first dose and the second dose is less than 1 week. In some embodiments, the mRNA encapsulated in LNPs is a therapeutic mRNA. In some embodiments, the mRNA encapsulated in LNPs is a mRNA encoding a vaccine antigen. In some embodiments, the mRNA encapsulated in LNPs encodes multiple proteins.

In some embodiments, the LNPs do not induce production of natural IgM molecules capable of binding to the LNPs. In some embodiments, the LNPs do not activate B1a cells. In some embodiments, the LNPs are free of an epitope that activates B1a cells. In some embodiments, the LNPs comprise a helper lipid, which comprises at least one fatty acid chain of at least 8C and at least one polar moiety, and wherein the helper lipid does not activate B1a cells. In some embodiments, the LNPs are free of phosphatidyl choline (PC).

In some embodiments, the helper lipid is a phosphatidyl choline analog. In some embodiments, the phosphatidyl choline analog comprises a modified PC head group, a modified PC core group, and/or a modified PC lipid tail. In some embodiments, the helper lipid competitively inhibits phosphatidylcholine from binding to CD36. In some embodiments, the helper lipid does not bind or has low binding activity to CD36.

In some embodiments, the LNPs comprise oleic acid or an oleic acid analog. In some embodiments, the LNPs are free of PEG or a PEGylated lipid. In some embodiments, the LNPs further comprise a PEGylated lipid. In some embodiments, the PEGylated lipid is an alkyl-PEGylated lipid. In some embodiments, the PEGylated lipid is a methoxy-PEGylated lipid. In some embodiments, the PEGylated lipid is DMG-PEG. In some embodiments, the PEGylated lipid is a hydroxy-PEGylated lipid. In some embodiments, the PEGylated lipid is less than 0.5% (w/w). In some embodiments, the PEGylated lipid is less than 0.25% (w/w). Each possibility represents a separate embodiment of the present invention.

In some embodiments, the LNPs further comprise a cationic lipid. In some embodiments, the cationic lipid is MC3 or DLin-MC3-DMA. In some embodiments, the LNPs further comprise a sterol. In some embodiments, the sterol is cholesterol.

In some aspects, the invention is a method for reducing accelerated blood clearance (ABC) in a subject being treated with a therapeutic regimen involving repeat dosing of lipid nanoparticles (LNPs), the method comprising administering to the subject LNPs and an agent that inhibits B1a cell-mediated immune responses induced by the LNPs, such that ABC is reduced upon repeat administration of the LNPs to the subject.

In some aspects, the invention is a method for reducing accelerated blood clearance (ABC) in a subject being treated with a therapeutic regimen involving multiple dosing of lipid nanoparticles (LNPs), the method comprising administering to the subject LNPs and an agent that inhibits B1a cell-mediated immune responses induced by the LNPs, such that ABC is reduced upon administration of one or more subsequent doses of the LNPs to the subject.

In some aspects, the invention is a method for reducing accelerated blood clearance (ABC) of lipid nanoparticles (LNPs) in a subject being treated with a multi-dose or repeat dosing therapeutic regimen, the method comprising administering to the subject LNPs and an agent that inhibits B1a cell-mediated immune responses induced by the LNPs, such that ABC is reduced upon subsequent or repeat dosing of LNPs in the subject.

In some aspects, the invention is a method for decelerating blood clearance of LNPs, the method comprising administering to a subject LNPs and an agent that inhibits B1a cell-mediated immune responses induced by the LNPs, such that upon administration of a subsequent dose of the LNPs to the subject blood clearance of the LNPs is decelerated.

In some aspects, the invention is a method for reducing or inhibiting accelerated blood clearance (ABC) of lipid nanoparticles (LNPs) in a subject, the method comprising administering to the subject LNPs and an agent that inhibits immune responses induced by the LNPs such that ABC of the LNPs is reduced or inhibited.

In some aspects, the invention is a method for reducing or inhibiting accelerated blood clearance (ABC) of lipid nanoparticles (LNPs) in a subject, the method comprising administering to the subject LNPs and an agent to inhibit immune responses induced by the LNPs such that ABC of the LNPs is reduced or inhibited. In some examples, the amount of the agent used in any of the methods described herein is sufficient to inhibit any of the immune responses described herein.

In some embodiments, the agent inhibits production of or neutralizes natural IgM capable of binding to the LNPs. In some embodiments, the immune response induced by the LNPs is activation of B1a cells. In some embodiments, the immune response induced by the LNPs is binding of natural IgM to the LNPs. In some embodiments, the agent binds and/or inhibits CD36 on B1a cells.

In some embodiments, the agent is administered to the subject prior to, after, or concurrently with the administration of the LNPs. In some embodiments, the LNPs encapsulate a therapeutic agent. In some embodiments, the therapeutic agent is a protein or a nucleic acid. In some embodiments, the therapeutic agent is a mRNA coding for a therapeutic protein.

In some embodiments, the subject is administered with the LNPs at multiple doses. In some embodiments, the interval between two consecutive doses is less than 2 weeks. In some embodiments, the interval between two consecutive doses is less than 1 week. In some embodiments, the interval between two consecutive doses is less than 21, 20, 19, 18, 17, 16, 15, 14, 13, 12, 11, 10, 9, 8, 7, 6, 5, 4, 3, 2 or 1 days. In some embodiments, the subject is administered a dose once daily, every 2, 3, 4, 5, 6, 7, 8, 9, 10, 11, 12, 13, 14, 15, 16, 17, 18, 19, 20 or 21 days. Each possibility represents a separate embodiment of the present invention.

In some aspects, the invention is a method for reducing dose-limiting toxicity (DLT) in a subject being treated with therapeutic regimen involving lipid nanoparticle (LNP)-mediated drug delivery, the method comprising administering LNPs to the subject, wherein the LNPs do not promote platelet activation, such that DLT is reduced in the subject being treated with therapeutic regimen.

In some aspects, the invention is a method for reducing toxicity associated with delivery of therapeutic doses of lipid nanoparticle (LNP)-encapsulated drug to a subject, the method comprising administering LNPs to the subject, wherein the LNPs do not promote platelet activation, such that the toxicity is reduced.

In some aspects, the invention is a method for delivering lipid nanoparticles (LNPs) to a subject without promoting toxicity associated with LNPs, the method comprising administering LNPs to the subject, wherein the LNPs do not promote LNP-related toxicity.

In some embodiments, the LNP-related toxicity comprises coagulopathy, disseminated intravascular coagulation (DIC), vascular thrombosis, complement activation-related pseudoallergy (CARPA), or a combination thereof. In some embodiments, the LNPs do not promote the classical pathway (CP). In some embodiments, the LNPs do not promote the alternative pathway (AP). In some embodiments, the LNPs do not promote platelet activation or aggregation. In some embodiments, the LNPs do not activate CD36. In some embodiments, the LNPs are free of an epitope that activates CD36.

In some embodiments, the LNPs comprise a helper lipid, which comprises at least one fatty acid chain of at least 8C and at least one polar moiety, and wherein the helper lipid does not activate B1a cells. In some embodiments, the LNPs are free of phosphatidyl choline (PC). In some embodiments, the helper lipid is a phosphatidyl choline analog. In some embodiments, the phosphatidyl choline analog comprises a modified PC head group, a modified PC core group, and/or a modified PC lipid tail. In some embodiments, the helper lipid competitively inhibits phosphatidylcholine from binding to CD36. In some embodiments, the helper lipid does not bind or has low binding activity to CD36. In some embodiments, the LNPs comprise oleic acid or an oleic acid analog. In some embodiments, the LNPs are free of PEG or a PEGylated lipid.

In some embodiments, the LNPs further comprise a PEGylated lipid. In some embodiments, the PEGylated lipid is an alkyl-PEGylated lipid. In some embodiments, the PEGylated lipid is a methoxy-PEGylated lipid. In some embodiments, the PEGylated lipid is DMG-PEG. In some embodiments, the PEGylated lipid is a hydroxy-PEGylated lipid. In some embodiments, the PEGylated lipid is less than 0.5% (w/w). In some embodiments, the PEGylated lipid is less than 0.25% (w/w). Each possibility represents a separate embodiment of the present invention.

In some embodiments, the LNPs further comprise a cationic lipid. In some embodiments, the cationic lipid is MC3 or DLin-MC3-DMA. In some embodiments, the LNPs further comprise a sterol. In some embodiments, the sterol is cholesterol.

In some embodiments, the LNPs encapsulate a therapeutic agent. In some embodiments, the therapeutic agent is a protein or a nucleic acid. In some embodiments, the therapeutic agent is a mRNA coding for a therapeutic protein.

In some aspects, the invention is a method for delivering lipid nanoparticles (LNPs) encapsulating an mRNA to a subject without promoting LNP-related toxicity, the method comprising administering an amount of the LNPs to a subject during a period, wherein the serum level of the LNPs in the subject during the administration period is not sufficient to induce LNP-related toxicity.

In some embodiments, the LNP-related toxicity comprises coagulopathy, disseminated intravascular coagulation (DIC), vascular thrombosis, activation-related pseudoallergy (CARPA), acute phase response (APR), or a combination thereof. In some embodiments, the serum level of the LNPs in the subject during the administration period is not sufficient to induce CARPA or APR. In some embodiments, the serum level of the LNPs in the subject during the administration period is not sufficient to induce the classical pathway (CP). In some embodiments, the serum level of the LNPs in the subject during the administration period is not sufficient to induce the alternative pathway (AP). In some embodiments, the serum level of the LNPs in the subject during the administration period is not sufficient to induce platelet activation or aggregation.

In some embodiments, the dose of the LNPs are lower than 0.1 mg/kg, 0.05 mg/kg, 0.02 mg·kg or 0.01 mg/kg. In some embodiments, the administration period is at least 96 hours, 72 hours, 48 hours, 24 hours, or 12 hours.

In some embodiments, the mRNA encapsulated in LNPs is a therapeutic mRNA. In some embodiments, the mRNA encapsulated in LNPs is a mRNA encoding a vaccine antigen. In some embodiments, the mRNA encapsulated in LNPs encodes multiple proteins. In some embodiments, the LNPs comprise a helper lipid, which comprises at least one fatty acid chain of at least 8C and at least one polar moiety, and wherein the helper lipid does not activate B1a cells.

In some embodiments, the LNPs are free of phosphatidyl choline (PC). In some embodiments, the helper lipid is a phosphatidyl choline analog. In some embodiments, the phosphatidyl choline analog comprises a modified PC head group, a modified PC core group, and/or a modified PC lipid tail. In some embodiments, the helper lipid competitively inhibits phosphatidylcholine from binding to CD36. In some embodiments, the helper lipid does not bind or has low binding activity to CD36. In some embodiments, the LNPs comprise oleic acid or an oleic acid analog. In some embodiments, the LNPs are free of PEG or a PEGylated lipid.

In some embodiments, the LNPs further comprise a PEGylated lipid. In some embodiments, the PEGylated lipid is an alkyl-PEGylated lipid, a methoxy-PEGylated lipid, a DMG-PEG, or a hydroxy-PEGylated lipid. In some embodiments, the PEGylated lipid is less than 0.5% (w/w). In some embodiments, the PEGylated lipid is less than 0.25% (w/w). In some embodiments, the LNPs further comprise a cationic lipid. In some embodiments, cationic lipid is MC3 or DLin-MC3-DMA. In some embodiments, the LNPs further comprise a sterol. In some embodiments, the sterol is cholesterol.

In some aspects, the invention is a method for reducing dose-limiting toxicity (DLT) in a subject being treated with therapeutic regimen involving lipid nanoparticle (LNP)-mediated drug delivery, the method comprising administering to the subject LNPs and an agent that inhibits platelet activation, such that DLT is reduced in the subject being treated with therapeutic regimen.

In some aspects, the invention is a method of increasing the therapeutic index in a subject being treated with lipid nanoparticle (LNP)-mediated drug delivery, the method comprising administering to the subject LNPs and an agent that inhibits platelet activation, such that dose-limiting toxicity (DLT) is reduced in the subject being treated with LNP.

In yet other aspects the invention is a method of a therapeutic regimen involving lipid nanoparticle (LNP)-mediated drug delivery, by administering LNPs to the subject, wherein the LNPs do not induce an immune response associated with B1 cell activation or platelet activation, and optionally administering an agent that inhibits immune responses induced by the LNPs, such that DLT is reduced in the subject being treated with the therapeutic regimen.

In some aspects, the invention is a method for reducing toxicity associated with delivery of therapeutic doses of lipid nanoparticle (LNP)-encapsulated drug to a subject, the method comprising administering to the subject LNPs and an agent that inhibits platelet activation, such that the toxicity is reduced.

In some aspects, the invention is a method for lessening lipid nanoparticle (LNP)-related toxicity in a subject, the method comprising administering to the subject LNPs and an agent in an amount effective to inhibit the LNP-related toxicity or alleviate at least one symptom thereof.

In some embodiments, the LNP-related toxicity comprises coagulopathy, disseminated intravascular coagulation (DIC), vascular thrombosis, activation-related pseudoallergy (CARPA), acute phase response (APR), or a combination thereof. In some embodiments, the agent is administered to the subject prior to, after, or currently with the administration of the LNPs. In some embodiments, the LNPs encapsulate a therapeutic agent. In some embodiments, the therapeutic agent is a protein or a nucleic acid. In some embodiments, the therapeutic agent is a mRNA coding for a therapeutic protein. In some embodiments, the agent alleviates at least one symptom associated with the LNP-related toxicity. In some embodiments, the agent is a non-steroidal anti-inflammatory drug (NSAID) or an antihistamine agent, wherein the anti-histamine is a histamine receptor blocker, such as an H1 antagonist or an H1 inverse agonist. In some embodiments, the NSAID is a COX-2 and/or 5-LOX inhibitor. In some embodiments, the antihistamine is a histamine receptor blocker. In some embodiments, the histamine receptor blocker is an H1 antagonist or an H1 inverse agonist. In some embodiments, the H1 antagonist is diphenhydramine (Benadryl), fexofenadine (Allegra) or loratadine (Claritin), and the H1 inverse agonist is cetirizine. In some embodiments, the agent inhibits CARPA or ARP. In some embodiments, the agent inhibits the classical pathway (CP). In some embodiments, the agent inhibits the alternative pathway. Each possibility represents a separate embodiment of the present invention.

In some embodiments, the agent inhibits platelet activation. In some embodiments, the agent is a platelet aggregation inhibitor. In some embodiments, the platelet aggregation inhibitor is an ADP receptor antagonist. In some embodiments, the platelet aggregation inhibitor is aspirin or clopidrogrel (PLAVIX®). In some embodiments, the platelet aggregation inhibitor is selected from aspirin/pravastatin, cilostazol, prasugrel, aspirin/dipyridamole, ticagrelor, cangrelor, elinogrel, dipyridamole, and ticlopidine. In some embodiments, the agent inhibits CD36. In some embodiments, the agent inhibits a TLR receptor, CD62P, properdin, a component of the complement system, C-reactive protein, or other proteins of the acute phase response. Each possibility represents a separate embodiment of the present invention.

In some aspects, the invention includes a method for reducing dose-limiting toxicity (DLT) and/or accelerated blood clearance (ABC) in a subject being treated with a therapeutic regimen involving lipid nanoparticle (LNP)-mediated drug delivery, the method comprising administering to the subject LNPs encapsulating the therapeutic agent, wherein the LNPs do not activate an immune cell thrombospondin receptor such as CD36, such that ABC is reduced upon repeat administration of the LNPs to the subject. In some embodiments, the immune cells are platelets and/or B cells, I particular, B1a cells.

In some aspects, the invention includes a method for delivering a therapeutically effective amount of a therapeutic agent via lipid nanoparticles to a subject, the method comprising administering to the subject LNPs encapsulating the therapeutic agent, wherein the LNPs do not activate CD36. In some embodiments, the LNPs are free of an epitope that activates CD36. In some embodiments, the LNPs are free of phosphatidyl choline (PC). In some embodiments, the LNPs comprise a helper lipid that does not bind or has low binding activity to CD36, or competitively inhibits phosphatidylcholine from binding to CD36. In some embodiments, the helper lipid comprises at least one fatty acid chain of at least 8C and at least one polar moiety. In some embodiments, the helper lipid is a phosphatidyl choline analog. In some embodiments, the phosphatidyl choline analog comprises a modified PC head group, a modified PC core group, and/or a modified PC lipid tail. In some embodiments, the LNPs comprise oleic acid or an oleic acid analog. In some embodiments, the LNPs are free of PEG or a PEGylated lipid.

In some embodiments, the LNPs further comprise a PEGylated lipid. In some embodiments, the PEGylated lipid is an alkyl-PEGylated lipid, a methoxy-PEGylated lipid, DMG-PEG or a hydroxy-PEGylated lipid. In some embodiments, the PEGylated lipid is less than 0.5% (w/w). In some embodiments, the PEGylated lipid is less than 0.25% (w/w). In some embodiments, the LNPs further comprise a cationic lipid. In some embodiments, the cationic lipid is MC3 or DLin-MC3-DMA. In some embodiments, the LNPs further comprise a sterol. In some embodiments, the sterol is cholesterol.

In some embodiments, the LNPs encapsulate a therapeutic agent. In some embodiments, the therapeutic agent is a protein or a nucleic acid. In some embodiments, the therapeutic agent is a mRNA coding for a therapeutic protein.

In some embodiments, the LNPs are administered to the subject at multiple doses. In some embodiments, the interval of two consecutive doses is less than 2 weeks. In some embodiments, the interval of two consecutive doses is less than 1 week.

In some aspects, the invention is a method for delivering a therapeutic level of a protein of interest to a subject, the method comprising administering to the subject lipid nanoparticles (LNPs), which encapsulate an mRNA coding for the protein of interest, wherein the LNPs do not activate B1a cells and/or do not activate platelets, such that a therapeutic level of the protein of interest is delivered to the subject.

In some aspects, the invention is a method for delivering a therapeutic level of a protein of interest to a subject, the method comprising administering to the subject lipid nanoparticles (LNPs), which encapsulate an mRNA coding for the protein of interest, wherein the LNPs do not induce drug responses associated with LNPs. In some embodiments, the drug response associated with LNPs is accelerated blood clearance. In some embodiments, the LNPs do not induce production of natural IgM molecules capable of binding to the LNPs. In some embodiments, the LNPs do not activate B1a cells. In some embodiments, the LNPs is free of an epitope that activates B1a cells.

In some embodiments, the LNPs are administered to the subject at multiple doses. In some embodiments, the interval of two consecutive doses is less than 2 weeks. In some embodiments, the interval of two consecutive doses is less than 1 week. In some embodiments, the drug response associated with LNPs is an adverse reaction induced by the LNPs. In some embodiments, the adverse reaction comprises coagulopathy, disseminated intravascular coagulation (DIC), vascular thrombosis, activation-related pseudoallergy (CARPA), acute phase response (APR), or a combination thereof. In some embodiments, the LNPs do not promote CARPA or APR. In some embodiments, the LNPs do not promote the classical pathway (CP). In some embodiments, the LNPs do not promote the alternative pathway (AP). In some embodiments, the LNPs do not promote platelet activation or aggregation. In some embodiments, the LNPs do not activate CD36.

In some embodiments, the LNPs comprise a helper lipid, which comprises at least one fatty acid chain of at least 8C and at least one polar moiety, and wherein the helper lipid does not induce production of natural IgM capable of binding to the LNPs, do not activate B1a cells, do not activate CD36, and/or do not activate platelet.

In some embodiments, the LNPs are free of phosphatidyl choline (PC). In some embodiments, the helper lipid is a phosphatidyl choline analog. In some embodiments, the phosphatidyl choline analog comprises a modified PC head group, a modified PC core group, and/or a modified PC lipid tail. In some embodiments, the helper lipid competitively inhibits phosphatidylcholine from binding to CD36. In some embodiments, the helper lipid does not bind or has low binding activity to CD36. In some embodiments, the LNPs comprise oleic acid or an oleic acid analog. In some embodiments, the LNPs are free of PEG or a PEGylated lipid.

In some embodiments, the LNPs further comprise a PEGylated lipid. In some embodiments, the PEGylated lipid is an alkyl-PEGylated lipid. In some embodiments, the PEGylated lipid is a methoxy-PEGylated lipid, DMG-PEG or a hydroxy-PEGylated lipid. In some embodiments, the PEGylated lipid is less than 0.5% (w/w). In some embodiments, the PEGylated lipid is less than 0.25% (w/w). In some embodiments, the LNPs further comprise a cationic lipid. In some embodiments, the cationic lipid is MC3 or DLin-MC3-DMA. In some embodiments, the LNPs further comprise a sterol. In some embodiments, the sterol is cholesterol.

In some embodiments, the mRNA encodes a therapeutic protein. In some embodiments, the mRNA encodes a vaccine antigen.

In some aspects, the invention is a method for delivering a therapeutic level of a protein of interest to a subject, the method comprising administering to the subject lipid nanoparticles (LNPs), which encapsulate an mRNA coding for the protein of interest, and an agent in amount effective to inhibit platelet activation and/or B cell activation, in particular, activation of B1a cells, induced by the LNPs, such that a therapeutic level of the protein of interest is delivered to the subject.

In some aspects, the invention is a method for delivering a therapeutic level of a protein of interest to a subject, the method comprising administering to the subject lipid nanoparticles (LNPs), which encapsulate an mRNA coding for the protein of interest, and an agent in amount effective to inhibit a drug response induced by the LNPs or alleviate at least one symptom thereof. In some embodiments, the drug response is accelerated blood clearance. In some embodiments, the agent inhibits production of or neutralizes natural IgM capable of binding to the LNPs. In some embodiments, the agent inhibits binding of natural IgM to a target. In some embodiments, the agent inhibits activation of B1a cells. In some embodiments, the agent binds CD36 on B1a cells.

In some embodiments, the agent is administered to the subject prior to, or currently with the administration of the LNPs. In some embodiments, an LNP is administered to the subject at multiple doses. In some embodiments, the interval between two consecutive doses is less than 2 weeks. In some embodiments, the interval between two consecutive doses is less than 1 week. In some embodiments, the drug response is LNP-related toxicity. In some embodiments, the LNP-related toxicity comprises coagulopathy, disseminated intravascular coagulation (DIC), vascular thrombosis, activation-related pseudoallergy (CARPA), acute phase response (APR), or a combination thereof.

In some embodiments, the agent is administered to the subject prior to, after, or currently with the administration of the LNPs. In some embodiments, the agent alleviates at least one symptom associated the LNP-related toxicity. In some embodiments, the agent is a nonsteroidal anti-inflammatory drug (NSAID) or an antihistamine agent. In some embodiments, the NSAID is a COX-2 and/or 5-LOX inhibitor. In some embodiments, the antihistamine is a histamine receptor blocker. In some embodiments, the histamine receptor blocker is an H1 antagonist or an H1 inverse agonist. In some embodiments, the H1 antagonist is diphenhydramine (Benadryl), fexofenadine (Allegra) or loratadine (Claritin), and the H1 inverse agonist is cetirizine. In some embodiments, the agent inhibits CARPA or ARP. In some embodiments, the agent inhibits the classical pathway (CP). In some embodiments, the agent inhibits the alternative pathway.

In some embodiments, the agent inhibits platelet activation. In some embodiments, the agent is a platelet aggregation inhibitor. In some embodiments, the platelet aggregation inhibitor is an ADP receptor antagonist. In some embodiments, the platelet aggregation inhibitor is aspirin or clopidrogrel (PLAVIX®). In some embodiments, the platelet aggregation inhibitor is selected from aspirin/pravastatin, cilostazol, prasugrel, aspirin/dipyridamole, ticagrelor, cangrelor, elinogrel, dipyridamole, and ticlopidine. In some embodiments, the agent inhibits CD36. In some embodiments, the agent inhibits a TLR receptor, CD62P, properdin, a component of the complement system, C-reactive protein, or other proteins of the acute phase response. Each possibility represents a separate embodiment of the present invention.

In some aspects, the invention is an accelerated blood clearance (ABC) insensitive lipid nanoparticle (LNP), comprising an ionizable cationic lipids, a PEG-lipid, a sterol, and a helper lipid, wherein the helper lipid does not comprise a phosphatidyl choline (PC). In some instances, the insensitive LNP consisting essentially of the components described herein. For example, such an LNP contains the components described herein, and optionally other components that do not materially affect the basic and novel characteristics of the LNPs described herein. For example, the additional components, if any, may not substantially affect the drug delivery function of the LNP (e.g., at a very low amount such that their functionality on drug delivery is insignificant).

In some embodiments, the helper lipid comprises a phosphatidyl choline (PC) analog. In some embodiments, the LNP is not subject to accelerated blood clearance (ABC) when administered at least twice to a subject in a time period of 10 days or less. In some embodiments, the PC analog comprises a modified PC head group, a modified PC core group, and/or a modified PC lipid tail. In some embodiments, the LNP has no or reduced B1a stimulating activity compared to an LNP comprising phosphatidyl choline. In some embodiments, the LNP has no or reduced binding to CD36 relative to an LNP comprising phosphatidyl choline. In some embodiments, the PC analog has no or reduced binding to CD36 relative to phosphatidyl choline (PC). In some embodiments, the PC analog has no or reduced CD36 binding relative to phosphatidyl choline (PC). In some embodiments, the helper lipid comprises oleic acid or an oleic acid analog.

In some embodiments, the LNP comprises less than 0.5% (w/w) of a PEGylated lipid. In some embodiments, the LNP comprises less than 0.25% of the PEGylated lipid. In some embodiments, the PEGylated lipid is an alkyl-PEGylated lipid, a methoxy-PEGylated lipid, DMG-PEG, a lipid conjugated to hydroxy-PEG (hydroxy-PEGylated lipid).

In some embodiments, the LNP has reduced platelet aggregation activity compared to an LNP comprising a methoxy-PEGylated lipid. In some embodiments, the cationic lipid is MC3 (or DLin-MC3-DMA).

In some aspects, the invention is a lipid nanoparticle (LNP) comprising or consisting essentially of a cationic lipid, a non-cationic, non-PC lipid, less than 0.5% (w/w) of a PEGylated lipid, and a sterol, and wherein the LNP is insensitive to accelerated blood clearance upon repeated administration in vivo within 10 days. In some embodiments, the LNP further comprises a protein or a nucleic acid. In some embodiments, the nucleic acid is DNA. In some embodiments, the nucleic acid is RNA. In some embodiments, the nucleic acid is mRNA.

In some aspects, the invention is a method for reducing ABC effect in a subject comprising contacting a blood sample from a subject with a lipid nanoparticle (LNP) formulation, measuring reactivity of the blood sample to the LNP formulation, and administering an LNP formulation comprising a therapeutic agent to the subject, provided the subject manifests no or low reactivity to the LNP formulation. In some embodiments, the therapeutic agent is administered at intervals of 2 weeks, 1 week, or less.

In some aspects, the invention is a method of delivering an agent to a subject, comprising administering to the subject an agent formulated in a lipid nanoparticle (LNP), wherein the subject is administered a platelet inhibitor. In some embodiments, the platelet inhibitor is administered to the subject at the same time as the agent formulated in a LNP. In some embodiments, the platelet inhibitor is administered to the subject 1 minute to 24 hours prior to the agent formulated in a LNP. In some embodiments, the platelet inhibitor is administered to the subject 24-48 hours prior to the agent formulated in a LNP. In some embodiments, the invention further comprises administering to the subject a histamine receptor blocker. In some embodiments, the invention comprises administering to the subject a non-specific inhibitor of COX enzyme.

In some embodiments, the agent is a nucleic acid. In some embodiments, the nucleic acid is a RNA. In some embodiments, RNA is siRNA or mRNA. In some embodiments, the LNP comprises a cationic lipid, a PEG. In some embodiments, the subject is not administered a corticosteroid.

In some embodiments, the platelet inhibitor is an inhibitor of P2Y12 subtype receptor. In some embodiments, the platelet inhibitor is clopidogrel. In some embodiments, the platelet inhibitor is ticagrelor. In some embodiments, is prasugrel, ticlopidine, cangrelor, or elinogrel. In some embodiments, the histamine receptor blocker is an antihistamine. In some embodiments, the antihistamine is Benadryl. In some embodiments, the non-specific inhibitor of COX enzyme is aspirin. In some embodiments, the non-specific inhibitor of COX enzyme is a COX-2 inhibitor. In some embodiments, the non-specific inhibitor of COX enzyme is a COX-2 and 5-lipoxygenase (5-LOX) inhibitor.

In other aspects the invention is method for reducing dose-limiting toxicity (DLT) in a subject being treated with a therapeutic regimen involving lipid nanoparticle (LNP)-mediated drug delivery, by administering to the subject an LNP comprising a therapeutic nucleic acid and administering to the subject an agent that agent removes or targets B cells, such that DLT is reduced in the subject being treated with the therapeutic regimen. In some embodiments the agent removes or targets B1a cells. In other embodiments the agent is Rituximab. In yet other embodiments the agent is administered to the subject prior to, after, or currently with the administration of the LNPs. The LNP may be administered to the subject at multiple doses. In other embodiments the therapeutic nucleic acid is an mRNA.

In other aspects the invention is a PEG lipid comprising a compound of Formula (V):

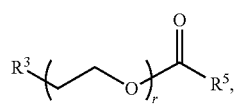

(V)

or a salts thereof, wherein:
R$^3$ is —OR$^O$;
R$^O$ is hydrogen, optionally substituted alkyl or an oxygen protecting group;
r is an integer between 1 and 100, inclusive;
R$^5$ is optionally substituted C$_{10-40}$ alkyl, optionally substituted C$_{10-40}$ alkenyl, or optionally substituted C$_{10-40}$ alkynyl; and optionally one or more methylene groups of R$^5$ are replaced with optionally substituted carbocyclylene, optionally substituted heterocyclylene, optionally substituted arylene, optionally substituted heteroarylene, —N(R$^N$)—, —O—, —S—, —C(O)—, —C(O)N(R$^N$)—, —NR$^N$C(O)—, —NR$^N$C(O)N(R$^N$)—, —C(O)O—, —OC(O)—, —OC(O)—, —OC(O)N(R$^N$)—, —NR$^N$C(O)O—, —C(O)S—, —SC(O)—, —C(=NR$^N$)—, —C(=NR$^N$)N(R$^N$)—, —NR$^N$C(=NR$^N$)—, —NR$^N$C(=NR$^N$)N(R$^N$)—, —C(S)—, —C(S)N(R$^N$)—, —NR$^N$C(S)—, —NR$^N$C(S)N(R$^N$)—, —S(O)—, —OS(O)—, —S(O)—, —OS(O)—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)—, —S(O)$_2$—, —N(R$^N$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—; and
each instance of R$^N$ is independently hydrogen, optionally substituted alkyl, or a nitrogen protecting group.

In some embodiments the compound of Formula (V) is of Formula (V-OH):

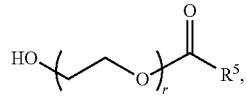

(V-OH)

or a salt thereof.

In other embodiments the compound of Formula (V) is of one of the following formulae:

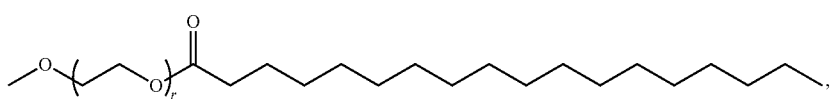

(Cmpd400)

-continued

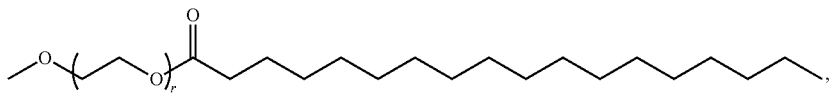
(Cmpd401)

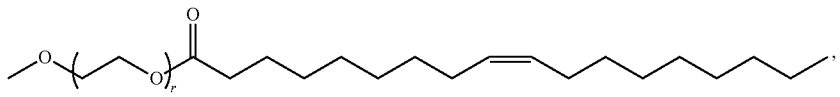
(Cmpd402)

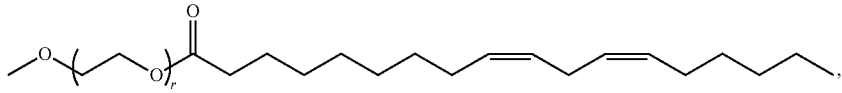
(Cmpd450)

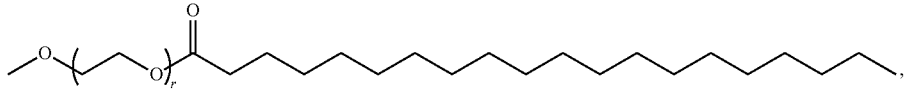
(Cmpd451)

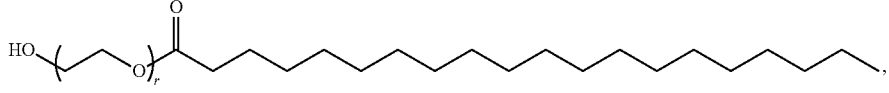
(Cmpd452)

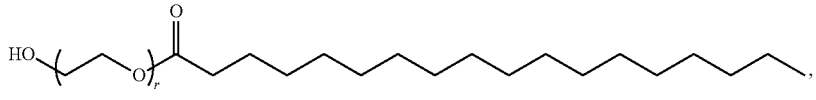
(Cmpd453)

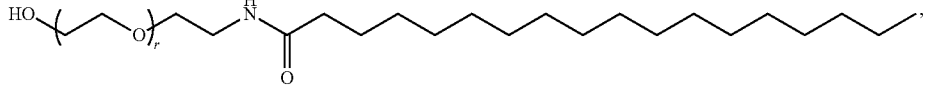
(Cmpd454)

or a salt thereof.

In yet other embodiments the compound of Formula (V) is:

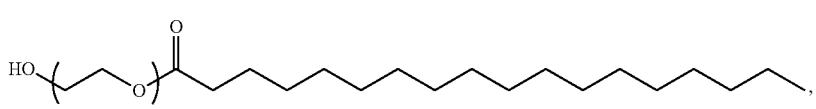
(Cmpd403)

or a salt thereof.

In some aspects the invention is a lipid nanoparticle (LNP) comprising a PEG lipid as described herein and optionally further comprising a lipid of Formula (V):

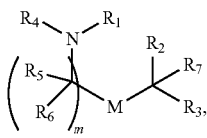
(V)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

These and other embodiments and aspects will be discussed in greater detail herein.

BRIEF DESCRIPTION OF DRAWINGS

The following Figures are provided in grey scale.

FIG. 29A shows B cell activation as a function of DMG-PEG mol % without Imiquimod and FIG. 29B shows B cell activation as a function of DMG-PEG mol % with Imiquimod.

FIGS. 31A-31D: Phospholipid designs of helper lipids that are analogs and substitutes of phosphatidyl choline (PC) and DSPC. The modifications reduce association, recognition for example by receptors, and/or uptake of LNP through for example modifying the PC head group (FIG. 31A), the PC core (FIG. 31B), or through reducing the planarity of the lipid (FIG. 31C). An oleic acid variant is also provided (FIG. 31D).

FIG. 32A shows Cmpd394, Cmpd395, Cmpd396, and Cmpd397. FIG. 32B shows Cmpd398 and Cmpd399. FIG. 32C shows Cmpd400-403.

FIG. 46A shows B1a (top) and B2b (bottom) cell levels following splenectomy or a sham operation. FIG. 46B shows B1a (to) and B2b (bottom) antibody levels following splenectomies. B1b cells lose the ability to secrete antibody.

FIGS. 49A-49B show the area under the curve (AUC) results from hEPO-mRNA-MC3 (FIG. 49A) and hEPO (FIG. 49B). $C_{max}$ values for hEPO-mRNA-MC3 (FIG. 49C) and hEPO (FIG. 49D) are also presented.

FIGS. 51A-51B: Cytokine expression in splenectomized NHPs. Levels of IL-6 (FIG. 51A) and IL-10 (FIG. 51B) are given.

Figure 56A:
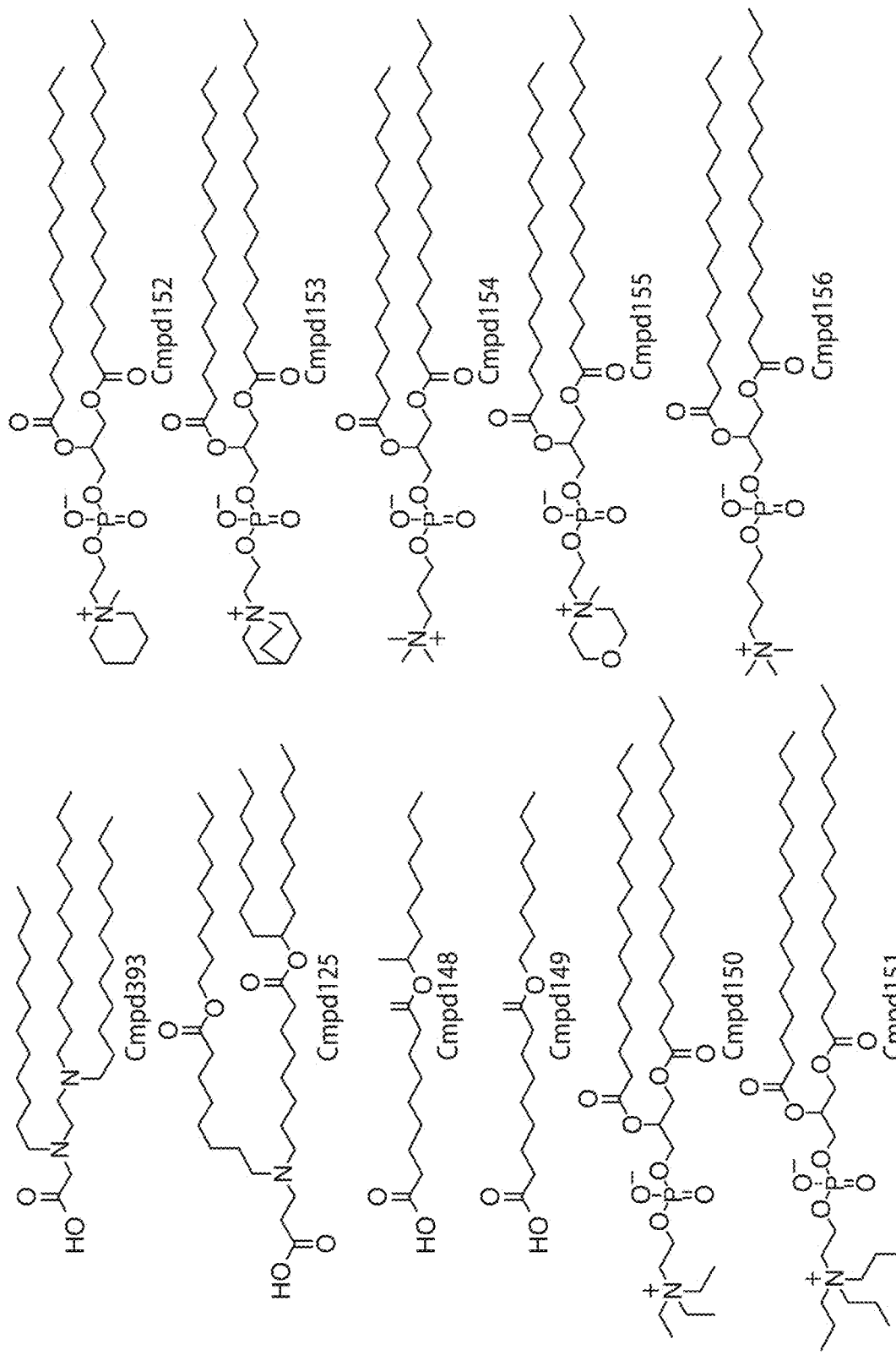
Figure 56B:
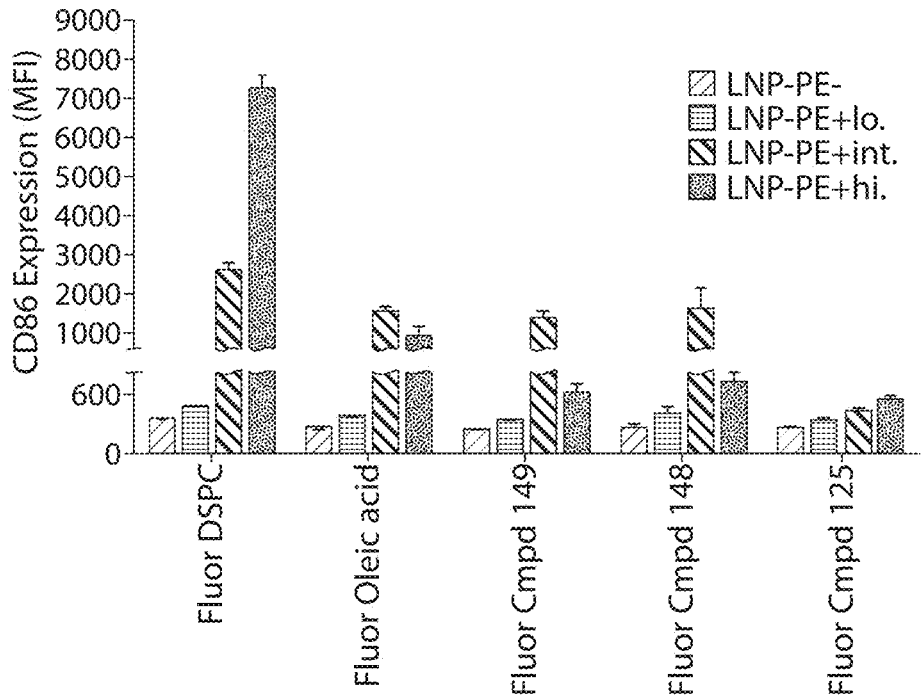
Figure 56C:
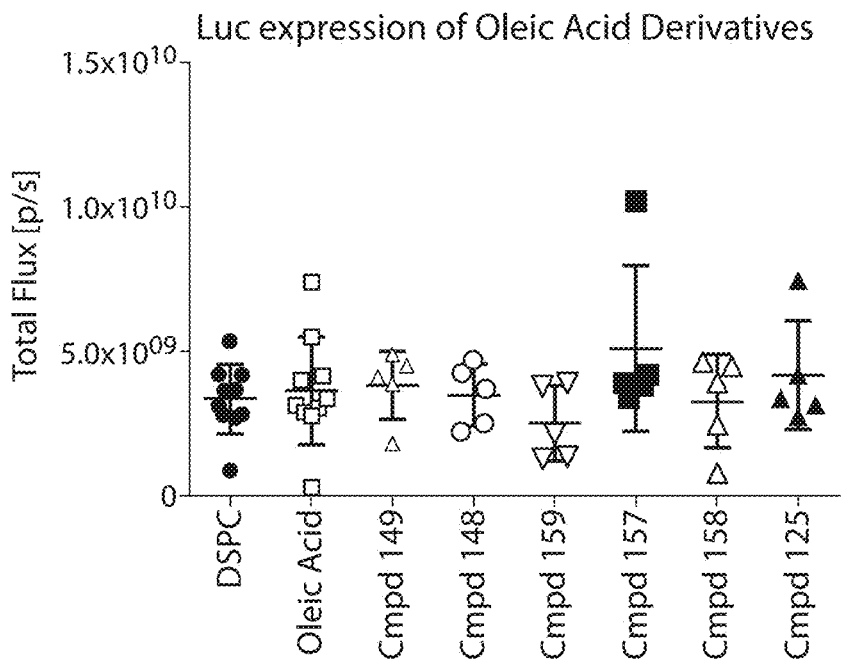
Figure 56D:
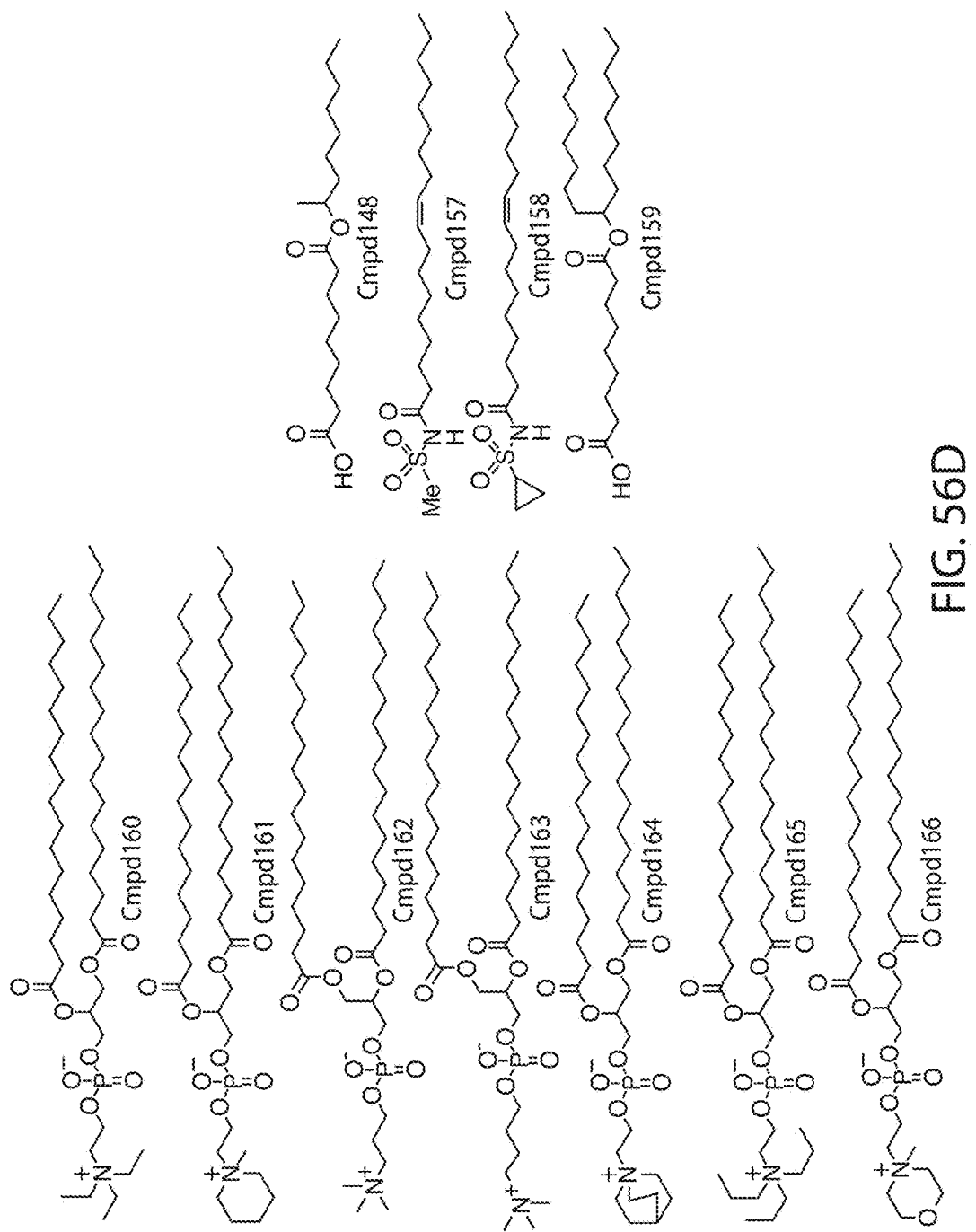
Figure 56E:
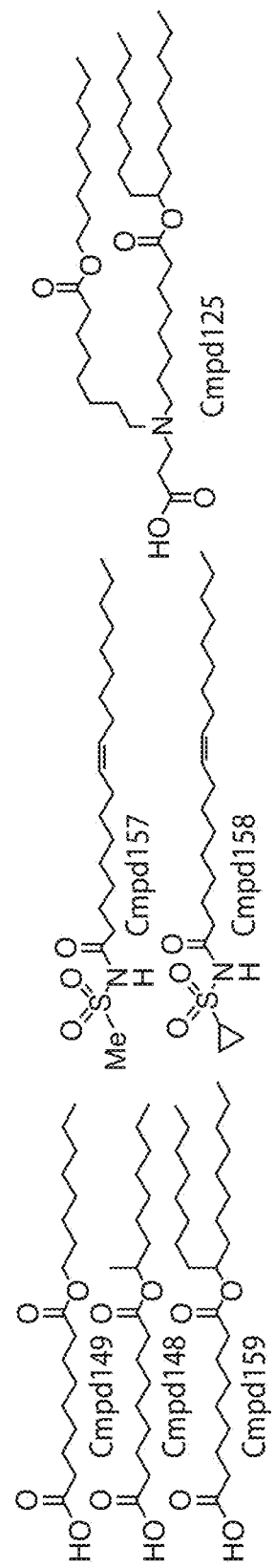

FIGS. 56A-56E depict effects of LNP formulation on Luc expression and B cell activation. FIG. 56B is a graph depicting CD86 expression (B cell activation) and FIG. 56C is a graph depicting expression levels of Luc as measured by total flux. The structures are shown in FIGS. 56A, 56D, and 56E.

Figure 57A:
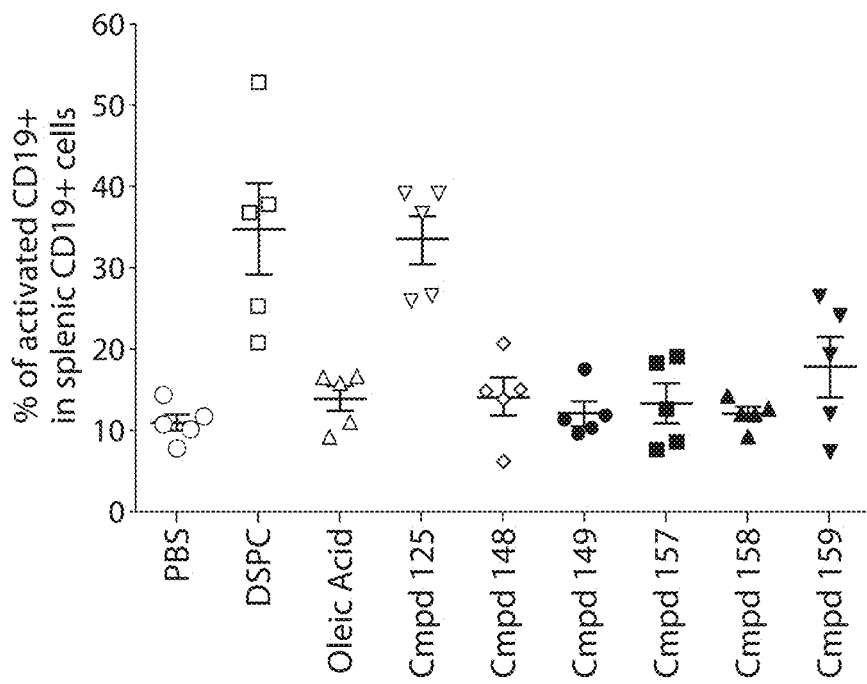
Figure 57B:
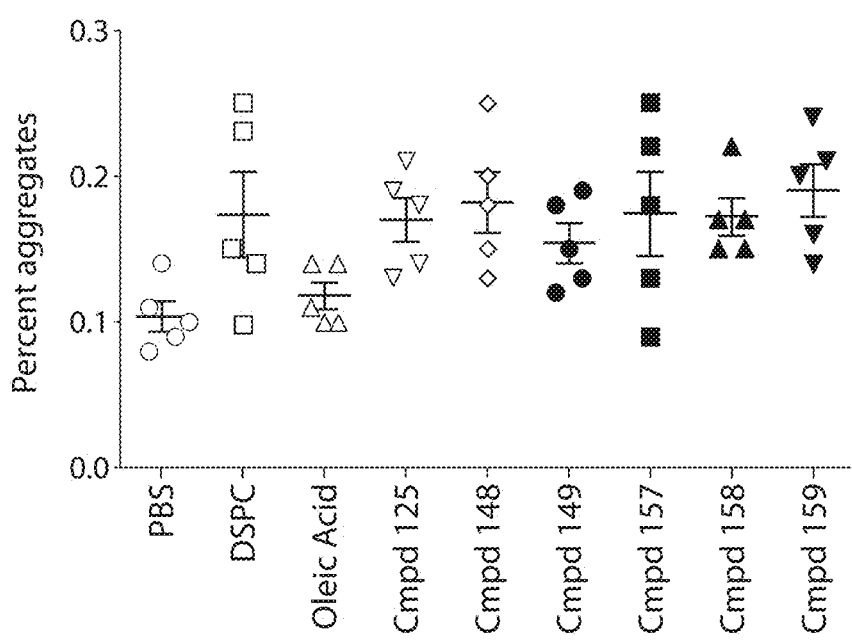
Figure 57C:
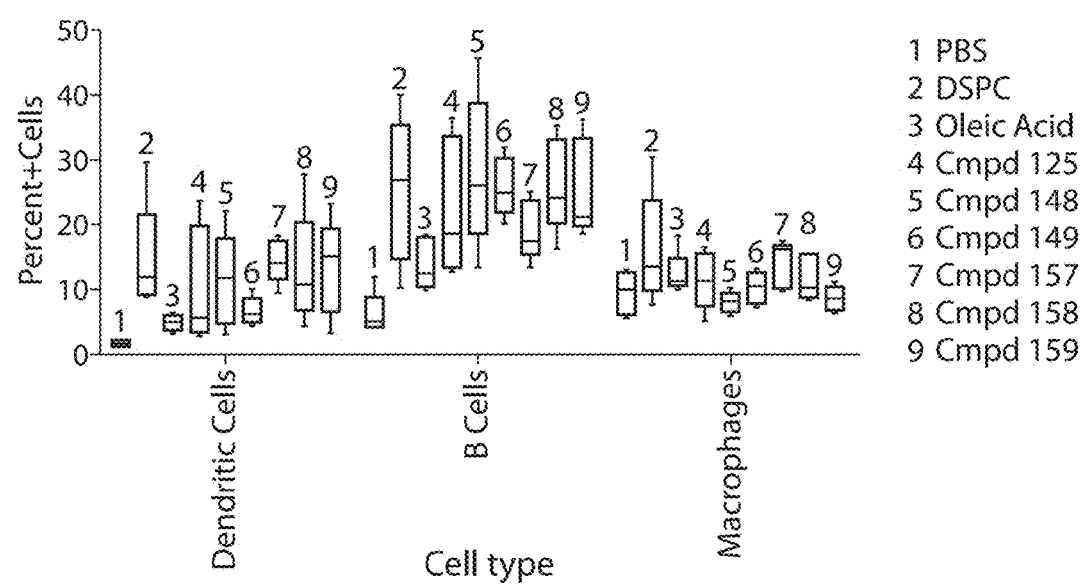

FIGS. 57A-57C depict the effects of various LNP formulations on B cells and platelets. FIG. 57A is a graph depicting activated B-cell frequencies 24 hours post dose. FIG. 57B is a graph depicting aggregation of platelets 15 minutes post dose. FIG. 57C is a graph depicting recruitment of cells in platelet aggregate.

Figure 58A:
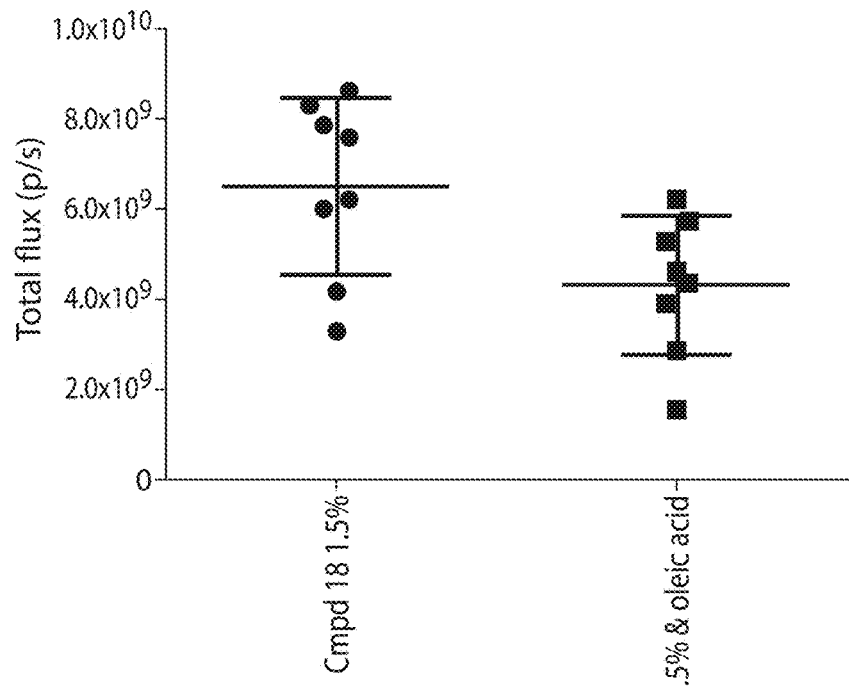
Figure 58B:
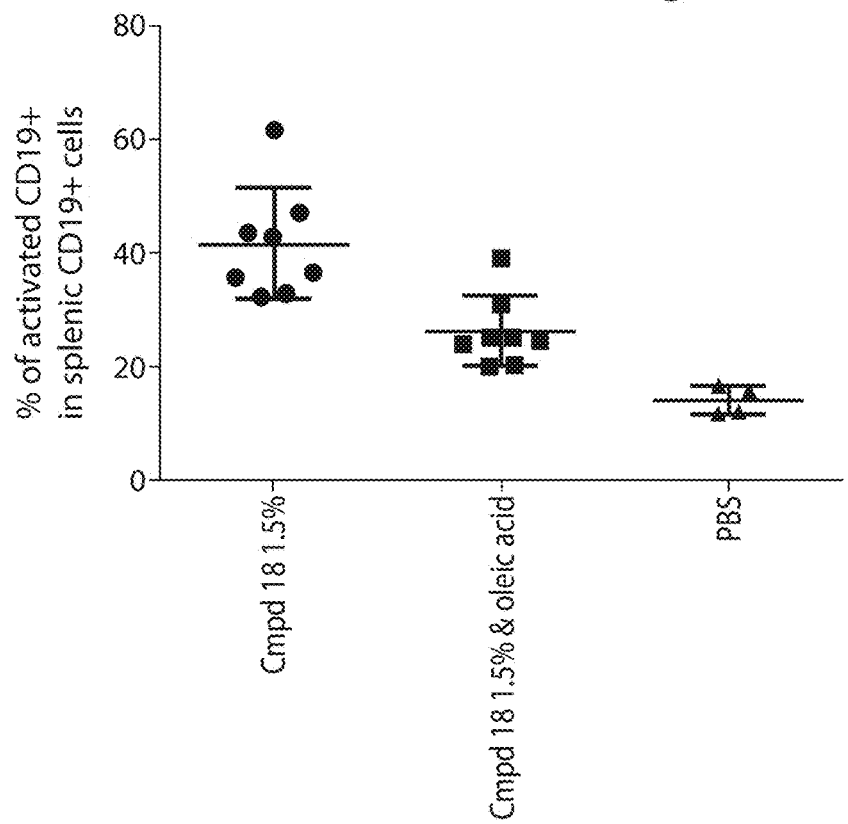

FIGS. 58A-58B depict the positive effects of oleic acid in an LNP. FIG. 58A depicts levels of luciferase expression as measured by total flux 6 hours after delivery to CD-1 mice. FIG. 58B depicts in vivo B-cell activation in mouse splenocytes 24 hours following the administration.

Figure 59:
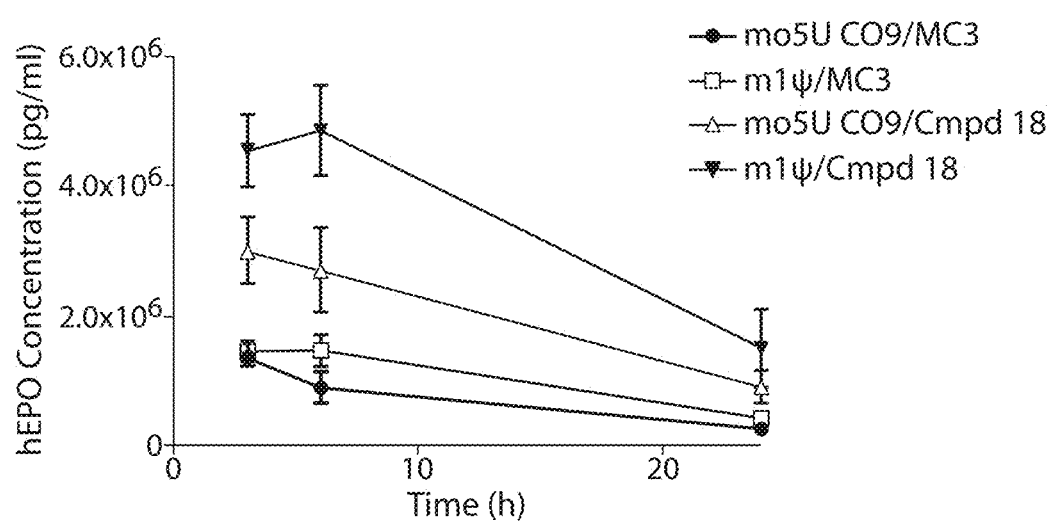

FIG. 59 is a graph depicting hEPO concentration over time. An improved margin of expression with a particle of the invention in contrast to MC3 was demonstrated with chemically modified mRNA.

Figure 60A:
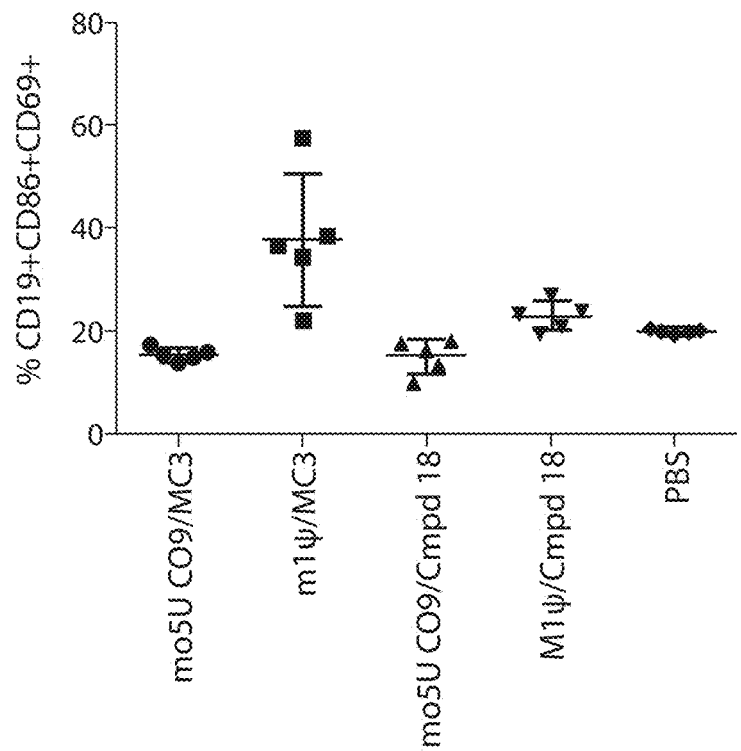
Figure 60B:
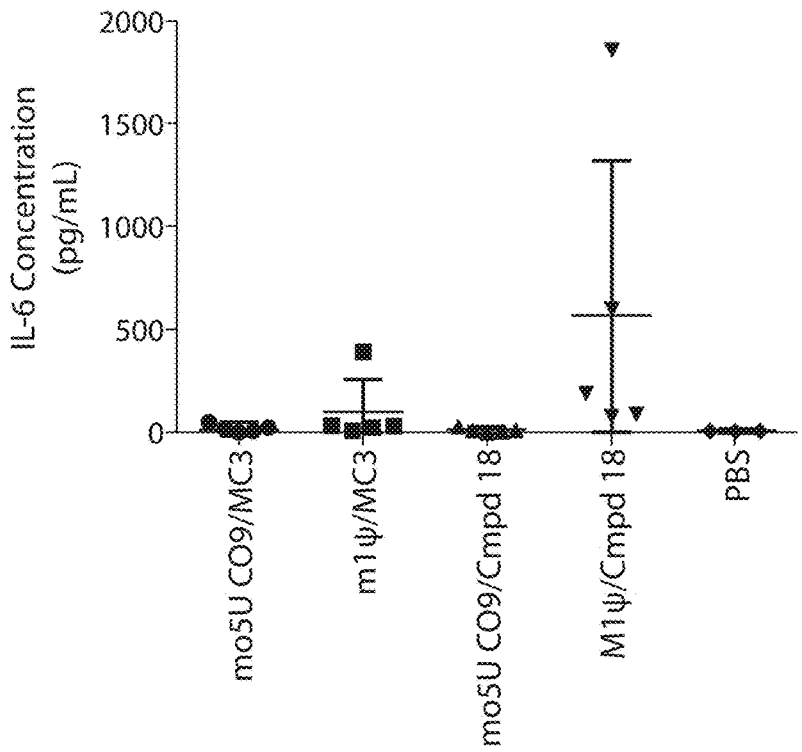
Figure 60C:
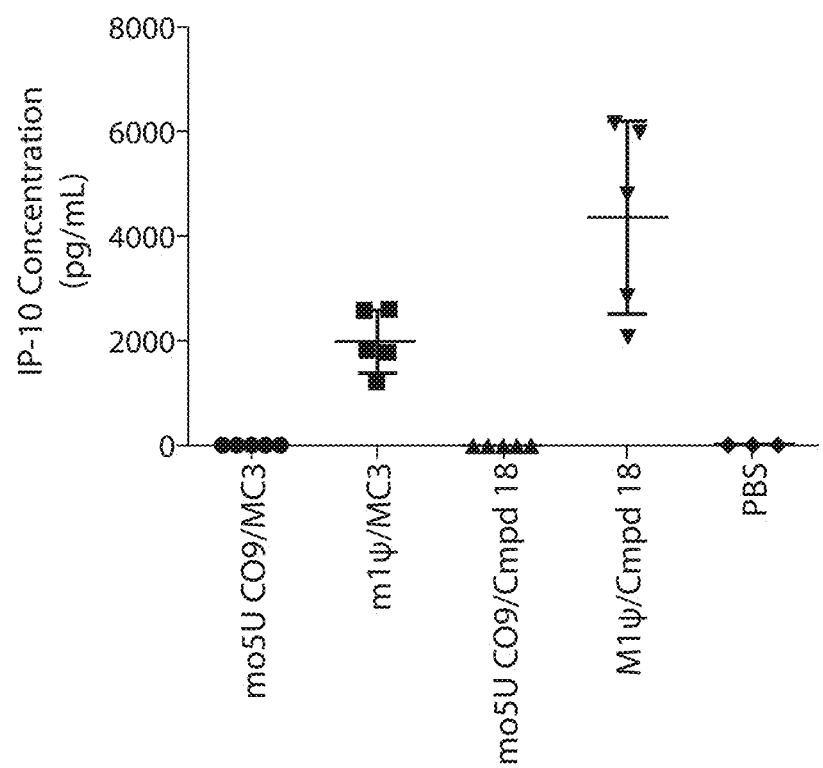

FIGS. 60A-60C are a set of graphs depicting improved immune activation profile with chemically modified mRNA in LNP formulations of the invention. FIG. 60A is a graph depicting in vivo B-cell activation 24 hours following administration of the hEPO loaded particles or PBS. FIG. 60B is a graph depicting in IL-6 concentration 6 hours following administration of the hEPO loaded particles or PBS. FIG. 60C is a graph depicting IP-10 concentration 6 hours following administration of the hEPO loaded particles or PBS.

Figure 61:
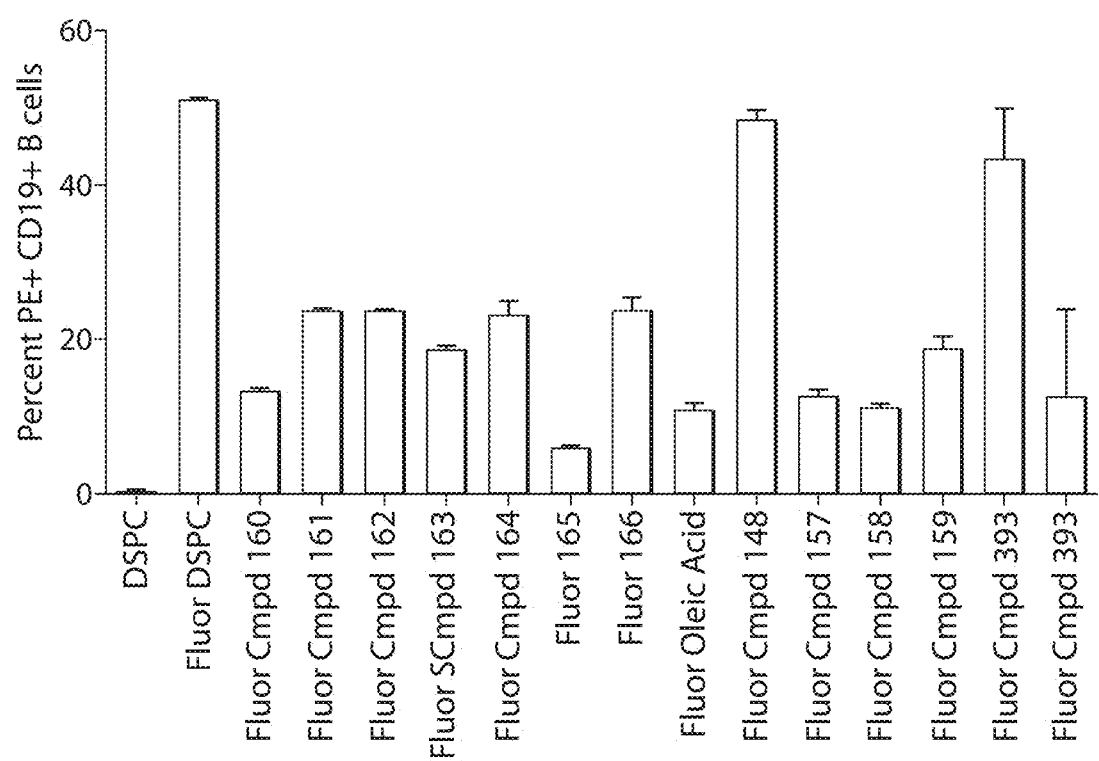

FIG. 61 is a graph depicting LNP Uptake by B cells as measured by percent PE+ CD19+ B cells.

Figure 62:
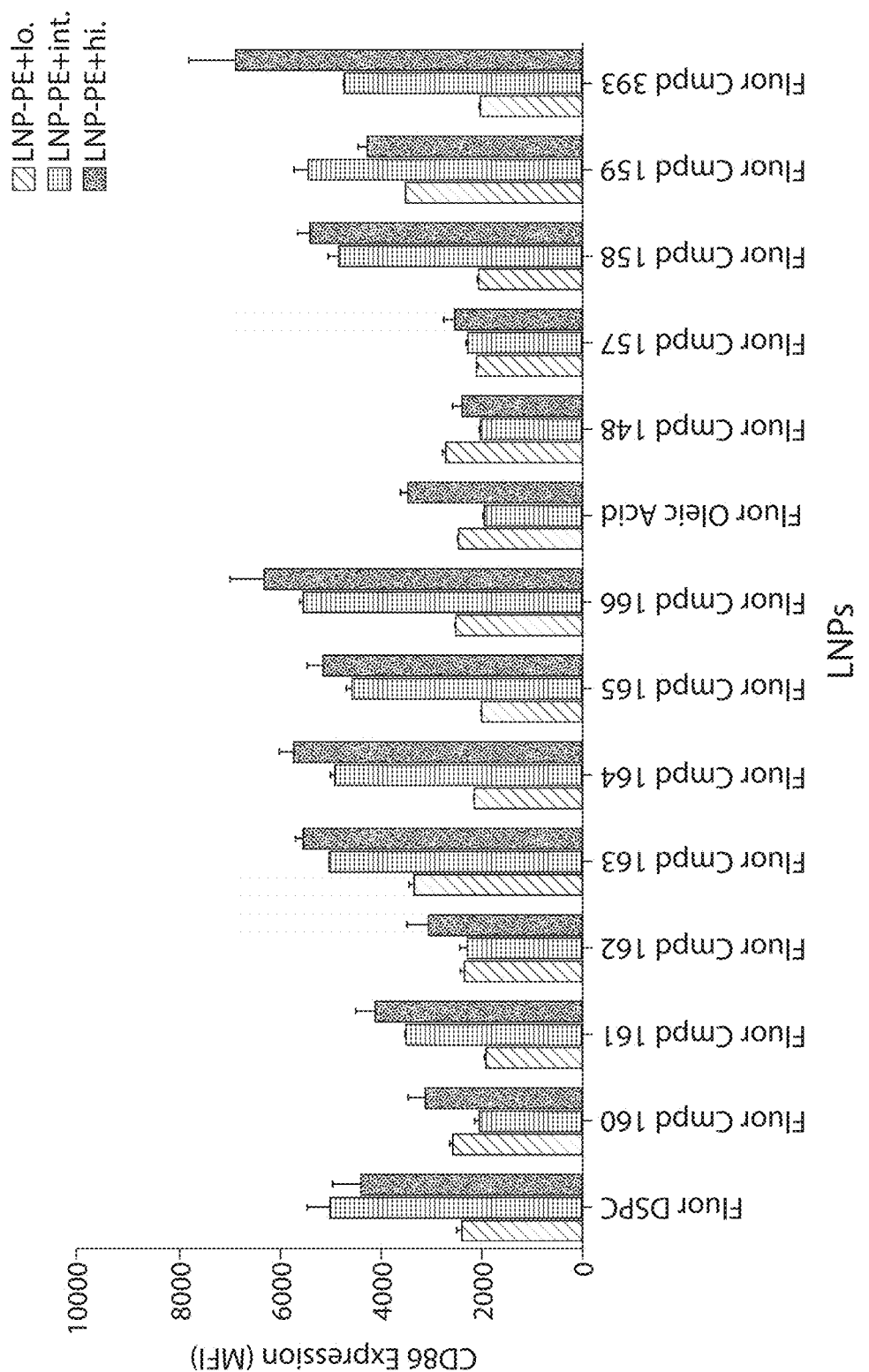

FIG. 62 is a graph depicting B cell activation by LNPs as measured by CD86 expression on B cells.

Figure 63A:
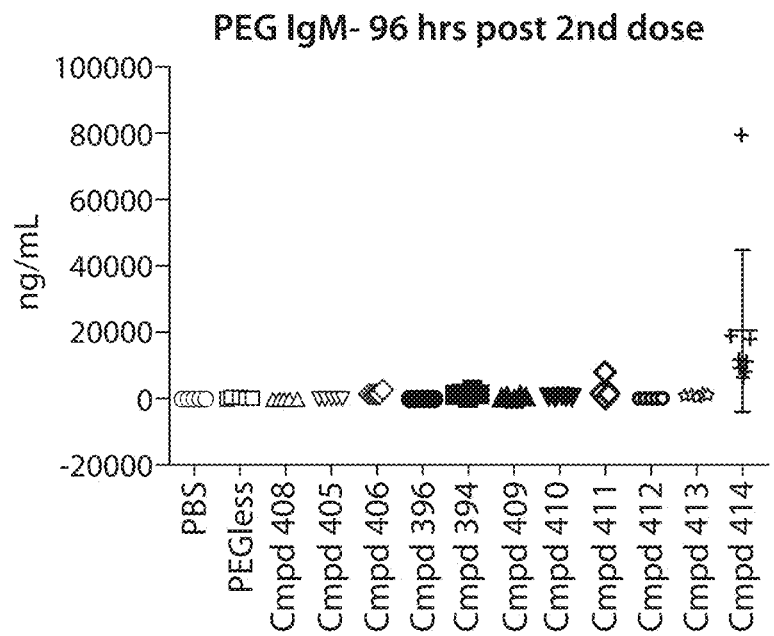
Figure 63B:
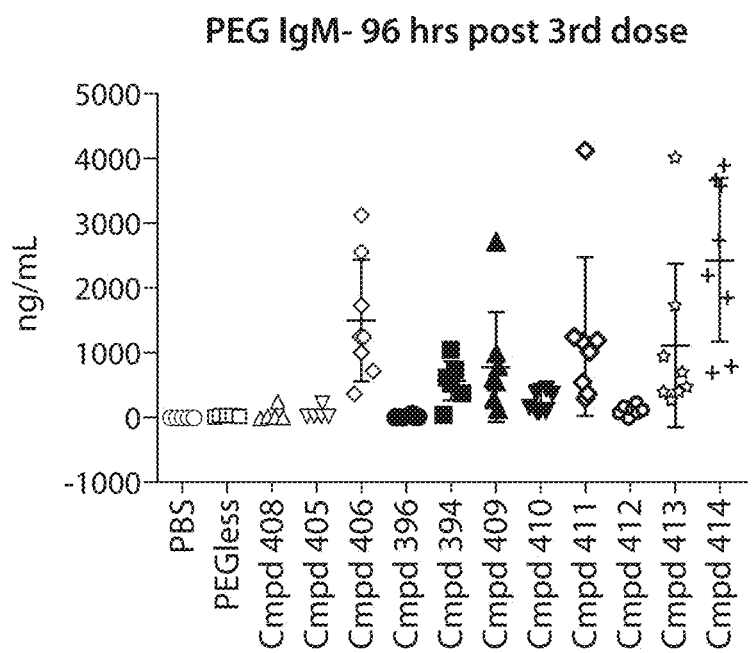

FIGS. 63A-63B are a set of graphs depicting the amount of PEG IgM produced 96 hours after a second dose of LNP (FIG. 63A) or 96 hours after a third dose of LNP (FIG. 63B).

Figure 64:
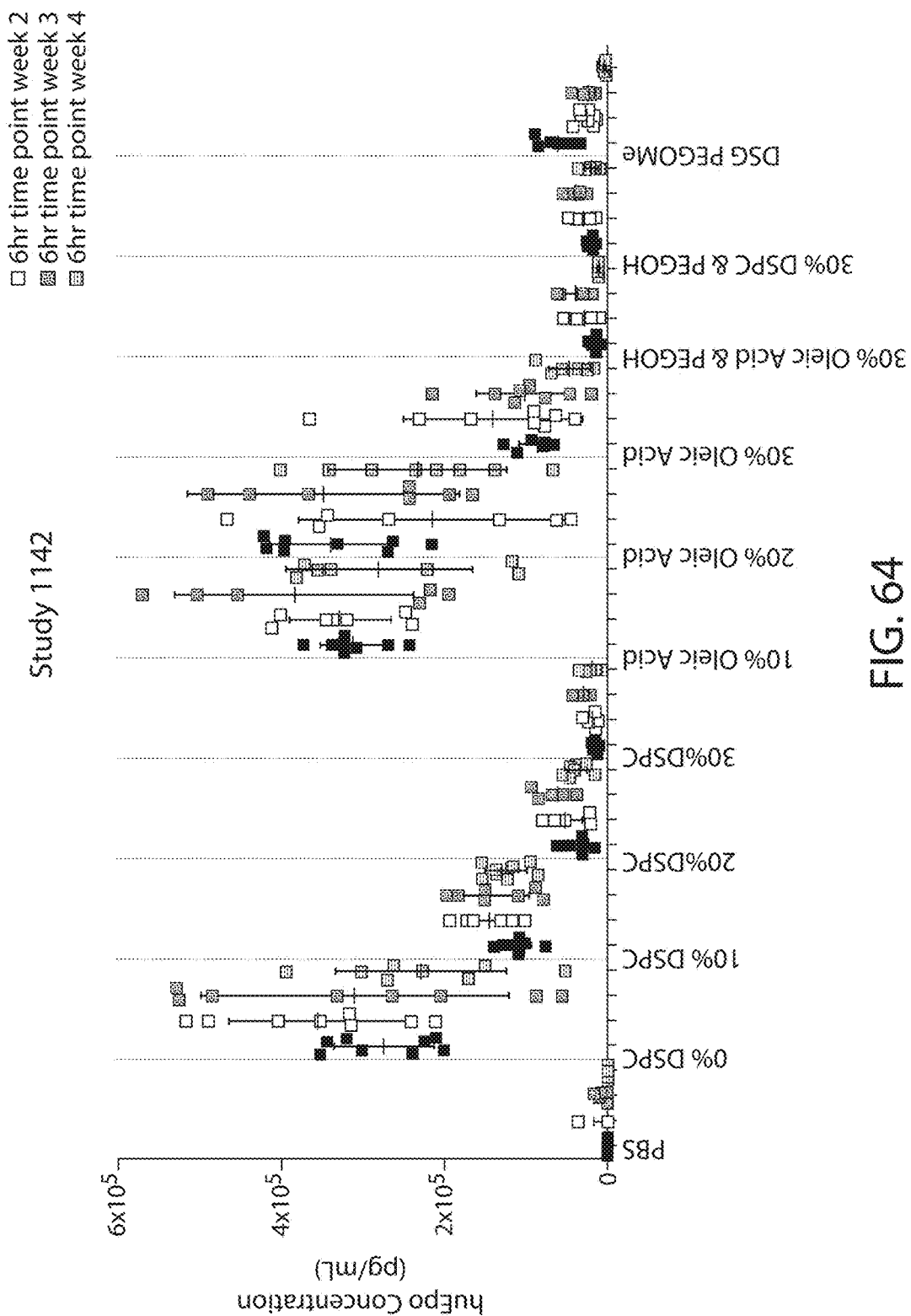

FIG. 64 is a graph depicting hEPO Expression 6 hours following once weekly administration by IV of hEPO mRNA-LNP formulations at weeks 1, 2, 3, and 4.

Figure 65:
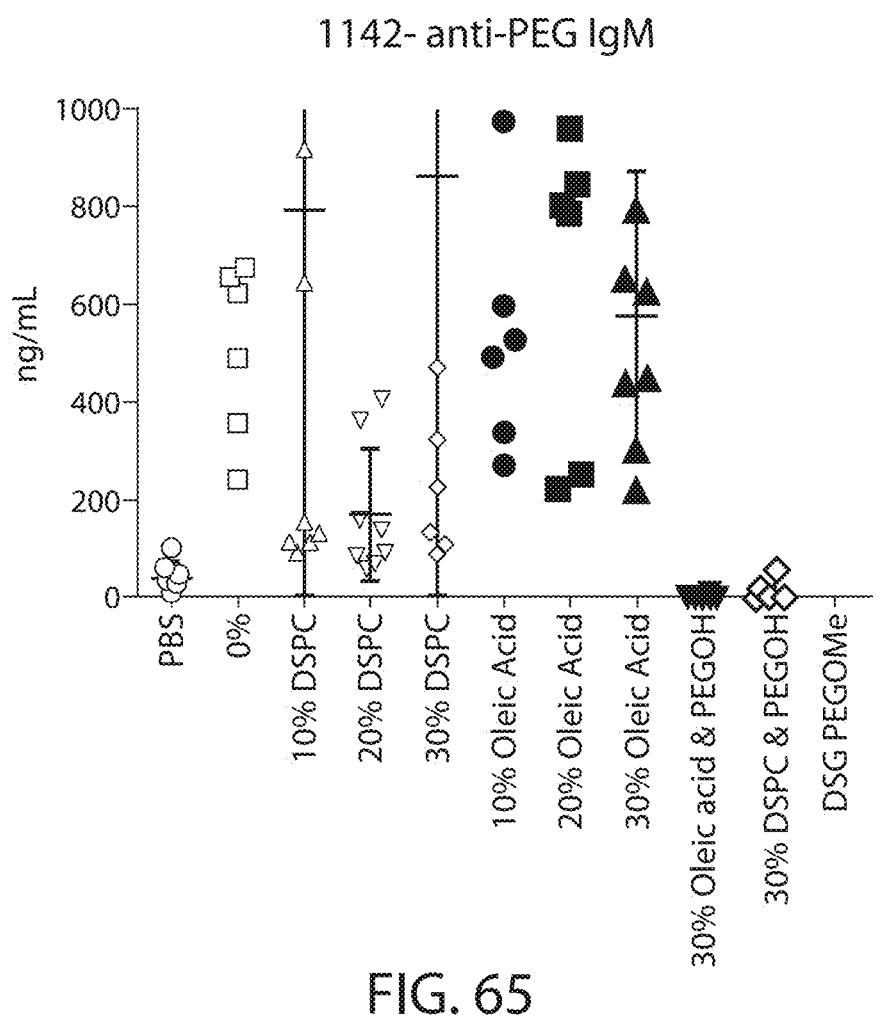

FIG. 65 is a graph depicting anti-PEG IgM production 96 hours following a third dose of hEPO mRNA-LNP formulations.

Figure 66:
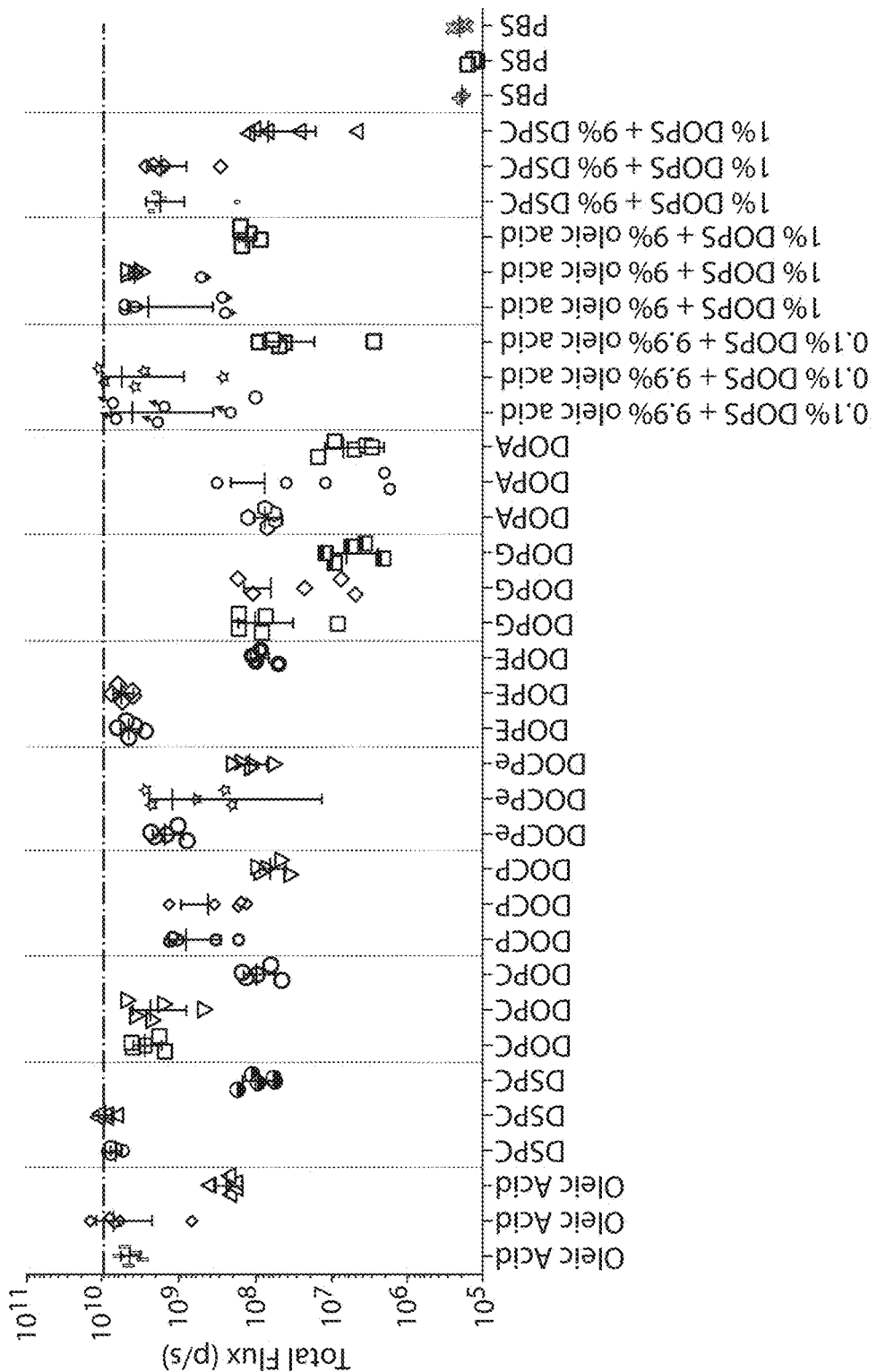

FIG. 66 is a graph depicting data from a single dose study of LNP having various phospholipids with different headgroups injected by IV in CD-1 Mice. Each phospholipid is measured at three time points (3, 6, and 24 hrs) following injection. Phospholipid structures are shown in FIG. 69.

Figure 67A:
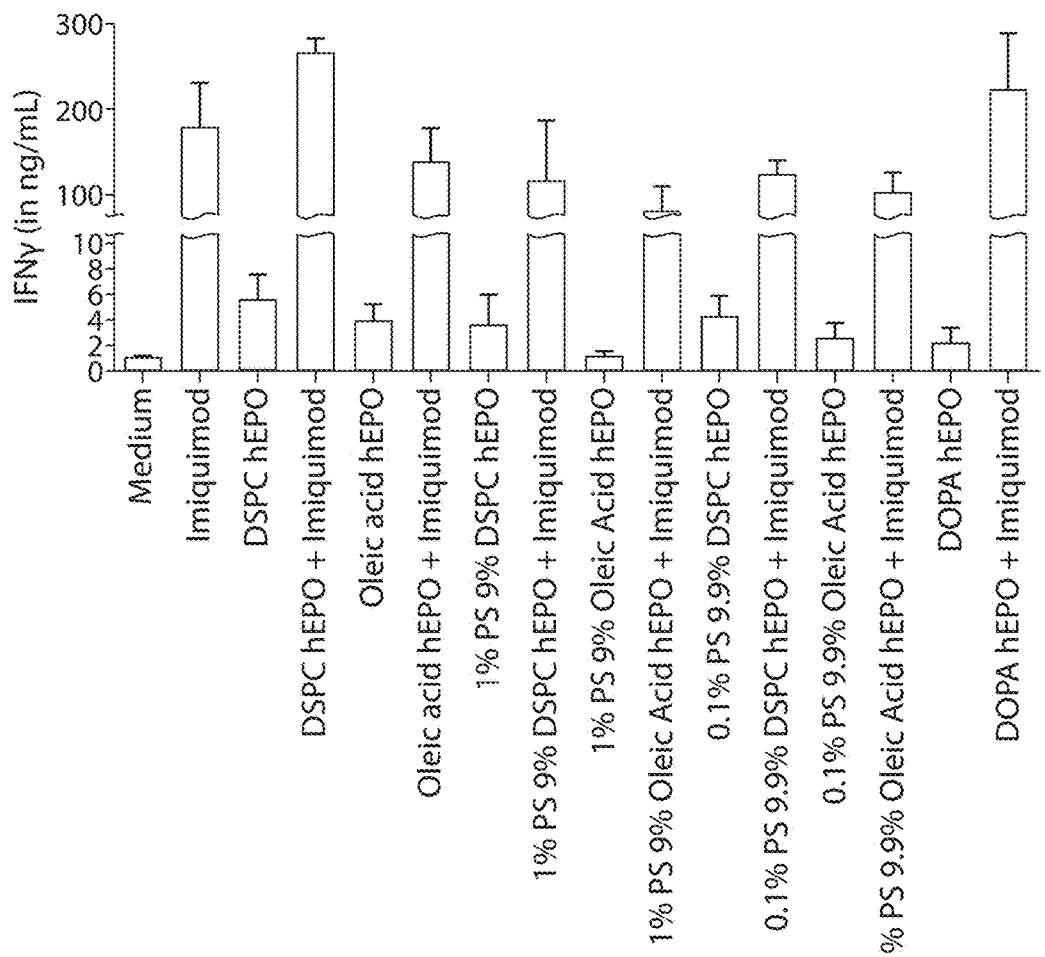
Figure 67B:
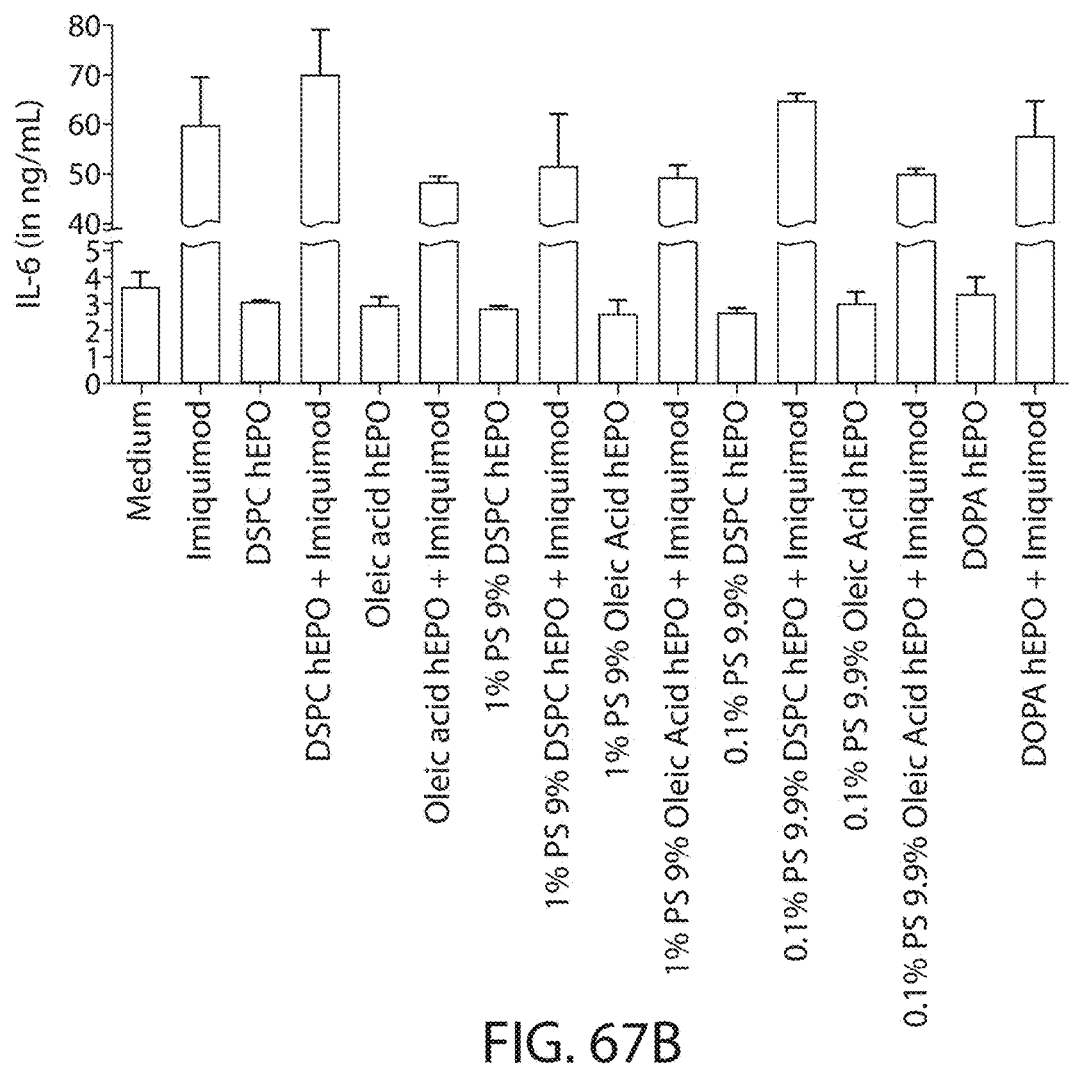
Figure 67C:
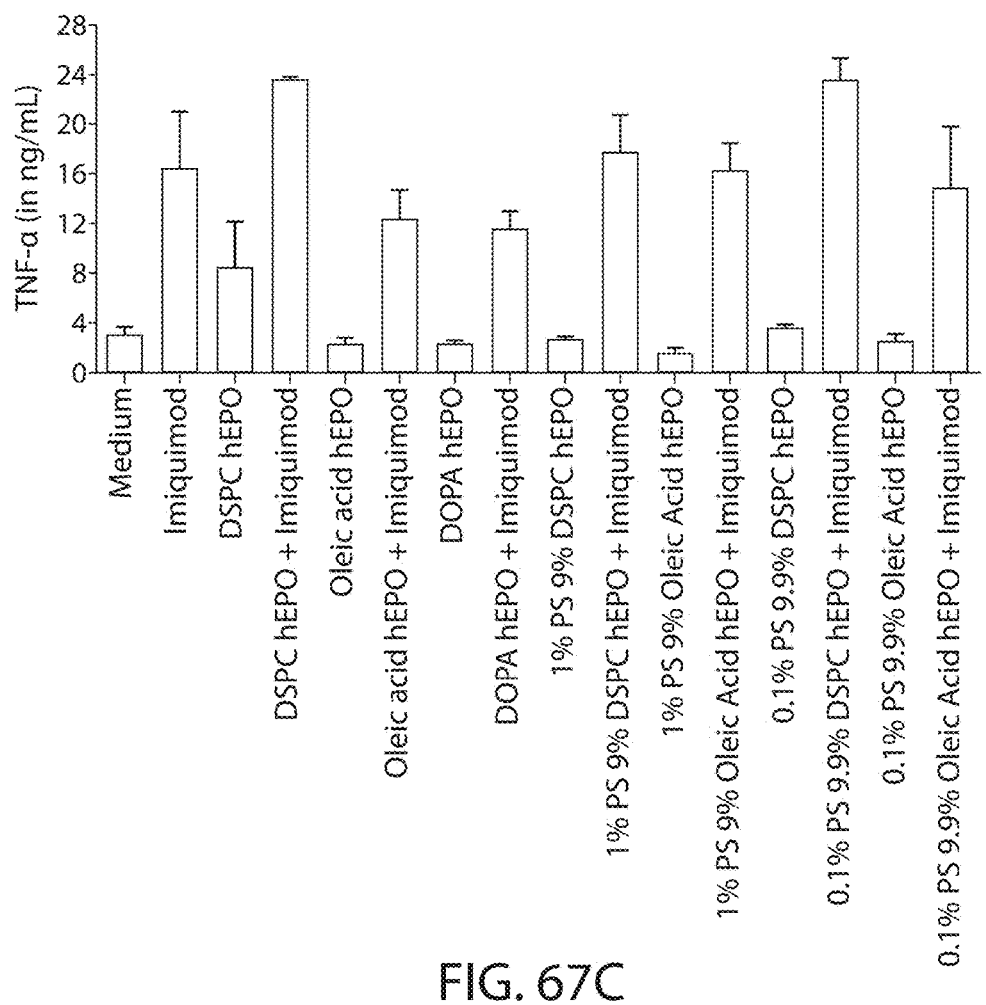

FIGS. 67A-67C are a set of graphs depicting cytokine release as a measure of ex vivo human B cell activation. Levels of IFN-gamma (FIG. 67A), LI-6 (FIG. 67) and TNF-alpha (FIG. 67C) were measured.

Figure 68:
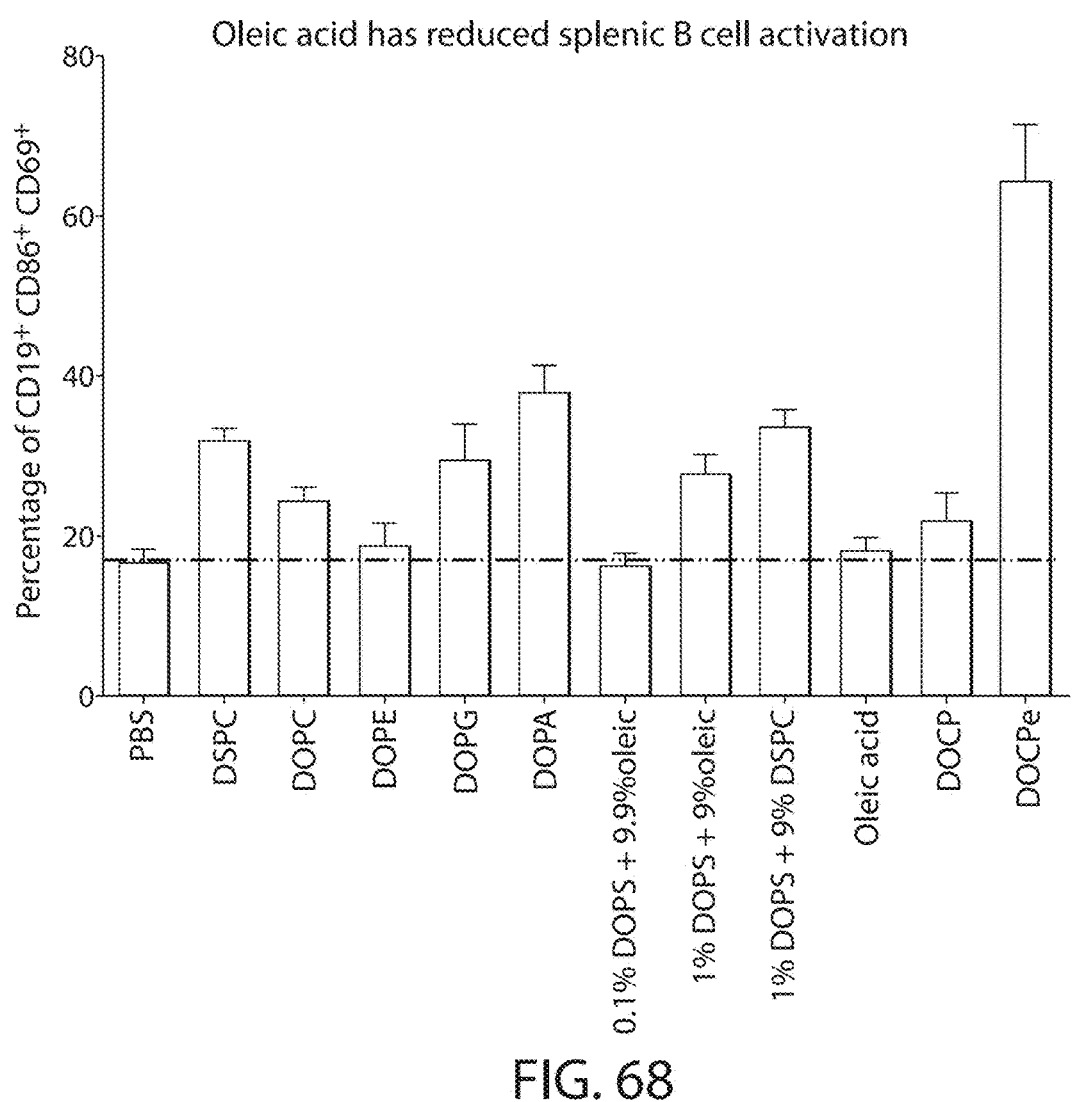

FIG. 68 is a graph depicting the amount of B cell activation as a result of various LNP formulations. LNP formulations including oleic acid demonstrated reduced splenic B cell activation.

Figure 69:
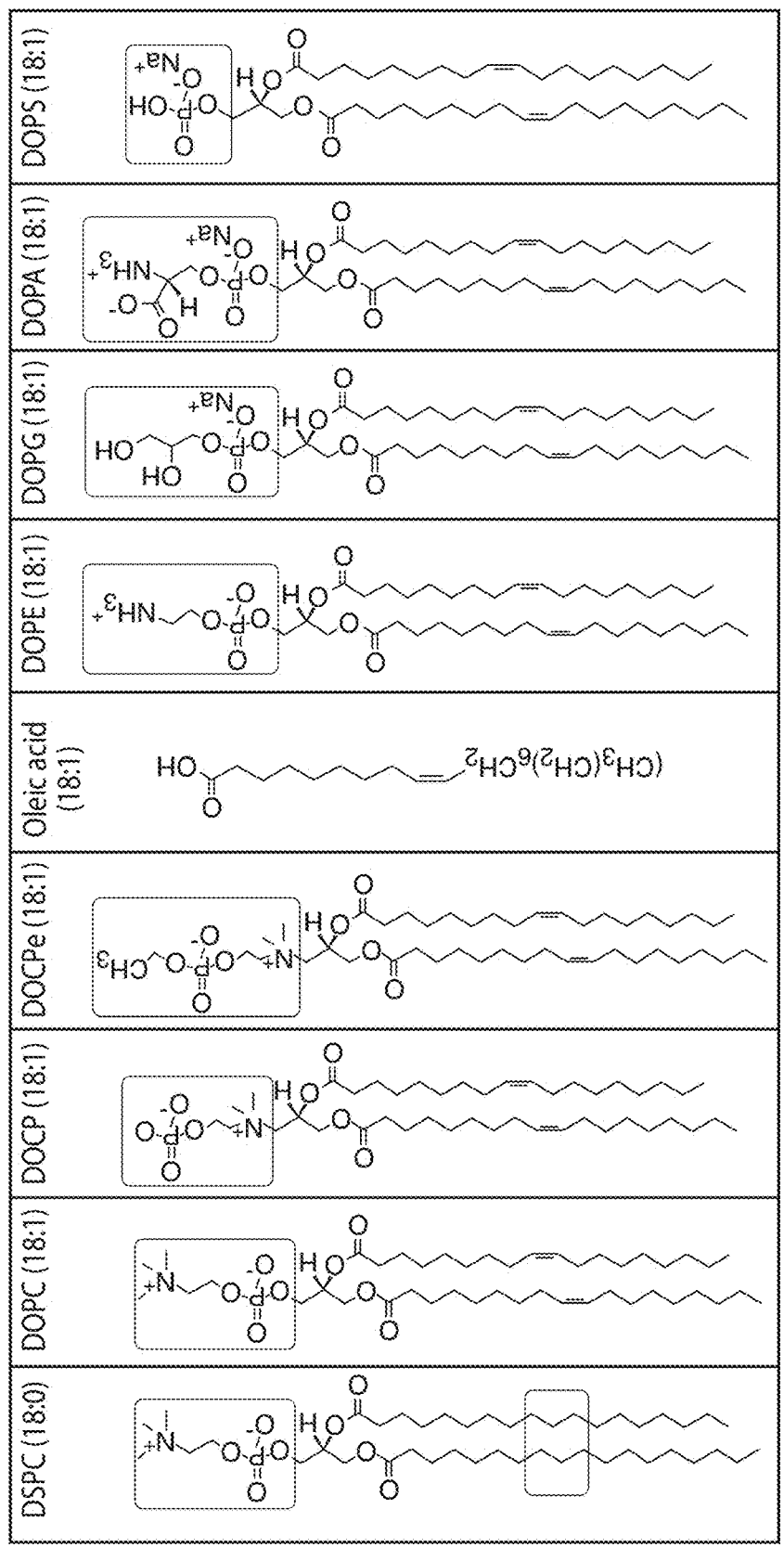

FIG. 69 shows phospholipid structures.

Figure 70:
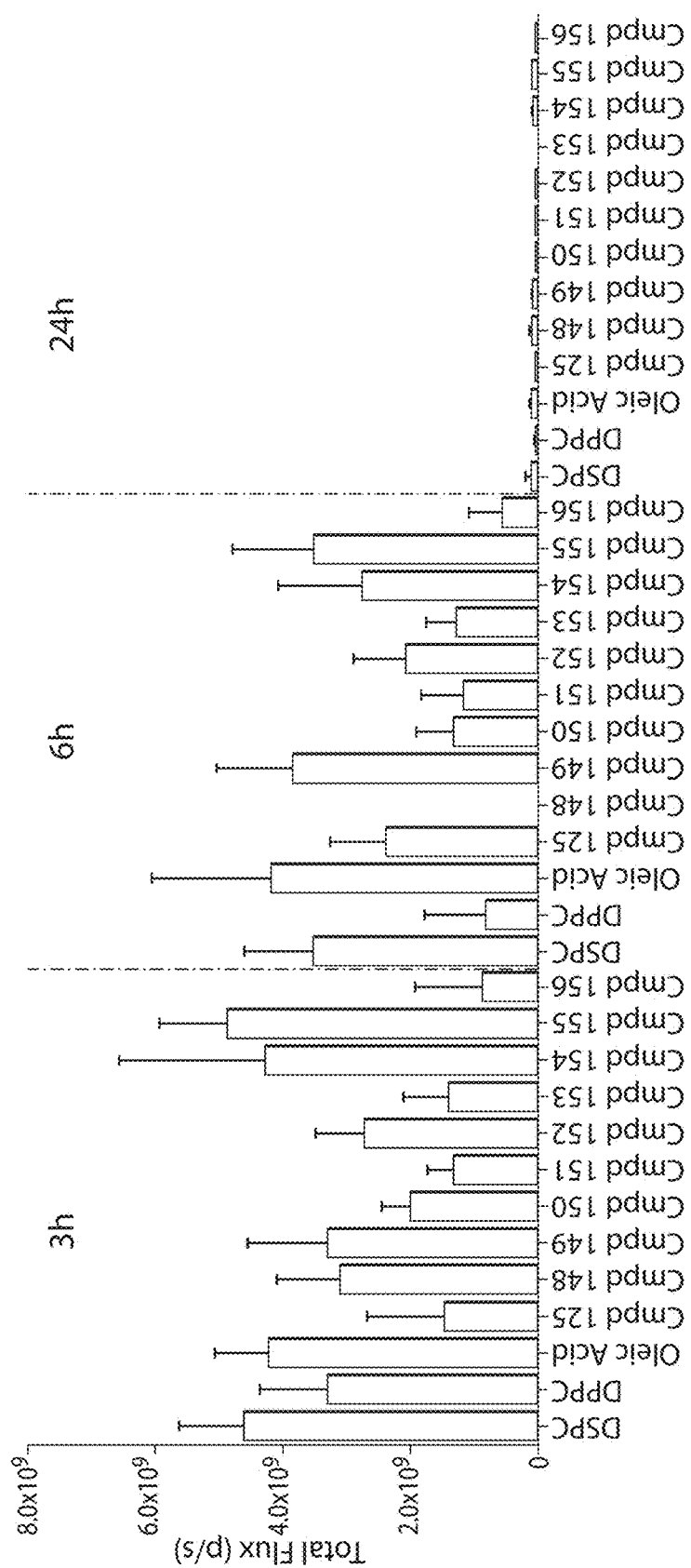

FIG. 70 is a graph depicting Luc expression levels following administration of LUC mRNA encapsulated in various LNP formulations composed of novel PC and Oleic Acid Derivatives at 3, 6 and 24 hours following.

Figure 71A:
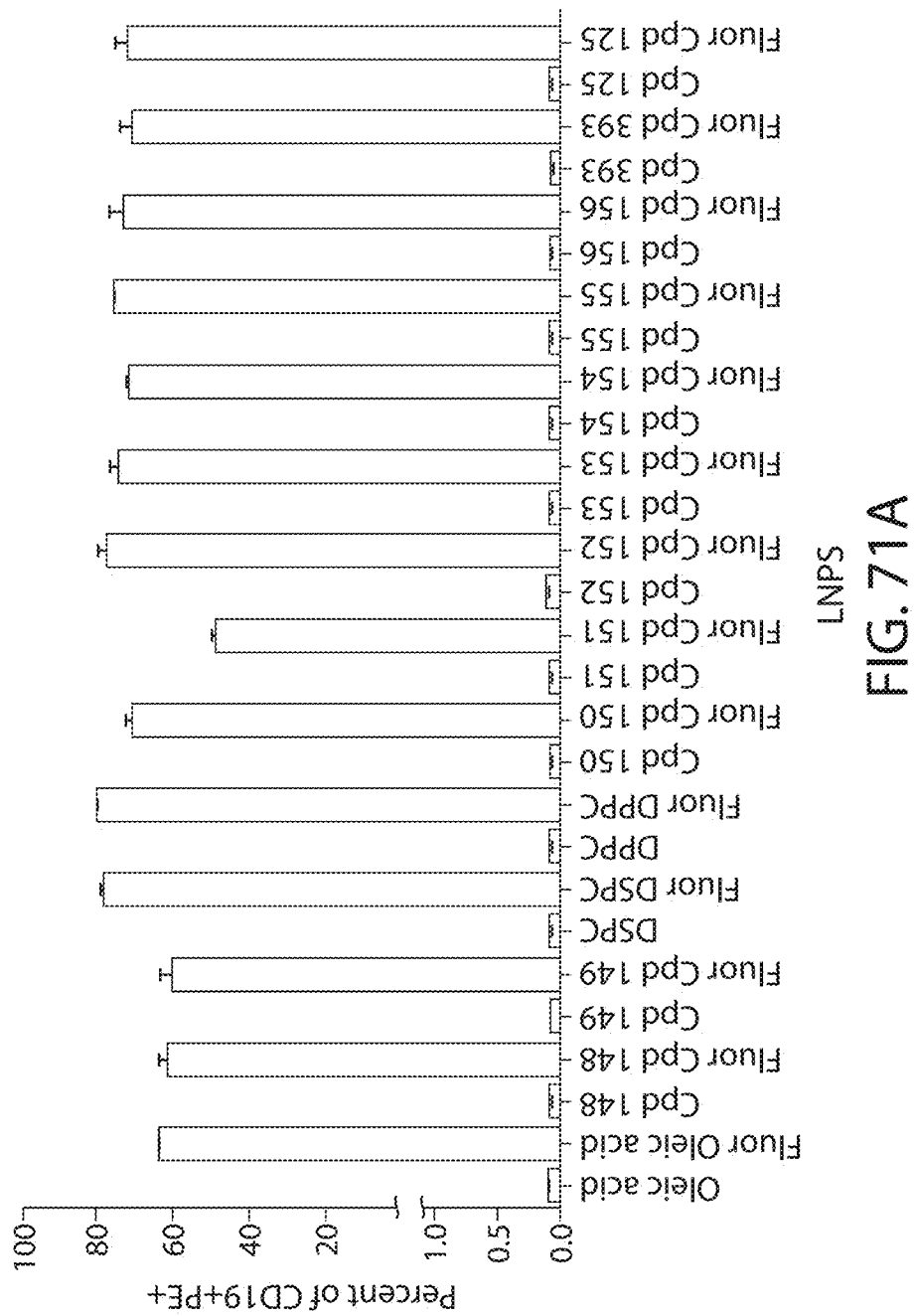
Figure 71B:
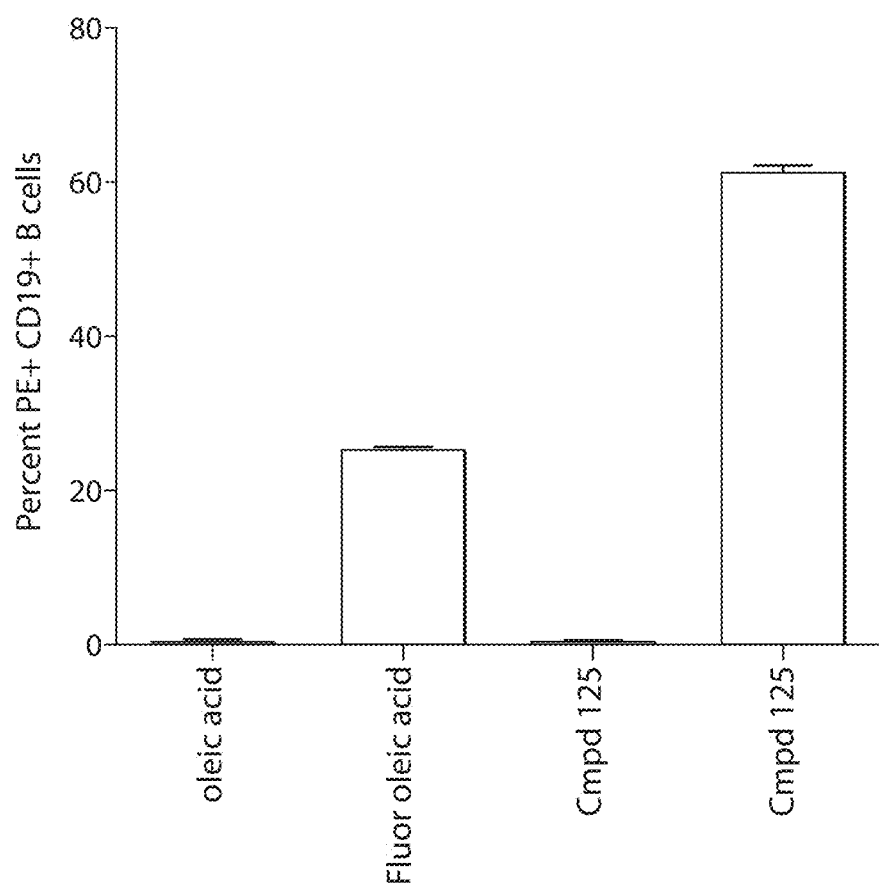

FIGS. 71A-71B are a set of graphs depicting B cell interaction/association with various LNP formulations as assessed by a percentage of CD19+PE+ cells. Several LNP formulations are depicted in FIG. 71A. Oleic acid and Cmpd125 are depicted in FIG. 71B.

Figure 72A:
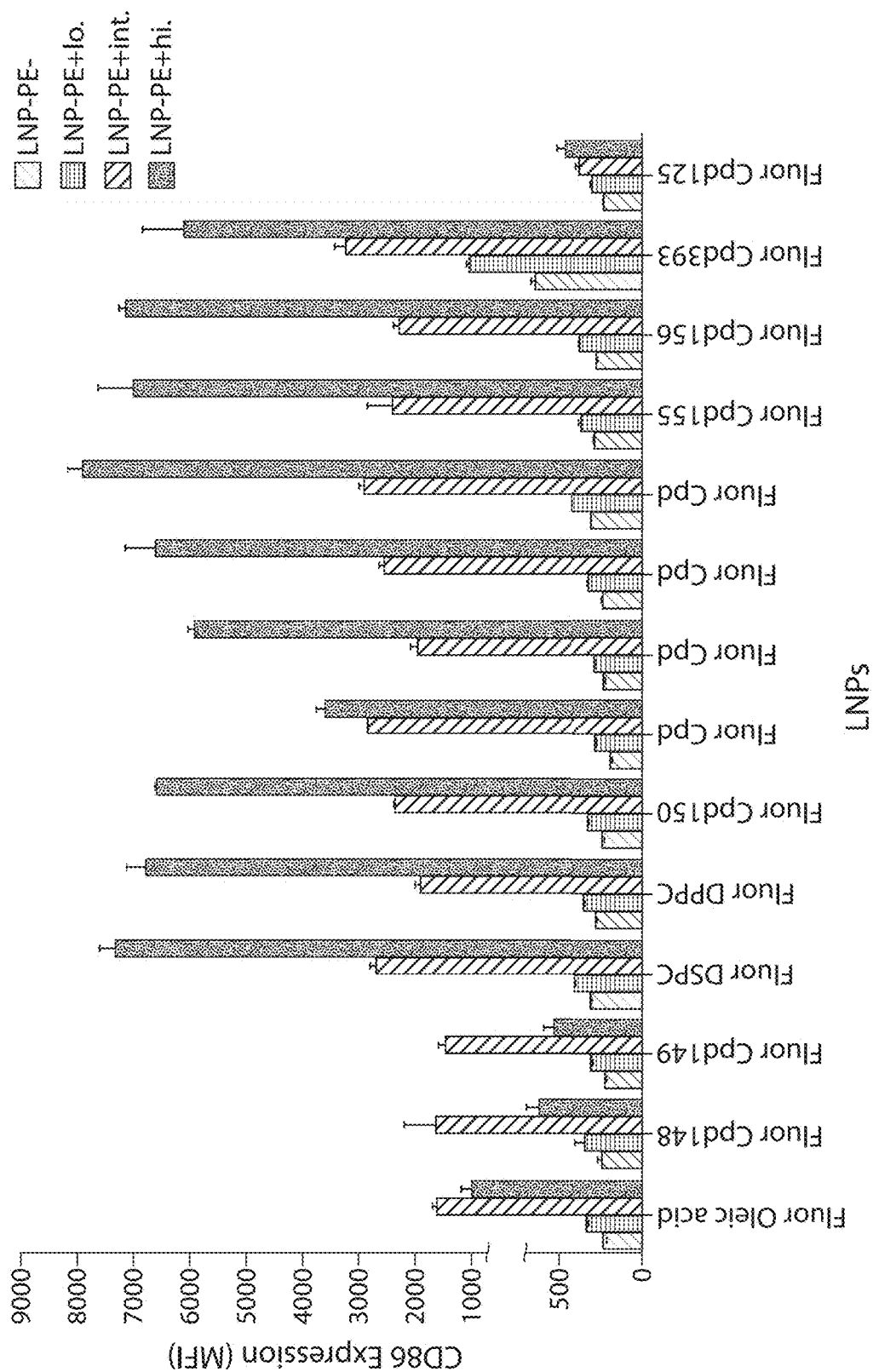
Figure 72B:
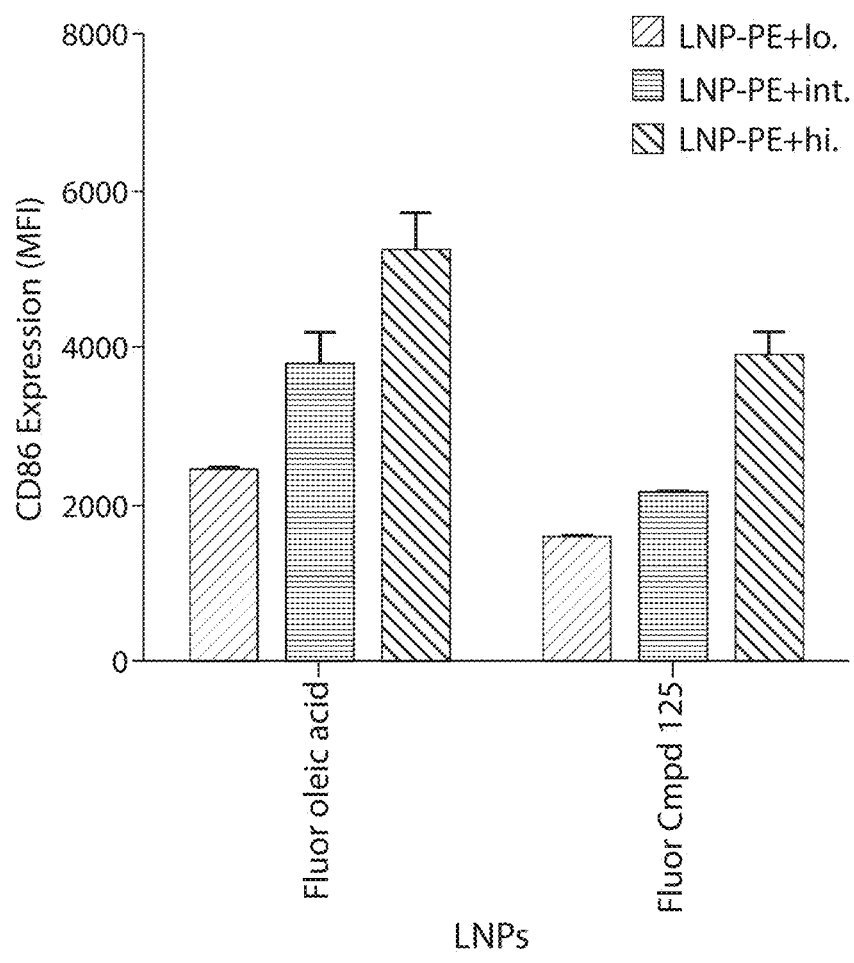

FIGS. 72A-72B are a set of graphs depicting B cell activation with various LNP formulations as assessed by CD86 Expression Median Fluorescence Intensity. Several LNP formulations are depicted in FIG. 72A. Oleic acid and Cmpd125 are depicted in FIG. 72B.

Figure 73A:
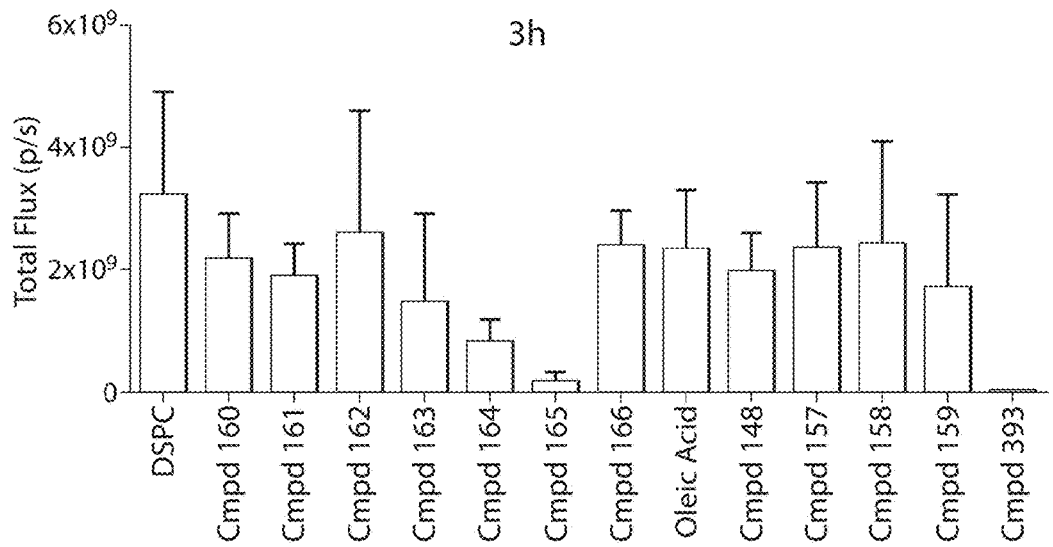
Figure 73B:
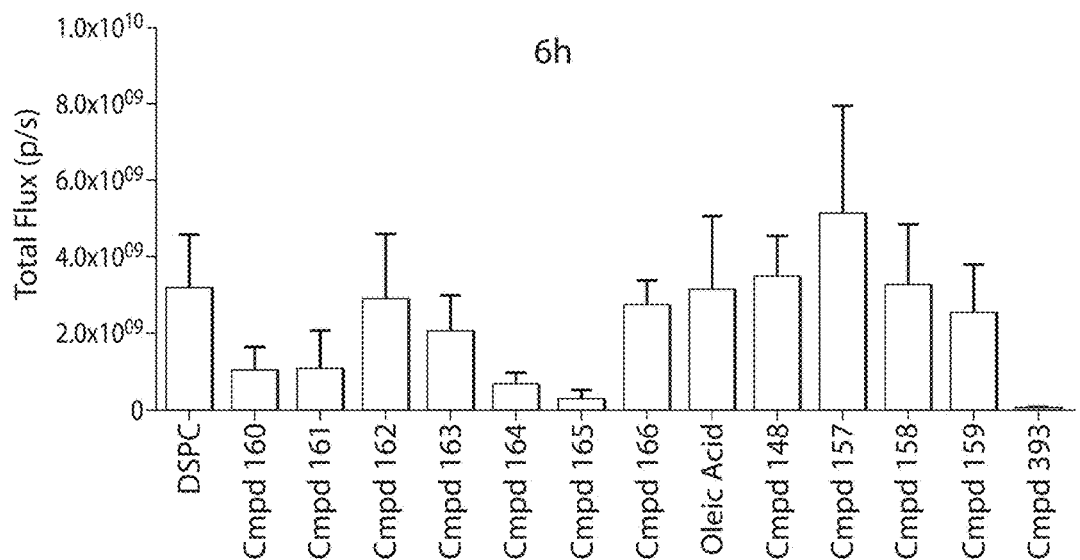
Figure 73C:
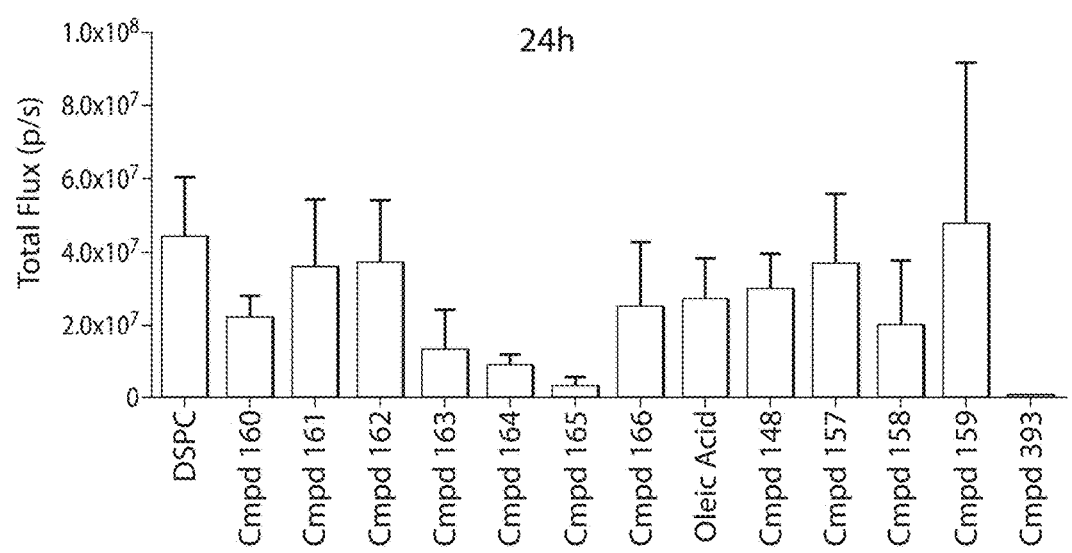

FIGS. 73A-73C are a set of graphs depicting Luc expression with various LNP formulations as assessed by a measurement of total flux at 3 hours (FIG. 73A), 6 hours (FIG. 73B), and 24 hours (FIG. 73C) following a dose.

Figure 74:
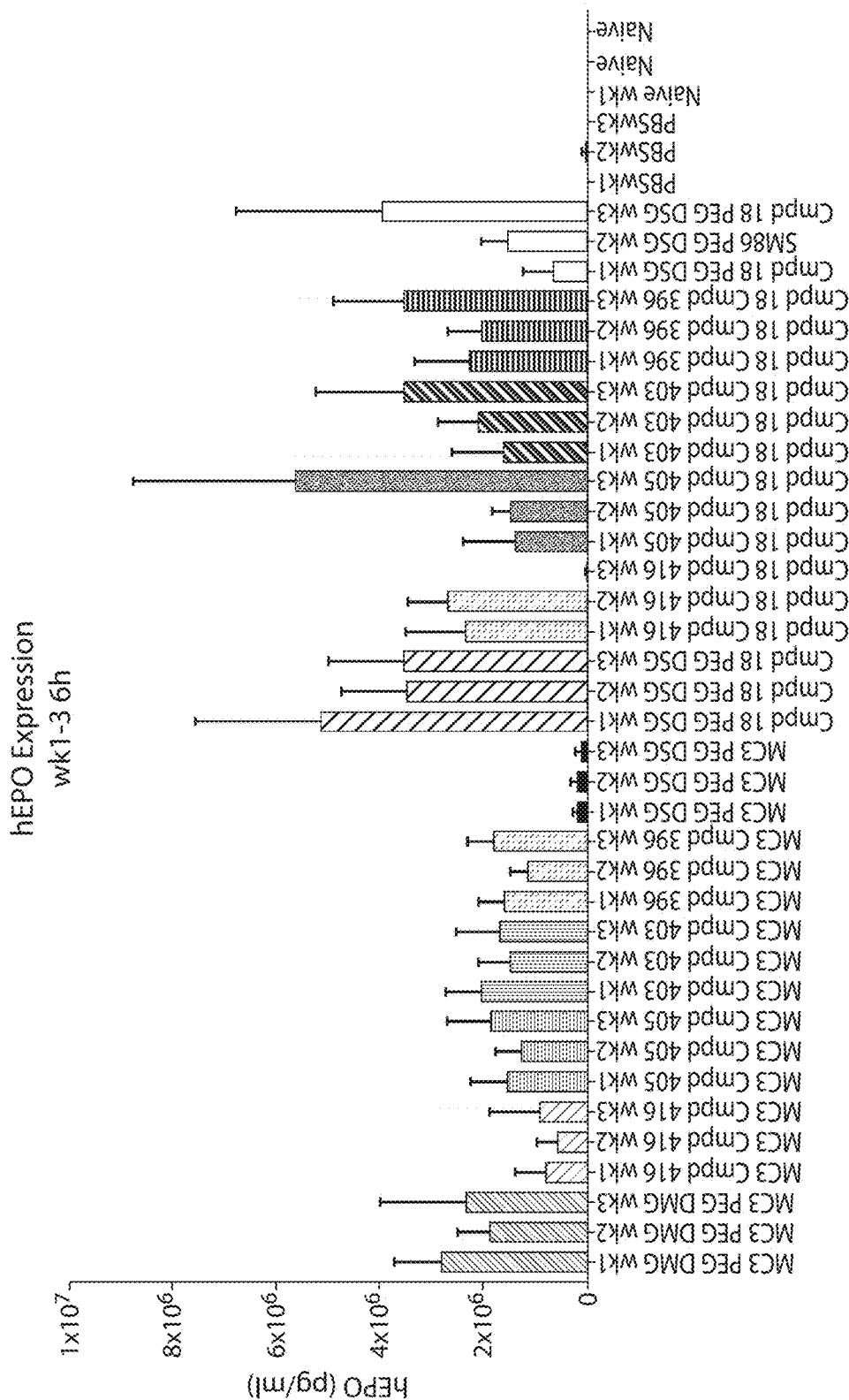

FIG. 74 is a graph depicting hEPO Expression (pg/mL) 6 hours following once weekly IV administration of hEPO mRNA-LNP formulations at weeks 1, 2, and 3.

Figure 75:
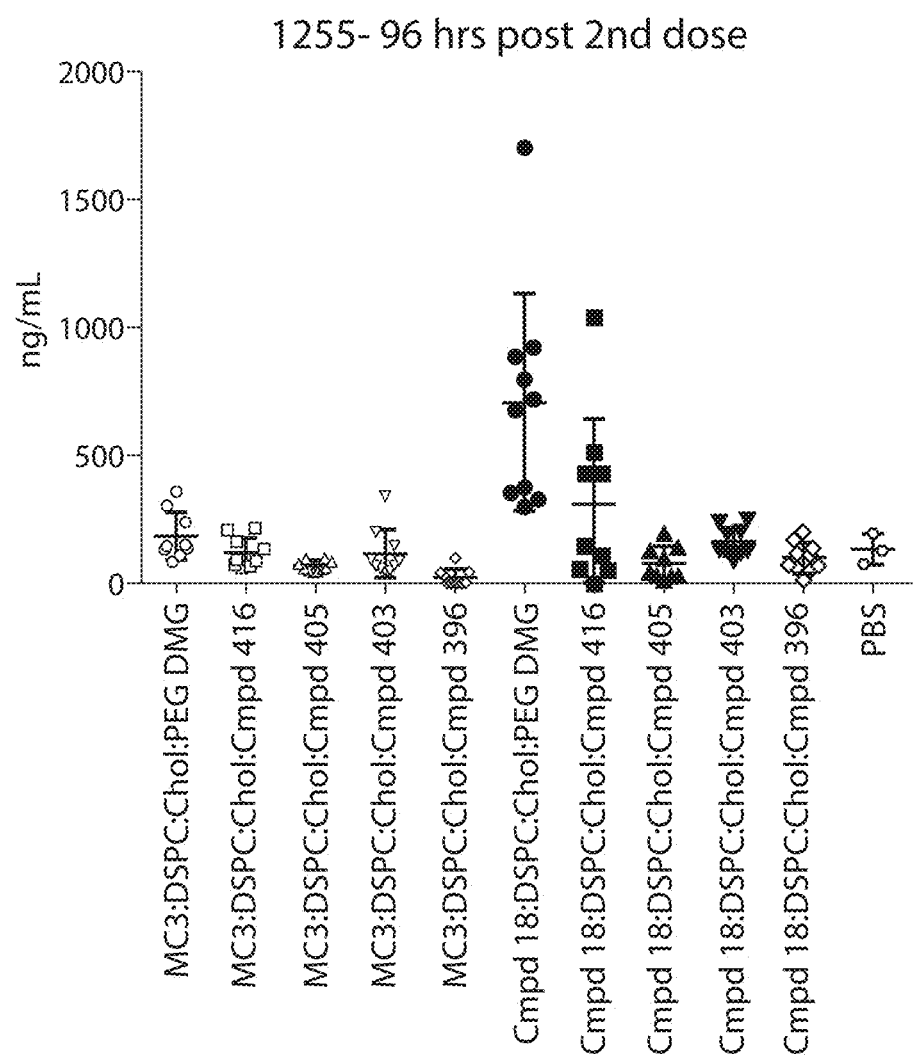

FIG. 75 is a graph depicting anti-PEG IgM production (ng/mL) 96 hours following administration of the second dose of LNP formulations.

Figure 76:
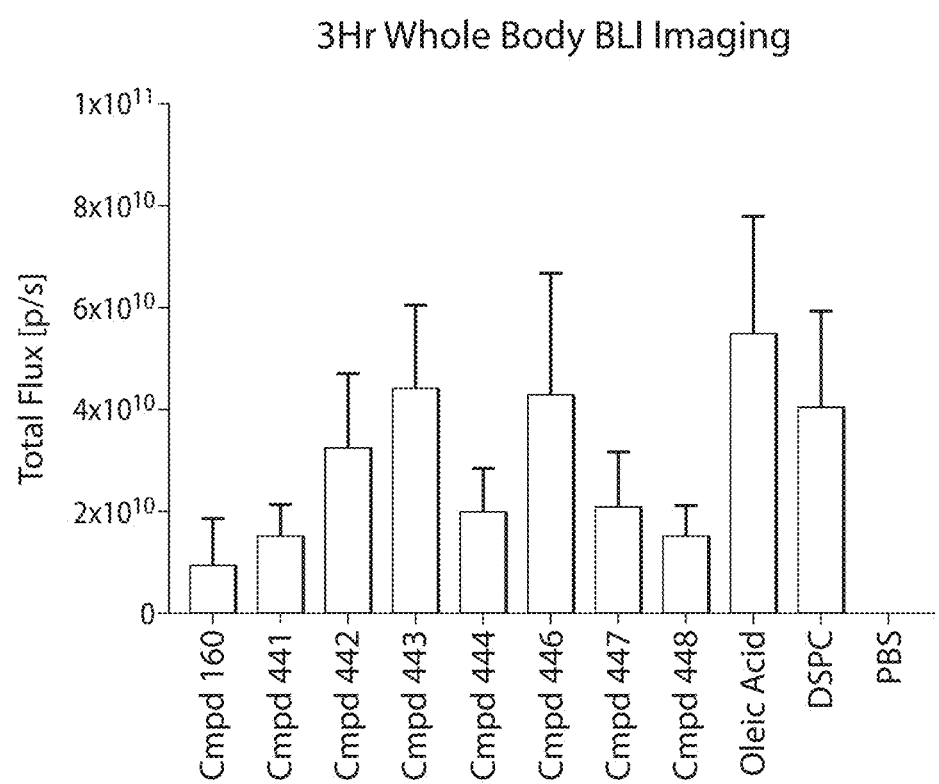

FIG. 76 is a graph depicting Luc expression of various LNP formulations. Luc expression was assessed by a measurement of total flux (p/s) at 3 hours following a dose, using whole body BLI imaging.

Figure 77:
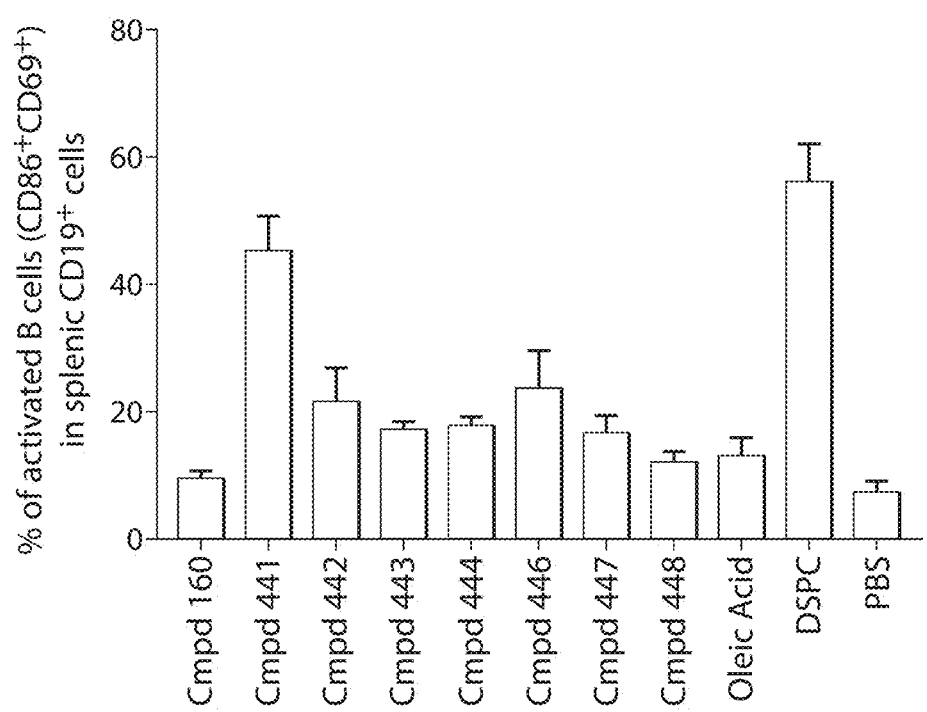

FIG. 77 is a graph depicting B cell activation. Percentage of activated B cells (CD86+CD69+) in splenic CD19+ cells for LNP formulations was measured.

Figure 78:
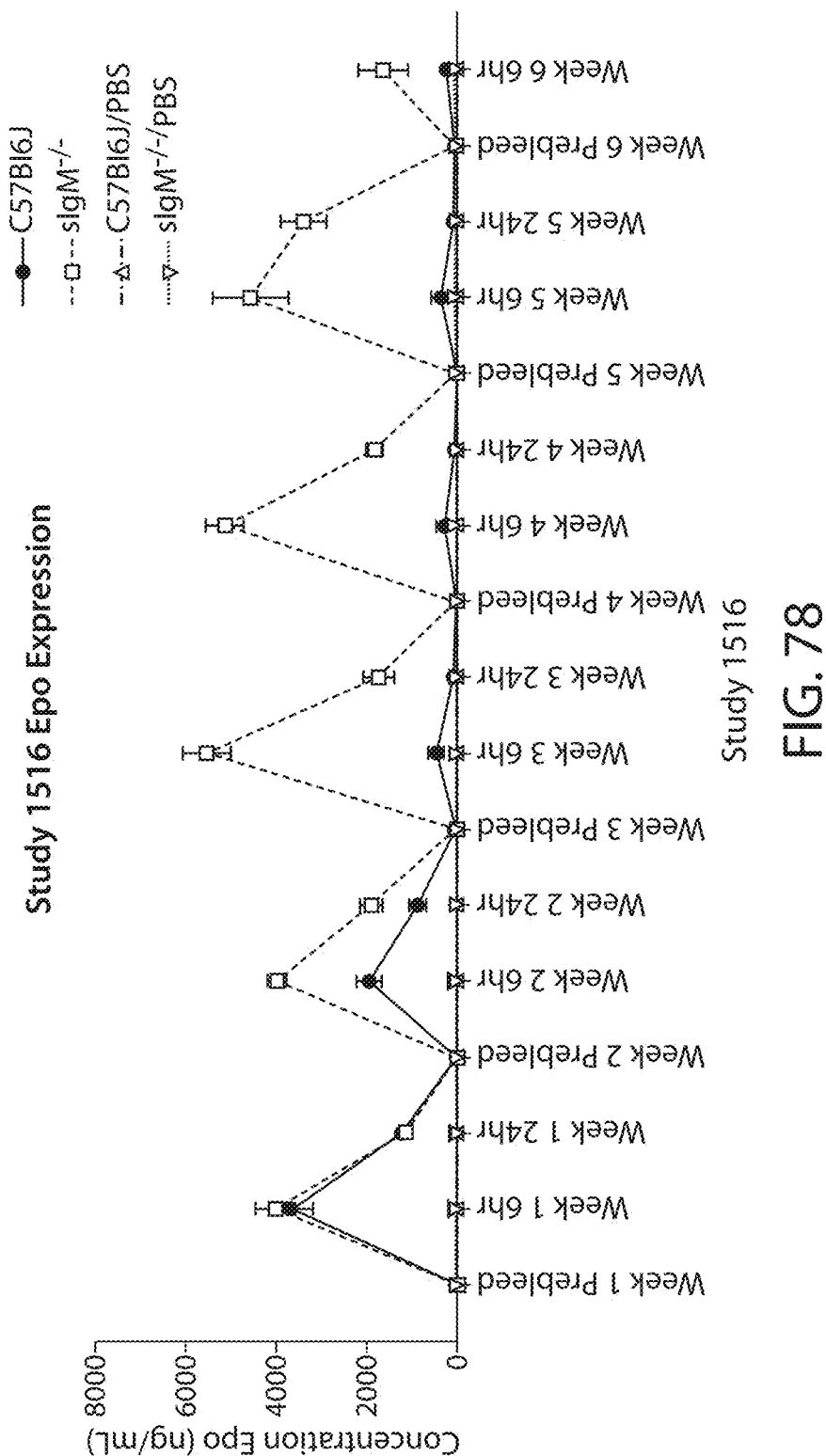

FIG. 78 is a graph depicting EPO expression. Concentration of EPO (ng/mL) was measured at prebleed, 6 hours, and 24 hours, each of the 6 weeks.

Figure 79:
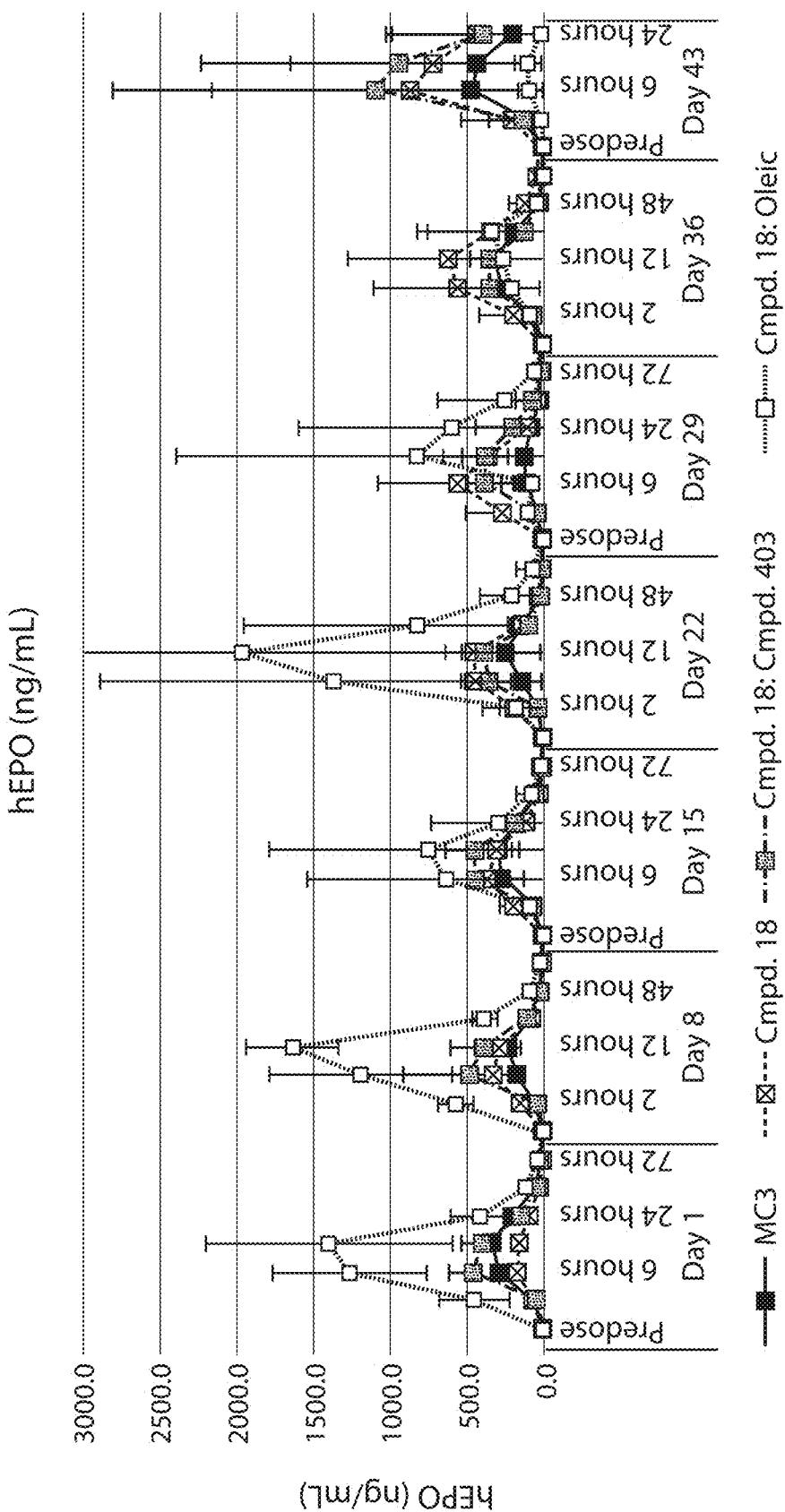

FIG. 79 is a graph depicting hEPO expression (ng/mL) at predose, 2 hours, 6 hours, 12 hours, 24 hours, 48 hours, and 72 hours following once weekly IV administration of hEPO mRNA-LNP formulations.

Figure 80:
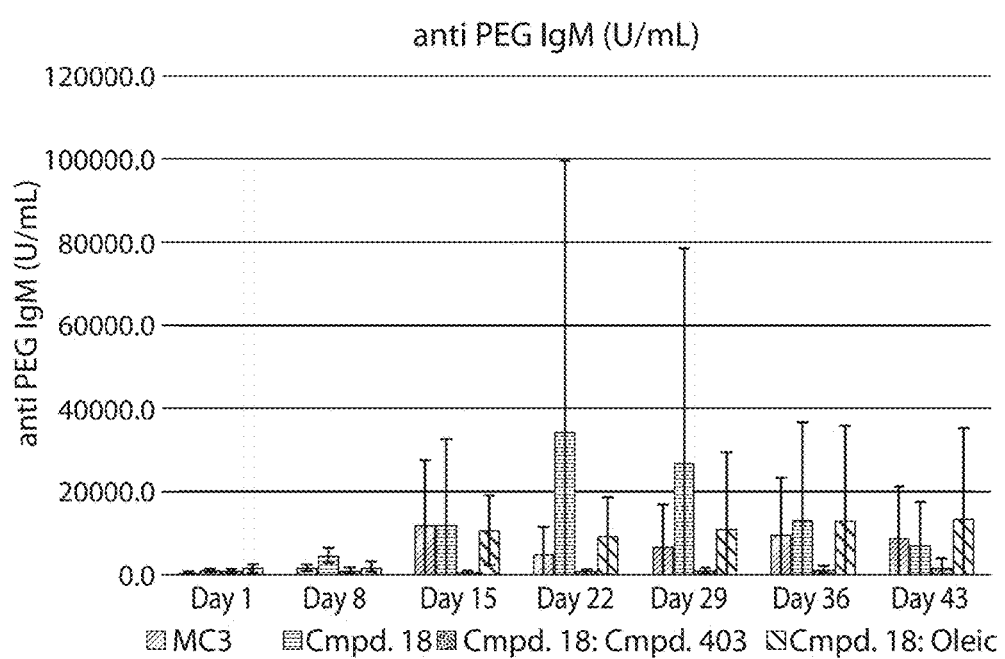

FIG. 80 is a graph depicting levels of anti-PEG IgM (U/mL) following once weekly IV administration of the hEPO mRNA-LNP formulations.

Figure 81:
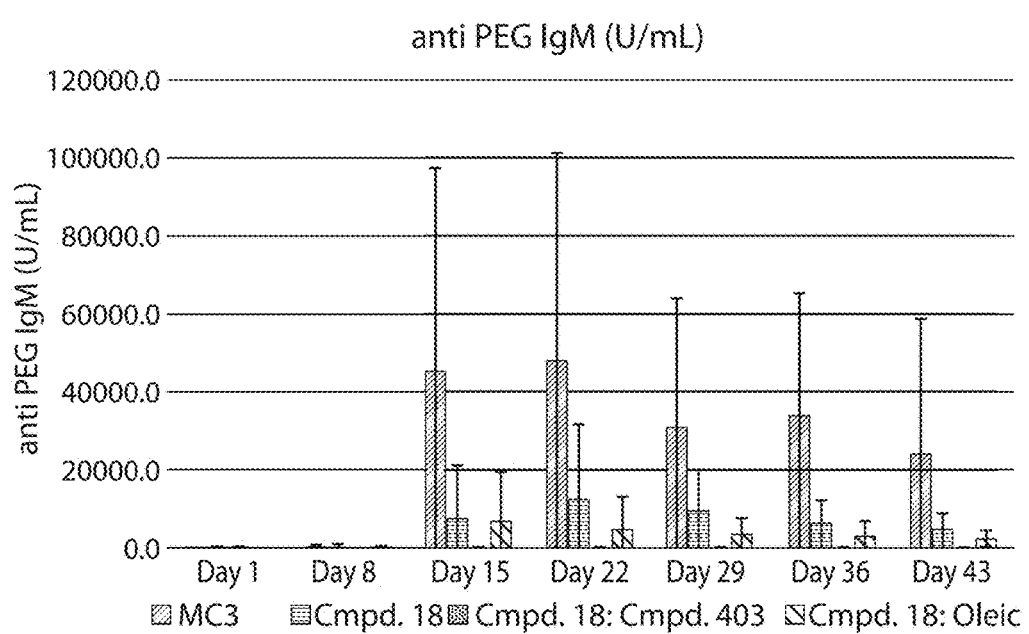

FIG. 81 is a graph depicting levels of anti-PEG IgG (U/mL) following once weekly IV administration of the hEPO mRNA-LNP formulations.

Figure 82:
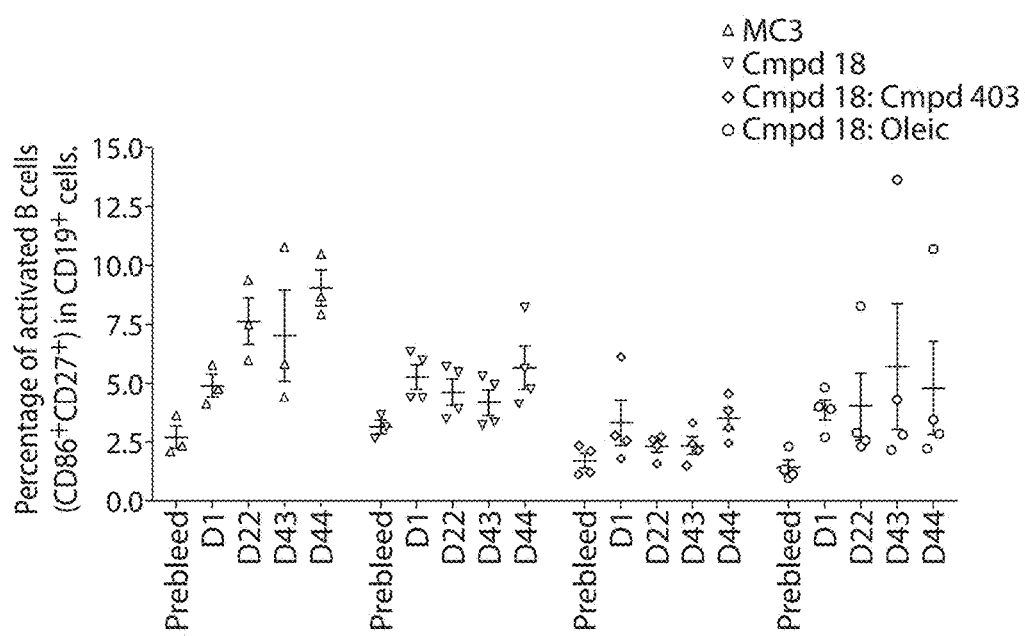

FIG. 82 is a graph depicting B cell activation. Percentage of activated B cells (CD86+CD27+) in CD19+ cells for LNP formulations was measured.

Figure 83:
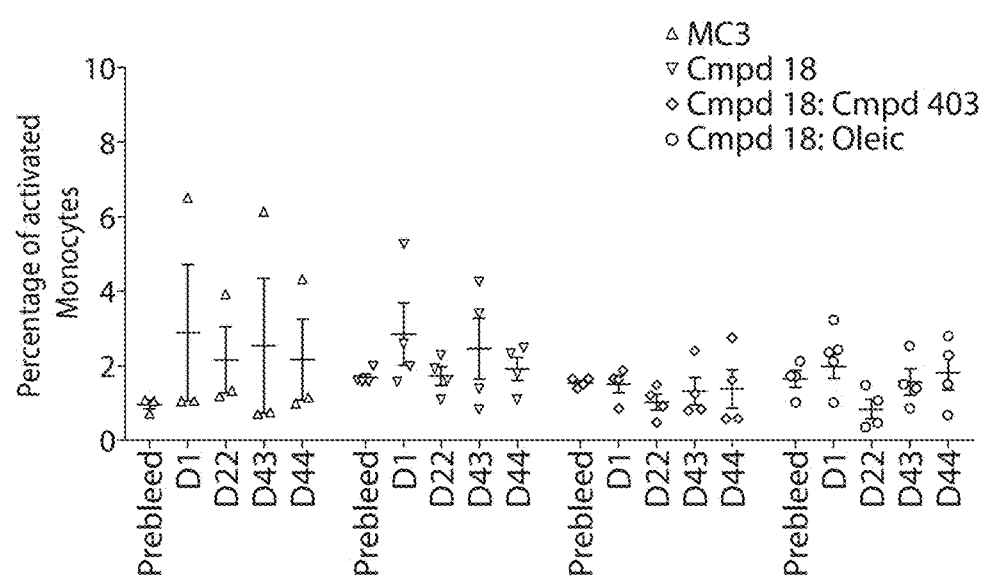

FIG. 83 is a graph depicting monocyte activation measured for LNP formulations.

Figure 84A:
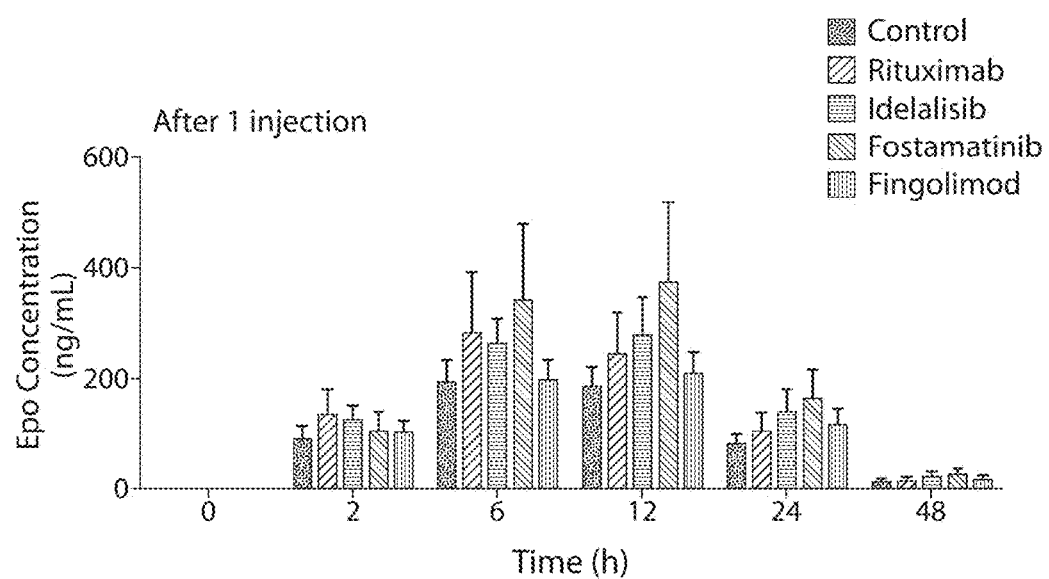
Figure 84B:
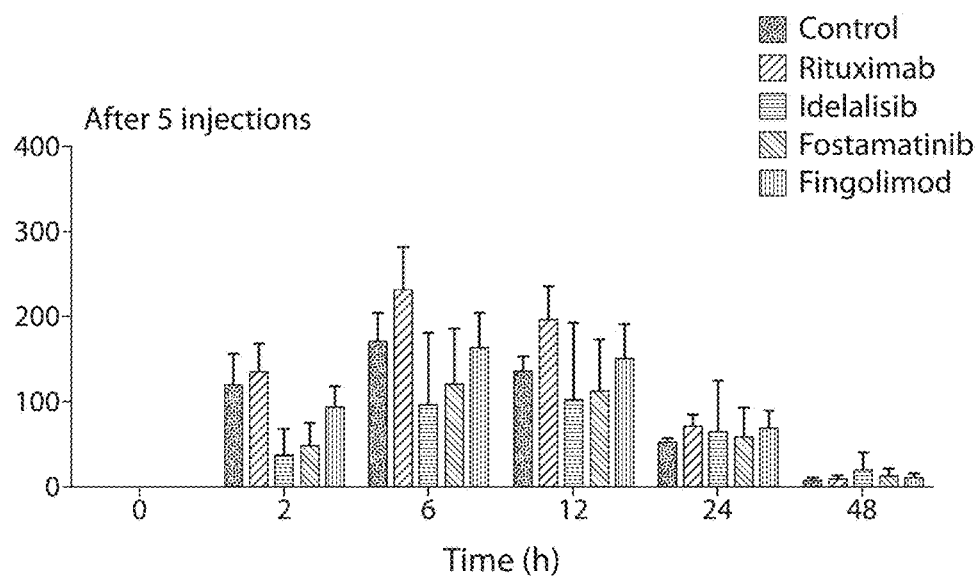
Figure 85A:
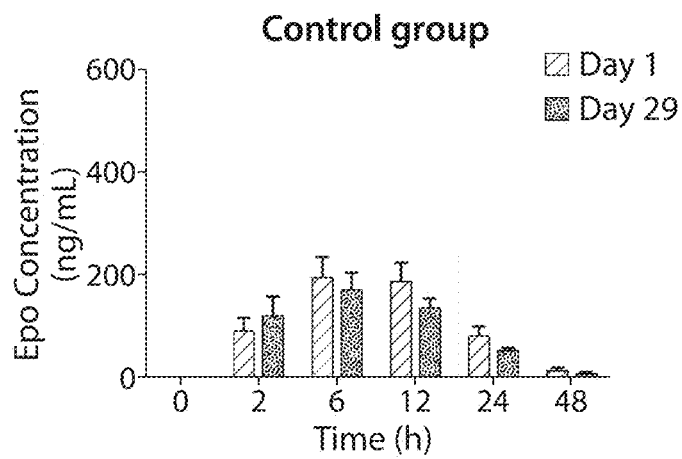
Figure 85B:
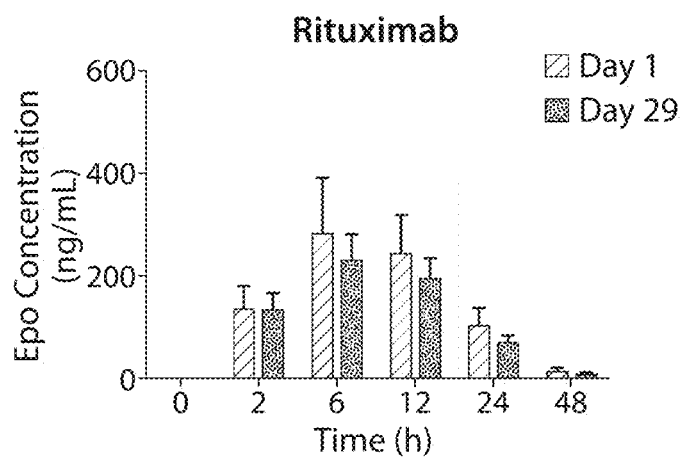
Figure 85C:
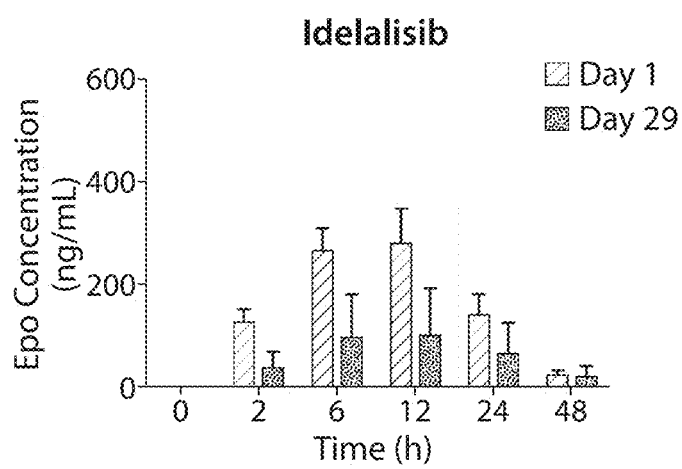
Figure 85D:
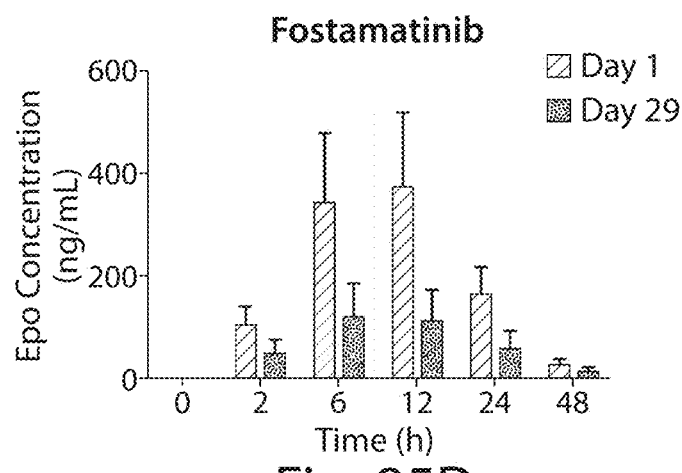
Figure 85E:
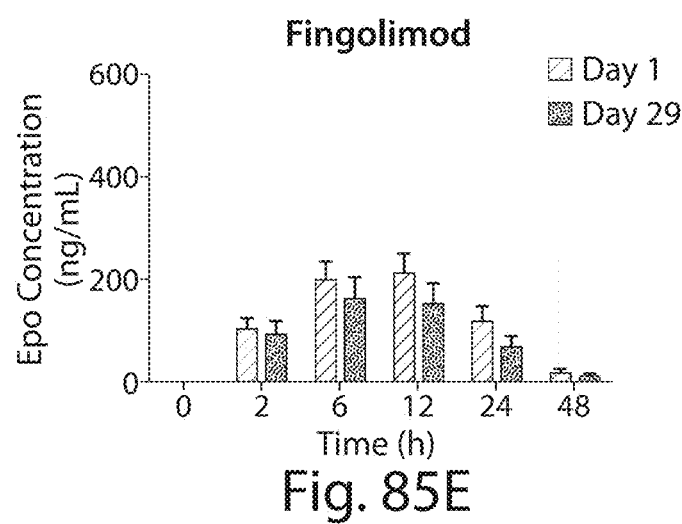

FIGS. 84A-84B are graphs depicting EPO expression. Concentration of EPO (ng/mL) was measured at 2 hours, 6 hours, 12 hours, 24 hours, and 48 hours following the first injection and the fifth injection.

FIGS. 85A-85E are graphs depicting EPO expression. Concentration of EPO (ng/mL) was measured on day 1 and day 29 at 2 hours, 6 hours, 12 hours, 24 hours, and 48 hours for each co-medication group.

Figure 86A:
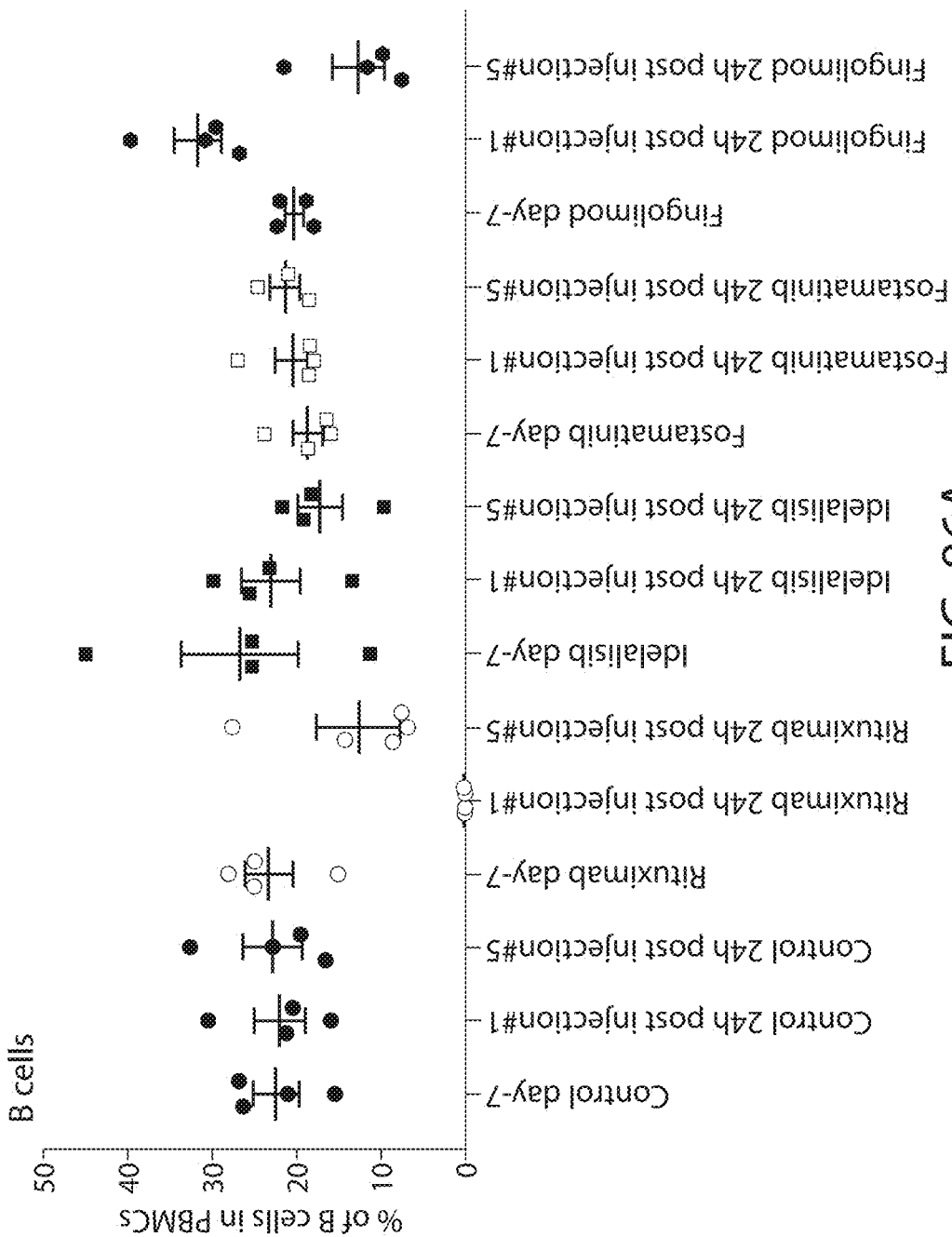
Figure 86B:
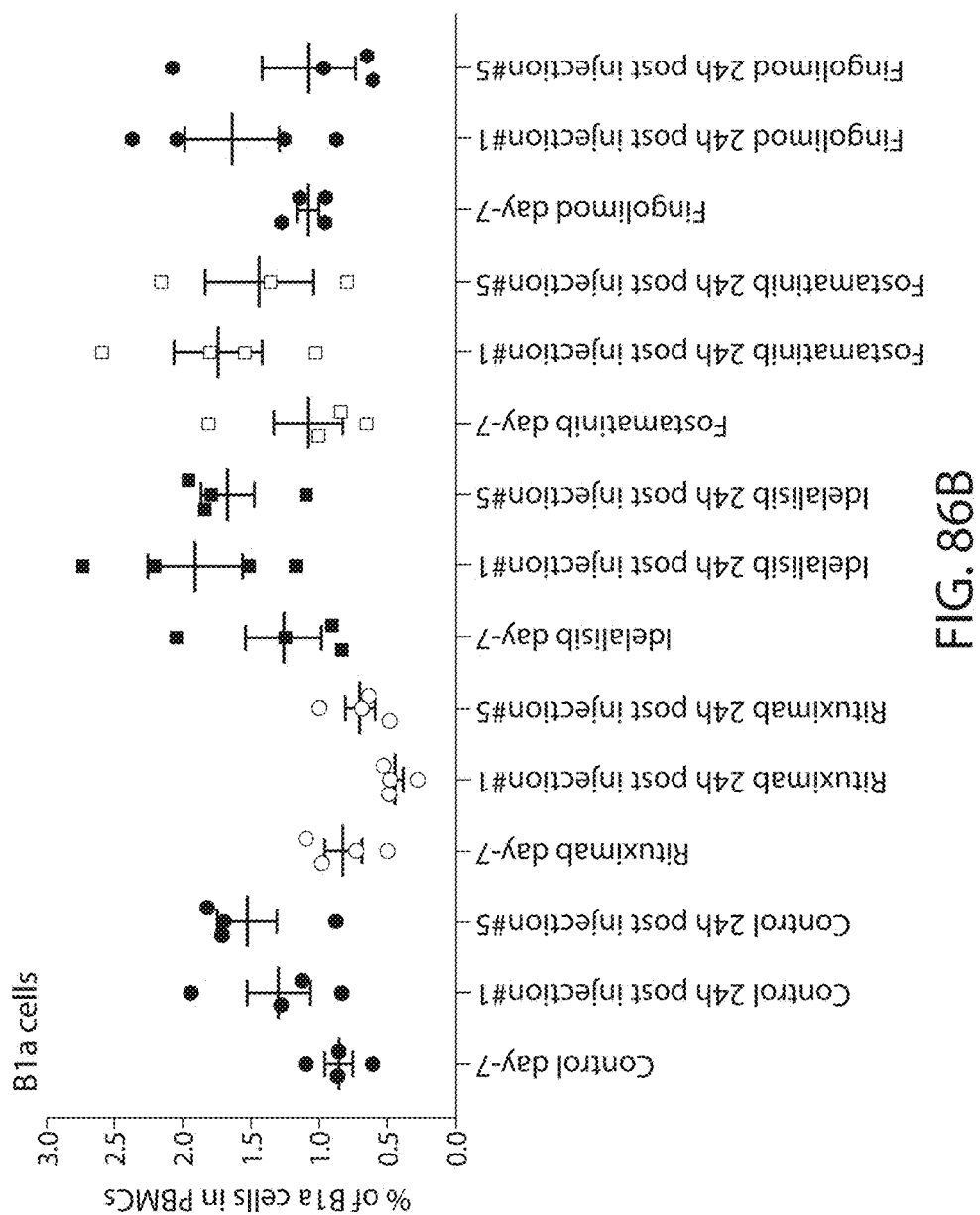
Figure 86C:
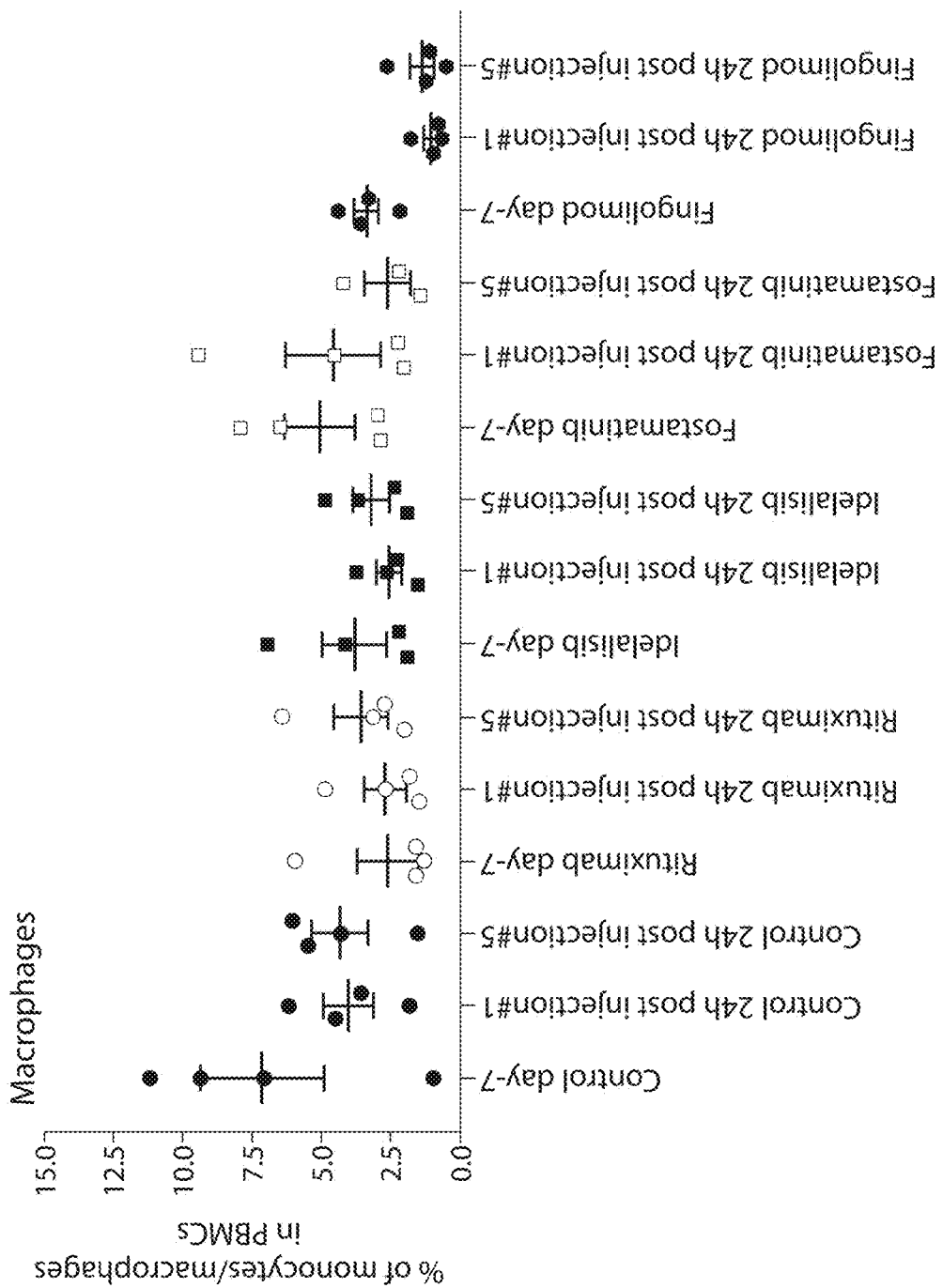

FIGS. 86A-86C are graphs depicting immune cell populations. Shows the percentage of B cells (FIG. 86A), B1a cells (FIG. 86B), and monocytes (FIG. 86C) in PBMCs for each co-medication group at day −7, 24 hours post first injection, and 24 hours post fifth injection.

Figure 87:
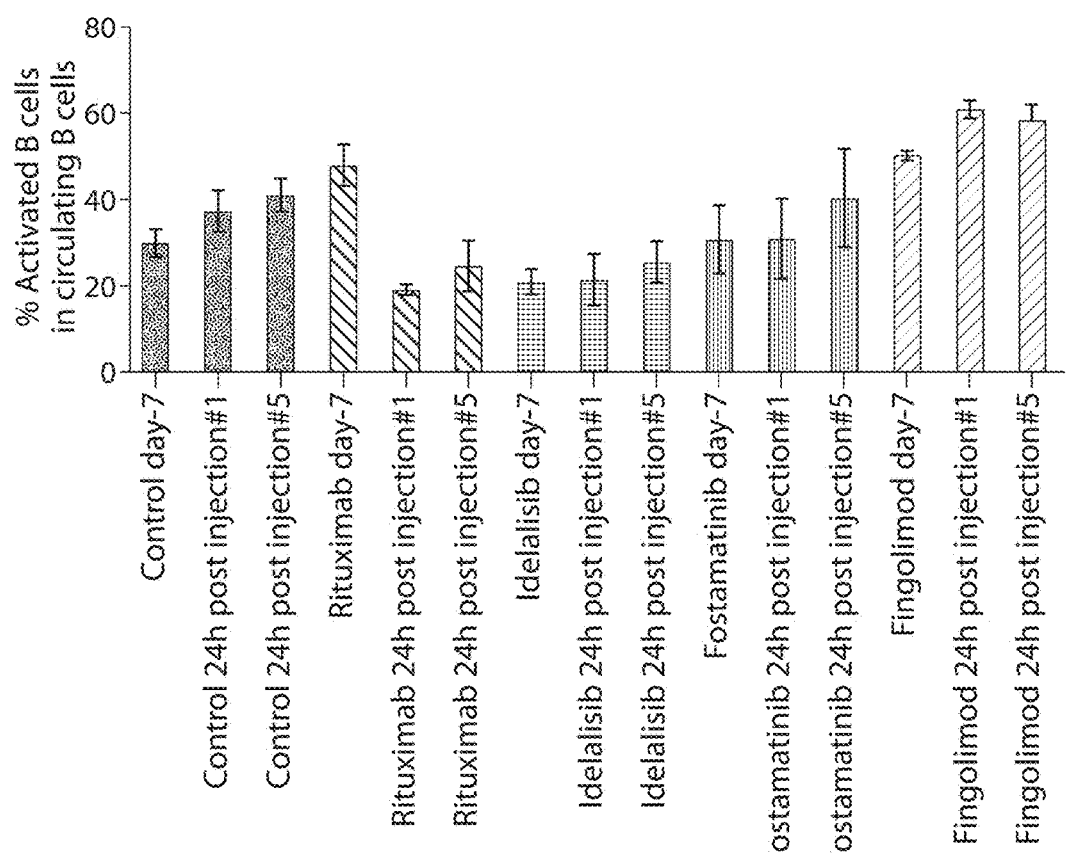

FIG. 87 is a graph depicting B cell activation. The percentage of activated B cells in circulating B cells was measured for each co-medication group at day −7, 24 hours post first injection, and 24 hours post fifth injection.

Figure 88:
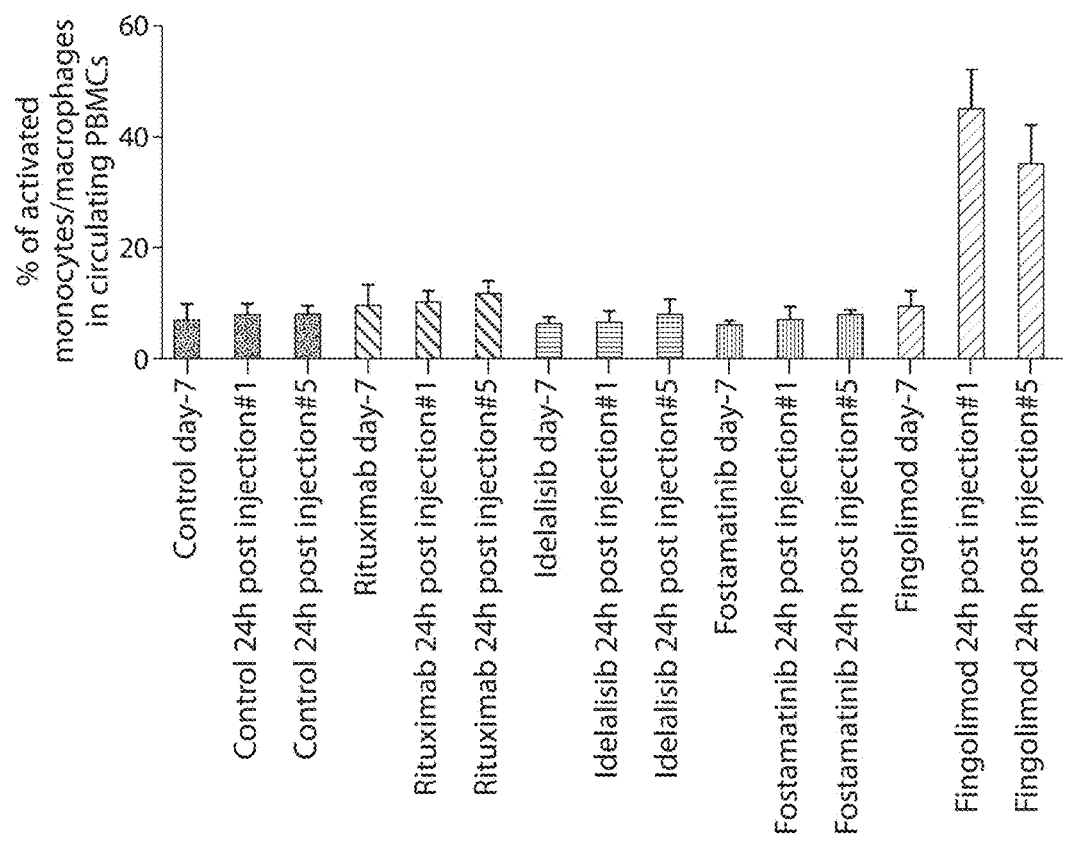

FIG. 88 is a graph depicting monocyte activation. The percentage of activated monocytes/macrophages in circulating PBMCs was measured for each co-medication group at day −7, 24 hours post first injection, and 24 hours post fifth injection.

Figure 89A:
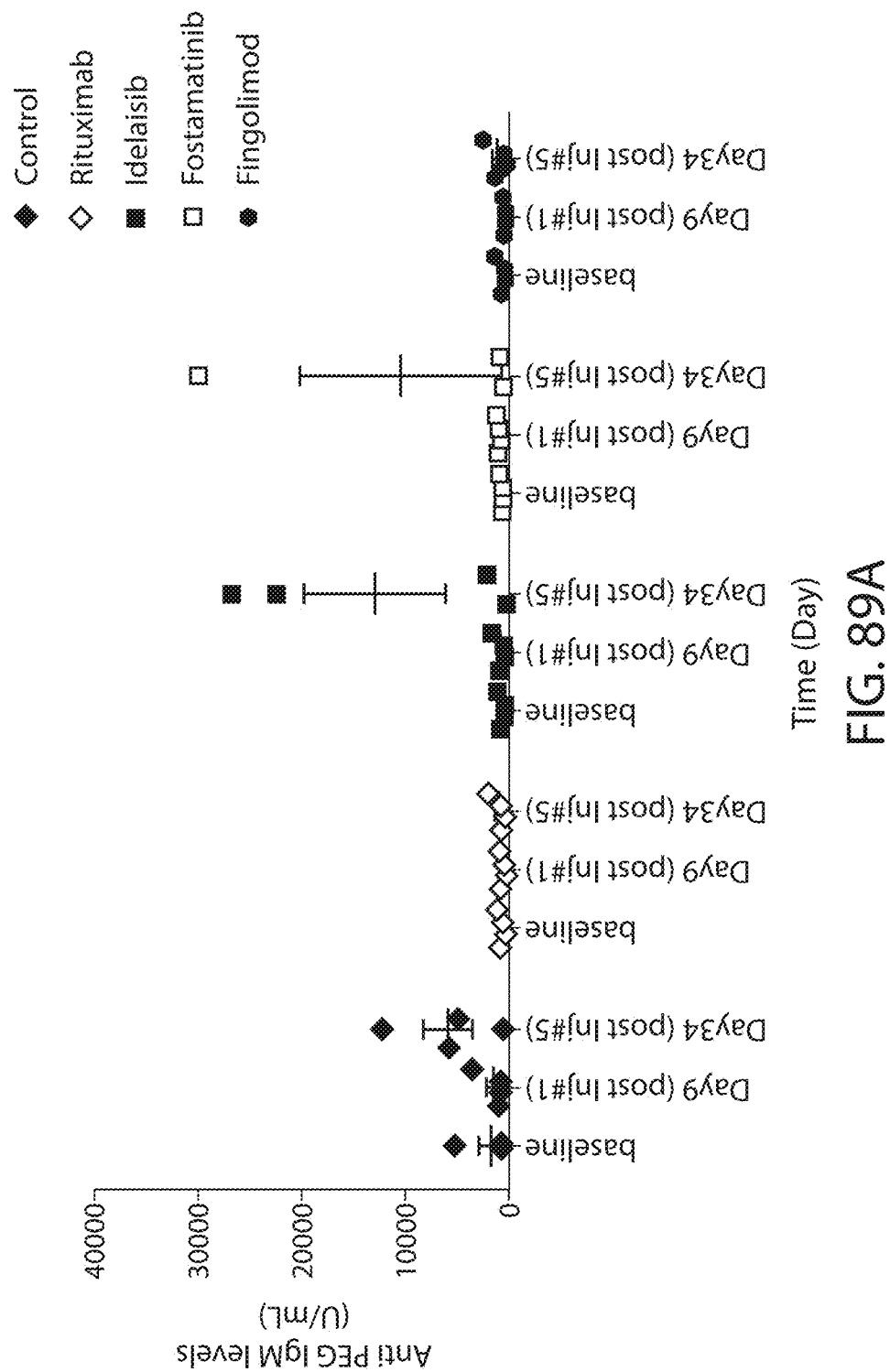
Figure 89B:
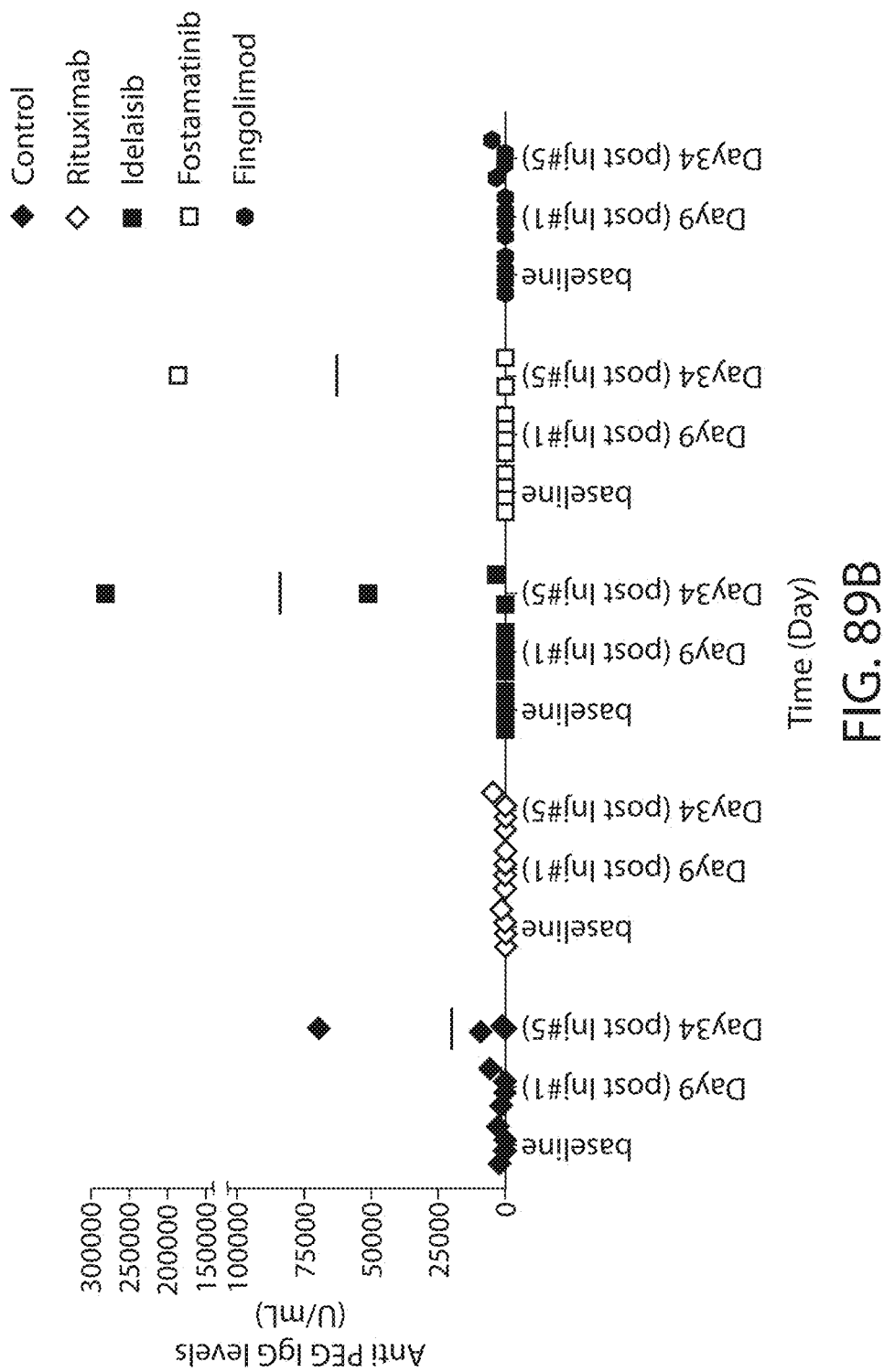

FIGS. 89A-89B are graphs depicting anti-PEG response. Anti-PEG IgM levels (U/mL) (FIG. 89A) and anti-PEG IgG levels (U/mL) (FIG. 89B) were measured for each co-medication group at baseline, day 9 post first injection, and day 34 post fifth injection.

Figure 90A:
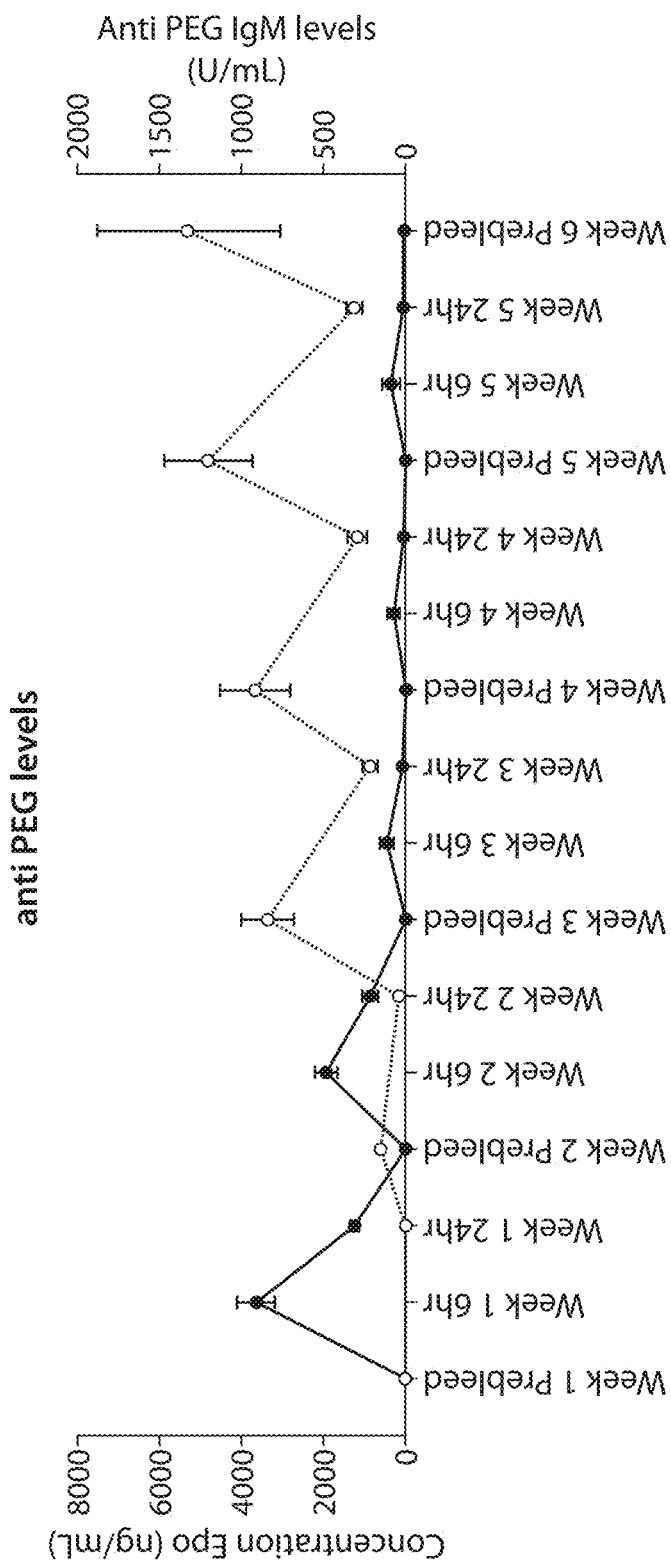
Figure 90B:
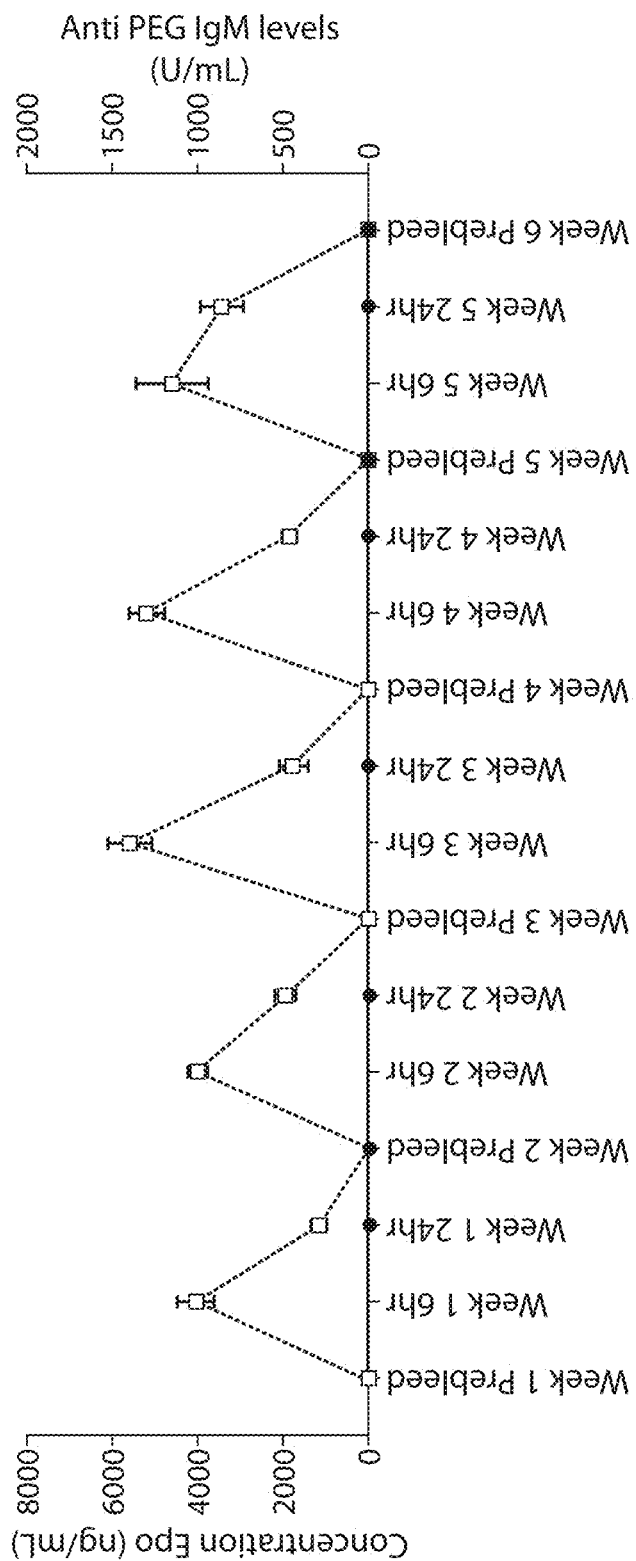

FIGS. 90A-90B are two graphs showing anti-PEG IgM levels (U/mL) and EPO levels (ng/mL) in two of the groups from FIG. 78: C57Bl6J (FIG. 90A) and sIgM–/–(FIG. 90B). In FIG. 90A, anti-PEG IgM levels are graphed as light grey circles; in FIG. 90B, they are represented by black circles. EPO concentrations are indicated by black circles (FIG. 90A) and black squares (FIG. 90B).

Figure 91A:
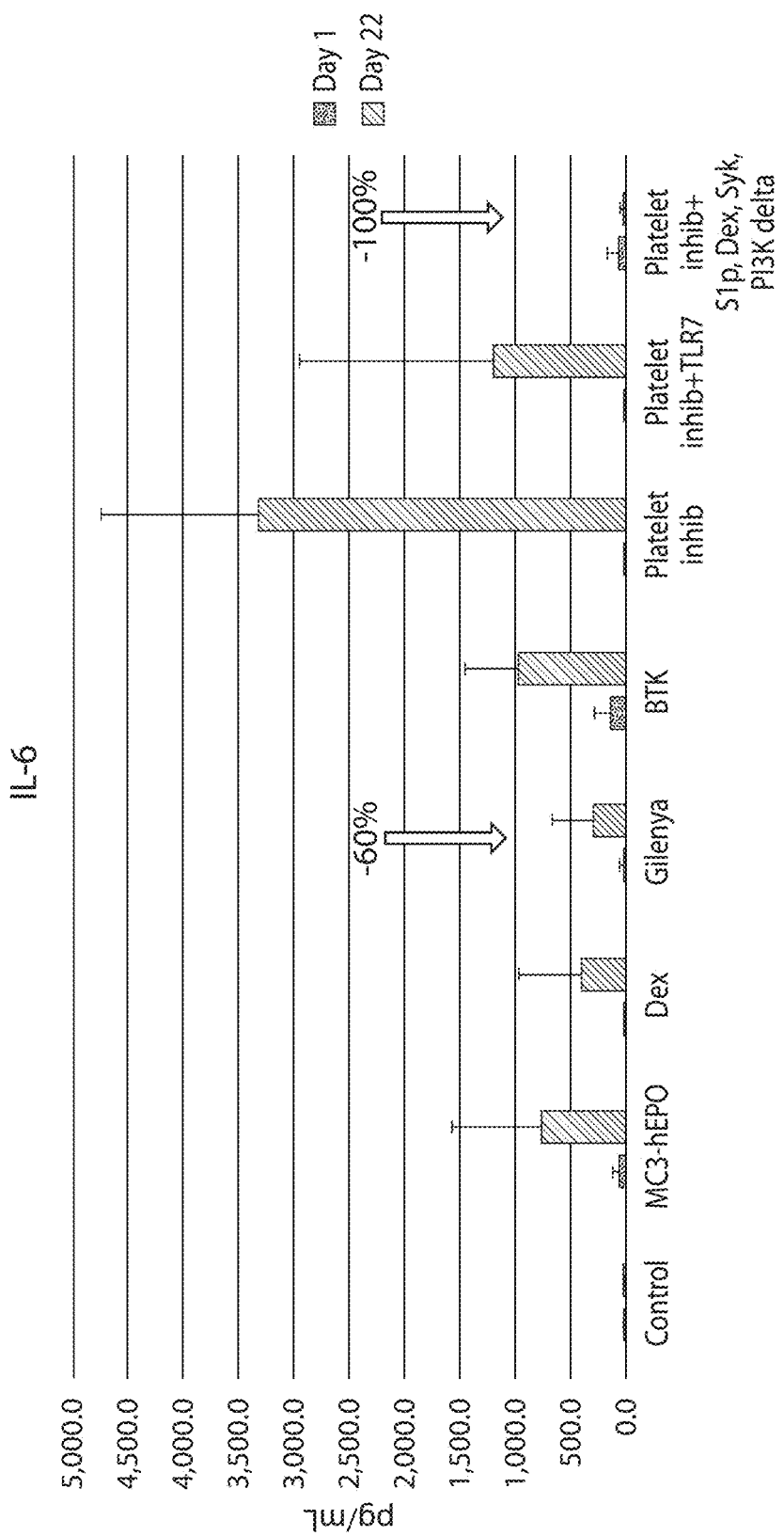
Figure 91B:
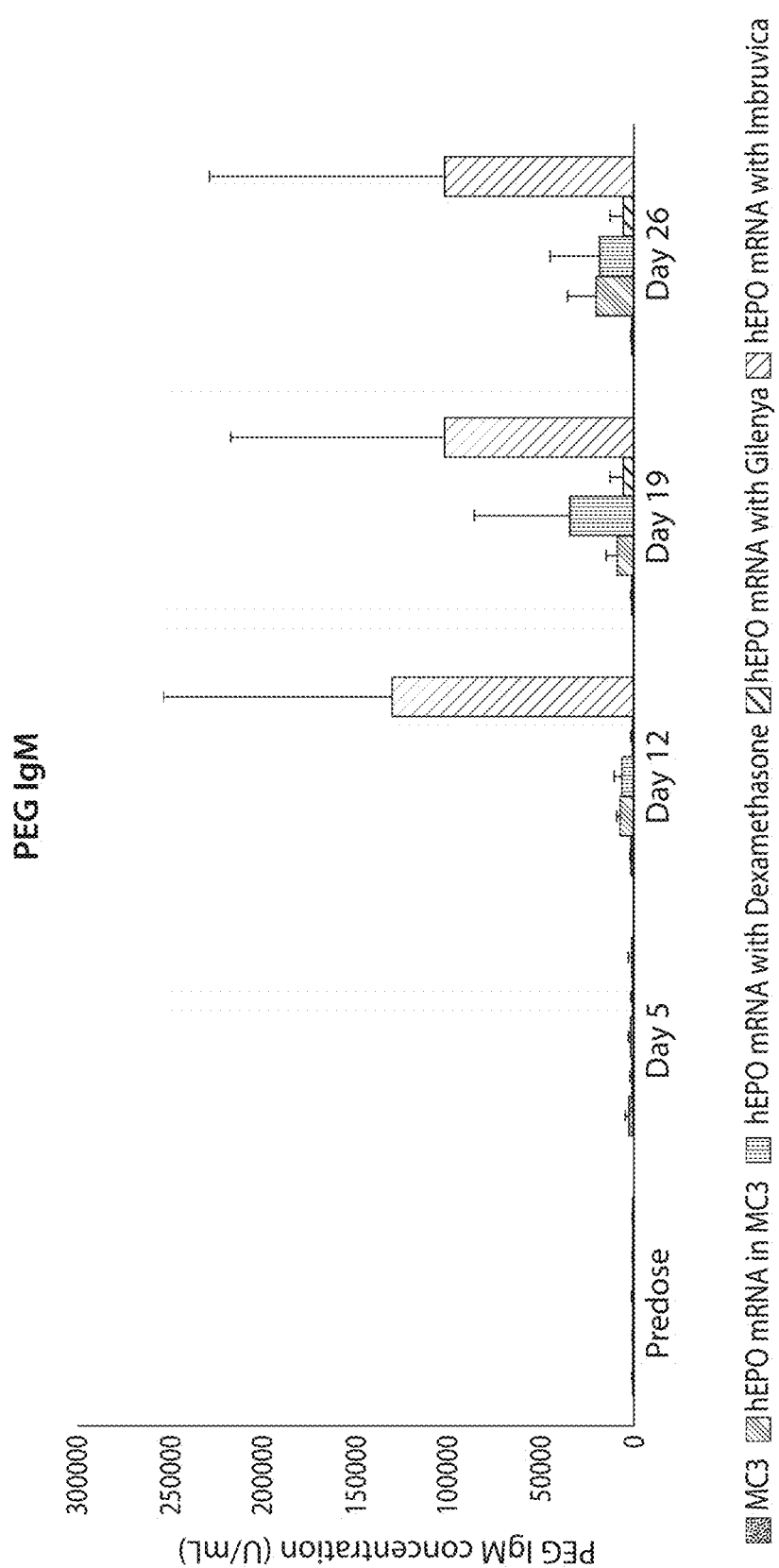

FIGS. 91A-91B: The effect of co-medication on ABC in NHP. Co-medication alleviates cytokine (IL-6) production in NHPs (FIG. 91A) and co-medication with Gilenya reduces anti-PEG IgM production, consistent with reduced ABC (FIG. 91B).

Figure 92:
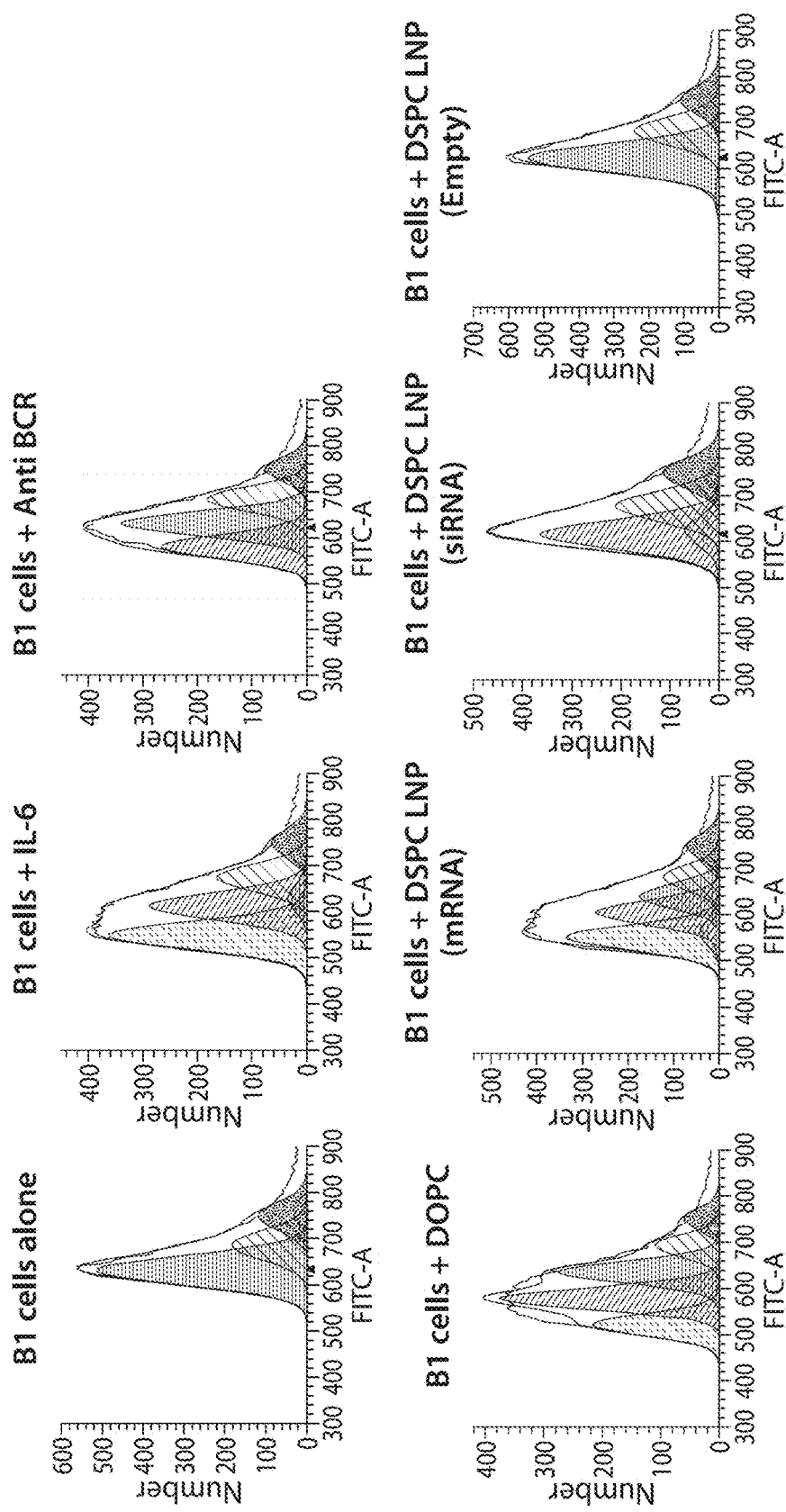

FIG. 92: B cells proliferate in the presence of DSPC LNPs. Splenic cells were stained with CFSE and after washing, incubated with IL-6, anti-BCR, DOPC liposomes, DSPC LNPs containing mRNA, DSPC LNPs containing siRNA or empty LNPs for 4 days at 37° C. On day 4, the cells were harvested, washed and stained for surface markers, (CD19 and CD3) before they were measured on a BDFortessa flow cytometer and analyzed with ModFit 4.1 software.

Figure 93:
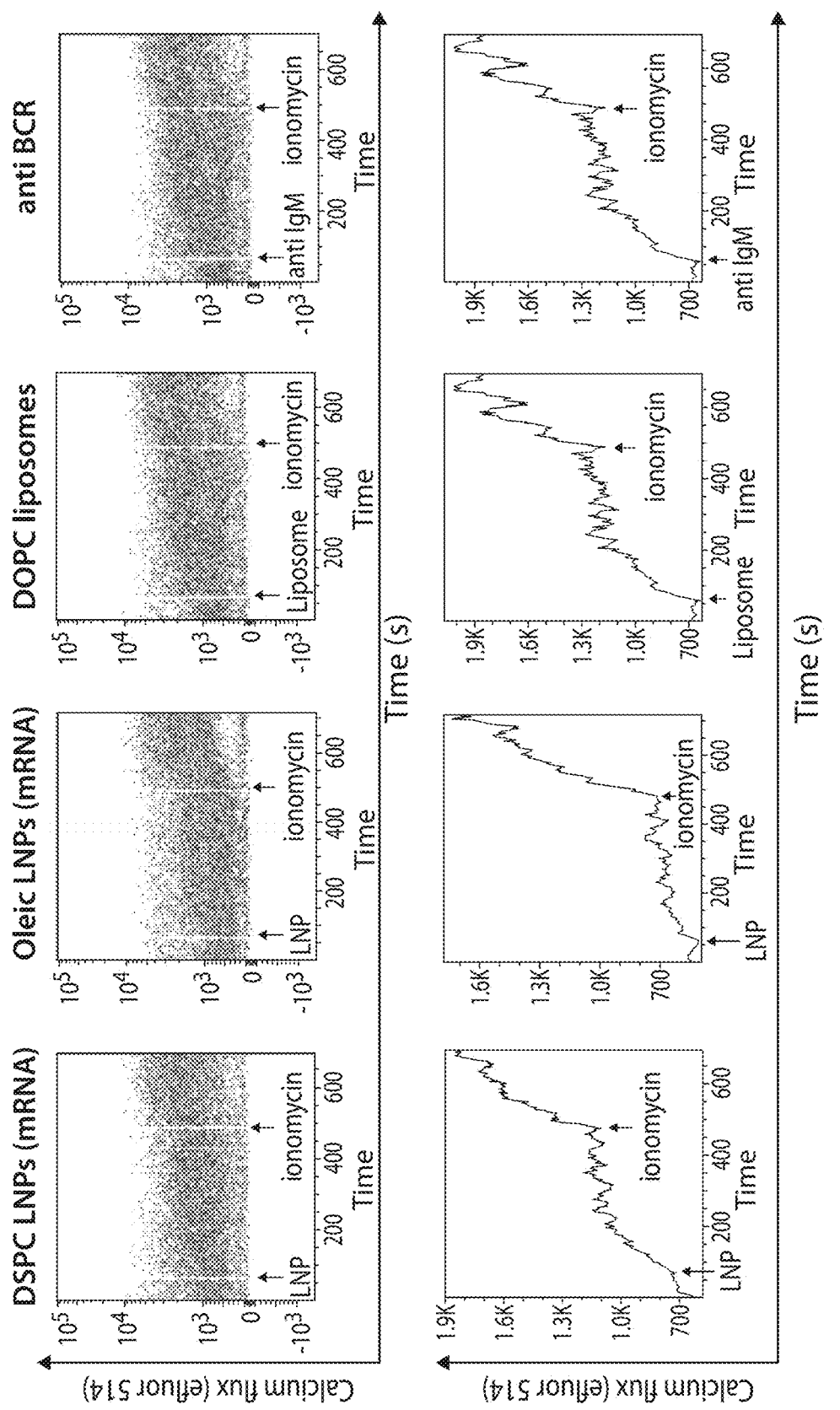

FIG. 93: DSPC LNPs induce calcium release in B cells. Splenic cells were stained with Calcium Sensor Dye eFluor® 514, CD19, and CD3. After washing, a calcium baseline was acquired for 30 seconds on a BDFortessa flow cytometer. Immediately after, the cells were incubated with DSPC LNPs containing mRNA, DOPC liposomes, oleic LNPs, or anti BCR and the calcium signal was acquired for 360 seconds. Then, the cell stimulation cocktail was added to the cells and the signal was acquired for an additional 30 seconds. The analysis was performed using ModFit 4.1 software.

DETAILED DESCRIPTION

This disclosure provides lipid-comprising compounds and compositions that are not subject to ABC and/or that have reduced toxicity, as well as methods for delivering LNPs to a subject without promoting LNP-related drug responses, including ABC and LNP-induced toxicity (e.g., coagulopathy, disseminated intravascular coagulation, vascular thrombosis, —CARPA, APR, or a combination thereof).

Lipid-comprising compounds and compositions are compounds and compositions that comprise or are conjugated to one or more lipids. These agents may be referred to herein as lipid-conjugated agents or lipidated agents. Alternatively such lipids may encapsulate agents such as prophylactic, therapeutic and diagnostic agents. These agents may be referred to herein as lipid-encapsulated agents or lipid nanoparticle (LNP) encapsulated agents.

Thus, it is to be understood that this disclosure provides improved compounds and compositions for reducing or eliminating ABC and toxicity upon in vivo administration. For brevity, this disclosure may however in some instances refer to compositions or formulations such as lipid nanoparticles or LNPs. This is intended for exemplary purposes and it is to be understood that the various teachings provided herein apply equally to individual compounds, such as lipid-conjugated compounds, unless explicitly stated otherwise.

Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC).

It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contenplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

B1a or B1b Activation Assay

Certain compositions provided in this disclosure do not activate B cells, such as B1a or B1b cells (CD19+ CD5+) and/or conventional B cells (CD19+ CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

Pro-inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

In some instances, the LNPs described herein may be free of an epitope that activates B1a cells, for example, free of an epitope that activates or interacts with CD36 or CD6. Such LNPs contain either no epitopes capable of activating B1a cells or CD36 or contain such epitopes at a substantially low amount, which is not sufficient to activate B1a or CD36 to a level high enough for inducing substantial ABC. In other embodiments, the LNPs described herein may be free of an epitope that activates B1b cells. By substantially free of, it is meaclassical pnt that a LNP includes less than 99% of the recited agent. In some embodiments the LNP may include none of the recited agent. In some instances, the LNPs described herein may contain one or more helper lipid as described herein, which may comprise at least one fatty acid chain of at least 8C and at least one polar moiety. In some examples, the helper lipid does not activate B1a and/or B1b cells. In other examples, the helper lipid does not bind or has low binding affinity to CD36. Alternatively, the helper lipid may competitively inhibit phosphatidylcholine from binding to CD36.

Alternatively the LNP may be coadminstered (administered with, before or after) or coformulated with an agent that removes or targets B or B1a cells. An agent that removes or targets B or B1a cells may be Rituximab. Rituximab (RITUXAN®, Genentech/Biogen) is a monoclonal antibody against the protein CD20, which is primarily found on the surface of immune system B cells. Rituximab interacts with CD20 on the surface of B cells and destroys B cells. As shown in the Examples, the combination of Rituximab and the LNP had significantly reduced ABC upon subsequent administration of LNP.

In other embodiments the agent may bind and/or inhibit CD6 on B1a cells. An exemplary agent that binds and/or inhibits CD6 on B1a cells is an anti-CD6 antibody, such as Alzumab. Alzumab (itolizumab, Biocon) is a humanized IgG1 monoclonal antibody that selectively targets CD6, a pan T cell marker involved in co-stimulation, adhesion and maturation of T cells. Alzumab also binds to CD6 on the surface of B1a cells.

In some instances such methods may comprise
(i) administering a first dose of an agent to a subject,
(ii) administering a second or subsequent dose of the agent to the subject, wherein the second or subsequent dose is administered within 2 weeks of the first or prior dose, and
(iii) repeating step (ii) one or more times, wherein the agent is formulated with an LNP that does not promote ABC.

Another method for delivering an agent to a subject involves
(i) administering a first dose of an agent to a subject,
(ii) administering a second or subsequent dose of the agent to the subject, wherein the second or subsequent dose is administered within 2 weeks of the first or prior dose, and
(iii) repeating step (ii) one or more times,
wherein the half-life of the agent after the second and subsequent dose is at least 50%, 60%, 70%, 80%, 85%, 90%, 95% or more of the half-life of the agent after the first dose.

Still another method for delivering an agent to a subject involves
(i) administering a first dose of an agent to a subject,
(ii) administering a second or subsequent dose of the agent to the subject, wherein the second or subsequent dose is administered within 2 weeks of the first or prior dose, and
(iii) repeating step (ii) one or more times,
wherein the activity or blood concentration of the agent after the second and subsequent dose is at least 50%, 60%, 70%, 80%, 85%, 90%, 95% or more of the activity or blood concentration of the agent after the first dose.

Second or subsequent doses may be administered within 1 week, or within 6 days, or within 5 days, or within 4 days, or within 3 days, or within 2 days, or within 1 day of the first or prior dose.

The agent may be a biologically active agent such as a diagnostic agent or a therapeutic agent, although it is not so limited.

Agents may be administered two or more times, three or more times, four or more times, etc. Agent administration may therefore be repeated once, twice, 3, 4, 5, 6, 7, 8, 9, 10, or more times. The agent may be administered chronically or acutely, depending on its intended purpose.

The method may be a method of treating a subject having or at risk of having a condition that benefits from the biologically active agent, particularly if the biologically active agent is a therapeutic agent. Alternatively, the method may be a method of diagnosing a subject, in which case the biologically active agent is a diagnostic agent.

The second and subsequent doses of biologically active agent may maintain an activity of at least 50% of the activity of the first dose, or at least 60% of the first dose, or at least 70% of the first dose, or at least 75% of the first dose, or at least 80% of the first dose, or at least 85% of the first dose, or at least 90% of the first dose, or at least 95% of the first dose, or more, for at least 1 day, 2 days, 3 days, 4 days, 5 days, 6 days, or 7 days post-administration of the second or subsequent dose.

When the biologically active agent is an mRNA (a therapeutic mRNA or a mRNA encoding a vaccine antigen), a method for reducing ABC of LNPs encapsulating the mRNA can be performed using a low amount of the LNPs for the first dose, and/or the second dose (as well as the subsequent doses). The low doses can be equal to or less than 0.3 mg/kg, e.g., 0.2 mg/kg, or 0.1 mg/kg. In some instances, the first dose, the second dose, or both range from 0.1 to 0.3 mg/kg.

The interval between the first dose and the second dose in any of the methods described herein may be equal to or less than two weeks, for example, less than 21, 20, 19, 18, 17, 16, 15, 14, 13, 12, 11, 10, 9, 8, 7, 6, 5, 4, 3, 2 or 1 days. In some instances, the subject can be administered a dose once daily, every 2, 3, 4, 5, 6, 7, 8, 9, 10, 11, 12, 13, 14, 15, 16, 17, 18, 19, 20 or 21 days in any of the methods described herein. Each possibility represents a separate embodiment of the present invention.

Further, inhibiting ABC of LNPs in a subject can be achieved by the use of one or more secondary agents that inhibit immune responses induced by LNPs, e.g., inhibit the binding to or activity of sensors e.g., natural IgM production, natural IgG production, activation of B1a cells, activation of B1b cells, and/or activation of platelets and or dendritic cells or the activity or production of any effectors. The secondary agents are referred to alternatively as agents that inhibit immune responses induced by LNPs. In some instances, the secondary agent may inhibit the production of natural IgM that binds the LNPs, or neutralize such natural IgMs. In other instances, the secondary agent may inhibit activation of B1a cells or remove B1a cells. For example, such a secondary agent may inhibit a surface receptor of B1a cells, including, but not limited to CD36. Alternatively or in addition, the secondary agent may interfere with the binding of IgM to its target. In other embodiments, the secondary agent may inhibit the production of natural IgG that binds the LNPs, or neutralize such natural IgGs or may interfere with the binding of IgG to its target. In other instances, the secondary agent may inhibit activation of B1b cells or remove B1b cells.

Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

Platelet aggregation is observed soon after LNP administration, and appears to occur at the same time as or potentially before platelet activation as evidenced through increased expression of platelet activation markers such as CD31 and CD62P. LNPs that do not associate with significant numbers of platelets but which are able to activate platelets to a lesser degree than the more robust LNPs (discussed above) also cause platelet aggregation very early after administration, and presumably prior to platelet activation. Thus, in vivo, LNP association with platelets appears to occur at about the same time as aggregation of platelets, and presumably prior to the peak of platelet activation.

Also significant is the additional observation that a subset of LNPs are able to activate platelets, even without appreciable physical association with platelets. This subset is also able to form platelet aggregates comprising B cells and macrophages.

Certain LNPs have also been shown to stimulate early interaction between platelets (whether or not activated) and macrophages and B cells, thereby activating these latter cells as well. The effect of LNPs on B cells and macrophages is therefore both direct and indirect, but ultimately can lead to increased activation of such cells.

Activation of platelets could mediate complement activation. It is therefore contemplated that certain LNPs may induce dose-limiting toxicity such as CARPA and APR via activation of platelets and subsequently the complement system. Certain lipid components of LNPs, such as phosphatidylcholine may bind to and activate CD36 on platelets, which would trigger the TLR2/4/6 signaling, leading to aggregation and activation of the platelets. Activated platelets express CD62P (P selectin), which is a C3b-binding protein and can trigger the complement cascade. Activated platelets also recruit immune cells such as macrophages and neutrophils, which lead to further immune responses including cytokine (e.g., IL-6) secretion. Further, properdin was found to bind directly to activated platelet via, e.g., CD62P and recruits C3b or $C3(H_2O)$, thus triggering the alternative pathway. Saggu et al., J. Immunol. 190:6457-6467 (2013).

Accordingly, uses of LNPs that do not induce platelet activation and/or aggregation; and/or do not promote the activation of the complement system (e.g., the classic pathway and/or the alternative pathway) could reduce the risk of LNP-related toxicity. Such LNPs may not induce the activation of platelets and/or the complement system at all. Alternatively, such LNPs may induce a substantially low level of platelet activation and/or complement system activation, which is not sufficient to result in substantial dose-limiting toxicity.

Alternatively or in addition, secondary agents that block the initial platelet activation/aggregation, the initial activation of the complement system, and/or the downstream complement cascade, either in the classic pathway or in the alternative pathway, could be used to prevent or reduce LNP-related toxicity. In some instances, such a secondary agent may inhibit platelet activation, for example, inhibit CD36 activation triggered by LNPs. In other instances, the secondary agent may inhibit CARPA or ARP, for example, inhibit the classical pathway and/or the alternative pathway. Such a secondary agent may target at least one component in the complement system or proteins involved in ARP, thereby blocking the reaction cascade. For example, the secondary agent may be an antagonist of a TLR receptor (TLR2. TLR4, or TLR6), CD62P, CD31, properdin, a component of the complement system (e.g., C1q, C3a, C3b, C5a, and C5b). In yet other instances, the secondary agent may be an agent that can alleviate at least one symptom of LNP-related toxicity. Such agents include, but are not limited to, nonsteroidal anti-inflammatory drug (NSAID) or an antihistamine agent, which can be a histamine receptor blocker such as an H1 antagonist or an H1 inverse agonist.

In some embodiments, dose-limiting toxicity and/or ABC can be reduced in a subject being treated with a therapeutic regimen involving LNP-mediated drug delivery by using LNPs that do not activate a thrombospondin receptor (e.g., CD36), which may be expressed on the surface of immune cells (e.g., B1a or B1b cells); or other surface receptors involved in triggering the immune responses that lead to dose-limiting toxicity and/or ABC. Such LNPs may not activate the thrombospondin receptor at all, or could only induce a substantially low level of its activity such that it is insufficient to induce clinically significant dose-limiting toxicity and/or ABC. Alternatively or in addition, dose-limiting toxicity and/or ABC can be reduced in a subject being treated with a therapeutic regimen involving LNP-mediated drug delivery by using one or more secondary agent that inhibits the activity of a thrombospondin receptor (e.g., CD36) expressed on the surface of immune cells and platelets. The thrombospondins (TSP) are a family of multifunctional proteins that are expressed on the surface of or secreted by cells such as blood platelets. The family consists of thrombospondins 1-5. TSP-1 is a inhibitory ligand of CD36.

Based on these findings, this disclosure contemplates and provides LNPs as well as LNP-formulated active agents that have reduced platelet association and/or reduced platelet activation and/or reduced platelet aggregation activity. Use of such LNPs, for example as a delivery vehicle for an active agent, reduces the risk of developing coagulopathy, such as disseminated intravascular coagulation (DIC, also referred to as consumptive coagulopathy), whether acute or chronic, and/or vascular thrombosis, as well as any toxicity related thereto. If such toxicity is dose-limiting, then use of these LNPs will enable administration of higher LNP doses and more importantly will enable the delivery of higher doses of the active agent cargo carried by such LNP.

The diminution of the platelet response after LNP administration has additional desirable effects, some of which may be synergistic. LNPs have been reported to activate complement shortly after administration. This activation may be direct or indirect. For example, it has been reported that activated platelets are able to activate complement. Thus LNPs that reduce or prevent platelet activation will also indirectly reduce or prevent complement activation. Complement activation can also contribute to coagulation, for example through complement-mediated generation of thrombin. Thrombin converts available fibrinogen to fibrin, which in turn forms clots together with platelets. Activated platelets have thrombin receptors on their surface and therefore are able to recruit and/or raise the local concentration of thrombin, thereby enhancing fibrin production and ultimately clot formation. The disclosure therefore contemplates and provides additional LNPs that do not activate complement or do not activate complement to the same degree as existing LNPs. Yet still additional LNPs provided herewith are those that do not activate platelet and do not activate complement.

Similarly, this disclosure contemplates LNPs that interfere with properdin binding to platelets. Properdin is a positive regulator of the alternative pathway of the complement system. It has been shown to bind to activated platelets, thereby activating the alternative pathway in response to and in the vicinity of the activated platelet. Thus further contemplated is the use of a properdin inhibitors in combination with LNPs provided herein whether such LNPs activate or do not activate platelets, as defined below. Properdin inhibitors include DNA and sulfated glucoconjugates, both of which are bound by properdin and may interfere with properdin binding to activated platelets.

This disclosure therefore contemplates and provides, in some aspects, LNPs and LNP formulations that have reduced platelet effects including reduced platelet association and/or reduced platelet activation and/or reduced platelet aggregation activity. Certain LNPs may affect one, two or all three of these platelet activities. For example, some LNP may have reduced platelet association activity, or reduced platelet aggregation activity, or reduced platelet activation activity. Some LNP may have reduced platelet association activity and or reduced platelet activation activity, or reduced platelet association activity and reduced platelet activation activity, or reduced platelet aggregation activity and reduced platelet activation activity. Some LNP may have reduced platelet association activity, reduced platelet aggregation activity, and reduced platelet activation activity.

The disclosure contemplates that some LNPs may be universal LNPs, intending that they will down-modulate (or not stimulate in the first instance) one or more of the afore-mentioned platelet activities upon administration in the majority of patients or in all patients.

Additionally, the disclosure contemplates that some LNPs may in some instances be defined and thus identified as patient-specific. That is, some LNPs may be effective at down-regulating a platelet response, as described herein, in some but not all patients. Thus, in some instances, some LNPs and LNP formulations may be identified for particular patients and may then be used only for those particular patients.

In some instances, the findings provided herein may be applied directly to biologically active agents. For example, the biologically active agent that is a lipid or is conjugated to a lipid or that is conjugated to a PEG moiety directly or indirectly, may be modified as described herein to render the agent unable to stimulate a platelet response or cascade.

Platelet Activity Assays

These various activities may be measured as described herein and/or as performed in the art. For example, platelet activation may be assessed by increased expression of activation markers such as CD31 and CD62P. Platelet aggregation may be assessed by flow cytometry. Similarly flow cytometry may be used to detect non-platelet types such as B cells and macrophages within such aggregates. It is to be understood that the platelet effects of LNP can be assessed in vivo, for example in an animal model, as well as in vitro using for example human blood. These assays may be used to screen for and/or identify LNP having one or more of the afore-mentioned activities.

Compounds and Compositions, Including LNP

The disclosure provides lipid-comprising compositions that are less susceptible to clearance and thus have a longer half-life in vivo. This is particularly important where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which lipid-containing exogenously administered agents are rapidly cleared from the blood upon second and subsequent administrations. This phenomenon has been observed for a variety of lipid-containing compositions, including, but not limited to, liposomes, lipid nanoparticles, and lipid-encapsulated agents. Heretofore, the basis of ABC has been poorly understood and accordingly strategies for avoiding it have remained elusive.

The lipid-containing compositions of this disclosure, surprisingly, do not experience or are minimally affected by ABC upon second and subsequent administration in vivo. This resistance to ABC renders these compositions particularly suitable for repeated use in vivo, including for repeated use within short periods of time, including days or 1-2 weeks.

This resistance to ABC is due in part to the inability of these compositions to activate B1a cells. Such compositions are therefore referred to herein as B1a inert compositions or compositions that do not activate substantial B1a, intending that these compositions, when combined with B1a cells, do not activate B1a cells. Activation of B1a cells may be determined in a number of ways including, but not limited to, increased expression of activation markers such as CD86, and expression and/or secretion of cytokines. These compositions may or may not bind to B1a cells, and they may or may not bind to circulating IgM. Thus, these compositions may evade detection by circulating IgM and/or by B1a cells.

B1a cells are a subset of B cells involved in innate immunity. These cells are the source of circulating IgM, referred to as natural antibody or natural serum antibody. These IgM antibodies are characterized as having weak affinity for a number of antigens, and therefore they are referred to as "poly-specific" or "poly-reactive", describing their ability to bind to more than one antigen. Although able to produce such IgM, B1a cells are not capable of producing IgG. Additionally, they do not develop into memory cells and thus do not contribute to an adaptive immune response. However, they are able to secrete IgM upon activation. The secreted IgM is typically cleared within about 12 days (half-life of IgM in sera is about 5-8 days, *Nature Review Drug Discovery* 2, 52-62, January 2003), at which point the immune system is rendered relatively naïve to the previously administered antigen. If the same antigen is presented after this time period (e.g., at about 2 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic compositions unsuitable for repeated use.

The compounds, particles, and compositions described herein overcome these limitations, thereby transforming a variety of lipid-containing compositions into efficacious therapeutic and diagnostic agents. The B1a lipid-compositions provided herein do not undergo accelerated blood clearance upon repeat administration and thus can be administered repeatedly to a subject, including within short periods of time, without loss of activity.

Resistance to ABC may also be due in part to the inability of these compositions to activate B1b cells, pDC and/or platelets. Such compositions are therefore referred to herein as B1b pDC and/or platelets inert compositions or compositions that do not activate substantial B1b pDC and/or platelets, intending that these compositions, when combined with B1b cells pDC and/or platelets, do not activate B1b cells pDC and/or platelets, respectively. Activation of B1b cells, pDC and/or platelets may be determined in a number of ways including, but not limited to, increased expression of activation markers such as CD11b (for B1b cells), and expression and/or secretion of cytokines, and ability to activate B cells (pDC). These compositions may or may not bind to B1b cells, pDC and/or platelets, and they may or may not bind to circulating IgM or IgG. Thus, these compositions may evade detection by circulating IgM, IgG and/or by B1a cells pDC and/or platelets.

Particles, such as LNP, typically comprise one or more of the following components: lipids (which may include cationic lipids, helper lipids which may be neutral lipids, zwitterionic lipid, anionic lipids, and the like), structural lipids such as cholesterol or cholesterol analogs, fatty acids, polymers, stabilizers, salts, buffers, solvent, and the like.

Certain of the LNPs provided herein comprise a cationic lipid, a helper lipid, a structural lipid, and a stabilizer which may or may not be provided conjugated to another lipid.

The cationic lipid may be but is not limited to DLin-DMA, DLin-D-DMA, DLin-MC3-DMA, DLin-KC2-DMA and DODMA. The cationic lipid may be an ionizable lipid.

The structural lipid may be but is not limited to a sterol such as for example cholesterol.

The helper lipid is a non-cationic lipid. The helper lipid may comprise at least one fatty acid chain of at least 8C and at least one polar headgroup moiety.

Certain of the LNPs lack any phosphatidyl choline (PC) lipids (i.e., are free of phosphatidyl choline (PC)). Certain of the LNPs provided herein lack specific phosphatidyl choline lipids such as but not limiting to DSPC. Certain of the LNPs comprise a phosphatidyl choline analog, such analogs comprising modified head groups (e.g., a modified quaternary amine head group), modified core group, and/or modified lipid tail group. Such analogs may comprise a zwitterionic group that is a non-PC zwitterionic group. The helper lipid may be a lipid of any one or any combination of Formulae I, I-a, I-b, I-b-1, I-b-2, I-b-3, I-b-4, I-c, I-c-1, I-c-2, I-c-3, or II as provided herein.

Certain of the LNP may include a 1,2-distearoyl-sn-glycero-3-phosphocholine (DSPC) substitute or include a minimal amount of DSPC. In certain embodiments, the DSPC substitute is a lipid that is not a phospholipid.

Certain LNPs comprise other helper non-cationic lipids including for example oleic acid or oleic acid analogs. The helper lipid may be a lipid of Formula IV as provided herein. The oleic acid may be a substitute or may be in addition to another lipid in the LNP. As would be appreciated by one of skill in the art, modified versions of oleic acid or related fatty acids may be used as well.

In some instances, the LNP comprise PEGylated lipids or lipids conjugated to other stabilizing moieties (or stabilizers) such as but not limited to XTEN and PAS polypeptides. Thus, the disclosure contemplates and provides LNPs or formulations thereof that do not include PEG. In certain embodiments, the LNPs include HO-PEG. In other embodiments, the LNPs include a PEG substitute such as a different polymer.

When PEG is used as the stabilizer, it may be conjugated to a lipid and thus may be provided as PEG-c-DOMG or PEG-DMG, for example. The stabilizer, whether provided in a conjugated or an unconjugated form, may comprise 1.5 mol % of the LNP, or it may comprise less than 0.5 mol % of the LNP. For example, it may comprise less than 0.4 mol %, less than 0.3 mol %, less than 0.2 mol %, or less than 0.1 mol %.

In still other embodiments, LNPs may contain less than 0.5% molar ratio of PEG lipid to the other components. Thus, an LNP may comprise at least 0.0001%, at least 0.0005%, at least 0.001%, at least 0.005%, at least 0.01%, at least 0.05%, at least 0.1%, at least 0.15%, at least 0.2%, at least 0.25%, at least 0.3%, at least 0.35%, at least 0.4%, at least 0.45%, and less than 0.5% (expressed as a molar percentage) of PEGylated lipid. Each possibility represents a separate embodiment of the present invention.

The LNP may comprise a PEGylated lipid of Formula III, including Formulae III-OH, III-a-1, III-a-2, III-b-1, IIII-b-2, III-b-1-OH, III-b-2-OH, V, V-OH. Each possibility represents a separate embodiment of the present invention.

Certain of the LNPs provided herein comprise no or low levels of PEGylated lipids, including no or low levels of alkyl-PEGylated lipids, and may be referred to herein as being free of PEG or PEGylated lipid. Thus, some LNPs comprise less than 0.5 mol % PEGylated lipid. In some instances, PEG may be an alkyl-PEG such as methoxy-PEG. Still other LNPs comprise non-alkyl-PEG such as hydroxy-PEG, and/or non-alkyl-PEGylated lipids such as hydroxy-PEGylated lipids.

The PEGylated lipid may be a Cmpd420, a Cmpd396, a Cmpd394, Cmpd397, Cmpd395, Cmpd417, Cmpd418, or Cmpd419.

In some instances, the LNP may comprise about 50 mol %, 10 mol % helper lipid, 1.5 mol % PEGylated lipid, and 38.5 mol % structural lipid.

In some instances, the LNP may comprise about 50 mol %, 10 mol % helper lipid, less than 0.5 mol % PEGylated lipid, and 39.5 mol % structural lipid.

In some embodiments, the stabilizer is a non-PEG moiety such as an XTEN peptide that may or may not be conjugated to a lipid. The XTEN peptide is capable of forming a hydrated shell around the LNP due to its hydrophilic nature. It further serves to increase the half-life of the LNP, compared to an LNP lacking (or free of) any stabilizer. Unlike PEG, however, it is biodegradable and has been reported to be non-immunogenic. The XTEN peptide may have an amino acid sequence of MAEPAGSPTSTEEGTPGSG-TASSSPGSSTPSGATGSPGASPGTSSTGS (SEQ ID NO:1) or MAEPAGSPTSTEEGASPGTSSTGSPGSSTPS-GATGSPGSSTPSGATGS (SEQ ID NO:2). Other XTEN amino acid sequences are known in the art, including for example those reported in U.S. Pat. No. 9,062,299. Examples of XTEN conjugated lipids include but are not limited to Cmpd431, and Cmpd432 and Cmpd433. Click chemistry may be used to conjugate the XTEN peptide to the lipid.

In some embodiments, the stabilizer is a non-PEG moiety such as a PAS peptide. A PAS peptide is a peptide comprising primarily if not exclusively proline, alanine and serine. Like PEG and XTEN peptides, the PAS peptide is capable of forming a hydrated shell around the LNP. It too serves to increase the half-life of an LNP, compared to an LNP lacking (or free of) a stabilizer. Unlike XTEN peptides, however, PAS peptides tend to be neutral in charge, and thus at least in this respect more similar to PEG. The PAS peptide may have an amino acid sequence of SAPSSPSPSAPSSPS-PASPSSAPSSPSPSAPSSPSPASPSSAPSSPSPSAPSSPSP-ASPS (SEQ ID NO:3 or AASPAAPSAPPAAASPAAPSAP-PAAASPAAPSAPPAAASPAAPSAPPA (SEQ ID NO:4). Other PAS amino acid sequences are known in the art, including for example, those reported in WO 2008155134.

Agents that inhibit immune responses induced by LNPs may also be used in the methods of the invention, together with a standard ABC inducing LNP or with a modified LNP of the invention. Agents that inhibit immune responses induced by LNPs, are compounds that inhibit the activation of a sensor, inhibit the interaction between an LNP and a sensor or between sensors (e.g, blocks interaction between pDC and B cells), and/or inhibit the production or activity of an effector. In some instances the agent will be specific for a particular sensor or effector. In other embodiments the agent that inhibits immune responses induced by LNPs functions to prevent the activation of multiple sensors by a more general mechanism, typically acting indirectly on other cellular components that can affect the sensors. An example of an agent that functions on multiple sensors indirectly is a miR binding site.

It has been discovered according to the invention that delivery of a miR binding site will inhibit an immune response associated with ABC and can be used to provide repeated dosing of a subject with an LNP during the window of susceptibility to ABC. The miR binding site may be incorporated into a therapeutic nucleic acid that is being delivered in the LNP. Alternatively the miR binding site may separately be incorporated into the same LNP that incorporates the therapeutic nucleic acid or into a different LNP. The miR binding site may be administered to the subject in a separate vehicle at the same or different time as the LNP and may or may not be incorporated into an LNP. In some embodiments the miR binding site may be a miR sponge.

Although Applicant is not bound by mechanism, it is believed that the miR binding site act to soak up endogenous, targeted miRNA of interest, preventing that miRNA from functioning in the cell. It is possible to target miRNA that play a positive role in regulation of immune cell function. By inhibiting the function of endogenous miRNA the miR binding site acts as an inhibitor to block the miRNA function and other downstream effects resulting from this targeting inhibition. The miRNA binding agent may also or alternatively be functioning by preventing protein translation in specific tissues or cells, such as the spleen or immune cells. By preventing translation of, for instance, an mRNA therapeutic encapsulated in the LNP, in specific tissues that are high in immune cells, the immune response in those tissues will be decreased, while not having an impact on mRNA expression in other tissues.

It has been demonstrated that introduction of miR binding sites such as miR 126 (highly abundant in pDC) results in a reduction in B cell activation, a reduction in pDC activation, a reduction in cytokine expression, such as IL6 and IFN-gamma, and a reduction in IgM relative to the response delivered by a corresponding LNP without the miR binding site.

In some embodiments the miR binding site is a miR 126, miR 155, and/or miR 142.3p binding site. In some embodiments, the mRNA can comprise at least one miR binding site to thereby reduce or inhibit ABC. The miR binding site may be found in, for instance, the 3' UTR of the mRNA. For example, in one embodiment, the mRNA comprises a miR-122 binding site, to thereby allow increased expression of a polypeptide encoded by the mRNA in a liver cancer cell (e.g., a hepatocellular carcinoma cell) as compared to a normal liver cell, and also comprises one or more miR binding sites, e.g., selected from the group consisting of miR-142, miR-146, miR-155, miR-126, miR-16, miR-21, miR-223, miR-24, miR-27.

A compound that inhibits the interaction between an LNP and a sensor as used herein will disrupt interaction between LNP and B1 cell, platelet or pDC. For instance, Some interactions between LNP and B1 cells are mediated through the CD36 receptor on the B1 cell and the PC on the LNP. The compound may block and neutralize the PC or the CD36. In some embodiments the compound is an antibody that recognizes and binds CD36, or an antigen-binding fragment or derivative thereof or a CD36 antagonist. A CD36 antagonist may be selected from the group consisting of antibodies or aptamers which bind to CD36 or fragments thereof; soluble ligands which bind to CD36 or fragments thereof; soluble CD36 which bind to its ligands; fusion polypeptides, peptides, small molecules, peptidomimetics inhibiting the CD36 activity; and nucleic acid molecules interfering specifically with CD36 expression. Such CD36 antagonist is preferably an antagonist which, preferably specifically, recognizes and binds to a CD36 molecule or fragment thereof, and is preferably selected from the group consisting of an antibody or an aptamer which specifically recognizes and binds to CD36 or a fragment thereof, a nucleic acid molecule interfering specifically with CD36 expression, and a small molecule inhibiting the CD36 activity. More preferably, said CD36 antagonist is a function-blocking monoclonal antibody against CD36. In other embodiments, said CD36 antagonist is a small molecule selected from the group consisting of salvianolic acid B, rosmarinic acid, sodium danshensu, 3-cinnamoyl indole, 13 pentyl berberine, hexarelin, nanoblockers, statins or antioxidants such as alpha-tocopherol and SS peptides, Sulfo-N-succinimidyl oleate and Ursolic acid, and any combination thereof. Alternatively, the CD36 antagonist may comprise an antibody that recognizes and binds CD36, or an antigen-binding fragment or derivative thereof. Preferably, said antibody or antigen-binding fragment or derivative thereof, is directed against the extracellular domain of CD36. Said antibody may be a full-length antibody. Preferably, said antibody is a monoclonal antibody. The antibody may be of the IgG, IgE or IgD type, preferably of the IgG type. The antibody may be a humanized, chimeric or human antibody. The antibody may also be camelid heavy-chain antibody, and in particular humanized camelid heavy-chain antibody. Preferably, said antibody, or antigen-binding fragment or derivative thereof, is bivalent. In particular, the antigen-binding fragment is selected from the group consisting of F(ab')2 di-scFvs, $sc(Fv)_2$ fragment, $(VHH)_2$ fragment and diabody.

A compound that inhibits the activity of an effector is a compound that prevents an effector from being produced by a sensor or functioning. For instance the agent may inhibit the production of natural IgM that binds the LNPs by interfering with the synthesis pathway in a B1 cell. Alternatively the agent may neutralize such natural IgMs or IgG. The agent may be an antibody or antigen-binding portion thereof, that binds to natural IgM or IgG and neutralizes it. Alternatively, the agent may interfere with the binding of IgM or IgG to its target. In other embodiments the agent that inhibits immune responses induced by the LNPs is an agent that inhibits IL6 activity. Agents that inhibit IL6 activity include for instance, antibodies, fragments thereof, specific humanized antibodies and fragments and variants thereof capable of binding to IL-6 and/or the IL-6/IL-6R complex. These antibodies may bind soluble IL-6 or cell surface expressed IL-6.

Lipid Nanoparticles, Generally

In some embodiments, the lipid nanoparticle comprises a cationic lipid, a PEG-modified lipid, a sterol and a non-cationic lipid. In some embodiments, the lipid nanoparticle carrier comprising a molar ratio of about 20-60% cationic lipid: 5-25% non-cationic lipid: 25-55% sterol; and 0.5-15% PEG-modified lipid. In some embodiments, the cationic lipid is an ionizable cationic lipid. In some embodiments, the non-cationic lipid is a neutral lipid. In some embodiments, the sterol is a cholesterol. In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm. Each possibility represents a separate embodiment of the present invention.

Lipid nanoparticles may comprise one or more lipid species, including, but not limited to, cationic/ionizable lipids, non-cationic lipids, structural lipids, phospholipids, and helper lipids. Any of these lipids may be conjugated to polyethylene glycol (PEG) and thus may be referred to as PEGylated lipids or PEG-modified lipids.

The formation of the lipid nanoparticle (LNP) may be accomplished by methods known in the art and/or as described in U.S. Pub. No. 2012/0178702, herein incorporated by reference in its entirety.

A lipid nanoparticle formulation may be influenced by, but not limited to, the selection of the cationic lipid component, the degree of cationic lipid saturation, the selection of the non-cationic lipid component, the degree of non-cationic lipid saturation, the selection of the structural lipid component, the nature of the PEGylation, ratio of all components and biophysical parameters such as size. In certain non-limiting examples, a LNP comprises four basic components: (1) a cationic lipid; (2) a non-cationic lipid (e.g., a phospholipid such as DSPC); (3) a structural lipid (e.g., a sterol such as cholesterol); and (4) PEG or a PEG-modified lipid. In one example by Semple et al. (*Nature Biotech.* 2010 28:172-176; herein incorporated by reference in its entirety), the lipid nanoparticle formulation is composed of molar ratios as follows: 57.1% cationic lipid, 7.1% dipalmitoyl-phosphatidylcholine, 34.3% cholesterol, and 1.4% PEG-c-DMA. As another example, changing the composition of the cationic lipid can more effectively deliver siRNA to various antigen presenting cells (Basha et al., *Mol Ther.* 2011 19:2186-2200; herein incorporated by reference in its entirety).

The lipid nanoparticles described herein comprise one or more lipids. In certain embodiments, the lipid nanoparticle formulation comprises a cationic lipid and a non-cationic lipid. In certain embodiments, the LNP formulation comprises a cationic lipid and a DSPC substitute. In certain embodiments, the LNP formulation comprises a cationic lipid and a fatty acid. In certain embodiments, the LNP formulation comprises a cationic lipid and oleic acid. In certain embodiments, the LNP formulation comprises a cationic lipid and an analog of oleic acid.

Cationic lipids are positively charged lipids that may associate with nucleic acids in the lipid/LNP-based delivery systems. A positive charge on the LNP promotes association with the negatively charged cell membrane to enhance cellular uptake. Cationic lipids may also combine with negatively charged lipids to induce nonbilayer structures that facilitate intracellular delivery. Suitable cationic lipids for use in making the LNPs disclosed herein can be ionizable cationic lipids, for example, amino lipid, and those disclosed herein.

In certain embodiments, the lipid nanoparticle formulation comprises a cationic lipid, a non-cationic lipid, and a structural lipid. In certain embodiments, the LNP formulation comprises a cationic lipid, a fatty acid, and a structural lipid. In certain embodiments, the LNP formulation comprises a cationic lipid, oleic acid, and a structural lipid. In certain embodiments, the LNP formulation comprises a cationic lipid, an analog of oleic acid, and a structural lipid. In certain embodiments, the LNP formulation comprises a cationic lipid, a fatty acid, and a sterol. In certain embodiments, the LNP formulation comprises a cationic lipid, oleic acid, and a sterol. In certain embodiments, the LNP formulation comprises a cationic lipid, oleic acid, and cholesterol.

In certain embodiments, the lipid nanoparticle formulation comprises a cationic lipid, a non-cationic lipid, and PEG or a PEG lipid. In certain embodiments, the LNP formulation comprises a cationic lipid, a non-cationic lipid, and a PEG lipid. In certain embodiments, the LNP formulation comprises a cationic lipid, a non-cationic lipid, and a PEG-OH lipid. In certain embodiments, the lipid nanoparticle formulation comprises a cationic lipid, a non-cationic lipid, and a PEG-OH lipid. In certain embodiments, the lipid nanoparticle formulation comprises a cationic lipid, a fatty acid, and a PEG-OH lipid. In certain embodiments, the lipid nanoparticle formulation comprises a cationic lipid, oleic acid, and a PEG-OH lipid. In certain embodiments, the lipid nanoparticle formulation comprises a cationic lipid, an analog of oleic acid, and a PEG-OH lipid.

In certain embodiments, the lipid nanoparticle formulation comprises a cationic lipid, a non-cationic lipid (e.g., a phospholipid or fatty acid), a structural lipid, and a PEG lipid. In certain embodiments, the lipid nanoparticle formulation comprises a cationic lipid, a non-cationic lipid (e.g., phospholipid or fatty acid), a structural lipid, and a PEG-OH lipid. In certain embodiments, the lipid nanoparticle formulation comprises a cationic lipid, a non-cationic lipid (e.g., phospholipid or fatty acid), and structural lipid. In certain embodiments, the lipid nanoparticle formulation comprises a cationic lipid, a fatty acid (e.g., oleic acid or an analog thereof), a structural lipid, and a PEG lipid. In certain embodiments, the lipid nanoparticle formulation comprises a cationic lipid, a fatty acid (e.g., oleic acid or an analog thereof), a structural lipid, and a PEG-OH lipid. In certain embodiments, the lipid nanoparticle formulation comprises a cationic lipid, oleic acid, a structural lipid (e.g., a sterol), and a PEG-OH lipid. In certain embodiments, the lipid nanoparticle formulation comprises a cationic lipid, oleic acid, and a structural lipid (e.g., cholesterol). In certain embodiments, the lipid nanoparticle formulation comprises one or more cationic or non-cationic lipids, a fatty acid (e.g., oleic acid), and a PEG lipid. In certain embodiments, the lipid nanoparticle formulation comprises one or more cationic or non-cationic lipids, a fatty acid (e.g., oleic acid), and a PEG-OH lipid.

In some embodiments, the LNP comprises a fatty acid. In certain embodiments, the fatty acid is a monounsaturated fatty acid. In certain embodiments, the fatty acid is a polyunsaturated fatty acid. In some embodiments, the LNP comprises oleic acid. In certain embodiments, the lipid nanoparticle formulation comprises one or more cationic or non-cationic lipids, and a fatty acid (e.g., oleic acid). In certain embodiments, the lipid nanoparticle formulation comprises one or more cationic or non-cationic lipids, and oleic acid. In certain embodiments, when the LNP includes oleic acid, the LNP does not include a phospholipid. In certain embodiments, when the LNP includes oleic acid, the LNP does not include DSPC. In certain embodiments, when the LNP includes a fatty acid, the LNP does not include a phospholipid. In certain embodiments, when the LNP includes a fatty acid, the LNP does not include DSPC.

In some embodiments, the LNP comprises PEG-OH lipids. In certain embodiments, the lipid nanoparticle formulation comprises one or more cationic or non-cationic lipids, and a PEG-OH lipid.

In some embodiments, lipid nanoparticle formulations may comprise, in molar percentages, 35 to 45% cationic lipid, 40% to 50% cationic lipid, 50% to 60% cationic lipid and/or 55% to 65% cationic lipid. In some embodiments, the ratio of lipid to nucleic acid (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. In certain embodiments, lipid nanoparticle formulations may contain 0.5% to 3.0%, 1.0% to 3.5%, 1.5% to 4.0%, 2.0% to 4.5%, 2.5% to 5.0%, and/or 3.0% to 6.0% of the lipid molar ratio of PEG lipid to the other components. As a non-limiting example, lipid nanoparticle formulations may contain 0.5% to 3.0%, 1.0% to 3.5%, 1.5% to 4.0%, 2.0% to 4.5%, 2.5% to 5.0%, and/or 3.0% to 6.0% of the lipid molar ratio of PEG-c-DOMG (R-3-[ω-methoxy-poly(ethyleneglycol)2000)carbamoyl)]-1,2-dimyristyloxypropyl-3-amine) (also referred to herein as PEG-DOMG) as compared to the cationic lipid, DSPC, and cholesterol. In some embodiments, the PEG-c-DOMG may be replaced with a PEG lipid such as, but not limited to, PEG-DSG (1,2-distearoyl-sn-glycerol, methoxypolyethylene glycol), DMG-PEG (1,2-dimyristoyl-sn-glycerol) and/or PEG-DPG (1,2-dipalmitoyl-sn-glycerol, methoxypolyethylene glycol). The cationic lipid may be selected from any lipid known in the art such as, but not limited to, DLin-MC3-DMA, DLin-DMA, C12-200, and DLin-KC2-DMA. In certain embodiments, the lipid nanoparticle does not contain a PEG lipid. In certain embodiments, the lipid nanoparticle contains a PEG lipid substitute such as a PEG-OH lipid. Incorporation of PEG-OH lipids in the nanoparticle formulation can improve the pharmacokinetics and/or biodistribution of the lipid nanoparticle formulations. For example, incorporation of PEG-OH lipids in the nanoparticle formulation can reduce the ABC effect. In certain embodiments, lipid nanoparticle formulations may contain 0.5% to 3.0%, 1.0% to 3.5%, 1.5% to 4.0%, 2.0% to 4.5%, 2.5% to 5.0%, and/or 3.0% to 6.0% of the lipid molar ratio of PEG-OH lipid to the other components (e.g., the cationic, neutral, and structural lipids). Each possibility represents a separate embodiment of the present invention.

In some embodiments, a LNP formulation is a nanoparticle that comprises at least one lipid. In certain embodiments, the lipids is selected from cationic/ionizable lipids, non-cationic lipids (e.g., fatty acids and phospholipids), PEG lipids, structural lipids (e.g., sterols), and PEG-OH lipids. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids, and amino alcohol lipids. In some embodiments, the lipid may be a cationic lipid, such as, but not limited to, DLin-DMA, DLin-D-DMA, DLin-MC3-DMA, DLin-KC2-DMA, DODMA, and amino alcohol lipids. The amino alcohol cationic lipid may be the lipids described in and/or made by the methods described in US Patent Publication No. US2013/0150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US2013/0150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US2013/0150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US2013/0150625); or any pharmaceutically acceptable salt or stereoisomer thereof. Each possibility represents a separate embodiment of the present invention.

Lipid nanoparticle formulations can comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a non-cationic lipid (e.g., phospholipid or fatty acid), a structural lipid (e.g., a sterol such as cholesterol), and a molecule capable of reducing particle aggregation, for example, a PEG or PEG-modified lipid (e.g., PEG-OH lipid). In certain embodiments, the formulation does not contain the PEG lipid.

In some embodiments, the LNP formulation consists essentially of a molar ratio of 20-60% cationic lipid; 5-25% non-cationic lipid; 25-55% sterol; 0.5-15% PEG lipid. In some embodiments, the LNP formulation consists essentially of a molar ratio of 20-60% cationic lipid; 5-25% non-cationic lipid; 25-55% sterol; 0.5-15% PEG-OH lipid. In some embodiments, the LNP formulation consists essentially of in a molar ratio of 20-60% cationic lipid; 5-25% non-cationic lipid; and 25-55% sterol. In certain embodiments, the non-cationic lipid is a fatty acid. In certain embodiments, the non-cationic lipid is oleic acid or an analog thereof. In certain embodiments, the PEG lipid is a PEG-OH lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a non-cationic lipid selected from DSPC, DPPC, POPC, DOPE, and SM; (iii) a sterol, e.g., cholesterol; and (iv) a PEG-lipid, e.g., PEG-DMG or PEG-cDMA, in a molar ratio of 20-60% cationic lipid; 5-25% non-cationic lipid; 25-55% sterol; 0.5-15% PEG-lipid. Each possibility represents a separate embodiment of the present invention.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a non-cationic lipid as a DSPC substitute (e.g., a different phospholipid, or a fatty acid); (iii) a structural lipid (e.g., a sterol such as cholesterol); and (iv) a PEG-lipid or a PEG-OH lipid (e.g., PEG-DMG or PEG-cDMA), in a molar ratio of 20-60% cationic lipid; 5-25% DSPC substitute; 25-55% structural lipid; 0.5-15% PEG-lipid. Each possibility represents a separate embodiment of the present invention.

In some embodiments, a lipid nanoparticle formulation includes 25% to 75% on a molar basis of a cationic lipid. The cationic lipid may be selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., 35 to 65%, 45 to 65%, 60%, 57.5%, 50% or 40% on a molar basis. Each possibility represents a separate embodiment of the present invention.

In some embodiments, a lipid nanoparticle formulation includes 0.5% to 15% on a molar basis of the non-cationic lipid, e.g., 3 to 12%, 5 to 10% or 15%, 10%, or 7.5% on a molar basis. In certain embodiments, the non-cationic lipid is a phospholipid. In certain embodiments, the non-cationic lipid is a DSPC substitute (e.g., a phospholipid other than DSPC, or a fatty acid). In certain embodiments, the non-cationic lipid is a fatty acid (e.g., oleic acid or an analog thereof). Other examples of non-cationic lipids include, without limitation, POPC, DPPC, DOPE and SM. In some embodiments, a lipid nanoparticle formulation includes 0.5% to 15% on a molar basis of a fatty acid, e.g., 3 to 12%, 5 to 10% or 15%, 10%, or 7.5% on a molar basis. In some embodiments, a lipid nanoparticle formulation includes 0.5% to 15% on a molar basis of oleic acid, e.g., 3 to 12%, 5 to 10% or 15%, 10%, or 7.5% on a molar basis. In some embodiments, a lipid nanoparticle formulation includes 0.5% to 15% on a molar basis of an analog of oleic acid, e.g., 3 to 12%, 5 to 10% or 15%, 10%, or 7.5% on a molar basis.

In some embodiments, the formulation includes 5% to 50% on a molar basis of the structural lipid, e.g., 15 to 45%, 20 to 40%, 40%, 38.5%, 35%, or 31% on a molar basis. In some embodiments, the formulation includes 5% to 50% on a molar basis of a sterol, e.g., 15 to 45%, 20 to 40%, 40%, 38.5%, 35%, or 31% on a molar basis. A non-limiting example of a sterol is cholesterol.

In some embodiments, a lipid nanoparticle formulation includes 0.5% to 20% on a molar basis of the PEG or PEG-modified lipid, e.g., 0.5 to 10%, 0.5 to 5%, 1.5%, 0.5%, 1.5%, 3.5%, or 5% on a molar basis. In some embodiments, a PEG or PEG-modified lipid comprises a PEG molecule of an average molecular weight of 2,000 Da. In some embodiments, a PEG or PEG modified lipid comprises a PEG molecule of an average molecular weight of less than 2,000, for example, around 1,500 Da, around 1,000 Da, or around 500 Da. Non-limiting examples of PEG-modified lipids include PEG-distearoyl glycerol (PEG-DMG) (also referred herein as Cmpd422), PEG-cDMA (further discussed in Reyes et al. *J. Controlled Release*, 107, 276-287 (2005) the contents of which are herein incorporated by reference in its entirety). As described herein, any PEG lipids or PEG-modified lipids may be PEG-OH lipids. In some embodiments, a lipid nanoparticle formulation includes 0.5% to 20% on a molar basis of a PEG-OH lipid, e.g., 0.5 to 10%, 0.5 to 5%, 1.5%, 0.5%, 1.5%, 3.5%, or 5% on a molar basis.

In some embodiments, lipid nanoparticle formulations include 25-75% of a cationic lipid, 0.5-15% of the non-cationic lipid; 5-50% of the structural lipid, and 0.5-20% of the PEG or PEG-modified lipid on a molar basis. In some embodiments, lipid nanoparticle formulations include 25-75% of a cationic lipid, 0.5-15% of the non-cationic lipid; 5-50% of the structural lipid, and 0.5-20% of a PEG-OH lipid on a molar basis. In some embodiments, lipid nanoparticle formulations include 25-75% of a cationic lipid, 0.5-15% of the non-cationic lipid, and 5-50% of the structural lipid on a molar basis. In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

In some embodiments, lipid nanoparticle formulations include 35-65% of a cationic lipid, 3-12% of the non-cationic lipid, 15-45% of the structural lipid, and 0.5-10% of the PEG or PEG-modified lipid on a molar basis. In some embodiments, lipid nanoparticle formulations include 35-65% of a cationic lipid, 3-12% of the non-cationic lipid, 15-45% of the structural lipid, and 0.5-10% of the PEG-OH lipid on a molar basis. In some embodiments, lipid nanoparticle formulations include 35-65% of a cationic lipid, 3-12% of the non-cationic lipid, and 15-45% of the structural lipid on a molar basis. In some embodiments, lipid nanoparticle formulations include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations include 45-65% of a cationic lipid, 5-10% of the non-cationic lipid, 25-40% of the structural lipid, and 0.5-10% of the PEG or PEG-modified lipid on a molar basis. In some embodiments, lipid nanoparticle formulations include 45-65% of a cationic lipid, 5-10% of the non-cationic lipid, 25-40% of the structural lipid, and 0.5-10% of a PEG-OH lipid on a molar basis. In some embodiments, lipid nanoparticle formulations include 45-65% of a cationic lipid, 5-10% of the non-cationic lipid, and 25-40% of the structural lipid on a molar basis. In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations include 60% of a cationic lipid, 7.5% of the non-cationic lipid, 31% of a structural lipid, and 1.5% of the PEG or PEG-modified lipid on a molar basis. In some embodiments, lipid nanoparticle formulations include 60% of a cationic lipid, 7.5% of the non-cationic lipid, 31% of a structural lipid, and 1.5% of a PEG-OH lipid on a molar basis. In some embodiments, lipid nanoparticle formulations include 60% of a cationic lipid, 9% of the non-cationic lipid, and 31% of a structural lipid on a molar basis. In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations include 50% of a cationic lipid, 10% of the non-cationic lipid, 38.5% of the structural lipid, and 1.5% of the PEG or PEG-modified lipid on a molar basis. In some embodiments, lipid nanoparticle formulations include 50% of a cationic lipid, 10% of the non-cationic lipid, 38.5% of a structural lipid, and 1.5% of a PEG-OH lipid on a molar basis. In some embodiments, lipid nanoparticle formulations include 50% of a cationic lipid, 10% of the non-cationic lipid, and 40% of a structural lipid on a molar basis. In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations include 40% of a cationic lipid, 15% of the non-cationic lipid, 40% of the structural lipid, and 5% of the PEG or PEG-modified lipid on a molar basis. In some embodiments, lipid nanoparticle formulations include 40% of a cationic lipid, 15% of the non-cationic lipid, 40% of the structural lipid, and 5% of a PEG-OH lipid on a molar basis. In some embodiments, lipid nanoparticle formulations include 40% of a cationic lipid, 20% of the non-cationic lipid, 40% of the structural lipid on a molar basis. In some embodiments, lipid nanoparticle formulations include 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations include 57.2% of a cationic lipid, 7.1% of the non-cationic lipid 34.3% of the sterol, and 1.4% of the PEG or PEG-modified lipid on a molar basis. In some embodiments, lipid nanoparticle formulations include 57.2% of a cationic lipid, 7.1% of the non-cationic lipid, 34.3% of the structural lipid, and 1.4% of the PEG-OH lipid on a molar basis. In some embodiments, lipid nanoparticle formulations include 57.2% of a cationic lipid, 8.5% of the non-cationic lipid, and 34.3% of the structural lipid on a molar basis. In some embodiments, lipid nanoparticle formulations include 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). Each possibility represents a separate embodiment of the present invention.

In some embodiments, lipid nanoparticle formulations consists essentially of a lipid mixture in molar ratios of 20-70% cationic lipid; 5-45% non-cationic lipid; 20-55% structural lipid; 0.5-15% PEG-modified lipid. In some embodiments, lipid nanoparticle formulations consists essentially of a lipid mixture in molar ratios of 20-70% cationic lipid; 5-45% non-cationic lipid (e.g., phospholipid or fatty acid); 20-55% structural lipid; and 0.5-15% PEG-OH lipid. In some embodiments, lipid nanoparticle formulations consists essentially of a lipid mixture in molar ratios of 20-70% cationic lipid; 5-45% non-cationic lipid (e.g., phospholipid or fatty acid); 20-55% structural lipid (e.g., sterols); and 0.5-15% PEG-OH lipid. In some embodiments, lipid nanoparticle formulations consists essentially of a lipid mixture in molar ratios of 20-70% cationic lipid; 5-45% non-cationic lipid (e.g., phospholipid or fatty acid); and 20-55% structural lipid (e.g., sterols). In some embodiments, lipid nanoparticle formulations consists essentially of a lipid mixture in molar ratios of 20-70% cationic lipid; 5-45% fatty acid (e.g., oleic acid or analog thereof); 20-55% structural lipid (e.g., sterols); and 0.5-15% PEG-OH lipid. In some embodiments, lipid nanoparticle formulations consists essentially of a lipid mixture in molar ratios of 20-70% cationic lipid; 5-45% fatty acid (e.g., oleic acid or analog thereof); and 20-55% structural lipid (e.g., sterols). In some embodiments, lipid nanoparticle formulations consists essentially of a lipid mixture in molar ratios of 20-70% cationic lipid; 5-45% oleic acid; 20-55% structural lipid (e.g., sterols); and 0.5-15% PEG-OH lipid. In some embodiments, lipid nanoparticle formulations consists essentially of a lipid mixture in molar ratios of 20-70% cationic lipid; 5-45% oleic acid; and 20-55% structural lipid (e.g., sterols).

In some embodiments, the molar lipid ratio is 50/10/38.5/1.5 (mol % cationic lipid/non-cationic lipid/structural lipid/PEG lipid). In some embodiments, the molar lipid ratio is 57.2/7.1134.3/1.4 (mol % cationic lipid/non-cationic lipid/structural lipid/PEG lipid). In some embodiments, the molar lipid ratio is 40/15/40/5 (mol % cationic lipid/non-cationic lipid/structural lipid/PEG lipid). In some embodiments, the molar lipid ratio is 50/10/35/4.5/0.5 (mol % cationic lipid/non-cationic lipid/structural lipid/PEG lipid). In some embodiments, the molar lipid ratio is 50/10/35/5 (mol % cationic lipid/non-cationic lipid/structural lipid/PEG lipid). In some embodiments, the molar lipid ratio is 40/10/40/10 (mol % cationic lipid/non-cationic lipid/structural lipid/PEG lipid). In some embodiments, the molar lipid ratio is 35/15/40/10 (mol % cationic lipid/non-cationic lipid/structural lipid/PEG lipid). In some embodiments, the molar lipid ratio is 52/13/30/5 (mol % cationic lipid/non-cationic lipid/structural lipid/PEG lipid). As described herein, any non-cationic lipid may be a DSPC substitute such as a non-DSPC phospholipid or a fatty acid (e.g., oleic acid). As described herein, any PEG lipid may be a PEG-OH lipid.

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.*, 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid (e.g., PEG-OH lipid) and optionally comprise a non-cationic lipid (e.g., phospholipid or fatty acid). In some embodiments, lipid nanoparticle formulations may comprise a cationic lipid, a PEG lipid (e.g., PEG-OH lipid) and a structural lipid (e.g., a sterol) and optionally comprise a non-cationic lipid (e.g., phospholipid or fatty acid).

Lipid nanoparticles described herein may comprise 2 or more components (e.g., lipids), not including the payload. In certain embodiments, the LNP comprises two components (e.g., lipids), not including the payload. In certain embodiments, the lipid nanoparticle comprises 5 components (e.g., lipids), not including the payload. In certain embodiments, the LNP comprises 6 components (e.g., lipids), not including the payload.

In some embodiments, the lipid nanoparticle formulations described herein may be four component lipid nanoparticles. A 4 component LNP may comprise four different lipids selected from any described herein. The four components do not include the payload. The lipid nanoparticle may comprise a cationic lipid, a non-cationic lipid, a PEG lipid, and a structural lipid. In certain embodiments, the lipid nanoparticle comprises a cationic lipid, a fatty acid, a PEG lipid, and a structural lipid. In certain embodiments, the lipid nanoparticle comprises a cationic lipid, a fatty acid, a PEG-OH lipid, and a structural lipid. Each possibility represents a separate embodiment of the present invention.

In some embodiments, the lipid nanoparticle formulations described herein may be three component lipid nanoparticles. A three component LNP may comprise three different lipids described herein. The lipid nanoparticle may comprise a cationic lipid, a non-cationic lipid (e.g., phospholipid or fatty acid), and a structural lipid. In certain embodiments, the lipid nanoparticle comprises a cationic lipid, a fatty acid, and a structural lipid. In certain embodiments, the lipid nanoparticle comprises a cationic lipid, a phospholipid, and a structural lipid.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm. or 80-200 nm.

In one embodiment, the LNP formulation may be formulated by the methods described in International Publication Nos. WO2011127255 or WO2008103276, the contents of each of which is herein incorporated by reference in their entirety. As a non-limiting example, LNP formulations as described in WO2011127255 and/or WO2008103276; each of which is herein incorporated by reference in their entirety.

In one embodiment, the lipid nanoparticle may be formulated by the methods described in US Patent Publication No US2013/0156845 or International Publication No WO2013/093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In one embodiment, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents (e.g., RNA); one or more cationic lipids comprising from about 50 mol % to about 85 mol % of the total lipid present in the particle; one or more non-cationic lipid lipids comprising from about 13 mol % to about 49.5 mol % of the total lipid present in the particle; and one or more structural lipids that inhibit aggregation of particles comprising from about 0.5 mol % to about 2 mol % of the total lipid present in the particle.

In one embodiment, the LNP formulation may be formulated by the methods described in International Publication Nos. WO2011127255 or WO2008103276, the contents of each of which are herein incorporated by reference in their entirety. As a non-limiting example, LNP formulations as described in WO2011127255 and/or WO2008103276; the contents of each of which are herein incorporated by reference in their entirety. In one embodiment, LNP formulations described herein may comprise a polycationic composition. As a non-limiting example, the polycationic composition may be selected from formula 1-60 of US Patent Publication No. US20050222064; the content of which is herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

As a non-limiting example, the LNP may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, the lipid nanoparticle includes a non-cationic lipid such as, but not limited to, cholesterol or dioleoyl phosphatidylethanolamine (DOPE).

In some embodiments, the lipid nanoparticles described herein can have a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um.

In another embodiment, LNPs may have a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm. Each possibility represents a separate embodiment of the present invention.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20. Each possibility represents a separate embodiment of the present invention.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV. Each possibility represents a separate embodiment of the present invention.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the nanoparticle composition before and after breaking up the nanoparticle composition with one or more organic solvents or detergents. Fluorescence may be used to measure the amount of free therapeutic agent (e.g., nucleic acids) in a solution. For the nanoparticle compositions described herein, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. Each possibility represents a separate embodiment of the present invention.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

In some embodiments, such LNPs are synthesized using methods comprising microfluidic mixers. Exemplary microfluidic mixers may include, but are not limited to a slit interdigitial micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In one embodiment, the lipid nanoparticles may be formulated using a micromixer such as, but not limited to, a Slit Interdigital Microstructured Mixer (SIMM-V2) or a Standard Slit Interdigital Micro Mixer (SSIMM) or Caterpillar (CPMM) or Impinging jet (IJMM) from the Institut für Mikrotechnik Mainz GmbH, Mainz Germany).

In one embodiment, the lipid nanoparticles are created using microfluidic technology (see Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647651; which is herein incorporated by reference in its entirety).

In one embodiment, the mRNA of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the lipid nanoparticles may have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm. In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. Each possibility represents a separate embodiment of the present invention.

In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm.

Lipids

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

Cationic/Ionizable Lipids

A nanoparticle composition may include one or more cationic and/or ionizable lipids (e.g., lipids that may have a positive or partial positive charge at physiological pH). Cationic and/or ionizable lipids may be selected from the non-limiting group consisting of 3-(didodecylamino)-N1, N1,4-tridodecyl-1-piperazineethanamine (KL10), N1-[2-(didodecylamino)ethyl] N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl-4-(dimethylamino)butanoate (DLin-MC3-DMA), 2,2-dilinoleyl-4-(2 dimethylaminoethyl)-[1,3]-dioxolane (DLin-KC2-DMA), 1,2-dioleyloxy-N,N-dimethylaminopropane (DODMA), 2-({8 [(3β)-cholest-5-en-3-yloxy]octyl}oxy) N,N dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S) 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, a cationic lipid may also be a lipid including a cyclic amine group. Each possibility represents a separate embodiment of the present invention. Each possibility represents a separate embodiment of the present invention.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and 520130225836; the contents of each of which are herein incorporated by reference in their entirety.

In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115, formula I of US Patent Publication No US20130123338; each of which is herein incorporated by reference in their entirety.

As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-1 0-amine, (15Z)—N,N-dimethyl eptacos-15-en-1 0-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-1 0-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcycIopropyl]methyl}cyclopropyl]nonadecan-10-amine,N,N-dimethyl-1-[(1S,2R)-2-octylcyclopropyl]hexadecan-8-amine, N,N-dimethyl-[(1R,2S)-2 undecylcyclopropyl]tetradecan-5-amine, N,N-dimethyl-3-{7-[(1S,2R)-2-octylcyclopropyl]heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexy- loxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1- yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxyl-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof. Each possibility represents a separate embodiment of the present invention.

Additional examples of cationic lipids include the following:

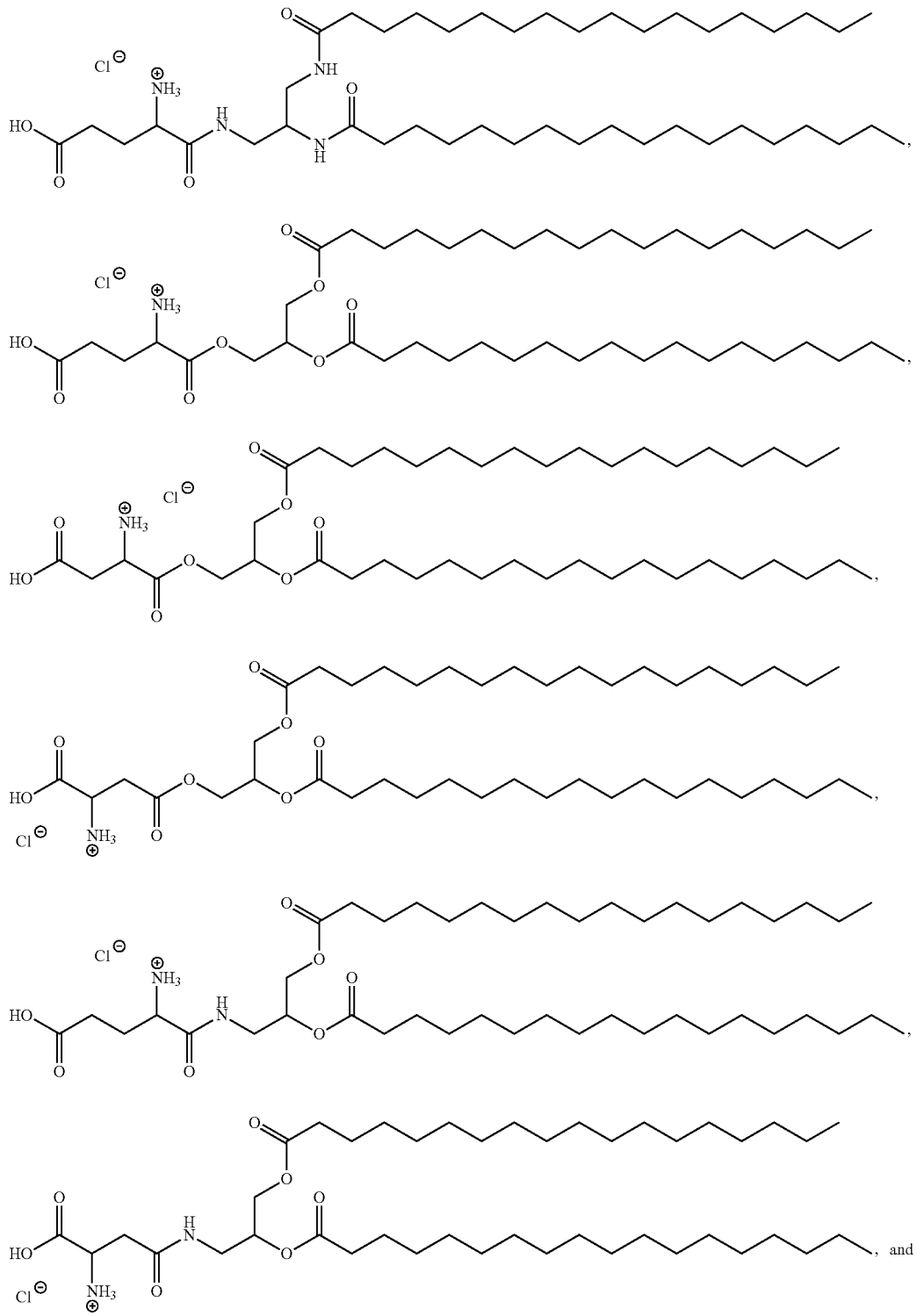

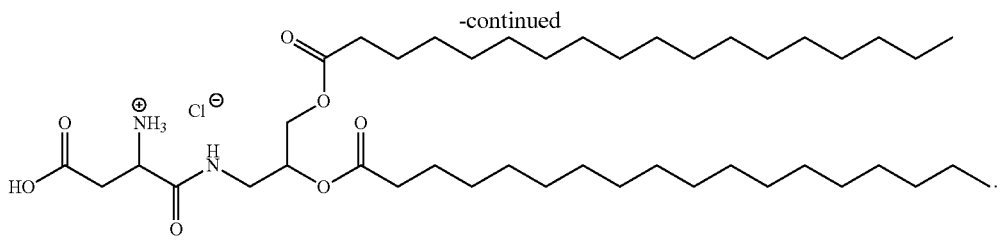

-continued

In one embodiment, the lipid may be a cleavable lipid such as those described in International Publication No. WO2012170889, herein incorporated by reference in its entirety. In another embodiment, the lipid may be a cationic lipid such as, but not limited to, Formula (I) of U.S. Patent Application No. US20130064894, the contents of which are herein incorporated by reference in its entirety. In one embodiment, the cationic lipid may be synthesized by methods known in the art and/or as described in International Publication Nos. WO2013086354; the contents of each of which are herein incorporated by reference in their entirety. In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In some embodiments, additional lipids may comprise a compound of Formula (X):

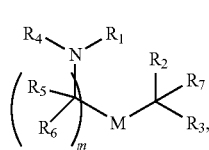

(X)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (X) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (X) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (X) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (X) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)—CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N (R)$_2$, —N(OR)C(=NR$_9$)N(R)$_2$, —N(OR)C(=CHR$_9$) N(R)$_2$, —C(=NR$_9$)R, —C(O)N(R)OR, and —C(=NR$_9$)N (R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (X) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (X) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —CQ(R)$_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (X) includes those of Formula (XA):

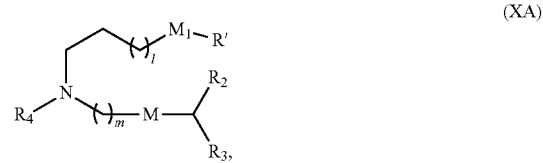

(XA)

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (X) includes those of Formula (XI):

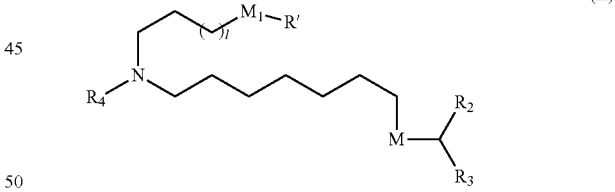

(II)

or a salt or isomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (X) includes those of Formula (XIa), (XIb), (XIc), or (XIe):

(XIa)

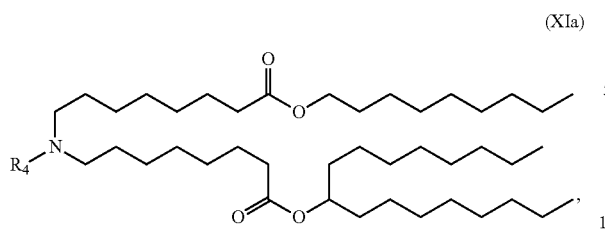

(XIb)

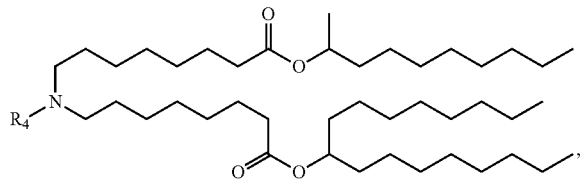

(XIc)

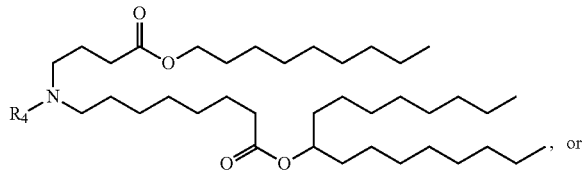

, or (XIe)

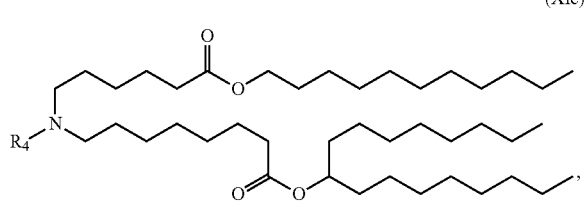

, or a salt or isomer thereof, wherein $R_4$ is as described herein.

In some embodiments, a subset of compounds of Formula (X) includes those of Formula (XId):

(IId)

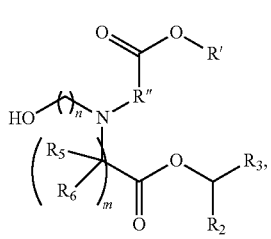

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (X) includes those of Formula (XIa), (XIb), (XIc), or (XIe):

(XIa)

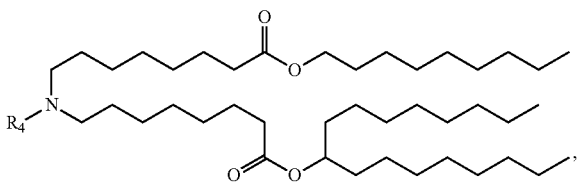

(XIb)

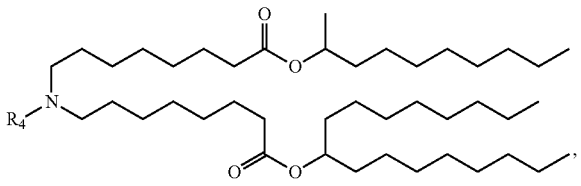

(XIc)

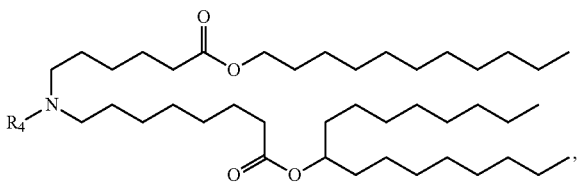

, or (XIe)

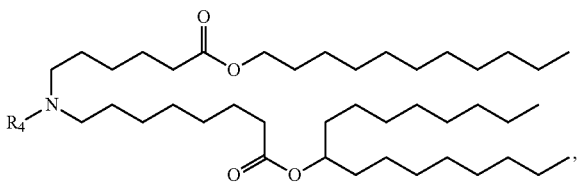

or a salt or isomer thereof, wherein $R_4$ is as described herein.

In some embodiments, a subset of compounds of Formula (X) includes those of Formula (XId):

(XId)

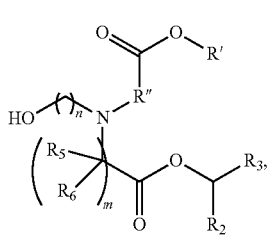

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (X) is selected from the group consisting of:

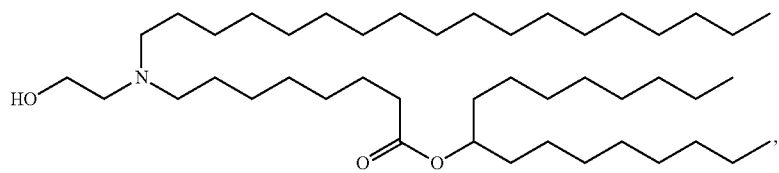
(Compound 500)
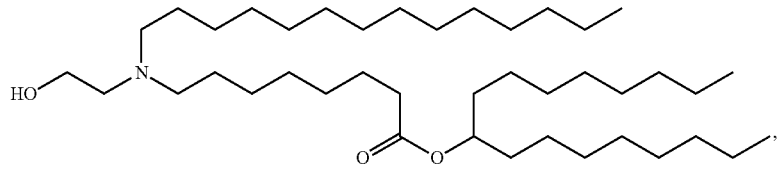
(Compound 501)
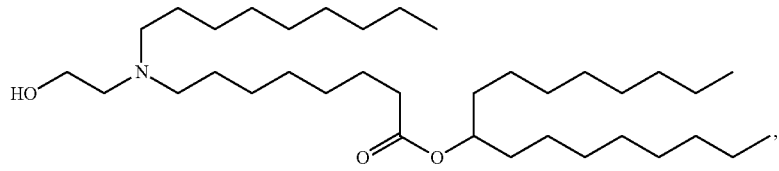
(Compound 502)
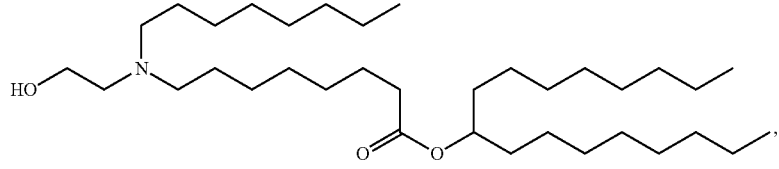
(Compound 503)
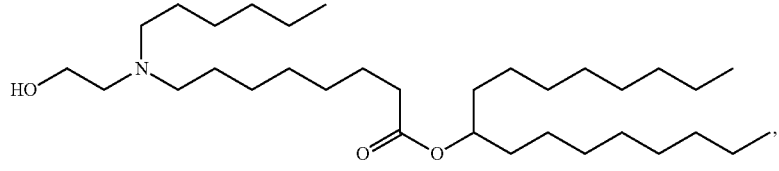
(Compound 504)
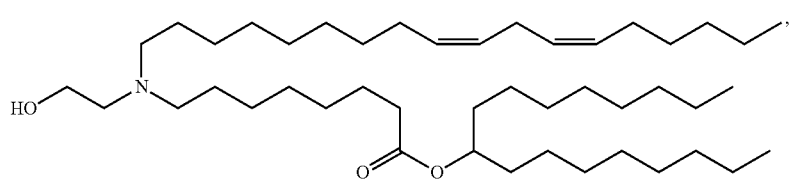
(Compound 505)
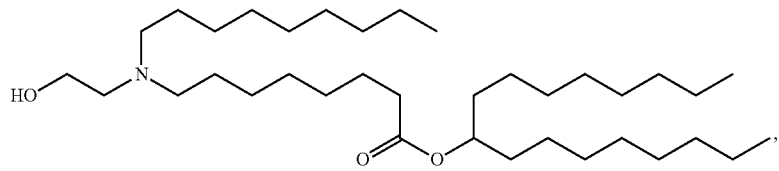
(Compound 506)
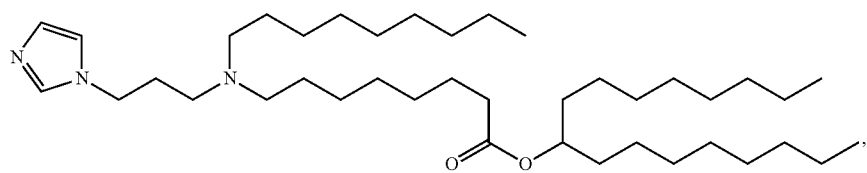
(Compound 507)

(Compound 508)
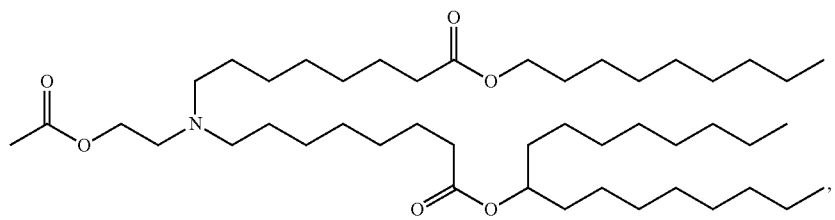
(Compound 509)
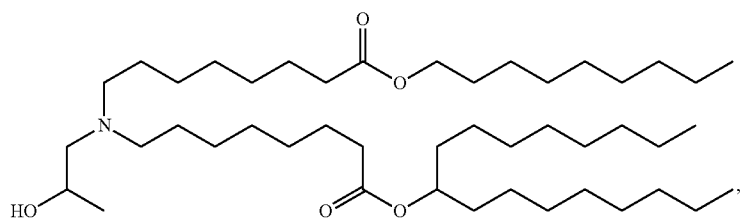
(Compound 510)
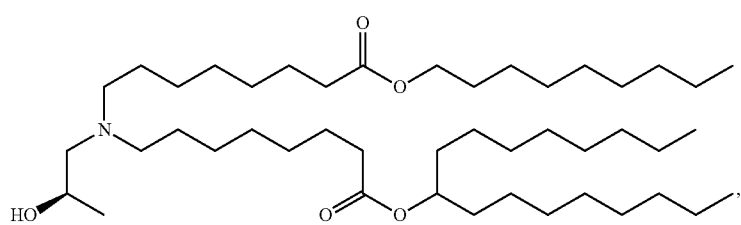
(Compound 511)
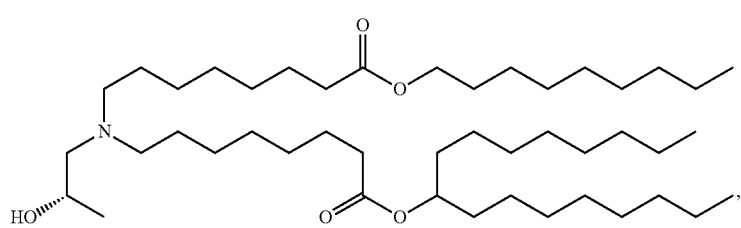
(Compound 512)
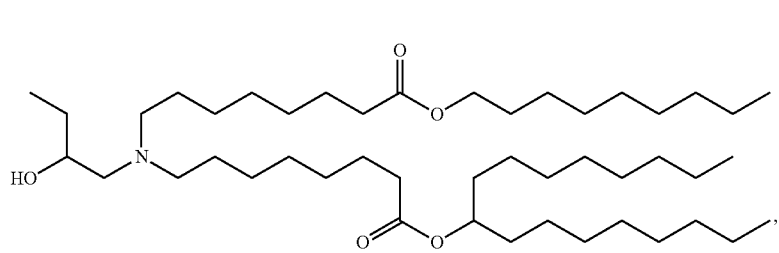
(Compound 513)
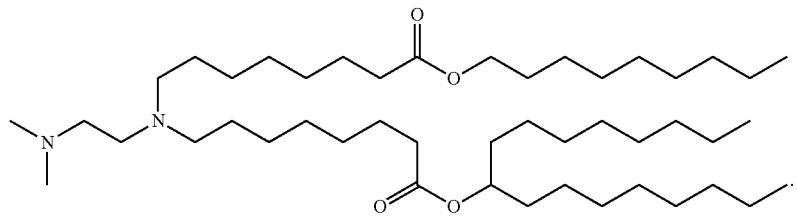
(Compound 514)
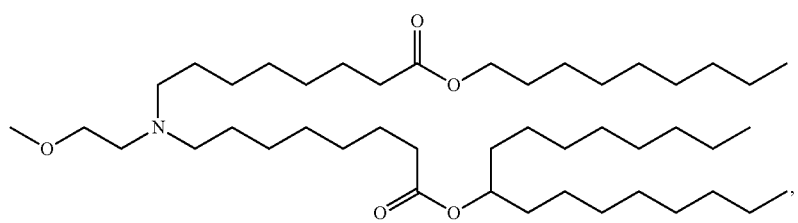

(Compound 515)
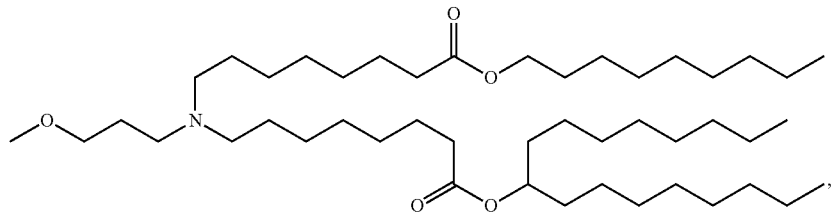
(Compound 516)
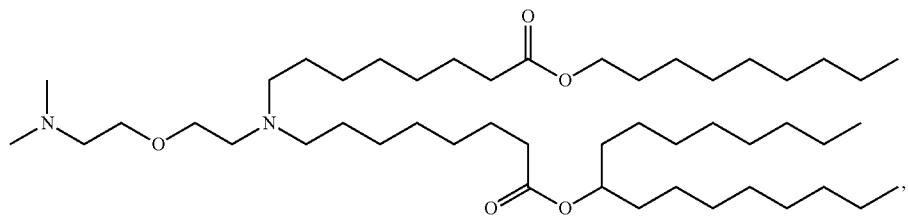
(Compound 517)
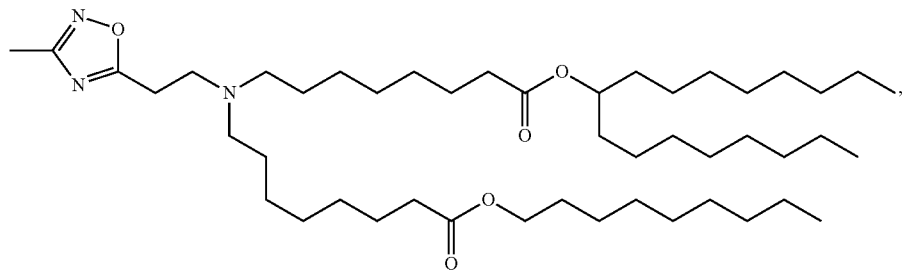
(Compound 518)
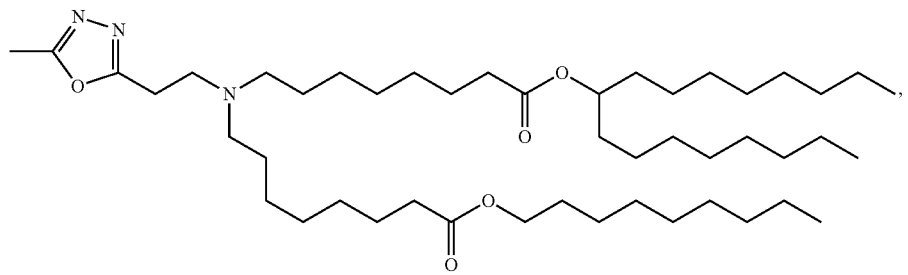
(Compound 18)
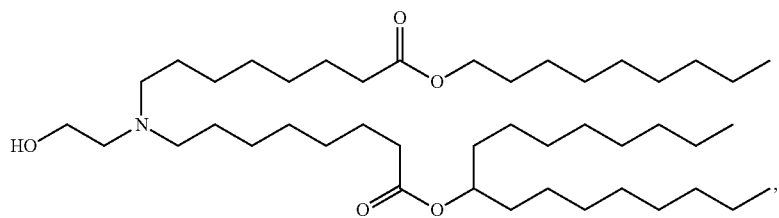
(Compound 519)
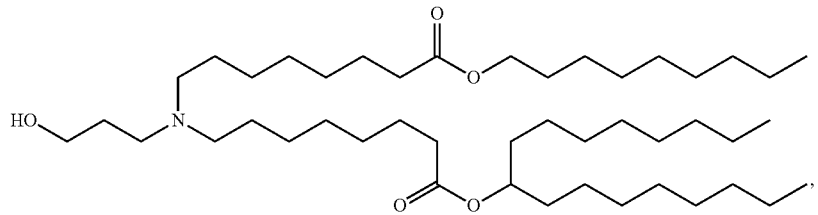

(Compound 520)
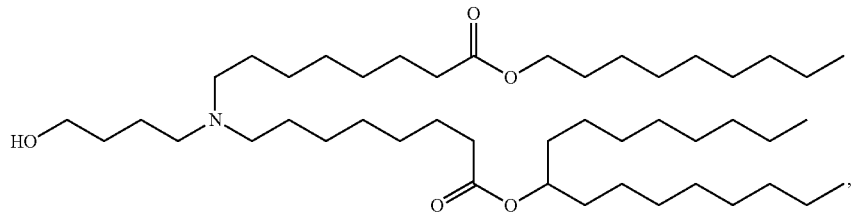
(Compound 521)
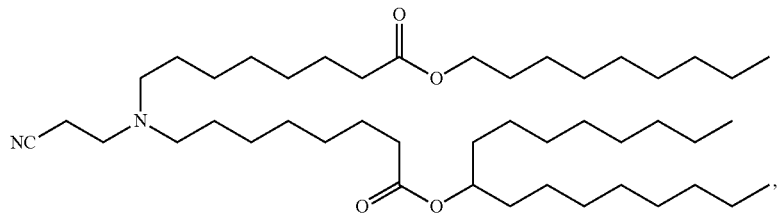
(Compound 522)
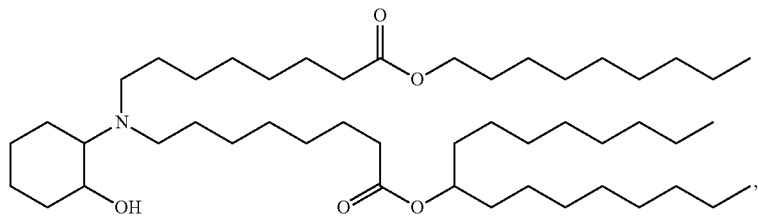
(Compound 523)
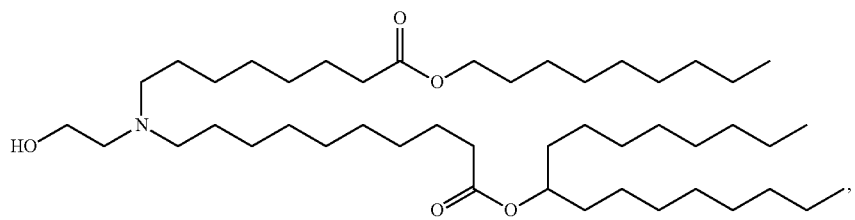
(Compound 524)
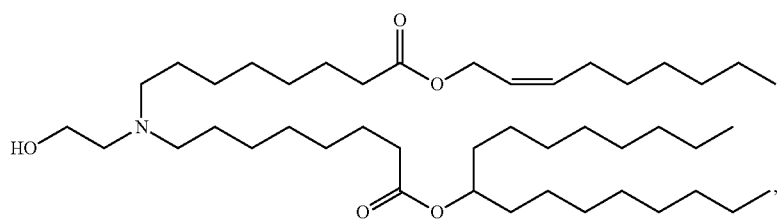
(Compound 525)
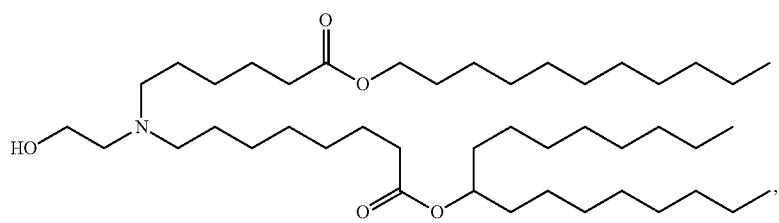
(Compound 526)
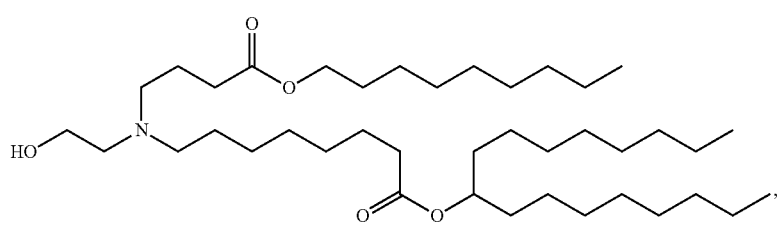

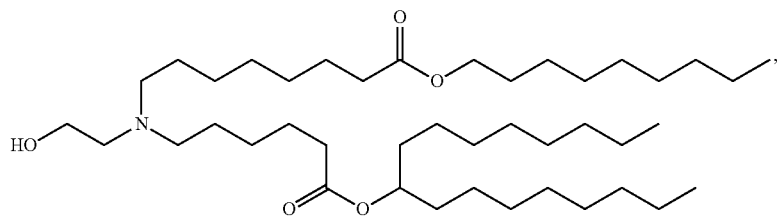
(Compound 527)
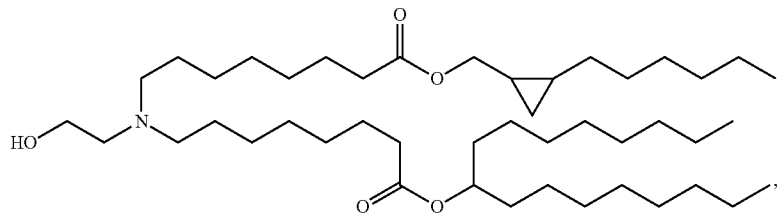
(Compound 528)
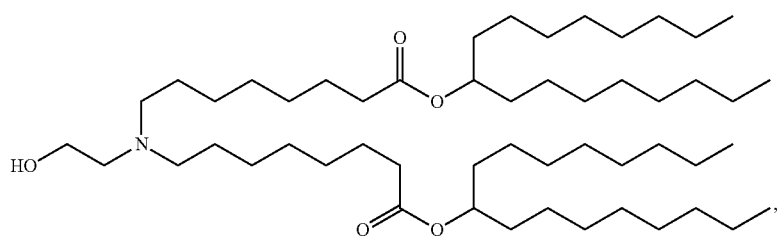
(Compound 529)
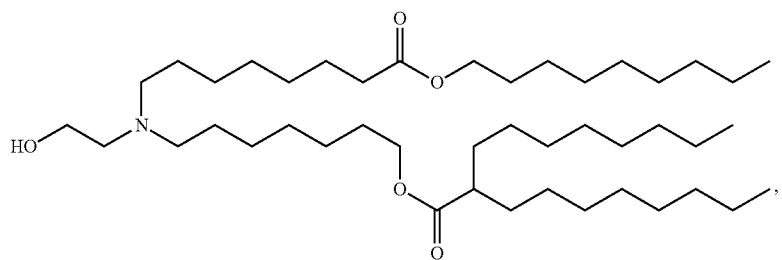
(Compound 530)
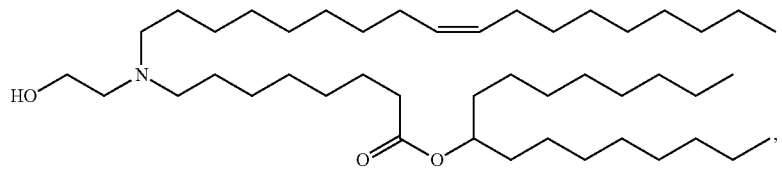
(Compound 531)
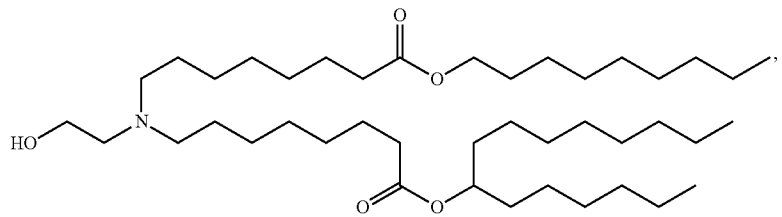
(Compound 532)
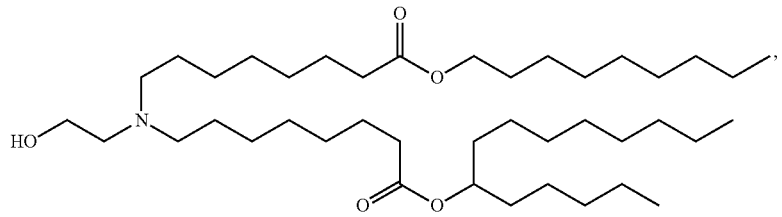
(Compound 533)

(Compound 534)
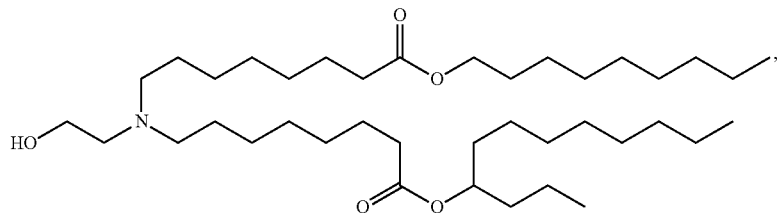
(Compound 535)
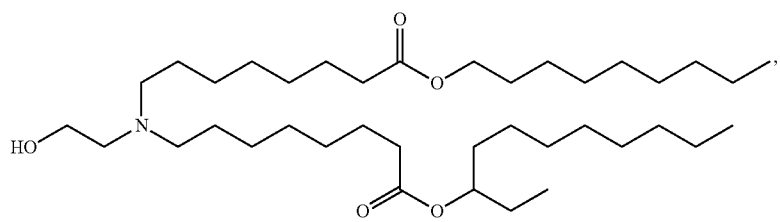
(Compound 536)
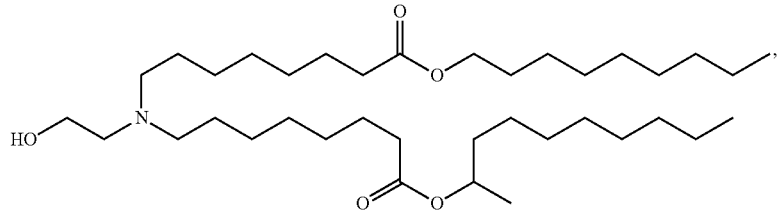
(Compound 537)
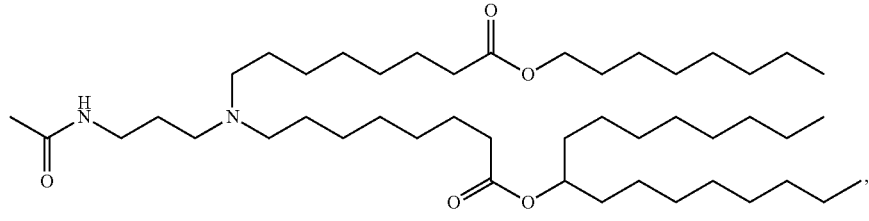
(Compound 538)
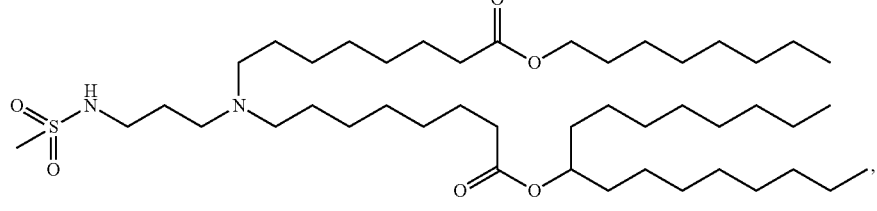
(Compound 539)
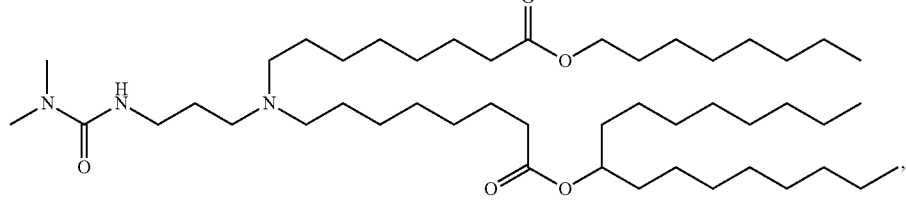
(Compound 540)
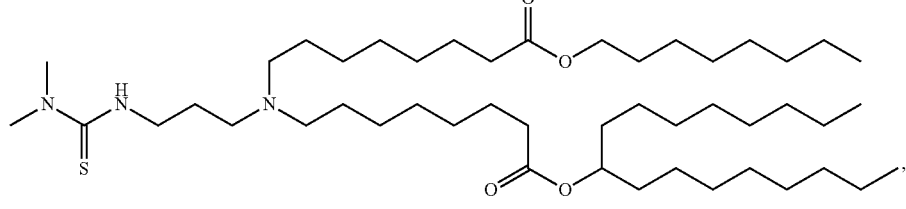

-continued
(Compound 541)
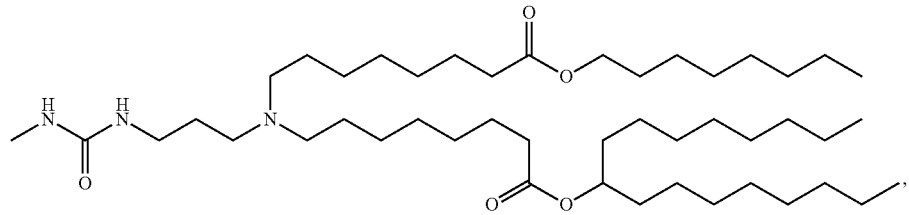
(Compound 542)
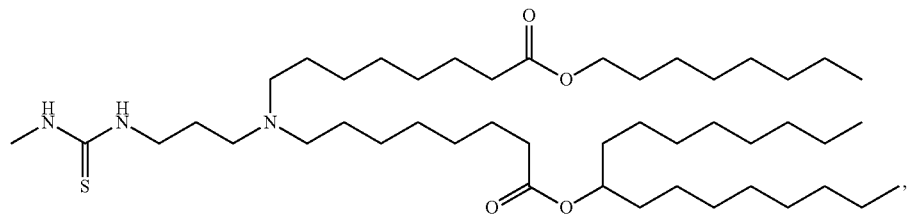
(Compound 543)
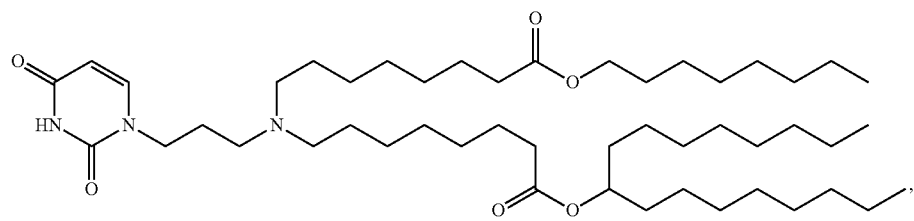
(Compound 544)
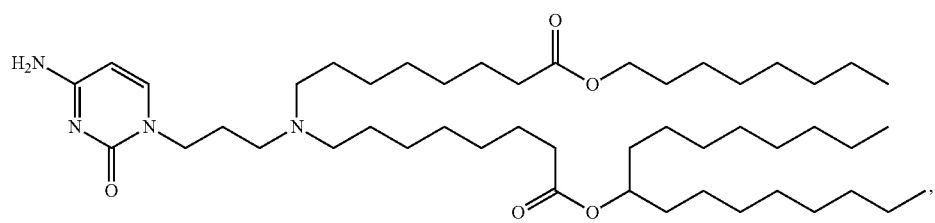
(Compound 545)
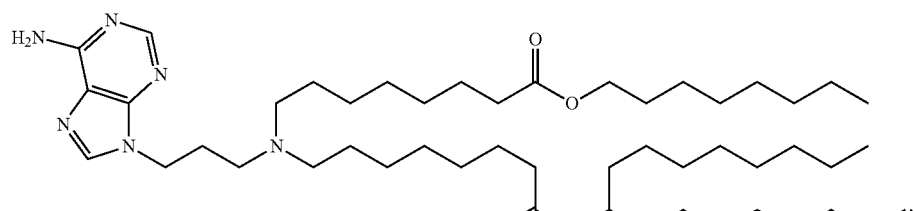
(Compound 546)
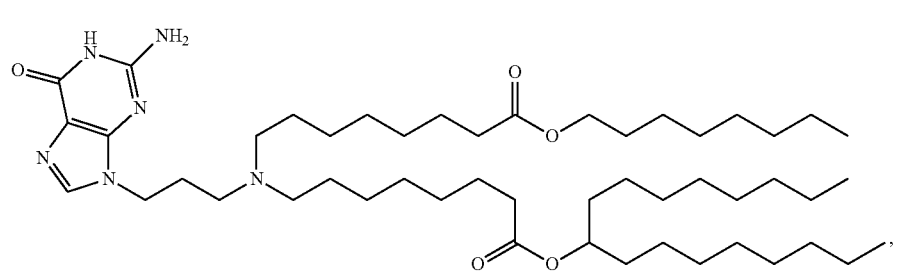
(Compound 547)
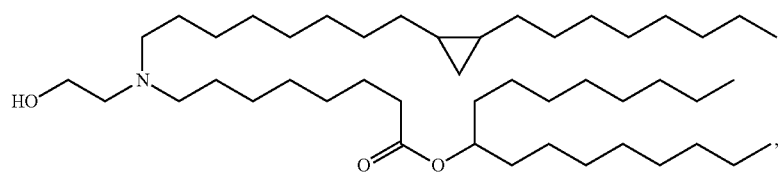

-continued
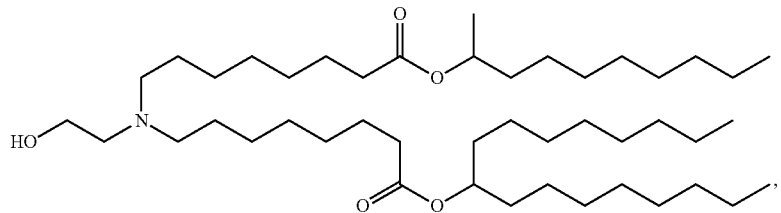
(Compound 548)
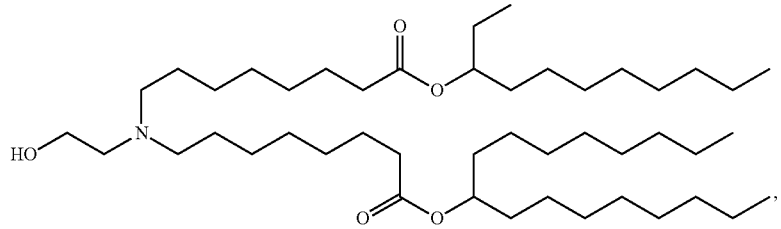
(Compound 549)
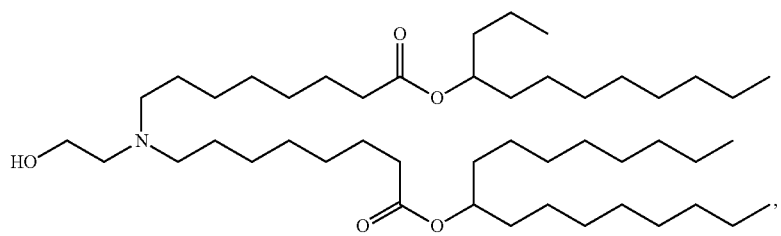
(Compound 550)
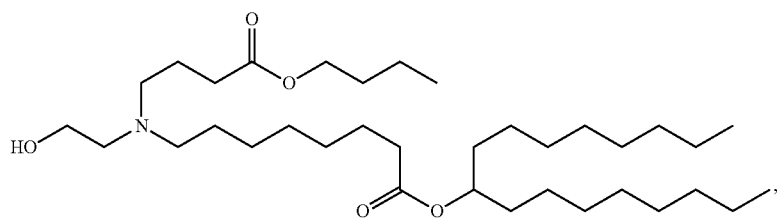
(Compound 551)
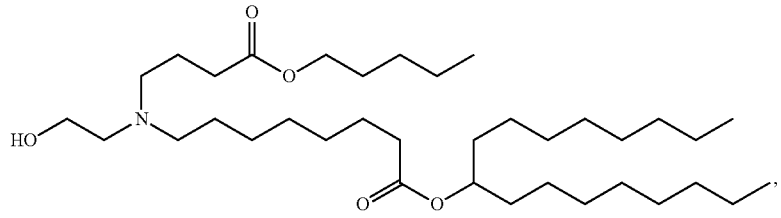
(Compound 552)
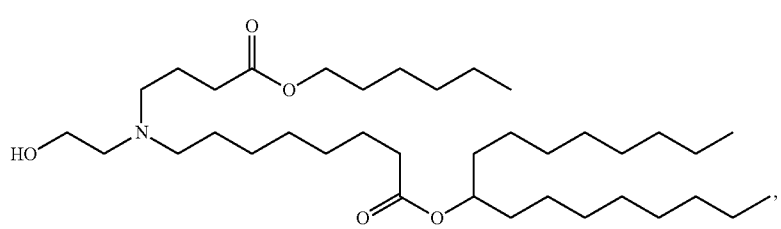
(Compound 553)
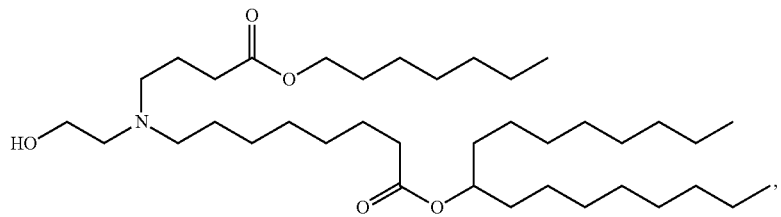
(Compound 554)

(Compound 555)
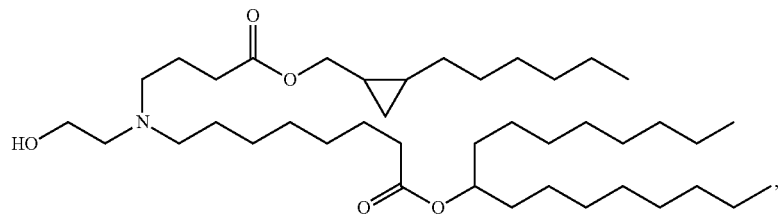
(Compound 556)
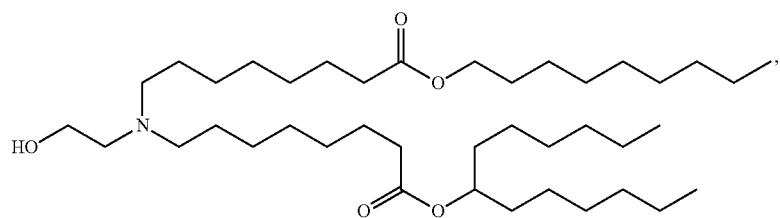
(Compound 557)
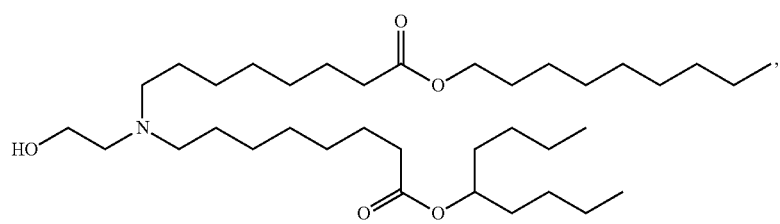
(Compound 558)
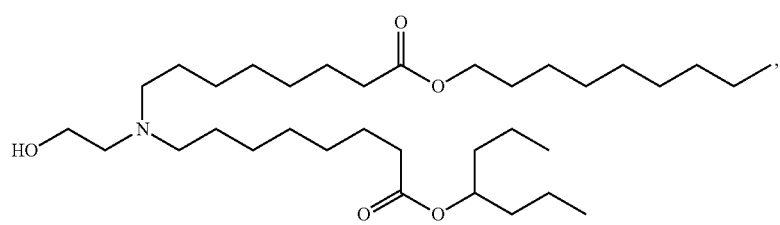
(Compound 559)
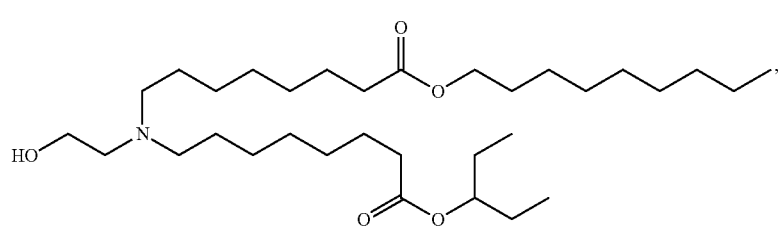
(Compound 560)
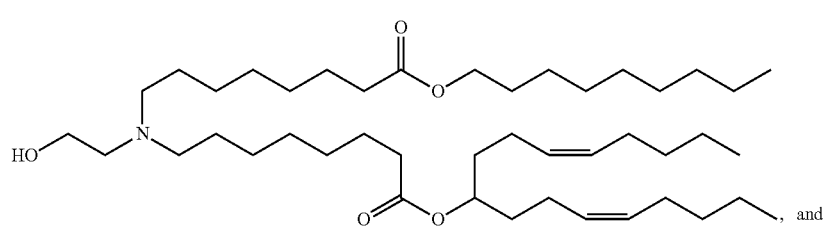, and
(Compound 561)
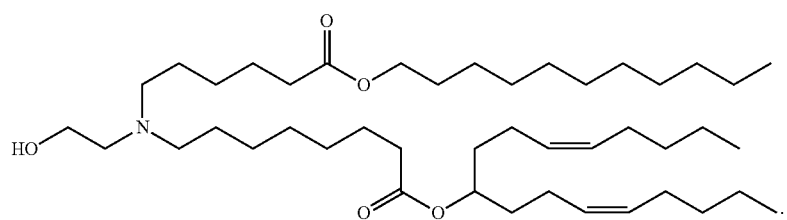.

In further embodiments, the compound of Formula (X) is selected from the group consisting of:
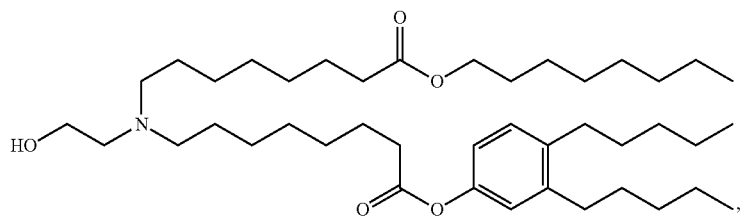
(Compound 562)
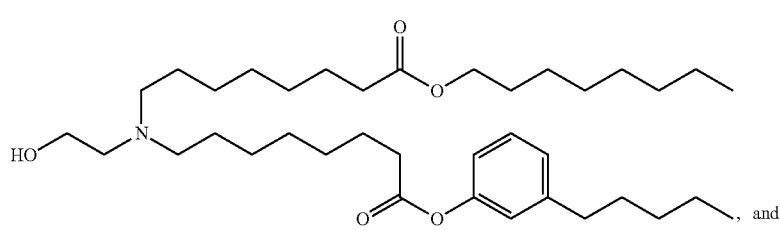
(Compound 563)
, and
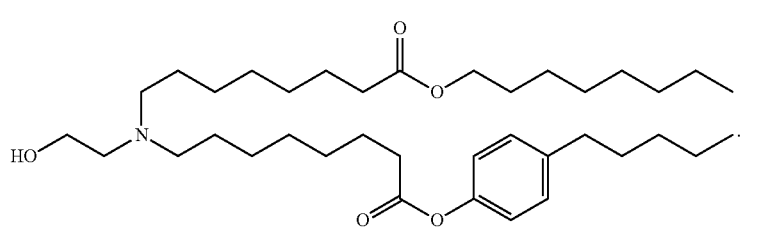
(Compound 564)
In some embodiments, the compound of Formula (X) is selected from the group consisting of:
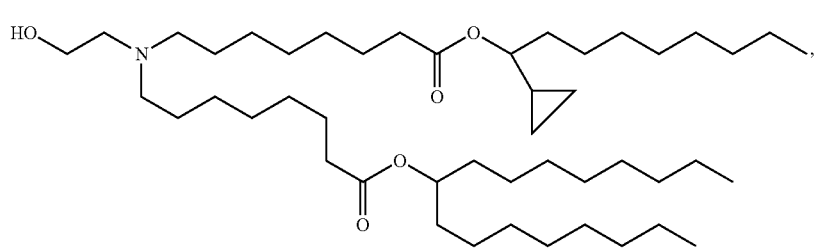
(Compound 565)
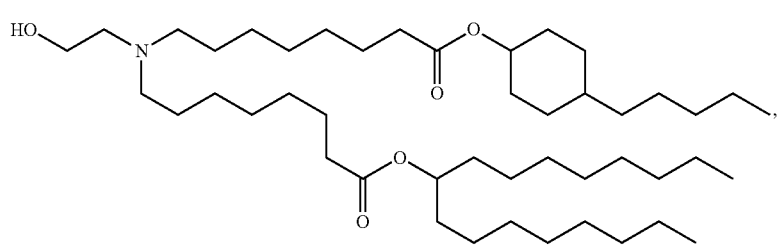
(Compound 566)
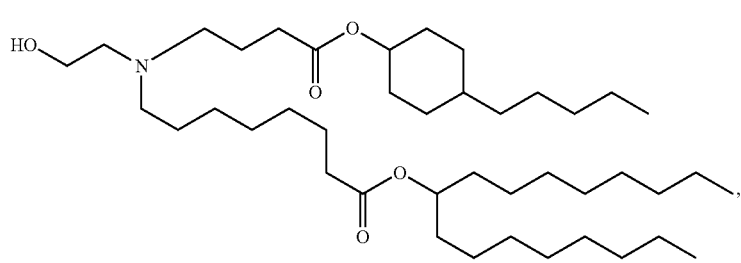
(Compound 567)

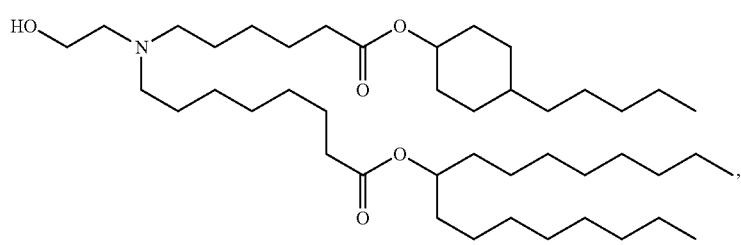
(Compound 568)
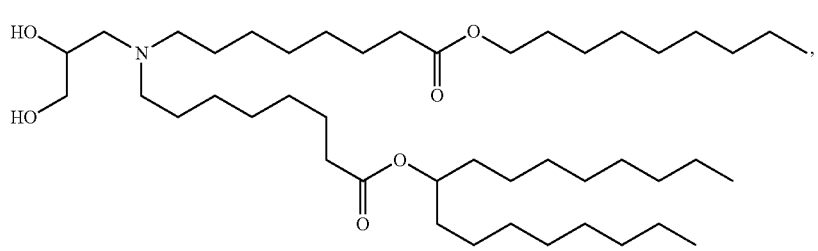
(Compound 569)
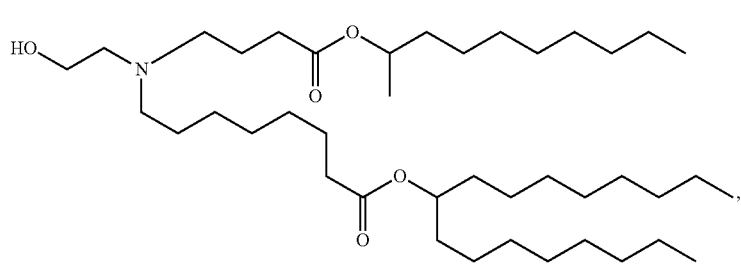
(Compound 570)
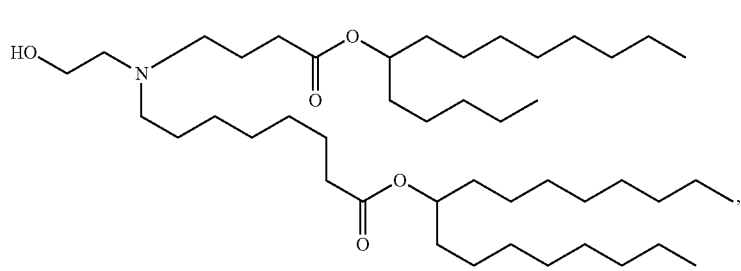
(Compound 571)
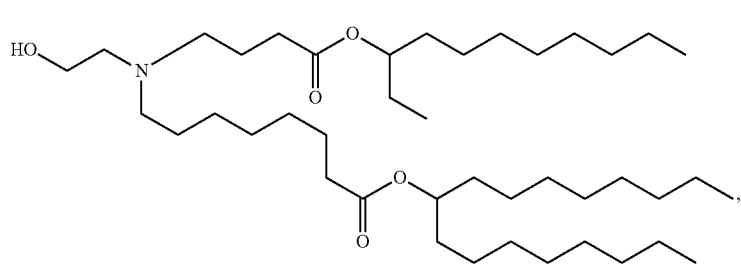
(Compound 572)
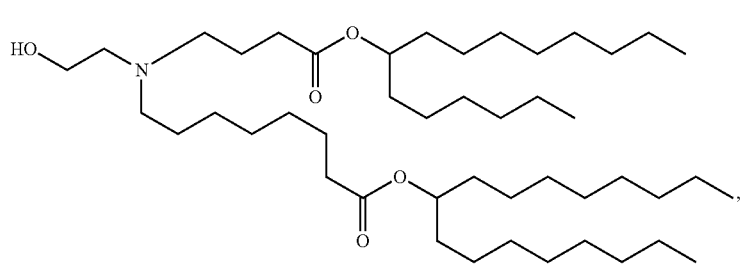
(Compound 573)

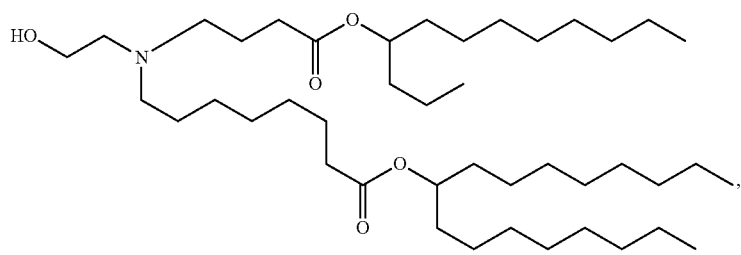
(Compound 574)
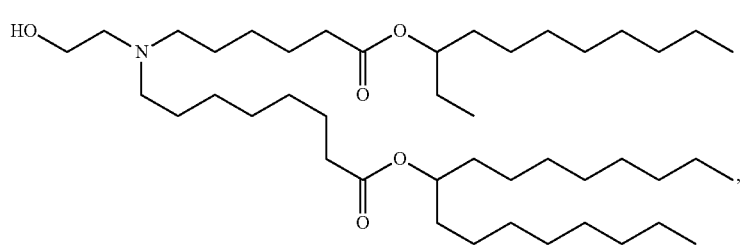
(Compound 755)
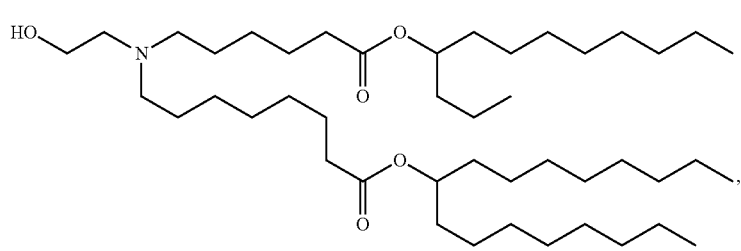
(Compound 576)
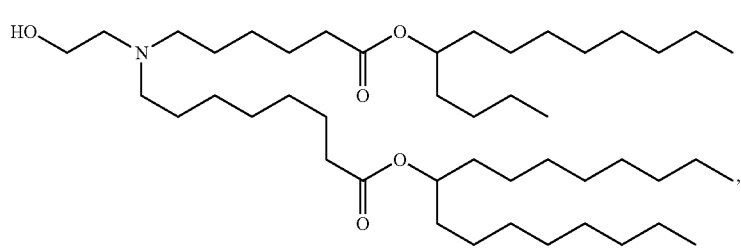
(Compound 577)
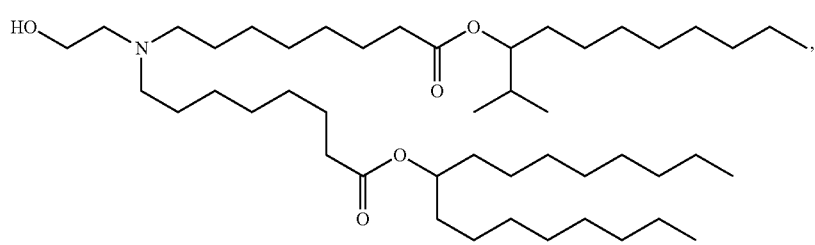
(Compound 578)
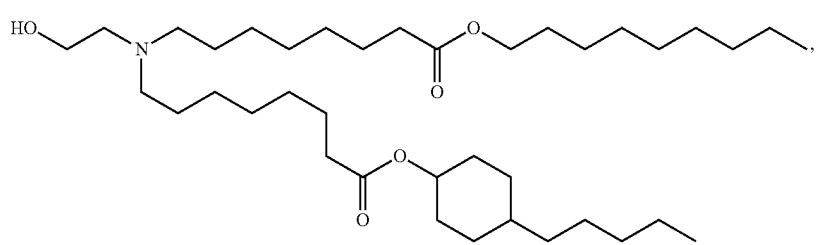
(Compound 579)

-continued
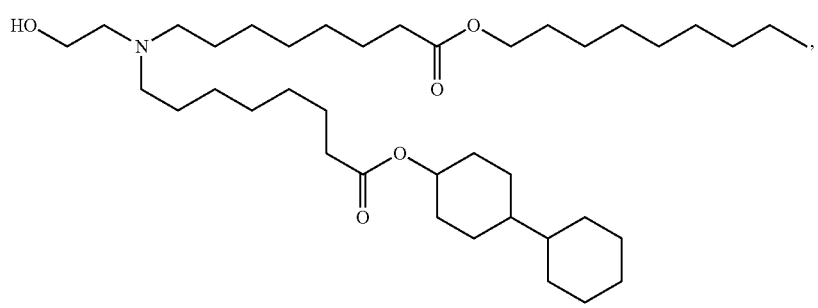
(Compound 580)
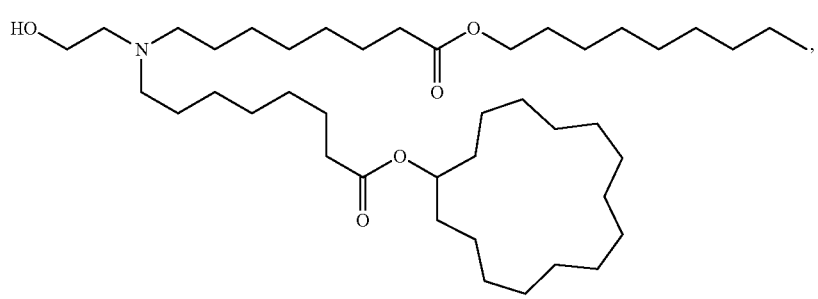
(Compound 581)
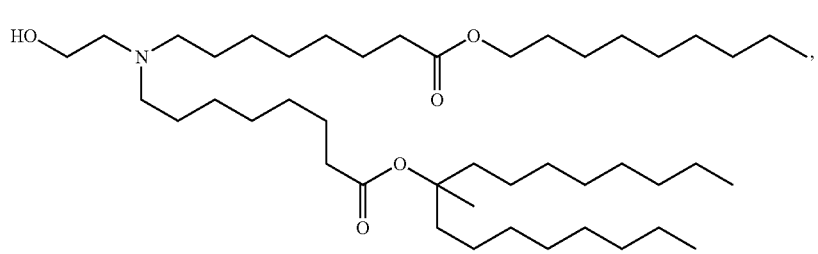
(Compound 582)
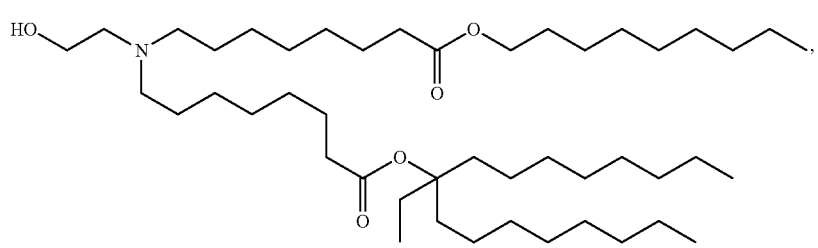
(Compound 583)
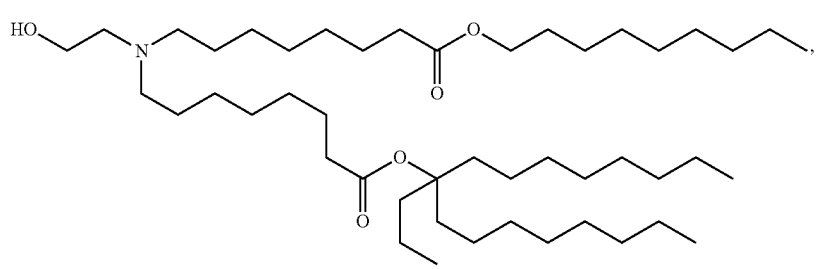
(Compound 584)
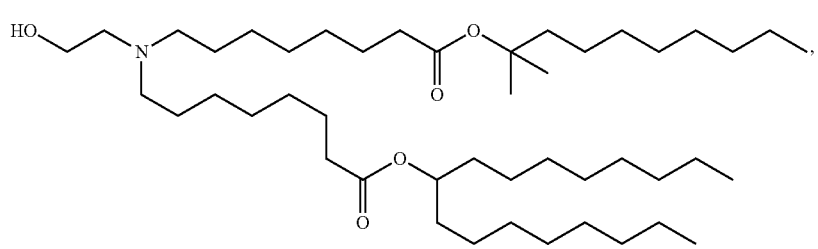
(Compound 585)

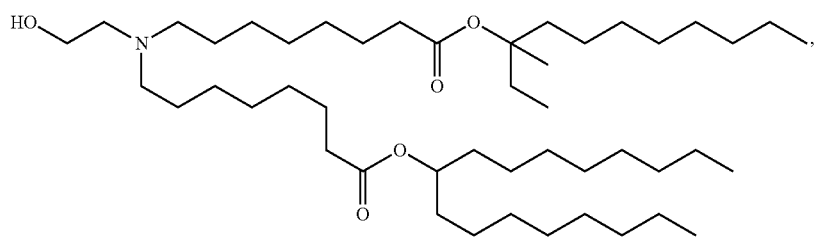
(Compound 586)
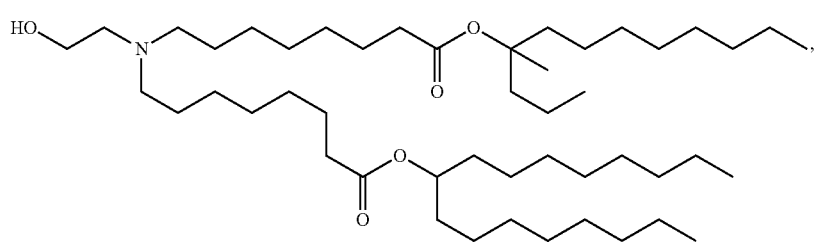
(Compound 587)
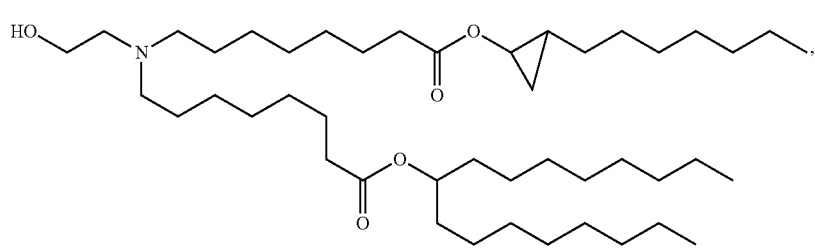
(Compound 588)
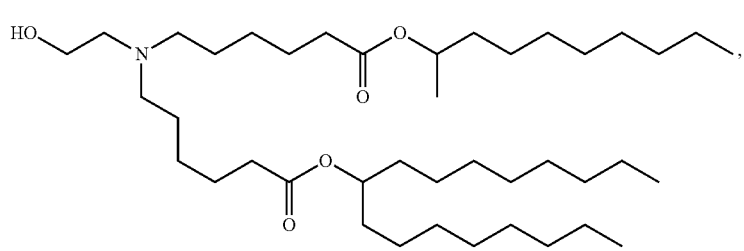
(Compound 589)
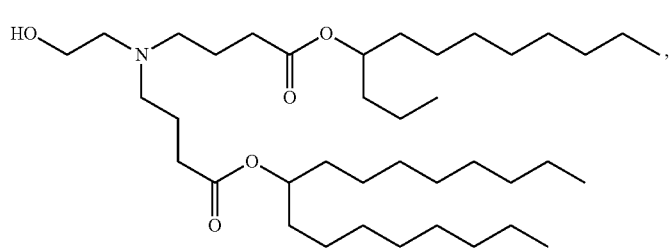
(Compound 590)
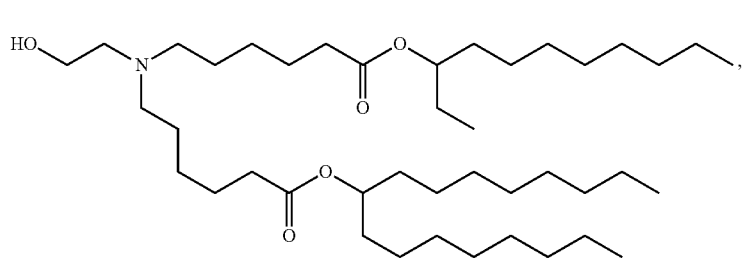
(Compound 591)

-continued
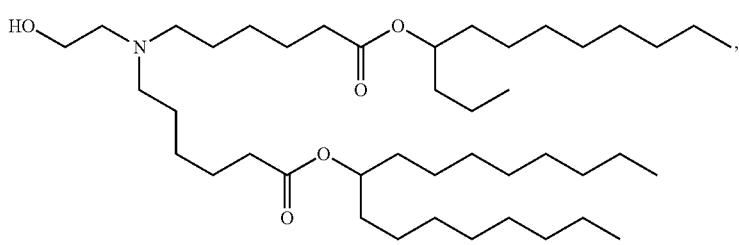
(Compound 592)
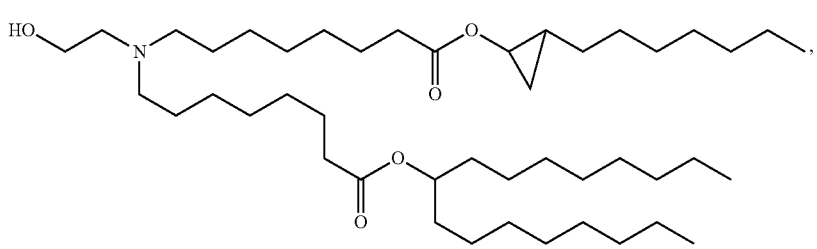
(Compound 593)
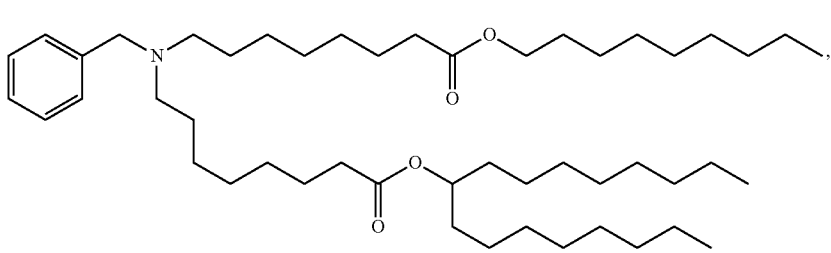
(Compound 594)
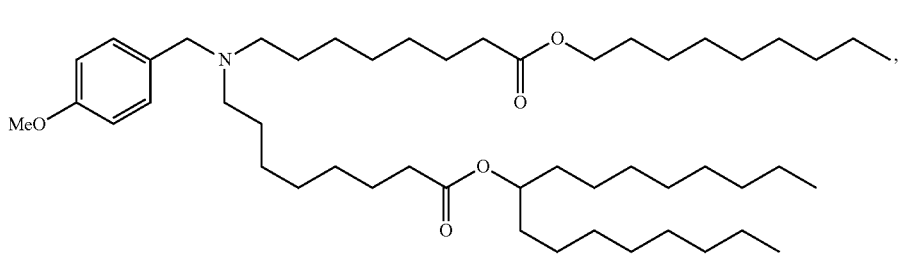
(Compound 595)
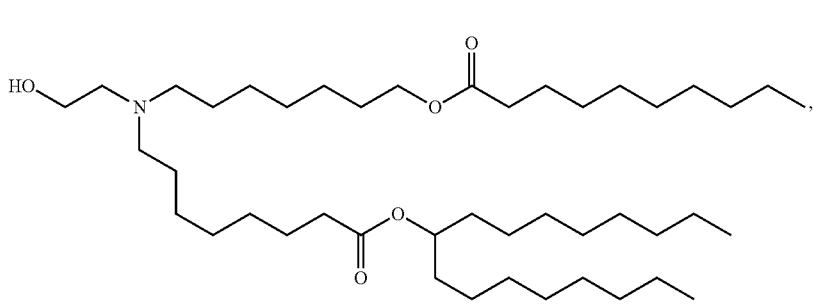
(Compound 596)
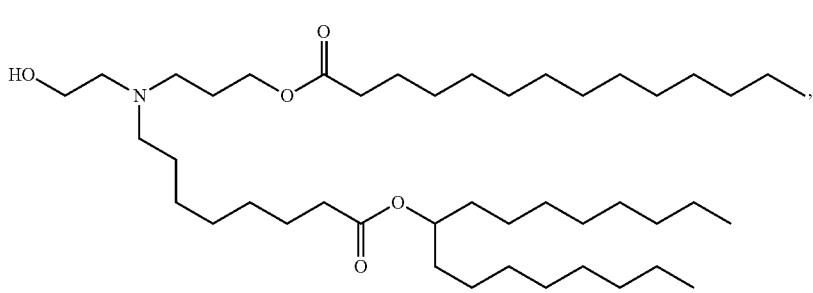
(Compound 597)

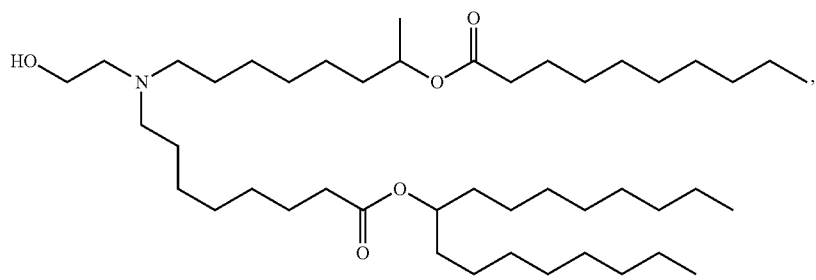
(Compound 598)
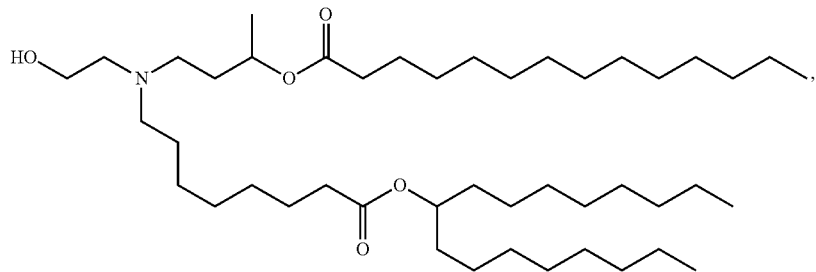
(Compound 599)
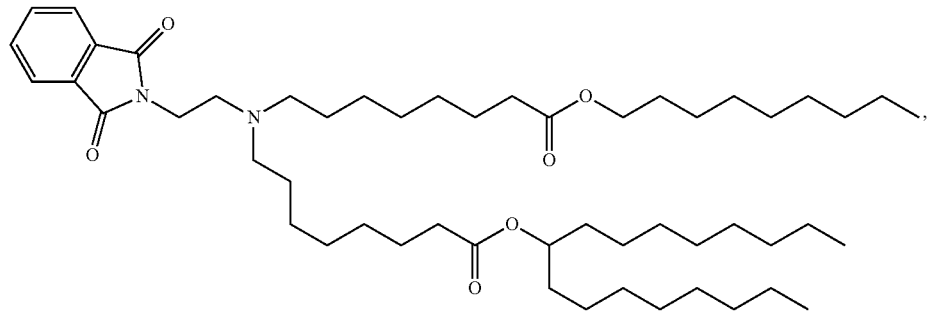
(Compound 600)
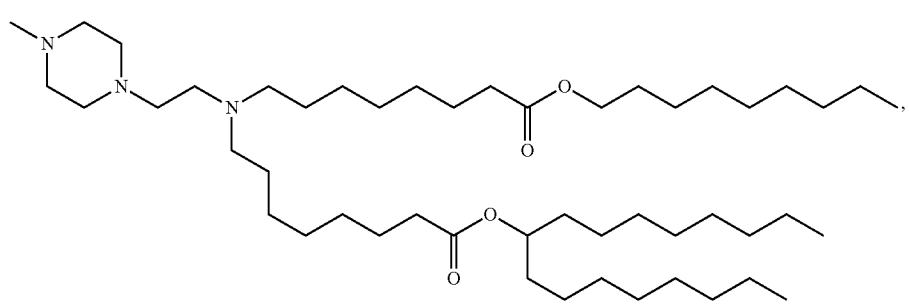
(Compound 601)
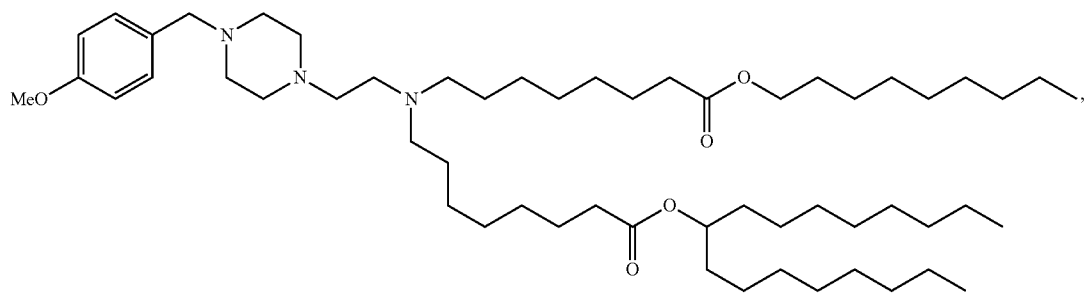
(Compound 602)

-continued
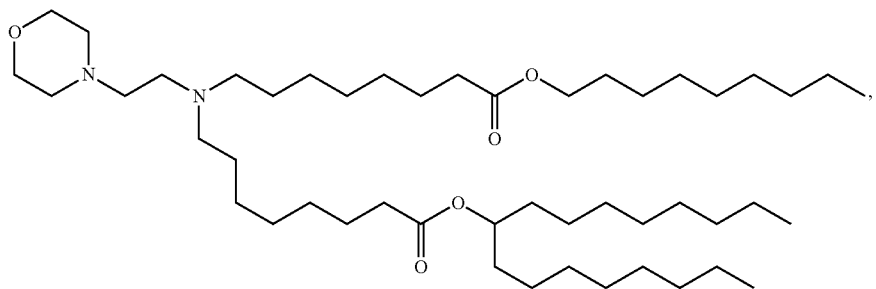
(Compound 603)
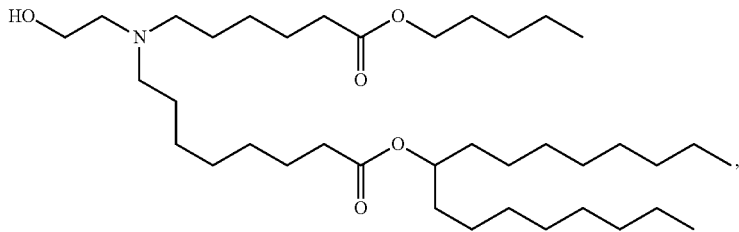
(Compound 604)
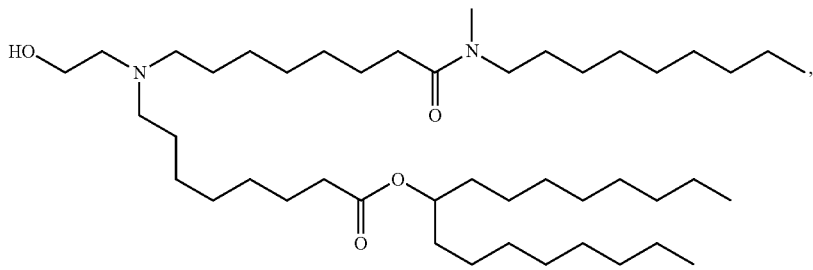
(Compound 605)
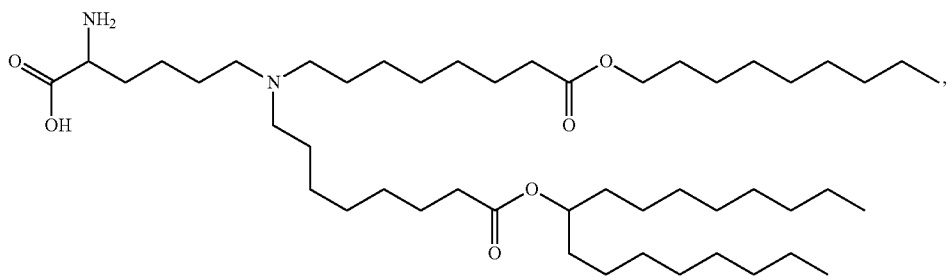
(Compound 606)
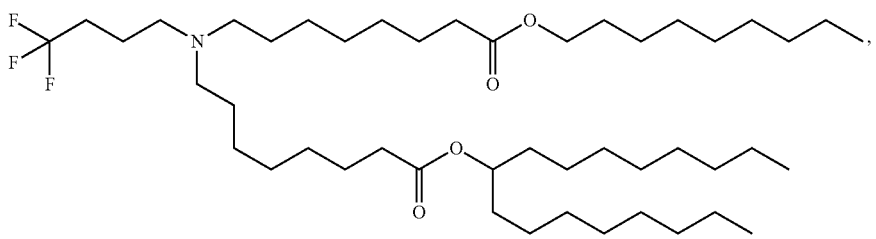
(Compound 607)
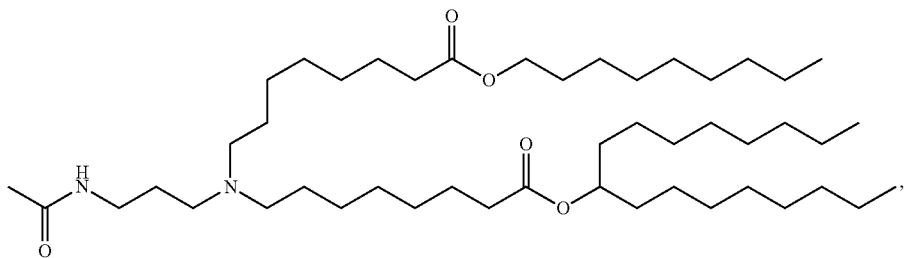
(Compound 608)

(Compound 609)
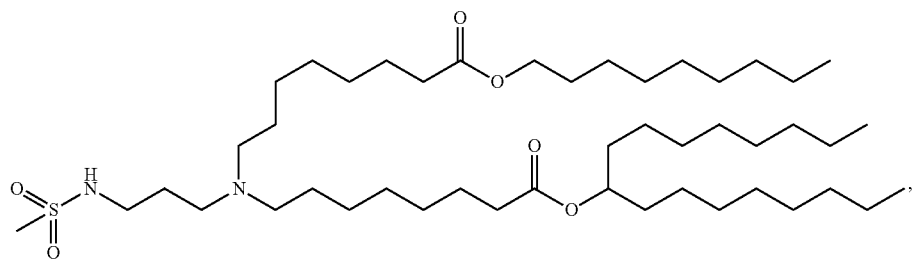
(Compound 610)
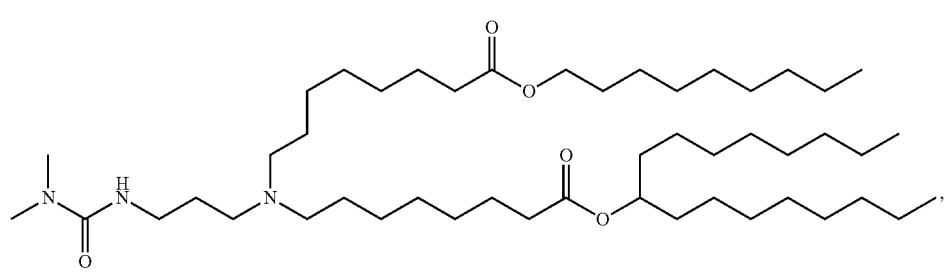
(Compound 611)
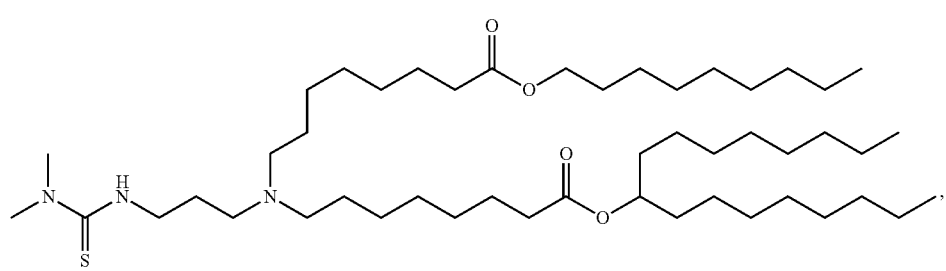
(Compound 612)
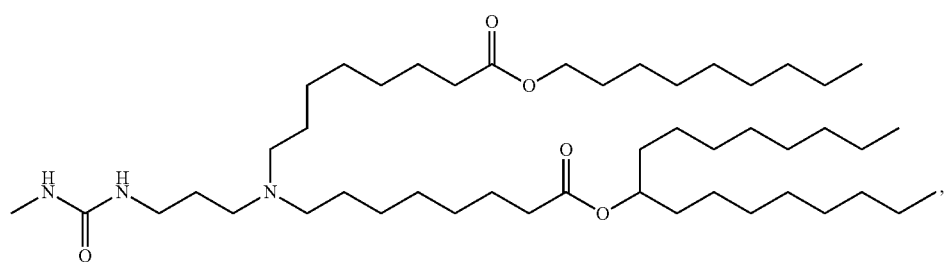
(Compound 613)
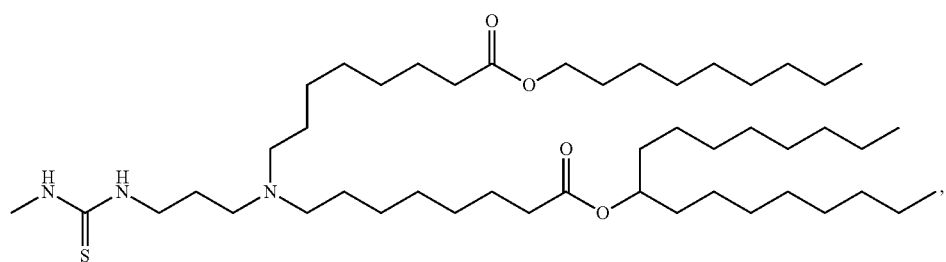
(Compound 614)
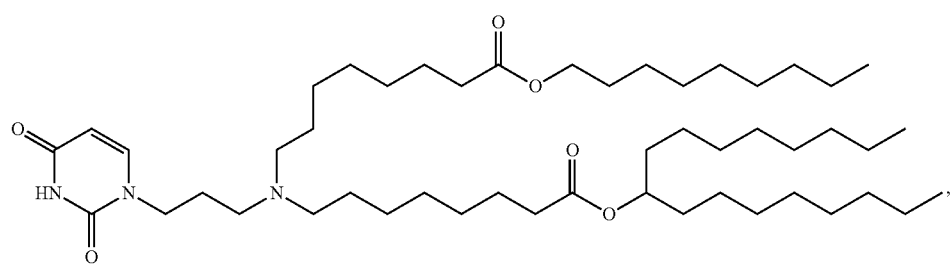

(Compound 615)
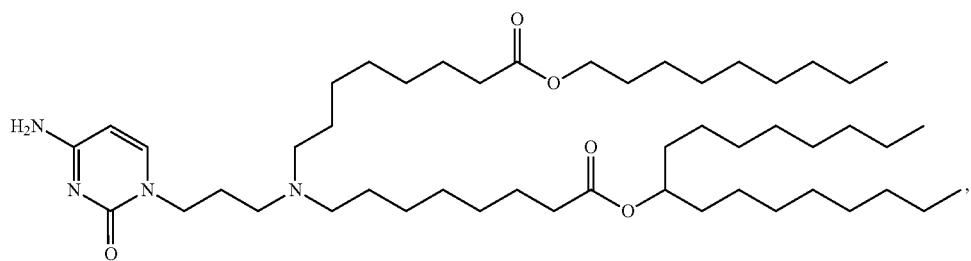
(Compound 616)
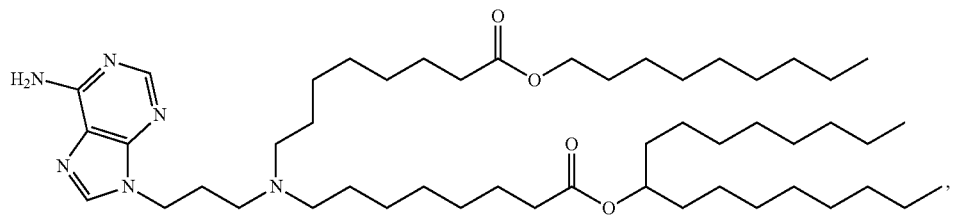
(Compound 617)
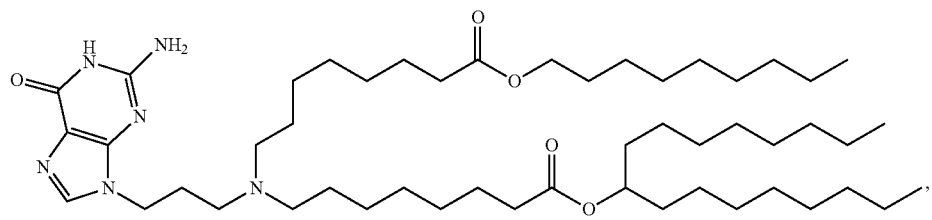
(Compound 618)
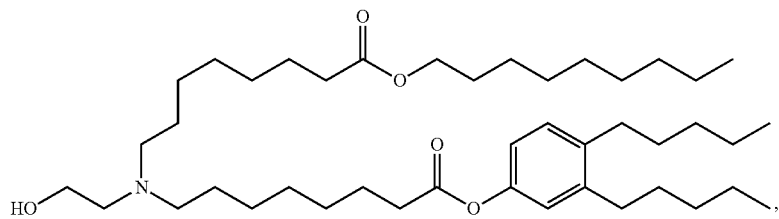
(Compound 619)
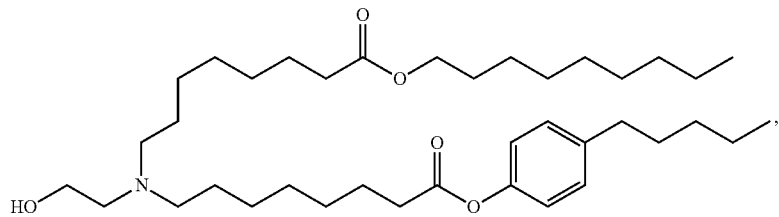
(Compound 620)
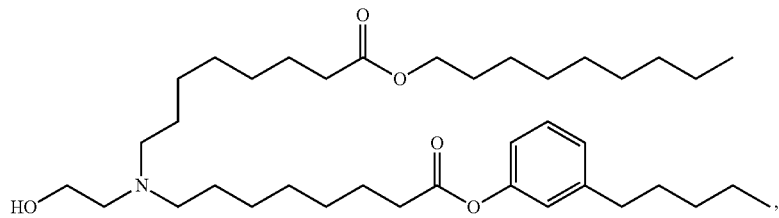
(Compound 621)
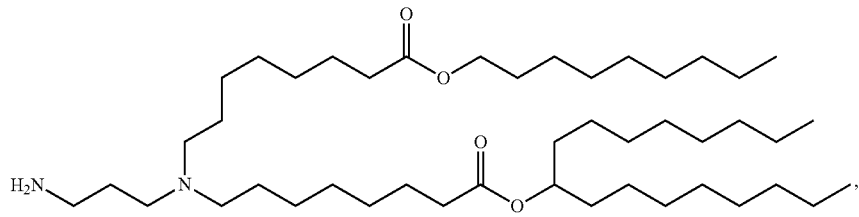

(Compound 622)
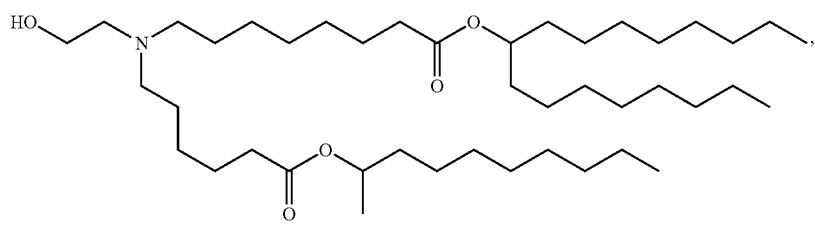
(Compound 623)
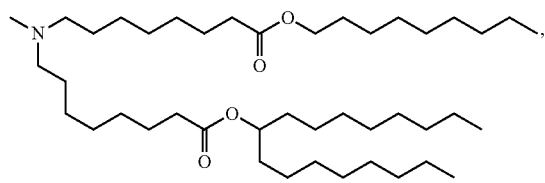
(Compound 624)
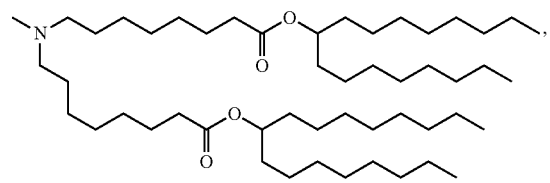
(Compound 625)
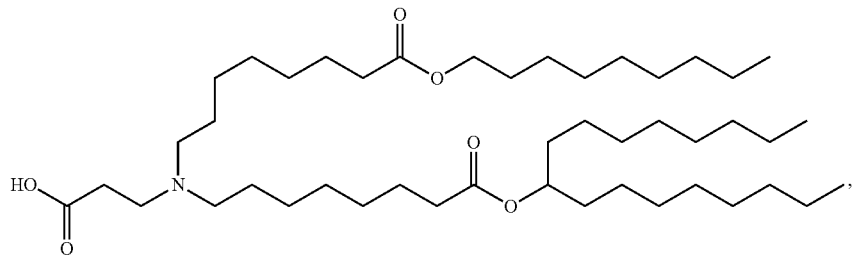
(Compound 626)
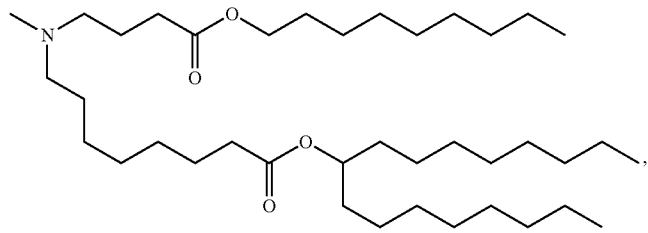
(Compound 627)
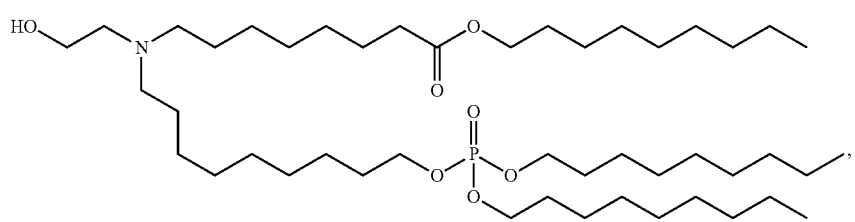
(Compound 628)
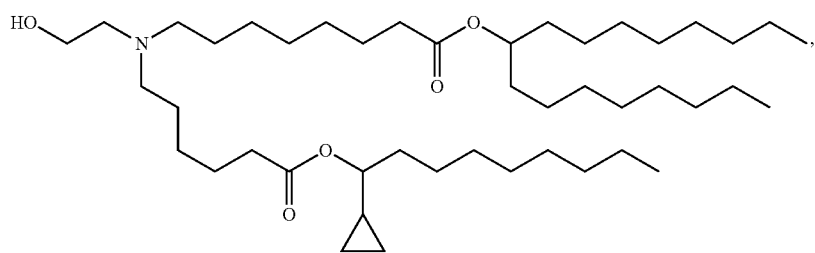

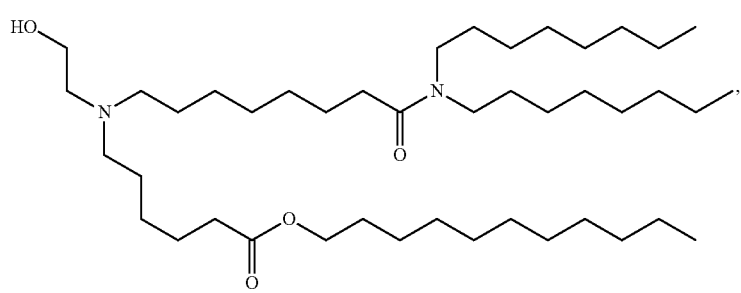
(Compound 629)
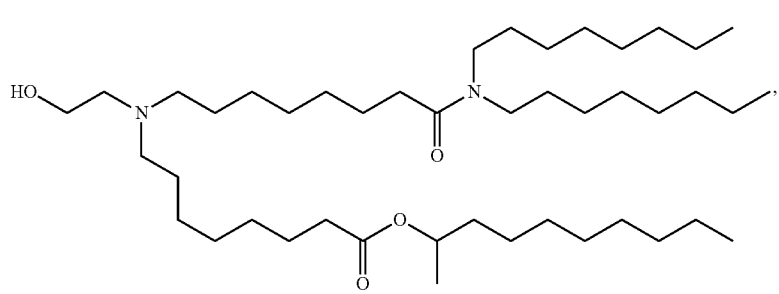
(Compound 630)
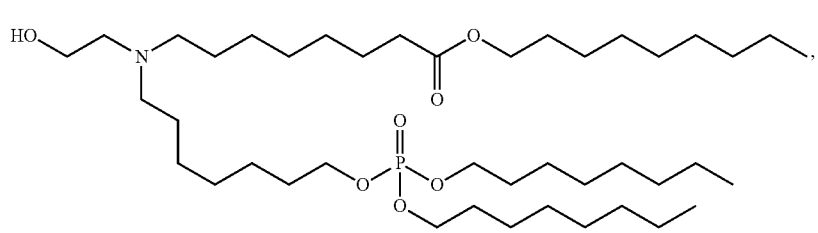
(Compound 631)
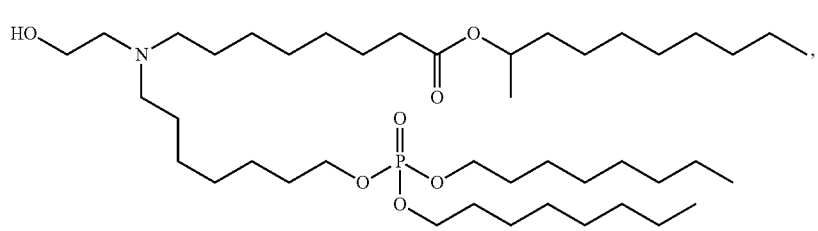
(Compound 632)
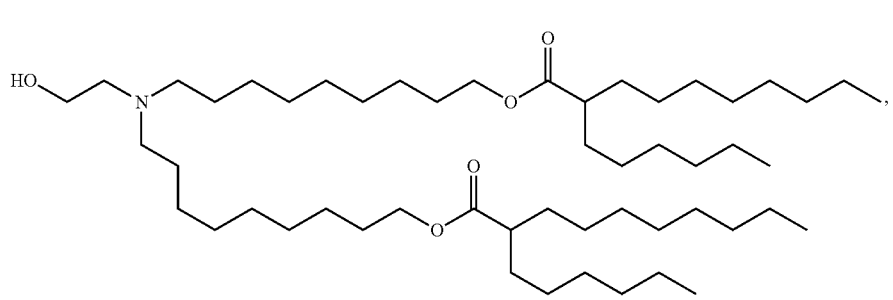
(Compound 633)
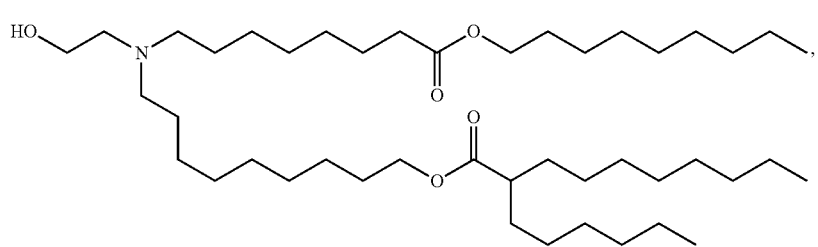
(Compound 634)

-continued
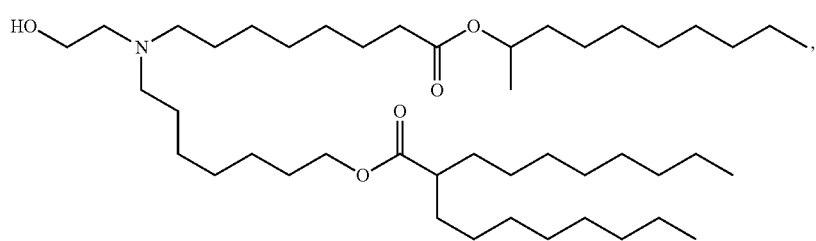
(Compound 635)
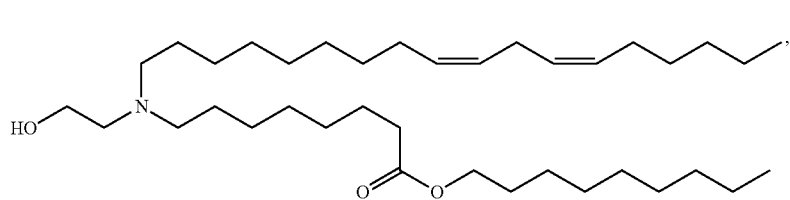
(Compound 636)
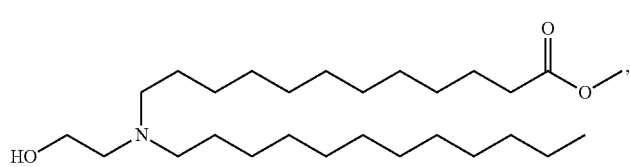
(Compound 637)
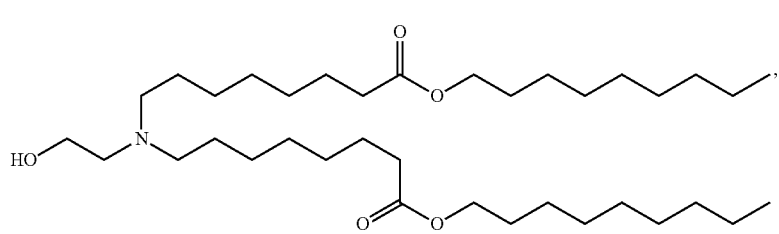
(Compound 638)
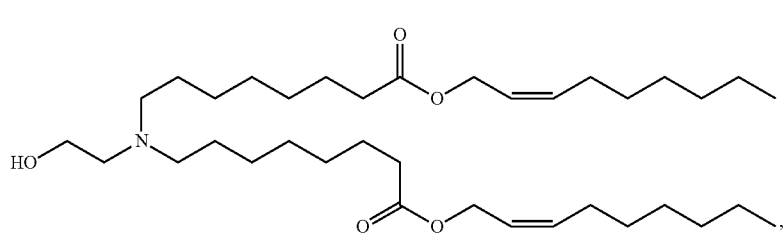
(Compound 639)
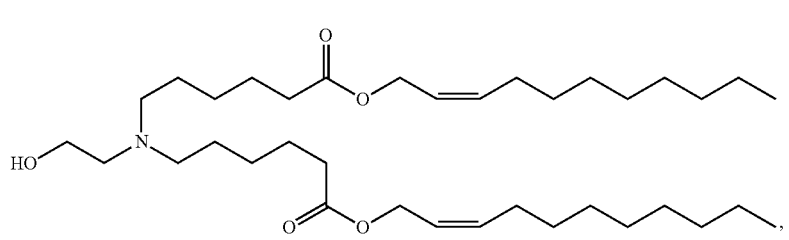
(Compound 640)
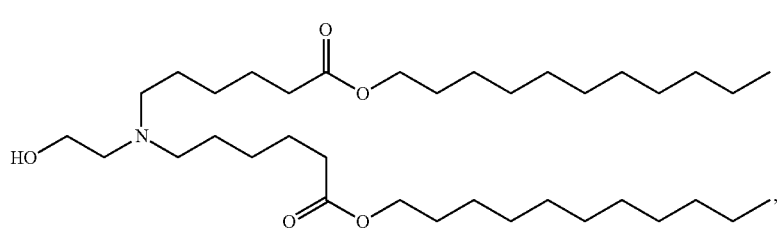
(Compound 641)

-continued
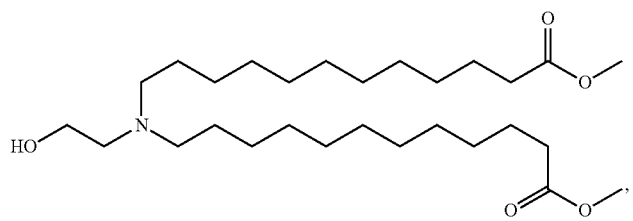
(Compound 642)
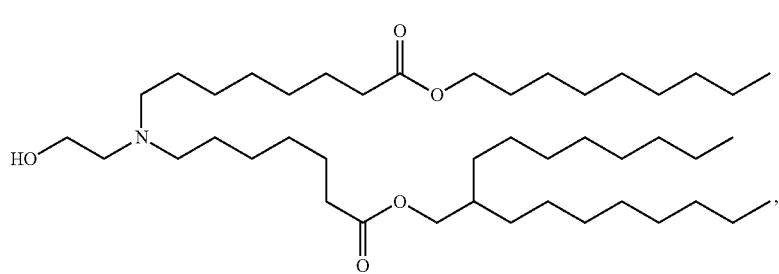
(Compound 643)
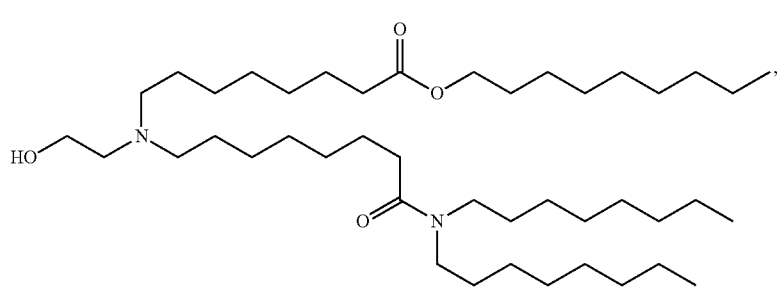
(Compound 644)
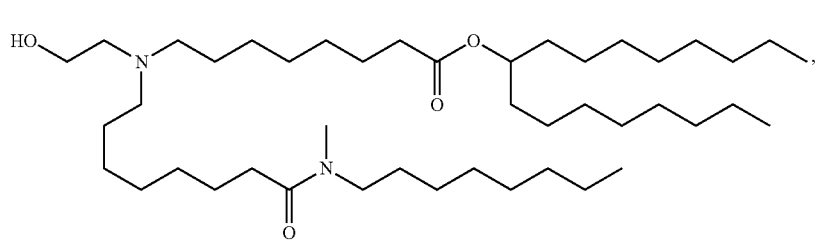
(Compound 645)
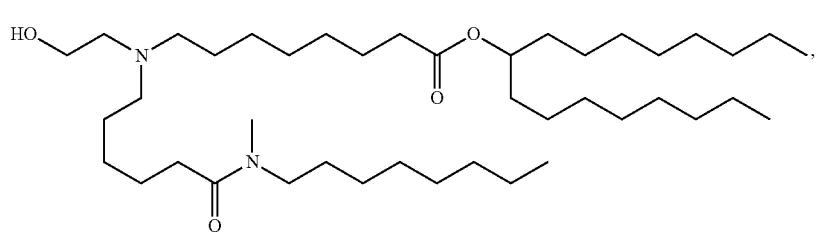
(Compound 646)
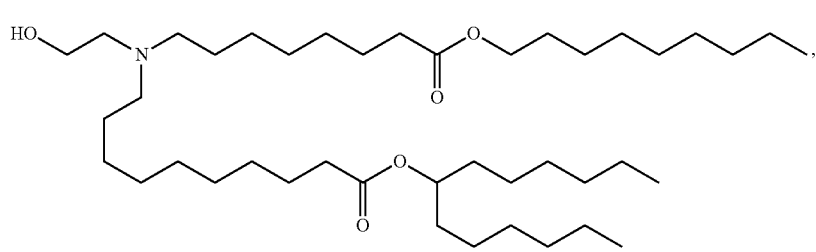
(Compound 647)

-continued
(Compound 648)
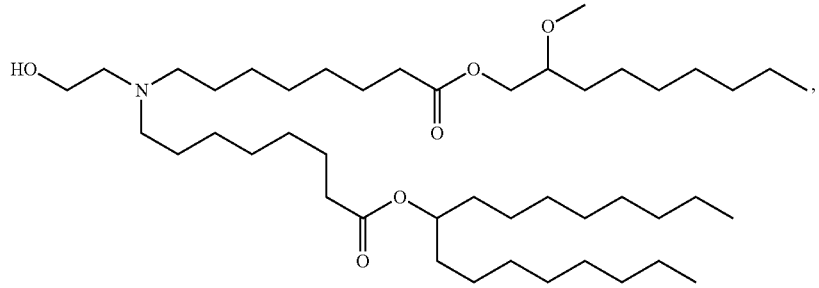
(Compound 649)
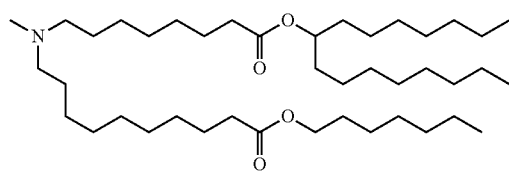
(Compound 650)
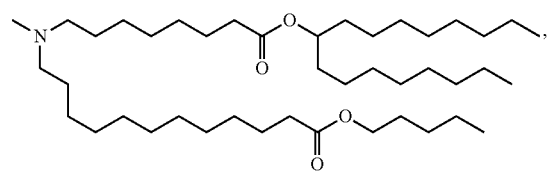
(Compound 651)
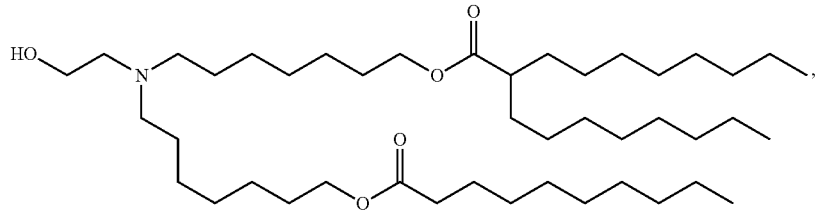
(Compound 652)
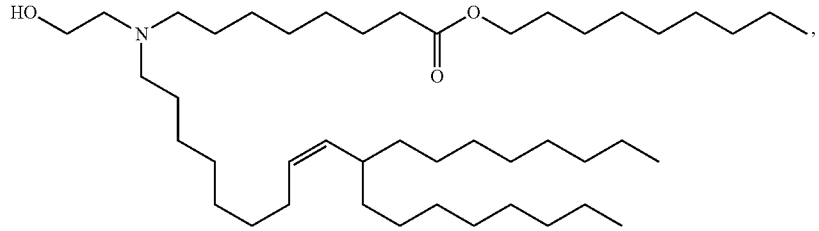
(Compound 653)
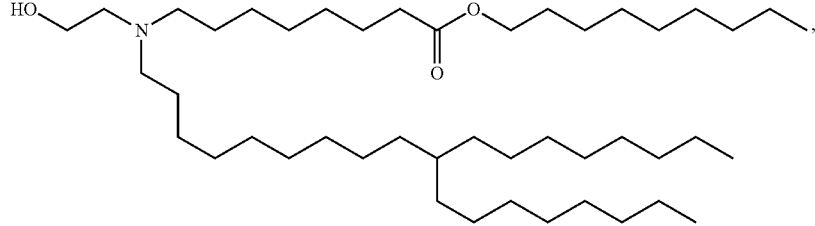
(Compound 654)
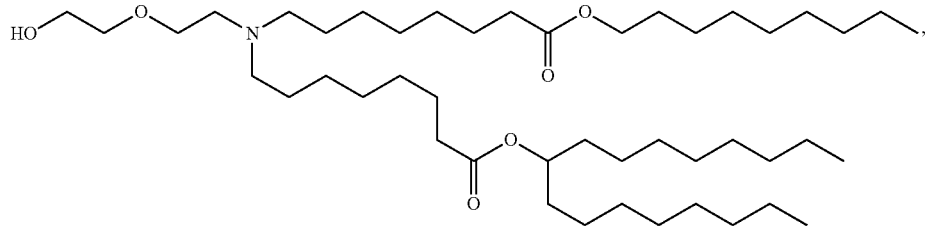

(Compound 655)
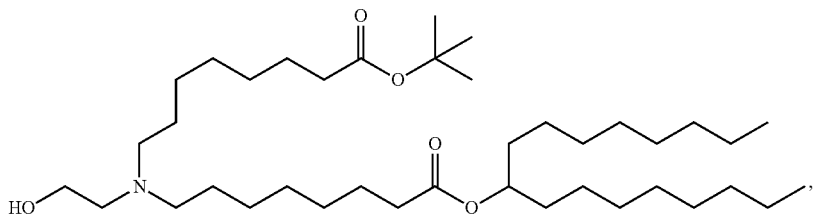
(Compound 656)
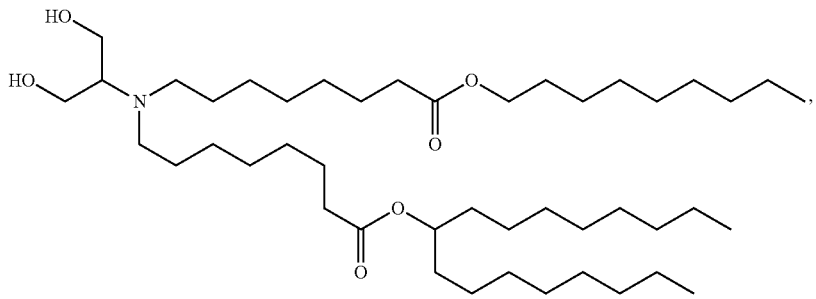
(Compound 657)
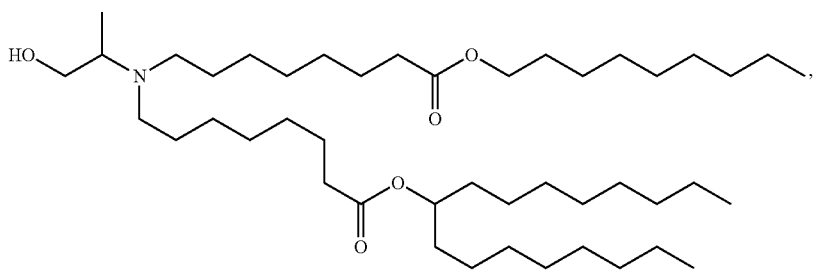
(Compound 658)
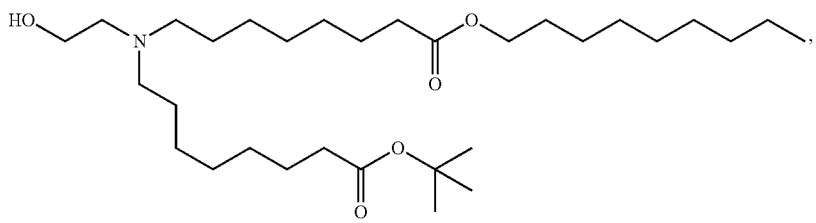
(Compound 659)
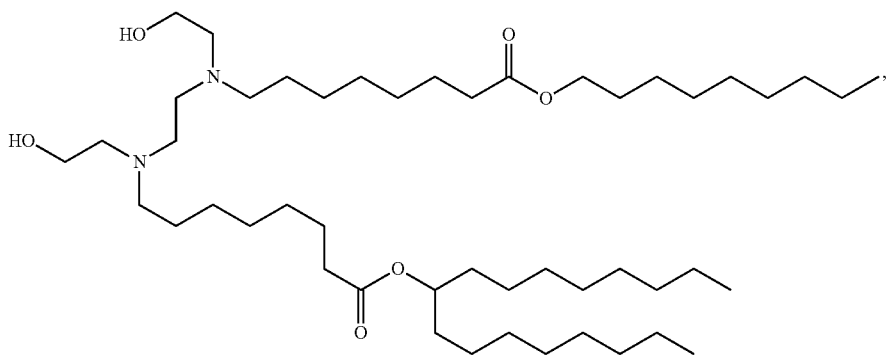

-continued
(Compound 660)
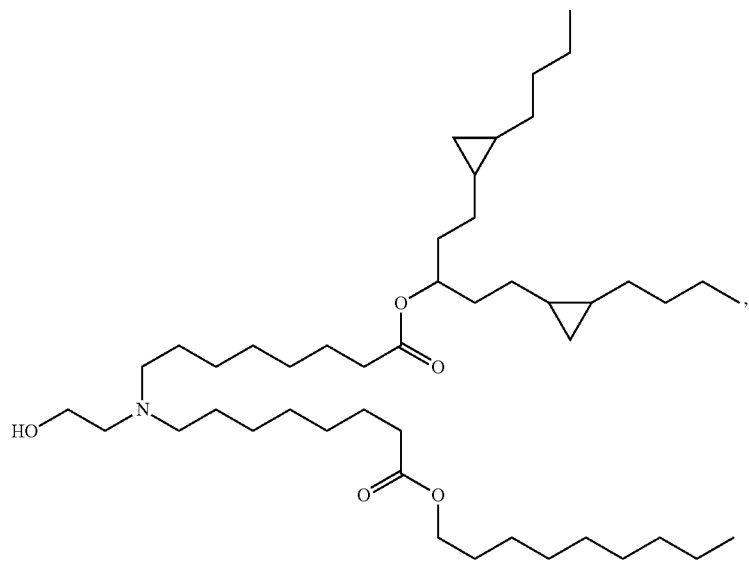
(Compound 661)
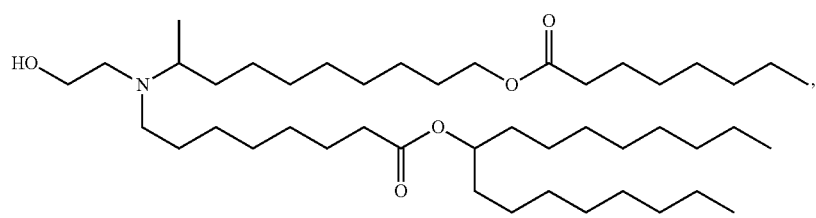
(Compound 662)
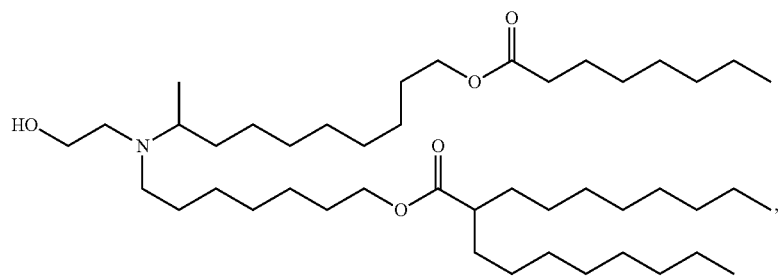
(Compound 663)
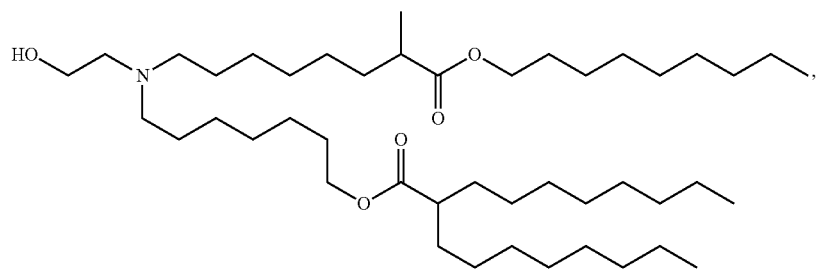
(Compound 664)
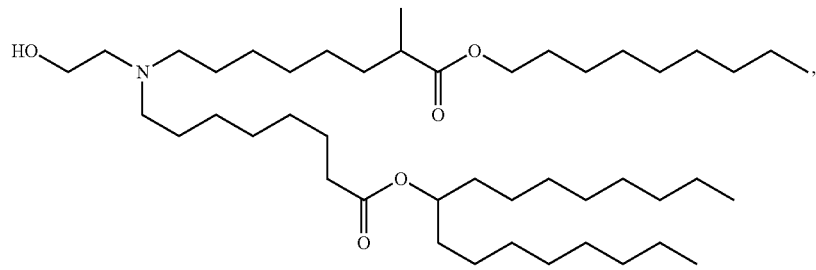

-continued
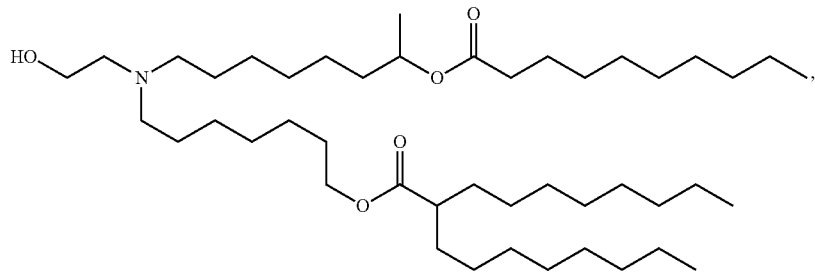
(Compound 665)
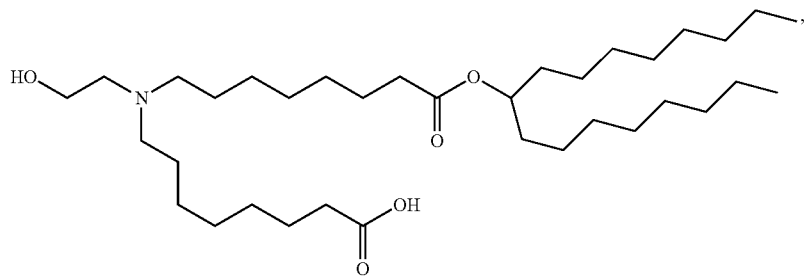
(Compound 666)
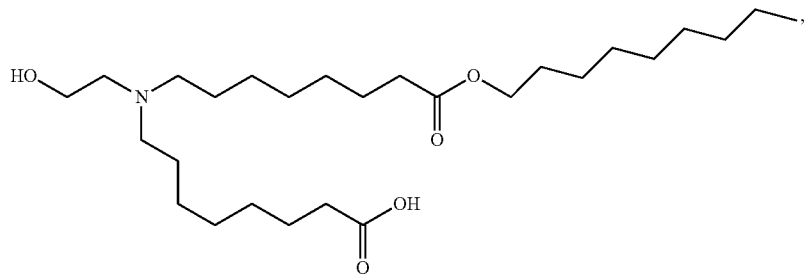
(Compound 667)
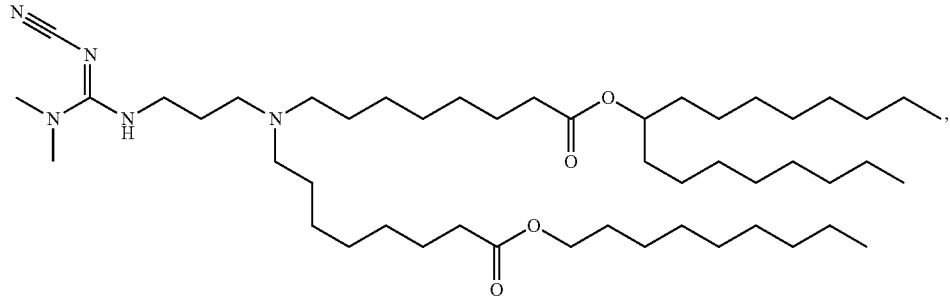
(Compound 668)
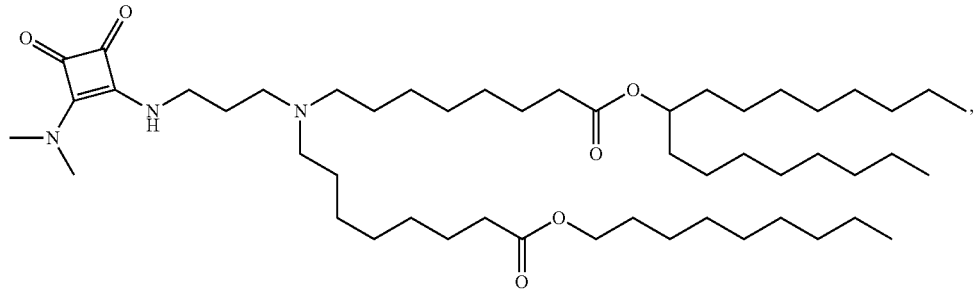
(Compound 669)

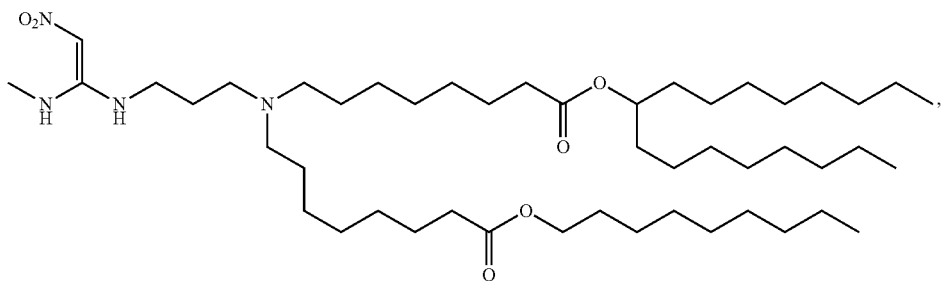
(Compound 670)
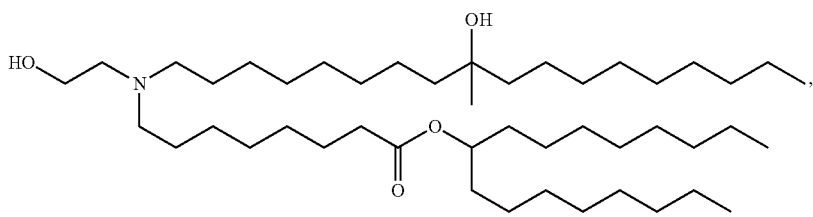
(Compound 671)
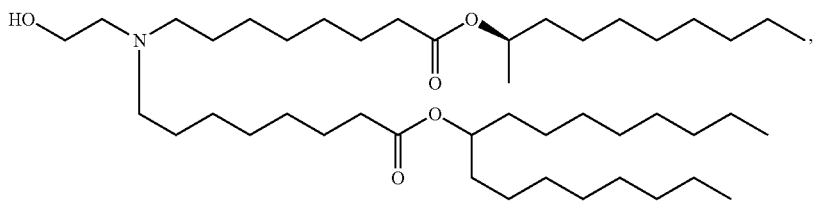
(Compound 672)
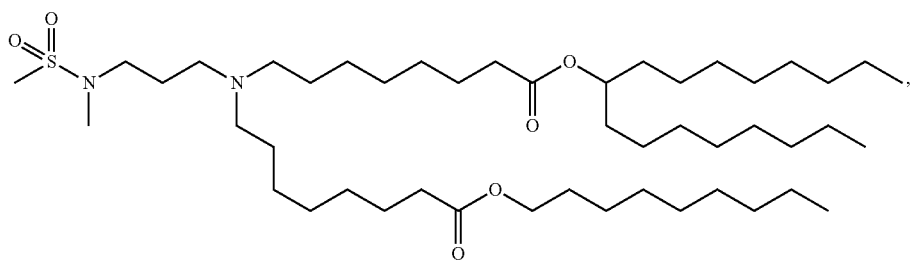
(Compound 673)
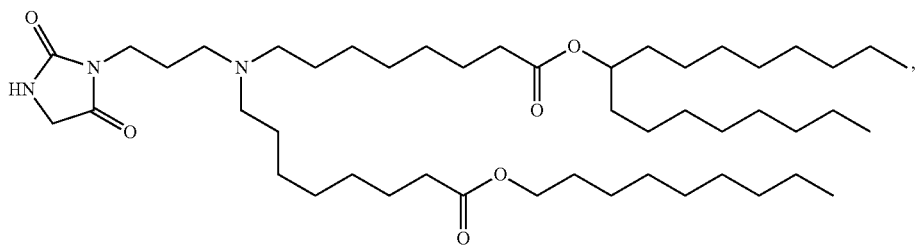
(Compound 674)
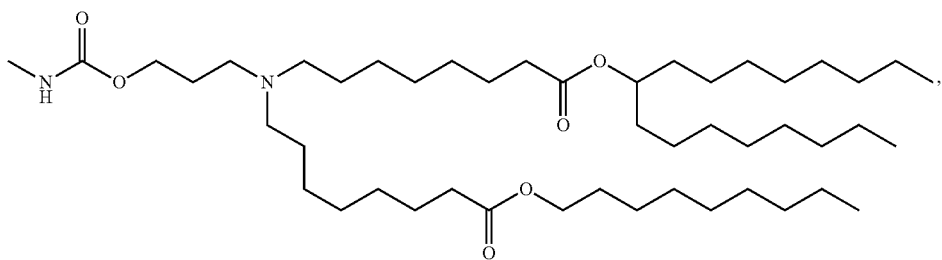
(Compound 675)

-continued
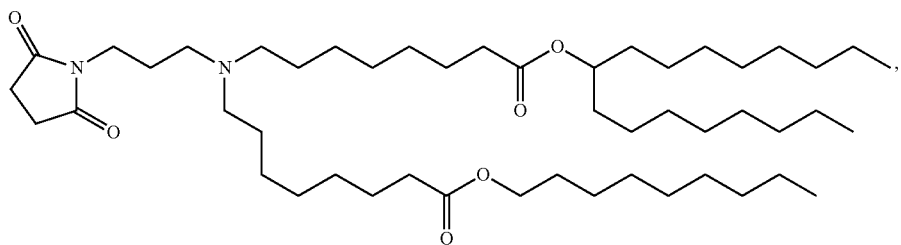
(Compound 676)
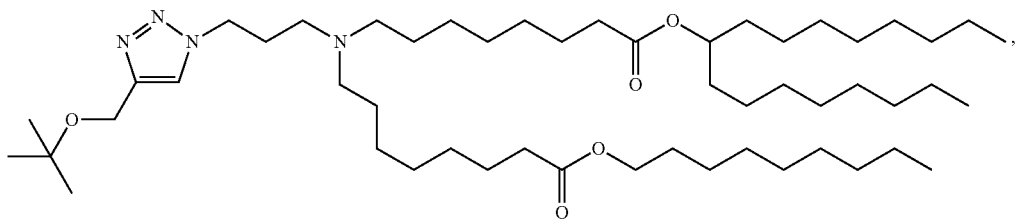
(Compound 677)
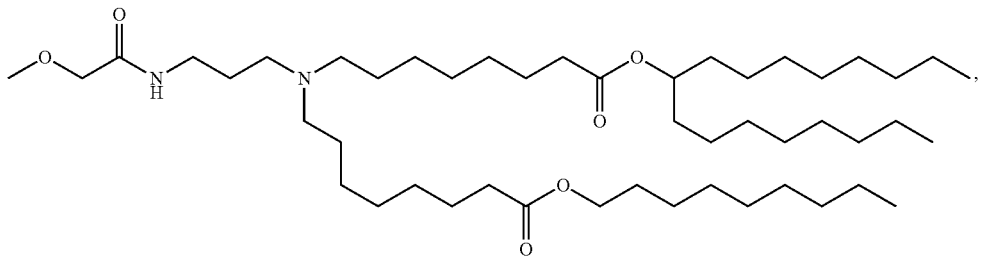
(Compound 678)
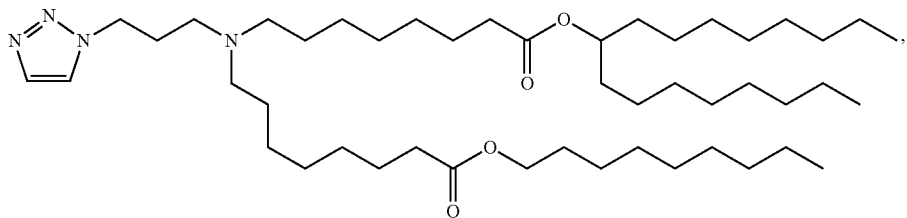
(Compound 679)
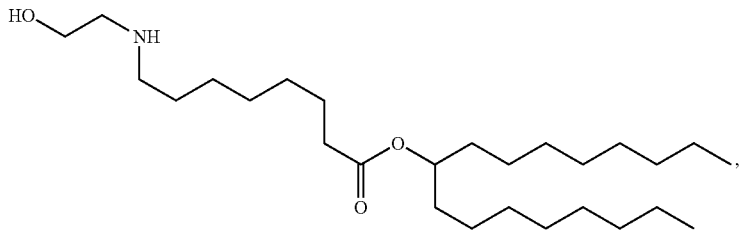
(Compound 680)
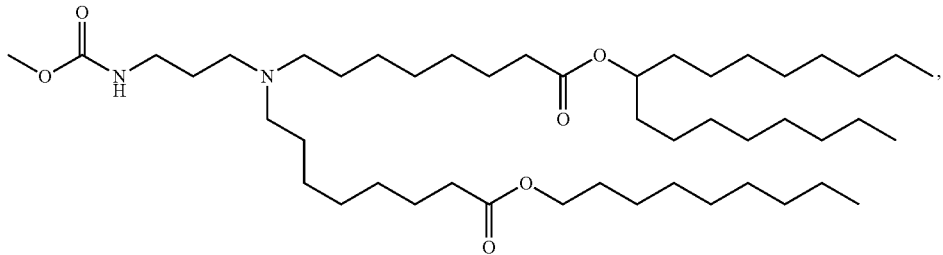
(Compound 681)

-continued
(Compound 682)
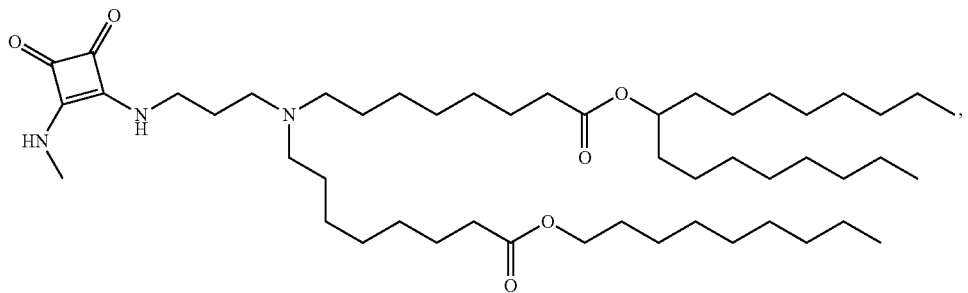
(Compound 683)
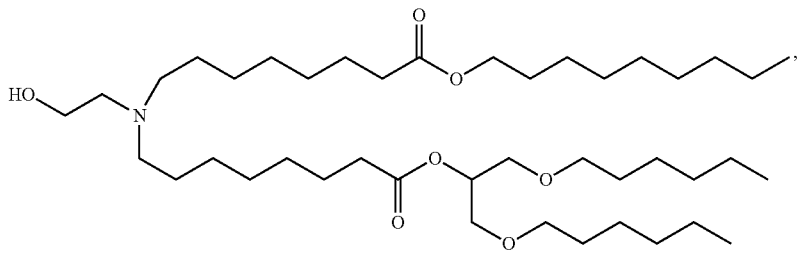
(Compound 684)
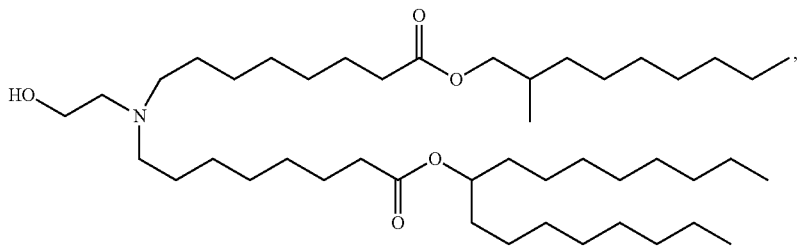
(Compound 685)
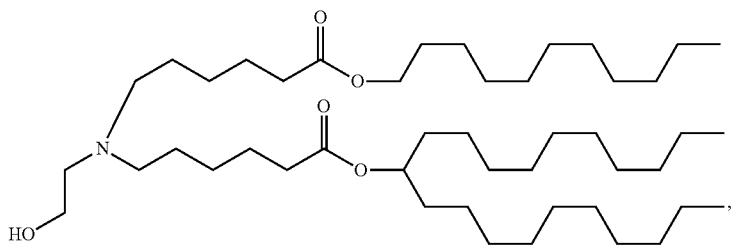
(Compound 686)
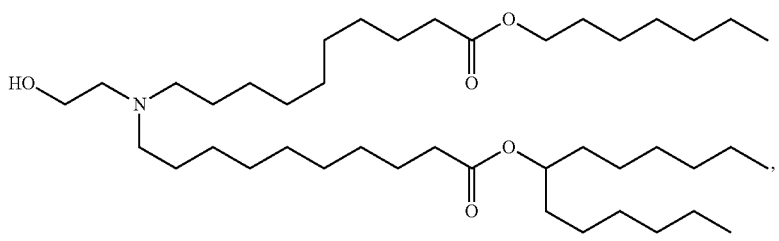
(Compound 687)
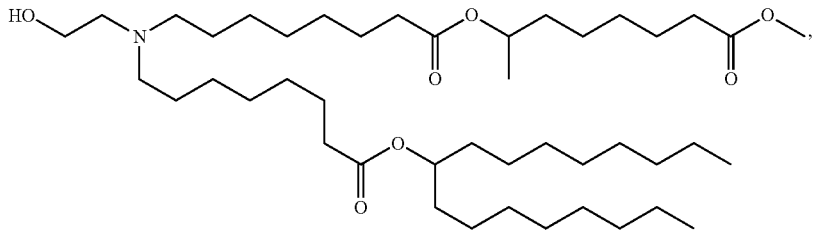

-continued
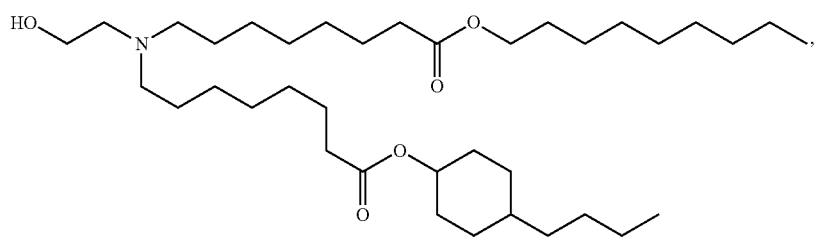
(Compound 688)
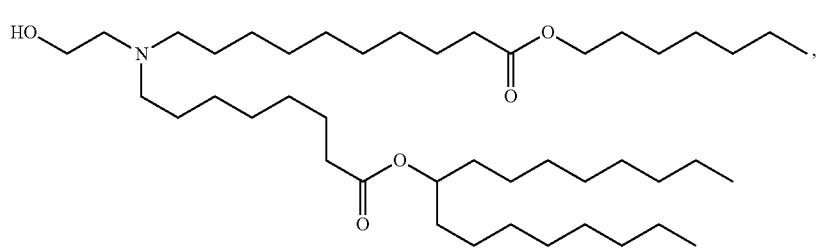
(Compound 689)
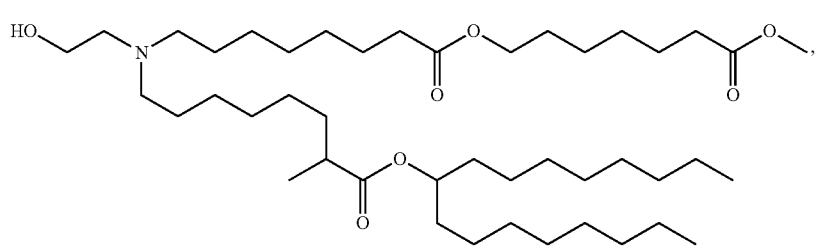
(Compound 690)
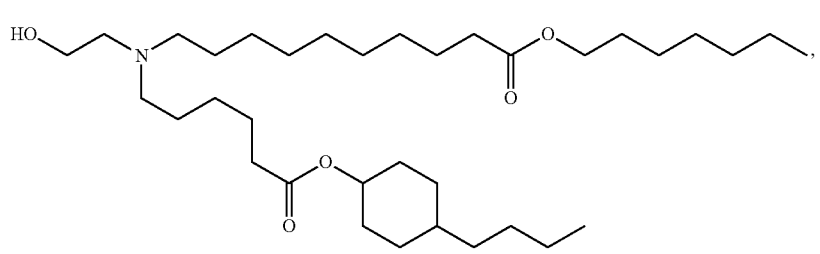
(Compound 691)
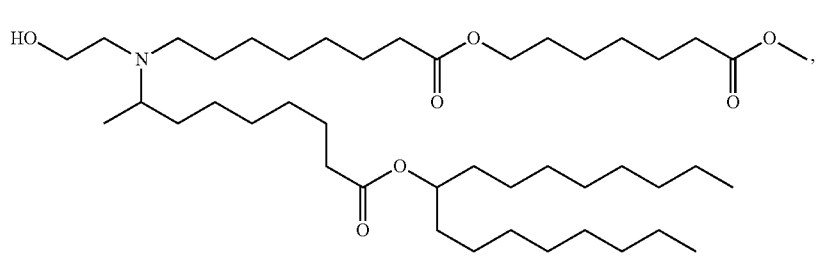
(Compound 692)
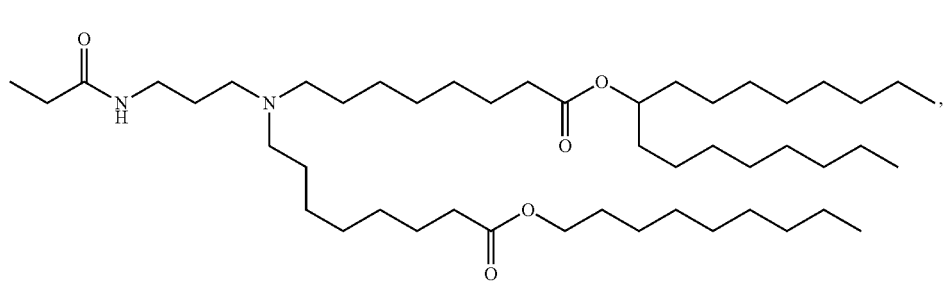
(Compound 693)

(Compound 694)
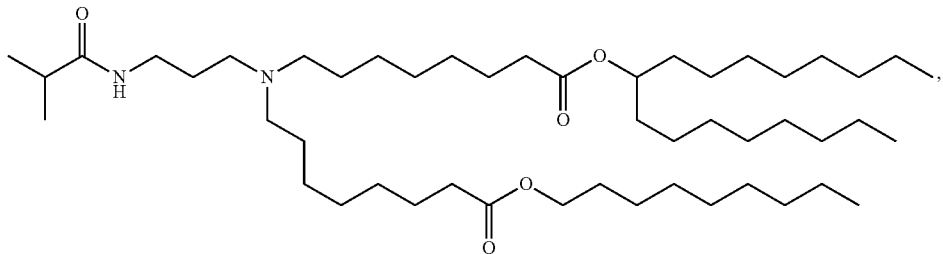
(Compound 695)
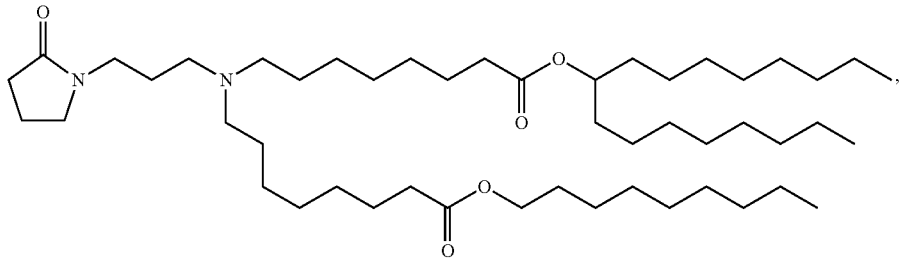
(Compound 696)
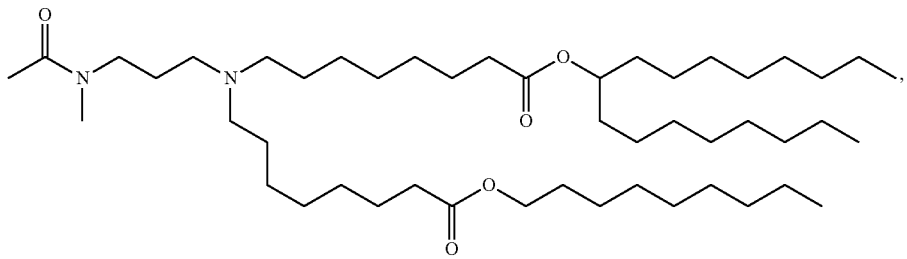
(Compound 697)
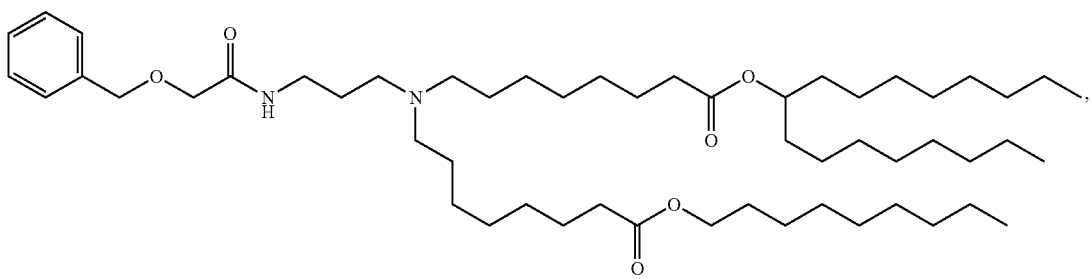
(Compound 698)
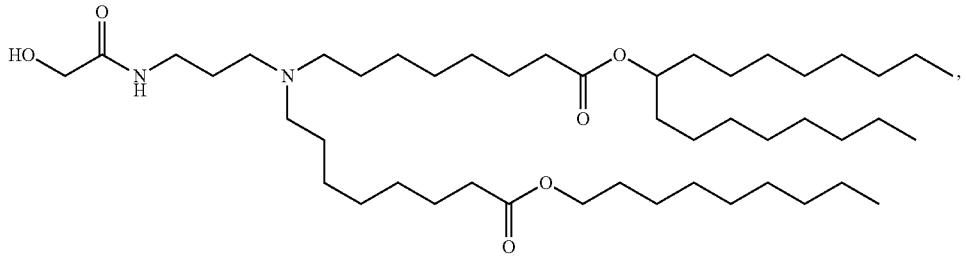
(Compound 699)
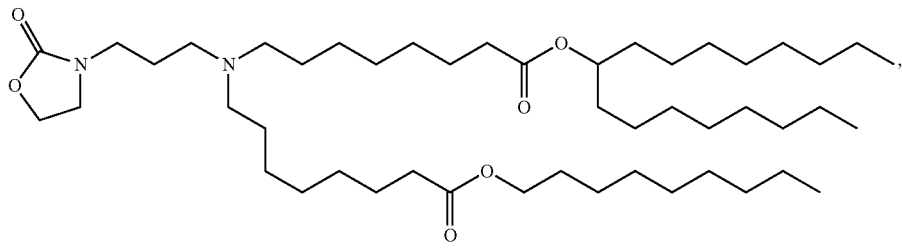

(Compound 700)
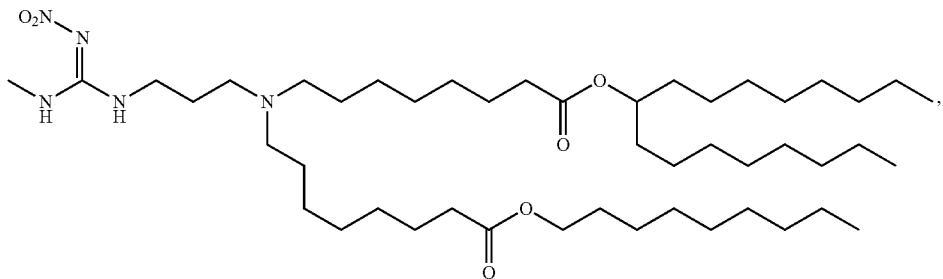
(Compound 701)
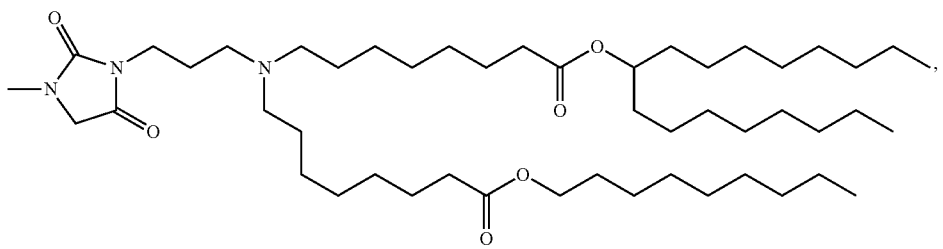
(Compound 702)
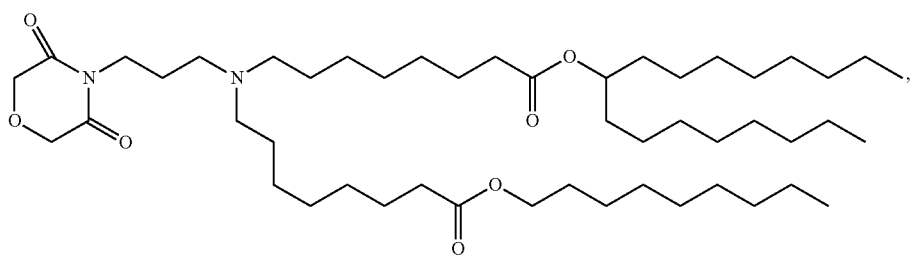
(Compound 703)
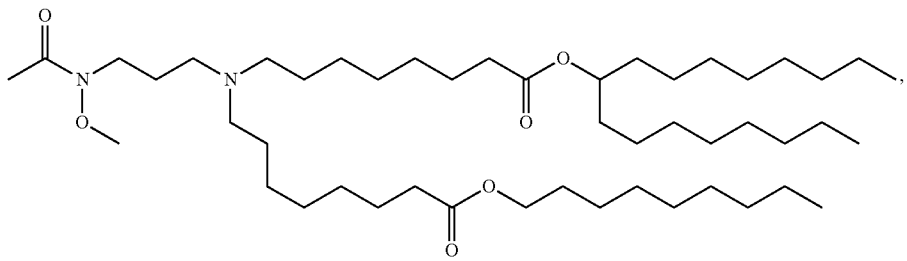
(Compound 704)
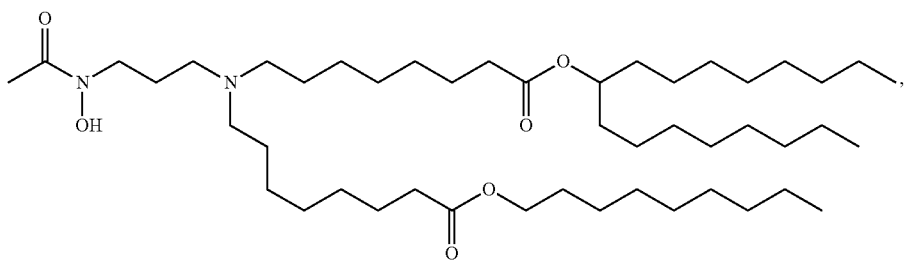
(Compound 705)
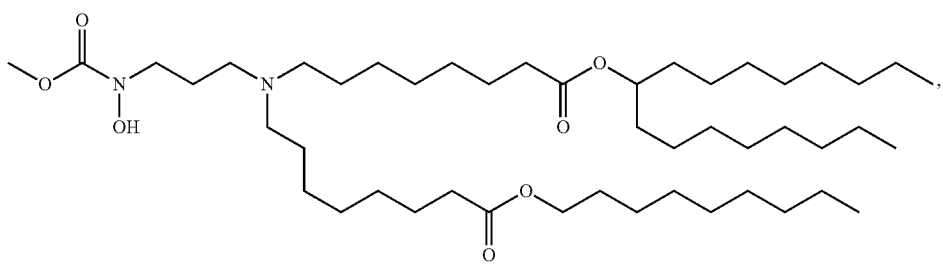

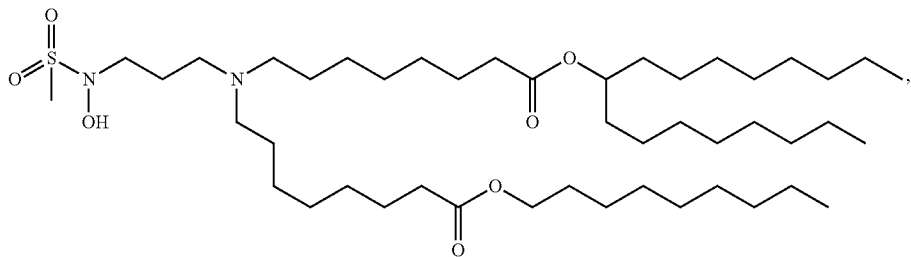
(Compound 706)
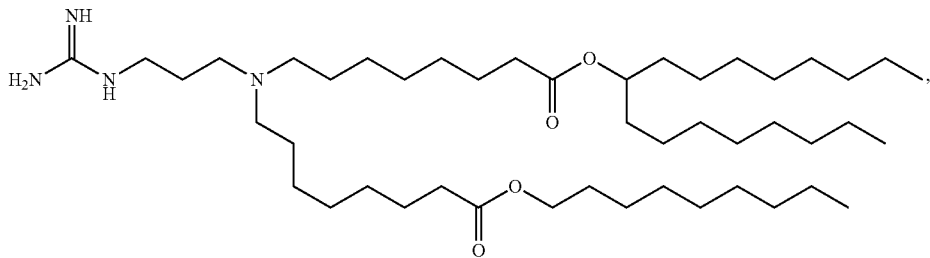
(Compound 707)
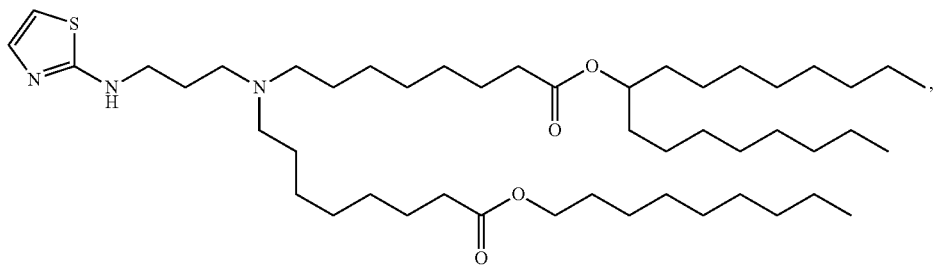
(Compound 708)
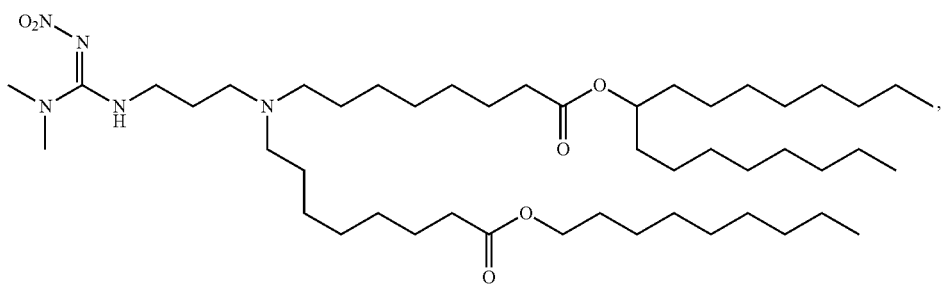
(Compound 709)
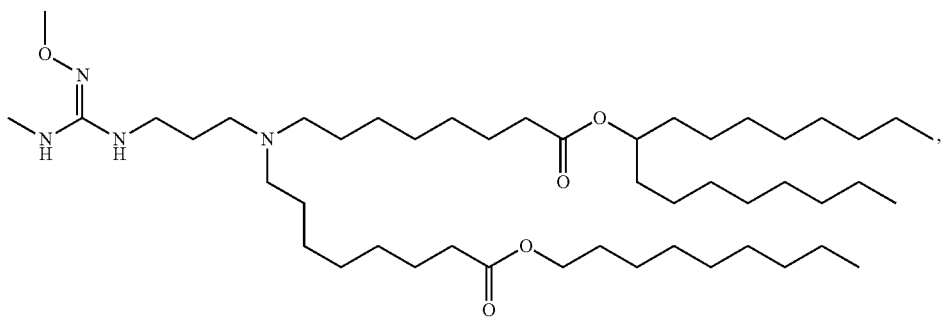
(Compound 710)

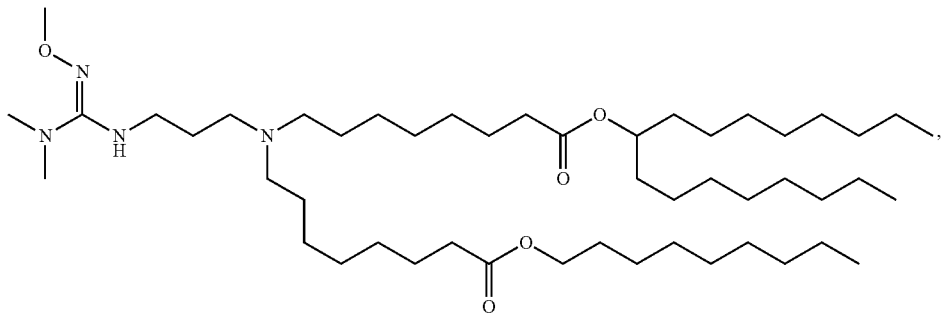
(Compound 711)
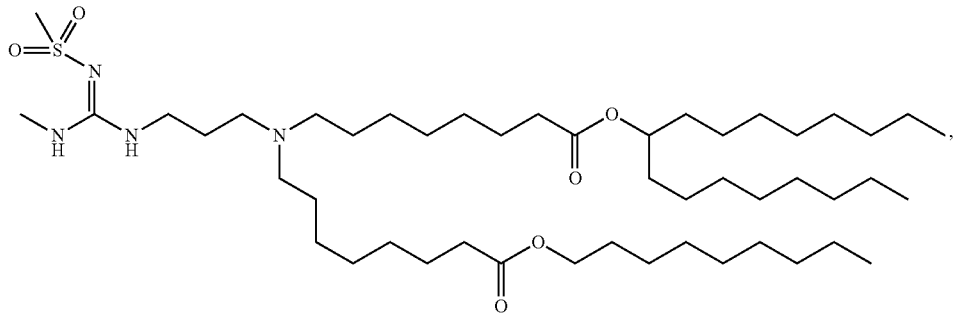
(Compound 712)
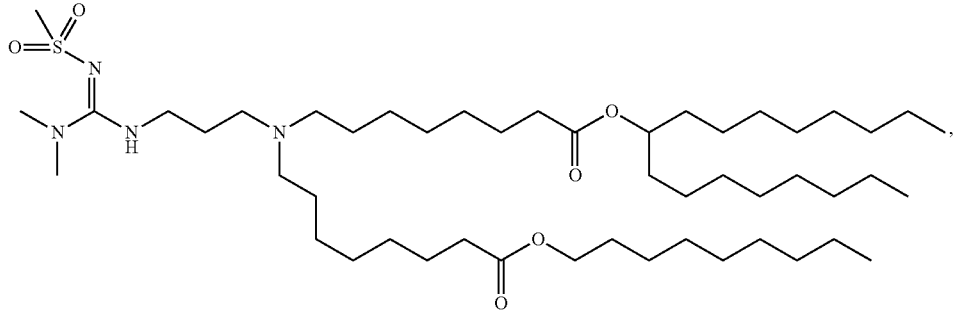
(Compound 713)
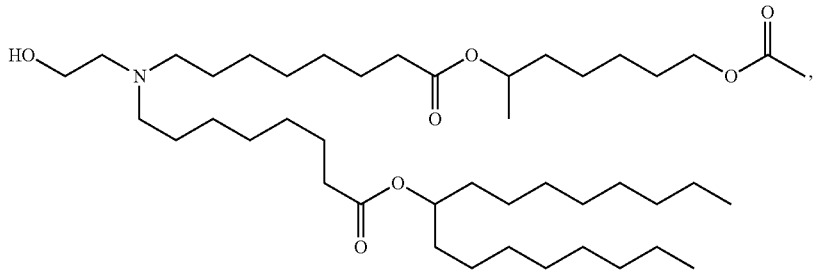
(Compound 714)
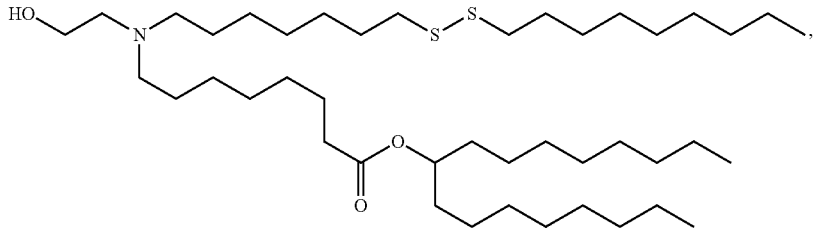
(Compound 715)

-continued
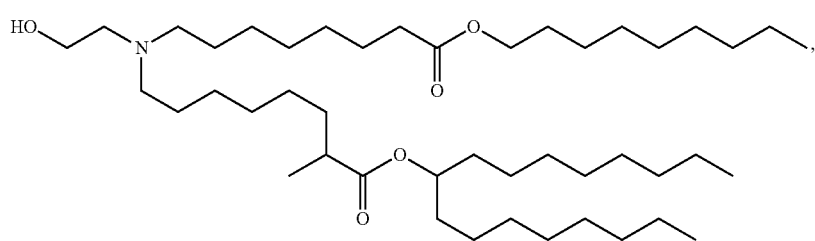
(Compound 716)
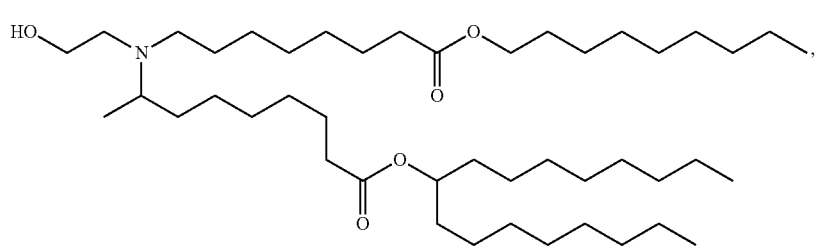
(Compound 717)
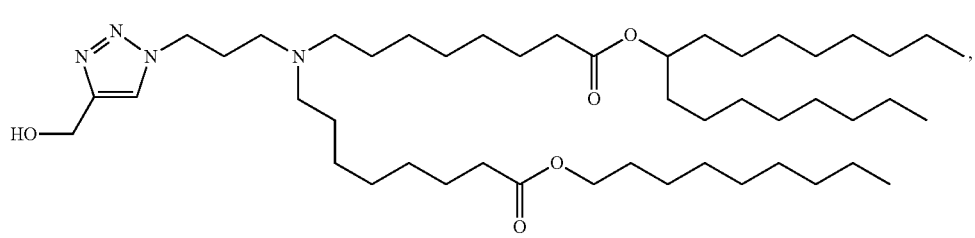
(Compound 718)
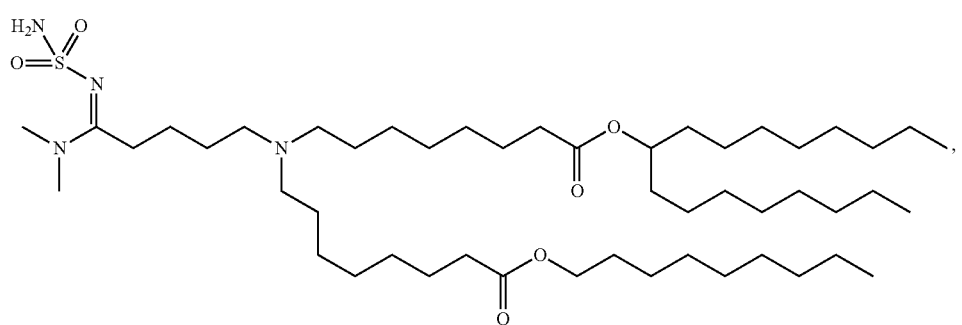
(Compound 719)
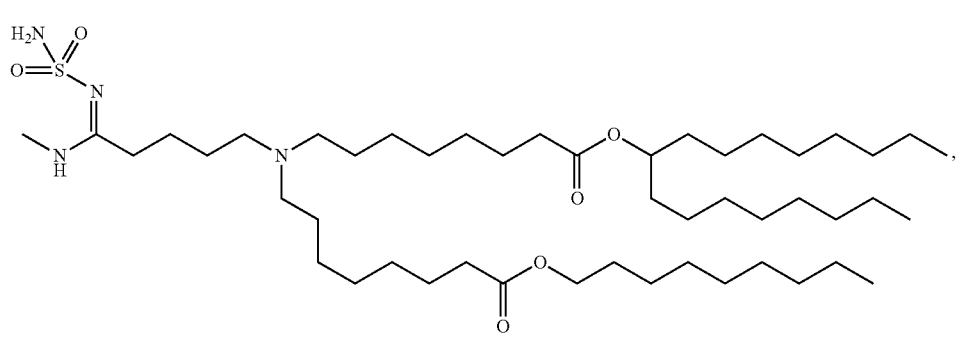
(Compound 720)

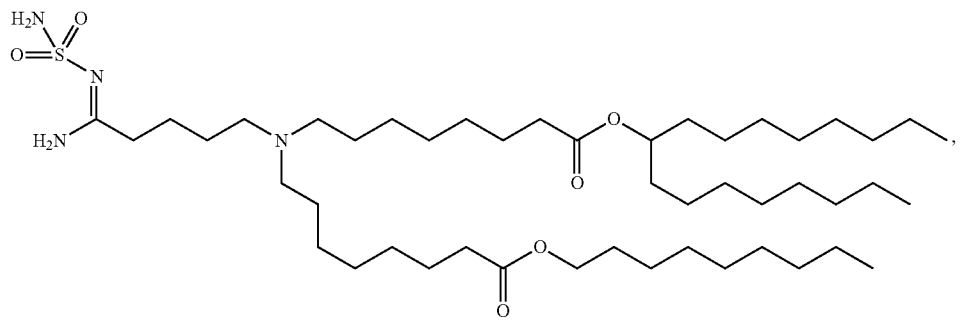
(Compound 721)
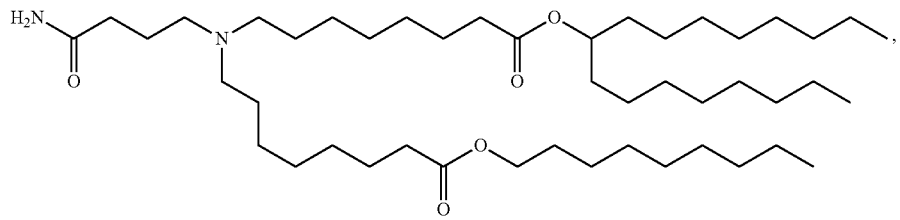
(Compound 722)
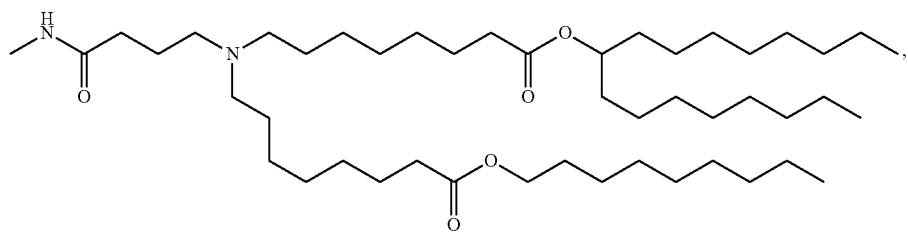
(Compound 723)
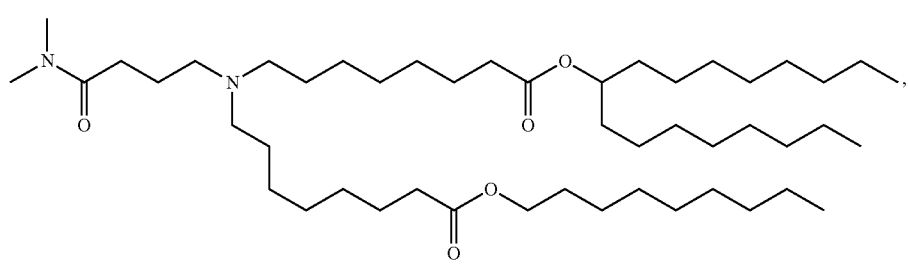
(Compound 724)
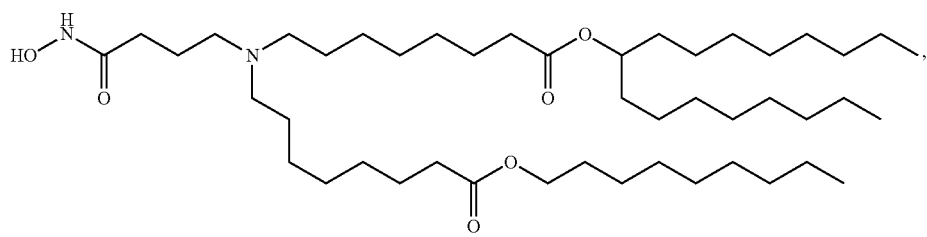
(Compound 725)
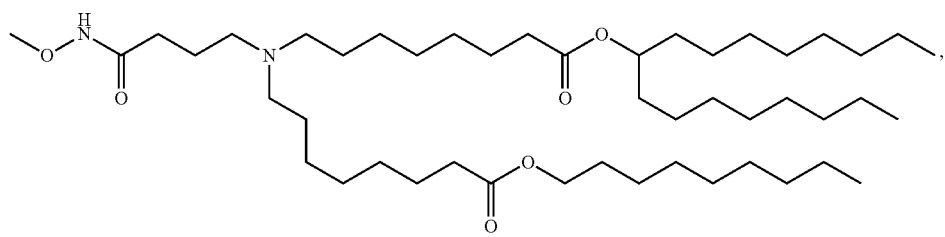
(Compound 726)

(Compound 727)

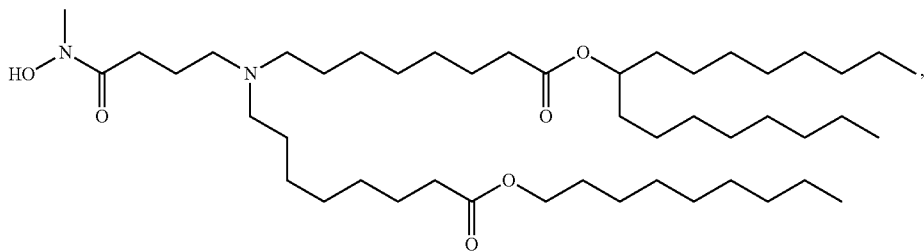

(Compound 728)

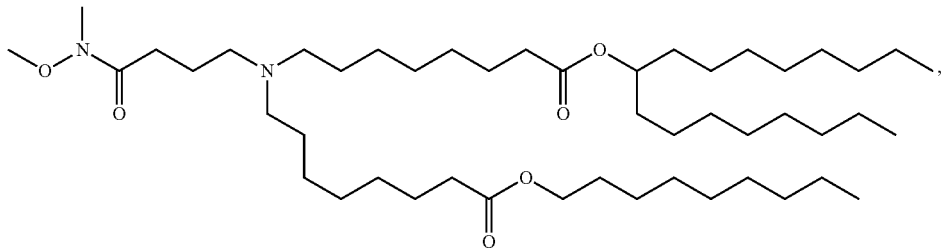

(Compound 729)

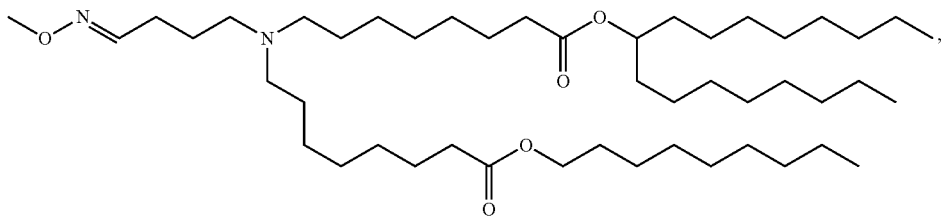

(Compound 730)

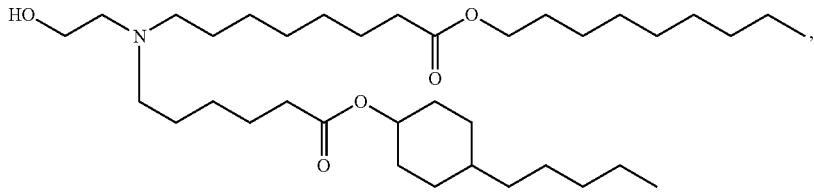

and salts and isomers thereof.

In some embodiments, a nanoparticle comprises the following compound:

(Compound 731)

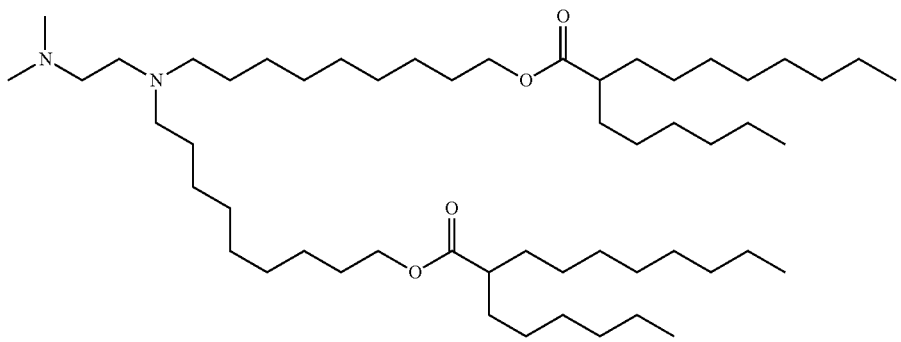

or salts and isomers thereof.

In some embodiments, the disclosure features a nanoparticle composition including a lipid component comprising a compound as described herein (e.g., a compound according to Formula (X), (XA), (XI), (XIa), (XIb), (XIc), (XId) or (XIe)).

Non-cationic Lipids, Including Non-cationic Helper Lipids

The lipid component of the nanoparticle may include any neutral and/or non-cationic lipid (e.g., lipids that are neutral or non-cationic lipid at physiological pH). Non-cationic lipid lipids may include, but are not limited to, fatty acids, glycerolipids, and prenol lipids. In certain embodiments, the non-cationic lipid is a fatty acid. The fatty acid may be saturated or unsaturated. Examples of unsaturated fatty acids include, but are not limited to, myristoleic acid, palmitoleic acid sapienic acid, oleic acid, elaidic acid, vaccenic acid, linoleic acid, linoelaidic acid, alpha-linoelaidic acid arachidonic acid, eicosapentaenoic acid, erucic acid, docosahexanoic acid, or any cis/trans double-bond isomers thereof. In certain embodiments, the lipid is oleic acid. In certain embodiments, the lipid is an isomer of oleic acid (e.g., the double bond is in a different location along the aliphatic chain relative to oleic acid). In certain embodiments, the lipid is an analog of oleic acid (e.g., the aliphatic chain is 1-10 carbons longer or 1-10 carbons shorter than the aliphatic chain of oleic acid). Examples of saturated fatty acids include, but are not limited to, caprylic acid, capric acid, lauric acid, myristic acid, palmitic acid, stearic acid, arachidic acid, behenic acid, lignoceric acid, and cerotic acid. In certain embodiments, the non-cationic lipid is a glycine derivative of a fatty acid (e.g., N-palitoylglycine or N-oleoglycine) In certain embodiments, the non-cationic lipid is a glycerolipid (e.g., monoglyceride, diglyceride, triglyceride). In certain embodiments, the non-cationic lipid is a monoglyceride. In certain embodiments, the non-cationic lipid is a diglyceride. In certain embodiments, the non-cationic lipid is a triglyceride. In certain embodiments, the non-cationic lipid comprises a sugar moiety (e.g., saccharide, disaccharide, polysaccharide). Examples of non-cationic lipids include, but are not limited to, the following:

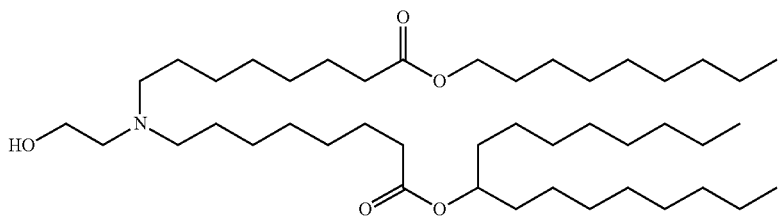

(Cmpd18)

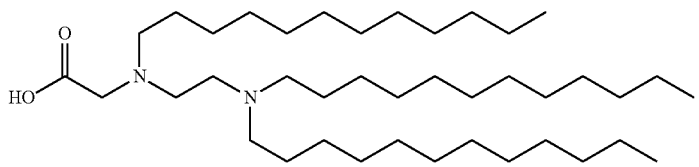

(Cmpd393)

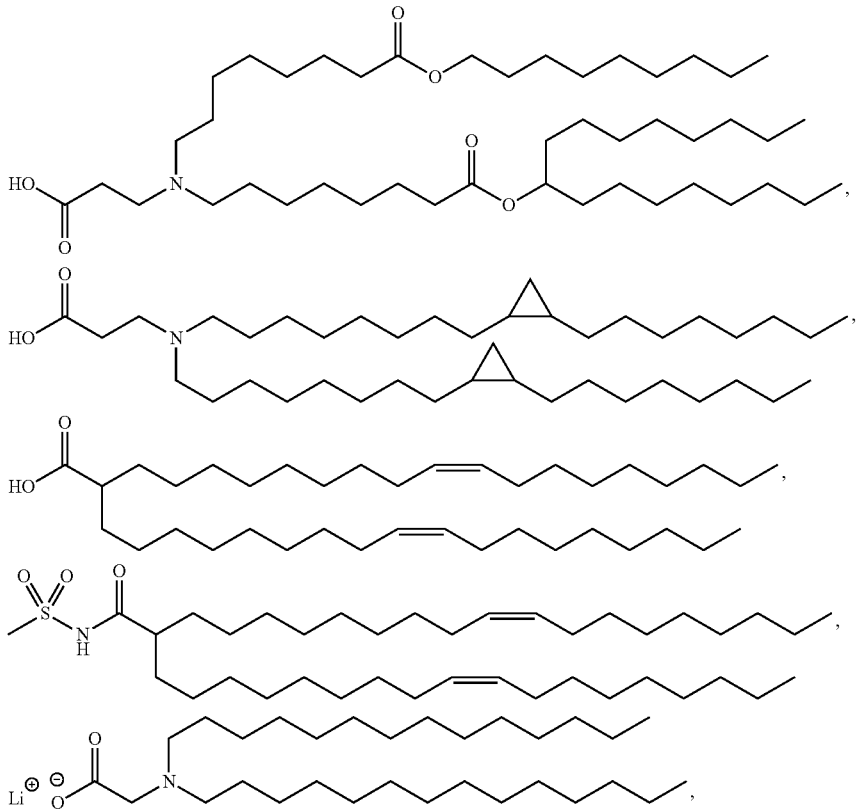

(Cmpd125)

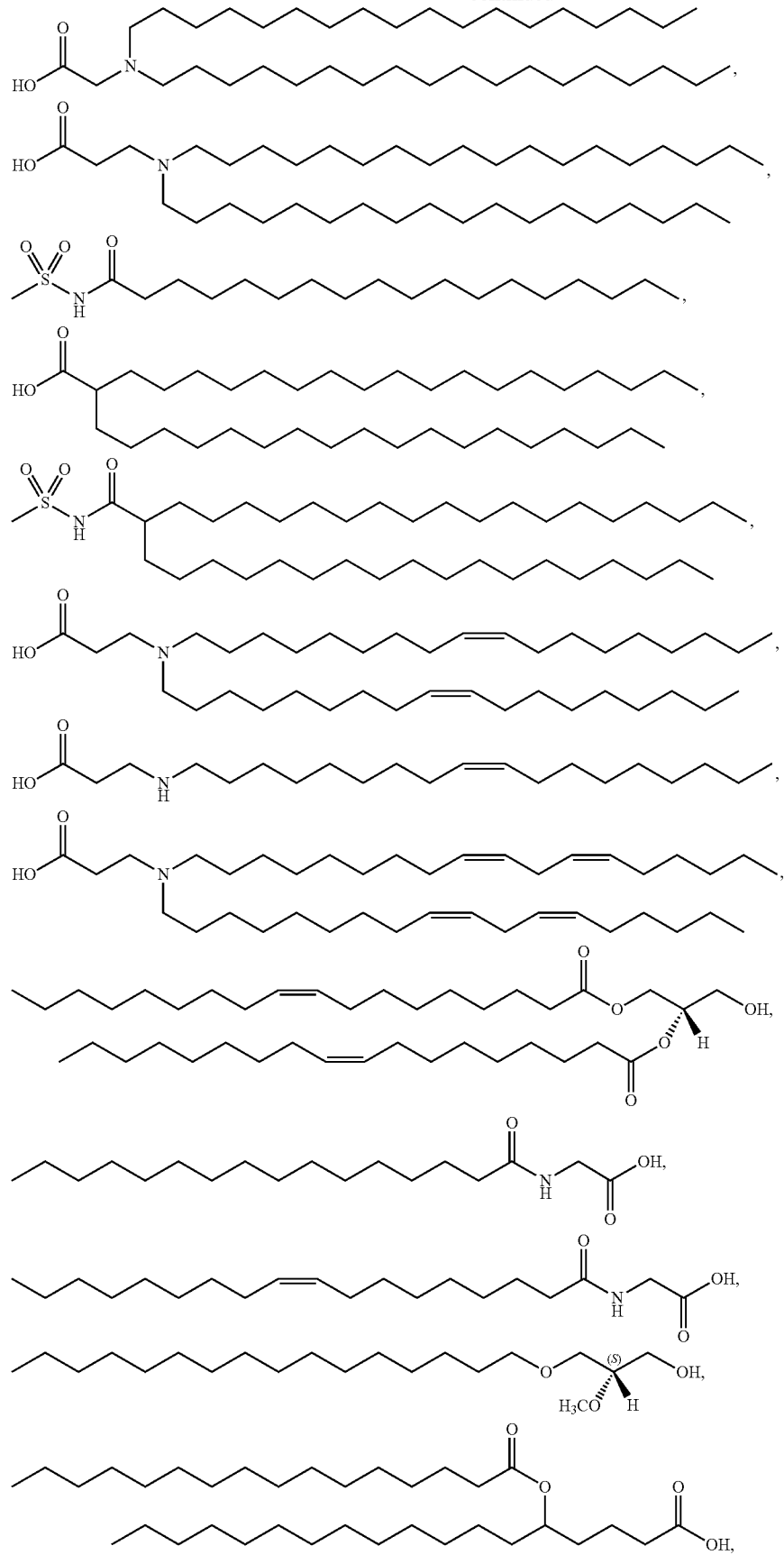

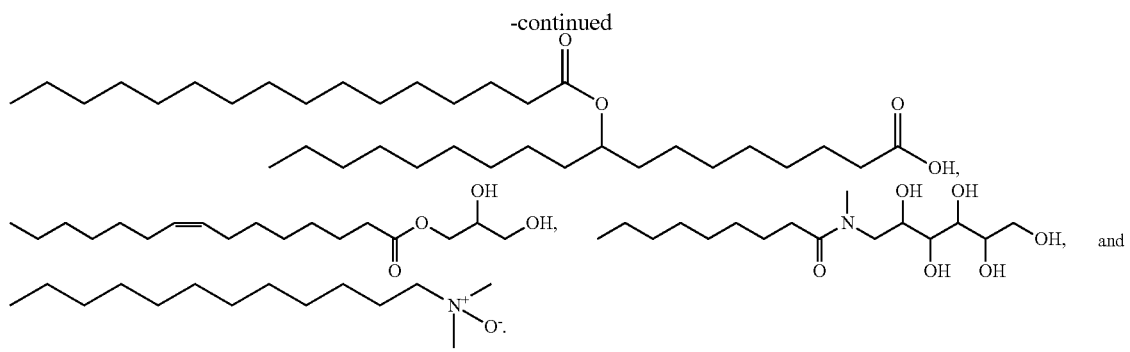
Examples of non-cationic lipids comprising sugars include, but are not limited to the following:
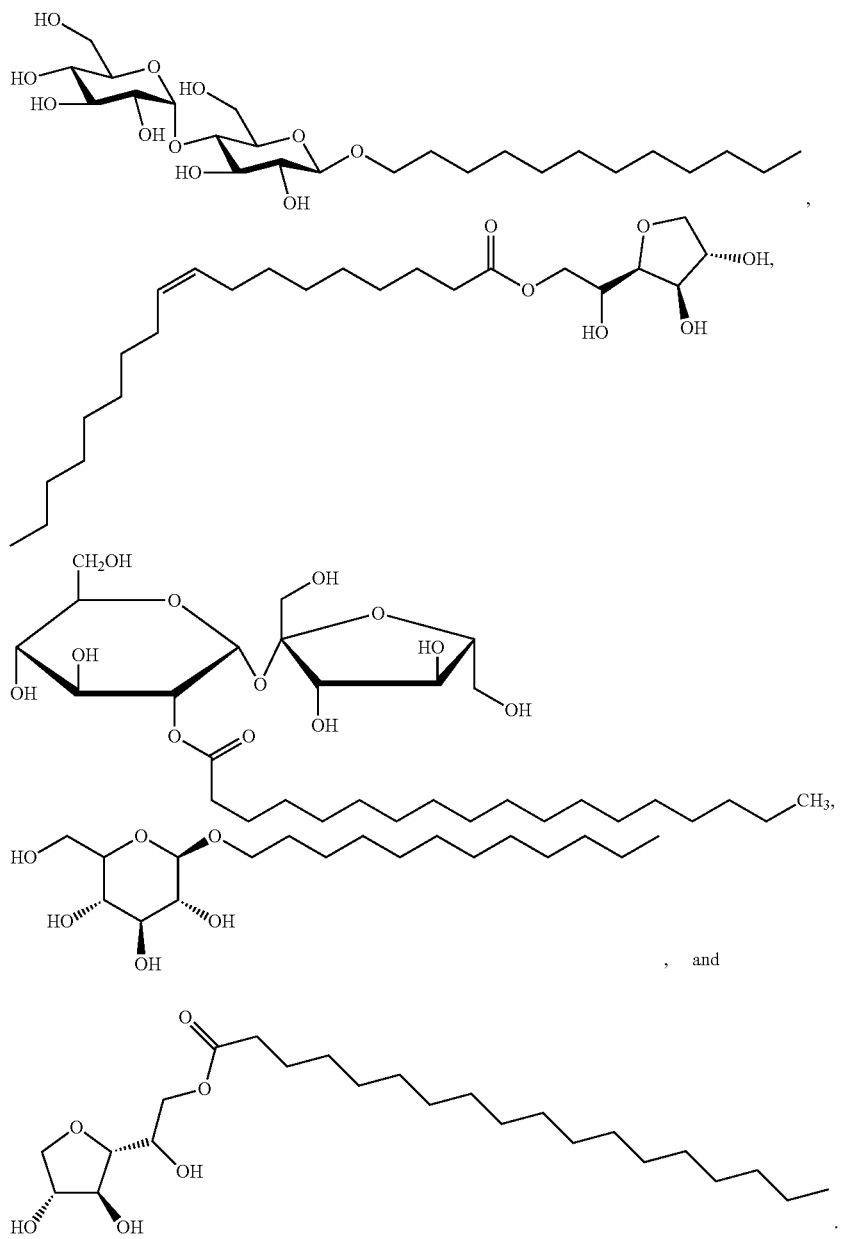

Zwitterionic Non-Cationic Lipids

In certain embodiments, non-cationic lipids useful in the present invention are DSPC analogs wherein the phosphocholine moiety is replaced by a different zwitterionic group.

DSPC has the following structure:

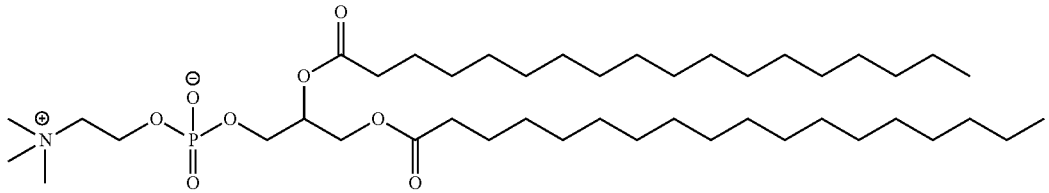 [SMILES: CCCCCCCCCCCCCCCCCC(=O)OCC(COP(=O)([O-])OCC[N+](C)(C)C)OC(=O)CCCCCCCCCCCCCCCCC]

The replacement with a different zwitterionic group is depicted in FIG. 73.

In certain embodiments, the different zwitterionic group is not a phosphocholine group. In certain embodiments, a non-cationic lipid useful in the present invention is a compound of Formula (II). Provided herein are compounds of Formula (II):

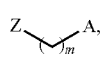

or a salts thereof, wherein:

Z is a zwitterionic moiety, wherein the zwitterionic moiety is not of the formula:

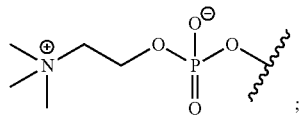 [SMILES: *OP(=O)([O-])OCC[N+](C)(C)C]

m is 0, 1, 2, 3, 4, 5, 6, 7, 8, 9, or 10;

A is of the formula:

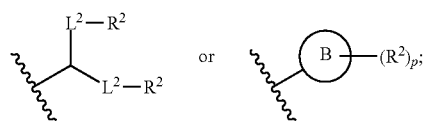

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, Z is an amino acid or a derivative thereof. In certain embodiments, Z is of one of the following formulae:

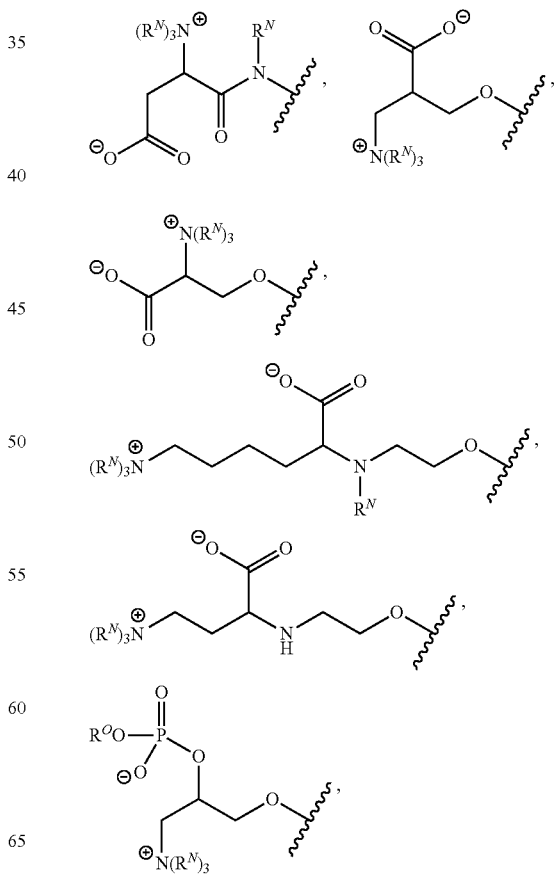

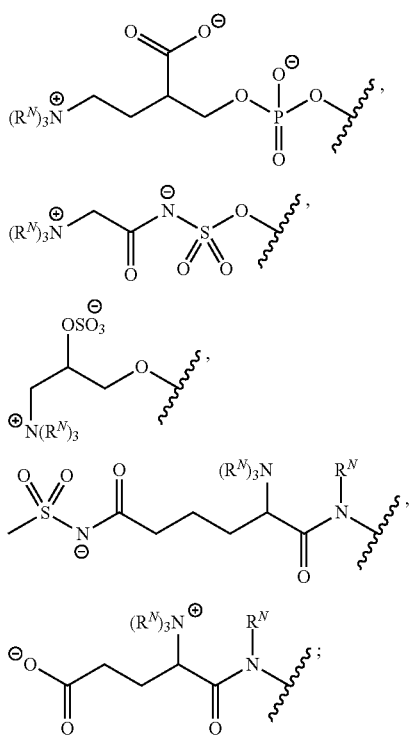
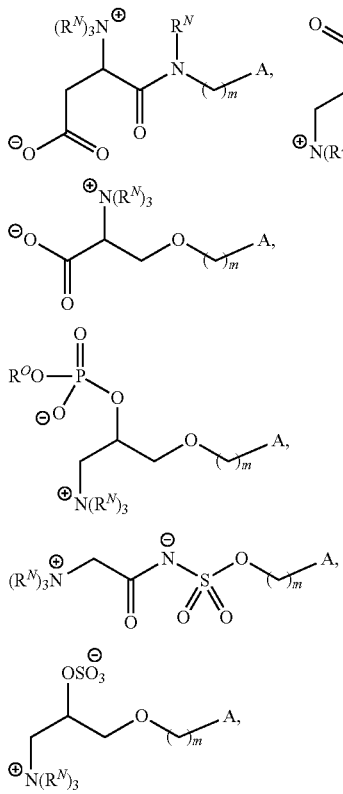
wherein $R^O$ is hydrogen, optionally substituted alkyl or an oxygen protecting group. In certain embodiments, a compound of Formula (II) is of one of the following formulae:
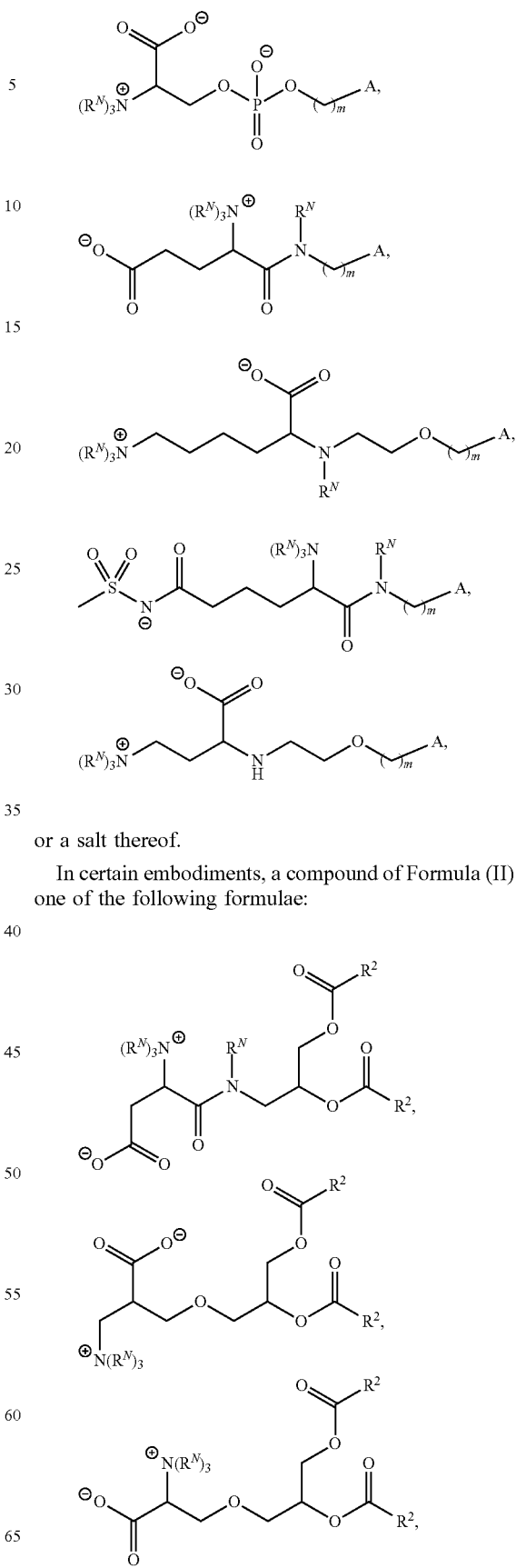
or a salt thereof.
In certain embodiments, a compound of Formula (II) is of one of the following formulae:

183
-continued
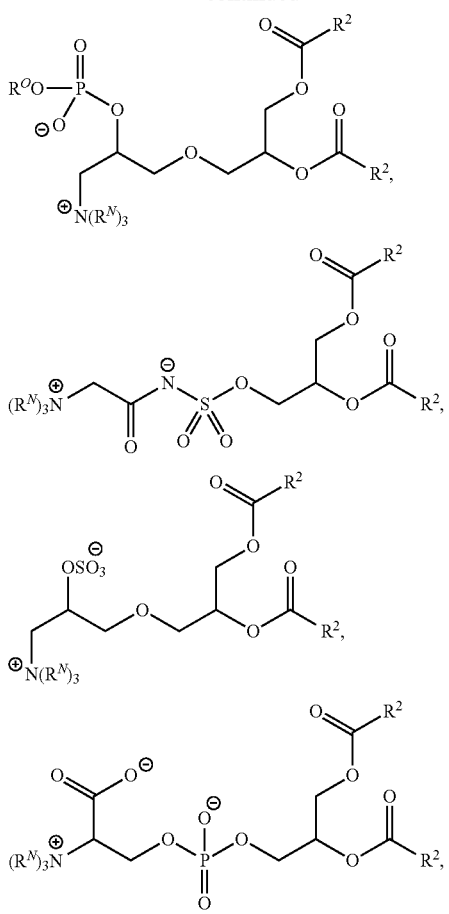
184
-continued
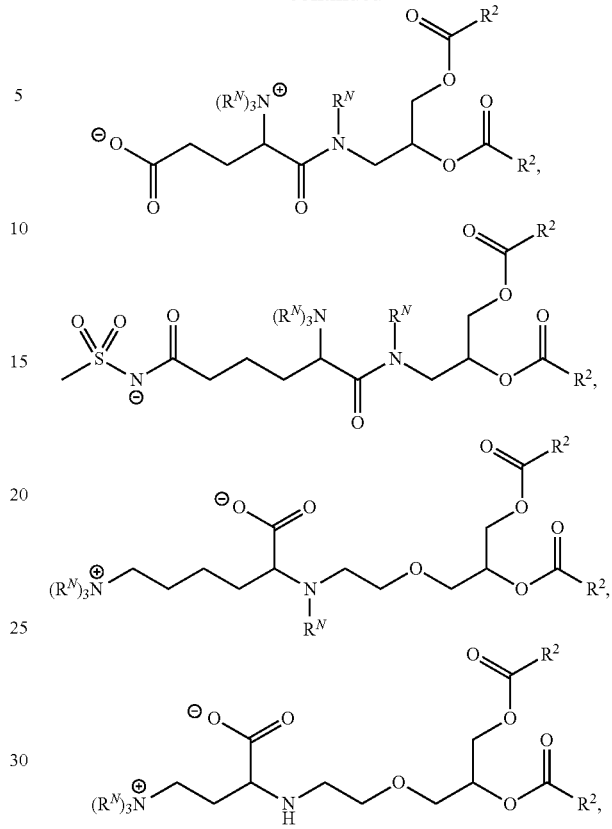
or a salt thereof.
For example, in certain embodiments, a compound of Formula (II) is one of the following:
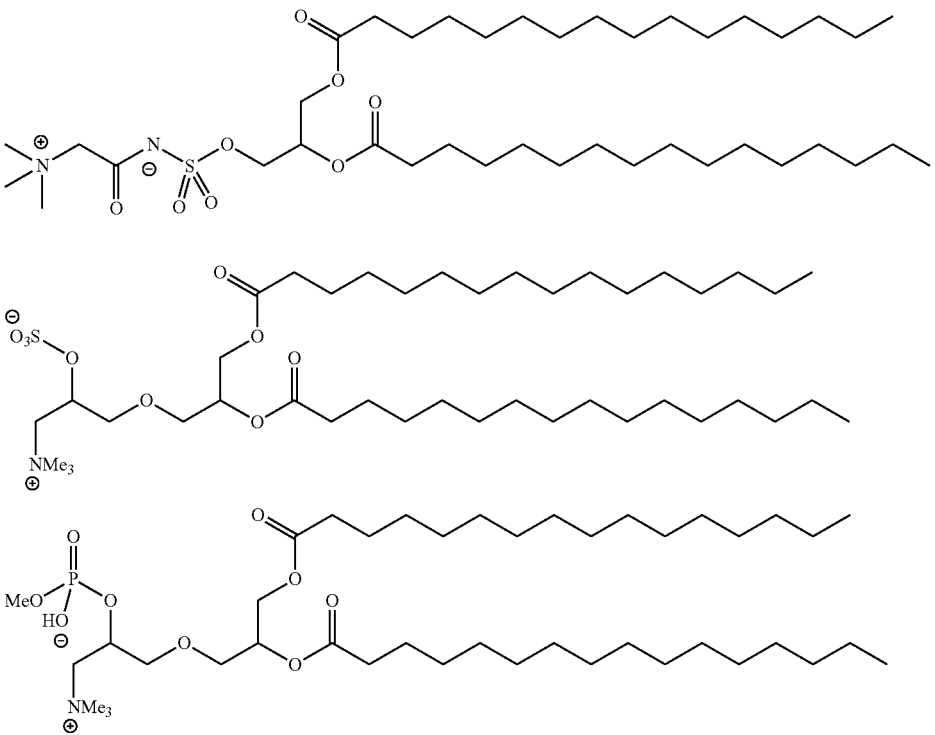

-continued
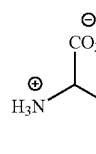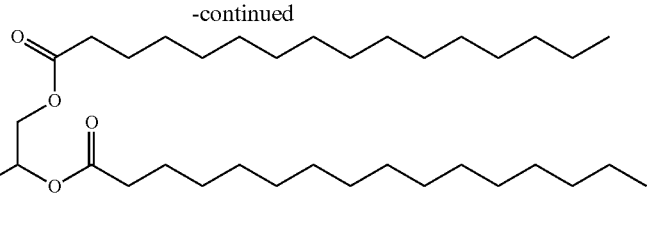
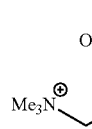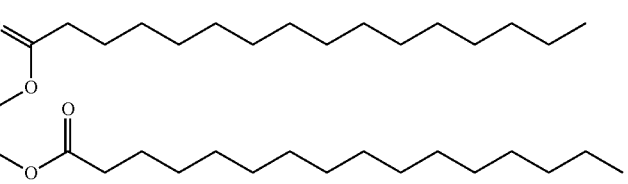
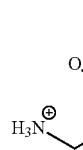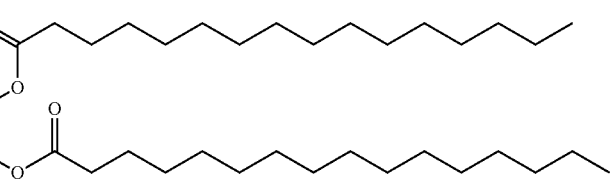
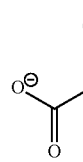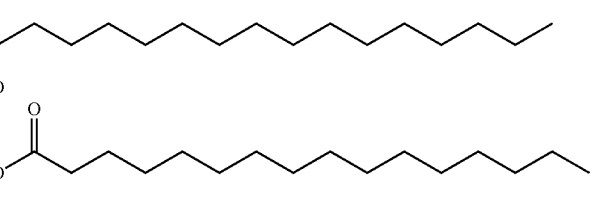
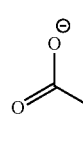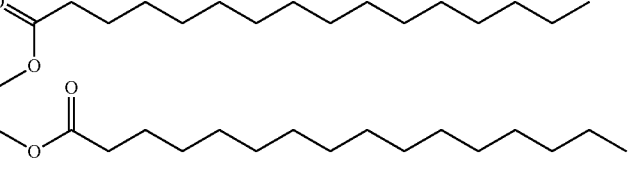
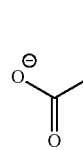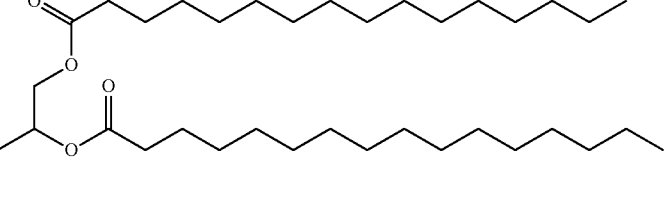
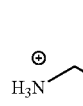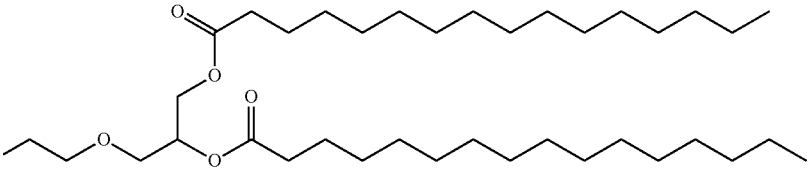
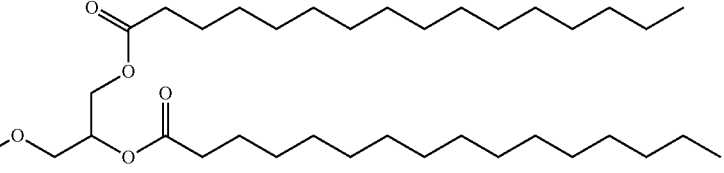

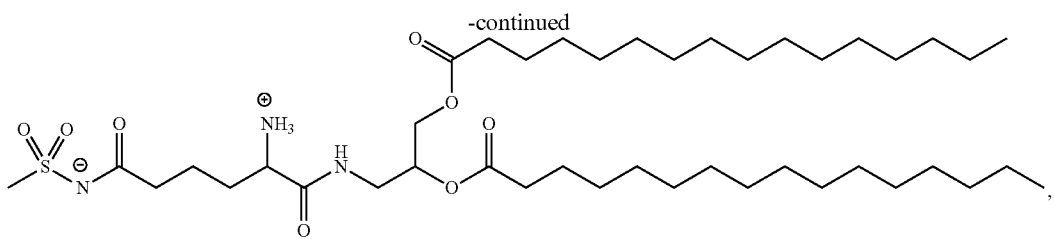

or salts thereof.

Oleic Acid Analogs

As described herein, non-cationic lipids useful in the present invention include analogs of oleic acid. As described herein, an oleic acid analog can comprise a modified oleic acid tail, a modified carboxylic acid moiety, or both. In certain embodiments, an analog of oleic acid is a compound of Formula (IV). Provided herein are compounds of Formula (IV):

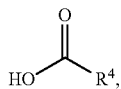

(IV)

or a salt thereof, wherein:

$R^4$ is optionally substituted, $C_{10\text{-}40}$ alkyl; optionally substituted, $C_{10\text{-}40}$ alkenyl; optionally substituted, $C_{10\text{-}40}$ alkynyl; wherein at least one methylene group of $R^4$ is independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)—, —OS(O)—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (IV) is one of the following:

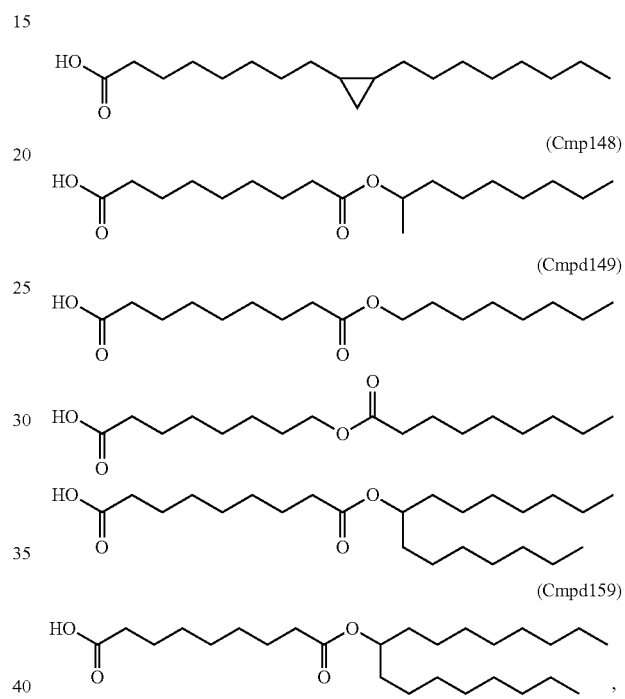

or salts thereof.

In certain embodiments, an oleic acid analog is a compound wherein the carboxylic acid moiety of oleic acid replaced by a different group. In certain embodiments, an oleic acid analog useful in the present invention is one of the following:

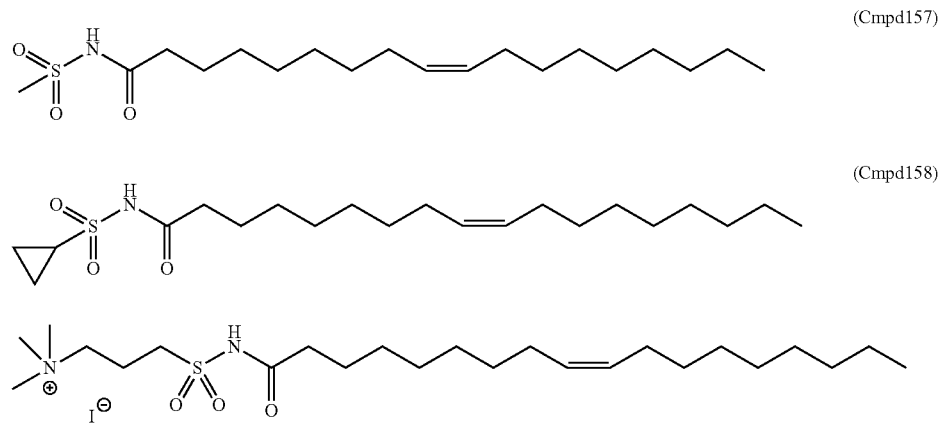

-continued

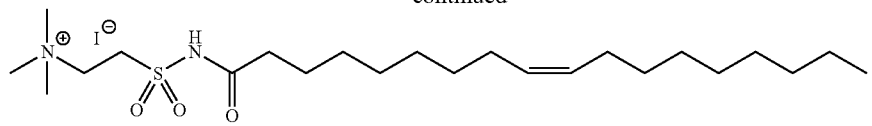

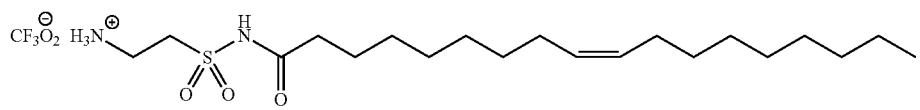

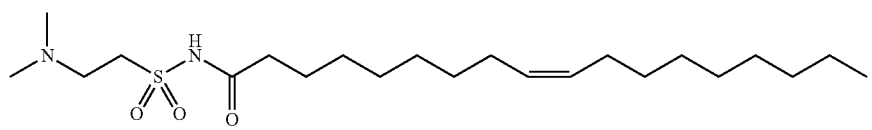

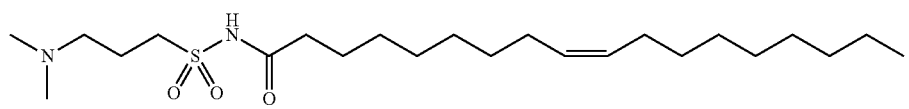

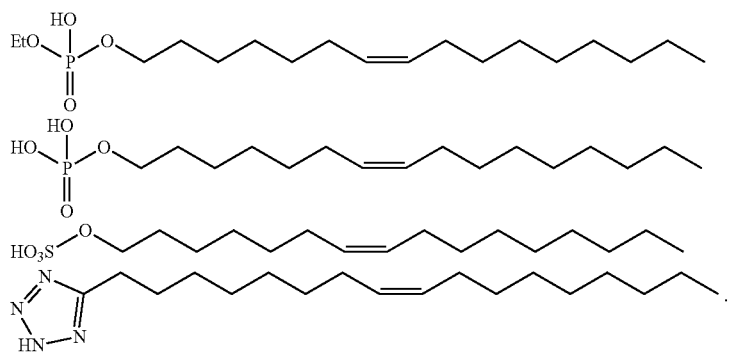

or salts thereof.

In certain embodiments, an oleic acid analog useful in the present invention is:

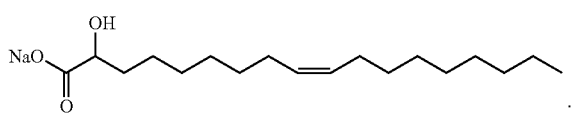

PEGylated Lipids

The lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

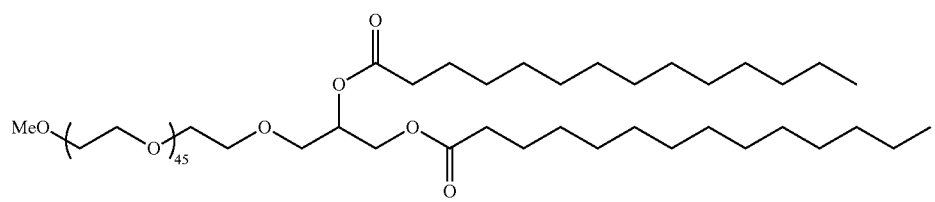

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

PEG and PEG-OH Lipids

In certain embodiments, a PEG lipid useful in the present invention is a compound of Formula (III). Provided herein are compounds of Formula (III):

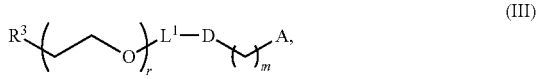
(III)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N($R^N$)—, —S—, —C(O)—, —C(O)N($R^N$)—, —N$R^N$C(O)—, —C(O)O—, —OC(O)—, —OC(O)O—, —OC(O)N($R^N$)—, —N$R^N$C(O)O—, or —N$R^N$C(O)N($R^N$)—;

D is a moiety obtained by click chemistry or a moiety cleavable under physiological conditions;

m is 0, 1, 2, 3, 4, 5, 6, 7, 8, 9, or 10;

A is of the formula:

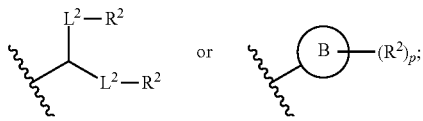

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —N$R^N$C(O)—, —C(O)O—, —OC(O)—, —OC(O)O—, —OC(O)N($R^N$)—, —N$R^N$C(O)O—, or —N$R^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (III) is a PEG-OH lipid (i.e., $R^3$ is —$OR^O$, and $R^O$ is hydrogen). In certain embodiments, the compound of Formula (III) is of Formula (III-OH):

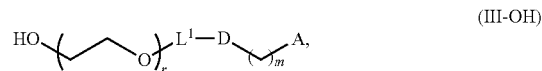
(III-OH)

or a salt thereof.

In certain embodiments, D is a moiety obtained by click chemistry (e.g., triazole). In certain embodiments, the compound of Formula (III) is of Formula (III-a-1) or (III-a-2):

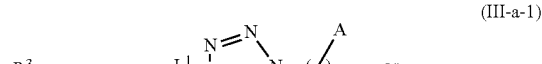
(III-a-1)

or

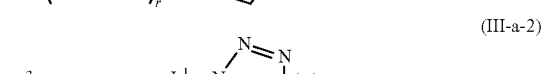
(III-a-2)

or a salt thereof.

In certain embodiments, the compound of Formula (III) is of one of the following formulae:

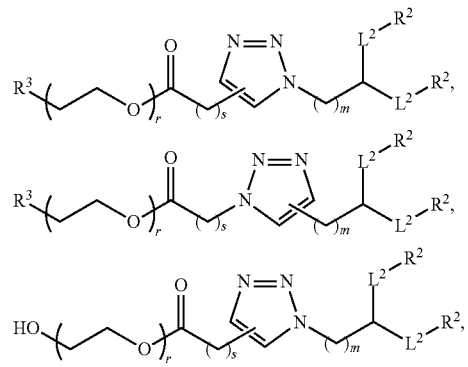

-continued
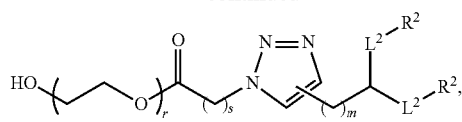
or a salt thereof, wherein
s is 0, 1, 2, 3, 4, 5, 6, 7, 8, 9, or 10.
In certain embodiments, the compound of Formula (III) is of one of the following formulae:
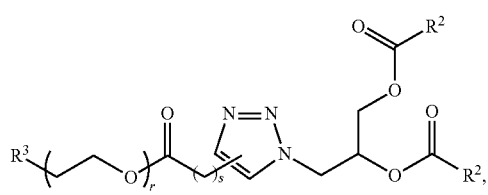
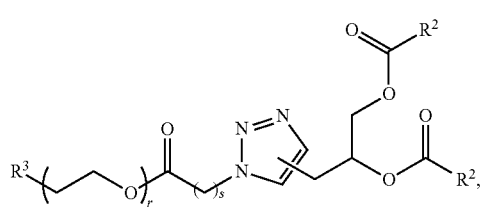
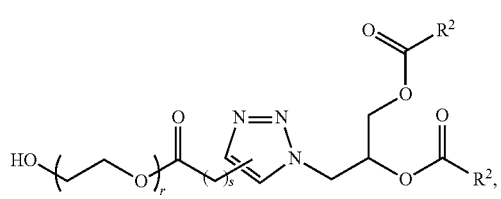
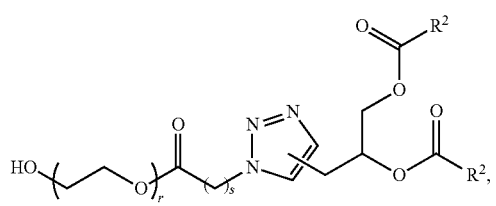
or a salt thereof.
In certain embodiments, a compound of Formula (III) is of one of the following formulae:
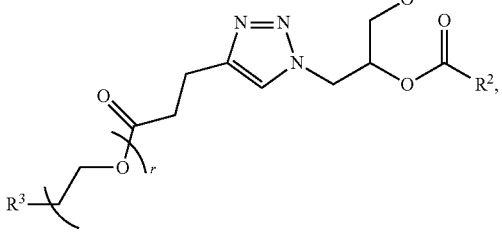
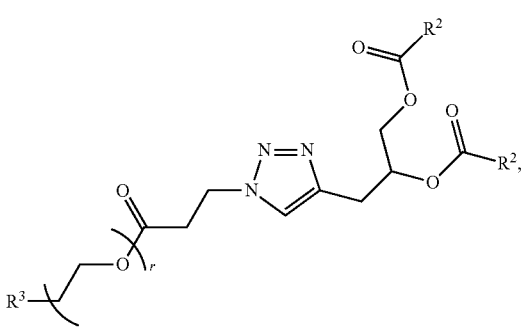
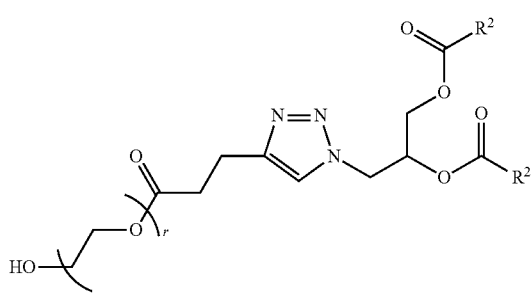
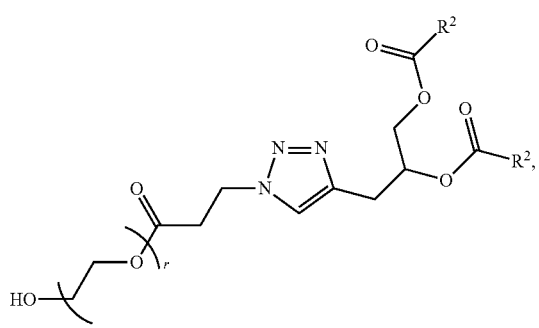
or a salt thereof.
In certain embodiments, a compound of Formula (III) is of one of the following formulae:

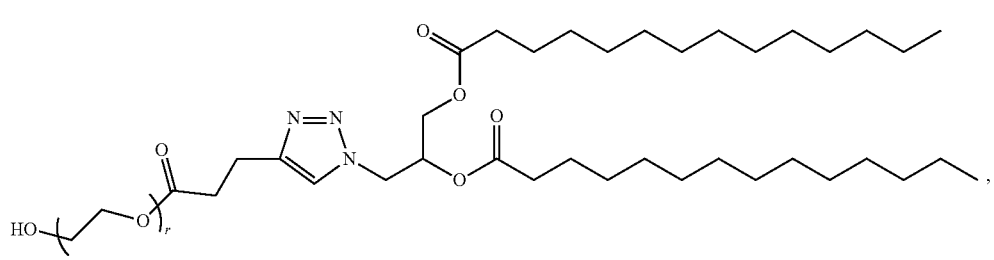
(Cmpd394)

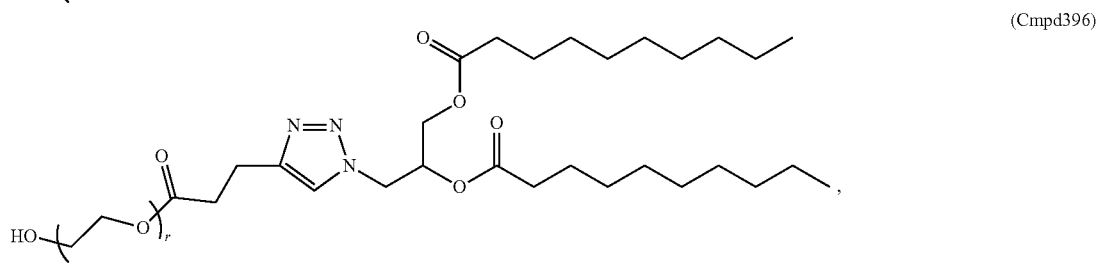
(Cmpd396)

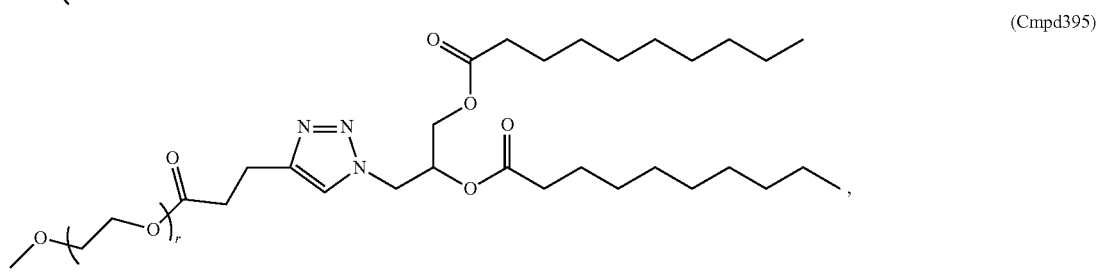
(Cmpd395)

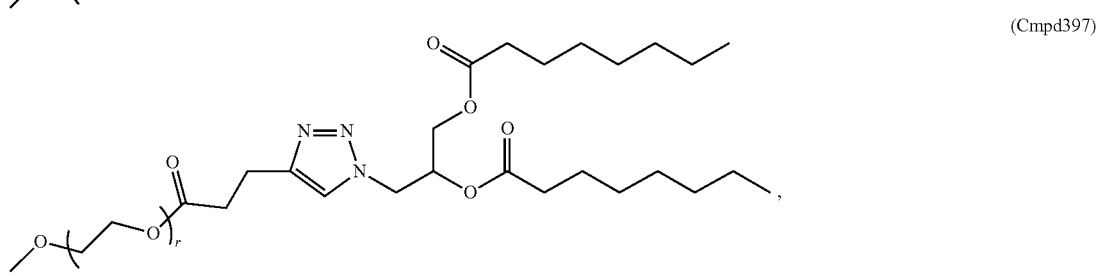
(Cmpd397)

or a salt thereof.

In certain embodiments, D is a moiety cleavable under physiological conditions (e.g., ester, amide, carbonate, carbamate, urea). In certain embodiments, a compound of Formula (III) is of Formula (III-b-1) or (III-b-2):

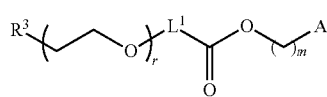
(III-b-1)

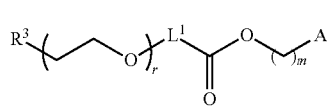
(III-b-2)

or a salt thereof.

In certain embodiments, a compound of Formula (III) is of Formula (III-b-1-OH) or (III-b-2-OH):

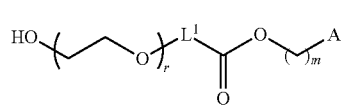
(III-b-1-OH)

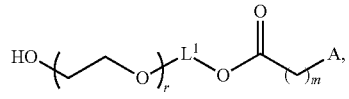
(III-b-2-OH)

or a salt thereof.

In certain embodiments, the compound of Formula (III) is of one of the following formulae:

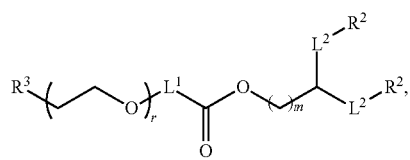

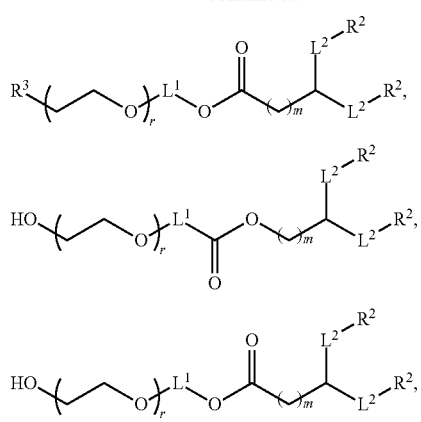
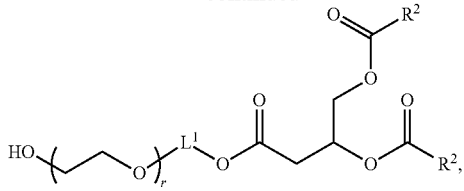
or a salt thereof.
In certain embodiments, a compound of Formula (III) is of one of the following formulae:
or a salt thereof.
In certain embodiments, a compound of Formula (III) is of one of the following formulae:
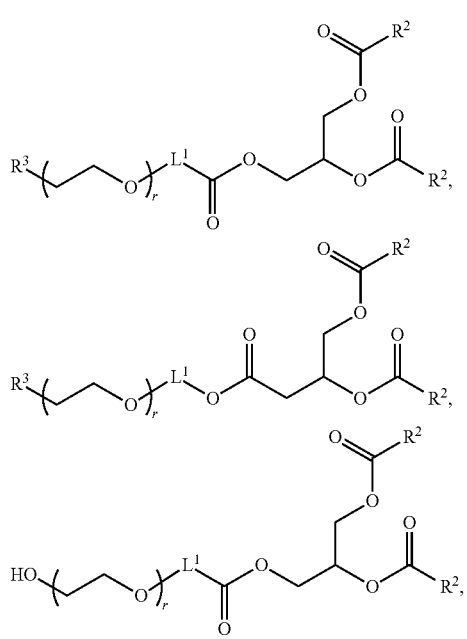
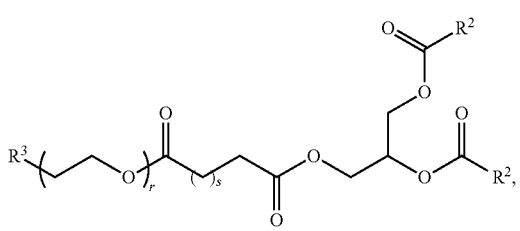
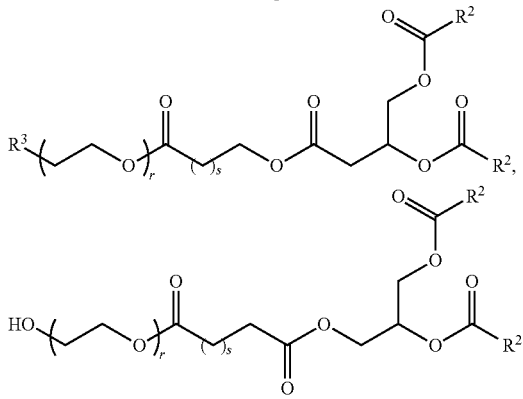
or a salt thereof.
In certain embodiments, a compound of Formula (III) is of one of the following formulae:
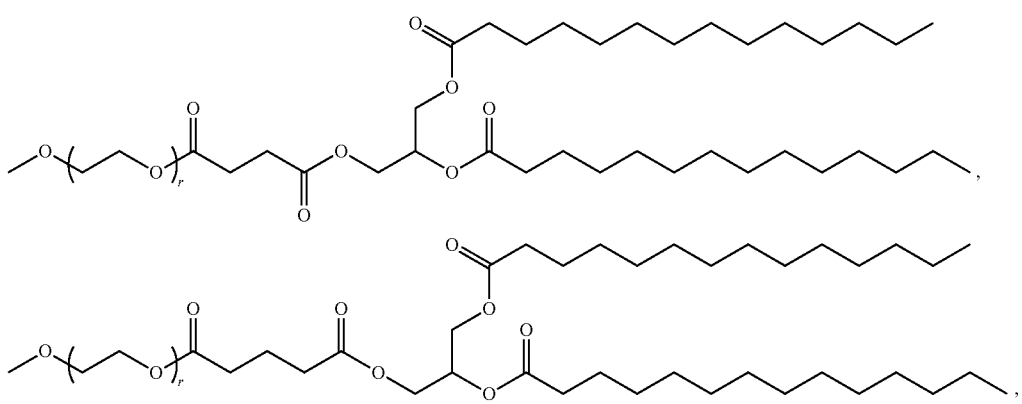

or salts thereof.

In certain embodiments, a PEG lipid useful in the present invention is a PEGylated fatty acid. In certain embodiments, a PEG lipid useful in the present invention is a compound of Formula (V). Provided herein are compounds of Formula (V):

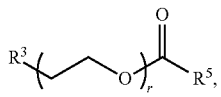
(V)

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (V) is of Formula (V-OH):

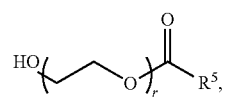
(V-OH)

or a salt thereof.

In certain embodiments, a compound of Formula (V) is of one of the following formulae:

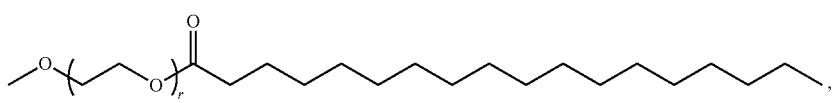
(Cmpd400)

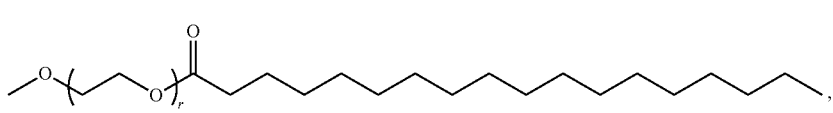
(Cmpd401)

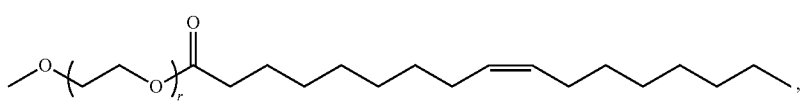
(Cmpd401)

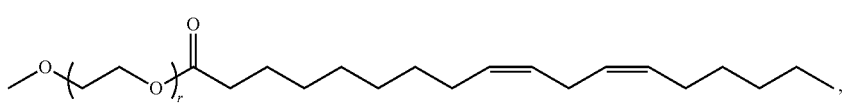
(Cmpd402)

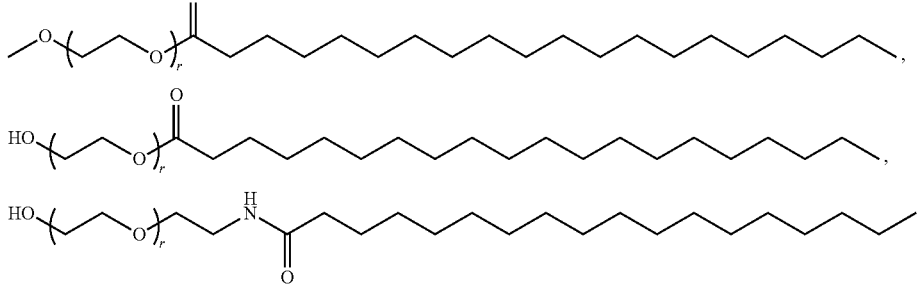

or a salt thereof.

Numerous LNP formulations having different PEG-lipids were prepared and tested for activity, as demonstrated in the Examples included below.

Phospholipids, Including Helper Phospholipids

Phospholipids, as defined herein, are any lipids that comprise a phosphate group. Phospholipids are a subset of non-cationic lipids. The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. A phospholipid moiety may be selected from the non-limiting group consisting of phosphatidyl choline, phosphatidyl ethanolamine, phosphatidyl glycerol, phosphatidyl serine, phosphatidic acid, 2-lyso-phosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye). Each possibility represents a separate embodiment of the present invention.

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. Each possibility represents a separate embodiment of the present invention.

In some embodiments, a nanoparticle composition includes DSPC. In certain embodiments, a nanoparticle composition includes DOPE. In some embodiments, a nanoparticle composition includes both DSPC and DOPE. Examples of phospholipids include, but are not limited to, the following:

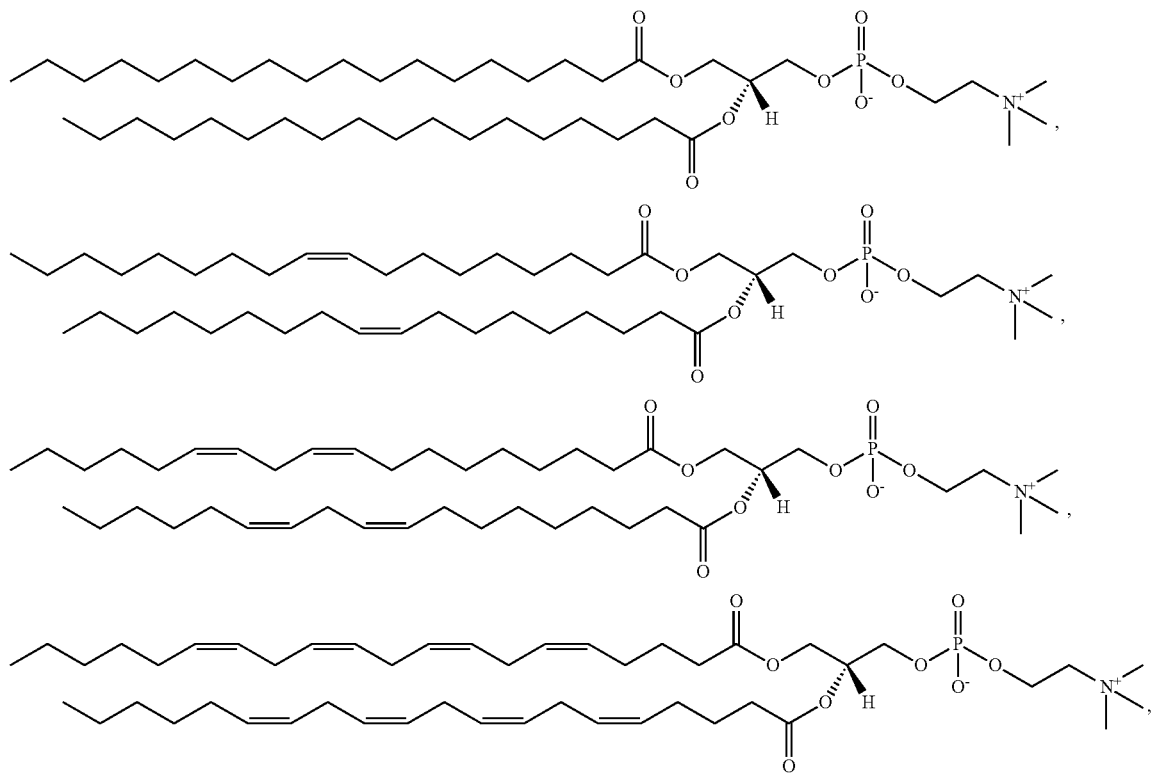

-continued
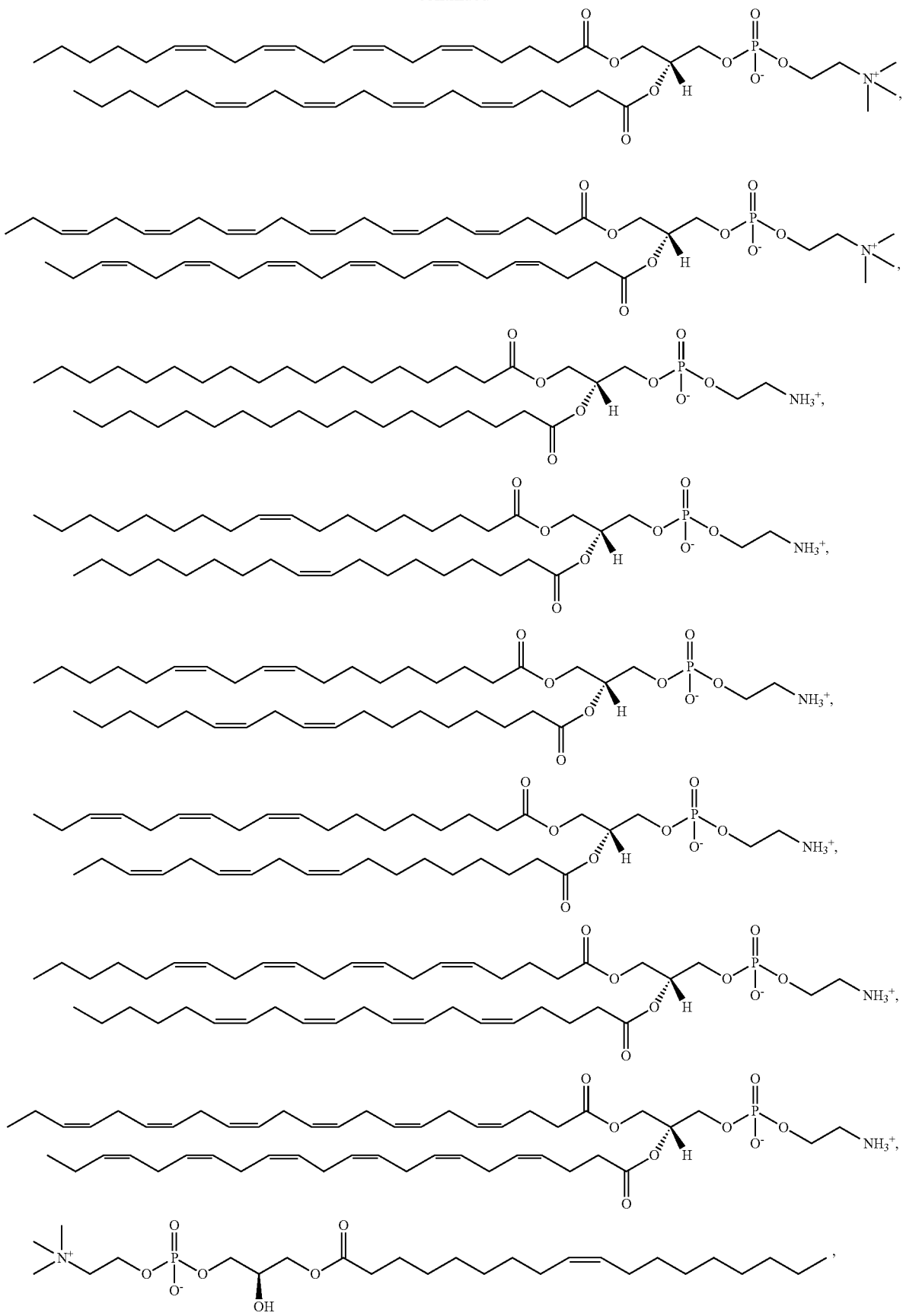

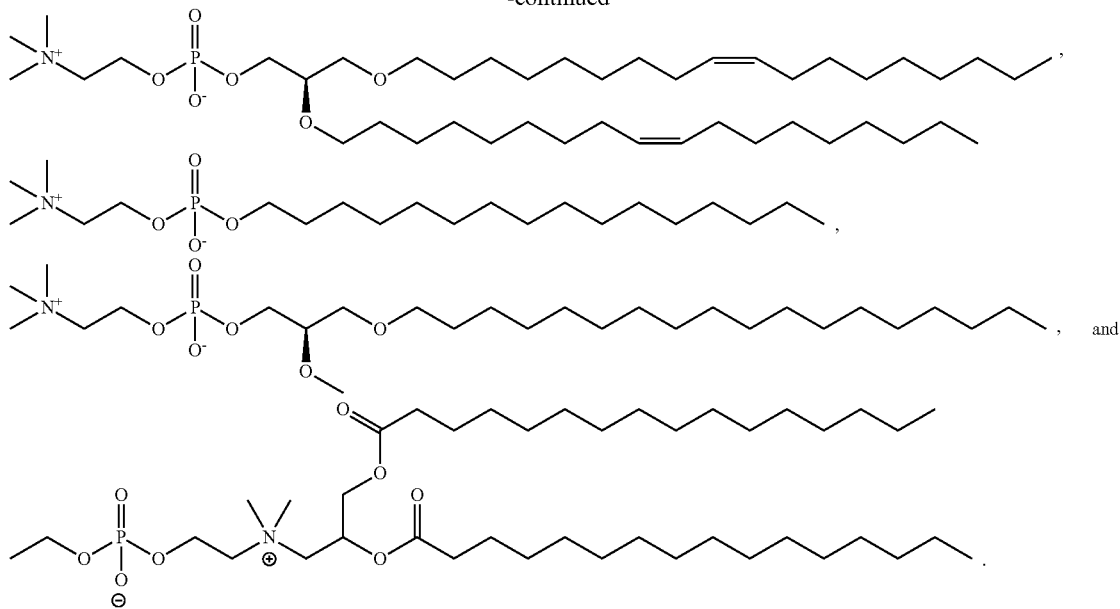

In certain embodiments, a phospholipid useful in the present invention is an analog or variant of DSPC. In certain embodiments, a phospholipid useful in the present invention is a compound of Formula (I):

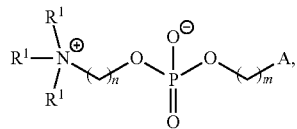

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;
m is 0, 1, 2, 3, 4, 5, 6, 7, 8, 9, or 10;
A is of the formula:

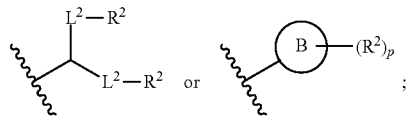

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —N$R^N$C(O)—, —C(O)O—, —OC(O)—, —OC(O)O—, —OC(O)N($R^N$)—, —N$R^N$C(O)O—, or —N$R^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

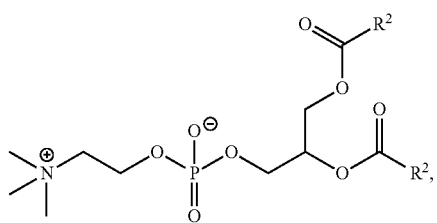

wherein each instance of $R^2$ is independently unsubstituted alkyl, unsubstituted alkenyl, or unsubstituted alkynyl.

Phospholipid Head Modifications

In certain embodiments, a phospholipid useful in the present invention comprises a modified phospholipid head (e.g., a modified choline group). In certain embodiments, a phospholipid with a modified head is DSPC, or analog thereof, with a modified quaternary amine. For example, in embodiments of Formula (I), at least one of $R^1$ is not methyl. In certain embodiments, at least one of $R^1$ is not hydrogen or methyl. In certain embodiments, the compound of Formula (I) is of one of the following formulae:

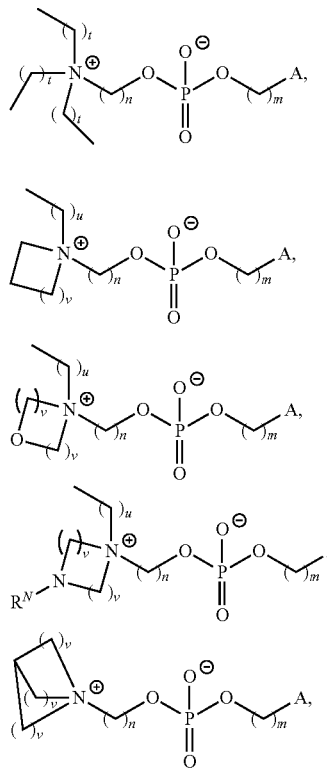

or a salt thereof, wherein:
each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.

In certain embodiments, the compound of Formula (I) is of one of the following formulae:

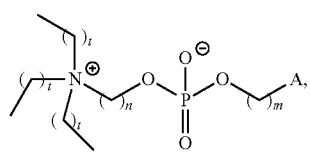

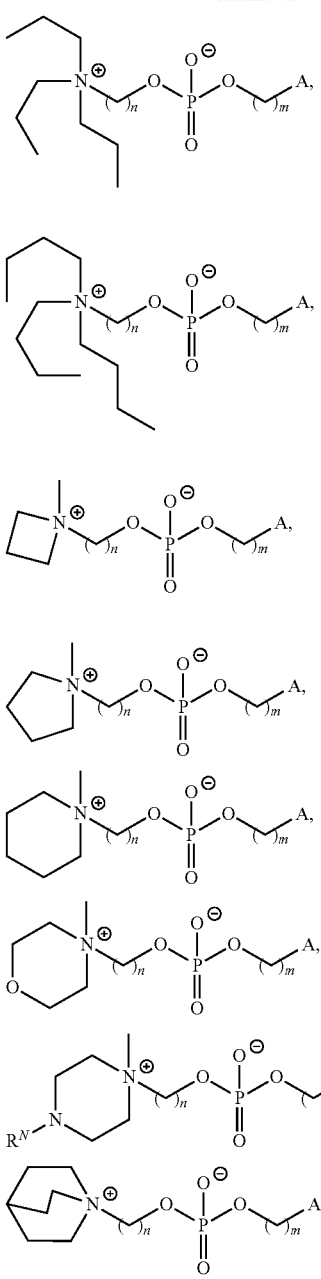

or a salt thereof.

In certain embodiments, a compound of Formula (I) is one of the following:

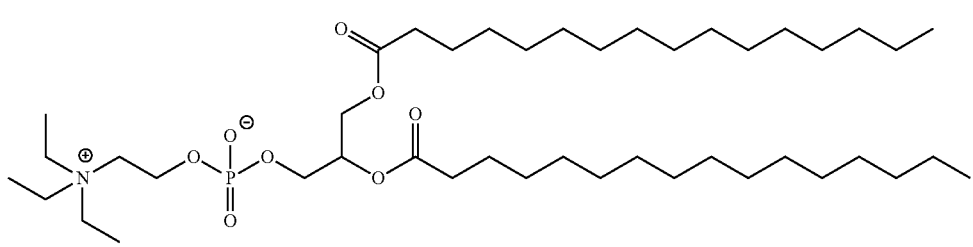

(Cmpd150)

-continued
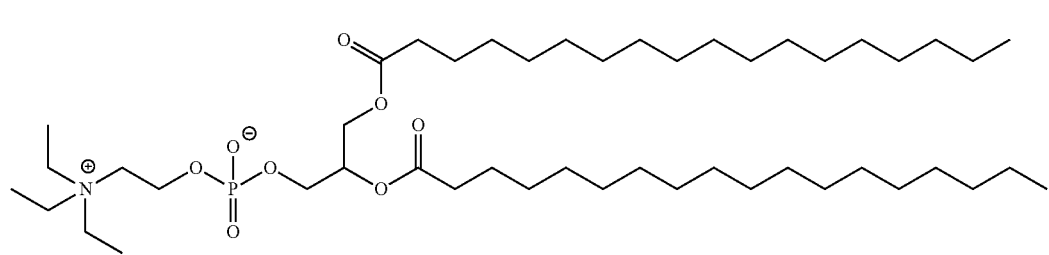
(Cmpd160)
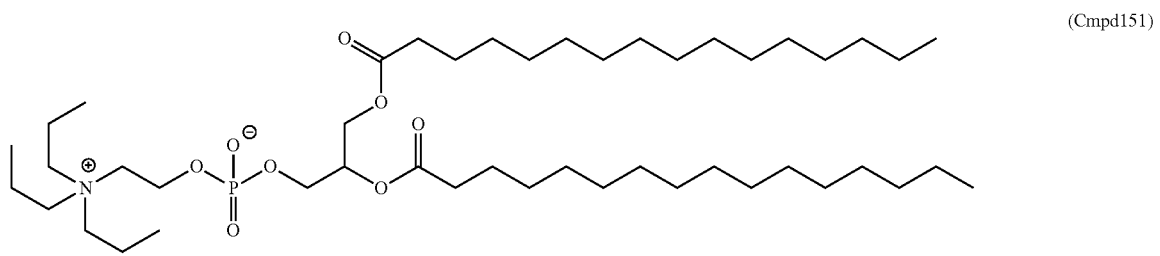
(Cmpd151)
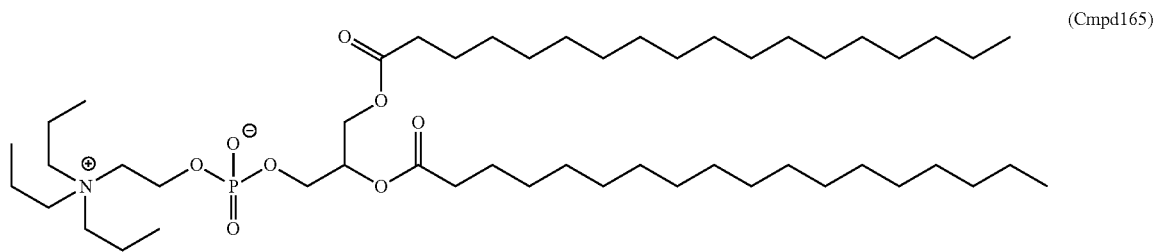
(Cmpd165)
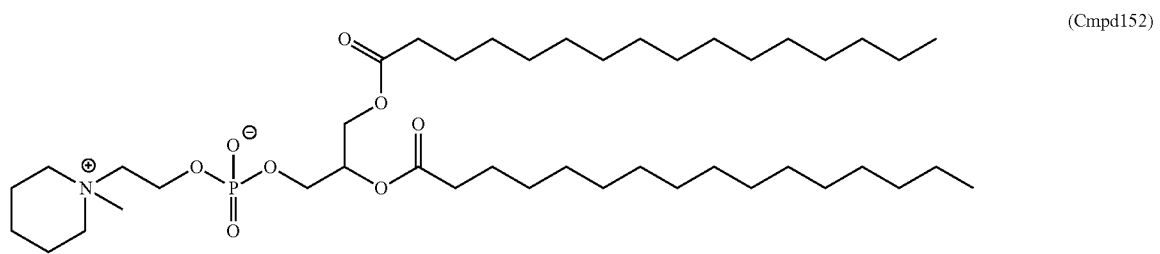
(Cmpd152)
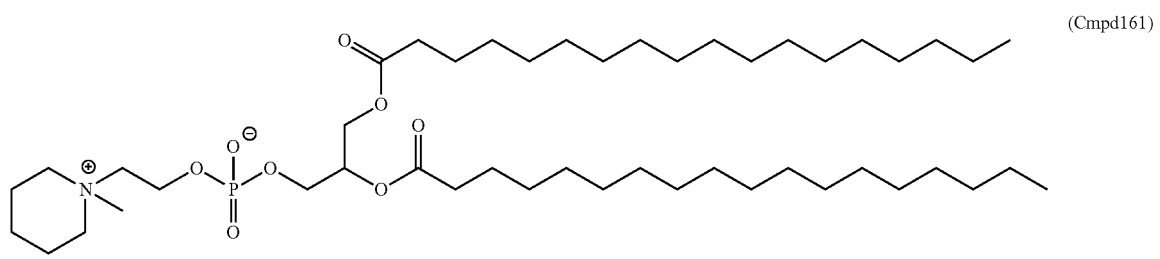
(Cmpd161)
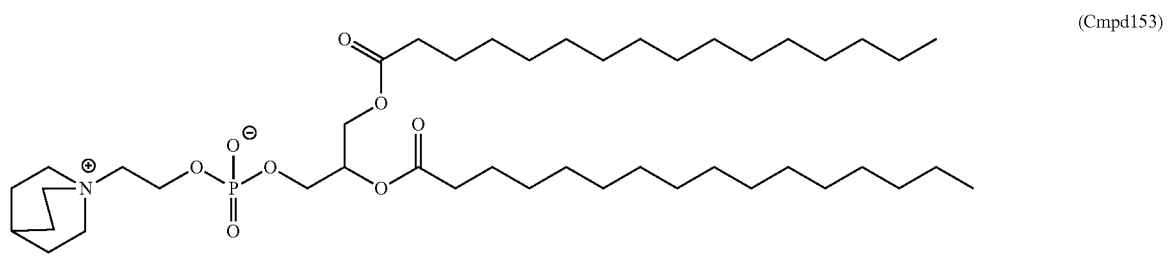
(Cmpd153)

-continued

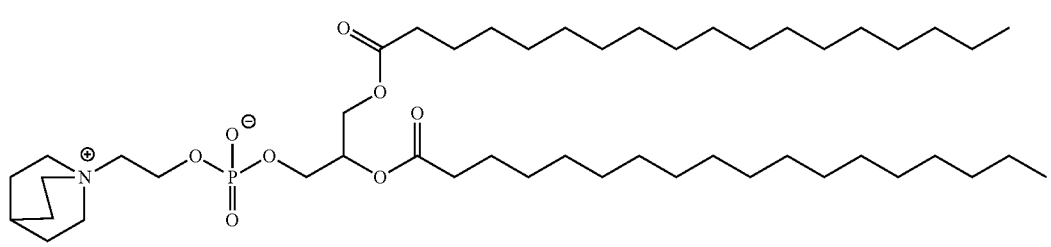
(Cmpd164)

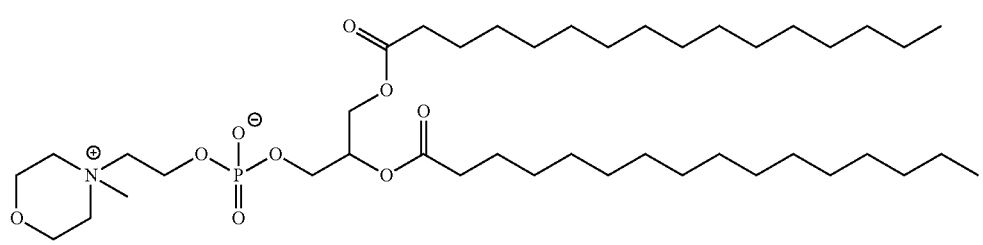
(Cmpd155)

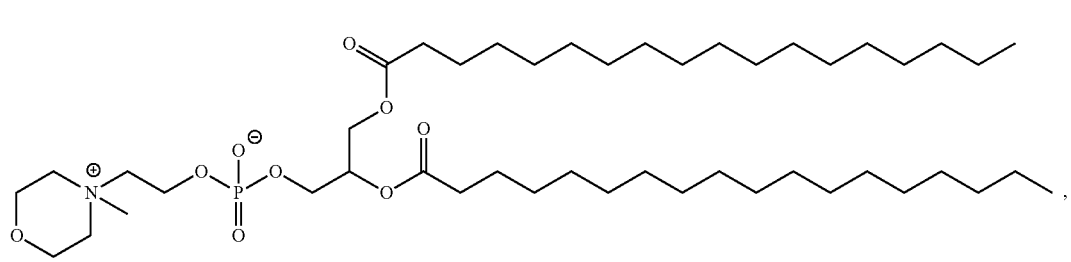
(Cmpd166)

or a salt thereof.

Phospholipid Core Modifications

In certain embodiments, a compound of Formula (I) is of Formula (I-a):

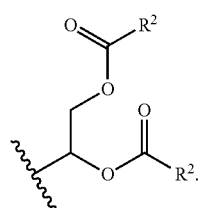

(I-a)

or a salt thereof.

Figure 47:
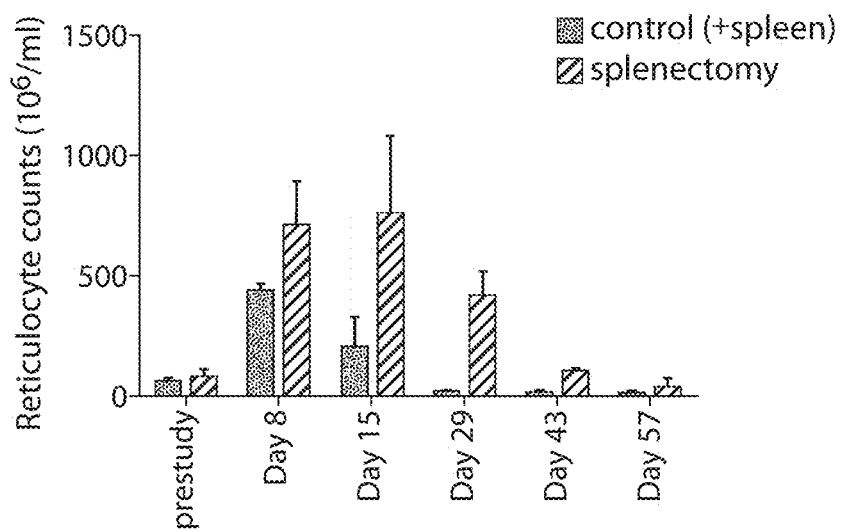
FIG. 47: Reticulocyte counts in intact and splenectomized non-human primates (NHPs).

In certain embodiments, phospholipids useful in the present invention comprise a modified core (see, e.g., FIG. 47). In certain embodiments, a phospholipid with a modified core described herein is DSPC, or analog thereof, with a modified core structure. For example, in certain embodiments of Formula (I-a), group A is not of the following formula:

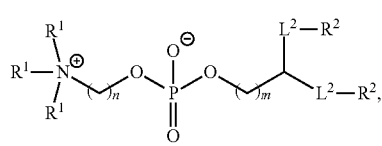

In certain embodiments, the compound of Formula (I-a) is of one of the following formulae:

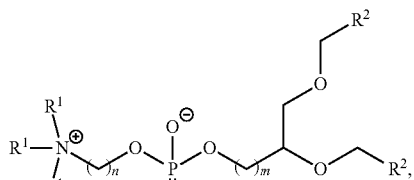

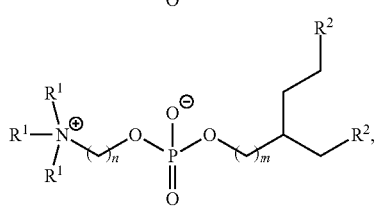

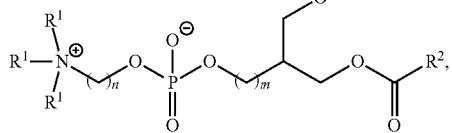

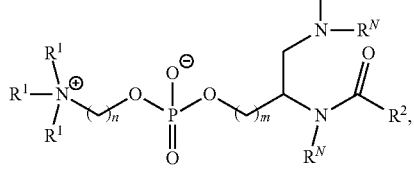

-continued

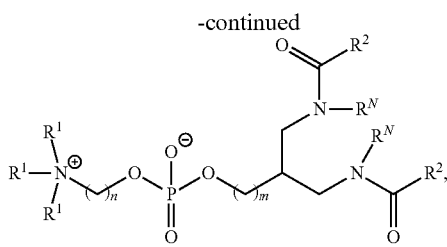

or a salt thereof.

In certain embodiments, a compound of Formula (I) is one of the following:

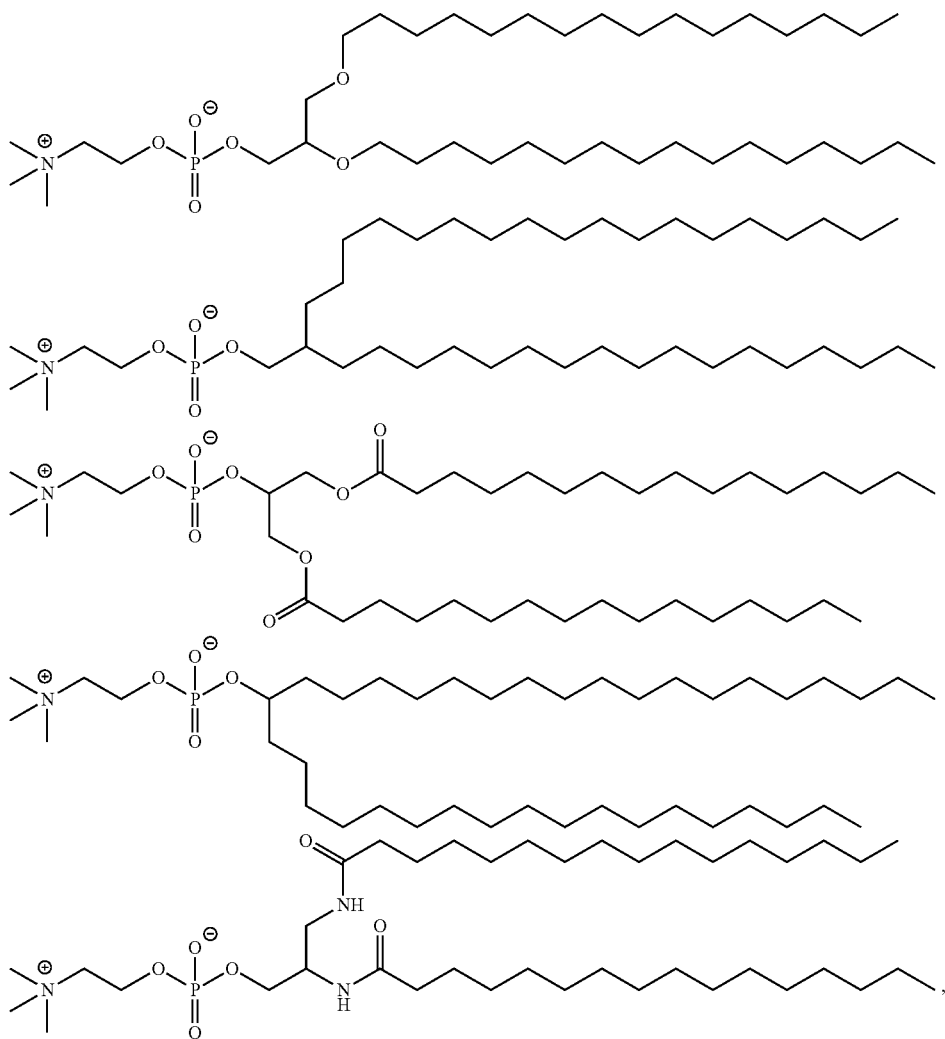

or salts thereof.

In certain embodiments, a phospholipid useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments In certain embodiments, the compound of Formula (I) is of Formula (I-b):

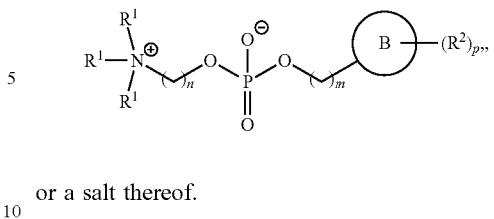

or a salt thereof.

In certain embodiments, the compound of Formula (I-b) is of Formula (I-b-1):

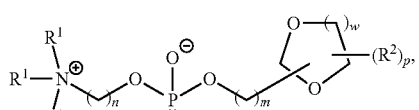

or a salt thereof, wherein:

w is 0, 1, 2, or 3.

In certain embodiments, the compound of Formula (I-b) is of Formula (I-b-2):

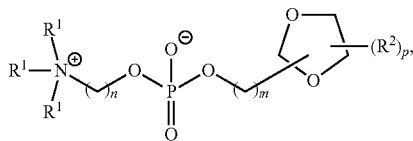

or a salt thereof.

In certain embodiments, the compound of Formula (I-b) is of Formula (I-b-3):

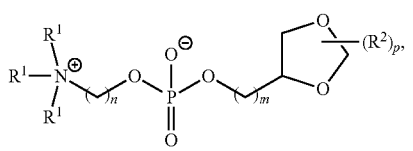

or a salt thereof.

In certain embodiments, the compound of Formula (I-b) is of Formula (I-b-4):

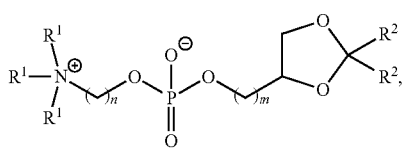

or a salt thereof.

In certain embodiments, the compound of Formula (I-b) is one of the following:

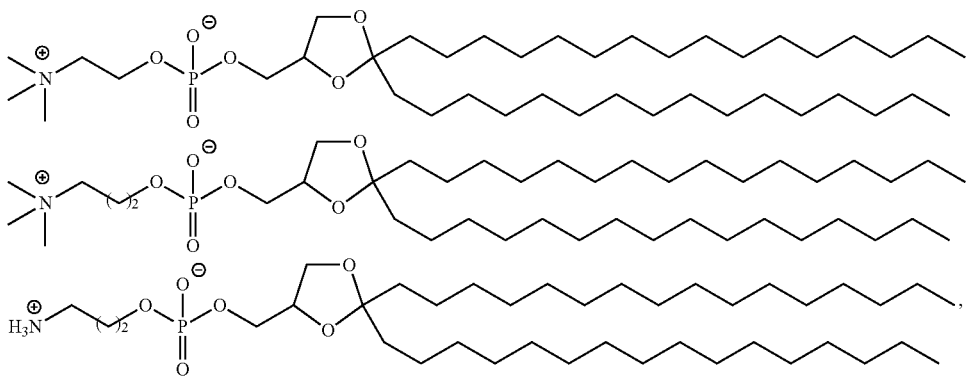

or salts thereof.

Phospholipid Tail Modifications

In certain embodiments, a phospholipid useful in the present invention comprises a modified tail. In certain embodiments, a phospholipid useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (I) is of Formula (I-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (I-a) is of Formula (I-c):

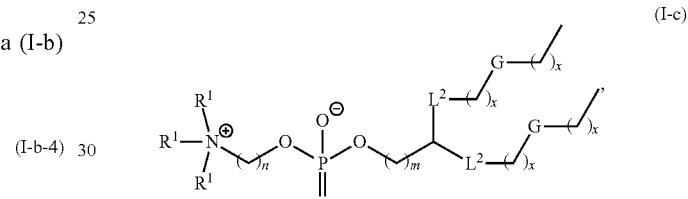

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N(R^N)S(O)O—, —S(O)₂—, —N(R^N)S(O)₂—, —S(O)₂N(R^N)—, —N(R^N)S(O)₂N(R^N)—, —OS(O)₂N(R^N)—, or —N(R^N)S(O)₂O—. Each possibility represents a separate embodiment of the present invention.

In certain embodiments, the compound of Formula (I-c) is of Formula (I-c-1):

(I-c-1)

or salt thereof, wherein:
each instance of v is independently 1, 2, or 3.

In certain embodiments, the compound of Formula (I-c) is of Formula (I-c-2):

(I-c-2)

or a salt thereof.

In certain embodiments, the compound of Formula (I-c) is of the following formula:

or a salt thereof.

In certain embodiments, the compound of Formula (I-c) is the following:

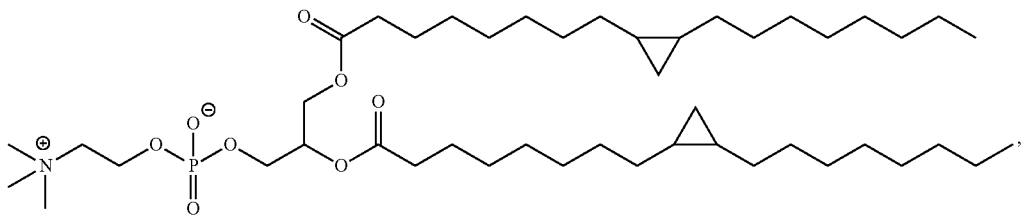 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (I-c) is of Formula (I-c-3):

(I-c-3)

or a salt thereof.

In certain embodiments, the compound of Formula (I-c) is of the following formulae:

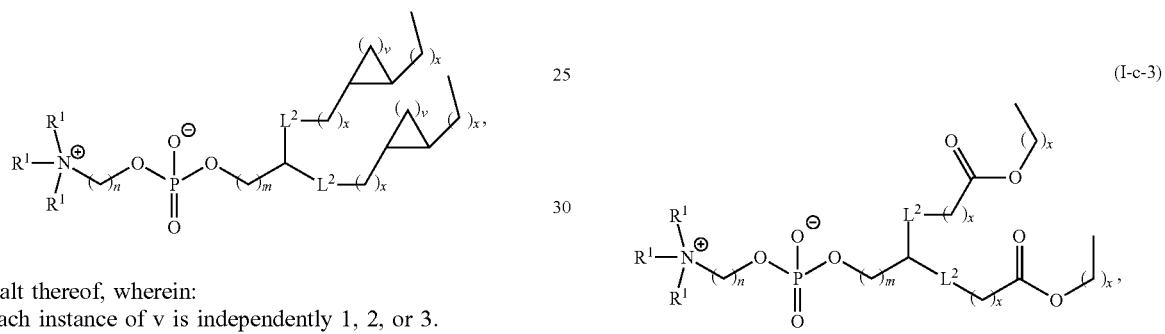

or a salt thereof.

In certain embodiments, the compound of Formula (I-c) is the following:

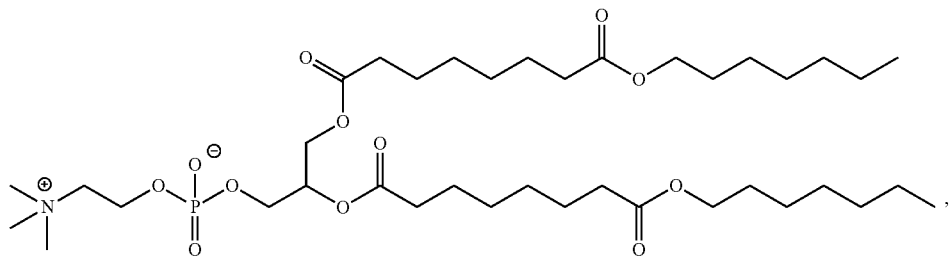 [SMILES: CCCCCCCOC(=O)CCCCCCC(=O)OCC(COP(=O)([O-])OCC[N+](C)(C)C)OC(=O)CCCCCCC(=O)OCCCCCCC]

or a salt thereof.

Phosphocholine Linker Modifications

In certain embodiments, a phospholipid useful in the present invention comprises a modified phosphocholine moiety, wherein the alkyl chain linking the quaternary amine to the phosphoryl group is not ethylene (e.g., n is not 2). Therefore, in certain embodiments, a phospholipid useful in the present invention is a compound of Formula (I), wherein n is 1, 3, 4, 5, 6, 7, 8, 9, or 10. For example, in certain embodiments, a compound of Formula (I) is of one of the following formulae:

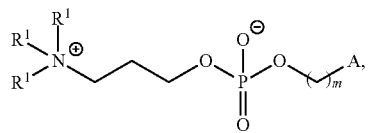

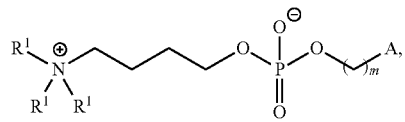

or a salt thereof.

In certain embodiments, a compound of Formula (I) is one of the following:

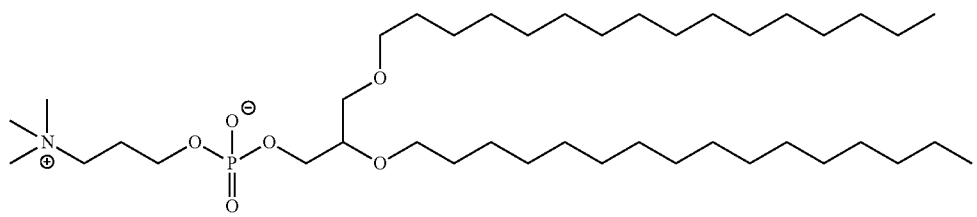

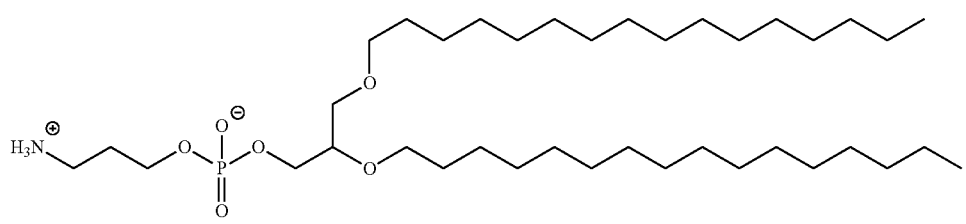

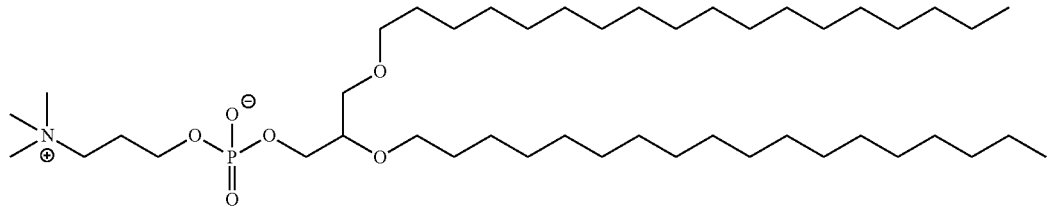

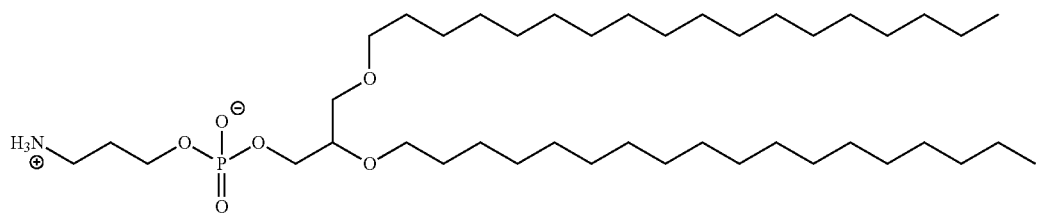

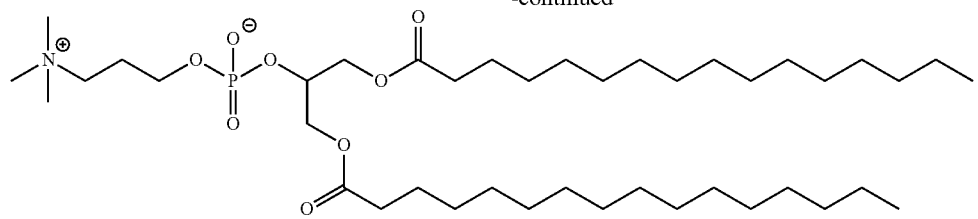
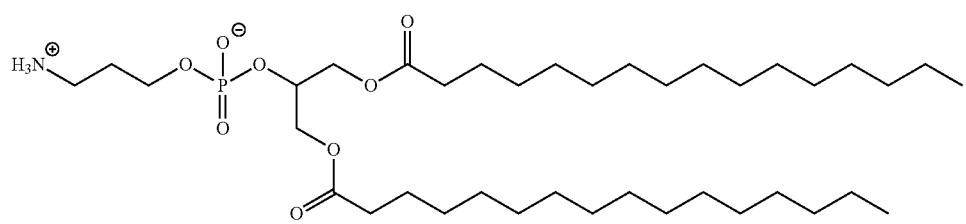
(Cmpd162)
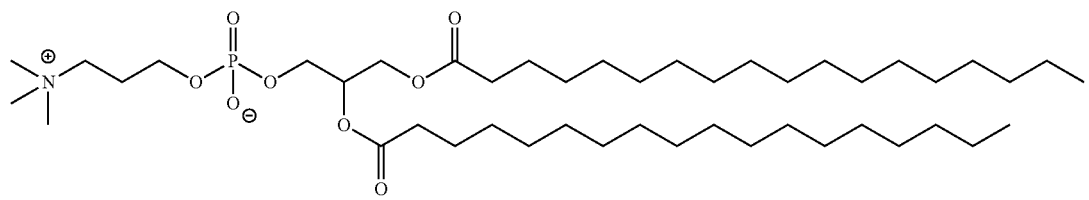
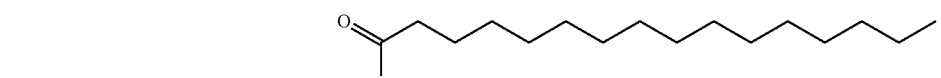
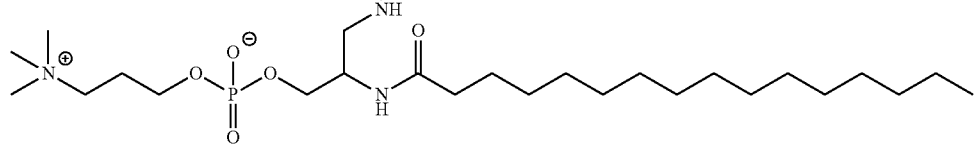
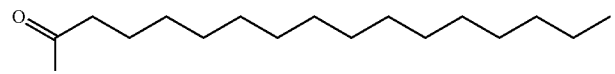
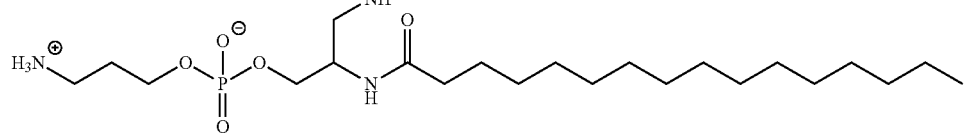
(Cmpd154)
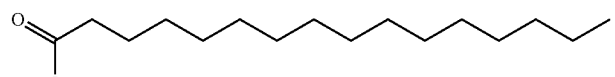
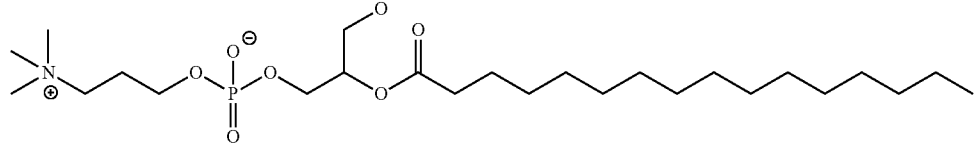
(Cmpd156)
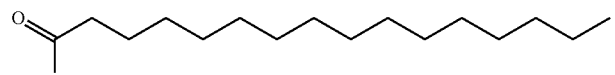
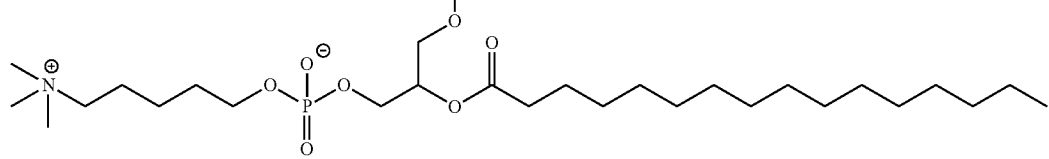

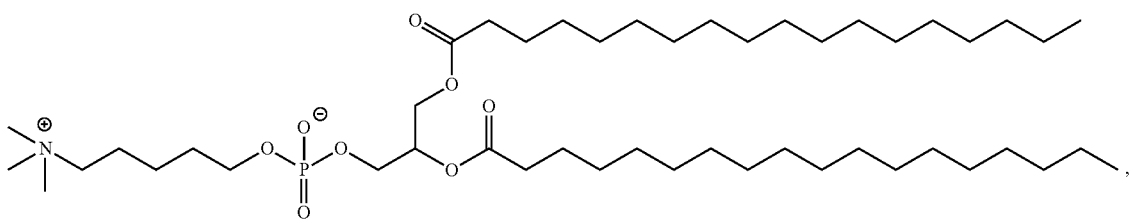

(Cmpd163)

or salts thereof.

Numerous LNP formulations having phospholipids other than DSPC were prepared and tested for activity, as demonstrated in the examples below. Exemplary phospholipids are shown in the Figures, including FIG. 75.

The following Table provides a summary of the phospholipids and indicates which examples include data on the phospholipids.

| Compound Name | Common Name | Example testing lipid | Formulation |
|---|---|---|---|
| Oleic acid | OL | 23 | MC3:OL:Chol:PEG-DMG |
| Cmpd393 | Trialkyl | 25 | MC3:PC:Chol:PEG-DMG |
| Cmpd125 | Dialkyl | 23 | MC3:PC:Chol:PEG-DMG |
| Cmpd-148 | OL | 25 | MC3:OL:Chol:PEG-DMG |
| Cmpd-149 | OL | 23 | MC3:OL:Chol:PEG-DMG |
| Cmpd-150 | PC | 23 | MC3:PC:Chol:PEG-DMG |
| Cmpd-151 | PC | 23 | MC3:PC:Chol:PEG-DMG |
| Cmpd-152 | PC | 23 | MC3:PC:Chol:PEG-DMG |
| Cmpd-153 | PC | 23 | MC3:PC:Chol:PEG-DMG |
| DOPC | PC | 22 | MC3:PC:Chol:PEG-DMG |
| Oleic acid | FA | 22 | MC3:PC:Chol:PEG-DMG |
| DOCP | PC | 22 | MC3:PC:Chol:PEG-DMG |
| DOCPe | PC | 22 | MC3:PC:Chol:PEG-DMG |
| DOPE | PE | 22 | MC3:PC:Chol:PEG-DMG |
| DOPG | PG | 22 | MC3:PC:Chol:PEG-DMG |
| DOPA | PA | 22 | MC3:PC:Chol:PEG-DMG |
| DOPS 0.1% | PS | 22 | MC3:OL:Chol:PEG-DMG |
| DOPS 1% | PS | 22 | MC3:OL:Chol:PEG-DMG |
| DOPS 1% | PS | 22 | MC3:PC:Chol:PEG-DMG |
| Cmpd-279 | PC | 23 | MC3:PC:Chol:PEG-DMG |
| Cmpd-280 | PC | 23 | MC3:PC:Chol:PEG-DMG |
| Cmpd-281 | PC | 23 | MC3:PC:Chol:PEG-DMG |
| Cmpd-160 | PC | 25 | MC3:PC:Chol:PEG-DMG |
| Cmpd-161 | PC | 25 | MC3:PC:Chol:PEG-DMG |
| Cmpd-162 | PC | 25 | MC3:PC:Chol:PEG-DMG |
| Cmpd-163 | PC | 25 | MC3:PC:Chol:PEG-DMG |
| Cmpd-157 | OL | 25 | MC3:OL:Chol:PEG-DMG |
| Cmpd-158 | OL | 25 | MC3:OL:Chol:PEG-DMG |
| Cmpd-159 | OL | 25 | MC3:OL:Chol:PEG-DMG |
| Cmpd-164 | PC | 25 | MC3:PC:Chol:PEG-DMG |
| Cmpd-165 | PC | 25 | MC3:PC:Chol:PEG-DMG |
| Cmpd-166 | PC | 25 | MC3:PC:Chol:PEG-DMG |
| DSPC | PC | 24 | Cmpd18:PC:Chol:PEG-DMG (50:1—:38.5:1.5) |
| DPPC | PC | 24 | Cmpd18:PC:Chol:PEG-DMG (50:1—:38.5:1.5) |
| DMPC | PC | 24 | Cmpd18:PC:Chol:PEG-DMG (50:1—:38.5:1.5) |
| SMPC | PC | 24 | Cmpd18:PC:Chol:PEG-DMG (50:1—:38.5:1.5) |
| OMPC | PC | 24 | Cmpd18:PC:Chol:PEG-DMG (50:1—:38.5:1.5) |
| SPPC | PC | 24 | Cmpd18:PC:Chol:PEG-DMG (50:1—:38.5:1.5) |
| OPPC | PC | 24 | Cmpd18:PC:Chol:PEG-DMG (50:1—:38.5:1.5) |
| PSPC | PC | 24 | Cmpd18:PC:Chol:PEG-DMG (50:1—:38.5:1.5) |
| POPC | PC | 24 | Cmpd18:PC:Chol:PEG-DMG (50:1—:38.5:1.5) |
| PLPC | PC | 24 | Cmpd18:PC:Chol:PEG-DMG (50:1—:38.5:1.5) |
| PMPC | PC | 24 | Cmpd18:PC:Chol:PEG-DMG (50:1—:38.5:1.5) |
| MSPC | PC | 24 | Cmpd18:PC:Chol:PEG-DMG (50:1—:38.5:1.5) |
| Steric acid | OL | 24 | |
| Oleic Acid | OL | 24 | |
| Linoleic Acid | OL | 24 | |

Structural Lipids

The lipid component of a nanoparticle composition may include one or more structural lipids. Incorporation of structural lipids in the lipid nanoparticle may help mitigate aggregation of other lipids in the particle. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

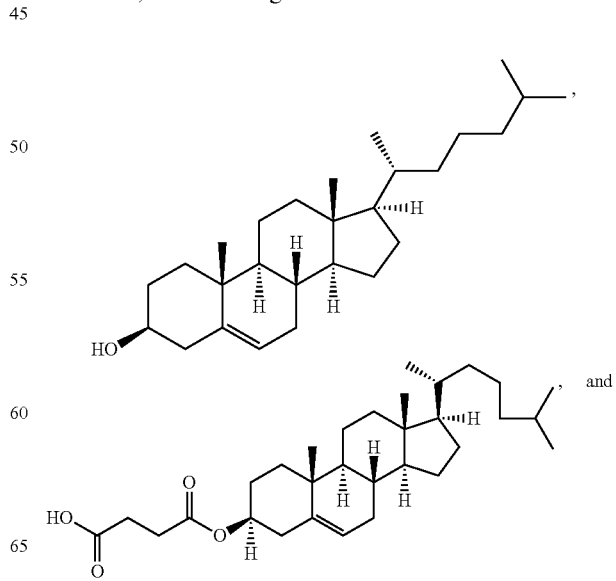

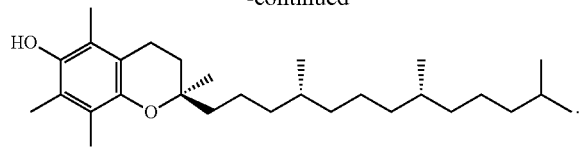

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

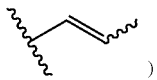

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Each possibility represents a separate embodiment of the present invention.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond. The term "unsaturated" or "partially unsaturated" refers to a moiety that includes at least one double or triple bond. The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SSR$^{cc}$, —C(=O) R$^{aa}$, —CO$_2$H, —CHO, —C(OR$^{cc}$)$_2$, —CO$_2$R$^{aa}$, —OC (=O)R$^{aa}$, —OCO$_2$R$^{aa}$, —C(=O)N(R$^{bb}$)$_2$, —OC(=O)N (R$^{bb}$)$_2$, —NR$^{bb}$C(=O)R$^{aa}$, —NR$^{bb}$CO$_2$R$^{aa}$, —NR$^{bb}$C (=O)N(R$^{bb}$)$_2$, —C(=NR$^{bb}$)R$^{aa}$, —C(=NR$^{bb}$)OR$^{aa}$, —OC (=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS (=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC (=O)SR$^{aa}$, —OC(=O)SR$^{aa}$, —SC(=O)OR$^{aa}$, —SC(=O) R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N (R$^{bb}$)$_2$)$_2$, —NR$^{bb}$P(=O)(R$^{aa}$)$_2$, —NR$^{bb}$P(O)(OR$^{cc}$)$_2$, —NR$^{bb}$P(O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP (R$^{cc}$)$_4$, —OP(OR$^{cc}$)$_4$, —B(R$^{aa}$)$_2$, —B(OR$^{cc}$)$_2$, —BR$^{aa}$ (OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, N$^{bb}$, or =NOR$^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of e is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —NR$^{bb}$C(=O)R$^{aa}$, —NR$^{bb}$CO$_2$R$^{aa}$, —NR$^{bb}$C(=O)N(R$_{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein $R^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein $R^{aa}$ and $R^{bb}$ are as defined herein.

The term "sulfinyl" refers to the group —S(=O)R$^{aa}$, wherein $R^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)S R$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-dip- henylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycycl- ohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), $NO_3^-$, $ClO_4^-$, $O^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

These and other exemplary substituents are described in more detail throughout. The invention is not intended to be limited in any manner by the above exemplary listing of substituents.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Biologically Active Agents

This disclosure contemplates that the LNPs provided herein and/or the various combination therapies provided herein may be used to deliver a variety of agents to a subject. Such agents typically will be biologically active agents. Biologically active agents are agents that have an effect in vivo, and preferably a beneficial effect, such as desirable immune modulation, immune stimulation, immune inhibition, cell killing, cell preservation, modified gene expression, protein replacement, and the like. Biologically active agents include but are not limited to prophylactic agents, therapeutic agents, and diagnostic agents. Biologically active agents include immunomodulatory agents such as immunostimulatory or immunoinhibitory agents, antigens, antibodies and antibody fragments such as antigen-binding antibody fragments, adjuvants, cytokines such as interleukins, anti-bacterial agents, anti-viral agents, anti-fungal agents, anti-parasitic agents, anti-cancer agents, anti-inflammatory agents, and the like.

Such agents may be, without limitation, nucleic acids, proteins or peptide, small organic compounds, carbohydrates and/or polysaccharides, and the like. They may be used to express nucleic acids and/or proteins in cells, particularly in cells that are deficient in such nucleic acids or proteins or have mutated versions of such nucleic acids or proteins. They may be used to introduce and express nucleic acids or proteins that are not native to the cell or organism, as may be done for example in the context of an immunization or vaccination protocol. In this respect, the nucleic acid or protein may be foreign to the subject to whom it is administered (e.g., not naturally occurring in such subject, or not naturally occurring at all), and it is administered to the subject to induce and/or boost an immune response to such nucleic acid or protein. The nucleic acids provided herein may be used for such a purpose.

Other biologically active agents may be used alone or together with such nucleic acids or proteins, including formulated together with such nucleic acids or proteins, including formulated in the LNPs of this disclosure.

Nucleic Acids

As used herein, the term "nucleic acid" refers to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. A nucleic acid sequence is presented in the 5' to 3' direction unless otherwise indicated.

Nucleic acids include any compound and/or substance that comprises a polymer of nucleotides. These polymers are referred to as polynucleotides. Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

Nucleic acids may be naturally occurring, for example, in the context of a genome, a transcript, an mRNA, tRNA, rRNA, siRNA, snRNA, plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Nucleic acids can be purified from natural sources, produced using recombinant expression systems and optionally purified, chemically synthesized, etc.

Furthermore, the terms "nucleic acid," "DNA," "RNA," and/or similar terms include nucleic acid analogs, i.e., analogs having other than a phosphodiester backbone.

Where appropriate, e.g., in the case of chemically synthesized molecules, nucleic acids can comprise nucleoside analogs such as analogs having chemically modified bases or sugars, and backbone modifications. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphdiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the therapeutic agents described herein include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladeno sine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalyl-carbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo) cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl)cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyo sine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine;

6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deaza-guanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudouridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2 (thio)-pseudouracil; 1 (aminocarbonylethylenyl)-2,4-(dithio)pseudouracil; 1 (aminocarbonylethylenyl)-4 (thio) pseudouracil; 1 (aminocarbonylethylenyl)-pseudouracil; 1 substituted 2(thio)-pseudouracil; 1 substituted 2,4-(dithio) pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonylmethyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio) uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; P seudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)p seudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP;

1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl)pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl)pseudouridine TP; 1-(4-Nitro-benzyl)pseudo-UTP; 1(4-Nitro-phenyl)pseudo-UTP; 1-(4-Thiomethoxybenzyl)pseudouridine TP; 1-(4-Trifluoromethoxybenzyl)pseudouridine TP; 1-(4-Trifluoromethylbenzyl)pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-p seudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl)pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methyl-amino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl; 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-aminopyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, modified nucleobases in the polynucleotide (e.g., RNA polynucleotide, such as mRNA polynucleotide) are selected from the group consisting of pseudouridine (ψ), N1-methylpseudouridine (m1ψ), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine,), 5-methoxyuridine and 2'-O-methyl uridine. In some embodiments, the polynucleotide (e.g., RNA polynucleotide, such as mRNA polynucleotide) includes a combination of at least two (e.g., 2, 3, 4 or more) of the aforementioned modified nucleobases. Each possibility represents a separate embodiment of the present invention.

In some embodiments, modified nucleobases in the polynucleotide (e.g., RNA polynucleotide, such as mRNA polynucleotide) are selected from the group consisting of 1-methyl-pseudouridine (m1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases. Each possibility represents a separate embodiment of the present invention. Each possibility represents a separate embodiment of the present invention.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C). Each possibility represents a separate embodiment of the present invention.

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above. Each possibility represents a separate embodiment of the present invention.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine. Each possibility represents a separate embodiment of the present invention.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenosine (m6A), and 2,6-Diaminopurine. Each possibility represents a separate embodiment of the present invention.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine. Each possibility represents a separate embodiment of the present invention.

In some embodiments, polynucleotides function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The basic components of an mRNA molecule typically include at least one coding region, a 5' untranslated region (UTR), a 3' UTR, a 5' cap and a poly-A tail. Polynucleotides may function as mRNA but can be distinguished from wild-type mRNA in their functional and/or structural design features which serve to overcome existing problems of effective polypeptide expression using nucleic-acid based therapeutics.

The mRNA, as provided herein, comprises at least one (one or more) ribonucleic acid (RNA) polynucleotide having an open reading frame encoding at least one polypeptide of interest. In some embodiments, a RNA polynucleotide of an mRNA encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 polypeptides. In some embodiments, a RNA polynucleotide of an mRNA encodes at least 10, 20, 30, 40, 50, 60, 70, 80, 90 or 100 polypeptides. In some embodiments, a RNA polynucleotide of an mRNA encodes at least 100 or at least 200 polypeptides.

In some embodiments, the nucleic acids are therapeutic mRNAs. As used herein, the term "therapeutic mRNA" refers to an mRNA that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following diseases and conditions: bacterial infections, viral infections, parasitic infections, cell proliferation disorders, genetic disorders, and autoimmune disorders.

Thus, the structures of the invention can be used as therapeutic or prophylactic agents. They are provided for use in medicine. For example, the mRNA of the structures described herein can be administered to a subject, wherein the polynucleotides are translated in vivo to produce a therapeutic peptide. Provided are compositions, methods, kits, and reagents for diagnosis, treatment or prevention of a disease or condition in humans and other mammals. The active therapeutic agents of the invention include the structures, cells containing structures or polypeptides translated from the polynucleotides contained in the structures.

The structures may be induced for translation in a cell, tissue or organism. Such translation can be in vivo, ex vivo, in culture, or in vitro. The cell, tissue or organism is contacted with an effective amount of a composition containing a structure which contains the mRNA polynucleotides each of which has at least one translatable region encoding a peptide.

An "effective amount" of the structures are provided based, at least in part, on the target tissue, target cell type, means of administration, physical characteristics of the polynucleotide (e.g., size, and extent of modified nucleosides) and other components of the nucleic acids, and other determinants. In general, an effective amount of the nucleic acids provides an induced or boosted peptide production in the cell.

The mRNA of the present invention may be designed to encode polypeptides of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery. "Therapeutic protein" refers to a protein that, when administered to a cell has a therapeutic, diagnostic, and/or prophylactic effect and/or elicits a desired biological and/or pharmacological effect.

The mRNA disclosed herein, may encode one or more biologics. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

According to the present invention, one or more biologics currently being marketed or in development may be encoded by the mRNA of the present invention. While not wishing to be bound by theory, it is believed that incorporation of the encoding polynucleotides of a known biologic into the mRNA of the invention will result in improved therapeutic efficacy due at least in part to the specificity, purity and/or selectivity of the construct designs.

The mRNA disclosed herein, may encode one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be encoded by the mRNA of the invention, including the heavy chains designated alpha, delta, epsilon, gamma and mu, respectively. Also included are polynucleotide sequences encoding the subclasses, gamma and mu. Hence any of the subclasses of antibodies may be encoded in part or in whole and include the following subclasses: IgG1, IgG2, IgG3, IgG4, IgA1 and IgA2. According to the present invention, one or more antibodies or fragments currently being marketed or in development may be encoded by the mRNA of the present invention.

Antibodies encoded in the mRNA of the invention may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

In one embodiment, mRNA disclosed herein may encode monoclonal antibodies and/or variants thereof. Variants of antibodies may also include, but are not limited to, substitutional variants, conservative amino acid substitution, insertional variants, deletional variants and/or covalent derivatives. In one embodiment, the mRNA disclosed herein may encode an immunoglobulin Fc region. In another embodiment, the mRNA may encode a variant immunoglobulin Fc region.

The mRNA disclosed herein, may encode one or more vaccine antigens. As used herein, a "vaccine antigen" is a biological preparation that improves immunity to a particular disease or infectious agent. According to the present invention, one or more vaccine antigens currently being marketed or in development may be encoded by the mRNA of the present invention. Vaccine antigens encoded in the mRNA of the invention may be utilized to treat conditions or diseases in many therapeutic areas such as, but not limited to, cancer, allergy and infectious disease.

The mRNA of the present invention may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides described herein may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, the anti-microbial polypeptide may have at least about 75%, 80%, 85%, 90%, 95%, 100% sequence homology to the corresponding viral protein sequence. In some embodiments, the anti-microbial polypeptide may have at least about 75%, 80%, 85%, 90%, 95%, or 100% sequence homology to the corresponding viral protein sequence.

In other embodiments, the anti-microbial polypeptide may comprise or consist of a synthetic peptide corresponding to a region, e.g., a consecutive sequence of at least about 5, 10, 15, 20, 25, 30, 35, 40, 45, 50, 55, or 60 amino acids of the binding domain of a capsid binding protein. In some embodiments, the anti-microbial polypeptide may have at least about 75%, 80%, 85%, 90%, 95%, or 100% sequence homology to the corresponding sequence of the capsid binding protein.

The anti-microbial polypeptides described herein may block protease dimerization and inhibit cleavage of viral proproteins (e.g., HIV Gag-pol processing) into functional proteins thereby preventing release of one or more enveloped viruses (e.g., HIV, HCV). In some embodiments, the anti-microbial polypeptide may have at least about 75%, 80%, 85%, 90%, 95%, 100% sequence homology to the corresponding viral protein sequence.

In other embodiments, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the binding domain of a protease binding protein. In some embodiments, the anti-microbial polypeptide may have at least about 75%, 80%, 85%, 90%, 95%, 100% sequence homology to the corresponding sequence of the protease binding protein.

A non-limiting list of infectious diseases that the mRNA vaccine antigens or anti-microbial peptides may treat is presented below: human immunodeficiency virus (HIV), HIV resulting in mycobacterial infection, AIDS related Cacheixa, AIDS related Cytomegalovirus infection, HIV-associated nephropathy, Lipodystrophy, AID related cryptococcal meningitis, AIDS related neutropaenia, Pneumocysitis jiroveci (*Pneumocystis carinii*) infections, AID related toxoplasmosis, hepatitis A, B, C, D or E, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), protozoan infectious diseases (malaria, sleeping sickness, leishmaniasis, toxoplasmosis, i.e. infections caused by *plasmodium*, trypanosomes, *leishmania* and *toxoplasma*), diphtheria, leprosy, measles, pertussis, rabies, tetanus, tuberculosis, typhoid, varicella, diarrheal infections such as Amoebiasis, *Clostridium difficile*-associated diarrhea (CDAD), Cryptosporidiosis, Giardiasis, Cyclosporiasis and Rotaviral gastroenteritis, encephalitis such as Japanese encephalitis, Wester equine encephalitis and Tick-borne encephalitis (TBE), fungal skin diseases such as candidiasis, onychomycosis, Tinea captis/scal ringworm, Tinea corporis/body ringworm, Tinea cruris/jock itch, sporotrichosis and Tinea pedis/Athlete's foot, Meningitis such as *Haemophilus* influenza type b (Hib), Meningitis, viral, meningococcal infections and pneumococcal infection, neglected tropical diseases such as Argentine haemorrhagic fever, Leishmaniasis, Nematode/roundworm infections, Ross river virus infection and West Nile virus (WNV) disease, Non-HIV STDs such as Trichomoniasis, Human papillomavirus (HPV) infections, sexually transmitted chlamydial diseases, Chancroid and Syphilis, Non-septic bacterial infections such as cellulitis, lyme disease, MRSA infection, *pseudomonas*, staphylococcal infections, Boutonneuse fever, Leptospirosis, Rheumatic fever, Botulism, Rickettsial disease and Mastoiditis, parasitic infections such as Cysticercosis, Echinococcosis, Trematode/Fluke infections, Trichinellosis, Babesiosis, Hypodermyiasis, Diphyllobothriasis and Trypanosomiasis, respiratory infections such as adenovirus infection, aspergillosis infections, avian (H5N1) influenza, influenza, RSV infections, severe acute respiratory syndrome (SARS), sinusitis, Legionellosis, Coccidioidomycosis and swine (H1N1) influenza, sepsis such as bacteraemia, sepsis/septic shock, sepsis in premature infants, urinary tract infection such as vaginal infections (bacterial), vaginal infections (fungal) and gonococcal infection, viral skin diseases such as B19 parvovirus infections, warts, genital herpes, orofacial herpes, shingles, inner ear infections, fetal cytomegalovirus syndrome, foodborn illnesses such as brucellosis (*Brucella* species), *Clostridium perfringens* (Epsilon toxin), *E. Coli* O157:H7 (*Escherichia coli*), Salmonellosis (*Salmonella* species), Shingellosis (Shingella), Vibriosis and Listeriosis, bioterrorism and potential epidemic diseases such as Ebola haemorrhagic fever, Lassa fever, Marburg haemorrhagic fever, plague, Anthrax Nipah virus disease, Hanta virus, Smallpox, Glanders (*Burkholderia mallei*), Melioidosis (*Burkholderia pseudomallei*), Psittacosis (*Chlamydia psittaci*), Q fever (*Coxiella burnetii*), Tularemia (Fancisella *tularensis*), rubella, mumps and polio.

The mRNA disclosed herein, may encode one or more validated or "in testing" therapeutic proteins or peptides. According to the present invention, one or more therapeutic proteins or peptides currently being marketed or in development may be encoded by the mRNA of the present invention. Therapeutic proteins and peptides encoded in the mRNA of the invention may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

The mRNA disclosed herein, may encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The mRNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the mRNA may also encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide encoded by the mRNA may form a complex after being translated. The complex may comprise a charged protein linked, e.g. covalently linked, to the cell-penetrating polypeptide.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the mRNA may be introduced. The cell-penetrating polypeptide may also be capable of penetrating the first cell.

In one embodiment, the mRNA may encode a cell-penetrating polypeptide which may comprise a protein-binding partner. The protein binding partner may include, but is not limited to, an antibody, a supercharged antibody or a functional fragment. The mRNA may be introduced into the cell where a cell-penetrating polypeptide comprising the protein-binding partner is introduced.

Some embodiments of the present disclosure provide a therapeutic mRNA that includes at least one ribonucleic acid (RNA) polynucleotide having an open reading frame encoding at least one antigenic polypeptide, in which the RNA polynucleotide of the RNA includes at least one chemical modification. In some embodiments, the chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine,), 5-methoxyuridine, and 2'-O-methyl uridine. Each possibility represents a separate embodiment of the present invention.

Any of the foregoing polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

As used herein, when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% or 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

The immunomodulatory agent may be an immunostimulatory agent or an immunoinhibitory agent.

An immunostimulatory agent is an agent that stimulates an immune response (including enhancing a pre-existing immune response) in a subject to whom it is administered, whether alone or in combination with another agent. Examples include antigens, adjuvants (e.g., TLR ligands such as imiquimod, imidazoquinoline, nucleic acids comprising an unmethylated CpG dinucleotide, monophosphoryl lipid A or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like.

An immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants.

Adjvants are agents that enhance an immune response. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy) phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic)

Adjuvants may be TLR ligands. Adjuvants that act through TLR3 include without limitation double-stranded RNA. Adjuvants that act through TLR4 include wihtout limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod, resiquimod). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The antigen may be without limitation a cancer antigen, a self-antigen, a microbial antigen, an allergen, or an environmental antigen. The antigen may be peptide, lipid, or carbohydrate in nature, but it is not so limited.

A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis *coli* protein (APC), fodrin, Connexin 37, Ig-idiotype, p15, gp75, GM2 ganglioside, GD2 ganglioside, human papilloma virus proteins, Smad family of tumor antigens, 1mp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2. Each possibility represents a separate embodiment of the present invention.

Microbial antigens are antigens derived from microbial species such as without limitation bacterial, viral, fungal, parasitic and mycobacterial species. As such, microbial antigens include bacterial antigens, viral antigens, fungal antigens, parasitic antigens, and mycobacterial antigens. Examples of bacterial, viral, fungal, parasitic and mycobacterial species are provided herein. The microbial antigen may be part of a microbial species or it may be the entire microbe.

An anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, *vinca* alkaloids. or epipodophyllotoxins.

Examples of anti-cancer agents include without limitation Acivicin; Aclarubicin; Acodazole Hydrochloride; Acronine;

Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4',5,7-trihydroxyisoflavone), Tyrphostin 25 (3,4,5-trihydroxyphenyl), methyleneFpropanedinitrile, Herbimycin A, Daidzein (4',7-dihydroxyisoflavone), AG-126, trans-1-(3'-carboxy-4'-hydroxyphenyl)-2-(2",5"-dihydroxyphenyl)ethane, or HDBA (2-Hydroxy5-(2,5-Dihydroxybenzylamino)-2-hydroxybenzoic acid. The CDK inhibitor may be without limitation p21, p2'7, p5'7, p15, p16, p18, or p19. The MAP kinase inhibitor may be without limitation KY12420 ($C_{23}H_{24}O_8$), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

The anti-cancer agent may be a VEGF inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-05, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

A diagnostic agent, which may be referred to herein as an imaging agent, is an agent that emits signal directly or indirectly thereby allowing its detection in vivo. Diagnostic agents such as contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203 Pb, and 11In; imaging agents for in vivo fluorescence imaging such as fluorescent dyes or dye-conjugated nanoparticles. In other embodiments, the agent to be delivered is conjugated, or fused to, or mixed or combined with an diagnostic agent.

The compounds and compositions may be administered to virtually any subject type that is likely to benefit from delivery of agents as contemplated herein. Human subjects are preferred subjects in some embodiments of the invention. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., mice, rats, rabbits, etc.), and the like. Subjects also include fish and other aquatic species.

The subjects to whom the agents are delivered may be normal subjects. Alternatively they may have or may be at risk of developing a condition that can be diagnosed or that can benefit from localized delivery of one or more particular agents. Such conditions include cancer (e.g., solid tumor cancers), infections (particularly infections localized to particular regions or tissues in the body), autoimmune disorders, allergies or allergic conditions, asthma, transplant rejection, and the like. In some embodiments, the subjects have been diagnosed with a genetic defect and are being administered a nucleic acid based therapeutic.

Agents may be administered systemically or locally. Agents may be administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

The invention provides pharmaceutical compositions. Pharmaceutical compositions are sterile compositions that comprise agents and may comprise delivery vehicles, nanoparticles and the like, preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and agent(s) are combined to facilitate administration. The components of the pharmaceutical compositions are commingled in a manner that precludes interaction that would substantially impair their desired pharmaceutical efficiency.

The compounds and compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions such as are known in the art or that will be readily apparent to those of ordinary skill in the art based on this disclosure.

This disclosure further contemplates use of LNPs together with one or more secondary agents, including agents that would normally be indicated for the subject.

In some instances, the LNPs may be administered substantially simultaneously with the secondary agents. By substantially simultaneously, it is meant that a LNP is administered to a subject close in time with the administration of the secondary agent, including for example with 1 hour, within 30 minutes, within 10 minutes, or within 5 minutes.

In some instances, the secondary agent(s) may be administered prior to the LNP. For example, the secondary agent(s) may be administered prior to and within 24 hours, or within 18 hours, or within 12 hours, or within 6 hours, or within 3 hours, or within 2 hours of the LNP administration. The secondary agent(s) may be administered 18-24 hours prior to LNP administration, or 12-18 hours prior to LNP administration, or 6-12 hours prior to LNP administration, or 2-6 hours prior to LNP administration.

Subjects who have been administered one or more secondary agents 2 or more hours prior to LNP administration may be referred to as having been pre-medicated with such agent(s). Subjects who have been administered one or more secondary agents within 1 hour prior to LNP administration may be referred to as having been co-mediated with such agent(s).

In some instances, the secondary agent(s) may be administered continuously to the subject, on an as needed basis or on a regular schedule (e.g., every day, every two days, etc.).

In other instances, the secondary agent may be administered before or after the administration of the LNP.

Such secondary agents may include but are not limited to anti-histamines, anti-platelet agents, and non-steroidal anti-inflammatory drugs. In certain embodiments, the LNPs are not formulated with and subjects are not pre- or co-medicated with a corticosteroid, such as but not limited to dexamethasone.

In certain embodiments, single secondary agents having anti-inflammatory and anti-platelet effects are used. An example of such an agent is aspirin.

In certain embodiments, a combination of aspirin, clopidrogrel (Plavix®), and an anti-histamine such as but not limited to diphenhydramine (Benadryl), fexofenadine (Allegra), loratadine (Claritin), or cetirizine is used. One or more of the secondary agents may be administered once per LNP administration while others may be administered more frequently. For example, clopidrogrel (Plavix®) may be administered once per LNP administration while aspirin and/or the anti-histamine may be administered daily.

Anti-histamines include H1 receptor antagonists and H1 receptor inverse agonists.

Examples of H1 receptor antagonists include but are not limited to acrivastine, alimemazine, alimemazine tartrate, antazoline, astemizole, azatadine, azatadine maleate, azelastine, bamipine, benzquinamide, bepotastine, bepotastine besilate, bilastine bromazine, bromopheniramine, buclizine, carbinoxamine, chlorphenoxamine, chlorcyclizine, cinnopentazone histapyrrodine, chlorodipheynhydramine, chloropyramine, chlorphenamine, Chlorpromazine, cinnarizine, clemastine, clemizole, clocinizine, cyclizine, cyproheptadine, desloratadine, deptropine, dexchlorpheniramine, dexbrompheniraine, dimenhydrinate, dimetindene, dimetotiazine, diphenhydramine (Benadryl), piphenylpyraline, doxepin, doxylamine, ebastine, efletirizine, embramine, emedastine, epinastine, fexofenadine (Allegra), flunarizine, homochlorcyclizine, hydroxyzine, isothipendyl, ketotifen, levocabastine (2nd genereation), loratadine (Claritin), mebhydroline, meclozine, mepyramine, mequitazine, methdilazine, mirtazapine, mizolastine, niaprazine, olopatadine, orphenadrine, oxatomide, oxomemazine, pemirolast, phenindamine, pheniramine, phenyltoloxamine, pimethixene, piprinhydrinate, promethazine, propiomazine, pyrrobutamine, quetiapine, quifenadine, rupatadine, setastine, terfenadine, thenyldiamine, thiethylperazine, thonzylamine, tolpropamine, trimethobenzamine, tripelennamine, triprolidine and tritoqualine.

Examples of H1 receptor inverse agonists include but are not limited to pyrilamine, cetirizine, levocetirizine, and desloratadine.

Anti-platelet agents include but are not limited to activation inhibitors, aggregation inhibitors, adhesion antagonists, anti-coagulation drugs (that do not target platelets directly), and agents that reduce platelet count or numbers.

Examples of activation inhibitors include but are not limited to (1) thrombin receptor PAR-1 inhibitors such as SCH 530348 (vorapaxar), E-5555 (atopaxar), SCH79797, FR 171113, RWJ 56110, BMS-200661, RWJ-58259, SCH205831, Pipal-7 pepducin, P1pal-12 pepducin; (2) thrombin receptor PAR-4 inhibitors such as ML 354, tcY-NH2, P4pal-10 pepducin, P4pal-i1 pepducin; (3) FSLLRY- NH2 (PAR-2 peptide antagonist); (4) TxA2 receptor antagonists such as AH 23,848, SQ 29,548, or R 68,070, S-1452, iosartan, seratrodast; (5) thromboxane receptor antagonists such as terutroban; (6) ADP P2Y12 receptor inhibitors such as ticlopidine, clopidogrel, prasugrel, ticagrelor, cangrelor, elinogrel, AZD6140, AR-C69931, CoA; (7) ADP P2Y1 receptor inhibitors such as A2P5P, A3P5P, MRS2179, MRS2279, MRS2500, palmitoyl-CoA (also acts on P2Y12), and other compounds from SAR study by Thalji et al. 2010; (8) 5-HT2A antagonists such as R-1012444, naftidrofuryl, sarpogrelate, AT-1015; (9) thromboxane syntahase inhibitors such as dazoxiben, CS-518 (TXA2 synthase inhibitor), SB 203580, U63557A, imidazo (1,5-2) pyridine-5-hexanoic acid; (10) COX-1 inhibitors such as aspirin, NCX-4016, ridogrel, S18886, picotamide, ramatroban (also TXA2 receptor antagonist), SC-560, FR122047, mofezolac, P6, TFAP, ibuprofen and naproxen (also Cox-2 inhibitors); (11) COX-2 inhibitors such as triflusal (also COX-1 and PDE inhibitor), Etoricoxib, rofecoxib, celecoxib, meloxicam; and (12) PI3K inhibitors such as AZD6482.

Examples of aggregation inhibitors include but are not limited to (1) GPIa/IIa Inhibitors such as EMS16; (2) GPVI inhibitors such as monoclonal antibodies and Fab fragments of mAb 12A5; (3) GPIIb/IIIa inhibitors such as abciximab, eptifibatide, tirofiban; (4) PDE inhibitors such as dipyridamole (also adenosine reuptake inhibitor), cilostazol (PDE3 inhibitor that results in increased cAMP, and activated PKA), and (5) ADP receptor antagonists. Other platelet aggregation inhibitors include aspirin, clopidrogrel (Plavix®), aspirin/pravastatin, cilostazol, prasugrel, aspirin/dipyridamole, ticagrelor, cangrelor, elinogrel, dipyridamole, and ticlopidine.

Examples of adhesion antagonists (to fibrinogen) include but are not limited to C1qTNF-related protein-1, DZ-697b, RG12986.

Examples of non-platelet anti-coagulation agents include but are not limited to warfarin; Xa inhibitors such as rivaroxaban, apixaban, edoxaban, betrixaban, darexaban, otamixaban; thrombin inhibitors such as bivalirudin, hirudin, dabigatran, lepirudin, desirudin, argatroban, melagatran, dabigatran, CDSO3, FDSO3, SDSO3, and additional sulphated benzofurans allorsteric inhibitors reported by Sidhu et al. paper.

Examples of agents that reduce platelet count or number include but are not limited to (1) cAMP phosphodiesterase inhibitors (e.g., anagrelide), 6,7-dichloro-1,5-dihydroimidazo-[2,1-b]quinazolin-2(3H)-one or 6,7-dichloro-1,2,3,5-tetrahydroimidazo[2,1-b]quinazolin-2-one (U.S. Pat. Nos. 3,932,407; 4,146,718; RE31,617, Haematologica 1992 77:40-3), (2) antibodies to cell surface receptors specifically expressed by platelets or megakaryocytes such as glycoprotein IIb/IIIa receptor antibodies, (3) most chemotherapeutic anti-cancer drugs such as busulphan (Br. J. Haematol. 1986 62:229-37), hydroxyurea (N Engl J Med 1995 332:1132-6), hepsulfan, phosphorus-32 (Br J Radiol 1997 70:1169-73), pipobroman (Scand J. Haematol 1986 37:306-9), cyclophosphamide (J Cell Physiol 1982 112:222-8), certain alkylating agents and certain antimetabolites, (4) cytokines, growth factors and interleukins such as alpha-interferon (Cancer Immunol Immunother 1987 25:266-73), gamma-interferon, transforming growth factor-beta, neutrophil activating peptide-2 and its analogs (U.S. Pat. No. 5,472,944), macrophage inflammatory protein and its analogs (U.S. Pat. No. 5,306,709), (5) compounds secreted by either platelets or megakaryocytes such as platelet-factor 4 (U.S. Pat. No. 5,185,323), transforming growth factor-beta, the 12-17 kD glycoprotein produced by megakaryocytes, thrombin and thrombospondin and its amino (1-174 amino acid) terminal fragment (J Lab Clin Med 1997 129:231-8), and (6) other agents including anti-cheloid agents such as Tranilast (Rizaben) (J Dermatol 1998 25:706-9); forskolin and spleen anti-maturation factor (U.S. Pat. No. 4,088,753).

Anti-platelet agents may also be characterized as anti-thrombotic agents, fibrinolytic agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, and angiotensin system inhibitors.

Anti-thrombotic agents are defined as agents which prevent the formation of a blood thrombus via a number of potential mechanisms and they include fibrinolytic agents, anti-coagulant agents, and inhibitors of platelet function.

Fibrinolytic agents are defined as agents that lyse a thrombus (e.g., a blood clot), usually through the dissolution of fibrin by enzymatic action. Examples of thrombolytic agents include but are not limited to ancrod, anistreplase, bisobrin lactate, brinolase, Hageman factor (i.e. factor XII) fragments, molsidomine, plasminogen activators such as streptokinase, tissue plasminogen activators (TPA) and urokinase, and plasmin and plasminogen. Anti-coagulant agents also include inhibitors of factor Xa, factor TFPI, factor VIIa, factor IXc, factor Va, factor VIIIa as well as inhibitors of other coagulation factors.

Anti-coagulant agents are agents which inhibit the coagulation pathway by impacting negatively upon the production, deposition, cleavage and/or activation of factors essential in the formation of a blood clot. Anti-coagulant agents include but are not limited to vitamin K antagonists such as coumarin and coumarin derivatives (e.g., warfarin sodium); glycosoaminoglycans such as heparins both in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, and tinzaparin sodium.

Other "anti-coagulant" and/or "fibrinolytic" agents include Plasminogen; Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Streptase; Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Still other anti-coagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bromindione; Desirudin; Dicumarol; Heparin Calcium; Heparin Sodium; Lyapolate Sodium; Nafamostat Mesylate; Phenprocoumon.

Clot lysing agents include, but are not limited to, tissue plasminogen activator, streptokinase, and nimodipine.

Inhibitors of platelet function are agents that impair the ability of mature platelets to perform their normal physiological roles (i.e., their normal function). Platelets are normally involved in a number of physiological processes such as adhesion, for example, to cellular and non-cellular entities, aggregation, for example, for the purpose of forming a blood clot, and release of factors such as growth factors (e.g., platelet-derived growth factor (PDGF)) and platelet granular components. One subcategory of platelet function inhibitors are inhibitors of platelet aggregation which are compounds which reduce or halt the ability of platelets to associate physically with themselves or with other cellular and non-cellular components, thereby precluding the ability of a platelet to form a thrombus.

Examples of useful inhibitors of platelet function include but are not limited to acadesine, anagrelide, anipamil, argatroban, aspirin, clopidogrel, cyclooxygenase inhibitors such as nonsteroidal anti-inflammatory drugs and the synthetic compound FR-122047, danaparoid sodium, dazoxiben hydrochloride, diadenosine 5',5'''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin (PGI2), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and anti-serotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

"Direct thrombin inhibitors" include hirudin, hirugen, hirulog, agatroban, PPACK, thrombin aptamers.

"Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotaloladolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazo1,7-(2-hydroxy-3-t-butylaminpropoxy) phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase" is an enzyme complex present in most tissues that produces various prostaglandins and thromboxanes from arachidonic acid. Nonsteroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity").

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2,3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419

"Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors." Aspirin is an example of a COX-2 inhibitor.

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

Non-steroidal anti-inflammatory drugs include but are not limited to naproxen sodium, diclofenac, sulindac, oxaprozin, diflunisal, aspirin, piroxicam, indomethocin, etodolac, ibuprofen, fenoprofen, ketoprofen, mefenamic acid, nabumetone, tolmetin sodium, and ketorolac tromethamine.

In some embodiments, the secondary agent may be an agent that inhibits the production of natural IgM, IgG, and/or activation of B1a and/or B1b cells by LNPs. Such agents may be antagonists of a surface receptor of B1a cells (e.g., CD36 and C5a) or B1b cells, for examples, antibodies or small molecule inhibitors that bind the surface receptor and interfere with its binding to its cognate ligands (e.g., lipid component such as phosphatidylcholine in certain LNPs).

In other embodiments, the secondary agent may be an agent that inhibits the activation of platelets and/or complement system (classical pathway or alternative pathway) by LNPs. Such agents may be CD36 antagonists, TLR antagonists, or antagonists of any component in the complement cascade. Such antagonists may be antagonistic antibodies specific to one of the targets. In some examples, the antagonists may be a protease inhibitor that targets one or more of the serine protease component in the complement system. Other CD36 antagonists include, but are not limited to, salvianolic acid or metabolites thereof (e.g., RA and DSS), 3-cinnamoyl indole, 13-pentyl berberine, hexarelin, or certain fatty acids such as DHA.

It is to be understood that the disclosure contemplates use of one or more of the foregoing secondary agents with any of the LNP provided herein, including for example those that comprise a cationic lipid such as MC3, a helper lipid such as DSPC or DOPE, a structural lipid such as cholesterol, and a methoxy-PEGylated lipid such as DMG-PEG, including when such methoxy-PEGylated lipid is used at a molar percentage of greater than 0.5% including 1.5%. Thus, the disclosure contemplates that LNPs that would otherwise trigger a platelet response may be used together with secondary agents that include one or more anti-platelet secondary agents. Such combinations are intended to reduce frequency and/or severity of ABC and toxicity related to LNP use in vivo.

Also provided herein are methods for reducing drug responses, including ABC and dose-limiting toxicity, associated with LNPs encapsulating mRNAs.

ABC is a threshold phenomenon, which means that the dose of an agent such as LNPs must reach a threshold to induce clinically signicant ABC (substantial). Accordingly, it is contemplated that using a dose lower than the threshold could reduce ABC or prevent its occurrence. Alternatively, the LNPs described herein can lower B1a and/or B1b and/or natural IgM stimulating activity and thus increase the dosing threshold.

In some embodiments, a method for reducing ABC of lipid LNPs encapsulating an mRNA can be performed by at least (i) administering to a subject in need thereof a first dose of the LNPs, and (ii) administering to the subject a second dose of the LNPs; wherein the first dose, the second dose, or both are equal to or less than about 0.3 mg/kg. For example, the first dose, the second dose, or both can be equal to or less than 0.2 mg/kg or 0.1 mg/kg. In some examples, the first dose, the second dose, or both, can range from about 0.1-0.3 mg/kg. The interval between the first dose and the second dose can be less than 2 weeks, e.g, less than 10 days, less than 1 week, less than 4 days, or less than 2 days. When subsequent doses are required, the same low doses described herein may be used. The interval between two consecutive doses may be less than 2 weeks, for example, less than 10 days, less than 1 week, less than 4 days, or less than 2 days.

Dose-limiting toxicity, such as CARPA, refers to side effects of a drug or other treatment that are serious enough to prevent an increase in dose or level of treatment. It is contemplated that using treatment regimens that could maintain the serum level of LNPs below the threshold for triggering clinically significant dose-limiting toxicity would reduce such toxicity or prevent its occurrence.

Accordingly, provided herein is a method for delivering lipid nanoparticles (LNPs) encapsulating an mRNA to a subject without promoting LNP-related toxicity. Such a method comprises administering an amount of the LNPs to a subject during a period, wherein the serum level of the LNPs in the subject during the administration period is not sufficient to induce LNP-related toxicity. The LNP-related toxicity may be coagulopathy, disseminated intravascular coagulation (DIC), vascular thrombosis, activation-related pseudoallergy (CARPA), acute phase response (APR), or a combination thereof.

It is within the knowledge of those skilled in the art to select suitable doses of the mRNA-encapsulating LNPs and the duration of the administration (e.g., infusion) so as to maintain the serum level of the LNPs below the threshold. For example, when a large dose is needed to reach the intended therapeutic effects, a longer administration period can be used. Occurrence of any of the dose-limiting toxicity can be monitored via conventional approaches in medical practice. The dose and administration period can be adjusted upon showing of any symptom associated with the toxicity. In some examples, the dose of the LNPs may be lower than 1 mg/kg, e.g., 0.5 mg/kg, 0.3 mg/kg, 0.2 mg/kg, or 0.1 mg/kg. In other examples, the LNP dose may range from 0.5 to 1 mg/kg (e.g., 0.3 to 0.5 mg/kg). The administration period may range from 30 minutes to 3 hours, for example 1-2 hours. In some instances, the administration period is no less than 1 hour, for example, no less than 1.5 hours, no less than 2 hours, no less than 2.5 hours, or no less than 3 hours.

In any of the methods described herein, the mRNA encapsulated in LNPs can be a therapeutic mRNA, which may code for a therapeutic protein. The mRNA encapsulated in LNPs may also be a mRNA encoding a vaccine antigen.

In some instances, the mRNA encapsulated in LNPs may encode multiple proteins. In some embodiments, the LNPs used in this method can be any of the LNPs described herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Exemplary Assay Methods:

1. Bead Assays by Flow Cytometry:

Streptavidin CML latex beads (Polysciences Inc) were coupled with biotinylated DSPC (6 mm beads) or biotinylated PEG (10 mm beads) following manufacturer's recommendations. Coupled Beads (DSPC coupled and PEG coupled) were incubated with diluted serum from mice injected with different LNPs for 30 minutes at room temperature. After washing, beads were then incubated with a rat anti-mouse IgM IgG (BD biosciences) for 15 minutes at room temperature. After washing, cells were resuspended in PBS+2% BSA and analyzed by flow cytometry with a BD Fortes ssa (BD Biosciences). Titers of anti LNP IgM were calculated based on standard curve obtained with an anti-PEG IgM monoclonal antibody. Analysis was performed with FlowJo and Prism Software.

2. In Vitro Platelet Activation Assay with LNPs or LNPs Components

Blood samples were collected in 6 mL BD Vacutainer containing 1 mL anticoagulant citrate dextrose (BD biosciences) and centrifuged with no acceleration and no brake at 200×g, 22° C., for 20 minutes. The top, transparent layer of platelet rich plasma (PRP) was transferred into a 15 mL conical tube and washed in PBS+2% fetal calf serum. After counting, $10^5$ cells were incubated at room temperature for different time points with different LNPs or LPS or different LNP components and stained with anti-CD41, CD31 and CD62P fluorescently labeled for 20 min on ice. After washing cells were fixed and analyzed by flow cytometry with a BD Fortessa (BD Biosciences). Analysis was performed with FlowJo and Prism Software.

3. In Vitro Platelet Aggregation with Macrophages, B Cells

Blood sample were collected in 6 mL BD Vacutainer containing 1 mL anticoagulant citrate dextrose (BD biosciences). 10-25 ml of blood were incubated at room temperature for different time points at room temperature with different LNPs or LPS and stained with anti-CD41, CD11b, CD19 and F4/80 fluorescently labeled for 20 min on ice. After washing cells were fixed and analyzed by flow cytometry with a BD Fortessa (BD Biosciences). Analysis was performed with FlowJo and Prism Software.

4. In Vivo Platelet Activation Assay

Mice were injected intravenously with different LNPs. After different time points, Blood sample were collected in 6 mL BD Vacutainer containing 1 mL anticoagulant citrate dextrose (BD biosciences) and centrifuged with no acceleration and no brake at 200×g, 22° C., for 20 minutes. The top, transparent layer of platelet rich plasma (PRP) was transferred into a 15 mL conical tube and washed in PBS+2% fetal calf serum. After counting, $10^5$ cells were stained with anti-CD41, CD31 and CD62P fluorescently labeled for 20 min on ice. After washing cells were fixed and analyzed by flow cytometry with a BD Fortessa (BD Biosciences). Analysis was performed with FlowJo and Prism Software.

5. In Vivo Platelet Aggregation with Macrophages, B Cells

Mice were injected intravenously with different LNPs. After different time points, Blood sample were collected in 6 mL BD Vacutainer containing 1 mL anticoagulant citrate dextrose (BD biosciences). 10-25 ml of blood were the stained with anti-CD41, CD11b, CD19 and F4/80 fluorescently labeled for 20 min on ice. After washing cells were fixed and analyzed by flow cytometry with a BD Fortessa (BD Biosciences). Analysis was performed with FlowJo and Prism Software.

6. In Vivo Splenic B Cell Activation Assay:

Spleen of injected animals with fluorescent LNPs were collected in saline buffer. Splenocytes cell suspension were prepared by gently pressing the spleen through a 70-µM mesh cell strainer (Fisher Scientific). After washing, red blood cells was lysed and cells were resuspended in PBS+2% fetal calf serum. After washing and counting, $10^5$ cells were stained with anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

7. In Vivo LNP Interaction with B Cells:

Spleen of injected animals with fluorescent LNPs were collected in saline buffer. Splenocytes cell suspension were prepared by gently pressing the spleen through a 70-µM mesh cell strainer (Fisher Scientific). After washing, red blood cells was lysed and cells were resuspended in PBS+2% fetal calf serum. After washing and counting, $10^5$ cells were stained with anti-CD19 and CD5 fluorescently labeled for 20 min on ice. After washing cells were fixed and analyzed by flow cytometry with a BD Fortessa (BD Biosciences). Analysis was performed with FlowJo and Prism Software.

8. In Vitro Splenic B Cell Activation Assay:

Spleen of injected animals with fluorescent LNPs were collected in saline buffer. Splenocytes cell suspension were prepared by gently pressing the spleen through a 70-µM mesh cell strainer (Fisher Scientific). After washing, red blood cells was lysed and cells were resuspended in PBS+2% Fetal calf serum. After counting, $10^5$ cells were incubated at 37 C for the indicated time points with different LNPs or medium. After incubation, cells were stained anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

9. In Vitro LNP Interaction with B Cells:

Spleen of injected animals with fluorescent LNPs were collected in saline buffer. Splenocytes cell suspension were prepared by gently pressing the spleen through a 70-µM mesh cell strainer (Fisher Scientific). After washing, red blood cells was lysed and cells were resuspended in PBS+2% Fetal calf serum. After counting, $10^5$ cells were incubated at 37 C for the indicated time points with different LNPs or medium. After incubation, cells were stained anti-CD19 and CD5 fluorescently labeled for 20 min on ice. After washing cells were fixed and analyzed by flow cytometry with a BD Fortessa (BD Biosciences). Analysis was performed with FlowJo and Prism Software.

10. Human B Cell Activation Assay:

Human PBMC were isolated post-Ficoll gradient separation. After counting, $10^5$ cells were incubated at 37 C for the indicated time points with different LNPs or medium. After incubation, cells were washed and stained with anti-CD19, CD86 and CD69 fluorescently labeled for 20 min on ice. After washing cells were fixed and analyzed by flow cytometry with a BD Fortessa (BD Biosciences). Analysis was performed with FlowJo and Prism Software.

Anti-PEG IgM: In several of the figures the terminology anti-PEG IgM is used generally to refer to IgM. If the IgM is detected at a time point earlier than 96 hours following delivery of the LNP, the IgM is natural IgM. If the IgM is measured after 96 hours, the IgM may be anti-PEG IgM and/or natural IgM. Natural IgM bind phosphocholine motif rather than PEG.

Example 1

$2 \times 10^5$ sterile unfractionated splenocytes were incubated with 200 ng of EGFP mRNA formulated with PE+ or PE− LNP PE-Rhodamine. LNP comprised MC3, DMG-PEG (1.5%), DSPC and cholesterol, mRNA expressing EGFP, and PE for visualizing LNP presence. After 2, 4, 6, 24, 48 or 120 h, cells were stained for CD3 and CD19 and analyzed by flow cytometry for PE uptake and EGFP expression. In parallel, $10^5$ HeLa cells were incubated with 100 ng of EGFP mRNA formulated with LNP PE-Rhodamine and EGFP expression was followed by microscopy with IncuCyte technology. PE=phycoerythrin, fluoresces at 562 nm. PE fluorescence demonstrates presence of the LNP. Enhanced green fluorescence protein (EGFP) once translated has a maximum emission wavelength of 509 nm. EGFP fluorescence demonstrates the LNP cargo was translated.

Figure 1:
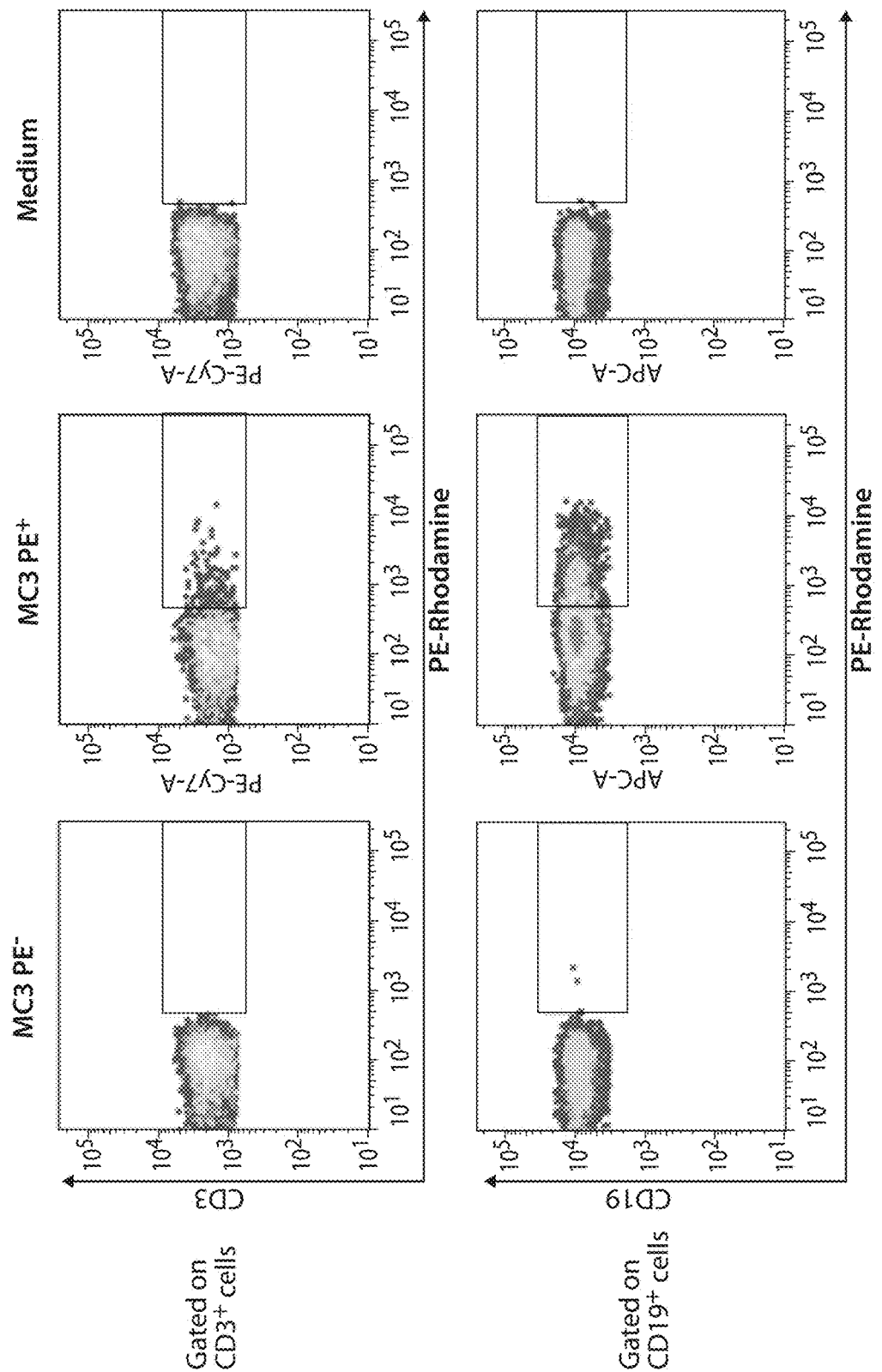
FIG. 1: Phycoerythrin (PE) fluorescence of CD3+ T cells and CD19+ B cells following incubation with PE− LNP, PE+ LNP or medium alone. The data show uptake of LNPs by splenic B cells but not T cells under ex vivo culture conditions.

LNPs associate or are taken up primarily by B cells (CD19+ cells) and not T cells (CD3+ cells) in ex vivo culture conditions, as shown in FIG. 1. Splenocytes incubated with LNPs lacking PE or with medium alone show no PE-Rhodamine fluorescence, as expected.

Figure 2A:
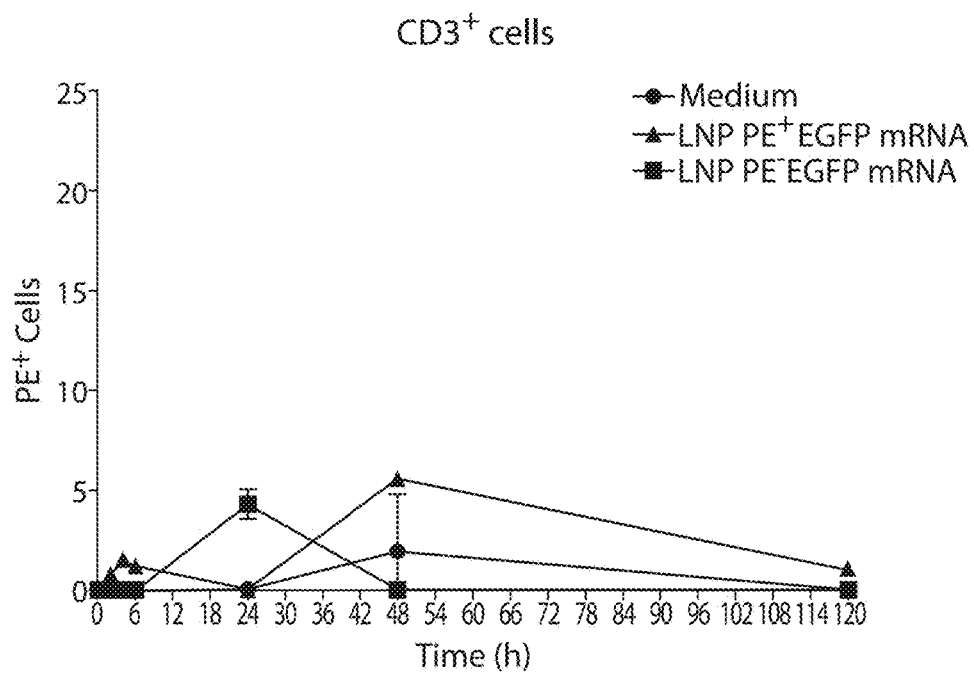
FIGS. 2A-2B: Phycoerythrin (PE) fluorescence of CD3+ T cells and CD19+ B cells as a function of time of incubation with PE− LNP, PE+ LNP or medium alone. The data show LNP uptake by B cells but not T cells occurs rapidly in these ex vivo culture conditions.
Figure 2B:
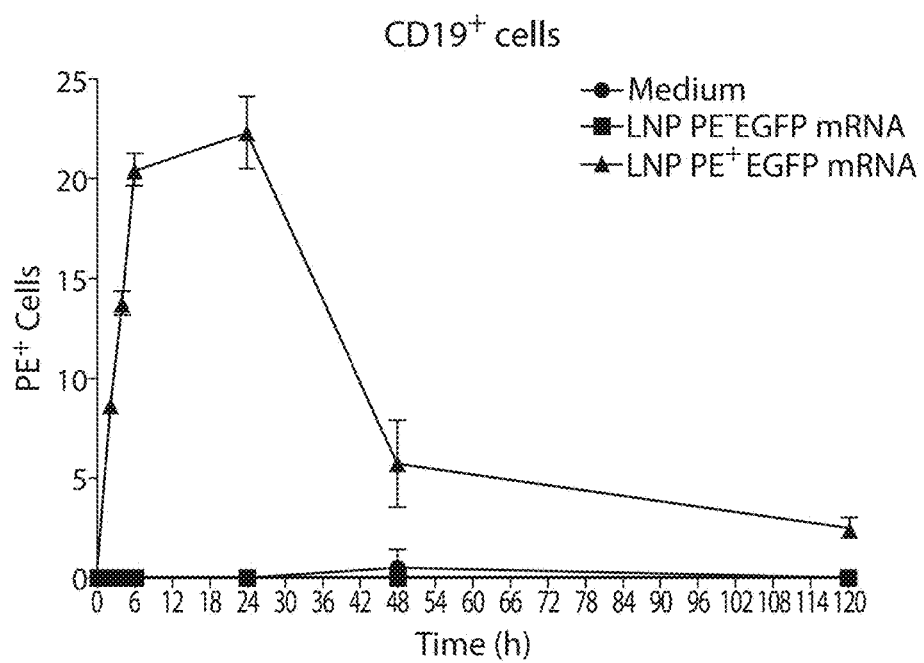

Time courses for LNP association or uptake by CD3+ T cells or CD19+ B cells are provided in FIGS. 2A and 2B, respectively. CD19+ B cells associate and/or uptake the LNP rapidly upon ex vivo culture incubation, and to a much greater extent than CD3+ T cells. About 20% of CD19+ B cells stain positive for PE up to about 48 hours of incubation. Only about 5% of CD3+ T cells stain with PE, and then only at after 48 hours of incubation. Thus, it appears that B cells associate and/or take up the LNPs to a much greater extent and more rapidly than do T cells.

Figure 3:
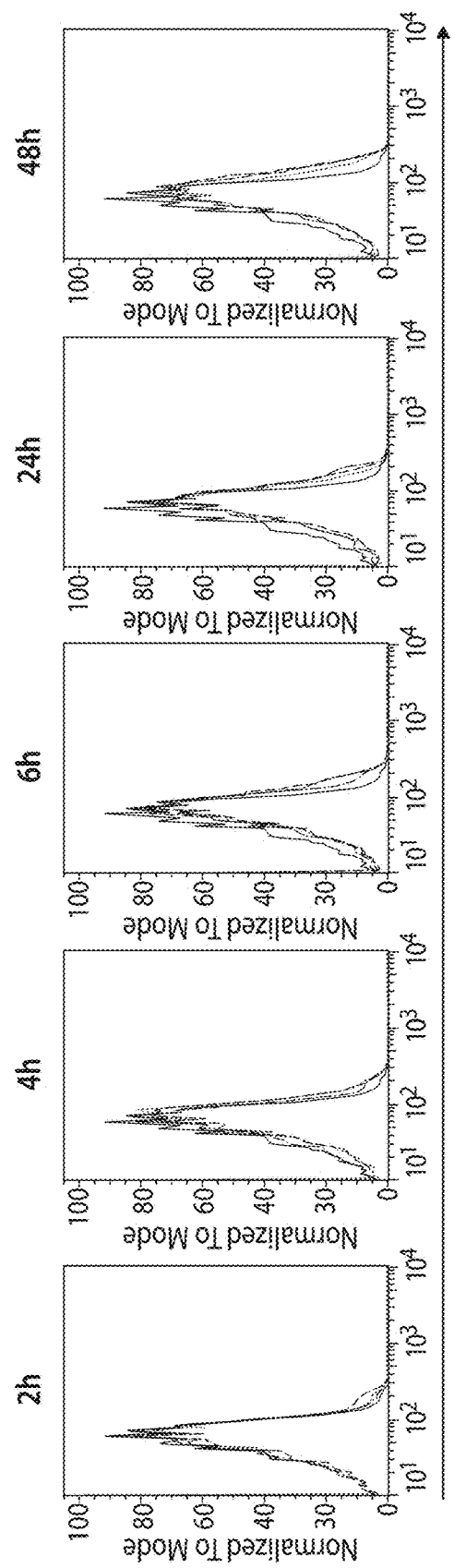
FIG. 3: EGFP fluorescence of CD19+ cells as a function of time of incubation with PE+ LNP comprising EGFP mRNA. No expression of EGFP by B cells is observed at any time point, despite massive LNP uptake by those cells.

However, CD19+ B cells do not however express the LNP mRNA cargo, as demonstrated in FIG. 3. No EGFP fluorescence is observed from CD19+ B cells. The times tested correspond to the time period in which maximum LNP association and/or uptake by CD19+ was observed (i.e., up to and including 48 hours). Thus, the B cells appear to associate and/or take up the LNP but do not express the LNP mRNA cargo.

In order to assess the integrity of the cargo EGFP mRNA in these experiments, a control experiment was performed in which HeLa cells were incubated with the PE+ and PE− LNPs, both comprising EGFP mRNA, and PE and EGFP fluorescence was tested. Images were obtained using IncuCyte. As expected, cells incubated with PE+ LNP showed red fluorescence, while cells incubated with PE− LNP did not. Both cell populations; however, fluoresced green, indicating that the LNP mRNA cargo was expressed in both populations.

Example 2

Figure 4A:
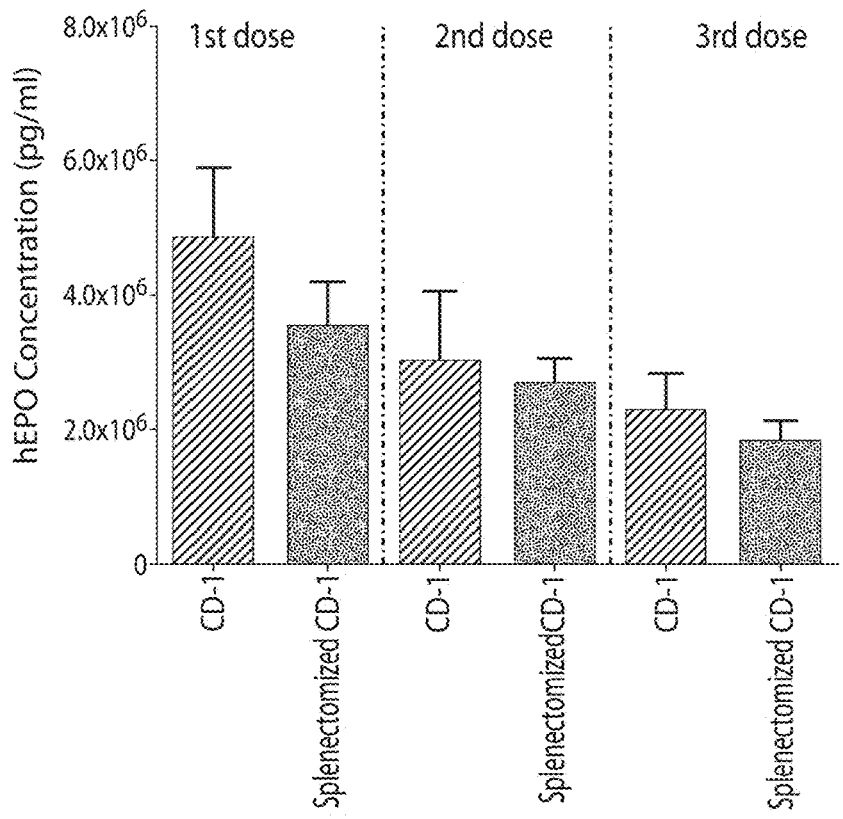
FIGS. 4A-4B: hEPO concentration and anti-PEG IgM levels in vivo following administration of first, second and third doses (hEPO) and first and second (IgM) of LNP carrying hEPO mRNA cargo into CD-1 non-splenectomized (CD-1) and splenectomized mice.

In another experiment, the effect of the spleen and splenocyte populations on LNP update and mRNA cargo expression was analyzed. CD-1 mice were splenectomized and then LNP were injected intravenously (i.v.). The LNP carried hEPO mRNA cargo and comprised MC3, DMG-PEG (1.5%), DSPC and cholesterol. hEPO protein concentration in the blood was measured after a first, second and third dose of LNP, as shown in FIG. 4A. The level of hEPO decreased with successive administrations, in both the non-splenectomized and splenectomized mice. The data are reminiscent of an accelerated blood clearance phenomenon.

Figure 4B:
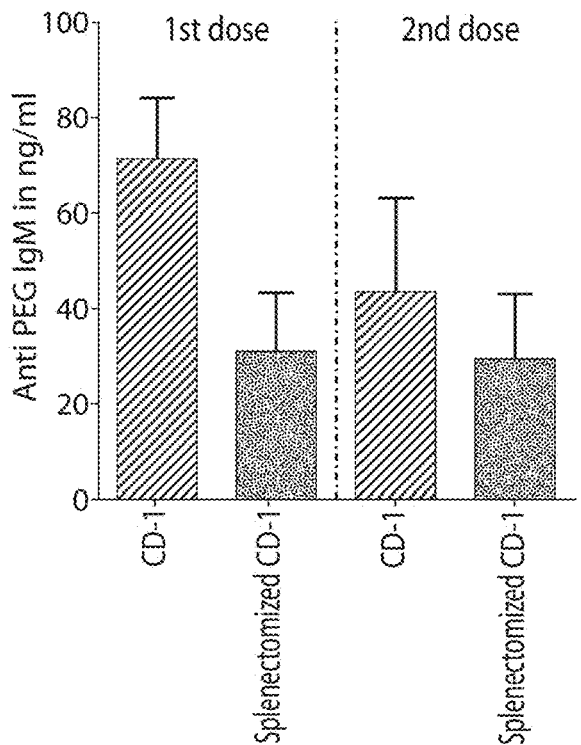

The level of anti-PEG IgM antibody was also measured in these mice after the first and second dose of LNP, as shown in FIG. 4B. The level of anti-PEG IgM decreased between the first and second doses but only in the non-splenectomized mice. The splenectomized mice, on the other hand, had lower levels of anti-EPG IgM at both time points and did not show such a decrease in the IgM level following the second dose.

Example 3

$2 \times 10^5$ Ficoll purified peripheral blood mononuclear cells (PBMCs) were incubated with 200 ng of EGFP mRNA formulated with LNP PE-Rhodamine. After 2, 4, 6, 24 hours, cells were stained for CD3 and CD19 and analyzed by flow cytometry for PE uptake and EGFP expression. The LNP comprised MC3, DMG-PEG (1.5%), DSPC and cholesterol.

Figure 5:
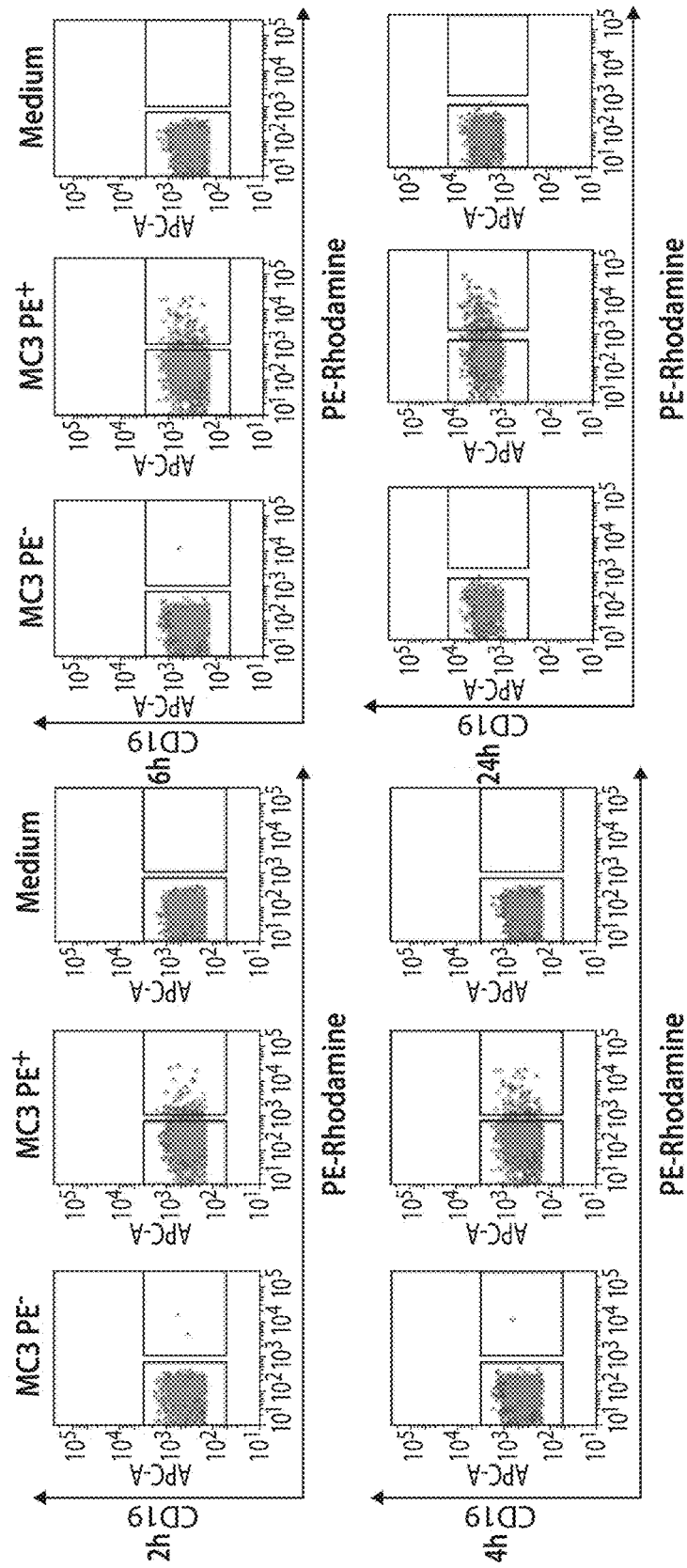
FIG. 5: PE-Rhodamine fluorescence in CD19+ circulating B cells after incubation for 2, 4, 6 and 24 hours with PE+ and PE− LNP.
Figure 6A:
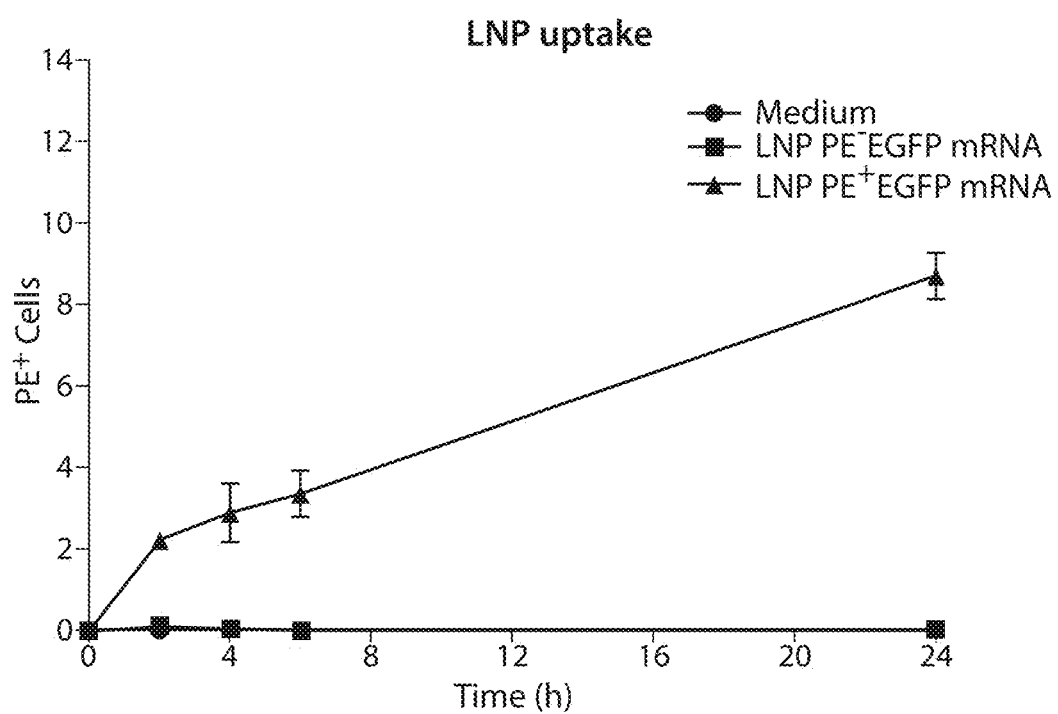
FIGS. 6A-6B: LNP uptake (FIG. 6A) and EGFP expression (FIG. 6B) by circulating B cells as a function of incubation time.
Figure 6B:
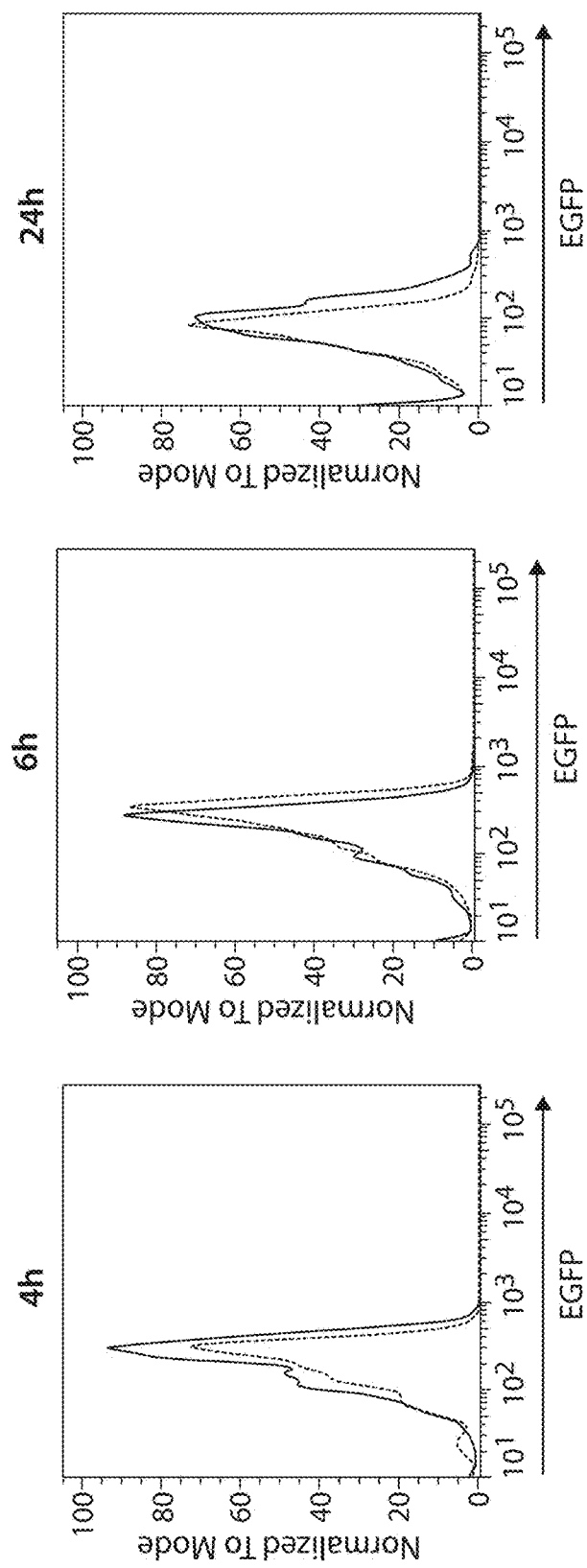

Increasing levels of PE+ LNP uptake by circulating CD19+ B cells were observed after 2 to 24 hours incubation, as shown in FIG. 5. As expected no PE fluorescence was observed in cells incubated with PE− LNP or with medium alone. The time course is illustrated in FIG. 6A which shows that LNP association and/or uptake increased steadily from 2 hours through to 24 hours. LNP uptake by circulating B cells is similar to that observed in splenic B cells. FIG. 6B shows that no EGFP expression occurs in the circulating CD19+ B cells, similar to the splenic B cells.

Example 4

$2 \times 10^5$ splenocytes or PBMCs were incubated with 200 ng of EGFP mRNA formulated with LNP comprising PE-Rhodamine or LNP lacking PE-Rhodamine ("non-PE-Rhodamine"). After 24 h, cells were stained for CD3, CD19 and CD86 and analyzed by flow cytometry for PE uptake and upregulation of CD86. CD86 expression was compared between B cells incubated with PE+ LNPs and PE− LNPs and between B cells that had taken up PE+ LNPs and B cells that had not taken up PE+ LNPs. IL-6 and TNF-alpha secretion into the cell culture supernatant was measured by ELISA after 24 h culture.

Figure 7:
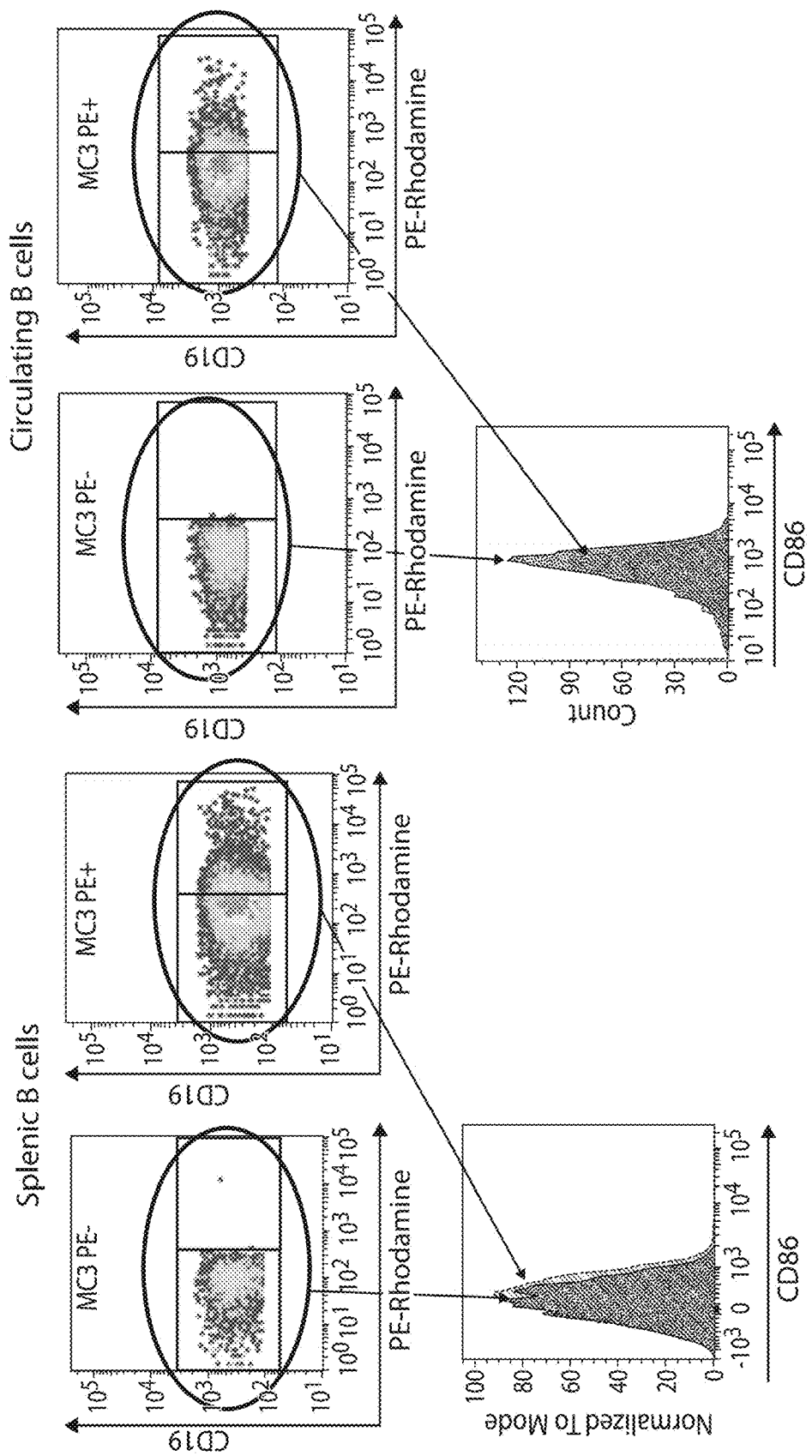
FIG. 7: CD86 expression in splenic and circulating B cells following incubation with PE− and PE+ LNP. Splenic and circulating B cells that take up LNPs are activated.
Figure 8:
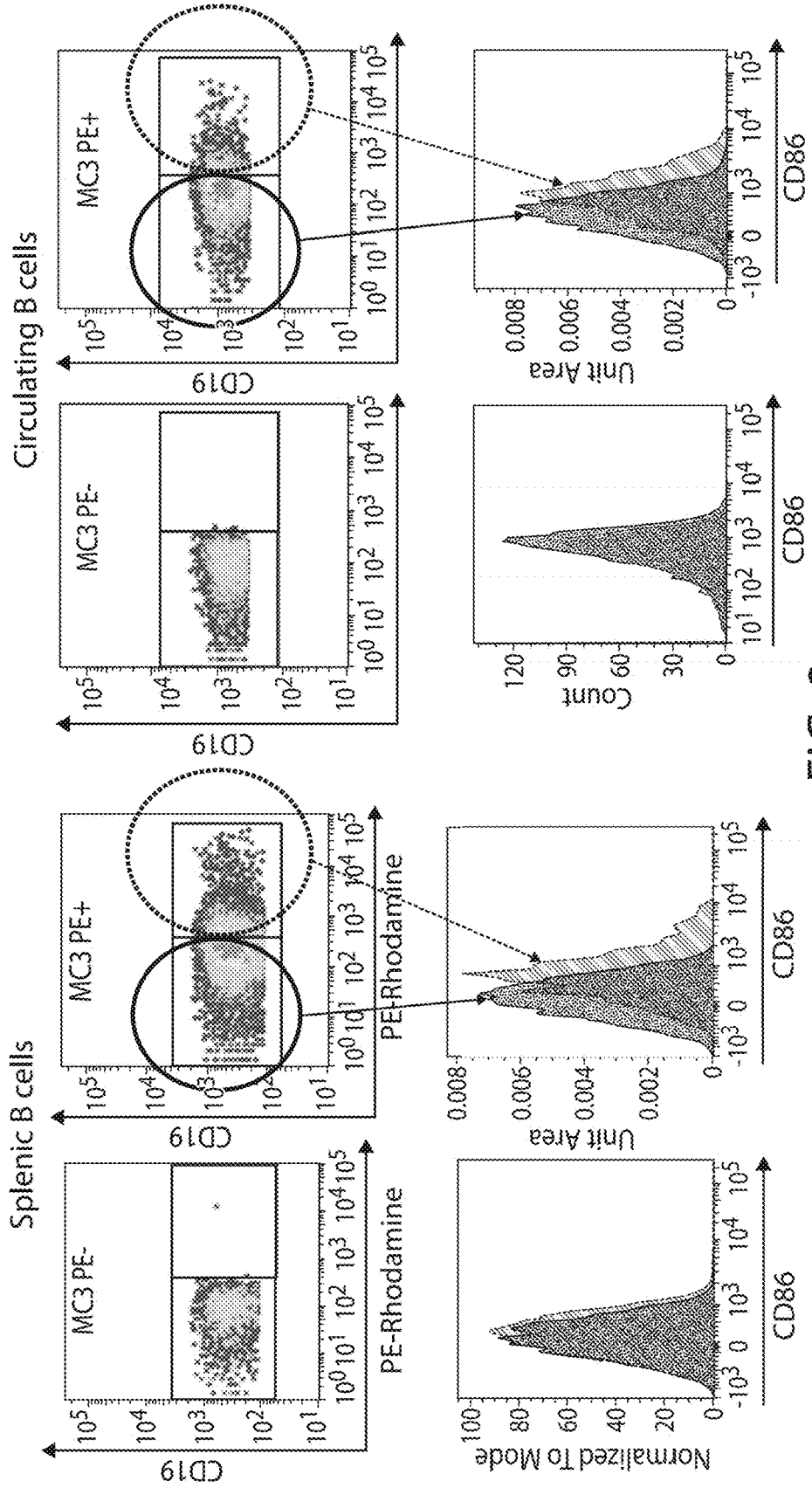
FIG. 8: CD86 expression in splenic and circulating B cells that take up or fail to take up PE+ LNPs. Splenic and circulating B cells that take up LNPs are activated, as evidenced by increased CD86 expression.
Figure 9:
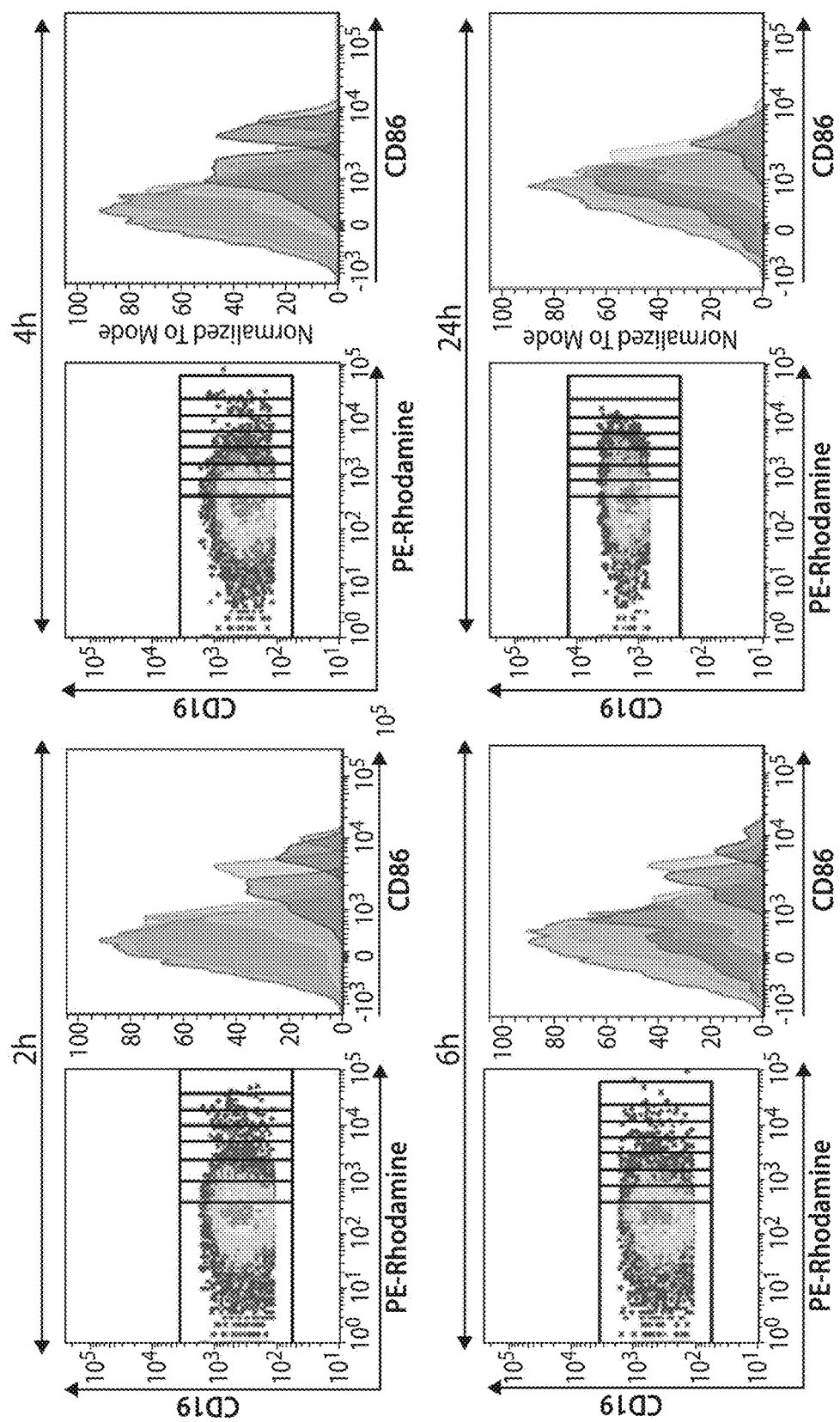
FIG. 9: CD86 expression as a function of LNP uptake by splenic B cells at various incubation times.
Figure 10:
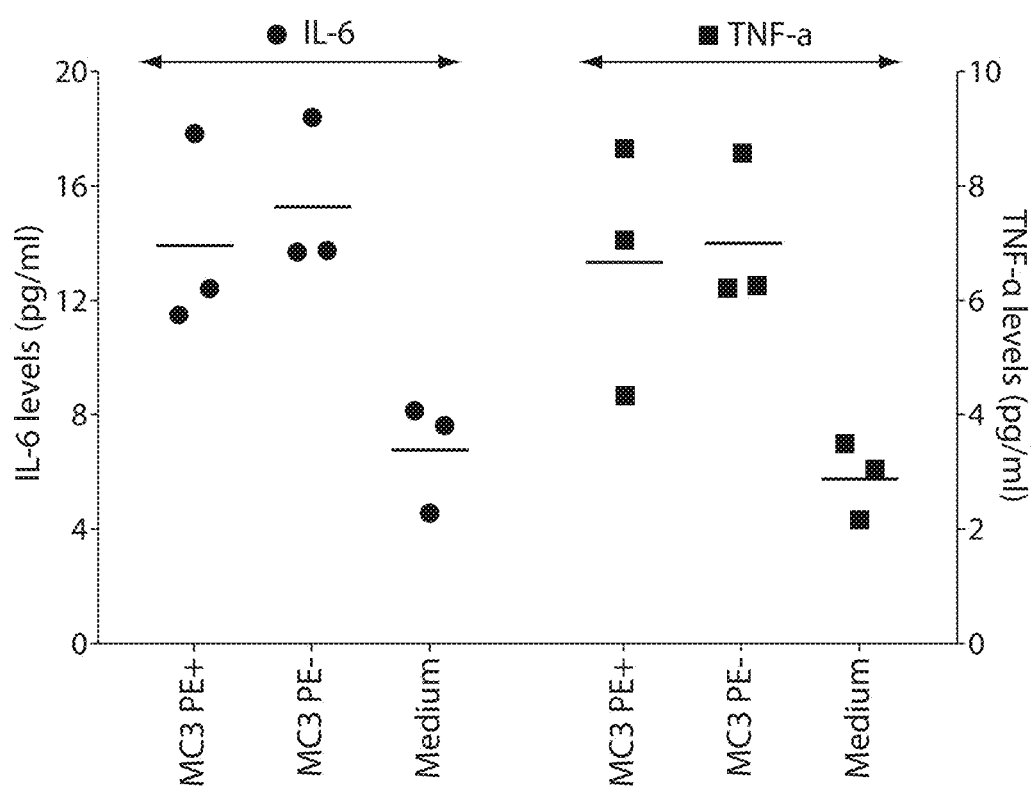
FIG. 10: IL-6 and TNF-alpha secretion by B cells incubated with PE+ and PE− LNP for 24 hours.

Splenic and circulating B cells that take up LNPs are activated as measured by CD86 upregulation. FIG. 7 shows that splenic and circulating B cells are activated after incubation with either PE+ or PE− LNP. FIG. 8 similarly shows increased CD86 expression correlates with LNP association or uptake by the splenic and circulating B cells. FIG. 9 shows that splenic B cells that take up LNPs are activated in an LNP-dose dependent manner. Activation is a transient phenomenon and begins to decrease after 24 hours. B cells incubated with PE+ or PE− LNP for 24 hours secrete increased levels of the inflammatory cytokines IL-6 and TNF-alpha (FIG. 10).

Example 5

$2 \times 10^5$ splenocytes were incubated with PE+ LNP. After 4 and 24 h, cells were stained for CD3, CD19 and CD86 and analyzed by flow cytometry for PE uptake and upregulation of CD86. IL-6 and TNF-alpha secretion into the cell culture supernatant was measured by ELISA after 24 h culture.

Figure 11A:
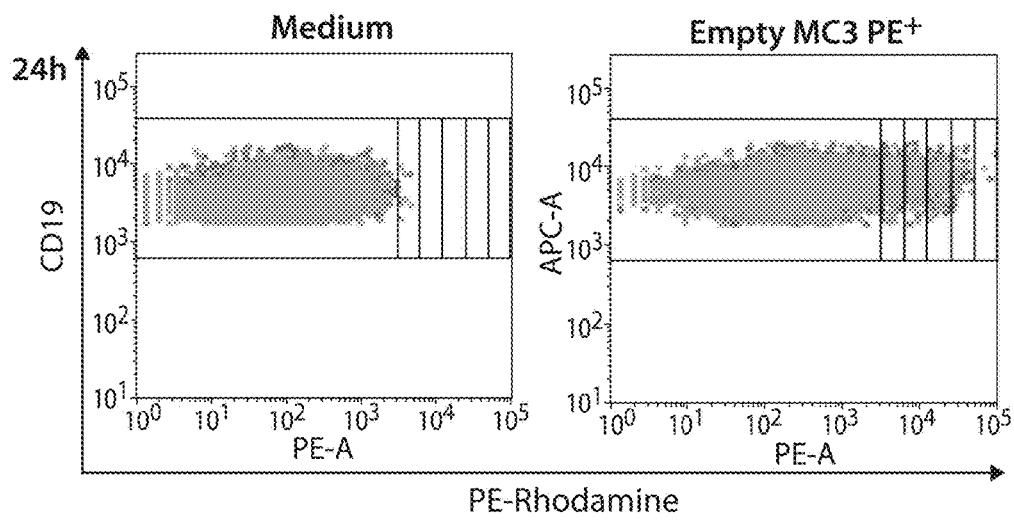
FIGS. 11A-11B: Empty PE+ LNP uptake by CD19+ B cells at 24 hours (FIG. 11A) and the time course at 4 and 24 hours (FIG. 11B).
Figure 11B:
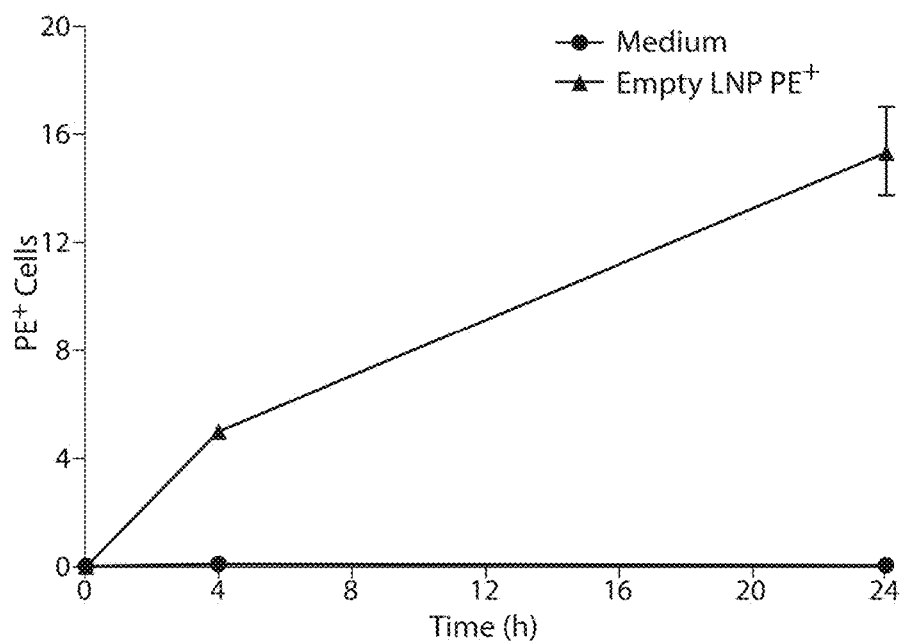
Figure 12A:
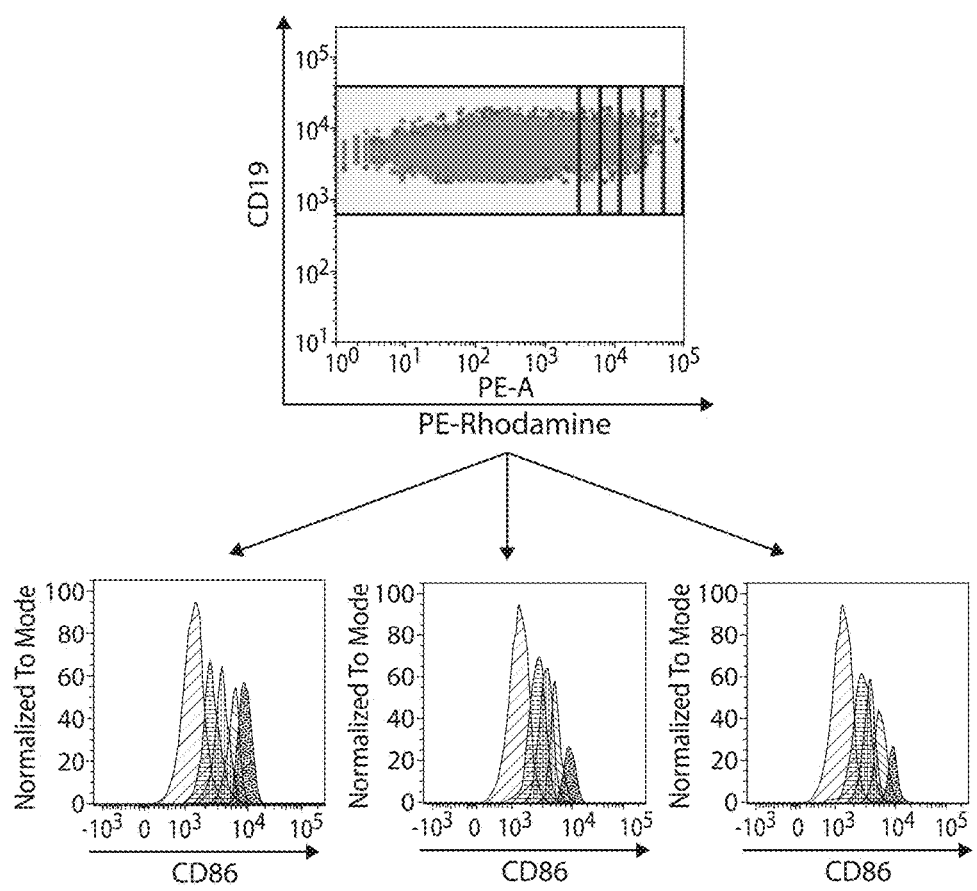
FIGS. 12A-12B: CD86 expression in B cells that have taken up empty PE+ LNP (FIG. 12A). Splenic B cells are activated by empty LNPs in a dose dependent manner. IL-6 and TNF-alpha secretion by B cells incubated with empty PE+ LNP (FIG. 12B).
Figure 12B:
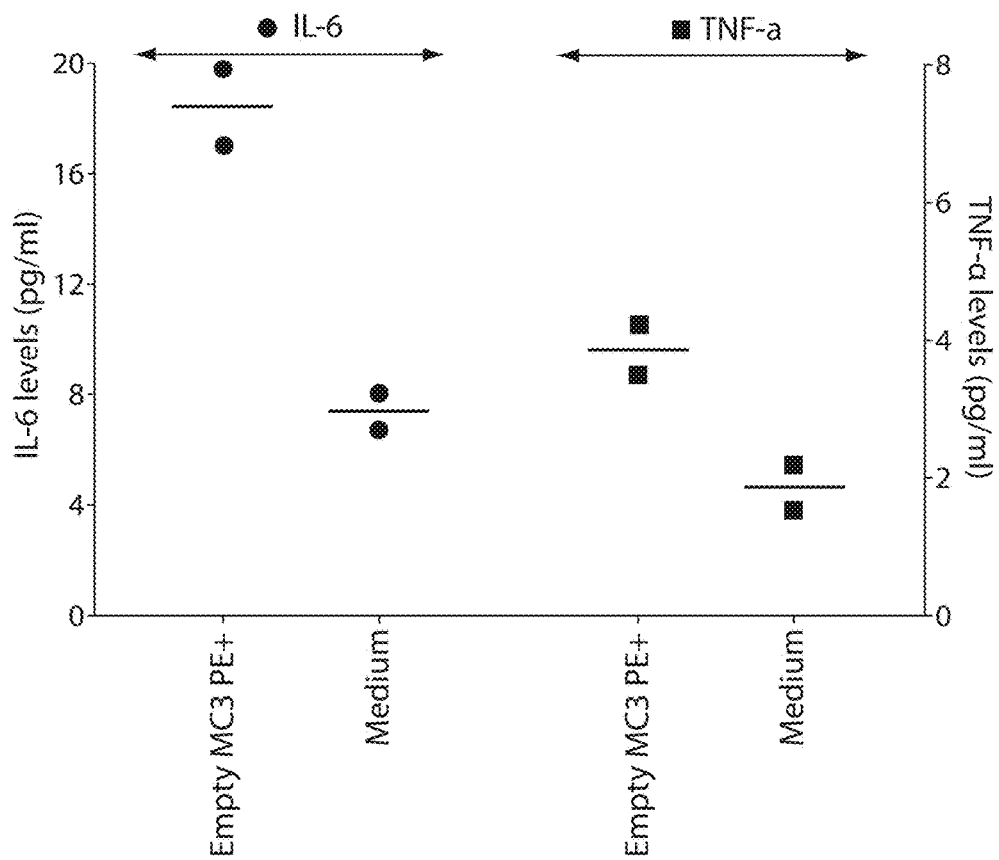

Splenic B cells are take up empty PE+ LNP at 4 hours (FIG. 11B) and 24 hours (FIGS. 11A and 11B). Empty PE+ LNP uptake by splenic B cells is similar to that observed with PE+ LNPs carrying EGFP mRNA cargo. The empty PE+ LNP were capable of activating the B cells as evidenced by increased CD86 expression. Splenic B cells are activated by empty PE+ LNPs in a dose dependent manner, as shown in FIG. 12A. Similarly, empty PE+ LNP were capable of inducing secretion of IL-6 and TNF-alpha from splenic B cells, as shown in FIG. 12B.

Example 6

$2 \times 10^5$ splenocytes from wild-type (WT), and ApoE−/− or LDL-R−/− knockout mice were incubated with 200 ng of EGFP mRNA formulated with PE+ or PE− LNP. After 24 h, cells were stained for CD3, CD19 and analyzed by flow cytometry for PE uptake. IL-1alpha, KC-GRO and TNF-alpha secretion into the cell culture supernatant was measured by ELISA.

Figure 13A:
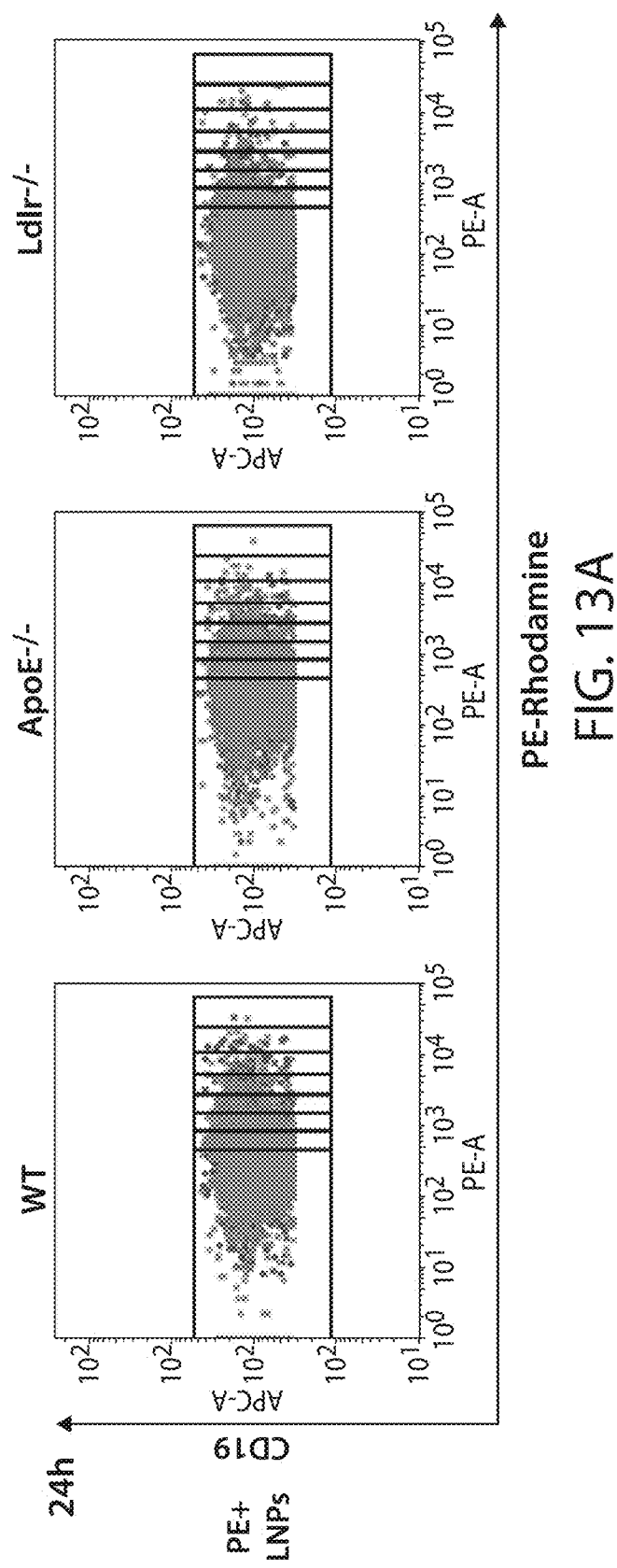
FIGS. 13A-13D: Uptake and cytokine secretion by B cells from wild type (WT), ApoE deficient, and LDL receptor deficient mice in PE+ LNPs (FIG. 13A) and PE− LNPs (FIG. 13B). The percentage of CD19+PE+ cells (FIG. 13C) and cytokine levels in pg/ml (FIG. 13D) are also given.
Figure 13B:
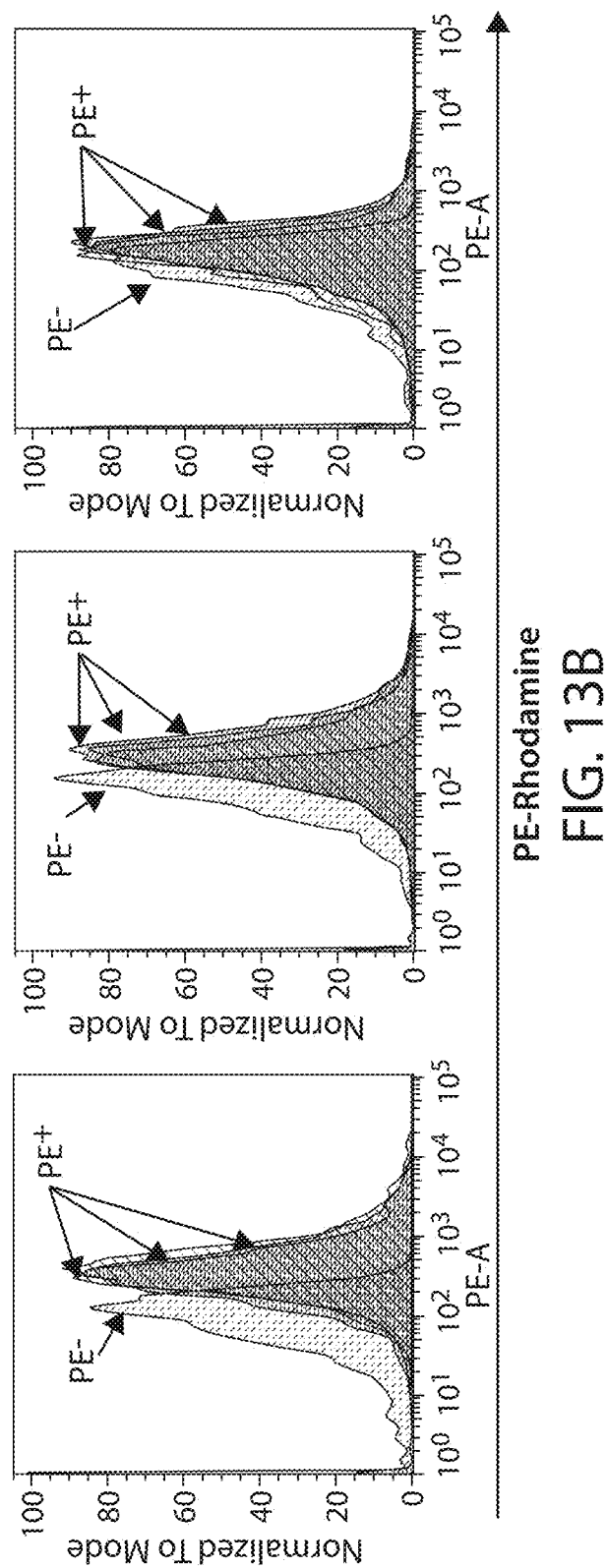
Figure 13C:
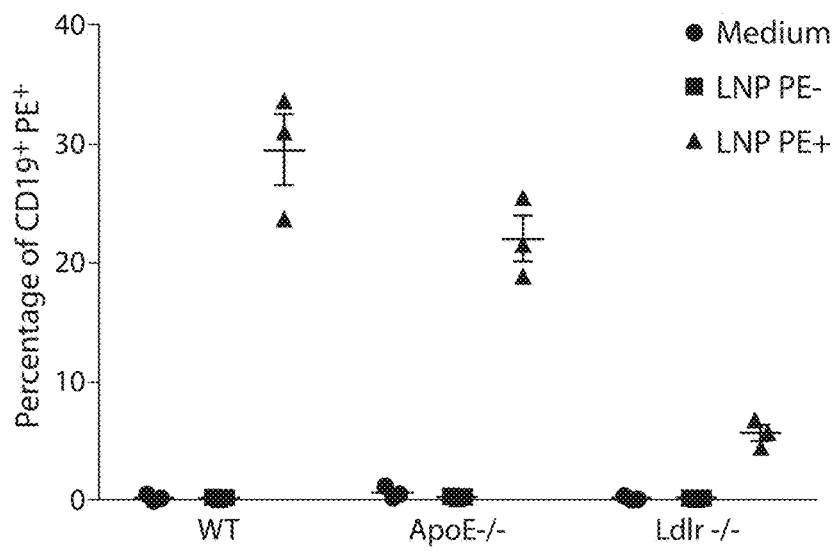
Figure 13D:
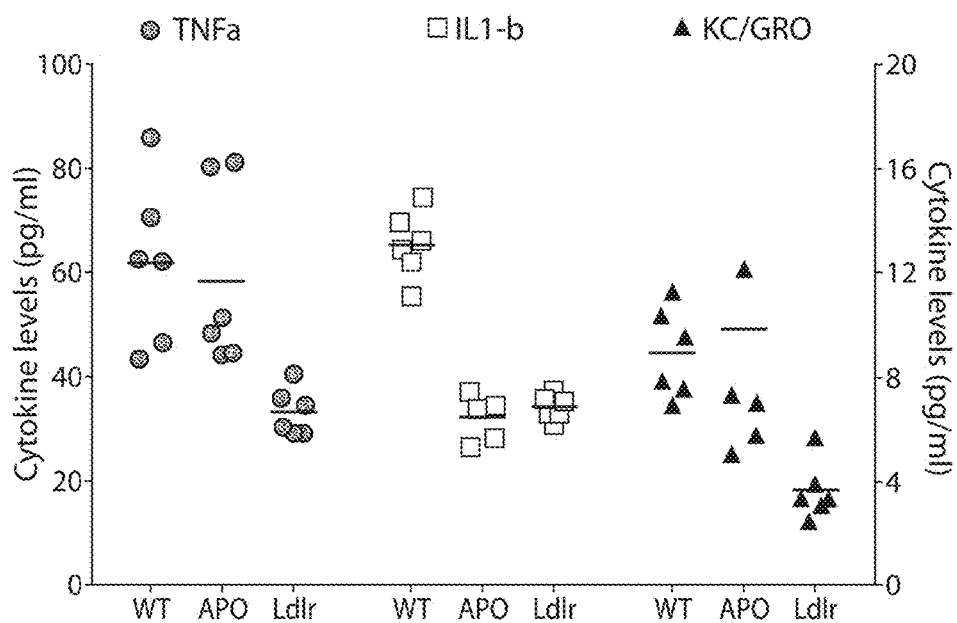

As shown in FIGS. 13A-13C, LNP uptake at 24 hours is partially abolished in the absence of ApoE or in the absence of the LDL receptor. FIG. 13D illustrates that wild type and Apo deficient B cells secrete similar levels of TNF-alpha and KC/GRO that are higher than the levels secreted by LDLR deficient B cells following incubation with LNP. Wild type B cells however secrete higher levels of IL-1beta than both of Apo deficient and LDL receptor deficient B cells following incubation with the LNP.

Example 7

$2 \times 10^5$ splenocytes were pre-incubated for 2 h with free PEG or with anti-PEG IgG and then incubated with 200 ng of EGFP mRNA formulated with PE+ or PE− LNP. After 24 h of LNP incubation, cells were stained for CD3, CD19 and analyzed by flow cytometry for PE uptake.

Figure 14:
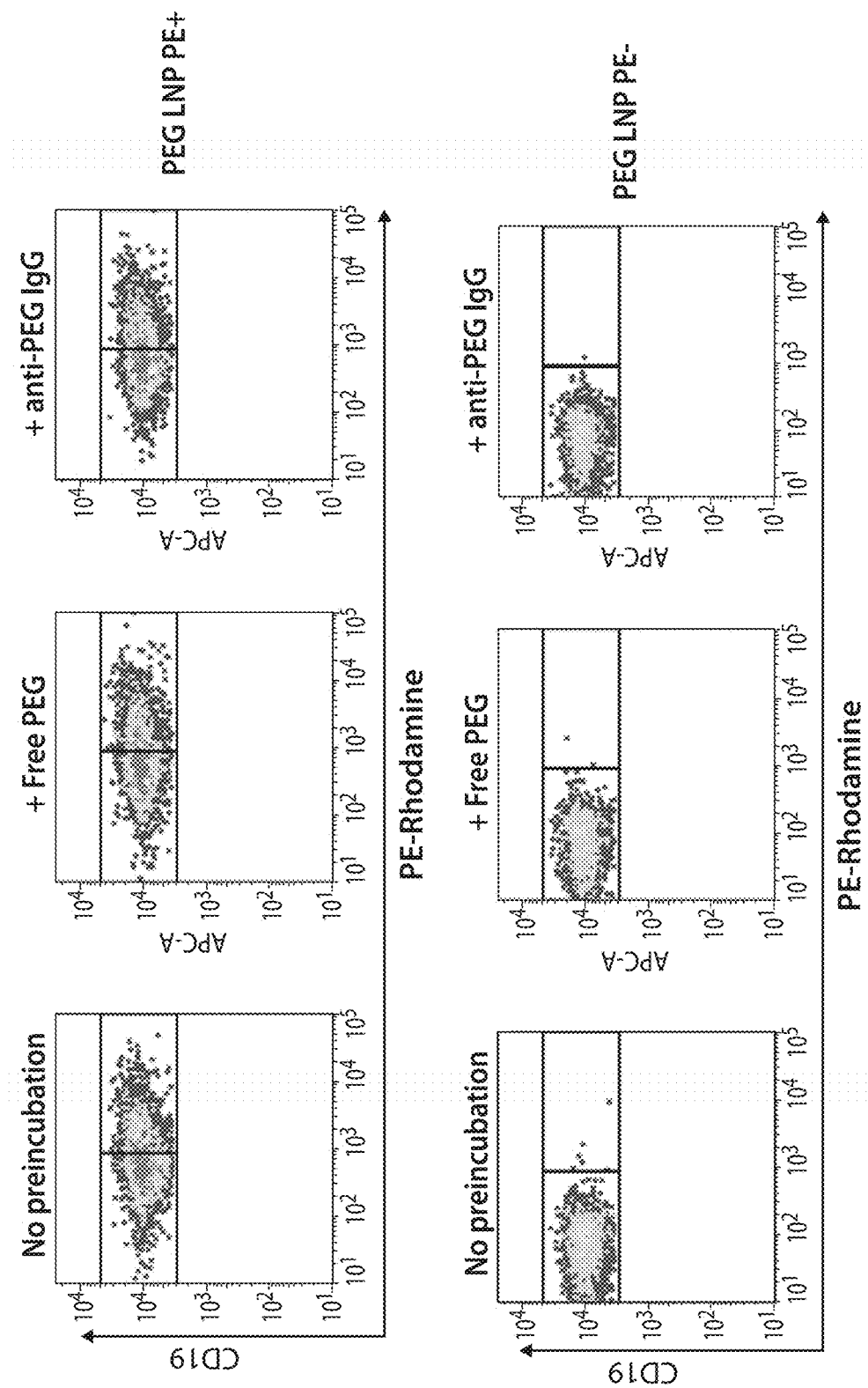
FIG. 14: LNP uptake following pre-incubation of B cells with free PEG or anti-PEG IgG.

LNP uptake still occurred even after pre-incubation of B cells with free PEG or with anti-PEG IgG antibody as shown in FIG. 14. Thus, such pre-incubation did not appear to compete with the PEG-comprising LNP for binding to B cells. Pre-incubation with anti-PEG antibody also did not appear to interfere with the ability of LNP to bind to B cells.

Example 8

Splenocytes were incubated with 200 ng of EGFP mRNA formulated with PE+ LNP comprising either PEG, PE-OH or no PEG (PEGless). After 24 h cells were stained for CD3, CD19 and analyzed by flow cytometry for PE uptake.

Figure 15:
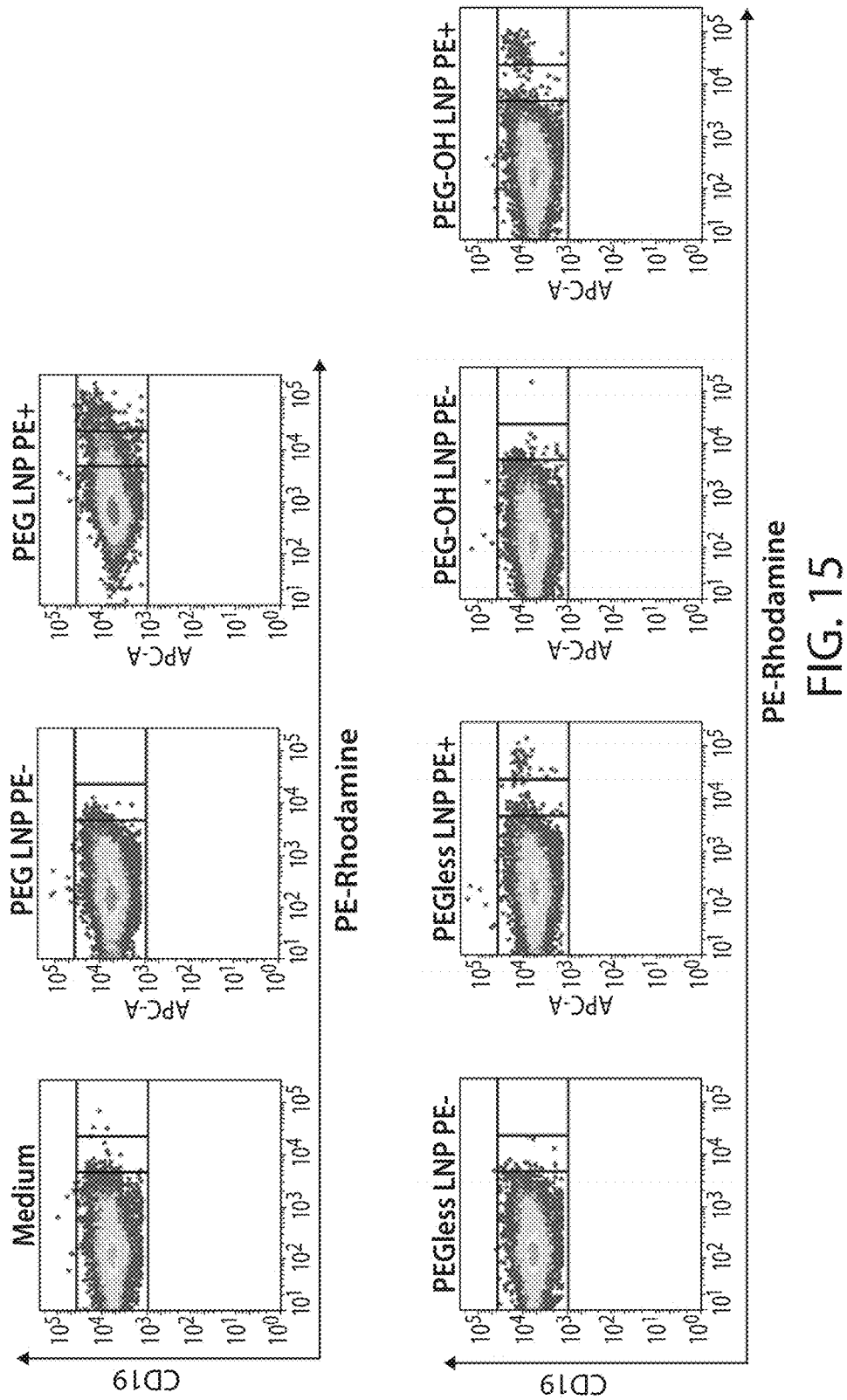
FIG. 15: Uptake of LNPs comprising PEG or PEG-OH or lacking PEG (PEGless) by B cells.
Figure 16:
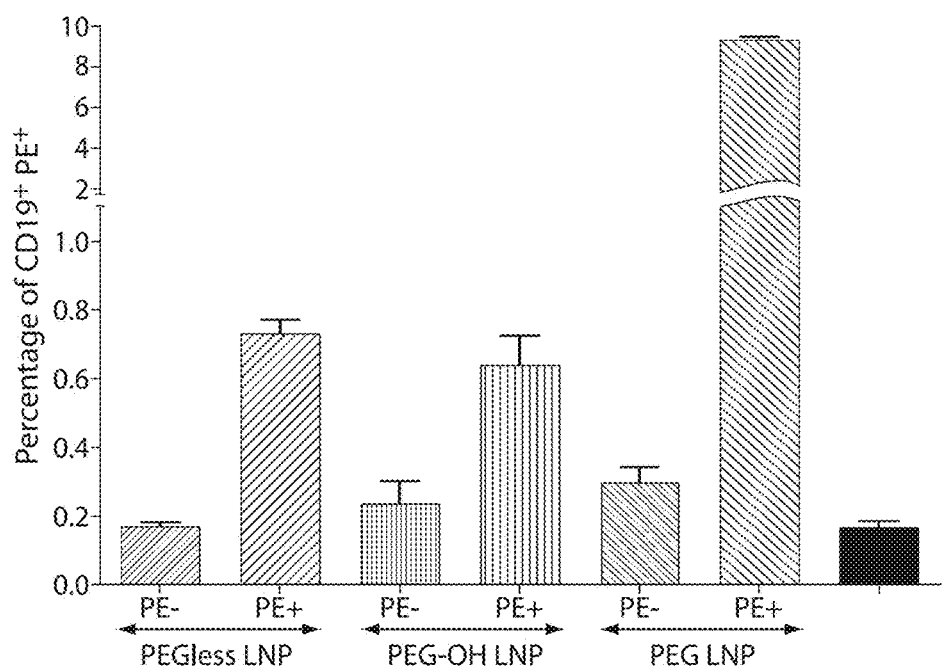
FIG. 16: Uptake of LNPs comprising PEG or PEG-OH or lacking PEG (PEGless) by B cells.
Figure 17:
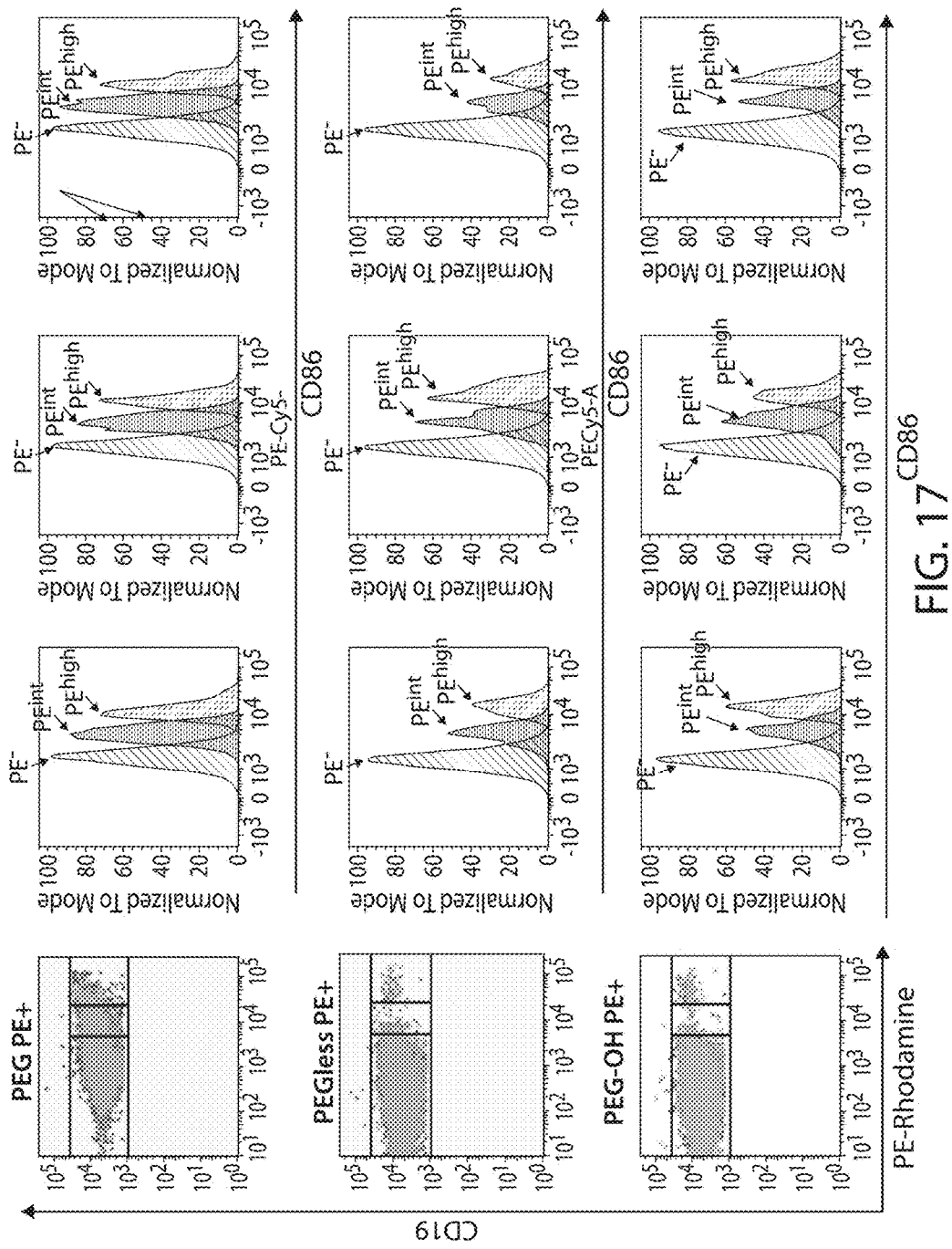
FIG. 17: CD86 expression in B cells incubated with PEG-less LNP or PEG-OH LNP, as a function of LNP uptake.

Uptake of LNP that lacked PEG ("PEGless" LNP) or LNP comprising hydroxy-PEG (PEG-OH) was partially abolished as compared to LNP comprising methoxy-PEG, as shown in FIGS. 15 and 16. PEG-less LNP and PEG-OH LNP however still activate a small fraction of B cells as is apparent in FIG. 17. Non-PEG mediated activation of B cells is apparent. Activation based on CD86 expression also appears to be dose dependent as B cells taking up greater amounts of LNP show higher CD86 expression levels.

Example 9

Splenocytes were incubated with 200 ng of EGFP mRNA formulated with different PE+ or PE− LNP. These LNPs lacked phospholipid ("phospholipid-less"), or comprised DSPC, oleic acid, DOPC or DOPE as a helper lipid. In other experiments, the LNPs comprised either PEG, PE-OH, DOPE PEG or no PEG (PEGless). After 24 hours, cells were stained for CD3, CD19, and CD5 and analyzed by flow cytometry for LNP uptake.

Figure 18:
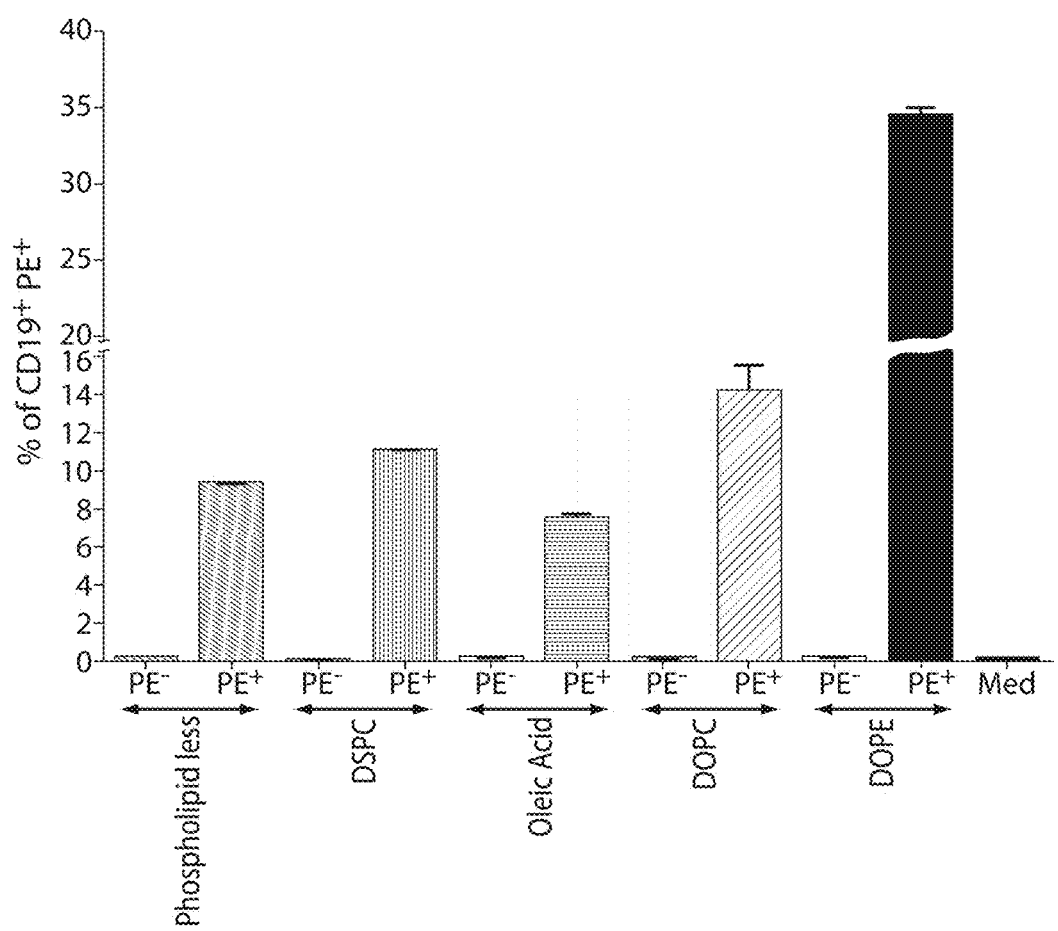
FIG. 18: LNP uptake as a function of phospholipid content of the LNP.

FIG. 18 shows LNP uptake for LNPs that comprise DSPC, oleic acid, DOPC and DOPE as helper lipid, or lacking a helper lipid. Uptake by B cells was greatest for LNPs comprising DOPE, followed by LNPs comprising DOPC, and LNPs comprising DSPC. Lowest uptake by B cells was seen for LNPs comprising oleic acid or lacking a helper lipid. These data indicate that B cell uptake of LNPs is partially dependent on the phospholipid content of the LNP.

Figure 19:
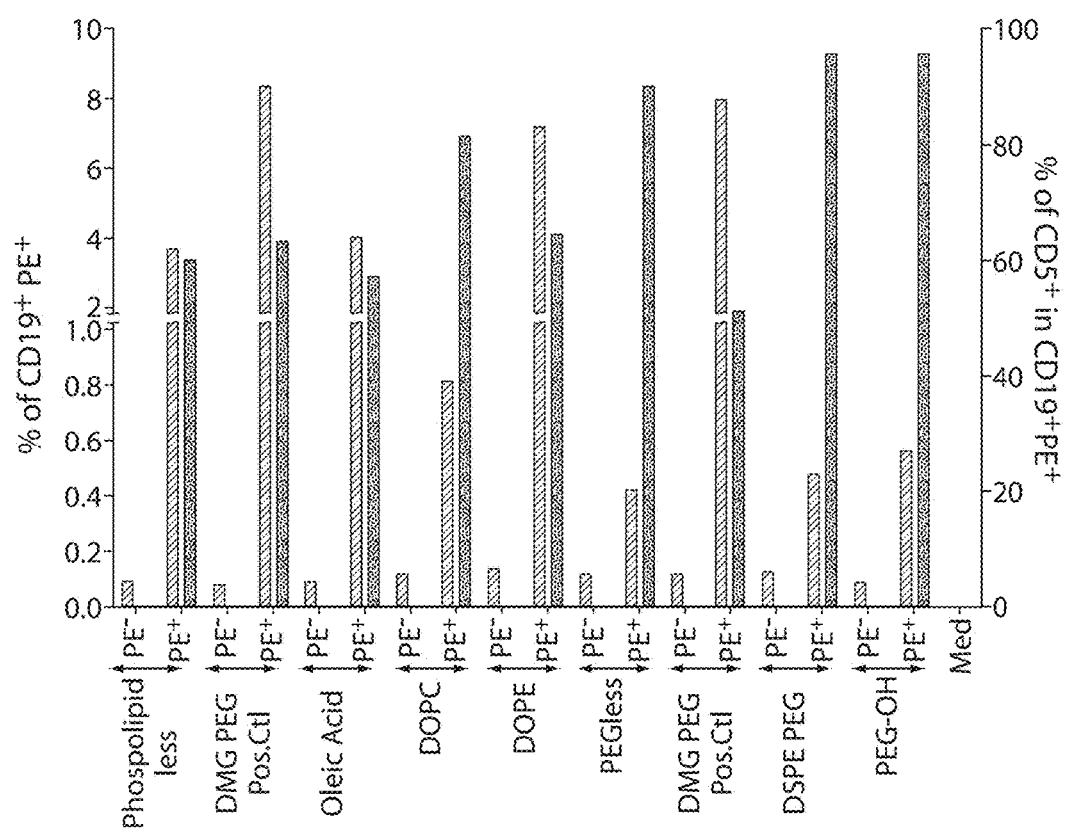
FIG. 19: LNP uptake as a function of phospholipid and PEG content of the LNP in CD19+ B cells and CD5+ B cells.

FIG. 19 indicates that PEGless or PEG-OH LNP uptake is mainly due to the presence of CD19+ CD5+ splenic B cells. This CD5+ B cell population represents the B1a cells. These cells are responsible for the production of natural IgM. The remaining uptake observed with PEGless and PEG-OH LNPs is mainly due to CD19+ CD5− conventional B cells. These data suggest that the combined use of hydroxy-PEG or the absence of PEG with oleic acid as the helper lipid could lead to no or low LNP uptake by B cells.

Figure 20:
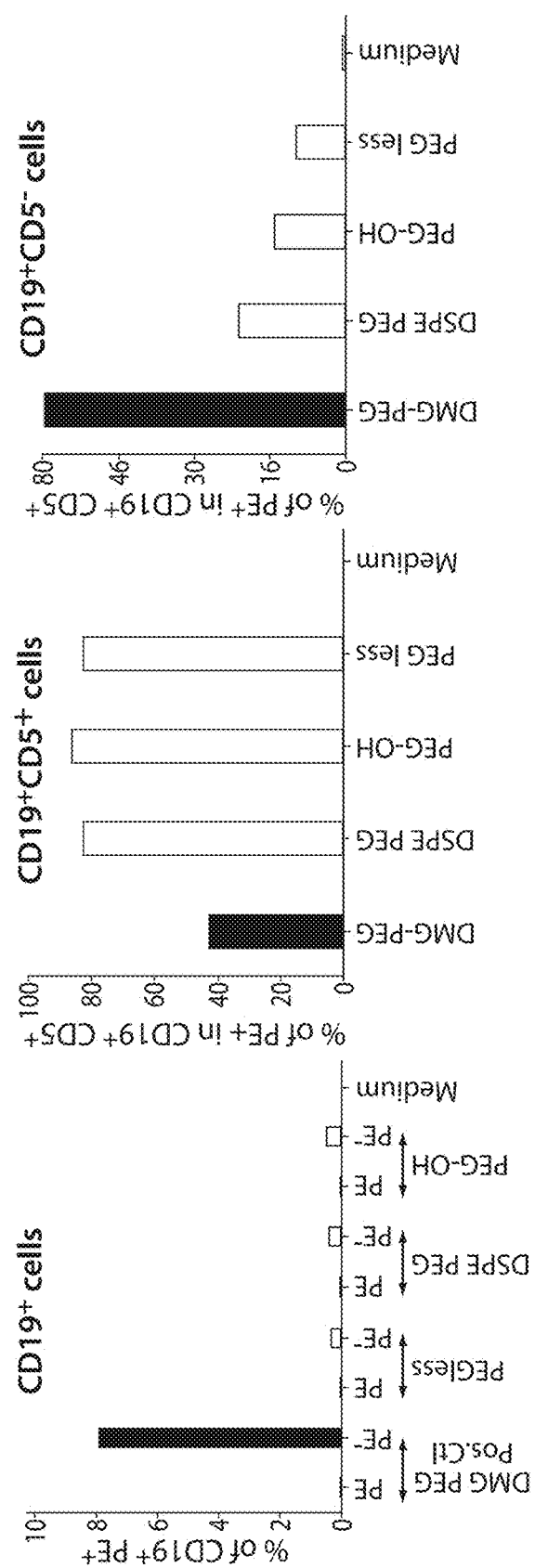
FIG. 20: LNP uptake by CD19+, CD19+ CD5+ or CD19+ CD5-B cells as a function of phospholipid and PEG content.

FIG. 20 indicates that CD5+ B cells are responsible for uptake of the majority of LNP comprising PEG-OH, DSPE and PEG, or being PEGless. CD5− cells were responsible for uptake of the majority of LNP comprising DMG-PEG. PEGless or PEG-OH LNPs uptake is mainly due to the presence of CD19+ CD5+ splenic murine B cells.

Example 10

An in vivo study of various LNPs was undertaken to assess the effect of various phospholipid and PEG combinations on LNP uptake by splenic B cells. The control and test groups are summarized in Table 2 below. The various LNPs comprised DMG-PEG and DSPC, PEG-OH and DSPC, or DSPC without PEG (PEGless). All LNPs further comprised cationic lipid MC3, and also carried EGFP mRNA. A single dose 0.1 mL dose of 0.1 mg/kg (concentration 0.02 mg/mL) was administered.

TABLE 2

Summary of Experimental Groups

| Group | Test/Control Material | Vehicle | Formulation | Route | # of Doses | # of females |
|---|---|---|---|---|---|---|
| 1 | PBS | N/A | | | 1 | 4 |
| 2 | mRNA EGFP Ψ | MC3 | DMG-PEG (DSPC) | IV | 1 | 6 |
| 3 | mRNA EGFP Ψ | MC3 | PEG-OH (DSPC) | IV | 1 | 6 |
| 4 | mRNA EGFP Ψ | MC3 | PEGless (DSPC) | IV | 1 | 6 |

Figure 21:
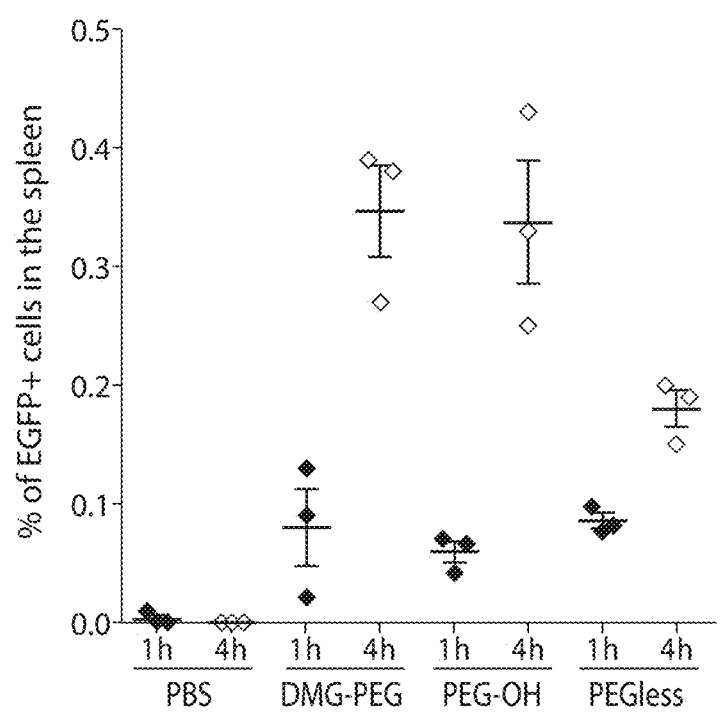
FIG. 21: EGFP expression in non-conventional T (CD3−) and B (CD19−) cells from the spleen 1 and 4 hours after administration of LNPs comprising DMG-PEG or PEG-OH and PEGless LNPs.

FIG. 21 shows that EGFP expression was observed in non-conventional T (CD3⁻) and B cells (CD19⁻) in the spleen as early as 1 hour after administration of DMG-PEG, PEG-OH and PEGless LNPs. At 4 hours post administration, expression levels of EGFP had increased relative to the 1 hour level in all the test groups. However, expression was the lowest in the PEGless group.

Figure 22A:
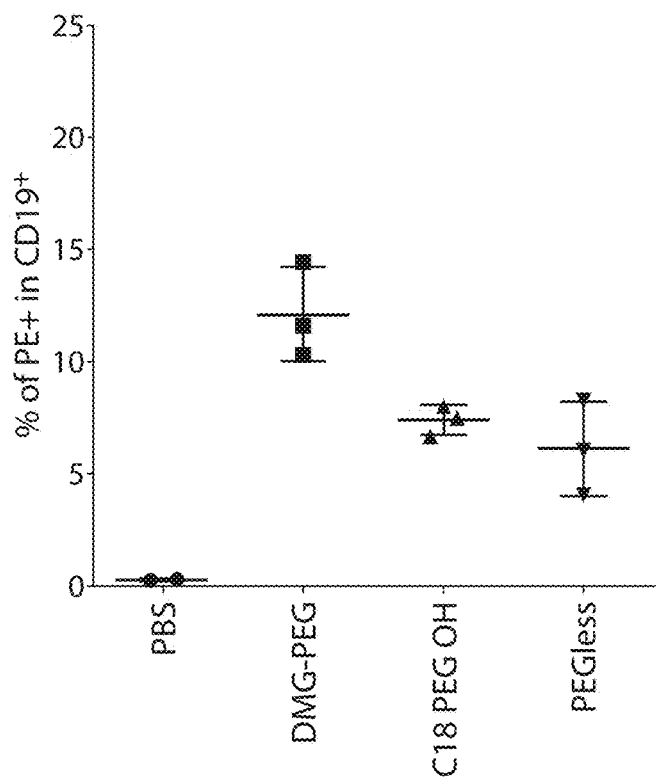
FIGS. 22A-22B: LNP uptake by B cells in vivo as a function of phospholipid and PEG content.
Figure 22B:
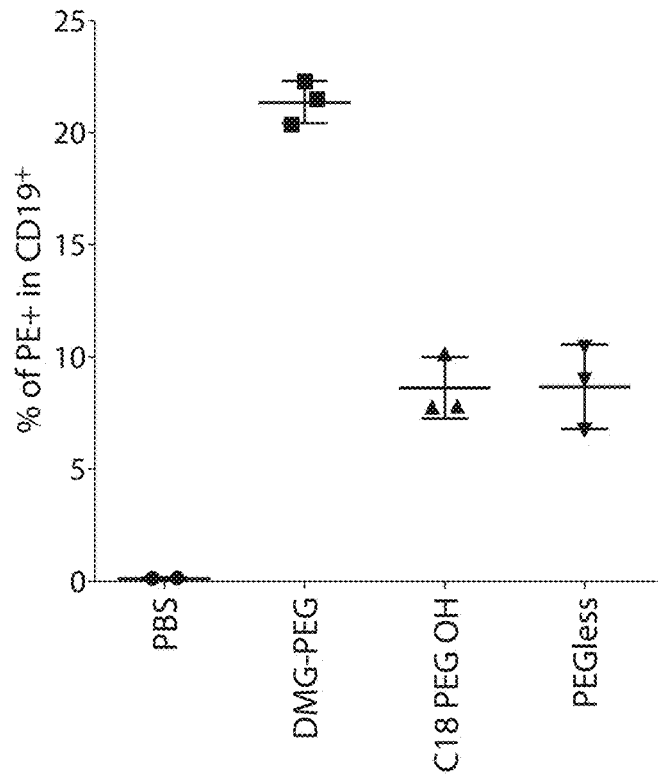

FIGS. 22A and 22B show that B cell uptake in vivo is similar to the uptake observed ex vivo and is partially dependent of DMG-PEG. B cell uptake was measured 1 hour post injection (FIG. 22A) and 4 hours post injection (FIG. 22B) with PBS or LNP comprising DMG-PEG or PEG OH, or LNP lacking PEG (PEGless LNPs).

Figure 23A:
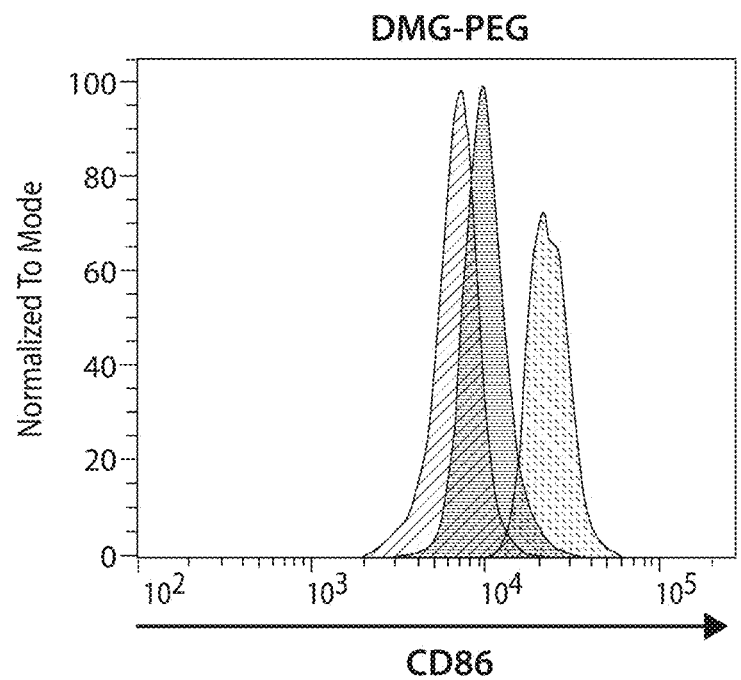
FIGS. 23A-23E: CD86 expression levels in B cells after injection of LNPs comprising DMG-PEG (FIG. 23A) or Cmpd418 (FIG. 23B), or PEGless LNP (FIG. 23C). CD86 expression level was assessed at 1 hour (FIG. 23D) and 4 hours (FIG. 12E) after injection of LNP.
Figure 23B:
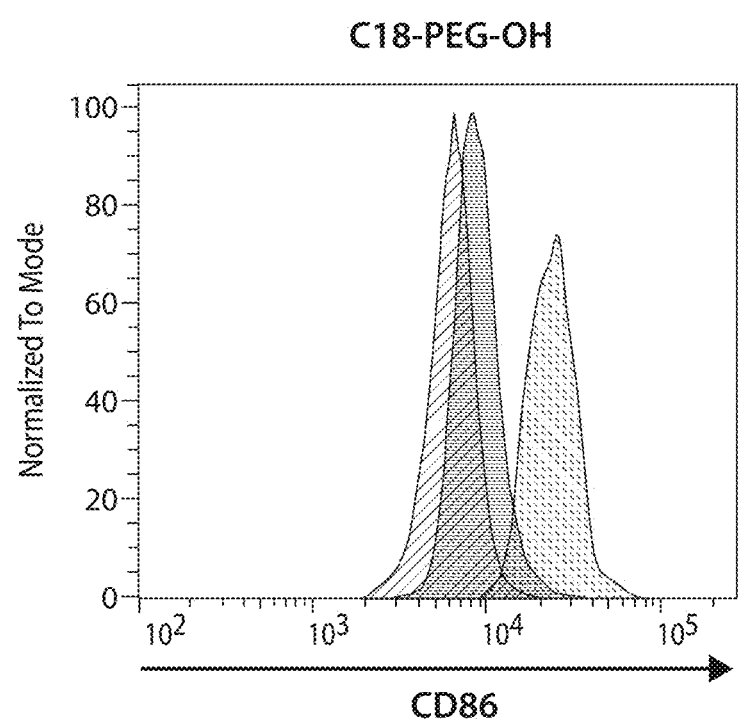
Figure 23C:
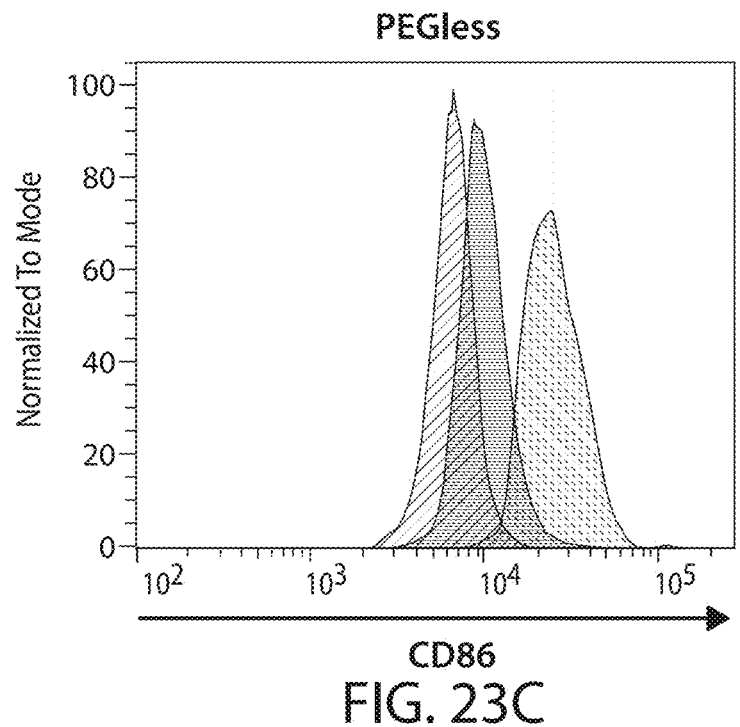
Figure 23D:
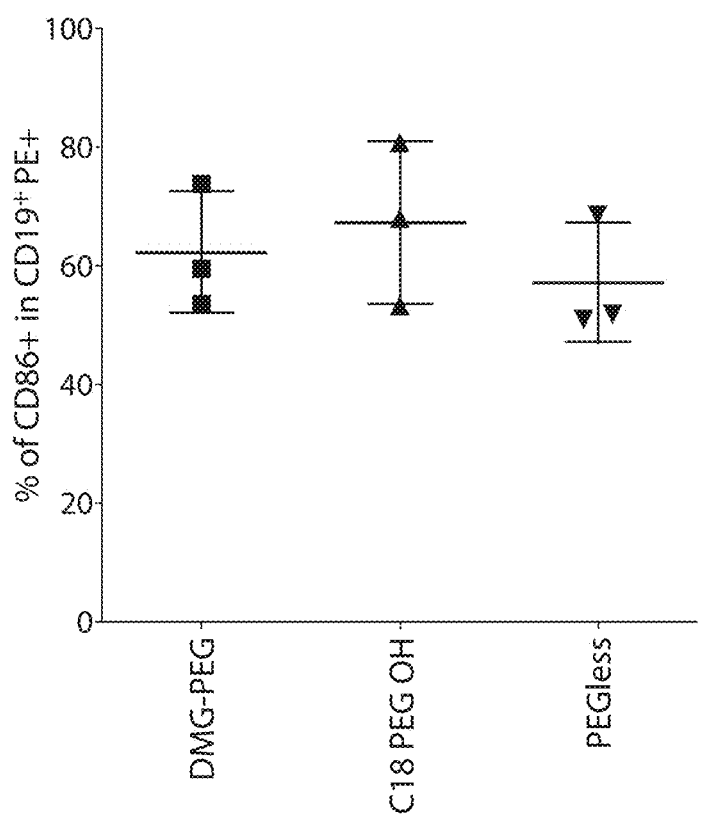
Figure 23E:
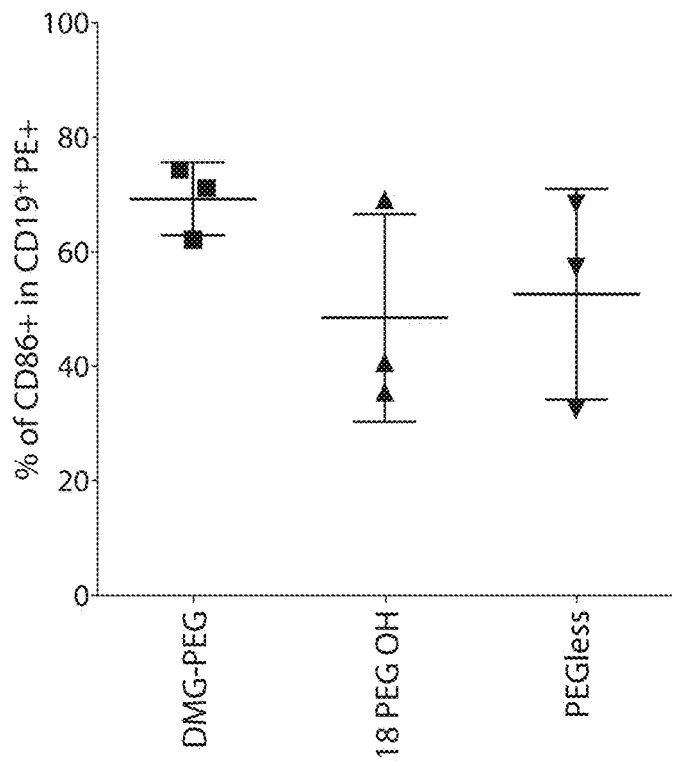

FIGS. 23A-23C show that uptake by B cells of LNP comprising DMG-PEG (FIG. 23A) or Cmpd418 (FIG. 23B) or PEGless LNP (FIG. 23C) results in B cell activation, as indicated by CD86 expression, in a LNP dose dependent manner. LNP uptake was measured 1 hour post injection (FIG. 23D) and 4 hours post injection (FIG. 23E) of PBS or LNP comprising DMG-PEG or PEG OH or PEGless LNPs. B cell uptake is also analyzed by flow cytometry (FIGS. 23A-23C). Activation levels are 1 hour post-injection were similar between the different LNPs. At 4 hours post-injection LNPs comprising PEG OH or lacking PEG were less stimulatory than were LNPs comprising DMG-PEG.

CD19+ B cells were stained and analyzed individually. LNP (PE, red) staining and the overlap between LNP and CD19 staining (green) were examined. LNPs are mainly located in the B cell membrane. Fewer PEGless LNPs and LNPs comprising Cmpd418 were observed at the membrane compared to LNPs comprising DMG-PEG.

Figure 24A:
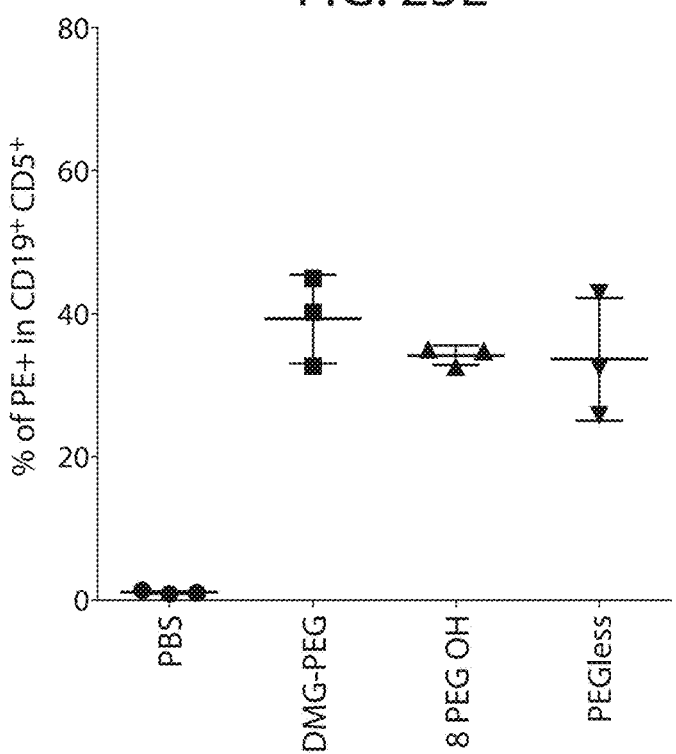
FIGS. 24A-24B: Uptake of PE+ LNP by B cells in vivo 1 hour (FIG. 24A) and 4 hours (FIG. 24B) after injection of LNP comprising DMG-PEG or PEG OH or PEGless LNPs.
Figure 24B:
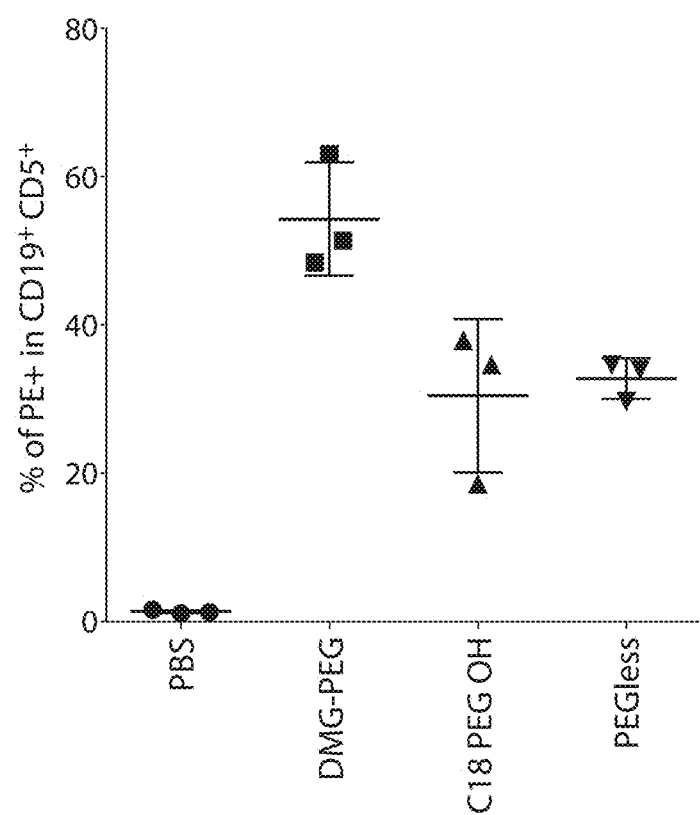

Next, uptake of LNPs by CD5+ B cells was analyzed. The results are shown in FIGS. 24A-24B. LNP uptake by CD5⁺ B cell uptake in vivo is slightly decreased when the LNP comprise PEG-OH or when the LNP lack PEG. LNP uptake is measured 1 hour post injection (FIG. 24A) and 4 hours post injection (FIG. 24B) of PBS, or LNP comprising DMG-PEG or PEG OH or PEGless LNPs.

CD5+ B cells were stained and analyzed individually. LNP (PE, red) staining and the overlap between LNP and CD19 staining (green) were examined. LNPs are mainly located in the B cell membrane. Fewer PEGless LNPs and LNPs comprising PEG-OH were observed at the membrane compared to LNPs comprising DMG-PEG.

Example 11

Table 3 outlines a study designed to analyze effects of LNPs comprising different amounts of DMG-PEG. All test LNPs comprised cationic lipid MC3, helper lipid DSPC, structural lipid cholesterol and carried hEPO mRNA cargo. The LNPs differed in their DMG-PEG contents with DMG-PEG content ranging from 0%, 0.25%, 0.5%, 0.75%, 1%, 1.25%, and 1.5%. Percentages reflect a theoretical mol %. The third column of the table provides the lipid composition of the LNP expressed as theoretical mol %.

TABLE 3

Study Design

| | Composition | Theoretical mol % | mRNA | Diameter (nm) | Pd Index | % EE | [final] ug/mL | For 200 ng |
|---|---|---|---|---|---|---|---|---|
| 0% PEG-DMG | MC3:DSPC:Chol | 50:11.5:38.5 | hEPO | 99.5 | 0.15 | 98 | 47 | 4.26 |
| 0.25% PEG-DMG | MC3:DSPC:Chol:PEG-DMG | 50:11.25:38.5:0.25 | hEPO | 56.2 | 0.12 | 98 | 52 | 3.84 |
| 0.5% PEG-DMG | MC3:DSPC:Chol:PEG-DMG | 50:11:38.5:0.5 | hEPO | 63 | 0.16 | 98 | 44 | 4.55 |
| 0.75% PEG-DMG | MC3:DSPC:Chol:PEG-DMG | 50:10.75:38.5:0.75 | hEPO | 61.8 | 0.13 | 98 | 50 | 4.00 |
| 1% PEG-DMG | MC3:DSPC:Chol:PEG-DMG | 50:10.5:38.5:1 | hEPO | 57.6 | 0.14 | 98 | 53 | 3.77 |
| 1.25% PEG-DMG | MC3:DSPC:Chol:PEG-DMG | 50:10.25:38.5:1.25 | hEPO | 53.7 | 0.076 | 98 | 53 | 3.77 |
| 1.5% PEG-DMG acetate | MC3:DSPC:Chol:PEG-DMG | 50:10:38.5:1.5 | hEPO | 51.5 | 0.043 | 98 | 54 | 3.70 |

Figure 25:
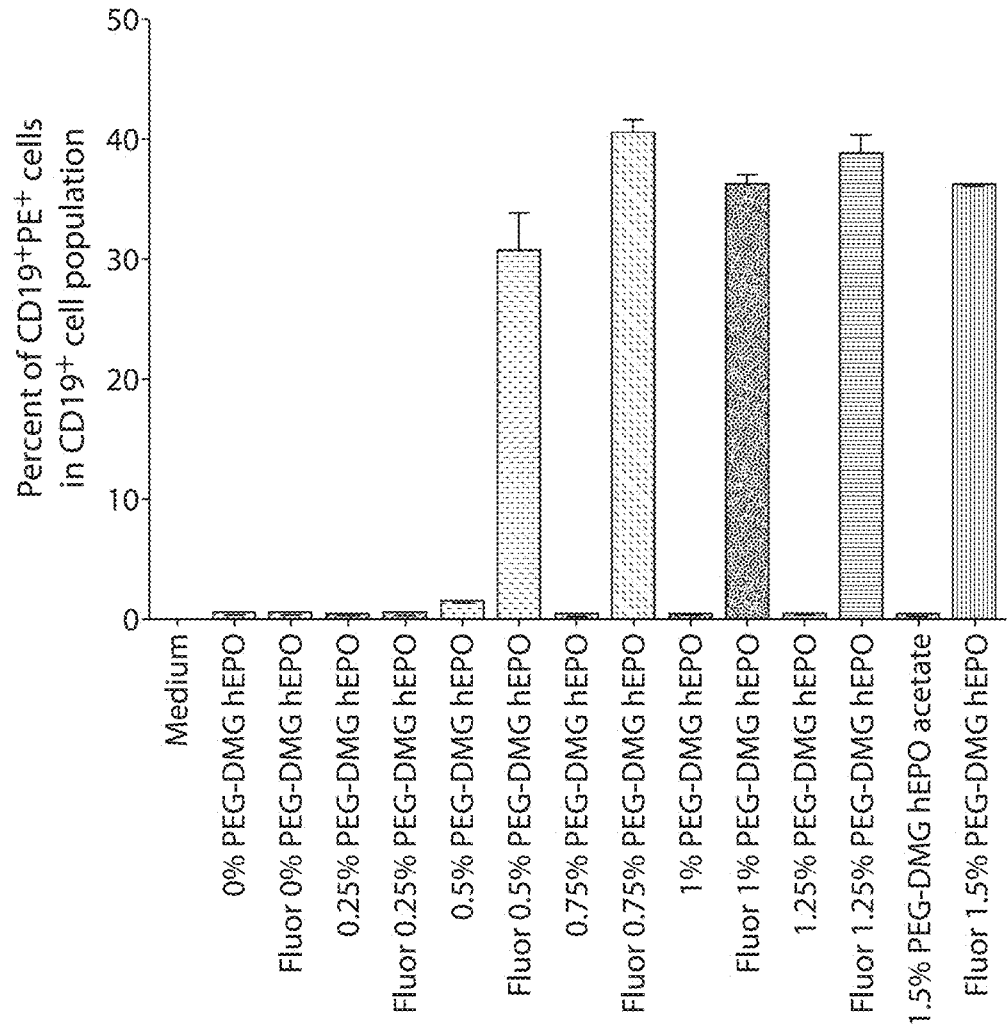
FIG. 25: LNP uptake in B cells as a function of DMG-PEG content in LNP (intermediate content study).

The following experiments were performed to determine the effect increasing DMG-PEG content of LNP on murine splenocyte and murine B cell activation and LNP uptake by murine B cells. PE+ staining (and thus association and/or uptake) of B cells was observed. LNP uptake is reduced significantly when the percentage of DMG-PEG is less than 0.25%. There is an increase of PE high cells (increased LNP uptake) when the percent of DMG-PEG is higher than 0.5%. The full data set is provided in FIG. 25, which shows that LNP uptake is reduced significantly when the percentage of DMG-PEG is less than 0.5%. The overall percentage of PE+ B cells is relatively constant for LNPs containing equal to or greater than 0.5% DMG-PEG.

Figure 26:
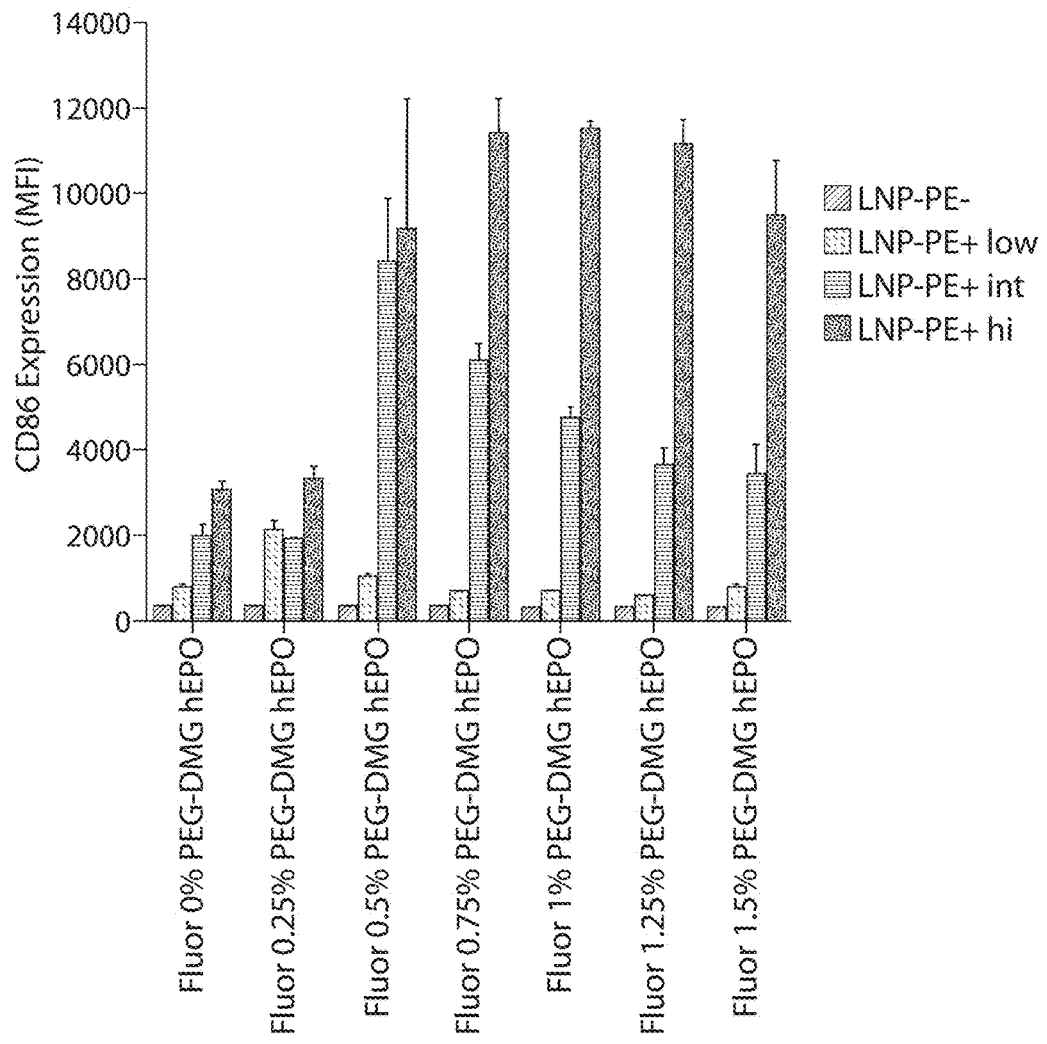
FIG. 26: B cell activation after LNP uptake as a function of DMG-PEG content in LNP. The data are presented in sets of 4 bars, the four bars in each set representing LNP PE negative, LNP-PE positive low, LNP-PE positive intermediate, and LNP-PE positive high, from left to right, respectively. Thus, the bars represent populations of cells that have associated or taken up an increasing amount of LNPs.

Next, B cell activation, measured by CD86 expression, after uptake of LNPs having differing amounts of DMG-PEG was analyzed. These data are shown in FIG. 26. CD86 expression increased on the surface of B cells as the mol percentage of DMG-PEG increased. B cell activation is consistent with B cell uptake. In addition, the most activated cells are those that have associated with or taken up the most LNP (indicated as LNP PE high).

Example 12

Table 4 outlines a study designed to analyze effects of LNPs comprising different amounts of DMG-PEG. Some of the tested LNPs comprised cationic lipid MC3, helper lipid DSPC, structural lipid cholesterol, and carried hEPO mRNA cargo. Some of the tested LNPs comprised cationic lipid MC3, helper lipid DOPE conjugated to Rhodamine, structural lipid cholesterol, and carried hEPO mRNA cargo. With each LNP subset, the amount of DMG-PEG varied from 0%, 0.05%, 0.1%, 0.15%, 0.2%, and 0.25%. Percentages reflect a theoretical mol %. The third column of the table provides the lipid composition of the LNP expressed as theoretical mol %.

There is a significant reduction of B cell activation, as measured by CD86 expression, for all LNPs tested compared to LNPs having 1.5 mol % DMG-PEG. CD86 expression in B cell populations showed no, low, intermediate, and high uptake of LNP comprising 0, 0.05, 0.1, 0.15, 0.2, and 0.25 mol % DMG-PEG (data not shown).

Example 13

Table 5 outlines a study designed to analyze the effect of LNPs comprising different helper lipids and different PEG conjugation chemistries on uptake of such LNP by B cells. All the tested LNPs comprised cationic lipid MC3 and structural lipid cholesterol. The LNPs differed in their helper

TABLE 4

Study Design

|  | Composition | mol % | mRNA | Diameter (nm) | Pd Index | % EE | [mRNA] ug/mL |
|---|---|---|---|---|---|---|---|
| 0% PEG DMG hEPO | MC3:DSPC:Chol | 50:11.5:38.5 | hEPO | 99.4 | 0.15 | 97 | 51 |
| 0.05% PEG DMG hEPO | MC3:DSPC:Chol:PEG-DMG | 50:11.45:38.5:0.05 | hEPO | 89.8 | 0.12 | 97 | 53 |
| 0.1% PEG DMG hEPO | MC3:DSPC:Chol:PEG-DMG | 50:11.4:38.5:0.1 | hEPO | 85.8 | 0.11 | 97 | 63 |
| 0.15% PEG DMG hEPO | MC3:DSPC:Chol:PEG-DMG | 50:11.35:38.5:0.15 | hEPO | 136.6 | 0.12 | 97 | 59 |
| 0.2% PEG DMG hEPO | MC3:DSPC:Chol:PEG-DMG | 50:11.3:38.5:0.2 | hEPO | 88.5 | 0.12 | 96 | 61 |
| 0.25% PEG DMG hEPO | MC3:DSPC:Chol:PEG-DMG | 50:11.25:38.5:0.25 | hEPO | 122.9 | 0.15 | 97 | 56 |
| Fluor 0% PEG DMG hEPO | MC3:DSPC:Rhodamine-DOPE:Chol | 50:11.4:0.1:38.5 | hEPO | 151.8 | 0.15 | 95 | 46 |
| Fluor 0.05% PEG DMG hEPO | MC3:DSPC:Rhodamine-DOPE:Chol:PEG-DMG | 50:11.35:0.1:38.5:0.05 | hEPO | 120.8 | 0.16 | 96 | 50 |
| Fluor 0.1% PEG DMG hEPO | MC3:DSPC:Rhodamine-DOPE:Chol:PEG-DMG | 50:11.3:0.1:38.5:0.1 | hEPO | 129.2 | 0.17 | 94 | 36 |
| Fluor 0.15% PEG DMG hEPO | MC3:DSPC:Rhodamine-DOPE:Chol:PEG-DMG | 50:11.25:0.1:38.5:0.15 | hEPO | 96 | 0.13 | 97 | 54 |
| Fluor 0.2% PEG DMGF hEPO | MC3:DSPC:Rhodamine-DOPE:Chol:PEG-DMG | 50:11.2:0.1:38.5:0.2 | hEPO | 93.5 | 0.14 | 97 | 47 |
| Fluor 0.25% PEG DMG hEPO | MC3:DSPC:Rhodamine-DOPE:Chol:PEG-DMG | 50:11.15:38.5:0.25 | hEPO | 88.6 | 0.12 | 97 | 54 |

Figure 27:
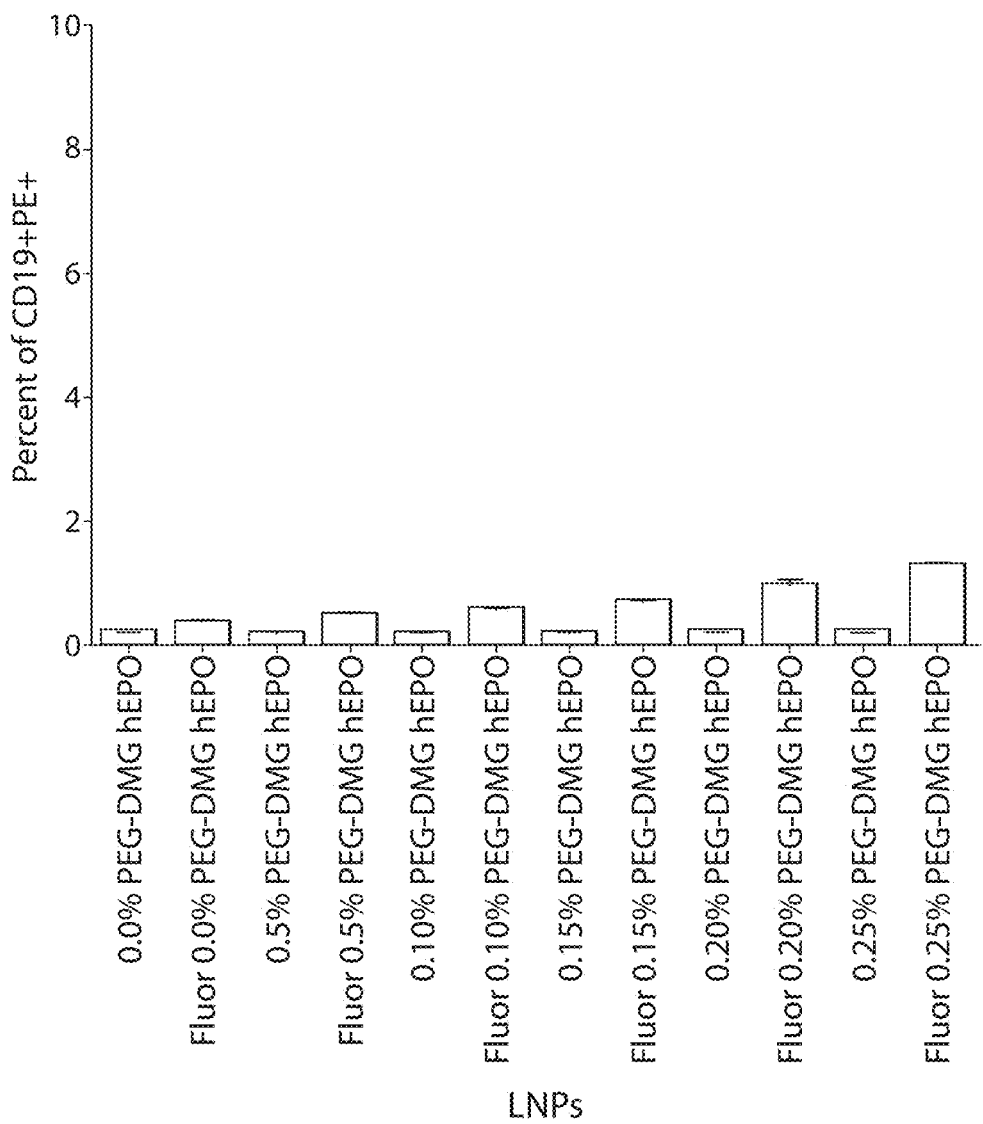
FIG. 27: LNP uptake in B cells as a function of DMG-PEG content in LNP (low content study).

The following experiments were performed to determine the effect decreasing DMG-PEG content of LNP on LNP uptake by B cells and B cell activation. PE+ staining (and thus association and/or uptake) of B cells was examined. LNP uptake is reduced significantly at all DMG-PEG concentrations tested (i.e., all below 0.5%). The full data set is provided in FIG. 27, which shows that LNP uptake is reduced significantly at all DMG-PEG mol % tested (i.e., 0-0.25 mol %). There is an absence or a significant reduction of LNP uptake by B cells at these lower DMG-PEG mol %.

lipids with some LNPs comprising oleic acid, DSPC, DOPE (conjugated to Rhodamine), oleic acid and DOPE, or DSPC and DOPE. The LNPs also differed in the PEGylated lipid component with some LNPs comprising DMG-PEG and others comprising variant Cmpd395. The second column provides details regarding the LNP lipid composition. The third column provides details regarding the mol % of each LNP component. The structure of the Cmpd395 variant is provided in FIG. 31A.

TABLE 5

Study Design

| | Composition | mol % | mRNA | Diameter (nm) | Pd Index | % EE | [mRNA] ug/mL |
|---|---|---|---|---|---|---|---|
| Oleic | MC3:Oleic Acid:Chol:PEG-DMG | 50:10:38.5:1.5 | hEPO | 101.6 | 0.11 | 97 | 65 |
| Click C10 | MC3:DSPC:Chol:PEG Click C10 | 50:10:38.5:1.5 | hEPO | 67.4 | 0.19 | 97 | 58 |
| Oleic Click C10 | MC3:Oleic Acid:Chol:PEG Click C10 | 50:10:38.5:1.5 | hEPO | 99.4 | 0.2 | 89 | 35 |
| Fluor Oleic | MC3:Oleic Acid:Rhodamine-DOPE:Chol:PEG-DMG | 50:9.9:0.1:38.5:1.5 | hEPO | 87.7 | 0.077 | 95 | 56 |
| Fluor Click C10 | MC3:DSPC:Rhodamine-DOPE:Chol:PEG Click C10 | 50:9.9:0.1:38.5:1.5 | hEPO | 74.6 | 0.19 | 97 | 57 |
| Fluor oleic click C10 | MC3:Oleic Acid:Rhodamine-DOPE:Chol:PEG Click C10 | 50:9.9:0.1:38.5:1.5 | hEPO | 84.2 | 0.19 | 91 | 38 |

Figure 28:
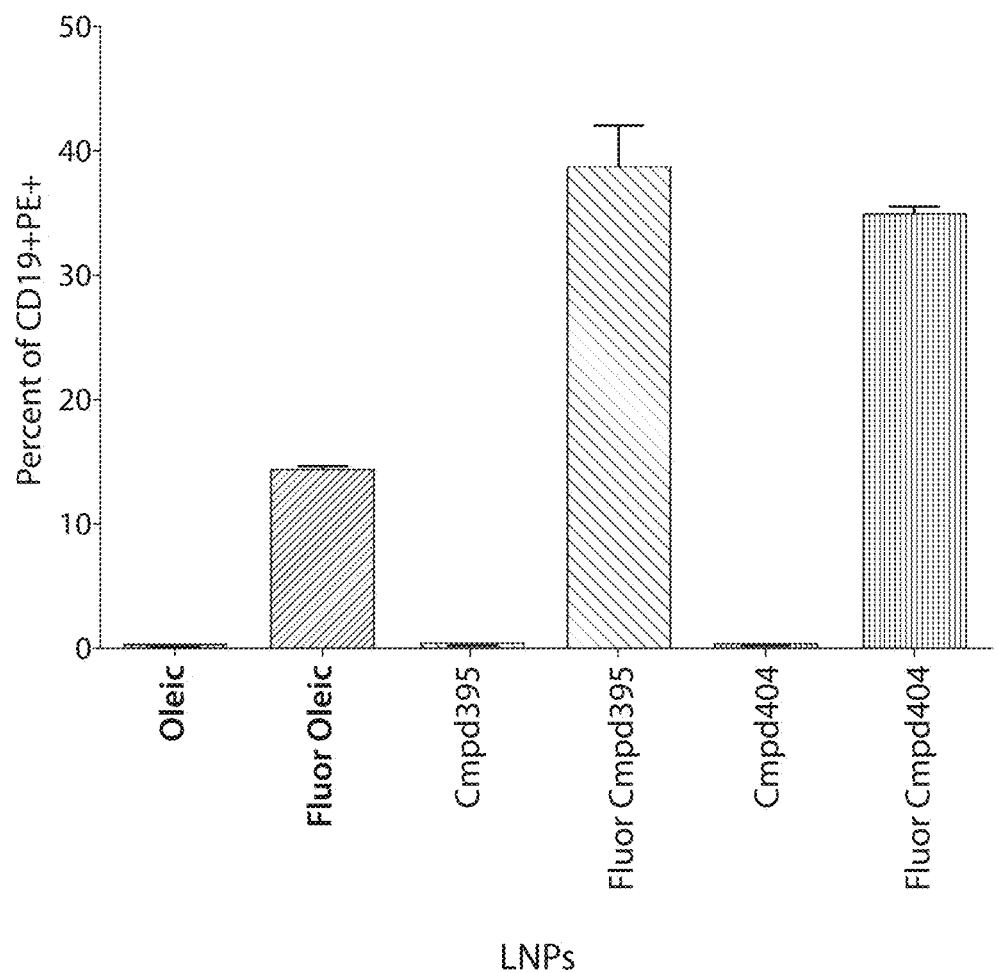
FIG. 28: PE+ staining of CD19+ B cells contacted with Cmpd395, Cmpd404, and oleic acid comprising LNPs.
Figure 40A:
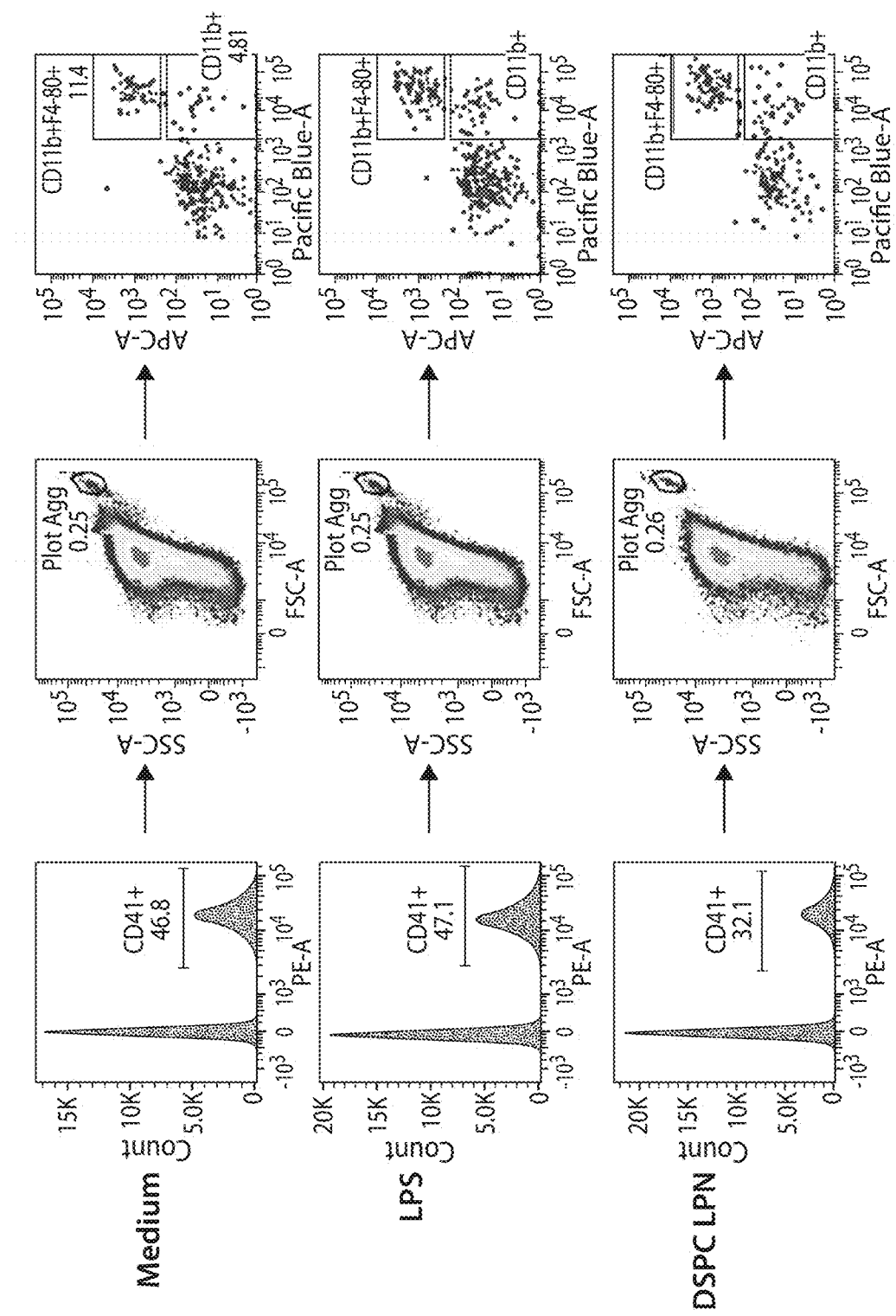
FIGS. 40A-40B: In vitro platelet aggregation using a whole blood assay. Aggregated cells were collected and gated based on CD41 expression (first column), high forward scatter and side scatter (second column) and F4/80 (y-axis) and CD11b (x-axis) expression (third column) after contact with medium (first row), LPS (second row) and DSPC LNP (third row). Platelet aggregates were isolated based on CD41+ expression and high FCS and high SSC, as shown in the second column for FIG. 40A. Percent of aggregated cells that are CD11b+F4/80+ double positive after administration of medium, LPS, and DSPC LNP (from left to right) is shown (FIG. 40B).

PE+ staining (and thus association and/or uptake) of CD19+ B cells for LNPs comprising the oleic acid, Cmpd395, and Cmpd404. The LNP compositions are identified in FIG. 40. The full data set is provided in FIG. 28. LNP comprising the Cmpd395 variant appears to have higher uptake by B cells. CD86 expression in B cell populations showed no, low, intermediate, and high uptake of LNP comprising Cmpd395, Cmpd404, and oleic acid, respectively. There was no activation in the presence of oleic acid.

Example 14

Figure 29A:
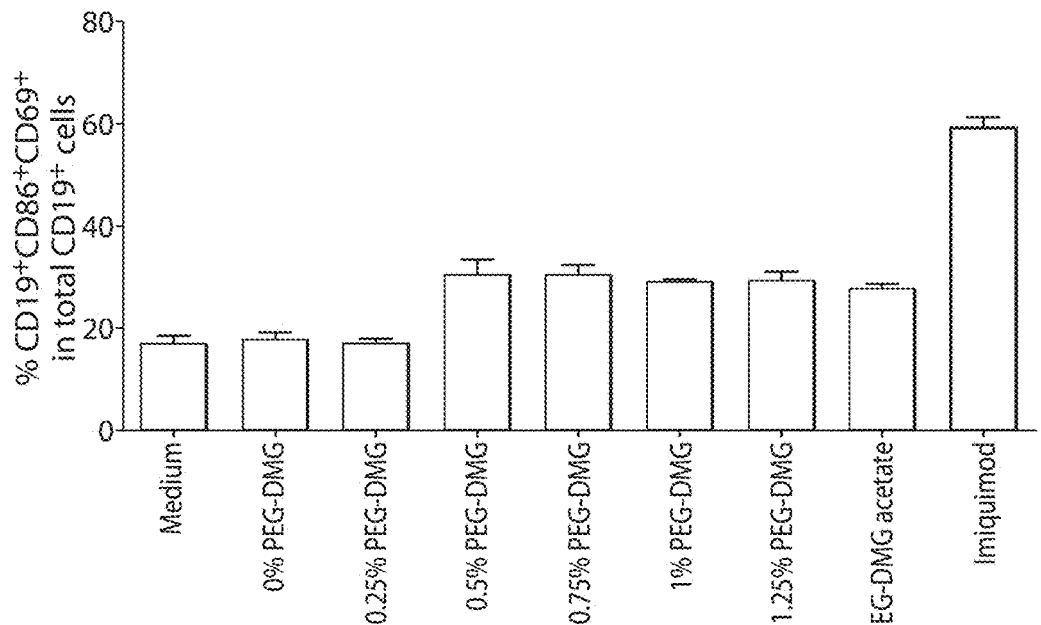
FIGS. 29A-29B: B cell activation measured through an increase in activated B cell population (CD19+CD86+ CD69+).
Figure 29B:
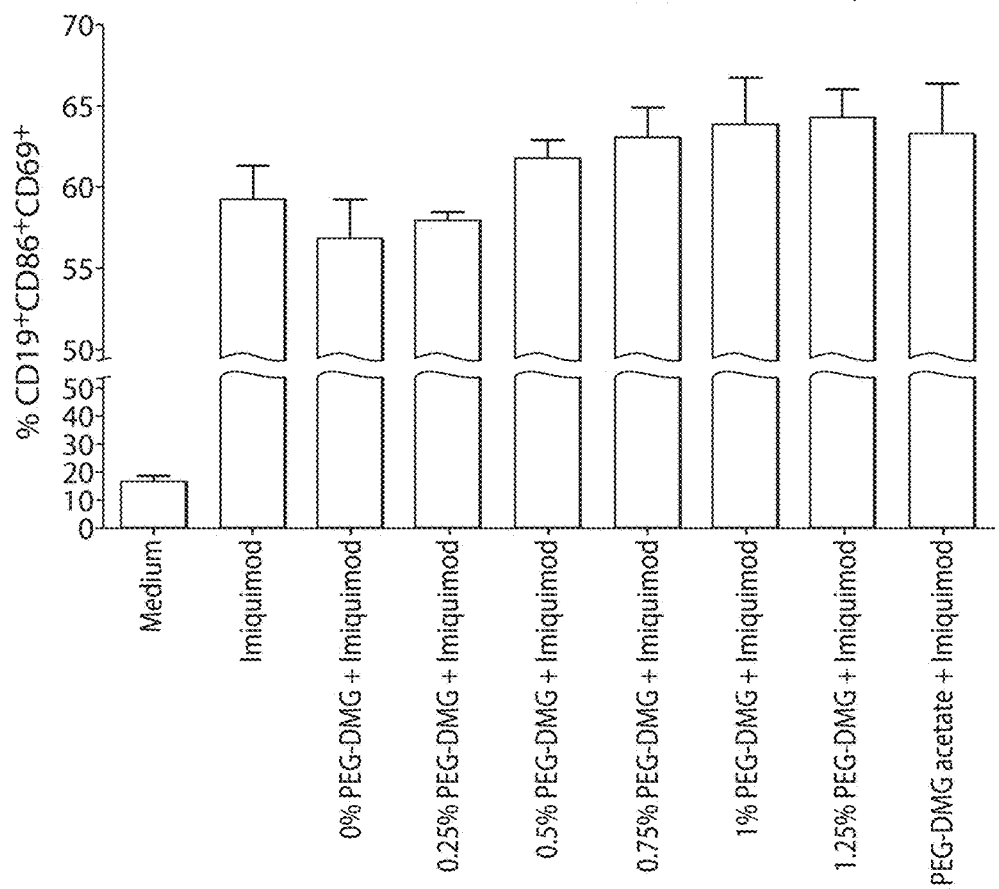
Figure 30A:
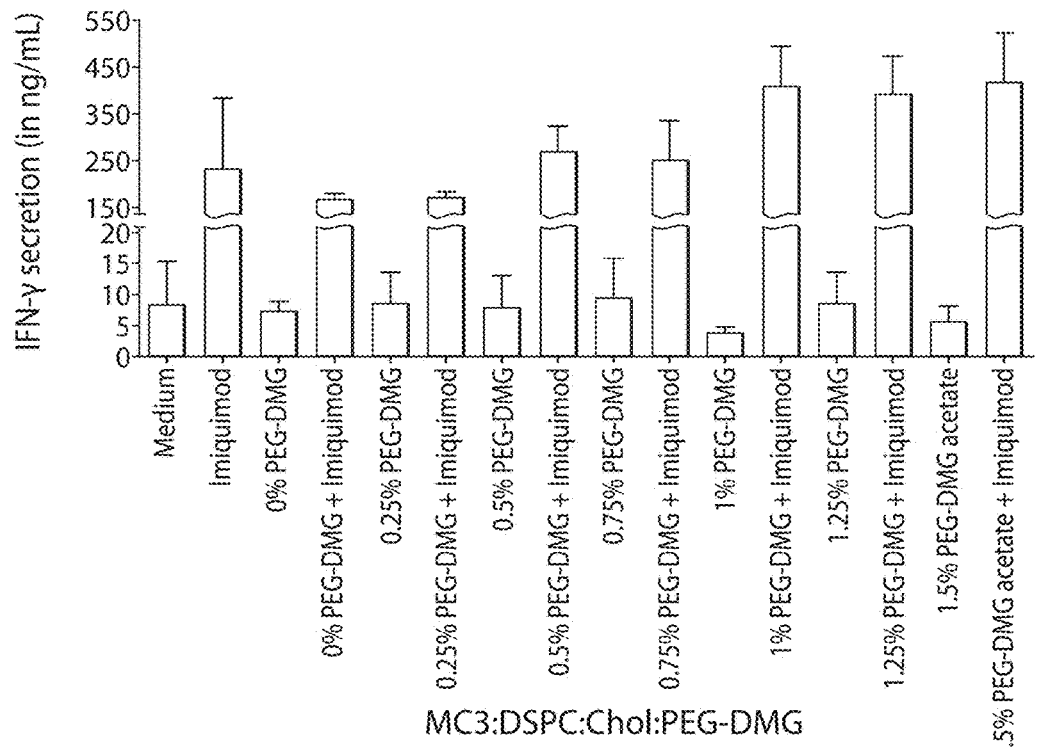
FIGS. 30A-30B: Pro-inflammatory cytokine release (IFN-γ in FIG. 30A, TNF-α in FIG. 30B) in an ex vivo human B cell culture as a function of DMG-PEG mol % in the presence or absence of Imiquimod.
Figure 30B:
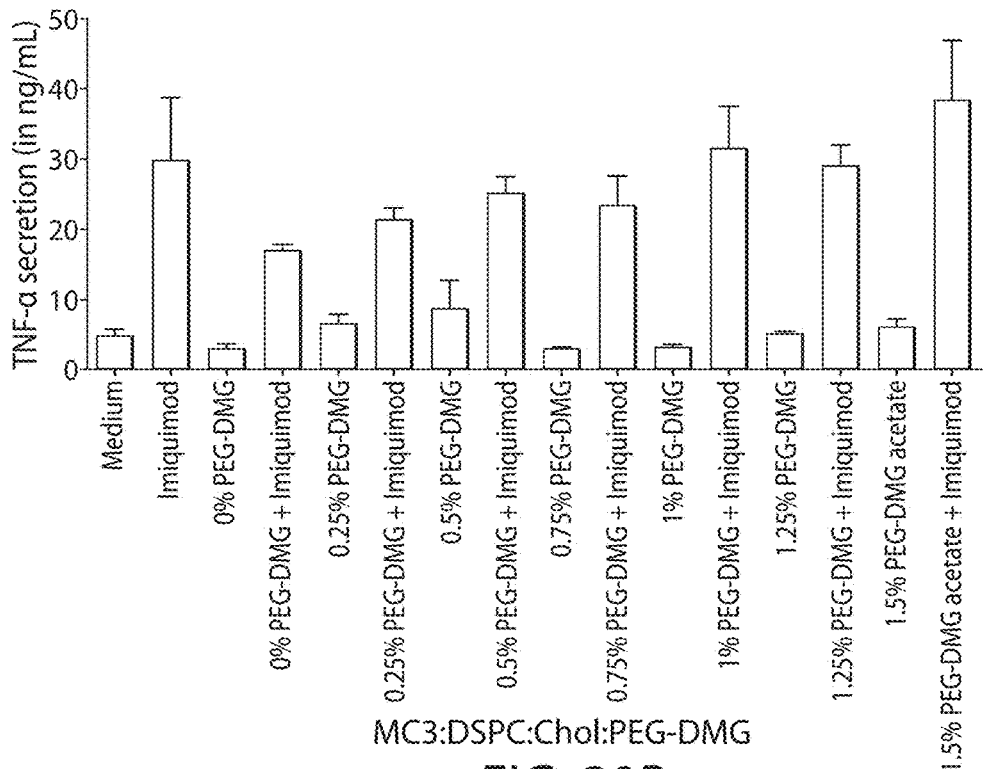

This experiment assessed the percentage of an activated B cell population defined as (CD19+CD86+CD69+) as a function of DMG-PEG content in LNPs, in the presence and absence of Imiquimod. DMG-PEG mol % were 0, 0.25, 0.5, 0.75, 1, 1.25 and 1.5 mol %. The data are shown in FIGS. 29A (without Imiquimod) and 29B (with Imiquimod). B cell activation is increased when the percentage of DMG-PEG is increased. 0.5% of DMG-PEG appears to constitute a threshold, below which B cells are no or minimally activated. Pro-inflammatory cytokine release induced by these same LNPs in an ex vivo culture is shown in FIG. 30A (IFN-gamma) and FIG. 30B (TNF-alpha). The cytokine secretion data are consistent with the B cell activation data. Increased cytokine secretion was observed when DMG-PEG mol % was increased, with 0.5% appearing to a threshold below which no or low levels of cytokine secretion were observed.

Example 15

Phospholipid design variations and substitutions for PC, including DSPC, lipids are provided in FIG. 31A-31D. The modifications may function to reduce LNP association with B cells, recognition of LNP by receptors, and ultimately uptake by B cells. The variations contemplated include but are not limited to modifying the PC head group (FIG. 31A), the PC core (FIG. 31B), or through reducing the planarity of the lipid (FIG. 31C). Other variants or substitutes include modified oleic acid, as shown in FIG. 31D.

Figure 32A:
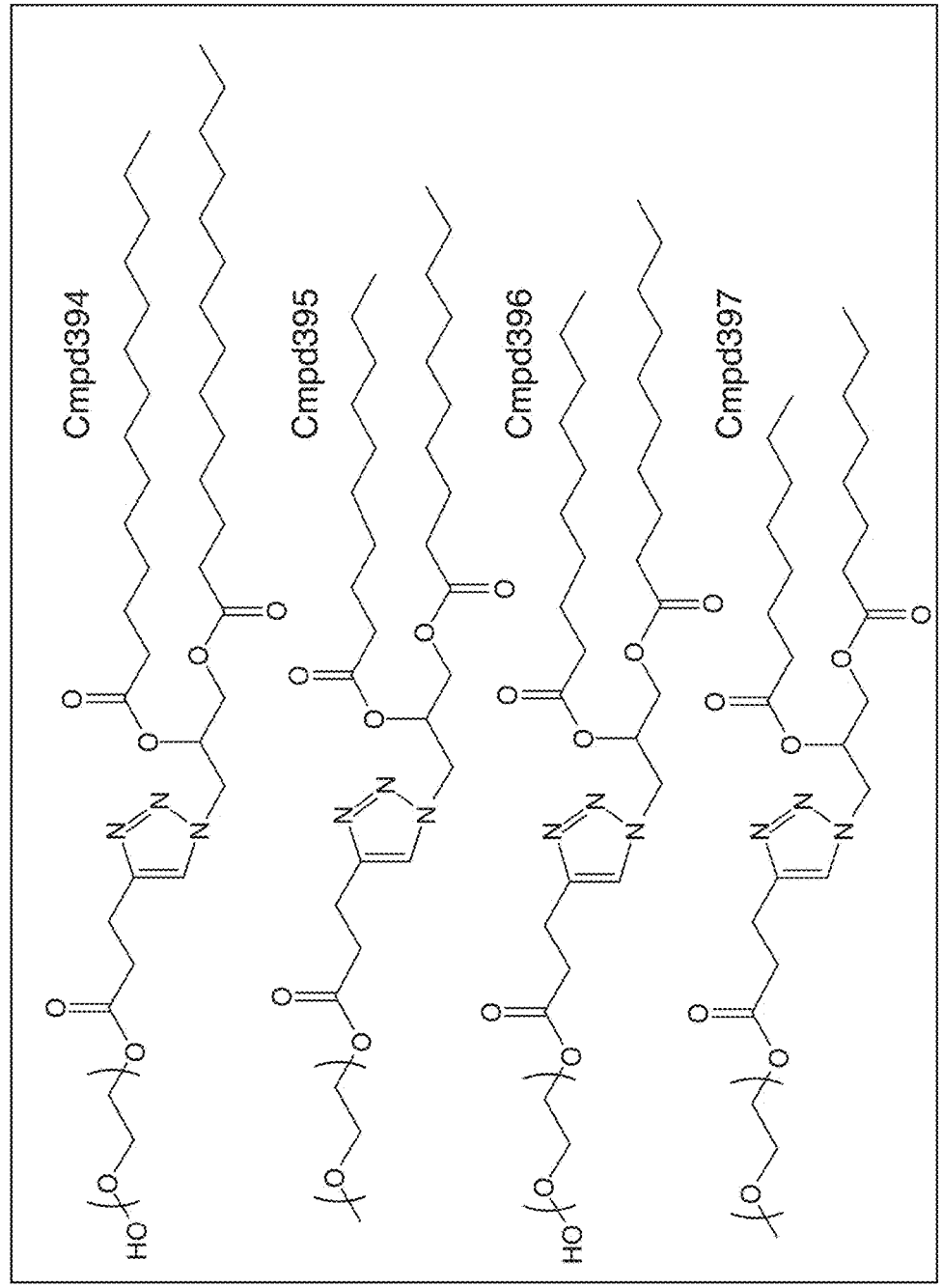
FIGS. 32A-32C: Examples of PEGylated lipids comprising short lipid tails, a click linker, and a hydroxy (OH) PEG end group.
Figure 32B:
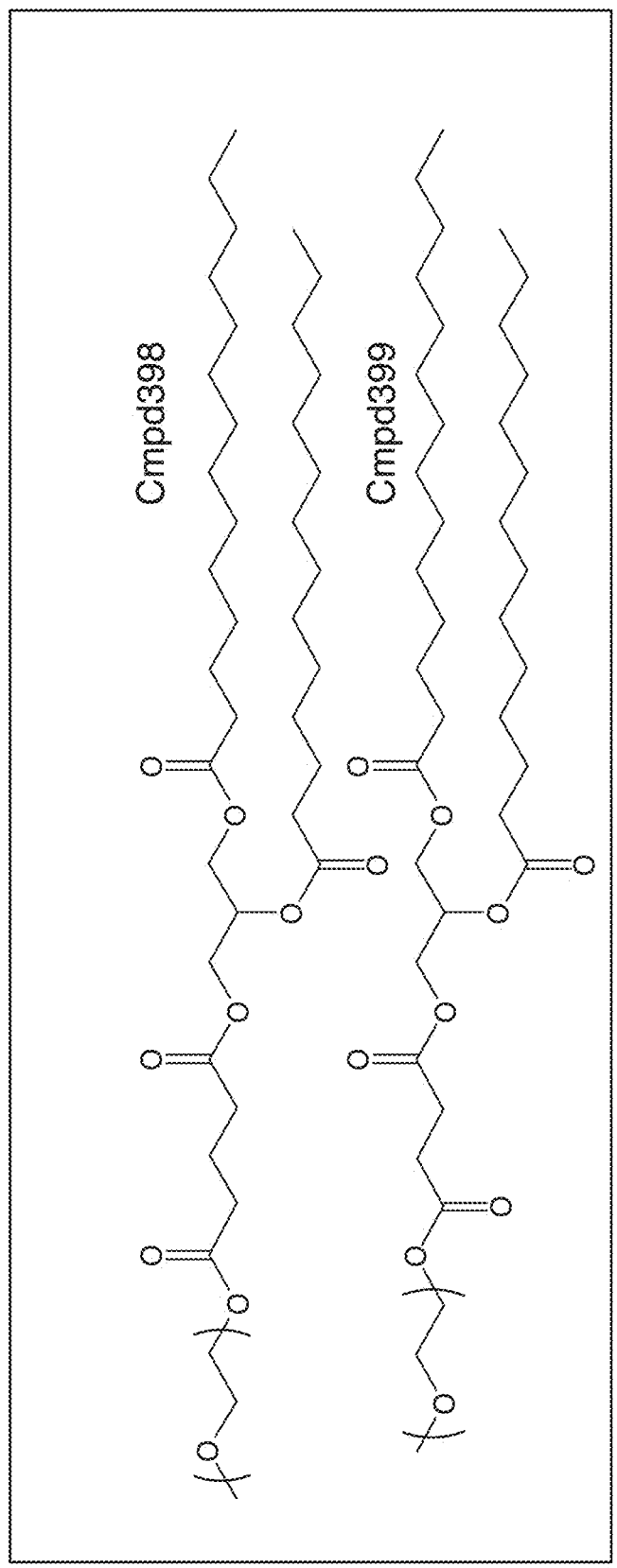
Figure 32C:
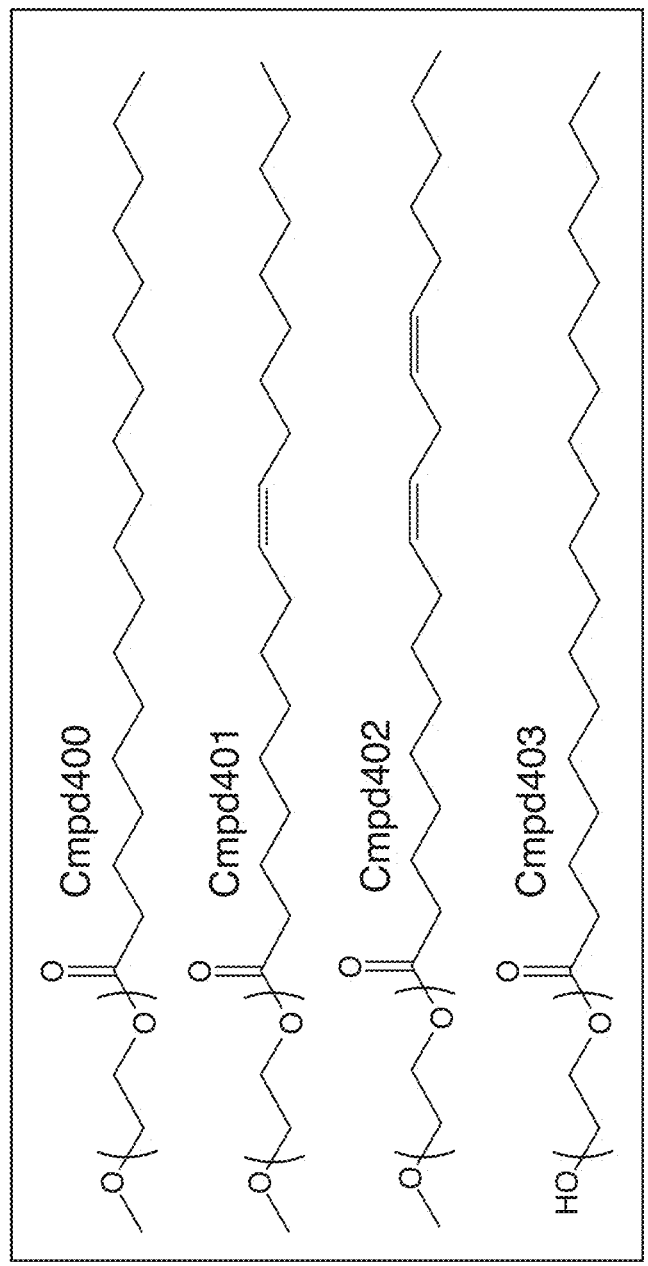

Variations of DMG-PEG are also contemplated and these include for example variants having shorter lipid tails, a click linker, and/or a hydroxy end group on the PEG moiety (PEG-OH, or hydroxy-PEG). FIG. 32A shows the structures for Cmpd394, Cmpd395, Cmpd396, and Cmpd397 variants. FIG. 32B shows exemplary Cmpd 398 and Cmpd 399.

Figure 33:
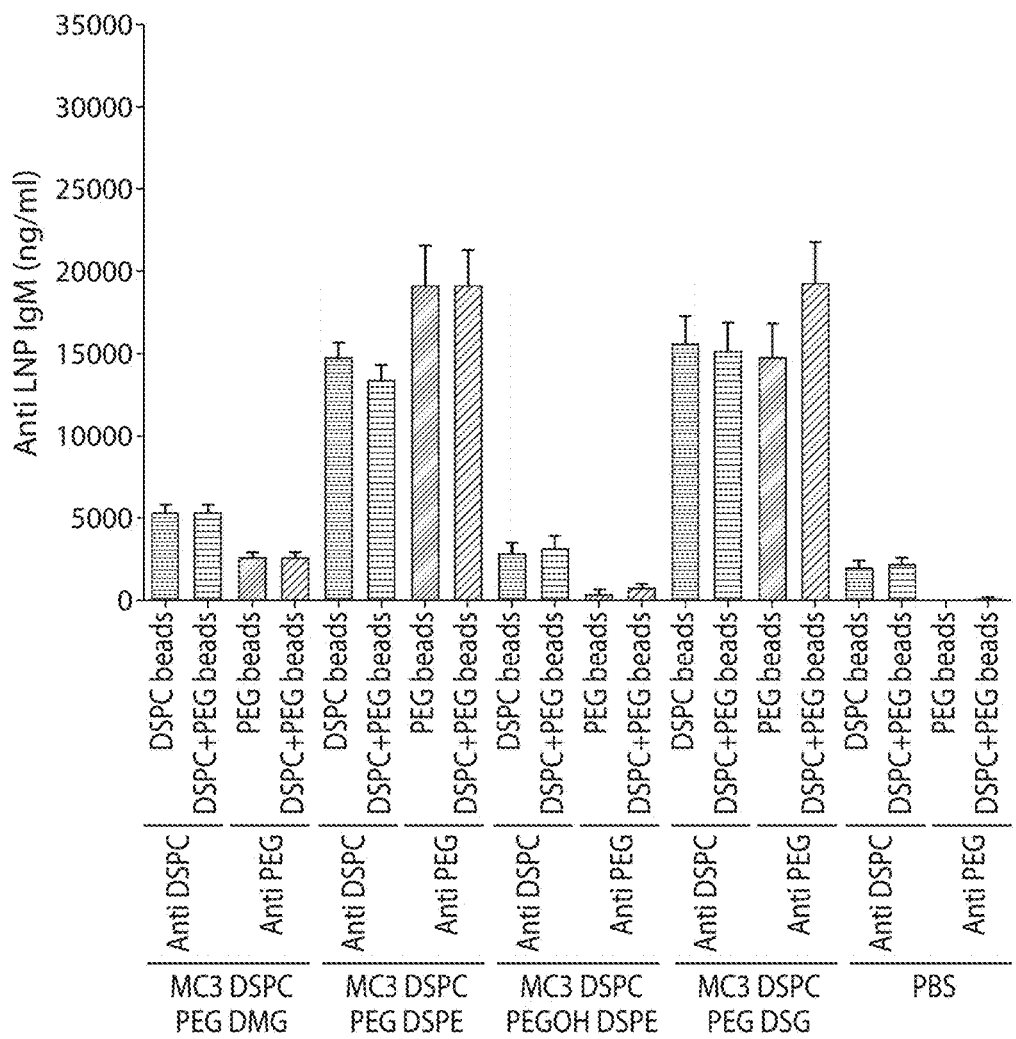
FIG. 33: Anti-PEG or anti-DSPC IgM response measured by flow cytometry (beads) 96 hours after administration of the second dose. The IgM responses against DSPC or PEG are measured identically when beads are used alone or together. PEG DMG, PEG DSPE or Cmpd430 LNPs induced anti-LNP responses. Anti-PEG IgM and anti DSPC IgMs were both observed suggesting that the IgM response is a natural IgM response.
Figure 34:
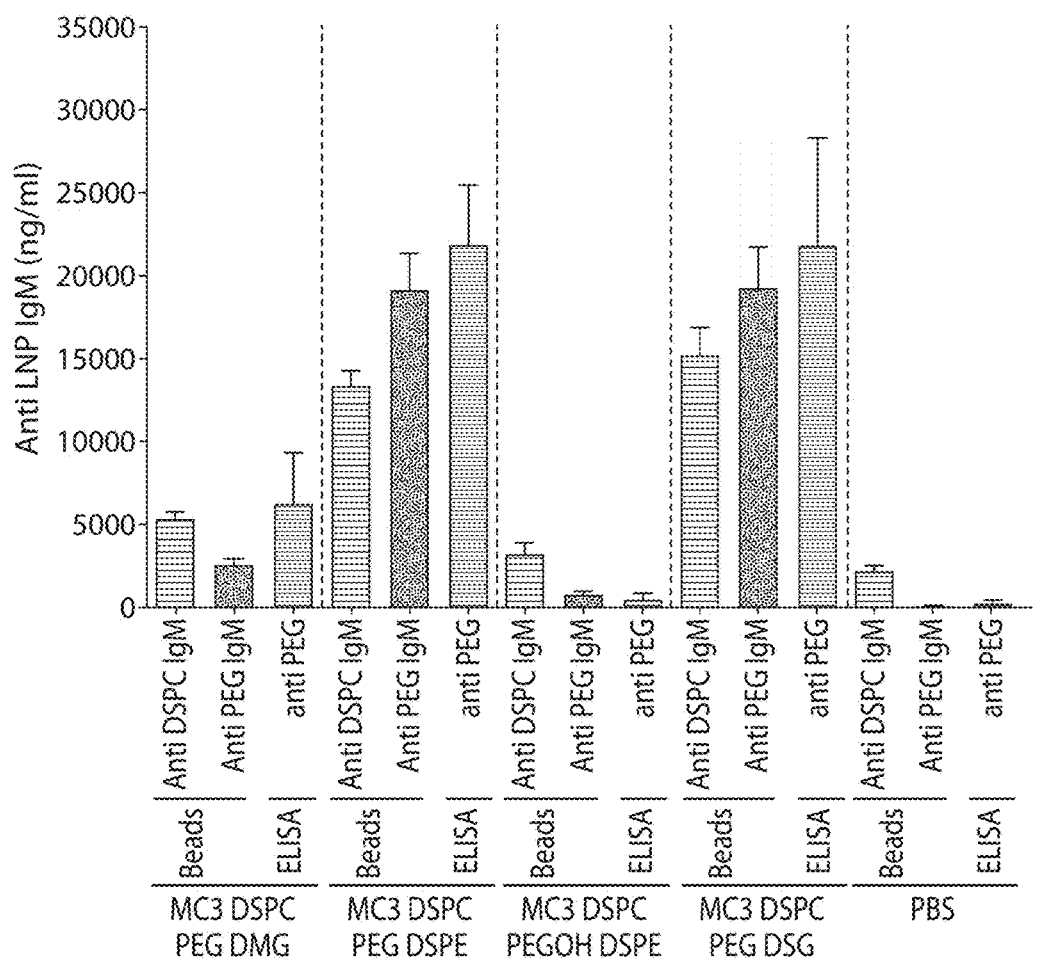
FIG. 34: Anti-PEG IgM measured by ELISA and anti-PEG or anti-DSPC IgM measured by flow cytometry (beads) 96 hours after administration of the second dose. The anti-PEG IgMs measured by ELISA and beads are similar and no significant differences were detected.

A table of parameters for an FFLuc repeat dose study with different PEG lipids and/or alternatives to PEG in mouse is shown in Table 6. This study was designed to test the effect of different surface stabilizing LNP components on IgG production. All the tested LNP comprised cationic lipid MC3, helper lipid DSPC and structural lipid cholesterol in the same proportions. They also all contained cargo Luc mRNA. The LNP differed in the PEGylated lipid. The anti-PEG or anti-DSPC IgM response measured by flow cytometry (beads) 96 hours after administration of the second dose is shown in FIG. 33. PEG DMG, PEG DSPE or PEG DSG LNPs induced anti-LNP responses. The data presented in FIG. 34 shows anti-PEG IgM measured by ELISA and anti-PEG or anti-DSPC IgM measured by flow cytometry (beads) 96 hours after administration of the second dose. The anti-PEG IgMs measured by ELISA and beads are similar and no significant differences were detected.

TABLE 6

Study Design

| Test/Control Material | Vehicle | Formulation | Route | Dosing Regimen | # of Doses | # of females |
|---|---|---|---|---|---|---|
| Luc, G5, C1 | MC3 | acetate MC3:DSPC:Chol:PEG-DMG_50:10:38.5:1.5 | IV | 1Xwk; 2 wk | 2 | 8 |
| Luc, G5, C1 | MC3 | MC3:DSPC:Chol:PG8 50:10:38.5:1.5 | IV | 1Xwk; 2 wk | 2 | 8 |
| Luc, G5, C1 | MC3 | MC3:DSPC:Chol:PEG Click (C12)_50:10:38.5:1.5 | IV | 1Xwk; 2 wk | 2 | 8 |
| Luc, G5, C1 | MC3 | MC3:DSPC:Chol:PEG DLPE (C12)_50:10:38.5:1.5 | IV | 1Xwk; 2 wk | 2 | 8 |
| Luc, G5, C1 | MC3 | MC3:DSPC:Chol:PEG DMPE (C14)_50:10:38.5:1.5 | IV | 1Xwk; 2 wk | 2 | 8 |
| Luc, G5, C1 | MC3 | MC3:DSPC:Chol:PEG Click DMG (C14)_50:10:38.5:1.5 | IV | 1Xwk; 2 wk | 2 | 8 |

TABLE 6-continued

Study Design

| | | | | | | |
|---|---|---|---|---|---|---|
| Luc, G5, C1 | MC3 | MC3:DSPC:Chol:PEGDMG (C14)_50:10:38.5:1.5 | IV | 1Xwk; 2 wk | 2 | 8 |
| Luc, G5, C1 | MC3 | MC3:DSPC:Chol:PEG DSPE (C18)_50:10:38.5:1.5 | IV | 1Xwk; 2 wk | 2 | 8 |
| Luc, G5, C1 | MC3 | MC3:DSPC:Chol:PEG-OH DSPE (C18)_50:10:38.5:1.5 | IV | 1Xwk; 2 wk | 2 | 8 |
| Luc, G5, C1 | MC3 | MC3:DSPC:Chol:PEGDSG_50:10:38.5:1.5 | IV | 1Xwk; 2 wk | 1 | 8 |
| Empty | PBS | MC3:DSPC:Chol:PEGDMG_50:10:38:1.5 | IV | 1Xwk; 2 wk | 2 | 8 |
| — | PBS | PBS | IV | 1Xwk; 2 wk | 2 | 3 |

| Test/Control Material | Dose Level (mg/kg) | Dose Vol (mL) | Dose Conc. (g/mL) | Total Vol Req (mL) | Total Min Mass Req (mg) |
|---|---|---|---|---|---|
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Lu, G5, C1 | 0.5 | 0.1 | 0.1 | 2.8 | 0.28 |
| Empty | 0 | 0.1 | 0 | 2.8 | 0 |
| — | 0 | 0.1 | 0 | 1.4 | 0 |

Example 16

Additional analyses were performed using the study design outlined in Table 7 to assess binding of various LNPs to platelets in vivo. The tested LNPs are denoted DMG-PEG LNP (comprising DMG-PEG, helper lipid DSPC, cationic lipid MC3, and structural lipid cholesterol), PEG-OH LNP (comprising PEG-OH, helper lipid DSPC, cationic lipid MC3, and structural lipid cholesterol), and PEGless LNP (comprising helper lipid DSPC, cationic lipid MC3, and structural lipid cholesterol, but lacking PEG).

TABLE 7

Study Design

| Group | Test/Control Material | Vehicle | Formulation | Route | Dosing Regimen | # of Doses | # of males | # of females | Dose Level (mg/kg) | Dose Vol (mL) | Dose Conc. (mg/mL | Total Vol Req | Total Min Mass |
|---|---|---|---|---|---|---|---|---|---|---|---|---|---|
| 1 | PBS | N/A | | | | 1 | | 6 | | | | | |
| 2 | mRNA EGFP G5 | MC3 | DMG-PEG (DSPC) | IV | | 1 | | 6 | 0.1 | 0.1 | 0.02 | 0.84 | 0.0168 |
| 3 | mRNA EGFP G5 | MC3 | PEG-OH (DSPC) | IV | | 1 | | 6 | 0.1 | 0.1 | 0.02 | 0.84 | 0.0168 |
| 4 | mRNA EGFP G5 | MC3 | PEGless (DSPC) | IV | | 1 | | 6 | 0.1 | 0.1 | 0.02 | 0.84 | 0.0168 |

Figure 35:
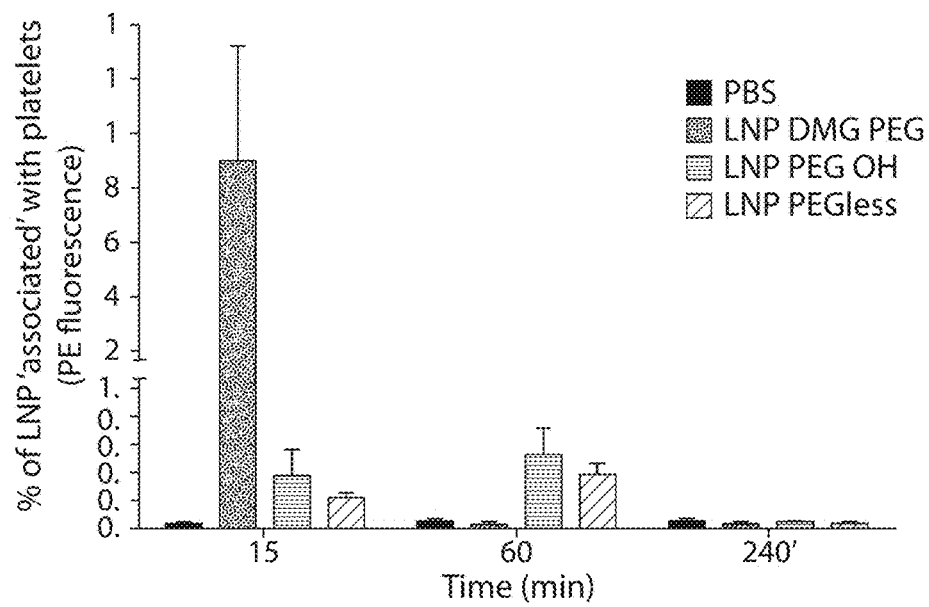
FIG. 35: LNP association with platelets as a function of time and LNP composition. The percent of LNP associated with platelets (as indicated by phycoerythrin (PE) fluorescence) is shown at three time points (15, 60 and 240 minutes) after administration of PBS, DMG-PEG containing LNP, PEG-OH containing LNP, and PEGless LNP (left to right for each time point). These experiments were performed on purified platelets harvested from the subject at the various time points shown.

LNP association to platelets is shown in FIG. 35. The percent LNP associated with platelets (as indicated by phycoerythrin (PE) fluorescence) is shown at three time points (15, 60 and 240 minutes) after administration of PBS, DMG-PEG containing LNP, PEG-OH containing LNP, and PEGless LNP (left to right for each time point). These experiments were performed on purified platelets harvested from the subject at the various time points. After intravenous injection, LNPs containing DMG-PEG associated with platelets. This association was rapid but transient; after 60 minutes, it was no longer visible. The DMG-PEG, and more specifically the methoxy-PEG moiety, was likely responsible for the observed LNP association since association did not occur when hydroxy-PEG (PEG-OH) was used instead of DMG-PEG and nor did it occur in the absence of any PEG (referred to as PEGless).

Figure 36:
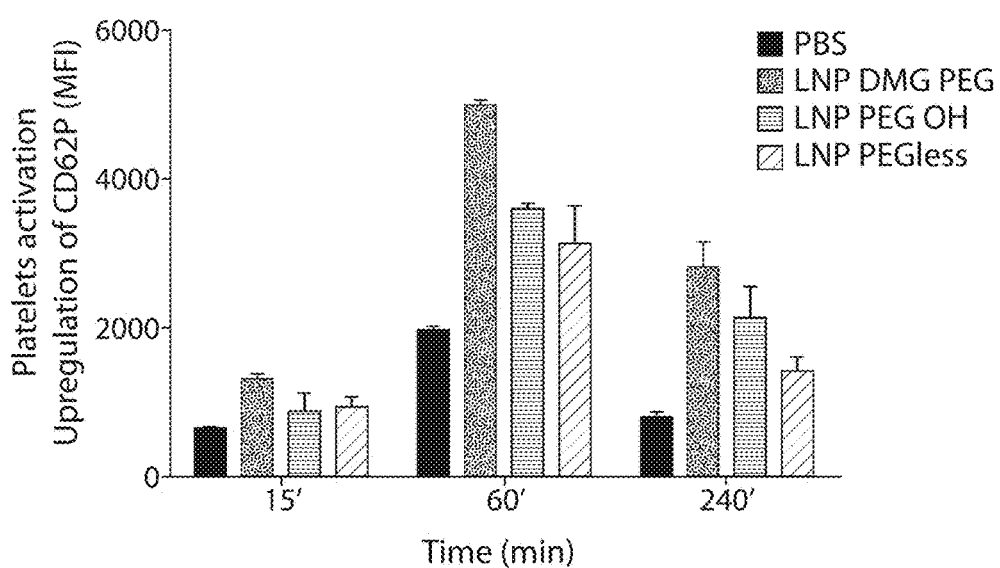
FIG. 36: Platelet activation as a function of LNP composition. Platelet activation (as indicated by expression of platelet activation marker CD62P (MFI)) was measured at three time points (15, 60 and 240 minutes) after administration of PBS, DMG-PEG LNP, PEG-OH LNP, and PEGless LNP (left to right).

Platelet activation after LNP administration is shown in FIG. 36. Platelet activation (as indicated by expression of platelet activation marker CD62P (MFI)) was measured at three time points (15, 60 and 240 minutes) after administration of PBS, DMG-PEG LNP, PEG-OH LNP, and PEGless LNP (left to right). The LNPs are as described in Table 7. Administration of LNPs led to increased expression of CD62P. The activation is highest in the DMG-PEG group but is also measurable in the PEG-OH and PEGless groups. Activation is detectable at 15 minutes after injection and is maximal at 60 minutes after injection. As with LNP association with platelets, activation is transient and decreases with time.

Thus, platelets appear to first associate with the injected LNP, following which such platelets are activated. LNPs comprising DMG-PEG are able to associate with platelets within 15 minutes of administration and then activate platelets within 60 and 240 minutes of administration. LNPs comprising PEG-OH and PEGless LNP, on the other hand, do not demonstrate significant association with platelets and yet are still able to activate platelets at the 60 and 240 minute time points. The level of platelet activation observed with the PEG-OH and PEGless LNP are slightly lower than that observed with DMG-PEG LNP. Thus it is possible for platelets to be activated even without appreciable association with the administered LNP. It may be that the association of DMG-PEG LNP to platelets is more stable than is the association of the other LNP types to platelets, and that while associated in vivo such association falls apart during the assay.

Figure 37A:
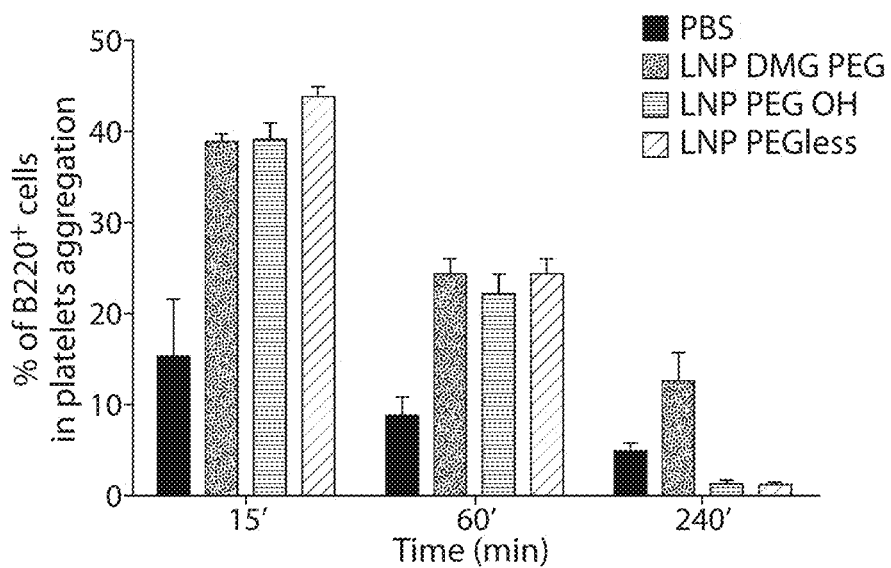
FIGS. 37A-37B: Presence of B220+ B cells and F4/80+ macrophages in platelet aggregates in vivo as a function of time and LNP composition. Percent of B cells (as indicated by B220+ staining, FIG. 37A) and percent of macrophages (as indicated by F4/80+ staining, FIG. 37B) at three time points (15, 60 and 240 minutes) after administration of PBS, DMG-PEG LNP, PEG-OH LNP, and PEGless LNP (left to right), is shown.
Figure 37B:
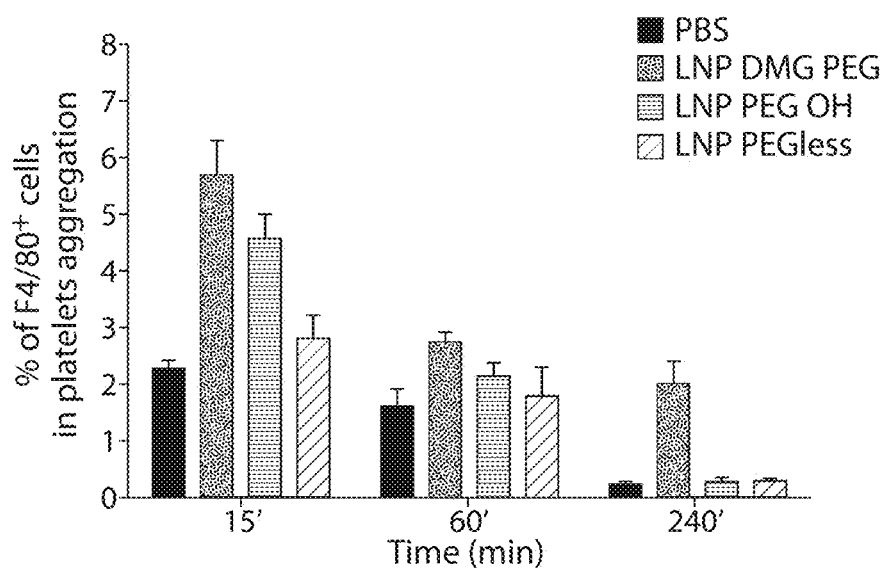
Figure 38:
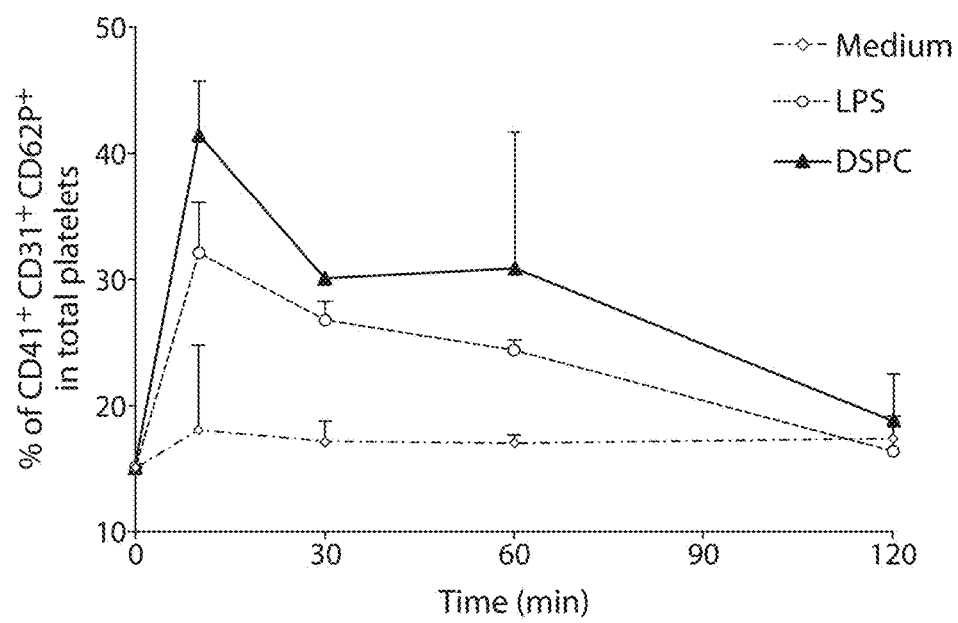
FIG. 38: In vitro activation of platelets as assessed by upregulation of CD31 and CD62P activation markers, after contact with LNPs.
Figure 39A:
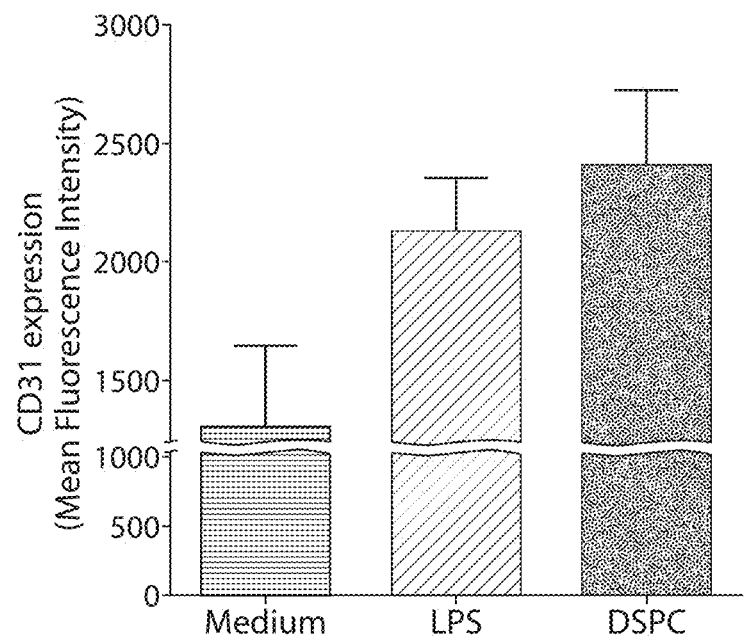
FIGS. 39A-39D: In vitro activation of platelets, as indicated by increased CD31 expression relative to control (medium), at 10 minutes (FIG. 39A), 30 minutes (FIG. 39B), 60 minutes (FIG. 39C), and 120 minutes (FIG. 39D) after administration of medium, LPS and LNP comprising DSPC.
Figure 39B:
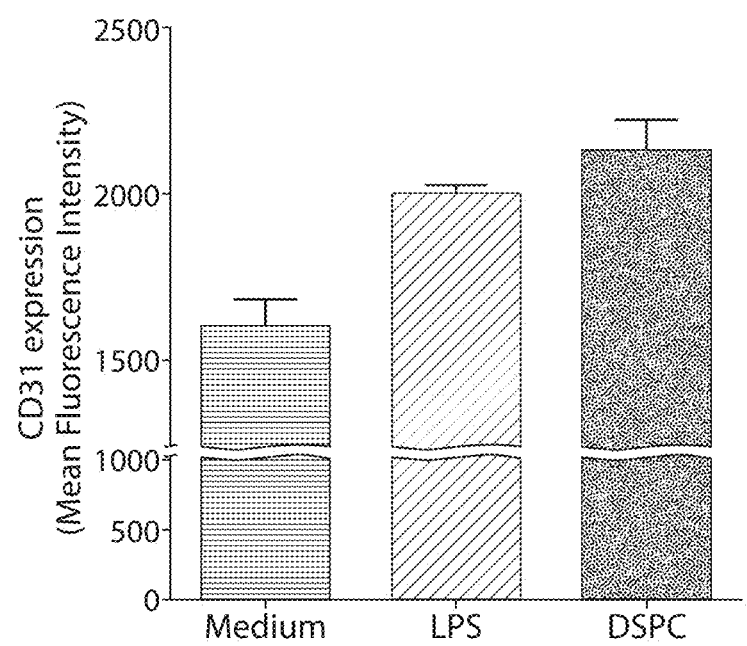
Figure 39C:
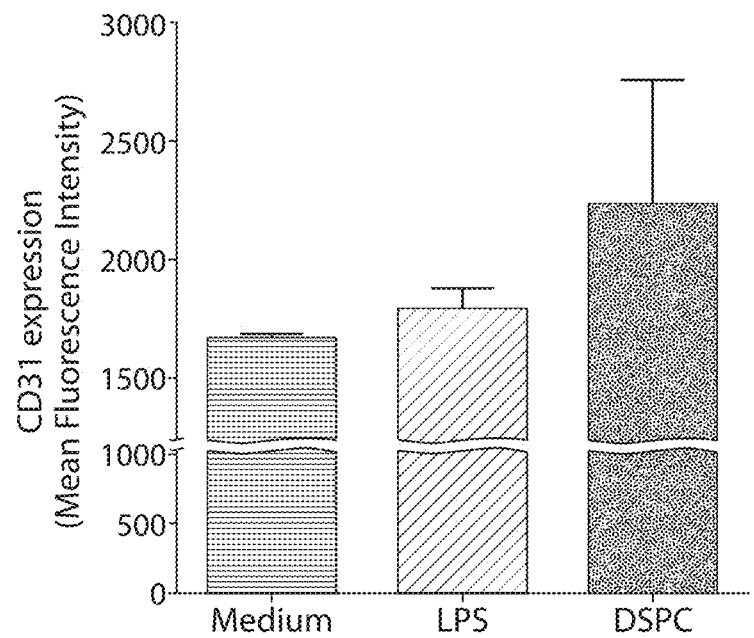
Figure 39D:
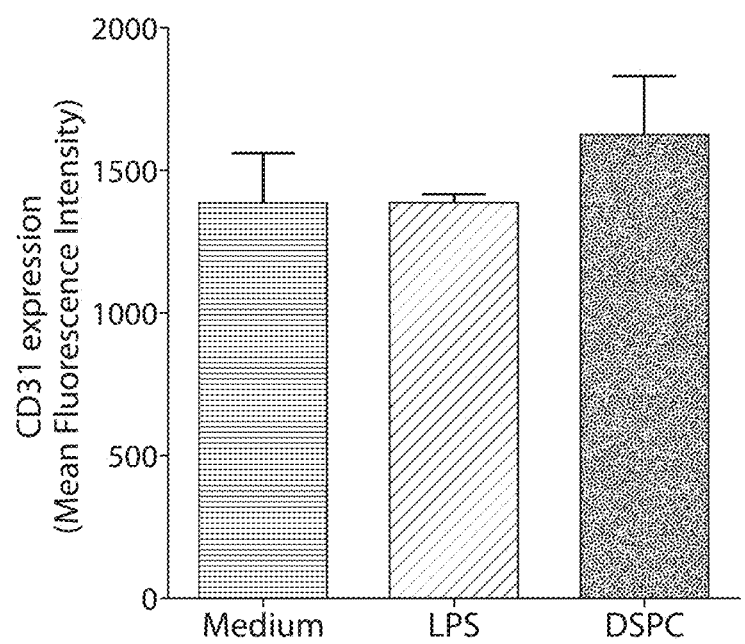

The presence of other cells in platelet aggregates was also assessed. FIGS. 37A and 37B show the percentage of B220+

B cells and F4/80+ macrophages present in platelet aggregates following intravenous injection of DMG-PEG LNP, PEG-OH LNP and PEGless LNP. Percent of B cells (as indicated by B220+ staining, FIG. 37A) and percent of macrophages (as indicated by F4/80+ staining, FIG. 37B) at three time points (15, 60 and 240 minutes) after administration of PBS, DMG-PEG LNP, PEG-OH LNP, and PEGless LNP (left to right), is shown. B cells and macrophages were associated with platelet aggregates. Macrophages and B cells associated with platelet aggregates following administration of all three LNP types (DMG-PEG LNP, PEG-OH LNP and PEGless LNP). B cell association was similar between the three LNP types, suggesting that PEG played a minimal or no role in this phenomenon. Macrophage association varied slightly between the three LNP types, with the highest macrophage association observed with LNPs comprising DMG-PEG. More significant differences were observed at the 240 minute time point for both cell types. Regardless of the LNP composition and PEG content, the association was transient and decreased with time. Interestingly, even in the absence of observable 'LNP association' with platelets in the presence of PEG-OH LNP and PEGless LNP (see FIG. 35), there is detectable B cell and macrophage presence in platelet aggregates.

Additional experiments were carried out in vitro to investigate these platelet interactions. Platelets were incubated in vitro with medium, LPS or LNPs comprising helper lipid DSPC (further comprising cationic lipid MC3, DMG-PEG, and structural lipid cholesterol). Platelet activation was assessed by expression of CD31 and CD62P in the CD41+ platelet population. Platelets were rapidly and strongly activated, as indicated by upregulation of CD31 and CD62P activation markers, after contact with LNPs. Peak platelet activation was observed by 15 minutes, as compared to 60 minutes when LNPs were administered in vivo. DSPC LNP stimulated platelets to a greater degree than LPS and medium at each time point tested. The data are shown in FIGS. 38 and 39A-39D.

Figure 40B:
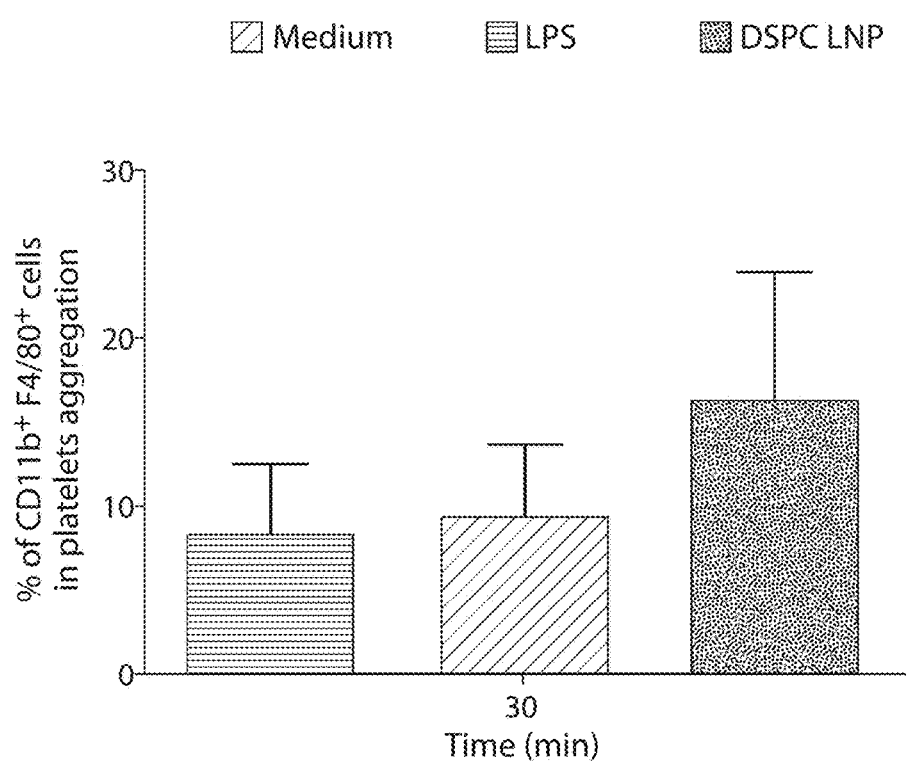

Next the ability of LNP to induce platelet aggregation in a whole blood assay was determined. The data are provide in FIGS. 40A-40B. Aggregated cells were collected and gated based on CD41 expression (first column), high forward scatter and side scatter (second column) and F4/80 (y-axis) and CD11b (x-axis) expression (third column) after contact with medium (first row), LPS (second row) and DSPC LNP (third row). Platelet aggregates were isolated based on CD41+ expression and high FCS and high SSC, as shown in the second column for FIG. 40A. Percent of aggregated cells that are CD11b+ F4/80+ double positive (macrophages) after administration of medium, LPS, and DSPC LNP (from left to right) is shown (FIG. 40B). DSPC LNPs resulted in a greater percentage of macrophages in platelet aggregates.

Figure 41A:
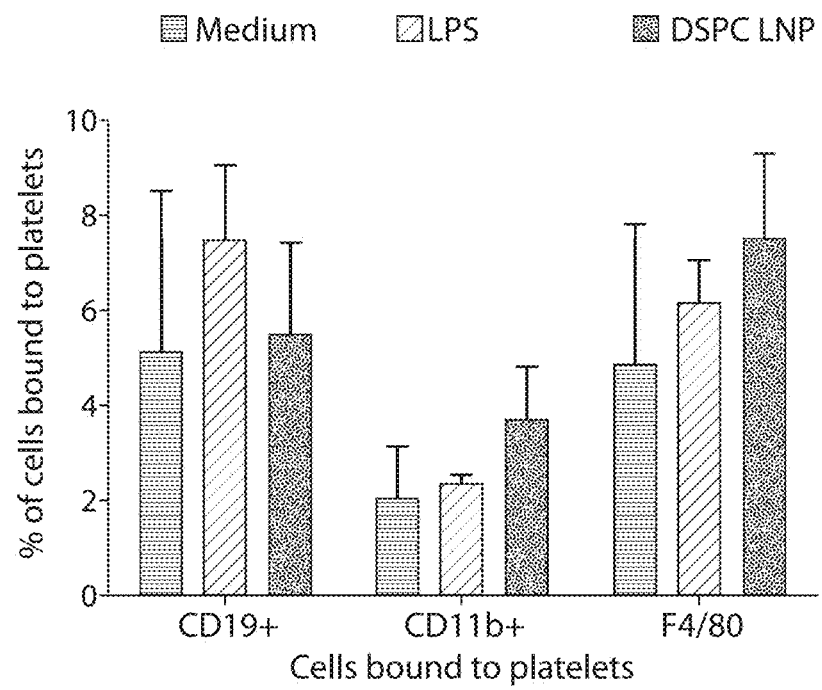
FIGS. 41A-41B: In vitro platelet aggregation with B cells (CD19+) and macrophages (CD11b+ and F4/80+) after incubation of whole blood with medium, LPS and DSPC LNP (from left to right) for 30 minutes (FIG. 41A) and 120 minutes (FIG. 41B).
Figure 41B:
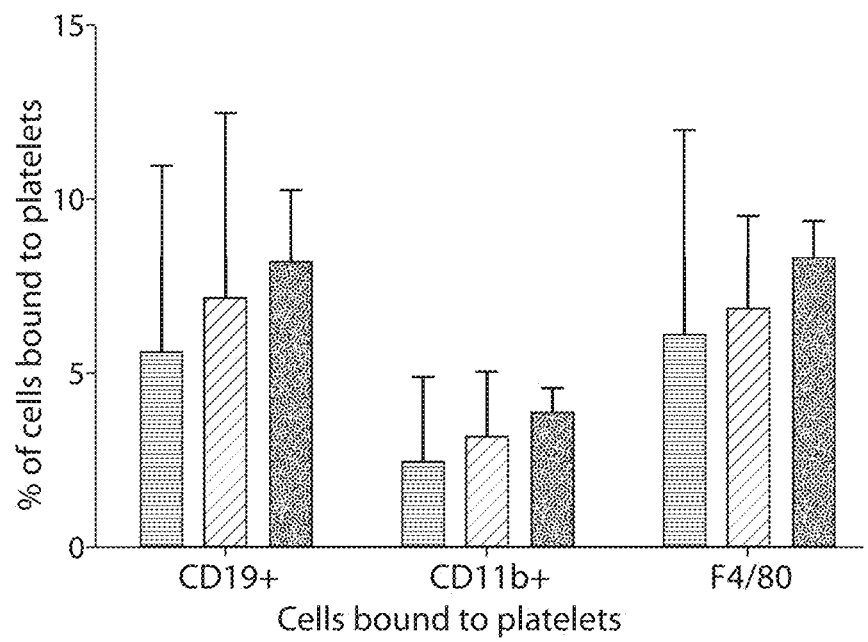
Figure 42A:
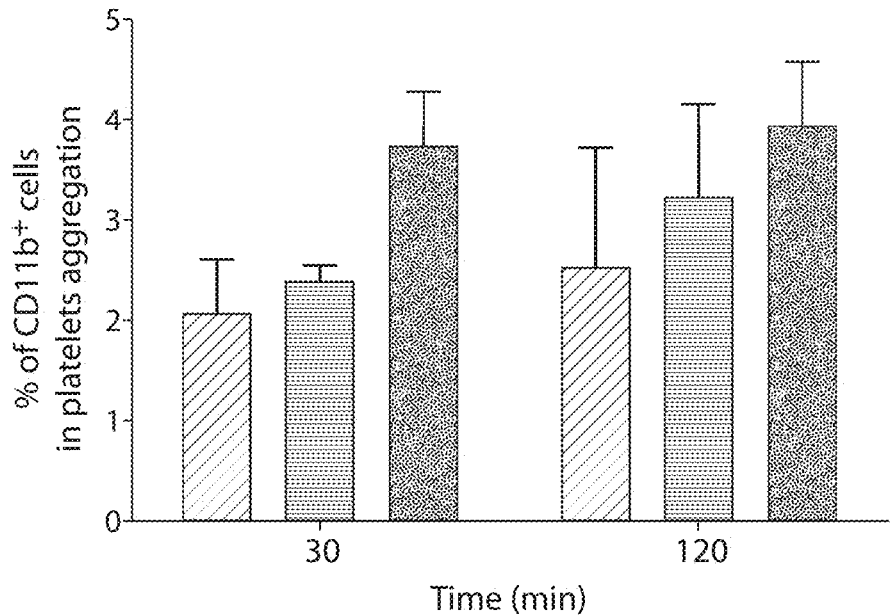
FIGS. 42A-42C: In vitro platelet aggregation with macrophages (FIGS. 42A and 42B) and B cells (FIG. 42C) after incubation of whole blood with medium, LPS, and DSPC LNP (from left to right) for 30 minutes and 120 minutes.
Figure 42B:
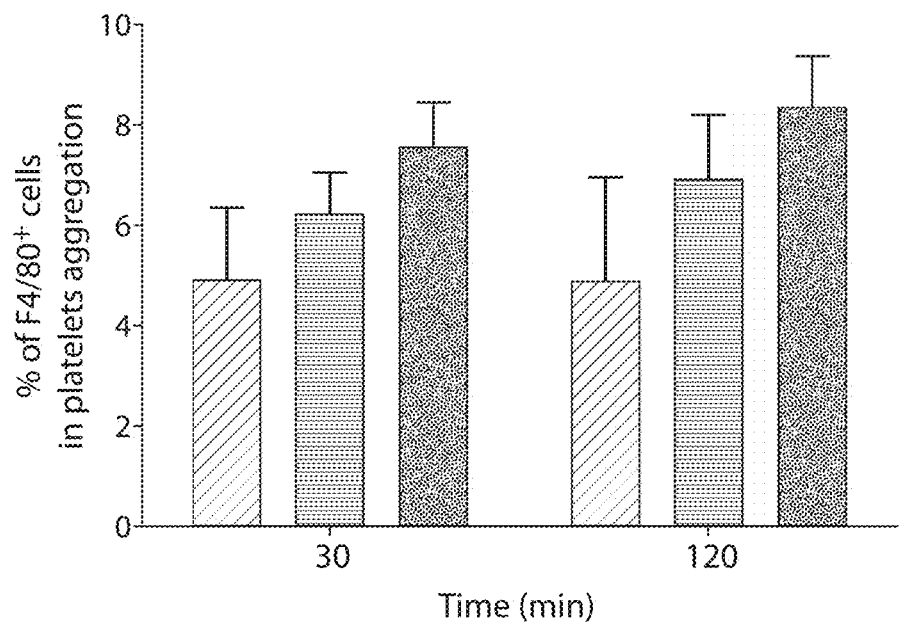
Figure 42C:
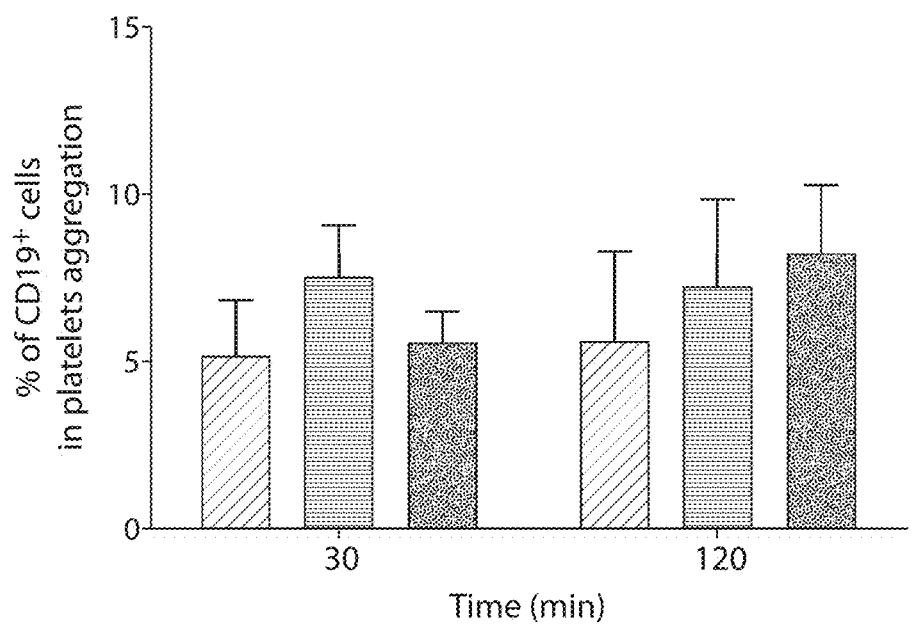

FIGS. 41A-41B show the degree of CD19+ B cells, CD11b+ macrophages and F4/80+ macrophages bound to platelets following incubation of whole blood with medium, LPS and DSPC LNP for 30 minutes (FIG. 41A) and 120 minutes (FIG. 41B). The data are also presented in FIGS. 42A and 42B (macrophages) and FIG. 42C (B cells).

Figure 43A:
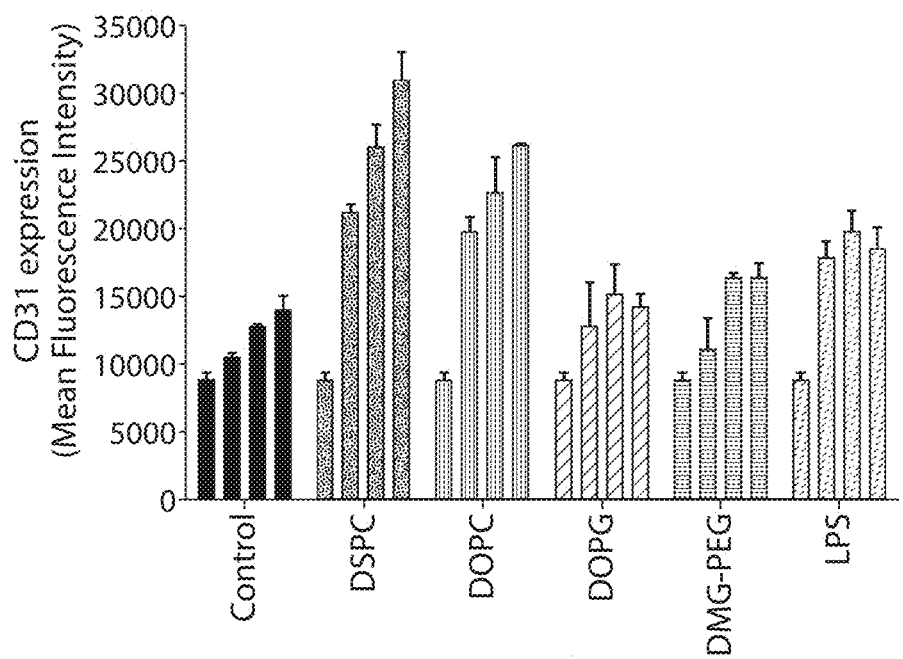
FIGS. 43A-43B: Upregulation of platelet activation markers CD31 (FIG. 43A) and CD62P (FIG. 43B) after incubation of platelets with medium (control), DSPC LNP, DOPC LNP, DOPG LNP, DMG-PEG LNP, and LPS (from left to right) in vitro, for 0, 10, 30 and 60 minutes, as measured by flow cytometry.
Figure 43B:
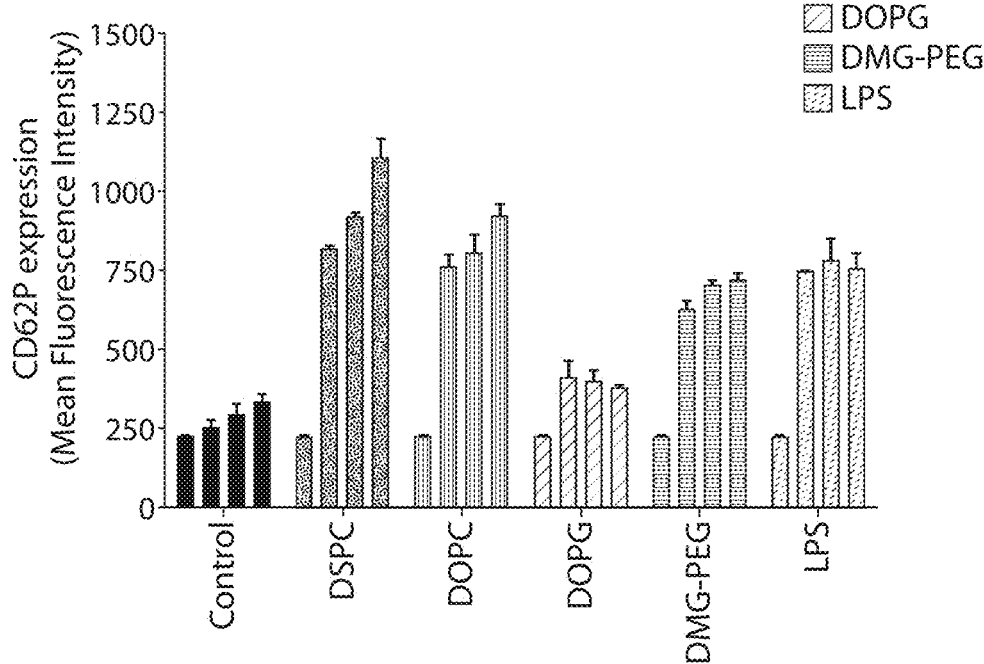
Figure 44A:
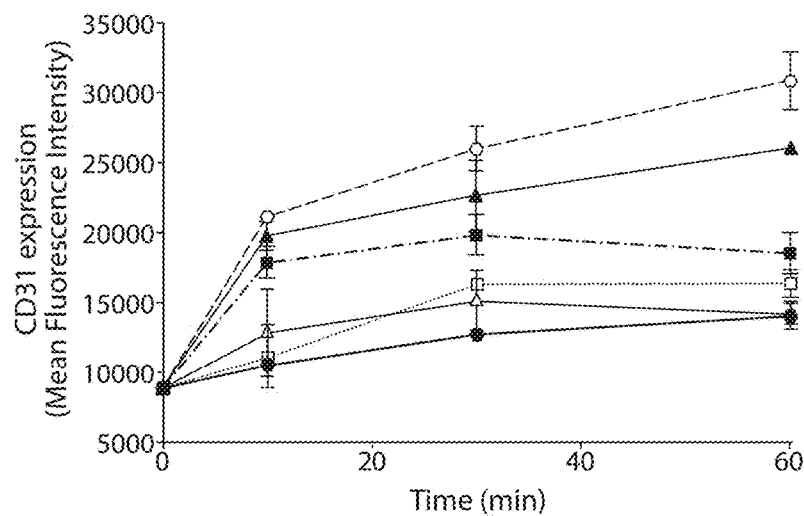
FIGS. 44A-44B: Upregulation of activation markers CD31 (FIG. 44A) and CD62P (FIG. 44B) after incubation of platelets in vitro with medium (control), DSPC LNP, DOPC LNP, DOPG LNP, DMG-PEG LNP and LPS, for 0, 10, 30 and 60 minutes, as measured by flow cytometry.
Figure 44B:
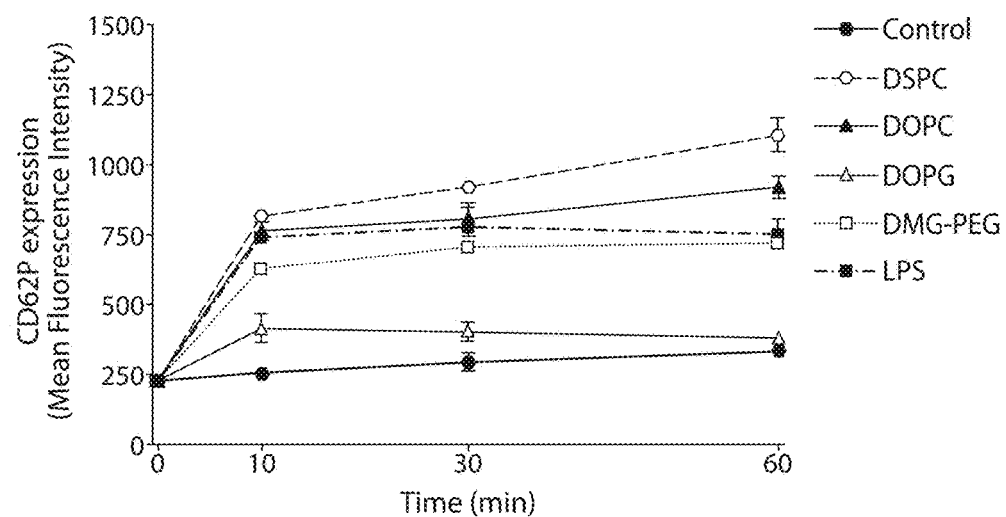
Figure 45:
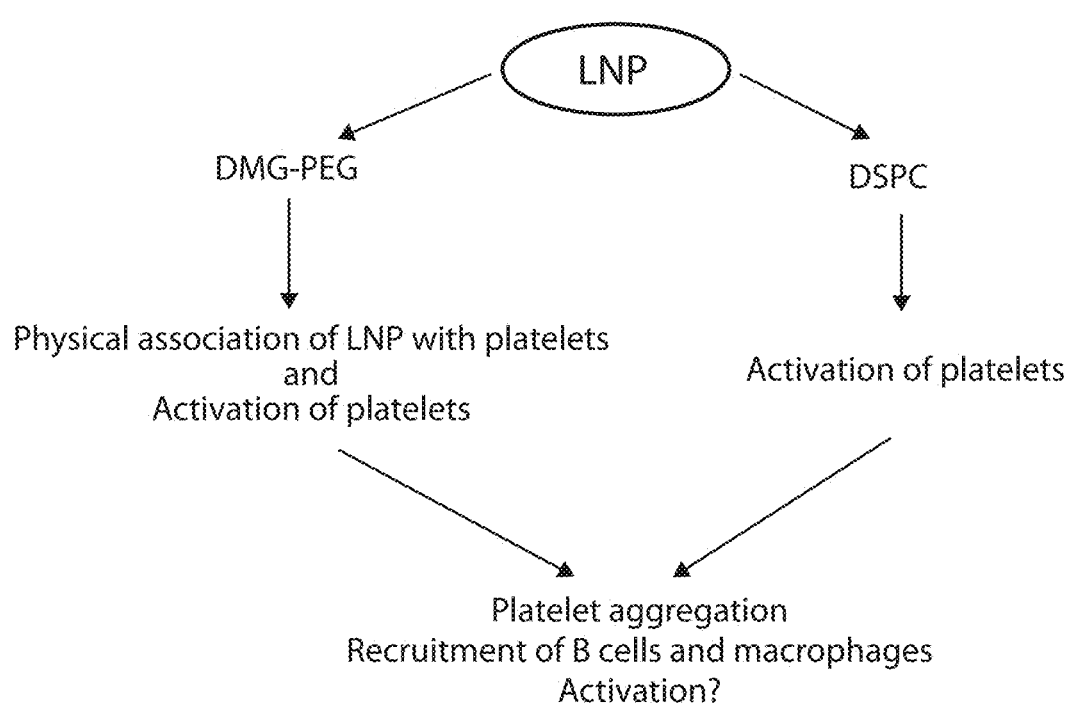
FIG. 45: Model of the effect of LNPs on platelets. DMG-PEG LNP physically associate with and activate platelets. DSPC LNP do not physically associate with platelets, but nevertheless are able to activate platelets. Both LNP types cause platelets to aggregate with concomitant recruitment of B cells and macrophages. PEG-OH and PEGless LNPs do not detectably associate with platelets, suggesting a role of the DMG-PEG in the LNP-platelet association. Even in the absence of DMG-PEG, however there is platelet activation, suggesting an interaction between platelets and the phospholipid component, and in particular the PC head group, in the LNP.

A further experiment was conducted to assess platelet activation, as indicated by CD31 and CD62P expression as measured by flow cytometry, as a function of LNP lipid content. FIGS. 43A-43B show activation based on CD31 (FIG. 43A) and CD62P (FIG. 43B) expression after LNP platelet incubation for 0, 10, 30 and 60 minutes (left to right) with medium (control), DSPC LNP, DOPC LNP, DOPG LNP, DMG-PEG LNP, and LPS (from left to right). The presence of DSPC and DOPC strongly activates platelets in vitro. DMG-PEG activates platelets, but the activation is lower than the activation with DSPC or DOPC. The absence of activation with DOPG, particularly as compared to the activation observed with DOPC, strongly suggests that the PC motif is responsible of the activation by DOPC and DSPC. The data are also presented in FIG. 44A-44B.

Example 17

Additional analyses were performed using the study design outlined in Table 8 to assess the pharmacokinetic and pharmocodynamic parameters of splenectomized non-human primates (NHPs).

TABLE 8

Study Design

| Group No. | Test Material | Dose Level (mg/kg/ week) | Dose Volume (mL/kg)$^a$ | Dose Concentration (mg/mL) | No. of Animals Splenectomized | Intact |
|---|---|---|---|---|---|---|
| 1 | rhEPO | 0.20 | 5 | 0.04 |  | 3 |
| 2 | mRNA-LNP |  |  |  | 3 |  |

$^a$Doses will be administered as a 60 minute infusion with an infusion rate of 5 mL/kg/hr.

Figure 46A:
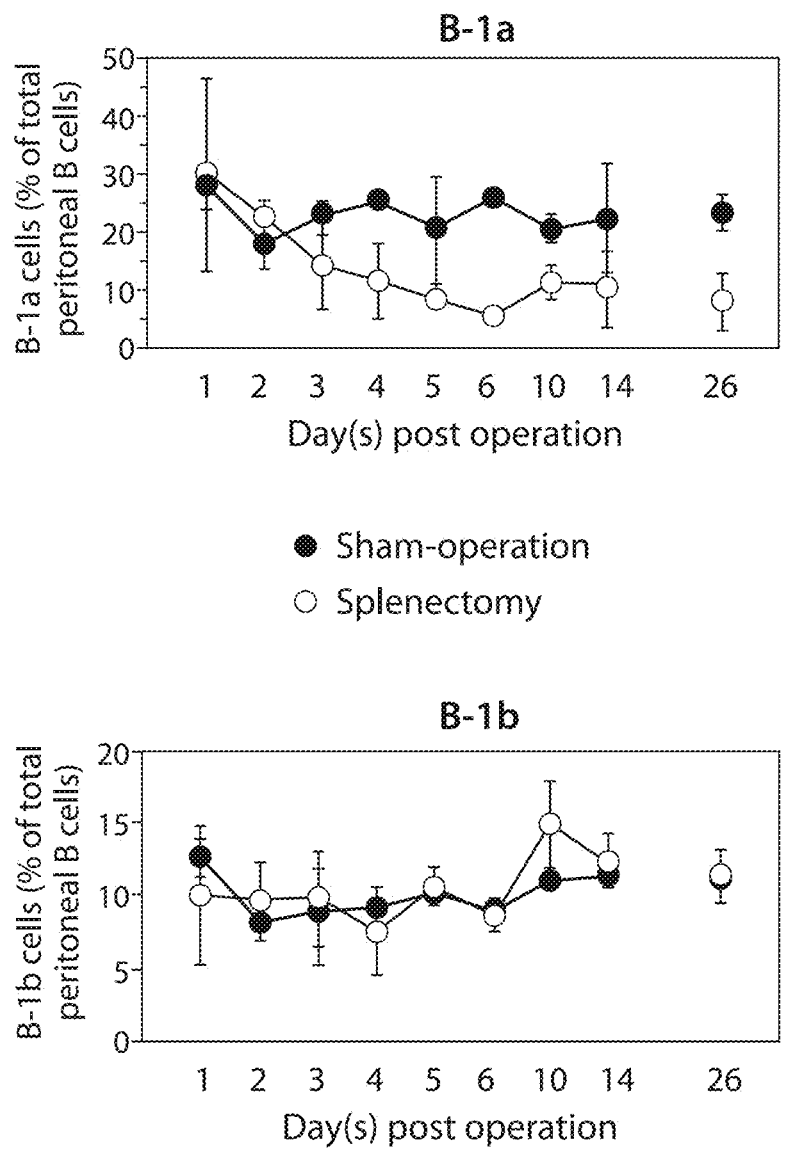
FIGS. 46A-46B: B1a and B1b cells require the spleen.
Figure 46B:
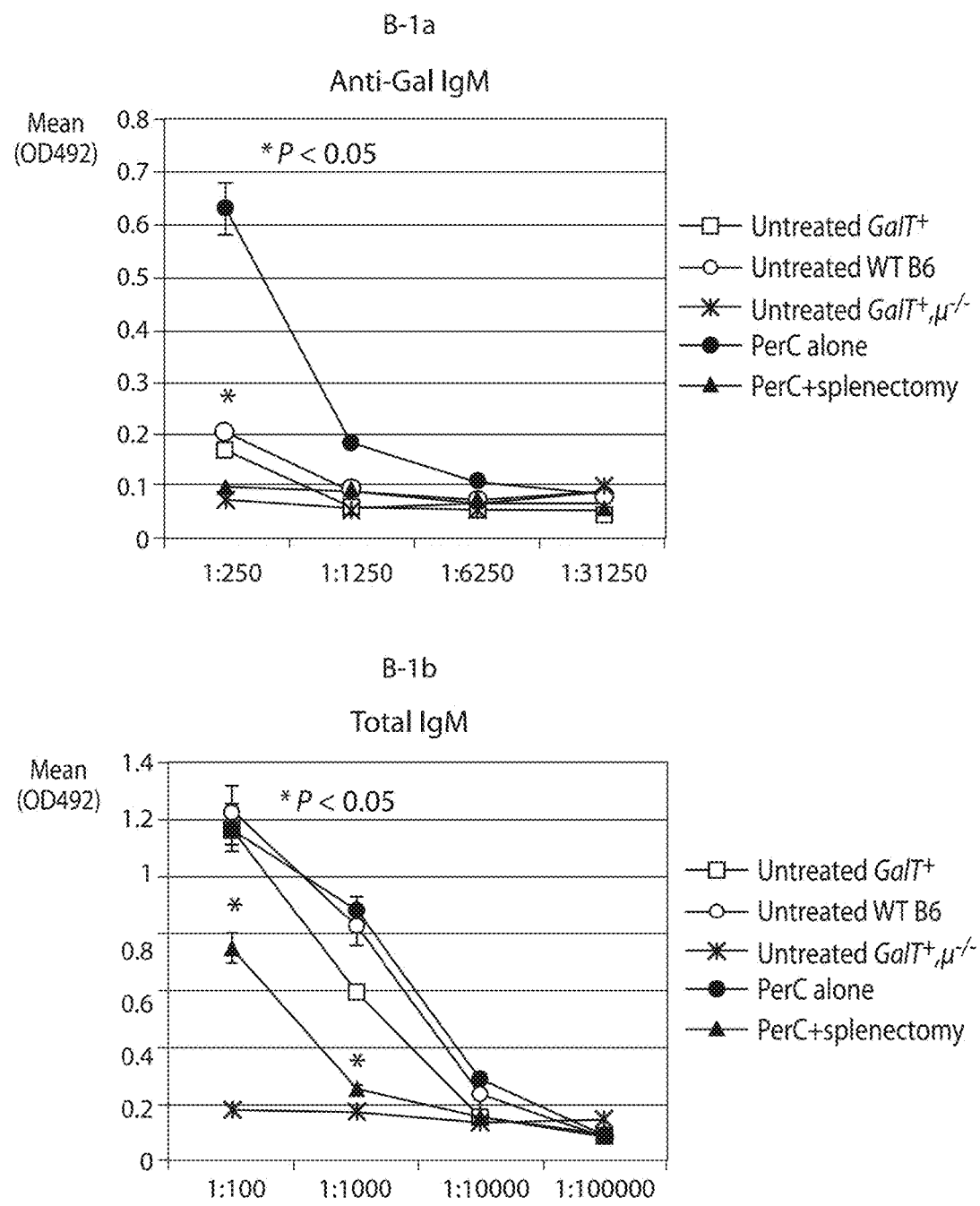

Generally, the spleen is the only location where platelets contact lymphocytes. Upon contact with lipid nanoparticles (LNPs), platelets are rapidly and strongly activated, as demonstrated by an upregaultion of both CD31 and CD62, two platelet activation markers (FIGS. 38, 39A-39D). A whole blood assay illustrated that thromocytes aggregate with macrophages in the presence of LNPs (FIGS. 40A-40B, 42A-42B). In the spleen, LNP uptake by B cells was shown to occur rapidly in a knetic manner under ex vivo culture conditions, while no specific uptake of LNPs by T cells was observed (FIGS. 2A-2B). Furthermore, B cells, particularly the B1 subset, were shown to be dose-dependently activated by empty LNPs (FIGS. 12A-12B). It has been shown that both B1a and B2b cells require the spleen, as B1a cells are lost and B1b cells lose the ability to secrete antibody following splenectomy (FIGS. 46A-46B).

Experiments were performed to compare the level of modified mRNA treatment and its production of erythropoietin in the presence of intact, functioning spleens (the control group) and splenectomized non-human primates (NHPs) (Table 8). Animals (n=3 per group) underwent 60 minute infusions of rhEPO mRNA-LNP at a rate of 5 mL/kg/hr (a dose concentration of 0.04 mg/mL), totaling 0.20 mg/kg/week. Blood samples were collected before and after the end of infusion (up to 48 hours) over 29 days. The PKPD mRNA levels and hEPO production were measured using bDNA and a protein ELISA.

Figure 48:
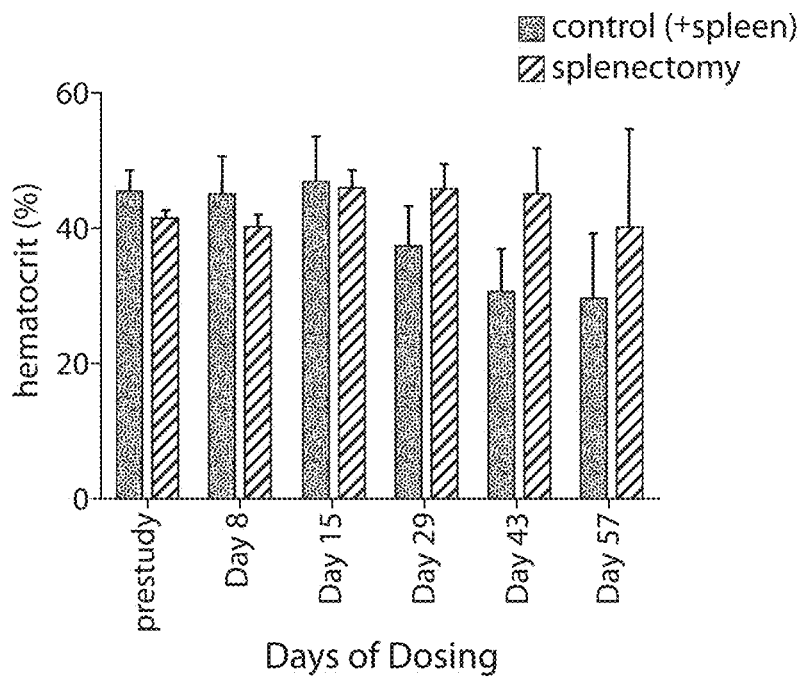
FIG. 48: Hematocrit is maintained in splenectomized NHPs.

First, the effect of splenectomies on reticulocyte counts was explored. Reticulocytes, immature red blood cells, undergo erythropoiesis to develop into mature red blood cells, a process controlled by the hormone erythropoietin (EPO). The spleen filters blood, removing infections and red blood cells from circulation, but it is not vital; splenectomized subjects show organ adaptation, resulting in an increased ability to fight infection and remove old red blood cells from circulation. After treatment with LNP-modRNA-hEPO as described above (days 1, 8, 15, and 29), the reticulocyte level increased with mRNA infusion, while the level decreased in the intact NHP (control) group after day 15. In the splenectomy group, the level gradually decreased after 15 days (FIG. 47). The hematocrit was found to be maintained in the splenectomized group as well under the same treatment conditions (FIG. 48).

Figure 49A:
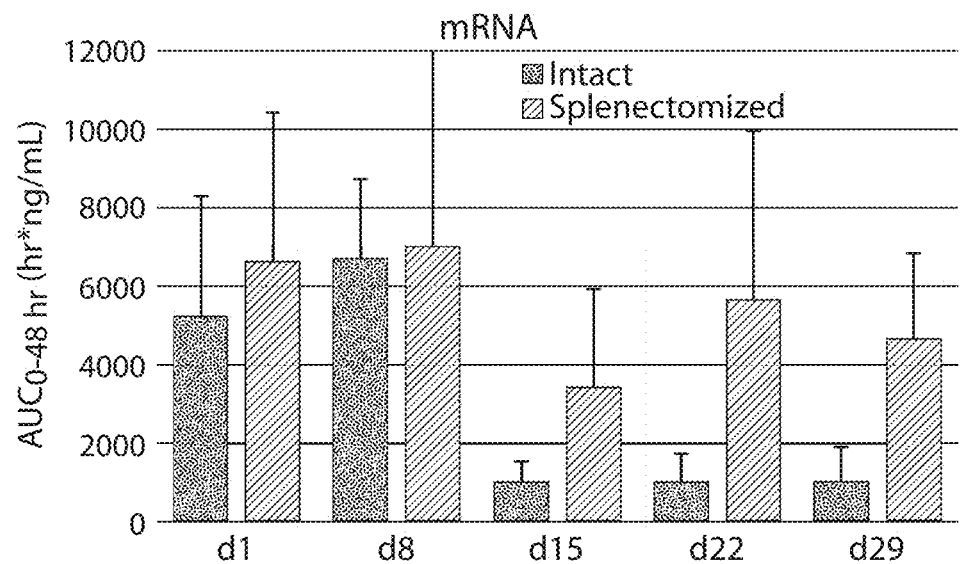
FIGS. 49A-49D: NHP splenectomy study results.
Figure 49B:
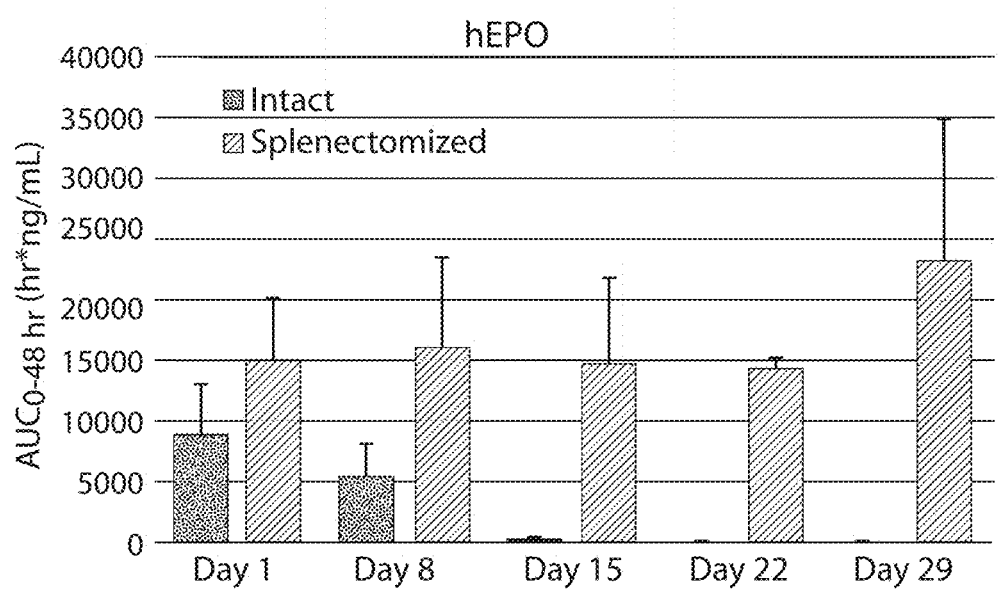
Figure 49C:
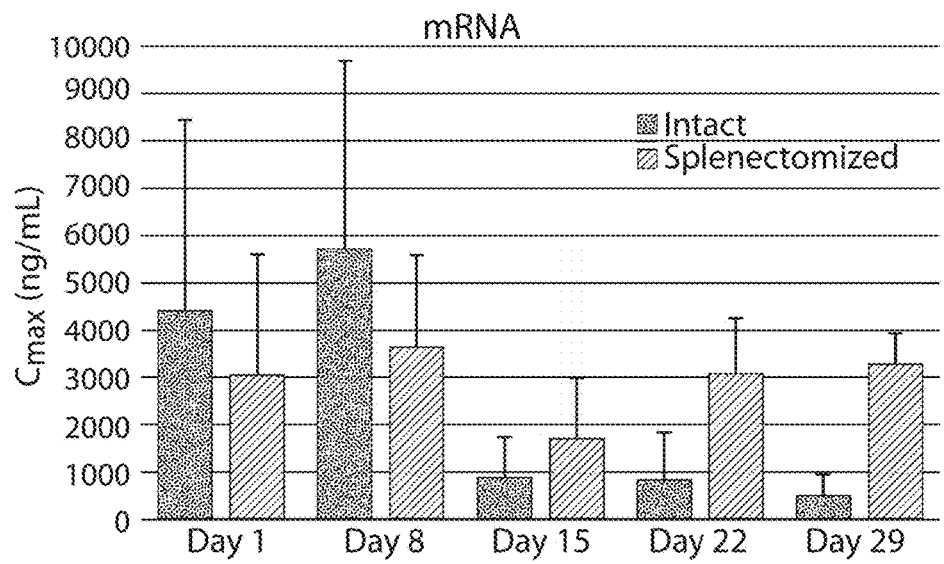
Figure 49D:
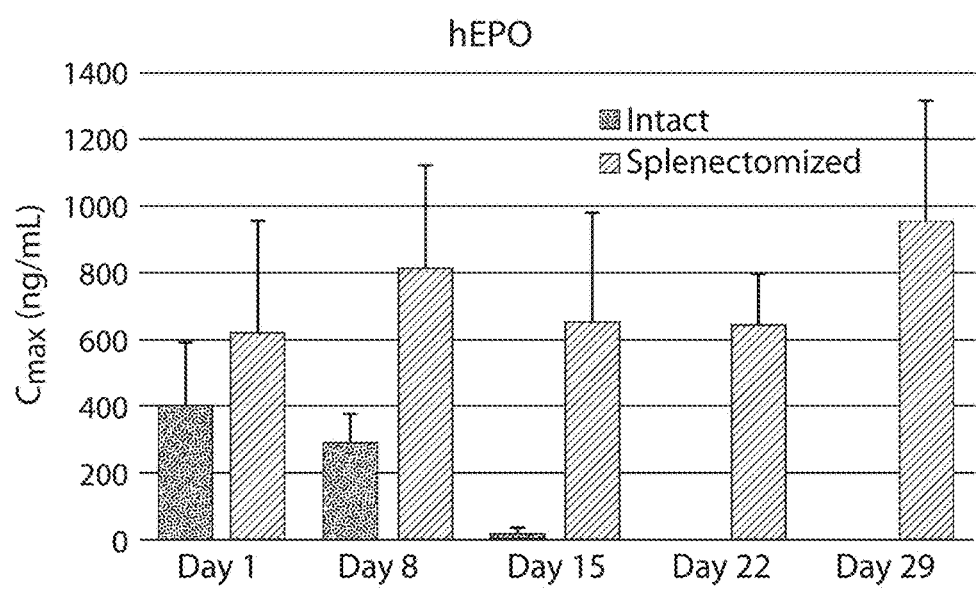

The mRNA and hEPO area under the curve (AUC) and $C_{max}$ values were determined over 29 days and 5 doses of mRNA-hEPO-LNP. AUC, a measure of the bioavailability of the measured substance over time, demonstrated that there was systemic exposure to the substance (FIGS. 49A-49B). $C_{max}$ represents the peak concentration of the substance or product of the substance after administration (FIGS. 49C-49D). In splenectomized NHPs, the levels of mRNA and hEPO are maintained systemically with repeat dosing (IV infusion) over the course of the study. In contrast to the intact (control) group, NHP mRNA and hEPO decline significantly starting on day 15 (FIGS. 49A-49D).

Figure 50A:
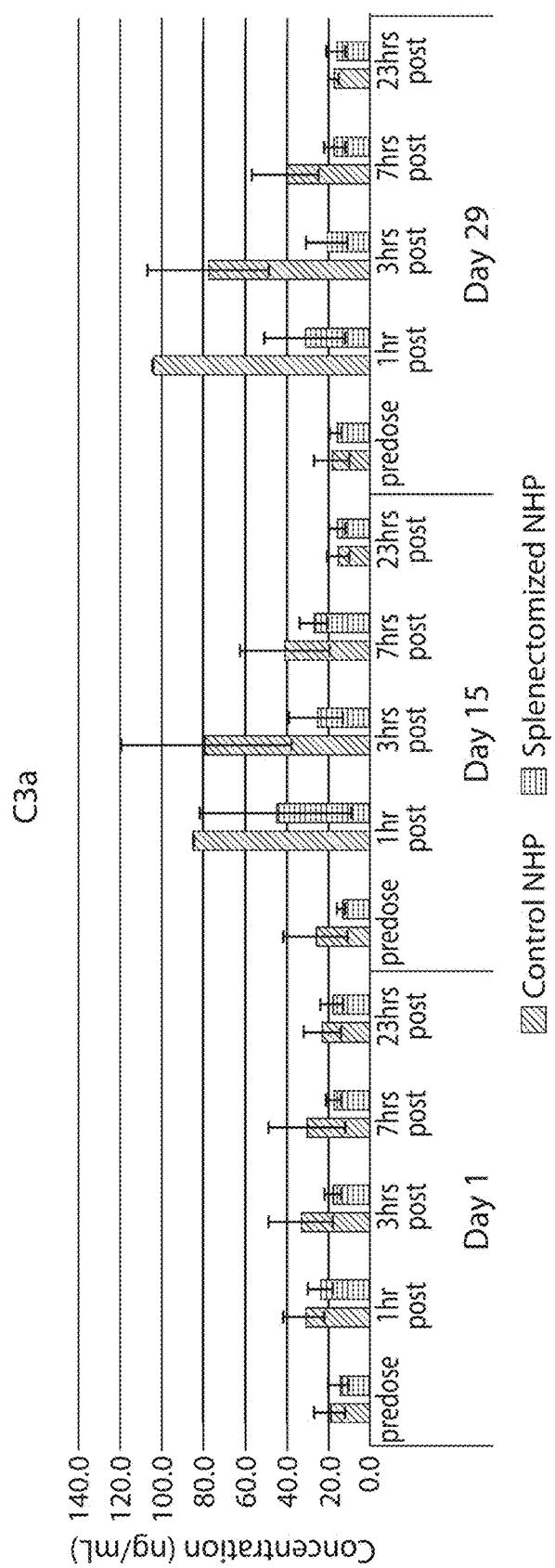
FIGS. 50A-50B: Suppression of complement activation in splenectomized NHPs as demonstrated by levels of complement activation indicators, C3a (FIG. 50A) and C5b9 (FIG. 50B).
Figure 50B:
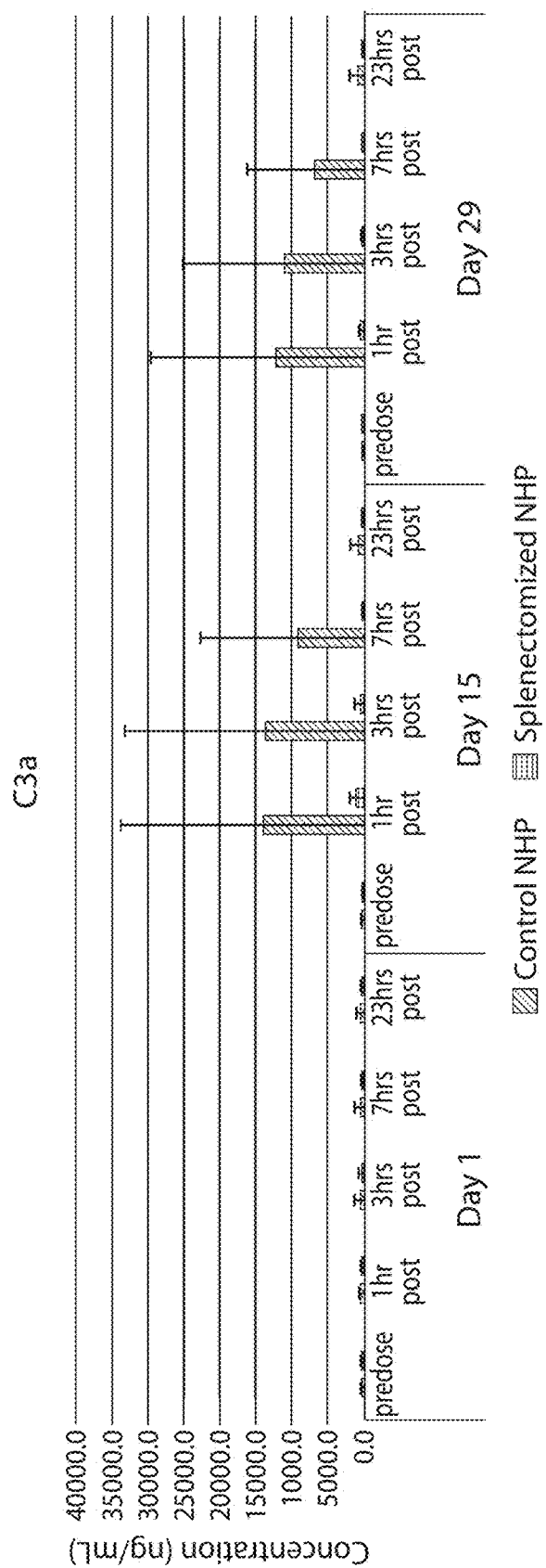
Figure 51B:
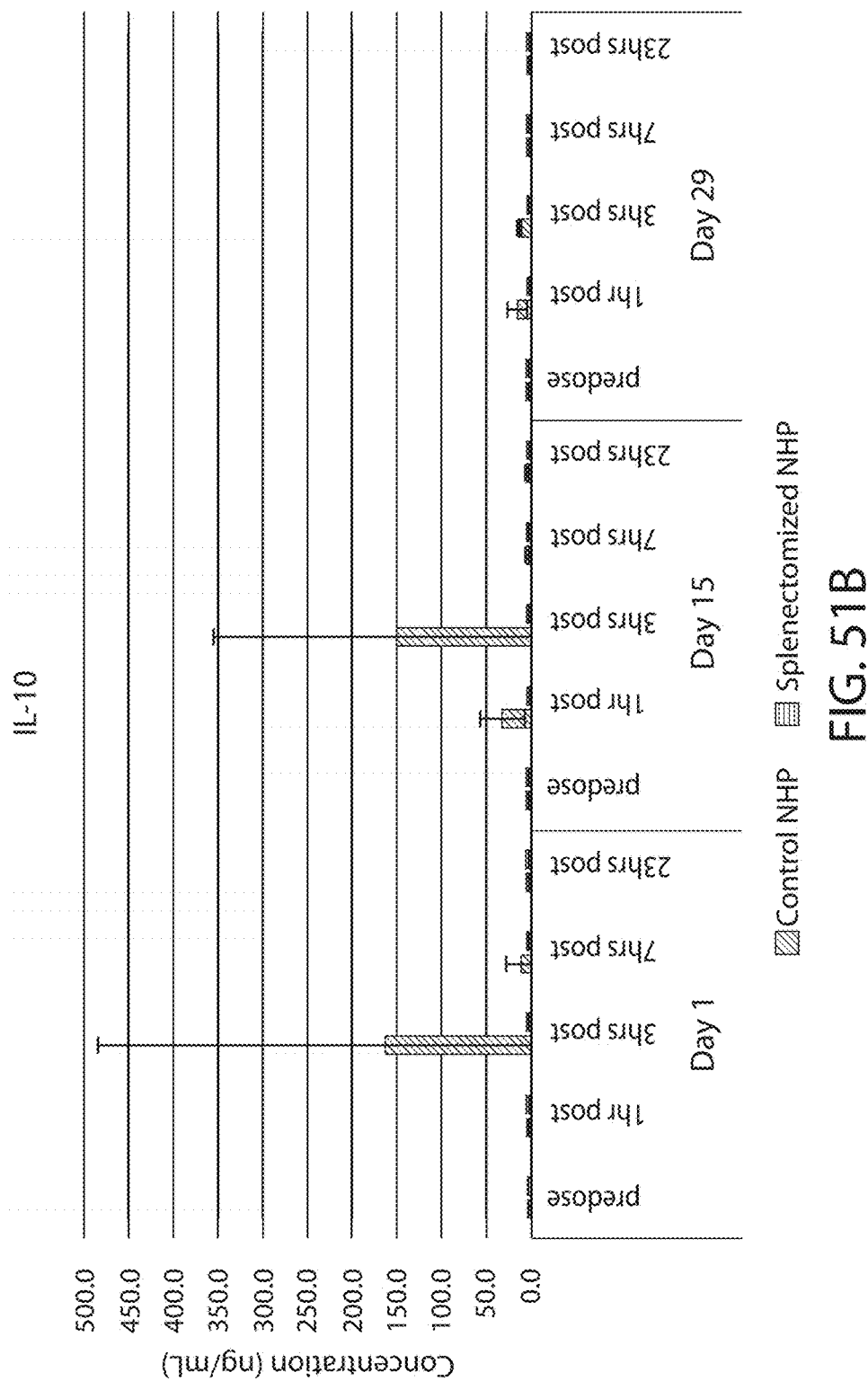
Figure 52A:
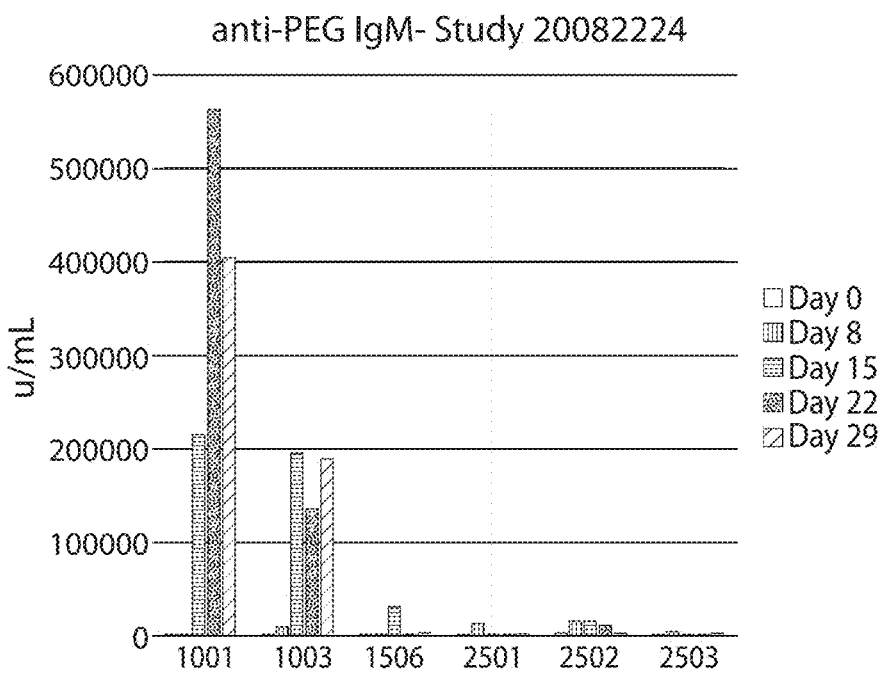
FIGS. 52A-52B: Anti-PEG IgM (FIG. 52A) and anti-PEG IgG (FIG. 52B) levels are greatly reduced in the absence of spleen.
Figure 52B:
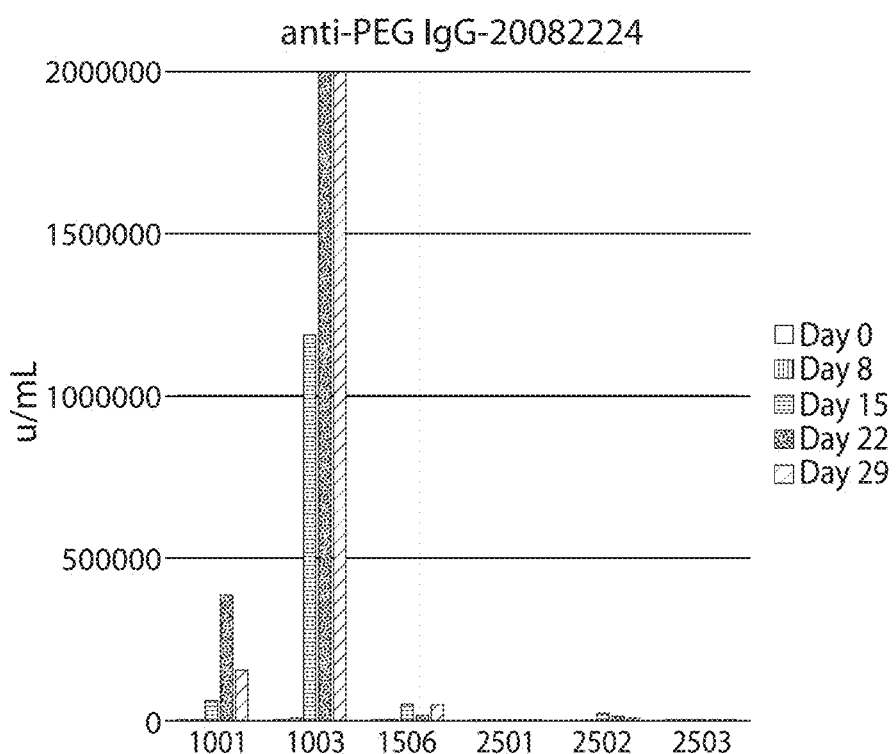

Complement activation was also measured and compared between the two groups. It was found that the splenectomized NHPs showed suppressed complement activation compared to the intact (control) NHPs, as measured by complement activation indicators, C3a (FIG. 50A) and C5b9 (FIG. 50B). Furthermore, cytokine expression was found to be nearly absent in splenectomzied NHPs (IL-6, FIG. 51A and IL-10, FIG. 51B). Anti-PEG IgM (FIG. 52A) and anti-PEG IgG (FIG. 52B) were also found to be greatly reduced in the absence of the spleen.

In summary, LNPs have multiple cellular interactions in vivo that drive the ABC effect, which likely includes a quorum-sensing event that includes platelets, monocytes, grulocytes, and B cells. A key node appears to be the spleen, which highly supports the hypothesis that ABC is driven by B1 cell function. B1 cells are responsible for natural IgMs, and can recognize PEG, phospholipids, and possibly cholesteral crystals, among others. B1b cells can also produce IgG when stimulated. As demonstrated above, removal of the spleen prevents activation of the B cells (including B1 cells) that likely contribute heavily to ABC. The splenectomized animals showed low to no IgM/IgG to PEG, no clearance of RNA or protein, and low to no cytokine/complement activation, showing that B1 cells drive accelerated blood clearance.

Example 18

Figure 54:
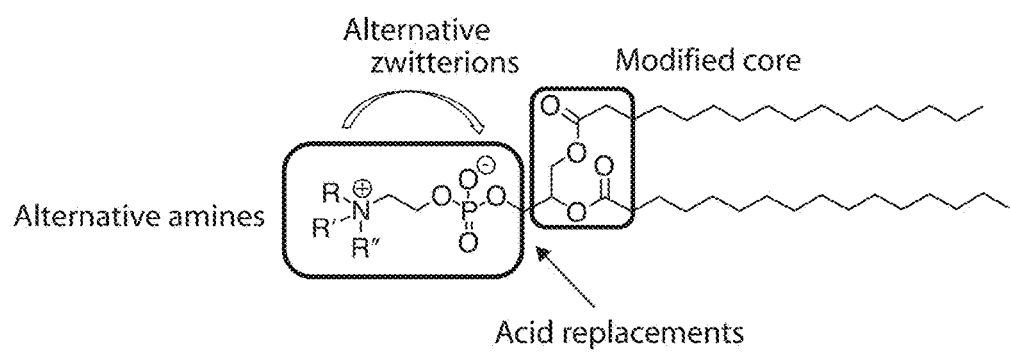
FIG. 54 is a schematic depicting the replacement of a phospholipid with a different zwitterionic group.

Example 18 shows LNP formulations designed to reduce CD36 binding and production of anti-PEG IgM. Numerous novel LNP formulations loaded with hEPO were prepared and tested to determine the effect of lipid changes on expression levels, B cell activation (e.g. through CD36) and anti-PEG IgM production. Commercially available natural phospholipid and fatty acids were incorporated into LNPs and screened in parallel with design and synthesis of unnatural DSPC analogs. FIG. 54 is a schematic depicting the replacement of a phospholipid with a different zwitterionic group.

CD-1 mice were dosed weekly with Cmpd405, Cmpd396, Cmpd406, Cmpd394, Cmpd407, Cmpd403, Cmpd434, Cmpd406, Cmpd405, and Cmpd407 LNPs. A repeat dose was administered at 3 weeks.

Figure 53A:
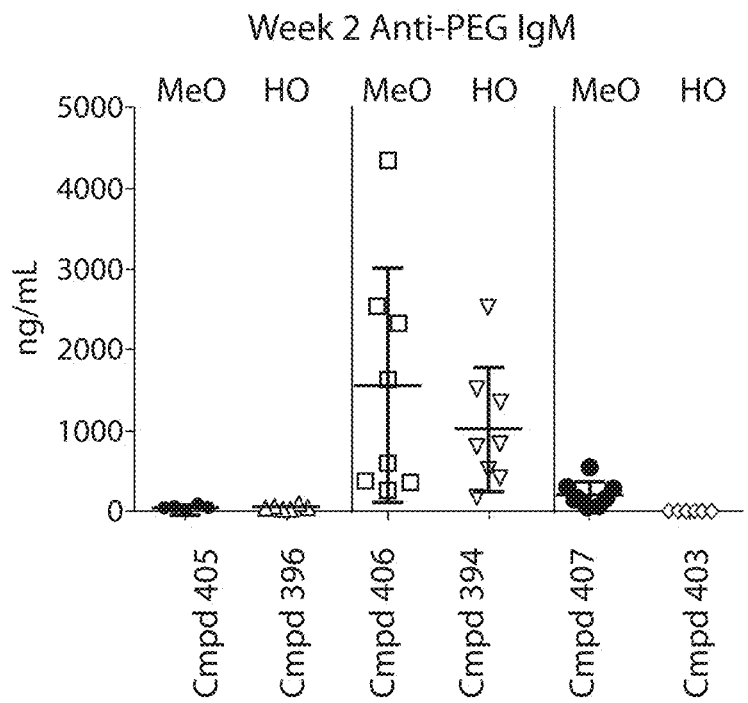
FIGS. 53A-53B are a set of graphs depicting anti-PEG IgM production following administration of LNP formulations.
Figure 53B:
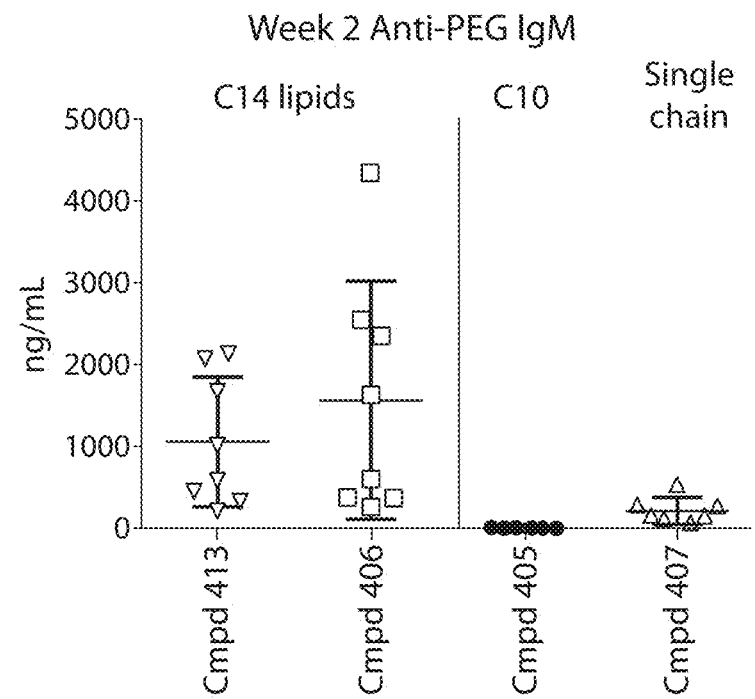

In the study hEPO expression was measured at 6 hours (pg/ml) and anti-PEG IgM was measured at week 2. The data is shown in FIGS. 53A-53B. FIGS. 53A-53B are a set of graphs depicting anti-PEG IgM production following administration of LNP formulations. The PEG-lipid effects the amount of Anti-PEG IgM generated in vivo upon repeat dose. Four PEG-lipids demonstrated low anti-PEG IgM levels with moderate levels of hEPO expression. Cmpd396, Cmpd416, Cmpd403, and Cmpd405. Cmpd413 produced relatively high PEG IgM. In general hydroxy-terminated and faster diffusing PEG Lipids afford reduced levels of anti-PEG IgM.

Several LNP formulations were designed to determine what type of DSPC modifications would reduce recognition of the LNP by CD36 on immune cells. It is believed according to aspects of the invention that activation of immune system by DSPC is caused by interaction with CD36 on platelets and B-cells and/or glycerol core. The head group and planarity of lipids tail on DSPC may play a role on the ability of the molecule to interact with CD36 ligands. Accordingly several modified DSPCs were generated, incorporated into lipids and tested for effects on B cells and platelets.

Figure 55A:
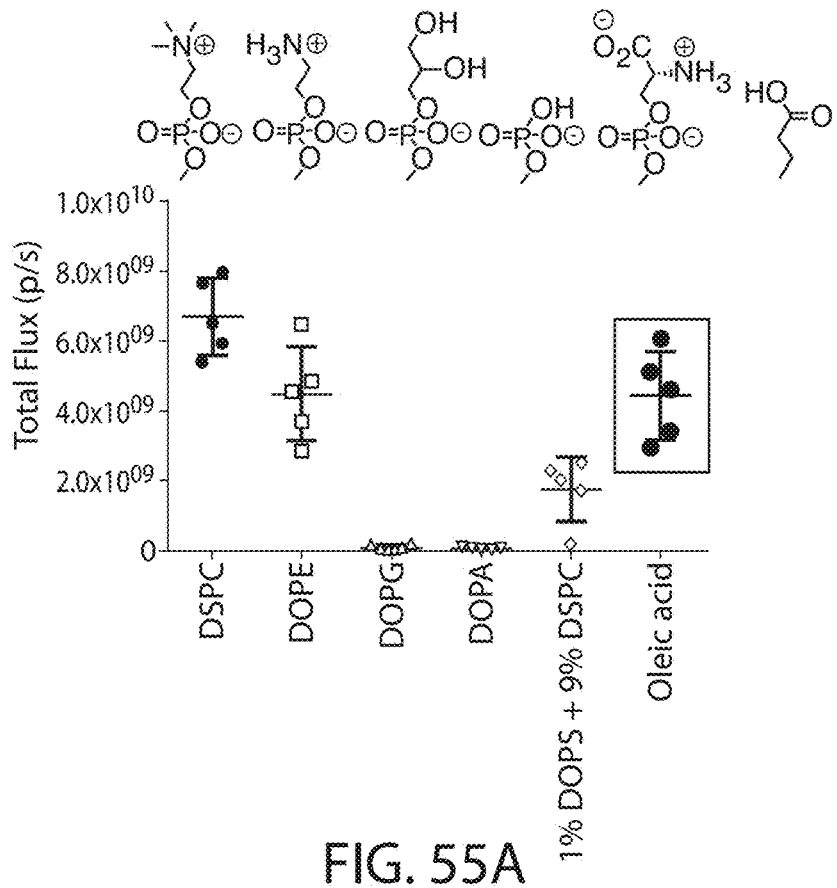
FIGS. 55A-55B are a set of graphs depicting Luc mRNA expression (FIG. 55A) and B cell activation (FIG. 55B) following administration of LNP formulations in CD-1 mice. CD-1 mice were administered 0.05 mg/kg Luc mRNA and Luc expression was measured six hours later.
Figure 55B:
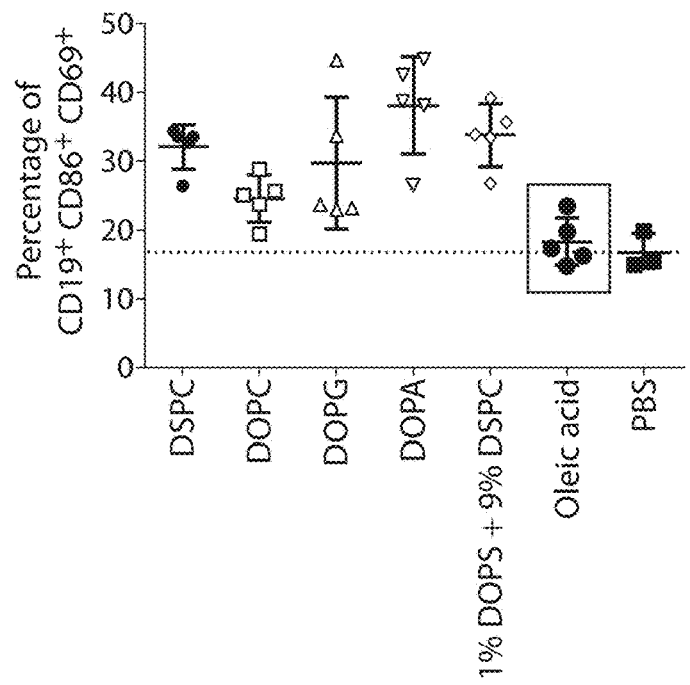

The effect of natural PC analogs on activation of cells and expression levels was tested. FIGS. 55A-55B depict Luc mRNA expression (FIG. 55A) and B cell activation (FIG. 55B) following administration of LNP formulations in the CD-1 mice. The natural PC analogs do result in activation of B-cells and some appear to interfere with expression (DOPG and DOPA) in the assay performed. However, oleic acid demonstrates significantly reduced B cell activation, while maintaining sufficient levels of Luc expression.

Several oleic acid derivatives were synthesized and tested for effects on expression levels, B cell activation and platelet aggregation. The data is shown in FIGS. 56A-56E and 57A-57C. The structures are shown in FIG. 56A. FIG. 56B is a graph depicting CD86 expression (B cell activation) and FIG. 56C is a graph depicting expression levels of Luc as measured by total flux. FIG. 57A is a graph depicting activated B-cell frequencies 24 hours post dose. FIG. 57B is a graph depicting aggregation of platelets 15 minutes post dose. FIG. 57C is a graph depicting recruitment of cells in platelet aggregate. Oleic acid derivatives show good expression and lower in vitro B-cell activation relative to DSPC, as shown in FIG. 56B (graph depicting CD86 expression) and FIG. 56C (graph depicting total flux).

The immune activation profiles for Cmpd18 LNPs containing oleic acid derivatives was examined. The oleic acid derivatives demonstrated improved immune activation profiles. The data is shown in FIGS. 58A-58B, 59, and 60A-60C. The positive effects of oleic acid were maintained with Cmpd18. FIG. 58A depicts levels of luciferase expression as measured by total flux 6 hours after delivery to CD-1 mice. FIG. 58B depicts in vivo B-cell activation in mouse solenocytes 24 hours following the administration. FIG. 59 is a graph depicting hEPO concentration over time. An improved margin of expression with a particle of the invention in contrast to MC3 was demonstrated with chemically modified mRNA. FIGS. 60A-60C are a set of graphs depicting improved immune activation profile with chemically modified mRNA in LNP formulations of the invention. FIG. 60A is a graph depicting in vivo B-cell activation 24 hours following administration of the hEPO loaded particles or PBS. FIG. 60B is a graph depicting in IL-6 concentration 6 hours following administration of the hEPO loaded particles or PBS. FIG. 60C is a graph depicting IP-10 concentration 6 hours following administration of the hEPO loaded particles or PBS.

The data demonstrate that several DSPC alternatives including oleic acid and oleic acid analogs can be formulated in LNPs and result in reduced B-cell activation in vivo. Additionally, PEG-lipid (PEG-DMG) alternatives having reduced anti-PEG IgM induction properties through faster diffusion and reduced surface hydrophobicity were identified.

Example 19

B cell association and activation using novel LNP formulations comprising oleic acid and PC derivatives are shown in Example 19. A study to determine the effect of the incorporation of oleic acid and PC derivatives in LNP on B cells as set up using the materials shown in Table 9. The characteristics of the resultant particles are also shown in Table 9.

TABLE 9

| | Composition | mol % | mRNA | Diameter (nm) | PDI | % EE | mRNA [ug/mL] |
|---|---|---|---|---|---|---|---|
| DSPC | MC3:DSPC:Chol:PEG-DMG | 50:10:38.5:1.5 | Luc | 80.8 | 0.1 | 99 | 63 |
| Cmpd160 | MC3:Cmpd 160:Chol:PEG-DMG | 50:10:38.5:1.5 | Luc | 76 | 0.1 | 98 | 65 |
| Cmpd161 | MC3:Cmpd 161:Chol:PEG-DMG | 50:10:38.5:1.5 | Luc | 74 | 0.098 | 99 | 66 |
| Cmpd162 | MC3:Cmpd 162:Chol:PEG-DMG | 50:10:38.5:1.5 | Luc | 76.3 | 0.085 | 99 | 65 |
| Cmpd163 | MC3:Cmpd 163Chol:PEG-DMG | 50:10:38.5:1.5 | Luc | 77.5 | 0.11 | 99 | 66 |
| Cmpd164 | MC3:Cmpd 164:Chol:PEG-DMG | 50:10:38.5:1.5 | Luc | 70.1 | 0.069 | 98 | 59 |
| Cmpd165 | MC3:Cmpd 165:Chol:PEG-DMG | 50:10:38.5:1.5 | Luc | 74.3 | 0.12 | 96 | 60 |
| Cmpd166 | MC3:Cmpd 166:Chol:PEG-DMG | 50:10:38.5:1.5 | Luc | 70.3 | 0.073 | 99 | 66 |
| Oleic Acid | MC3:Oleic Acid Acid:Chol:PEG-DMG | 50:10:38.5:1.5 | Luc | 80.6 | 0.093 | 97 | 67 |
| Cmpd148 | MC3:Cmpd 148:Chol:PEG-DMG | 50:10:38.5:1.5 | Luc | 79.7 | 0.092 | 95 | 66 |
| Cmpd157 | MC3:Cmpd 157:Chol:PEG-DMG | 50:10:38.5:1.5 | Luc | 75.8 | 0.094 | 97 | 63 |
| Cmpd158 | MC3:Cmpd 158:Chol:PEG-DMG | 50:10:38.5:1.5 | Luc | 76.4 | 0.13 | 97 | 65 |
| Cmpd159 | MC3:Cmpd 159:Chol:PEG-DMG | 50:10:38.5:1.5 | Luc | 97.5 | 0.11 | 97 | 69 |
| Cmpd393 | MC3:Cmpd 393:Chol:PEG-DMG | 50:10:38.5:1.5 | Luc | 134 | 0.12 | 80 | 60 |
| Fluor DSPC | MC3:DSPC:Rhodamine-DOPE:Chol:PEG-DMG | 50:9.9:0.1:38.5:1.5 | Luc | 78.1 | 0.075 | 99 | 68 |
| Fluor Cmpd160 | MC3:Cmpd160:Rhodamine-DOPE:Chol:PEG-DMG | 50:9.9:0.1:38.5:1.5 | Luc | 73.4 | 0.099 | 99 | 68 |
| Fluor Cmpd161 | MC3:Cmpd161:Rhodamine-DOPE:Chol:PEG-DMG | 50:9.9:0.1:38.5:1.5 | Luc | 69.6 | 0.11 | 99 | 64 |
| Fluor Cmpd162 | MC3:Cmpd162:Rhodamine-DOPE:Chol:PEG-DMG | 50:9.9:0.1:38.5:1.5 | Luc | 72 | 0.1 | 99 | 64 |
| Fluor Cmpd163 | MC3:Cmpd163:Rhodamine-DOPE:Chol:PEG-DMG | 50:9.9:0.1:38.5:1.5 | Luc | 72.6 | 0.046 | 99 | 64 |
| Fluor Cmpd164 | MC3:Cmpd164:Rhodamine-DOPE:Chol:PEG-DMG | 50:9.9:0.1:38.5:1.5 | Luc | 67.3 | 0.11 | 99 | 63 |
| Fluor Cmpd165 | MC3:Cmpd165:Rhodamine-DOPE:Chol:PEG-DMG | 50:9.9:0.1:38.5:1.5 | Luc | 74.8 | 0.16 | 97 | 66 |
| Fluor Cmpd166 | MC3:Cmpd166:Rhodamine-DOPE:Chol:PEG-DMG | 50:9.9:0.1:38.5:1.5 | Luc | 69.5 | 0.083 | 99 | 68 |
| Fluor Oleic Acid | MC3:Acid:Rhodamine-DOPE:Chol:PEG-DMG | 50:9.9:0.1:38.5:1.5 | Luc | 83.7 | 0.12 | 97 | 78 |
| Fluor Cmpd148 | MC3:Cmpd148:Rhodamine-DOPE:Chol:PEG-DMG | 50:9.9:0.1:38.5:1.5 | Luc | 81.2 | 0.11 | 97 | 73 |
| Fluor Cmpd157 | MC3:Cmpd157:Rhodamine-DOPE:Chol:PEG-DMG | 50:9.9:0.1:38.5:1.5 | Luc | 78.8 | 0.11 | 98 | 67 |
| Fluor Cmpd158 | MC3:Cmpd158:Rhodamine-DOPE:Chol:PEG-DMG | 50:9.9:0.1:38.5:1.5 | Luc | 83.8 | 0.078 | 98 | 60 |
| Fluor Cmpd159 | MC3:Cmpd159:Rhodamine-DOPE:Chol:PEG-DMG | 50:9.9:0.1:38.5:1.5 | Luc | 99 | 0.13 | 97 | 58 |
| Fluor Cmpd393 | MC3:Cmpd393:Rhodamine-DOPE:Chol:PEG-DMG | 50:9.9:0.1:38.5:1.5 | Luc | 122.4 | 0.09 | 83 | 67 |

The data is presented in FIGS. 61-62. FIG. 61 is a graph depicting LNP uptake by B cells as measured by percent PE+ CD19+ B cells. FIG. 62 is a graph depicting B cell activation by LNPs as measured by CD86 expression on B cells.

Example 20

In vivo assessment of hEPO containing LNP formulations composed of novel PEG lipids is shown in Example 20. An in vivo study to examine the effects of different PEG lipids on expression levels and anti-PEG IgM production was conducted. The study involved a comparison of different lipid tail lengths (diffusion) and terminal groups—e.g., —OH (versus oMe) with click linkers or an amide group. The tested structures and experimental design are shown in Table 10.

TABLE 10

| Group | Test/ Control Material | Vehicle | Cmpd #/lipid | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 1 | PBS | N/A | N/A | IV | once weekly | 4 | 8 | | 0.05 | 0.1 | 0.01 | 4.48 | 0.0448 |
| 2 | hEPO | MC3 | Pegless | IV | once weekly | 4 | 8 | | 0.05 | 0.1 | 0.01 | 4.48 | 0.0448 |
| 3 | hEPO | MC3 | 408 | IV | once weekly | 4 | 8 | | 0.05 | 0.1 | 0.01 | 4.48 | 0.0448 |
| 4 | hEPO | MC3 | 405 | IV | once weekly | 4 | 8 | | 0.05 | 0.1 | 0.01 | 4.48 | 0.0448 |
| 5 | hEPO | MC3 | 406 | IV | once weekly | 4 | 8 | | 0.05 | 0.1 | 0.01 | 4.48 | 0.0448 |

TABLE 10-continued

| Group | Test/ Control Material | Vehicle | Cmpd #/lipid | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 6 | hEPO | MC3 | 396 | IV | once weekly | 4 | 8 | | 0.05 | 0.1 | 0.01 | 4.48 | 0.0448 |
| 7 | hEPO | MC3 | 394 | IV | once weekly | 4 | 8 | | 0.05 | 0.1 | 0.01 | 4.48 | 0.0448 |
| 8 | hEPO | MC3 | 409 | IV | once weekly | 4 | 8 | | 0.05 | 0.1 | 0.01 | 4.48 | 0.0448 |
| 9 | hEPO | MC3 | 410 | IV | once weekly | 4 | 8 | | 0.05 | 0.1 | 0.01 | 4.48 | 0.0448 |
| 10 | hEPO | MC3 | 411 | IV | once weekly | 4 | 8 | | 0.05 | 0.1 | 0.01 | 4.48 | 0.0448 |
| 11 | hEPO | MC3 | 412 | IV | once weekly | 4 | 8 | | 0.05 | 0.1 | 0.01 | 4.48 | 0.0448 |
| 12 | hEPO | MC3 | 413 | IV | once weekly | 4 | 8 | | 0.05 | 0.1 | 0.01 | 4.48 | 0.0448 |
| 13 | hEPO | MC3 | 414 | IV | once weekly | 4 | 8 | | 0.05 | 0.1 | 0.01 | 4.48 | 0.0448 |

Expression levels of hEPO from the mRNA delivered in the LNP were measured at weeks 1, 2, 3, and 4 following the IV administration of the LNP. hEPO was expressed by each of the mRNA-LNP formulations. The levels of expression were diminished in the DSG PEG OMe LNP relative to the other formulations.

Anti-PEG IgM levels were also detected 96 hours following the second and third doses of LNP. FIGS. 63A-63B are a set of graphs depicting the amount of PEG IgM produced 96 hours after a second dose of LNP (FIG. 63A) or 96 hours after a third dose of LNP (FIG. 63B). The compounds tested correspond to the lanes in the following order from left to right in both FIGS. 63A and 63B: PBS, Pegless, Cmpd408, Cmpd405, Cmpd406, Cmpd409, Cmpd410, Cmpd411, Cmpd412, Cmpd413, and Cmpd414. DSG and DMG serve as relative known controls. The DMG control is increased by the third3rd dose. Many of the novel formulations produced less IgM than the DMG control. The Cmpd405, Cmpd396, Cmpd403 (single C18 tail), Cmpd416 (di-lipid tail), all showed low anti-PEG IgM induction. Cmpd405 and Cmpd396 after both doses exhibited only minimal PEG IgM. The Cmpd396 appeared to be the best candidate tested at producing minimal PEG IgM.

While hEPO expression was generally maintained for all groups, OH terminal PEGs exhibited reduced anti-PEG IgM levels. C10 PEG lipids also demonstrated reduced anti-PEG IgM production.

Example 21

Titration data was generated to determine the effect of titration with oleic and DSPC on the immune components of ABC/toxicity. Levels of oleic and DSPC in MC3 LNPs were reduced (e.g. providing reduced levels of choline). The LNPs were loaded with hEPO and formulated as shown in Table 11. The LNPs were administered by IV once weekly for 4 weeks to mice.

TABLE 11

| Group | Test/ Control Material | Vehicle | Formulation | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 1 | PBS | N/A | N/A | IV | once weekly | 4 | 8 | | 0.05 | 0.1 | 0.01 | 4.48 | 0.0448 |
| 2 | hEPO | MC3 | 0% | IV | once weekly | 4 | 8 | | 0.05 | 0.1 | 0.01 | 4.48 | 0.0448 |
| 3 | hEPO | MC3 | 10% DSPC | IV | once weekly | 4 | 8 | | 0.05 | 0.1 | 0.01 | 4.48 | 0.0448 |
| 4 | hEPO | MC3 | 20% DSPC | IV | once weekly | 4 | 8 | | 0.05 | 0.1 | 0.01 | 4.48 | 0.0448 |
| 5 | hEPO | MC3 | 30% DSPC | IV | once weekly | 4 | 8 | | 0.05 | 0.1 | 0.01 | 4.48 | 0.0448 |
| 6 | hEPO | MC3 | 10% Oleic Acid | IV | once weekly | 4 | 8 | | 0.05 | 0.1 | 0.01 | 4.48 | 0.0448 |
| 7 | hEPO | MC3 | 20% Oleic Acid | IV | once weekly | 4 | 8 | | 0.05 | 0.1 | 0.01 | 4.48 | 0.0448 |
| 8 | hEPO | MC3 | 30% Oleic Acid | IV | once weekly | 4 | 8 | | 0.05 | 0.1 | 0.01 | 4.48 | 0.0448 |
| 9 | hEPO | MC3 | 30% Oleic acid & PEGOH | IV | once weekly | 4 | 8 | | 0.05 | 0.1 | 0.01 | 4.48 | 0.0448 |
| 10 | hEPO | MC3 | 30% DSPC & PEGOH | IV | once weekly | 4 | 8 | | 0.05 | 0.1 | 0.01 | 4.48 | 0.0448 |

TABLE 11-continued

| Group | Test/ Control Material | Vehicle | Formulation | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 11 | hEPO | MC3 | DSG PEGOMe | IV | once weekly | 4 | 8 | | 0.05 | 0.1 | 0.01 | 4.48 | 0.0448 |

The data is shown in FIGS. 64-65. FIG. 64 is a graph depicting hEPO Expression 6 hours following once weekly administration by IV of hEPO mRNA-LNP formulations at weeks 1, 2, 3, and 4. The results indicate a dose response rather than a binary switch. For oleic acid, 10-20% appears to be optimal. Increasing the amount of oleic acid may provide further benefits in the production of stable particles since it is only about half the size of DSPC. FIG. 65 is a graph depicting anti-PEG IgM production 96 hours following a third dose of hEPO mRNA-LNP formulations.

Example 22

LNPs comprised of phospholipids having different head groups were prepared and tested in a single dose study. The objective of the study was to evaluate expression for different phospholipid headgroups relative to the standard DSPC formulation. A single dose of MC3 LNPs having various phospholipids with different headgroups were administered by IV to CD-1 mice. At 3, 6, and 24 hours post injection 100 ul blood 15 minutes was collected.

The results are shown in FIG. 66. Each phospholipid is measured at three time points (3, 6, and 24 hrs) following injection. Phospholipid structures are shown in FIG. 69. All of the formulations expressed well (DOPA and DOPG had the lowest expression).

Several new LNPs were synthesized to test B1a/B cell activation. The formulations are shown in Table 12.

decreased level of B cell activation. Ex vivo human B cell activation was also assessed by measuring cytokine release. FIGS. 67A-67C are a set of graphs depicting cytokine release as a measure of ex vivo human B cell activation. Levels of IFN-gamma (FIG. 67A), LI-6 (FIG. 67B) and TNF-alpha (FIG. 67C) were measured. In FIG. 67A, significant differences in IFNg release were observed with non-DSPC LNPs. Substitution of DSPC by oleic acid leads to significant decrease in IFN-g release. In FIG. 67B, significant differences in IL-6 were observed with non-DSPC LNPs. Substitution of DSPC by oleic acid led to significant decrease in IL-6 secretion. Substitution of DSPC by oleic acid also led to significant decrease in TNF-a secretion (FIG. 67C). This decrease was more significant than the decreases observed with IFN-g and IL-6.

Splenic VB cell activation was also assessed. The results are shown in FIG. 68. FIG. 68 is a graph depicting the amount of B cell activation as a result of various LNP formulations. LNP formulations including oleic acid demonstrated reduced splenic B cell activation.

Example 23

LNPs comprised of novel PC and oleic acid derivatives were prepared and tested for impact on Luc expression, platelet aggregation and B cell activation. The LNPs were formulated as listed in Table 13 and administered IV as a single dose to CD-1 mice. The lipids were DSPC replacements having structures as shown in FIG. 56A. Some of the

TABLE 12

| | Composition | mol % | mRNA | Diameter (nm) | Pd Index | % EE | [mRNA] ug/mL |
|---|---|---|---|---|---|---|---|
| DSPC | MC3:DSPC:Chol:PEG-DMG | 50:10:38.5:1.5 | hEPO | 69.7 | 0.12 | 98 | 57 |
| Oleic acid | MC3:Oleic Acid:Chol:PEG-DMG | 50:10:38.5:1.5 | hEPO | 101.7 | 0.088 | 96 | 50 |
| 0.1% PS 9.9% Oleic Acid | MC3:DOPS:Oleic Acid:Chol:PEG-DMG | 50:0.1:9.9:38.5:1.5 | hEPO | 81 | 0.079 | 97 | 53 |
| 1% PS 9% Oleic Acid | MC3:DOPS:Oleic Acid:Chol:PEG-DMG | 50:1:9:38.5:1.5 | hEPO | 74.4 | 0.083 | 98 | 51 |
| DOPA | MC3:DOPA:Chol:PEG-DMG | 50:10:38.5:1.5 | hEPO | 103.9 | 0.15 | 98 | 43 |
| 0.1% PS 9.9% DSPC | MC3:DOPS:DSPC:Chol:PEG-DMG | 50:0.1:9.9:38.5:1.5 | hEPO | 77.6 | 0.11 | 98 | 48 |
| 1% PS 9% DSPC | MC3:DOPS:DSPC:Chol:PEG-DMG | 50:1:9:38.5:1.5 | hEPO | 73 | 0.12 | 99 | 46 |

All formulations resulted in an increase in activated B cell population (CD19+CD86+CD69+) compared to a negative control. However, substituting DSPC by oleic acid led to lipids have a modified PC-like head group. Others have modified tails to test for stabilization. Cmpd125 has a Zwitterionic head group.

TABLE 13

| Group | Test/Control Material | Vehicle | Formulation | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 1 | LUC C1 | DSPC | MC3:PC:Chol:PEG-DMG; 50:10:38:5:1.5 | IV | Once on Day 1 | 1 | | 5 | 0.05 | 0.1 | 0.01 | 0.7 | 0.007 |
| 2 | LUC C1 | DPPC | MC3:PC:Chol:PEG-DMG; 50:10:38:5:1.5 | IV | Once on Day 1 | 1 | | 5 | 0.05 | 0.1 | 0.01 | 0.7 | 0.007 |
| 3 | LUC C1 | Oleic Acid | MC3:PC:Chol:PEG-DMG; 50:10:38:5:1.5 | IV | Once on Day 1 | 1 | | 5 | 0.05 | 0.1 | 0.01 | 0.7 | 0.007 |
| 4 | LUC C1 | Cmpd125 | MC3:PC:Chol:PEG-DMG; 50:10:38:5:1.5 | IV | Once on Day 1 | 1 | | 5 | 0.05 | 0.1 | 0.01 | 0.7 | 0.007 |
| 5 | LUC C1 | Cmpd148 | MC3:PC:Chol:PEG-DMG; 50:10:38:5:1.5 | IV | Once on Day 1 | 1 | | 5 | 0.05 | 0.1 | 0.01 | 0.7 | 0.007 |
| 6 | LUC C1 | Cmpd149 | MC3:PC:Chol:PEG-DMG; 50:10:38:5:1.5 | IV | Once on Day 1 | 1 | | 5 | 0.05 | 0.1 | 0.01 | 0.7 | 0.007 |
| 7 | LUC C1 | Cmpd150 | MC3:PC:Chol:PEG-DMG; 50:10:38:5:1.5 | IV | Once on Day 1 | 1 | | 5 | 0.05 | 0.1 | 0.01 | 0.7 | 0.007 |
| 8 | LUC C1 | Cmpd151 | MC3:PC:Chol:PEG-DMG; 50:10:38:5:1.5 | IV | Once on Day 1 | 1 | | 5 | 0.05 | 0.1 | 0.01 | 0.7 | 0.007 |
| 9 | LUC C1 | Cmpd152 | MC3:PC:Chol:PEG-DMG; 50:10:38:5:1.5 | IV | Once on Day 1 | 1 | | 5 | 0.05 | 0.1 | 0.01 | 0.7 | 0.007 |
| 10 | LUC C1 | Cmpd153 | MC3:PC:Chol:PEG-DMG; 50:10:38:5:1.5 | IV | Once on Day 1 | 1 | | 5 | 0.05 | 0.1 | 0.01 | 0.7 | 0.007 |
| 11 | LUC C1 | Cmpd154 | MC3:PC:Chol:PEG-DMG; 50:10:38:5:1.5 | IV | Once on Day 1 | 1 | | 5 | 0.05 | 0.1 | 0.01 | 0.7 | 0.007 |
| 12 | LUC C1 | Cmpd155 | MC3:PC:Chol:PEG-DMG; 50:10:38:5:1.5 | IV | Once on Day 1 | 1 | | 5 | 0.05 | 0.1 | 0.01 | 0.7 | 0.007 |
| 13 | LUC C1 | Cmpd156 | MC3:PC:Chol:PEG-DMG; 50:10:38:5:1.5 | IV | Once on Day 1 | 1 | | 5 | 0.05 | 0.1 | 0.01 | 0.7 | 0.007 |

The RNAs are modified with N1-methylpseudouridine. The lipid structures are shown in FIG. 56A.

The results are shown in FIG. 70. FIG. 70 is a graph depicting Luc expression levels following administration of LUC mRNA encapsulated in various LNP formulations composed of novel PC and oleic acid derivatives at 3, 6 and 24 hours following administration. Expression levels varied. As the molecules became more sterically hindered, expression appeared to decrease. Expression levels for oleic acid and its derivatives remained high.

In vitro Cmpd-LNPs and B cell interaction and activation were also assessed. The data is shown in FIGS. 71A-71B and 72A-72B.

FIGS. 71A-71B are a set of graphs depicting B cell interaction/association with various LNP formulations as assessed by a percentage of CD19+PE+ cells. Several LNP formulations are depicted in FIG. 71A. Oleic acid and Cmpd125 are depicted in FIG. 71B. FIGS. 72A-72B are a set of graphs depicting B cell activation with various LNP formulations as assessed by CD86 expression median fluorescence intensity. Several LNP formulations are depicted in FIG. 72A. Oleic acid and Cmpd125 are depicted in FIG. 72B.

Example 24

LNPs comprised of novel PC and oleic acid derivatives were prepared and tested for expression, platelet activation, and B cell activation in a single dose study relative to the standard DSPC formulation. The LNPs were formulated as listed in Table 14 and administered IV as a single dose to CD-1 mice.

TABLE 14

| Group | Test/Control Material | Vehicle | Formulation | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 1 | LUC C1 | DSPC | MC3:PC:Chol:PEG-DMG; 50:10:38:5:1.5 | IV | Once on Day 1 | 1 | | 5 | 0.05 | 0.1 | 0.01 | 0.7 | 0.007 |
| 2 | LUC C1 | Cmpd160 | MC3:PC:Chol:PEG-DMG; 50:10:38:5:1.5 | IV | Once on Day 1 | 1 | | 5 | 0.05 | 0.1 | 0.01 | 0.7 | 0.007 |
| 3 | LUC C1 | Cmpd161 | MC3:PC:Chol:PEG-DMG; 50:10:38:5:1.5 | IV | Once on Day 1 | 1 | | 5 | 0.05 | 0.1 | 0.01 | 0.7 | 0.007 |
| 4 | LUC C1 | Cmpd162 | MC3:PC:Chol:PEG-DMG; 50:10:38:5:1.5 | IV | Once on Day 1 | 1 | | 5 | 0.05 | 0.1 | 0.01 | 0.7 | 0.007 |
| 5 | LUC C1 | Cmpd163 | MC3:PC:Chol:PEG-DMG; 50:10:38:5:1.5 | IV | Once on Day 1 | 1 | | 5 | 0.05 | 0.1 | 0.01 | 0.7 | 0.007 |
| 6 | LUC C1 | Cmpd164 | MC3:PC:Chol:PEG-DMG; 50:10:38:5:1.5 | IV | Once on Day 1 | 1 | | 5 | 0.05 | 0.1 | 0.01 | 0.7 | 0.007 |
| 7 | LUC C1 | Cmpd165 | MC3:PC:Chol:PEG-DMG; 50:10:38:5:1.5 | IV | Once on Day 1 | 1 | | 5 | 0.05 | 0.1 | 0.01 | 0.7 | 0.007 |
| 8 | LUC C1 | Cmpd166 | MC3:PC:Chol:PEG-DMG; 50:10:38:5:1.5 | IV | Once on Day 1 | 1 | | 5 | 0.05 | 0.1 | 0.01 | 0.7 | 0.007 |

TABLE 14-continued

| Group | Test/Control Material | Vehicle | Formulation | Route | Dosing Regimen | # of Doses | # of males | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|---|---|
| 9 | LUC C1 | Oleic Acid | MC3:PC:Chol:PEG-DMG; 50:10:38:5:1.5 | IV | Once on Day 1 | 1 | | 5 | 0.05 | 0.1 | 0.01 | 0.7 | 0.007 |
| 10 | LUC C1 | Cmpd148 | MC3:PC:Chol:PEG-DMG; 50:10:38:5:1.5 | IV | Once on Day 1 | 1 | | 5 | 0.05 | 0.1 | 0.01 | 0.7 | 0.007 |
| 11 | LUC C1 | Cmpd157 | MC3:PC:Chol:PEG-DMG; 50:10:38:5:1.5 | IV | Once on Day 1 | 1 | | 5 | 0.05 | 0.1 | 0.01 | 0.7 | 0.007 |
| 12 | LUC C1 | Cmpd158 | MC3:PC:Chol:PEG-DMG; 50:10:38:5:1.5 | IV | Once on Day 1 | 1 | | 5 | 0.05 | 0.1 | 0.01 | 0.7 | 0.007 |
| 13 | LUC C1 | Cmpd159 | MC3:PC:Chol:PEG-DMG; 50:10:38:5:1.5 | IV | Once on Day 1 | 1 | | 5 | 0.05 | 0.1 | 0.01 | 0.7 | 0.007 |

The RNAs are modified with N1-methylpseudouridine. The structures of the tested lipids are shown in FIG. 56D.

The data is shown in FIGS. 73A-73C. Luc expression with various LNP formulations was assessed by a measurement of total flux at 3 hours (FIG. 73A), 6 hours (FIG. 73B), and 24 hours (FIG. 73C) following a dose.

Example 25

Monkeys were administered hEPO mRNA (chemically modified) in MC3-LNP 1× weekly for 4 weeks. The co-medication regimen of oral Dexamethasone at equal mg/kg dose of human, COX-2 inhibitor (vet), ranitidine, and cetirizine was administered as described in literature. Methotrexate was administered weekly to assess targeted B cell inhibition. The experimental design is shown in Table 15.

TABLE 15

| Group No. | Test Material | Dose Level (mg/kg) | Co-medication | Dose rate (mL/kg/h) | Dose Concentration (mg/mL) | Number of Males |
|---|---|---|---|---|---|---|
| 1 | MC3[a] | 0 | N/A | 5 | 0 | 3 |
| 2 | hEPO mRNA in MC3 | 0.3 | N/A | 5 | 0.06 | 3 |
| 3 | hEPO mRNA in MC3 | 0.3 | Methotrexate | 5 | 0.06 | 3 |

[a]The concentration of MC3 for Group 1 is equivalent to the concentration of MC3 in Groups 2 to 3.
N/A = not applicable.

The data is shown in FIGS. 91A-91B. FIG. 91A is a graph depicting cytokine (IL-6) production in NHPs at day 1 and day 22 of co-medication regimens. FIG. 91B is a graph illustrating that co-medication with Gilenya reduces anti-Peg IgM production, consistent with reduced ABC. The results show that previously treated animals appear to have a high baseline positive IgM or IgG titer. However, some animals did not show an increase in IgM and/or IgG post LNP administration. NHPs exhibit a high frequency of Anti-PEG response, either IgM or IgG (~50%). Several co-medication regimens appear to ameliorate ABC in primates, including Gilenya and anti-platelet/Syk/Dex/PI3Kdelta. This results in reduced IL-6 production and reduced anti-PEG Ig responses as shown in FIGS. 91A-91B. Co-medication appears to enhance day 1 expression indicating there are baseline ABC responses occurring (FIG. 91A). The results of the co-medication regimens are shown in Table 16.

TABLE 16

| | | MC3 | hEPO in MC3 | hEPO in MC3 with methotrexate |
|---|---|---|---|---|
| Cmax (ug/mL) | Day 1 | 0.001 | 0.162 | 0.144 |
| | Day 8 | 0.001 | 0.155 | 0.141 |
| | Day 15 | 0.001 | 0.102 | 0.052 |
| | Day 22 | 0.001 | 0.056 | 0.056 |
| AUC (ug*hr/mL) | Day 1 | 0.150 | 8.998 | 6.735 |
| | Day 8 | 0.150 | 7.620 | 5.694 |
| | Day 15 | 0.150 | 3.811 | 3.211 |
| | Day 22 | 0.150 | 2.196 | 4.252 |

Example 26

1. CFSE Assay

Cells were isolated from spleens by crushing the tissue through a 70 nm filter in the presence of PBS. After washing, red blood cells were lysed by ACK buffer. After an additional washing with PBS, 2×10[6] cells per sample were stained with CFSE in PBS at room temperature for 5 minutes. Immediately after incubation, the staining reaction was quenched with 15 mL of media at room temperature. The cells were then centrifuged and washed twice with media. The cells were then incubated for 3 days at 37° C. in the presence of diverse stimuli. The analysis was performed using ModFit 4.1 software. FIG. 92 shows that B cells proliferate in the presence of DSPC LNPs.

2. Calcium Flux

Cells were isolated from spleens by crushing the tissue through a 70 nm filter in the presence of PBS. After washing, red blood cells were lysed by ACK buffer. After an additional washing, 2×10[6] cells per sample were stained with 5 uM of Calcium Sensor Dye eFluor® 514(#65-0859-39, ebioscience) for 30 minutes at 37° C. After an additional washing, cells were stained with CD19 on ice for 20 minutes. The cells were then analyzed by flow cytometry. A baseline was acquired for 30 seconds, then after stimulus addition, the signal was measured for 360 seconds. After adding a positive stimulus (Cell stimulation cocktail #00-4970-03 ebioscience), the signal was recorded for an additional 30 seconds. The analysis was performed using FlowJo software. FIG. 93 shows that DSPC LNPs induce calcium release in B cells.

Example 27

Previous studies have characterized, in detail, the reduced efficacy of PEGylated nanoparticles upon repeat dosing, known as the ABC phenomenon. Anti-PEG IgM generated in response to LNP administration, recognize the PEG lipid component of the LNP, bind to LNP, and remove them from circulation. The phospholipid component of the LNP, in particular DSPC, activates both platelets and B cells causing the release of cytokines and "natural IgM" which further potentiate the immune response to administered LNPs, contributing to ABC. Oleic acid has been identified as a DSPC alternative. Replacement of DSPC with oleic acid results comparable protein expression from encapsulated mRNA, but provides reduced B cell activation as compared to standard LNP formulation, e.g., MC3-based LNP formulation. Also identified above, are novel PEG lipids which can be sued as PEG-lipid, e.g., PEG DMG alternatives. Without being bound in theory, it is believed that such novel PEG-lipids provide for reduction of anti-PEG IgM generation through faster diffusion (shorter lipid tails) and reduced surface hydrophobicity (—OH vs —OMe).

Recent multi-dose studies in mice with hEPO have identified PEG-lipids which afford good levels of protein expression and low levels of Anti-PEG IgM. This study was designed to test such lipids in a repeat administration study in mice, optionally in combination with novel cationic amino lipids, in LNP-formulations for mRNA administration. Specific parameters such as protein expression, anti-PEG IgM, in vivo B-cell activation and cytokine expression were tested to differentiate LNPs based on preferred efficacy.

A three-week study of novel PEG/Cmpd18 and PEG/MC3 combinations by intravenous (IV) administration with hEPO was conducted in mice. In particular, MC3 novel PEG LNPs and Cmpd18 novel PEG LNPs were prepared and tested head-to-head for expression, anti-PEG IgM, in vivo B cell activation, and cytokine expression in a multi-dose study. The LNP formulations were administered by IV in three fixed volume doses to CD-1 mice. Size in diameter (nm), polydispersity index (PDI), encapsulation efficiency (EE), mRNA concentration (ug/mL), and endotoxin concentration (EU/mL) were measured for the novel LNPs. Table 1 shows the foregoing measurements of the MC3 and Cmpd18 LNPs with the novel PEG lipids after the first dose was administered. As shown by the data in Table 17, the LNPs had a size, PDI, and EE sufficient for in vivo administration.

TABLE 17

Week 1 Data

| Animal | | Diameter (nm) | Pd Index | % EE | [final] ug/mL |
|---|---|---|---|---|---|
| 1 | MC3:Cmpd422 | 62.5 | 0.098 | 98 | 88 |
| 2 | MC3:Cmpd416 | 106 | 0.14 | 97 | 80 |
| 3 | MC3:Cmpd405 | 76 | 0.14 | 97 | 78 |
| 4 | MC3:Cmpd403 | 68.4 | 0.16 | 98 | 79 |
| 5 | MC3:Cmpd396 | 76.5 | 0.18 | 97 | 66 |

TABLE 17-continued

Week 1 Data

| Animal | | Diameter (nm) | Pd Index | % EE | [final] ug/mL |
|---|---|---|---|---|---|
| 6 | MC3:Cmpd430 | 69 | 0.13 | 98 | 75 |
| 7 | Cmpd18:Cmpd422 | 78 | 0.085 | 94 | 80 |
| 8 | Cmpd18:Cmpd416 | 129 | 0.081 | 95 | 97 |
| 9 | Cmpd18:Cmpd405 | 103.8 | 0.18 | 91 | 71 |
| 10 | Cmpd18:Cmpd403 | 87.3 | 0.13 | 96 | 79 |
| 11 | Cmpd18:Cmpd396 | 98.8 | 0.16 | 92 | 78 |
| 12 | Cmpd18:Cmpd430 | 87.5 | 0.065 | 97 | 89 |
| 13 | PBS | | | | |

The size in diameter (nm), polydispersity index (PDI), encapsulation efficiency, mRNA concentration (ug/mL), and endotoxin concentration of the MC3 novel PEG LNPs and Cmpd18 novel PEG LNPS were also measured three weeks after dosing. This data is shown in Table 18 below. The data in Tables 17 and 18 show that the physiochemical characteristics for both MC3 and Cmpd18 LNPs remained constant throughout the study. Additionally, the EE and size of the novel LNPS shown in Tables 17 and 18 are within art-recognized ranges.

TABLE 18

(Week 3)

| Animal | | Diameter (nm) | Pd Index | % EE | [final] ug/mL |
|---|---|---|---|---|---|
| 1 | MC3:Cmpd422 | 63.8 | 0.089 | 98 | 93 |
| 2 | MC3:Cmpd416 | 108 | 0.045 | 98 | 81 |
| 3 | MC3:Cmpd405 | 76.7 | 0.16 | 97 | 71 |
| 4 | MC3:Cmpd403 | 65.8 | 0.14 | 98 | 68 |
| 5 | MC3:Cmpd396 | 77.2 | 0.16 | 97 | 67 |
| 6 | MC3:Cmpd430 | 69.1 | 0.074 | 98 | 80 |
| 7 | Cmpd18:Cmpd422 | 77.1 | 0.082 | 95 | 71 |
| 8 | Cmpd18:Cmpd416 | 130.4 | 0.1 | 96 | 103 |
| 9 | Cmpd18:Cmpd405 | 103.1 | 0.18 | 91 | 68 |
| 10 | Cmpd18:Cmpd403 | 89.4 | 0.13 | 96 | 77 |
| 11 | Cmpd18:Cmpd396 | 96 | 0.17 | 93 | 77 |
| 12 | Cmpd18:Cmpd430 | 86.5 | 0.11 | 97 | 86 |

Additional data is shown in FIG. 74. FIG. 74 depicts hEPO expression 6 hours following once weekly IV administration of hEPO mRNA-LNP formulations at weeks 1, 2, and 3. The data show superior expression for Cmpd 18-based LNPs and further evidence appreciable protein expression with several of the novel PEG lipids tested.

Cytokine expression in the MC3 and Cmpd 18 LNPs is shown in Tables 19-22. IFN-γ-inducible protein 10 (IP-10) is a chemokine involved in inflammation and interlukin 6 (IL-6) is a pro-inflammatory cytokine. Concentrations (pg/mL) of IP-10 (Table 19) and IL-6 (Table 20) 6 hours following administration of the MC3 and Cmpd 18 LNPs at week 1 are given.

TABLE 19

Week 1 IP-10 (pg/mL)

| MC3: Cmpd422 | MC3: Cmpd416 | MC3: Cmpd405 | MC3: Cmpd403 | MC3: Cmpd396 | MC3: Cmpd430 | Cmpd18: Cmpd422 |
|---|---|---|---|---|---|---|
| 2316 | 7127 | 1648 | 1411 | 2509 | 86 | 3327 |
| 2765 | 9000 | 1385 | 1168 | 733 | 29 | 3209 |
| 2670 | 3264 | 1710 | 155 | 1824 | 0 | 6584 |
| 1486 | 359 | 1168 | 1168 | 978 | 9 | 4907 |
| 1598 | 758 | 1598 | 1322 | 1039 | 54 | 2726 |
| 866 | 3848 | 1966 | 839 | 1202 | 0 | 3475 |
| 1335 | 3425 | 2099 | 959 | 815 | 9 | 794 |

TABLE 19-continued

Week 1 IP-10 (pg/mL)

| 1673 | 2184 | 2387 | 592 | 1734 | 9  | 1574 |
|------|------|------|-----|------|----|------|
| 1636 | 1245 | 3722 | 893 | 825  | 9  | 1574 |
| 1398 | 648  | 3275 | 648 | 1514 | 17 | 2785 |

| Cmpd18: Cmpd416 | Cmpd18: Cmpd405 | Cmpd18: Cmpd403 | Cmpd18: Cmpd396 | Cmpd18: Cmpd430 | PBS | Naive |
|---|---|---|---|---|---|---|
| 12028 | 3752 | 3849 | 7402 | 3730 | 49 | 0 |
| 6310  | 1208 | 3698 | 3568 | 4574 | 49 | 16 |
| 897   | 3309 | 4693 | 6943 | 2727 | 58 | 57 |
| 16027 | 3957 | 1445 | 4433 | 2350 | 30 | 151 |
| 6300  | 9375 | 3039 | 6257 | 4596 | 98 | 72 |
| 2528  | 5778 | 3590 | 2921 | 4498 | 85 | 44 |
| 7824  | 3493 | 3687 | 3795 | 3449 | | |
| 10757 | 5007 | 3514 | 9871 | 4661 | | |
| 14677 | 4314 | 1240 | 2921 | 1531 | | |
|       |      | 3190 | 5691 | 4098 | | |

TABLE 20

Week 1 Il-6 (pg/mL)

| MC3: Cmpd422 | MC3: Cmpd416 | MC3: Cmpd405 | MC3: Cmpd403 | MC3: Cmpd396 | MC3: Cmpd430 | Cmpd18: Cmpd422 |
|---|---|---|---|---|---|---|
| 41  | 500   | 460  | 1254 | 198  | 5  | 937  |
| 163 | 500*  | 79   | 264  | 49   | 19 | 500* |
| 55  | 2084  | 186  | 195  | 60   | 31 | 283  |
| 72  | 207   | 38   | 476  | 31   | 29 | 1477 |
| 78  | 27    | 81   | 360  | 62   | 0  | 897  |
| 41  | 95    | 83   | 1988 | 1015 | 0  | 22   |
| 21  | 41    | 1015 | 1034 | 950  | 78 | 27   |
| 39  | 10    | 1189 | 18   | 500* | 261| 5    |
| 166 | 130   | 820  | 933  | 60   | 5  | 11   |
| 58  | 123   | 104  | 67   | 2393 | 9  | 61   |

| Cmpd18: Cmpd416 | Cmpd18: Cmpd405 | Cmpd18: Cmpd403 | Cmpd18: Cmpd396 | Cmpd18: Cmpd430 | PBS | Naive |
|---|---|---|---|---|---|---|
| 216  | 51   | 987  | 1124 | 72  | 193 | 272 |
| 322  | 35   | 26   | 500* | 185 | 33  | 1113 |
| 52   | 177  | 1881 | 500* | 53  | 31  | 35 |
| 500* | 500* | 681  | 578  | 44  | 62  | 1954 |
| 40   | 2424 | 177  | 92   | 219 | 82  | 75 |
| 221  | 159  | 500* | 26   | 41  | 283 | 58 |
| 1850 | 40   | 65   | 64   | 41  | | |
| 343  | 84   | 1651 | 57   | 50  | | |
|      | 139  | 1091 | 31   | 251 | | |
|      |      | 618  |      | 665 | | |

Concentrations (pg/mL) of IP-10 and IL-6 6 hours following administration of the MC3 and Cmpd18 LNPs at week 2 are given in Tables 21 and 22, respectively. These data demonstrate that several of the novel PEG lipids tested provide for low levels of inflammatory chemokine/cytokine expression, in particular, when certain novel PEG lipids are formulated in combination with Cmpd 18 as the cationic amino lipid.

TABLE 21

Week 2 IP-10 (pg/mL)

| MC3: Cmpd422 | MC3: Cmpd416 | MC3: Cmpd405 | MC3: Cmpd403 | MC3: Cmpd396 | MC3: Cmpd430 | Cmpd18: Cmpd422 |
|---|---|---|---|---|---|---|
| 462 | 953  | 587 | 323  | 525  | 2885 | 636  |
| 537 | 1229 | 686 | 126  | 348  | 1253 | 1455 |
|     | 661  | 500 | 386  | 512  | 1348 | 500  |
|     | 661  | 297 | 348  | 258  |      | 1098 |
|     | 1134 | 448 | 1122 | 1158 |      |      |
|     | 929  | 336 |      | 166  |      |      |
|     | 550  | 649 |      | 243  |      |      |
|     | 796  | 832 |      | 525  |      |      |
|     |      | 1133|      |      |      |      |

TABLE 21-continued

| Week 2 IP-10 (pg/mL) | | | | | | |
|---|---|---|---|---|---|---|
| Cmpd18: Cmpd416 | Cmpd18: Cmpd405 | Cmpd18: Cmpd403 | Cmpd18: Cmpd396 | Cmpd18: Cmpd430 | PBS | Naive |
| 4901 | 928 | 2496 | 2311 | 533 | 0 | |
| 1504 | 3219 | 1394 | 939 | | 0 | |
| | 1723 | 2906 | 2582 | | 0 | |
| | | 1657 | 1162 | | | |
| | | 1679 | 1822 | | | |
| | | | 1206 | | | |

TABLE 22

| Week 2 IL-6 (pg/mL) | | | | | | |
|---|---|---|---|---|---|---|
| MC3: Cmpd422 | MC3: Cmpd416 | MC3: Cmpd405 | MC3: Cmpd403 | MC3: Cmpd396 | MC3: Cmpd430 | Cmpd18: Cmpd422 |
| 57 | 613 | 19 | 87 | 39 | 500 | 24 |
| 107 | 0* | 45 | 13 | 0* | 252 | 0* |
| 114 | 53 | 48 | 0* | 22 | 0* | 27 |
| 8 | 49 | 45 | 260 | 35 | 36 | 0* |
| 10 | 0* | 35 | 74 | 264 | 93 | 21 |
| 34 | 28 | 51 | 0* | 18 | 22 | 7 |
| 0* | 85 | 171 | 140 | 63 | 30 | 343 |
| 0* | 62 | 29 | 500 | 0* | 388 | 13 |
| 0* | 622 | 43 | 0 | 98 | 100 | 5 |
| | 70 | 0* | 284 | 11 | 34 | 49 |

| Cmpd18: Cmpd416 | Cmpd18: Cmpd405 | Cmpd18: Cmpd403 | Cmpd18: Cmpd396 | Cmpd18: Cmpd430 | PBS | Naive |
|---|---|---|---|---|---|---|
| 355 | 0* | 36 | 0* | 11 | 49 | |
| 147 | 0* | 125 | 0* | 159 | 33 | |
| 263 | 140 | 18 | 451 | 39 | 9 | |
| 431 | 6 | 38 | 0* | 84 | 19 | |
| 33 | 40 | 194 | 43 | 2 | 435 | |
| 325 | 0* | 75 | 0* | 0* | 168 | |
| 46 | 67 | 269 | 153 | 57 | | |
| 420 | 0* | 58 | 500 | 0* | | |
| 154 | | 38 | 0* | 16 | | |
| | | | 43 | 0* | | |

In FIG. 75, levels of anti-PEG IgM (ng/mL) 96 hours post second dose were measured. The data in this graph shows reduced levels of anti-PEG IgM generated for the novel PEG lipids. The above-discussed data show that accelerated blood clearance was not observed when certain novel PEG lipids were used in LNP formulations. Interestingly, most of the MC3 groups maintained expression while most of the Cmpd18 groups increased expression over the 3 week study. Of the novel PEG lipids tested, Cmpd405, Cmpd396 and Cmpd403 had the lowest levels of anti-PEG IgM. It was quite surprisingly observed in this study, as well as in previously described studies, that Cmpd160, which differs from DSPC by just one methyl group in the had group was essentially immune silent when tested in LNPs administered IV in vivo.

Example 28

LNPs comprised comprising of novel DSPC and/oleic acid derivatives were prepared and tested for expression of luciferase (m1ψ-modified mRNA-encoded luciferase) and B cell activation in a single dose study relative to the standard DSPC formulation. The DSPC/oleic analogs tested are shown in Table 23 below.

TABLE 23

| Group | Phospholipid (PL) | Formulation | Route | Dosing Regimen | # of Doses | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|
| 1 | Cmpd162 | MC3:PL:Chol:PEG-DMG; 50:10:38:5:1.5 | IV | Once on Day 1 | 1 | 5 | 0.5 | 0.1 | 0.1 | 0.7 | 0.07 |
| 2 | Cmpd441 | MC3:PL:Chol:PEG-DMG; 50:10:38:5:1.5 | IV | Once on Day 1 | 1 | 5 | 0.5 | 0.1 | 0.1 | 0.7 | 0.07 |
| 3 | Cmpd442 | MC3:PL:Chol:PEG-DMG; 50:10:38:5:1.5 | IV | Once on Day 1 | 1 | 5 | 0.5 | 0.1 | 0.1 | 0.7 | 0.07 |

TABLE 23-continued

| Group | Phospholipid (PL) | Formulation | Route | Dosing Regimen | # of Doses | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|
| 4 | Cmpd443 | MC3:PL:Chol:PEG-DMG; 50:10:38:5:1.5 | IV | Once on Day 1 | 1 | 5 | 0.5 | 0.1 | 0.1 | 0.7 | 0.07 |
| 5 | Cmpd444 | MC3:PL:Chol:PEG-DMG; 50:10:38:5:1.5 | IV | Once on Day 1 | 1 | 5 | 0.5 | 0.1 | 0.1 | 0.7 | 0.07 |
| 6 | Cmpd445 | MC3:PL:Chol:PEG-DMG; 50:10:38:5:1.5 | IV | Once on Day 1 | 1 | 5 | 0.5 | 0.1 | 0.1 | 0.7 | 0.07 |
| 7 | Cmpd446 | MC3:PL:Chol:PEG-DMG; 50:10:38:5:1.5 | IV | Once on Day 1 | 1 | 5 | 0.5 | 0.1 | 0.1 | 0.7 | 0.07 |
| 8 | Cmpd447 | MC3:PL:Chol:PEG-DMG; 50:10:38:5:1.5 | IV | Once on Day 1 | 1 | 5 | 0.5 | 0.1 | 0.1 | 0.7 | 0.07 |
| 9 | Cmpd448 | MC3:PL:Chol:PEG-DMG; 50:10:38:5:1.5 | IV | Once on Day 1 | 1 | 5 | 0.5 | 0.1 | 0.1 | 0.7 | 0.07 |
| 10 | Oleic Acid | MC3:Oleic Acid:Chol:PEG-DMG; | IV | Once on Day 1 | 1 | 5 | 0.5 | 0.1 | 0.1 | 0.7 | 0.07 |
| 11 | DSPC | MC3:DSPC:Chol:PEG-DMG; 50:10:38:5:1.5 | IV | Once on Day 1 | 1 | 5 | 0.5 | 0.1 | 0.1 | 0.7 | 0.07 |
| 12 | PBS | | IV | Once on Day 1 | 1 | 3 | | 0.1 | 0 | 0.42 | 0 |
| 13 | Naïve | | | | | 3 | | | | | |

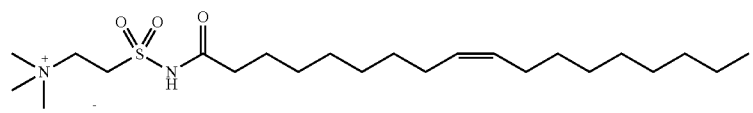

Cmpd 364

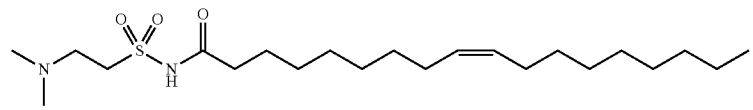

Cmpd 368

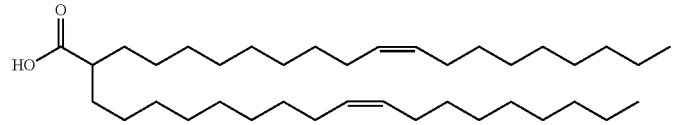

Cmpd 376

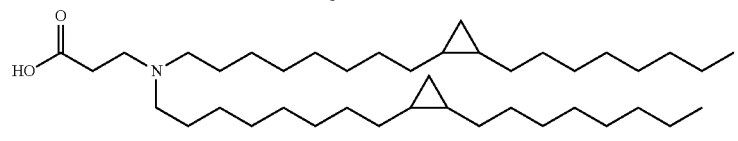

Cmpd 443

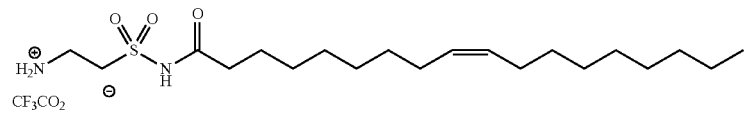

Cmpd442

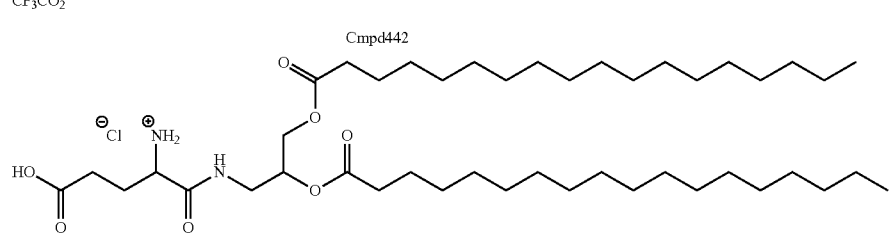

Cmpd441

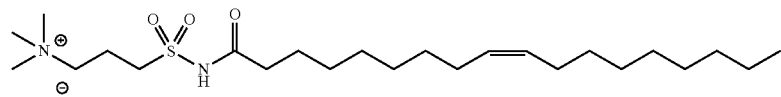

Cmpd 378

TABLE 23-continued

| Group | Phospholipid (PL) | Formulation | Dosing Route | Regimen | # of Doses | # of females | Dose Level (mg/kg) | Dose Vol (mL) | Dose Conc. (mg/mL) | Total Vol Req (mL) | Total Min Mass Req (mg) |
|---|---|---|---|---|---|---|---|---|---|---|---|

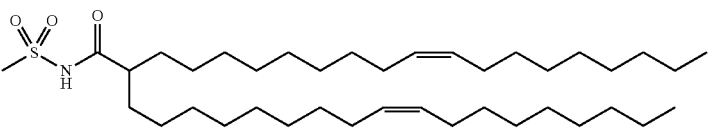

Cmpd 377

As shown in Table 23, the LNPs were administered by IV as a single dose to mice. The data is shown in FIGS. 76 and 77. Luc expression with various LNP formulations was assessed by a measurement of total flux (p/s) at 3, 6, and 9 hours following dosing, using whole body BLI imaging (see FIG. 76). The percentage of activated B cells (CD86+ CD69+) in splenic CD19+ cells was also measured. These activated B cell frequencies are shown in FIG. 77.

In general, flux increased from three to six hours, showing a decline in expression by 24 hours. All of the formulations tested showed appreciable luciferase expression in vivo, although some variability in expression was observed. The % of CD86+CD69+ B cells in splenic CD19+ cells (B lymphocytes) in the spleen was also measured for the LNP formulations as an indicator of B cell activation. All formulations tested showed B cell activation at levels below, and often significantly below, that of DSCP control formulations.

Example 29

A repeat dose of hEPO mRNA in Cmpd18-containing LNPs with modified PEG lipids was next performed in non-human primates. Briefly, cynomolgus monkeys were treated with LNP-encapsulated mRNA administered by intravenous (IV) infusion. Oleic acid- and Cmpd403-containing LNPs were analyzed to determine their effect on accelerated blood clearance (ABC). In particular, it was an objective to determine if the DSPC and PEG-lipid replacements demonstrate low B cell activation, low anti-PEG IgM, and maintenance of protein expression in higher species. The following four groups were compared: MC3/DSPC/Chol/Cmpd422 (control), Cmpd18/DSPC/Chol/Cmpd422 (control), Cmpd18/DSPC/Chol/Cmpd403 (test group), and Cmpd18/Oleic Acid/Chol/Cmpd422 (test group). The monkeys were administered a pseudouridine modified hEPO mRNA (0.2 mg/kg) weekly dosing in the foregoing LNPs for 6 weeks.

Pharmokinetic parameters including AUC were determined for Cmpd 18: Cmpd 403 combinations. Contsitutive AUC was seen over time with baseline complement and cytokine levels and low to no levels of IgM observed.

The particle characteristics for each of the formulations are shown in Table 24 below. mRNA used for this study was m1ψ-modified mRNA encoding EPO. Formulations includes components at the following mol %-50:10:38.5:1.5. Table 24 shows size, encapsulation efficiency (EE) and polydispersity index (PDI). Particles had characteristics within acceptable limits for in vivo testing.

TABLE 24

| Group | Sample | Composition | Theoretical mol % | mRNA | pH | Osmolality (mOsm/kg) |
|---|---|---|---|---|---|---|
| 1 | Std MC3 | MC3:DSPC:Chol:Cmpd427 | 50:10:38.5:1.5 | modified hEPO | 7.502 | 307 |
| 2 | Std Cmpd18 | Cmpd18:DSPC:Chol:Cmpd427 | 50:10:38.5:1.5 | modified hEPO | 7.453 | 307 |
| 3 | Cmpd18: Oleic Acid | Cmpd18:Oleic Acid:Chol:Cmpd427 | 50:10:38.5:1.5 | modified hEPO | 7.455 | 307 |
| 4 | Cmpd18: Cmpd403 | Cmpd18:DSPC:Chol:Cmpd403 | 50:10:38.5:1.5 | modified hEPO | 7.446 | 306 |

Throughout the 6 weeks of experimentation, hEPO protein expression, anti-PEG IgM and IgG levels, IgM, IgG and cytokine and complement levels were measured for the novel LNPs. FIG. 79 depicts hEPO expression (ng/mL) at predose, 2 hours, 6 hours, 12 hours, 24 hours, 48 hours, and 72 hours following once weekly IV administration of the hEPO mRNA-LNP formulations at day 1, day 8, day 15, day 22, day 29, day 36, and day 43.

In FIG. 80, levels of anti-PEG IgM (U/mL) were measured following once weekly IV administration of the hEPO mRNA-LNP formulations at day 1, day 8, day 15, day 22, day 29, day 36, and day 43. FIG. 81 shows the levels of anti-PEG IgG (U/mL) measured following once weekly IV administration of the hEPO mRNA-LNP formulations at day 1, day 8, day 15, day 22, day 29, day 36, and day 43. The Cmpd403 group demonstrated maintenance of protein expression across the 6 weeks, maintenance of baseline levels of anti-PEG IgM and anti-PEG IgG, no complement activation, and minimal cytokine activation. Levels of anti-PEG IgM and IgG, complement, and cytokine elevations appeared to inversely correlate with a loss of protein expression. The MC3 and Cmpd18 controls and oleic acid group all showed reduced hEPO protein expression at week 6. The oleic acid group demonstrated the highest levels of initial of protein production. The MC3 and Cmpd18 controls and Cmpd403 groups showed similar levels of hEPO expression. Cmpd18/DSPC at 0.2 mg/kg did not show increased hEPO expression relative to MC3/DSPC; however, Cmpd18/oleic acid did show increased protein expression (3-fold) relative to MC3/DSPC and Cmpd18/DSPC. Table 25 shows hEPO expression as measured by AUC of the four LNP groups. In particular, the hEPO AUC (ng/mL*h) was measured each week of the 6 week study.

TABLE 25

| | hEPO AUC (ng/mL*h) | | | |
|---|---|---|---|---|
| Day | MC3 | Cmpd18 | Cmpd403 | Oleic Acid |
| 1 | 9134 | 4059 | 9861 | 31258 |
| 8 | 4754 | 6272 | 8554 | 31739 |
| 15 | 8031 | 4059 | 10922 | 17132 |
| 22 | 4951 | 6272 | 7562 | 44124 |
| 29 | 2607 | 9414 | 10822 | 21015 |
| 36 | 2824 | 17585 | 7870 | 6105 |
| 43 | 7491 | 14102 | 16622 | 689.3 |

Particles formulated with Cmpd18 as the cationic amino lipid outperformed standard MC3-based LNPs in terms of protein expression throughout repeated dosing in primates. Oleic acid as a DSPC replacement resulted in initially high protein expression but did not fully ameliorate ABC over the course of the study. Compound 403 as a PEG-lipid replacement resulted in reduced ABC as evidenced by maintenance of hEPO AUC over the course of the study. Taken together, these data show that deletion of B cells leads to absence of to ABC after 5 injections. In particular, a single injection of anti CD20, 7 days before LNP injection lead to (1) low/no IgM/IgG to PEG; (2) no clearance of RNA or protein; and (3) low/no cytokines/complement activation, making this an attractive candidate for co-administration regimens featuring LNP-encapsulated mRNAs.

FIG. 82 shows the percentage of activated B cells (CD86+ CD27+) in CD19+ cells at pre-bleed, day 1, day 22, day 43, and day 44 of the study. As shown in FIG. 82, all LNP groups demonstrated low B cell activation. Nearly all of the subjects administered the Cmpd18/DSPC/Chol/Cmpd403 or the Cmpd18/Oleic Acid/Chol/Cmpd422 had less than 5% B cell activation in CD19+ cells and demonstrated an average B cell activation percentage close to 2.5%, which was maintained through the course of the study. The percentage of monocyte activation was also measured at pre-bleed, day 1, day 22, day 43, and day 44 of the study. These results are reflected in FIG. 83. All of the LNP groups demonstrated low monocyte activation and all of the subjects administered the Cmpd18/DSPC/Chol/Cmpd403 or the Cmpd18/Oleic Acid/Chol/Cmpd422 maintained an average of less than 3% monocyte activation through the course of the study.

Example 30

The above data show that B cell activation is a key contributor to the ABC phenomenon in animal administered LNP-encapsulated nucleic acids, e.g., mRNAs. Prior art studies attempted to mitigate the ABC phenomenon with compounds such as dexamenthsone and/or corticosteroids. The instant inventors have provided a detailed mechanistic understanding of the ABC phenomenon, in particular as it pertains to LNP-encapsulated mRNA administration. LNPs have multiple cellular interactions in vivo that have been demonstrated to drive the ABC effect. IV injection of LNPs leads to increased secretion of anti PC IgM (natural IgM) and induced development of anti-PEG IgM response. Moreover, repeat IV injection of LNPs leads to increase levels of natural IgM. A key node appears to be the spleen and highly supports the hypothesis that ABC is driven by B1 cell function. These cells are responsible for secreting "natural IgMs" (e.g., B1a cells), but B1b cells can also produce IgG when stimulated. These immunoglobulins recognize PEG, phospholipids, and most likely, cholesterol domains, present on the surface of the LNPs. It is shown herein that natural IgM likely recognize a PC motif present on the surface of standard LNP (e.g., DSPC-containing LNPs).

IV injection of LNPs leads to rapid activation of B1a cells resulting in increased secretion of anti-PC IgM (natural IgM) and repeat IV injection of LNPs leads increase level of natural IgM. Removal of the spleen prevents activation of B cells (B1 specifically) that likely contribute heavily to ABC. In particular, splenectomized animals show (1) low/no IgM/IgG to PEG; (2) no clearance of RNA or protein; and (3) low/no cytokines/complement activation. Based on the mechanisms and cell types herein implicated in the ABC effect, the instant inventors hypothesized that certain B cell targeted co-administration regimens might be useful for treatment of subjects with LNP-encapsulated mRNAs, in particular, where repeat of chronic dosing is required for the desired therapeutic index.

A repeat-dose study of hEPO mRNA by IV infusion with co-administration was conducted in cynomolgus monkeys. Monkeys were administered hEPO mRNA in MC3-LNPs according to the experimental design shown in Table 26 and were co-administered one of rituximab, idealalisib, fostamatinib, or fingoimod according to the regimen shown in Table 27.

TABLE 26

| Group No. | Test Material | Dose Level (mg/kg) | Comedication | Dose Volume (mL/kg) | Dose Conc. (mg/mL) | Number of Males |
|---|---|---|---|---|---|---|
| 1 | hEPO mRNA in MC3 | 0.2 | NA | 5.0 | 0.04 | 4 |
| 2 | hEPO mRNA in MC3 | 0.2 | rituximab | 5.0 | 0.04 | 4 |
| 3 | hEPO mRNA in MC3 | 0.2 | idealalisib | 5.0 | 0.04 | 4 |
| 4 | hEPO mRNA in MC3 | 0.2 | fostamatinib | 5.0 | 0.04 | 4 |
| 5 | hEPO mRNA in MC3 | 0.2 | fingolimod | 5.0 | 0.04 | 4 |

TABLE 27

| Comedication | Route | Dose Level (mg/kg/dose) | Dose Volume (mL/kg) | Dose Concentration (mg/mL) | Dose Rate (mL/h) | Regimen |
|---|---|---|---|---|---|---|
| rituximab | IV infusion | 20 | 2 | 10 | 5 | Once on Day −7 |
| idelalisib | PO; in capsules | 2 | N/A | N/A | N/A | BID on Days −2, −1, 1, 6, 7, 8, 13, 14, 15, 20, 21, 22, 27, 28, 29; 60 min prior to and 11 hours after the start of infusion on dosing days |
| fostamatinib | PO; in capsules | 3 | N/A | N/A | N/A | BID daily starting on Day −4; 60 min prior to and 11 hours after the start of infusion on dosing days |
| fingolimod | PO; 0.5 mg hard capsules | 0.5 | N/A | N/A | N/A | SID daily starting on Day −4; 60 min prior to the start of infusion on dosing days |

PO = per os; IV = Intravenous; N/A = not applicable

The experimental data is shown in FIGS. 84A-90. FIGS. 84A and 84B show the EPO expression after the first injection and after the fifth injection. In particular, the concentration of EPO (ng/mL) was measured at 2 hours, 6 hours, 12 hours, 24 hours, and 48 hours following the first injection and the fifth injection. FIGS. 85A-85E show the EPO expression for each of the co-medications on day 1 and day 29 of the study. In particular, the concentration of EPO (ng/mL) was measured on day 1 and day 29 at 2 hours, 6 hours, 12 hours, 24 hours, and 48 hours for each co-medication group. Immune cell populations were also measured. Specifically, the percentage of B cells (FIG. 86A), B1a cells (FIG. 86B), and monocytes (FIG. 86C) in PBMCs was measured for each co-medication group at day −7, 24 hours post first injection, and 24 hours post fifth injection. B cell activation is reflected in FIG. 87. The percentage of activated B cells in circulating B cells was measured for each co-medication group at day −7, 24 hours post first injection, and 24 hours post fifth injection.

In the control group, the percentage of activated B cells increased 24 hours post first injection and again 24 hours post fifth injection, thus, showing that more LNP injection leads to higher B cell activation. The percentage of activated B cells was reduced drastically in the rituximab group 24 hours post first injection, due to the fact that B cells were deleted in the subjects of this group. B cell depletion correlated with reduction of anti-PEG IgM and IgG, even at day 34 (post 5th injection). B cell depletion also correlated well with maintenance of protein expression. In particular, B cell depletion provided for loss of expression after 5 injections indicating there was no ABC and B cell depletion further provided for no anti PEG response. B cell activation was not observed in the idelalisib group and B cells frequencies were slightly reduced (see FIG. 86A). The fostamatinib and fingolimid groups displayed normal B cell activation similar to that of the control group. With regard to the B1a cells, B1a cell frequencies were normal before injection in all co-medication groups (see FIG. 86B). Except for the rituximab group where B1a cells frequencies dropped slightly, all co-medication groups displayed increased B1a cells frequencies after LNP injection, meaning that LNP injection leads to B1a activation and proliferation.

Monocyte activation is reflected in FIG. 88. The percentage of activated monocytes/macrophages in circulating PBMCs was measured for each co-medication group at day −7, 24 hours post first injection, and 24 hours post fifth injection. As shown in FIG. 86C, the frequencies of monocytes were normal in all co-medication groups except for fingolimod, where a significant decrease was observed. An increase in the percentage of activated monocytes/macrophages post injection was only observed in the fingolimod co-medication group. As the frequency of monocytes in the fingolimod group dropped significantly post injection, the data suggests monocyte activation before apoptosis.

FIGS. 89A and 89B show the anti-PEG response. Anti-PEG IgM levels (U/mL) (FIG. 89A) and anti-PEG IgG levels (U/mL) (FIG. 89B) were measured for each co-medication group at baseline, day 9 post first injection, and day 34 post fifth injection.

Example 31

To further study the role of IgM in the ABC phenomenon, LNP-encapsulated mRNA encoding EPO was administered to control mice and to that lack secreted IgM (sIgM−/− mice). FIG. 78 shows the impact of removing circulating IgM on EPO EPO expression over the course of the 6 week study. In particular, the concentration of EPO (ng/mL) was measured at pre-bleed, 6 hours, and 24 hours, at each of the 6 weeks. In the two negative control groups, c57Bl6J/PBS and sIgM−/−PBS, EPO levels remained at baseline throughout the study, while in the mRNA treatment groups, EPO concentrations peaked at 6 hours post-dose, and then receded back to baseline by two weeks following mRNA administration. Note that, in Week 1, the EPO concentration was approximately the same in the c57Bl6J mice and the sIgM−/− mice at the 6 hour time point (peak expression post dose). However, over the time course of the experiment, the ABC phenomenon was observed, as evidenced by the decreasing AUC for EPO expression in the c57Bl6J mice. By contrast, the sIgM−/− mice produced consistently high levels of EPO following each repeat administration of LNP-encapsulated mRNA throughout the duration of the experiment. Thus, in the absence of circulating IgM, no loss of expression was observed even after five injections of mRNA evidencing a complete lack of ABC.

FIG. 90 further demonstrates the importance of anti-PEG IgM in the ABC phenomenon. FIGS. 90A-90B are two graphs showing anti-PEG IgM levels (U/mL) and EPO levels (ng/mL) in two of the groups from FIG. 78: C57Bl6J (FIG. 90A) and sIgM−/− mice (FIG. 90B). The anti-PEG IgM levels are graphed as light grey circles in FIG. 90A and an increase in anti-PEG IgM correlates with the onset of ABC. In the sIgM−/− mouse this is shown by black circles which remain at the baseline (FIG. 90B). EPO concentrations are indicated by black circles (FIG. 90A) and black squares (FIG. 90B). The data clearly demonstrate the inverse correlation between protein expression and anti-PEG IgM levels. When IgM levels are high EPO expression is suppressed, indicating ABC is occurring. When IgM levels are suppressed, for instance in the knockout mice, the EPO expression is significantly enhanced and ABC is reduced. Thus, in the absence of circulating IgM, no loss of expression was observed (no ABC) correlating with the absence of an anti-PEG response.

Example 32

Exemplary compound synthesis follows:

Compound 393:
N-(2-(Didodecylamino)ethyl)-N-dodecylglycine

Methyl N-(tert-butoxycarbonyl)-N-dodecylglycinate

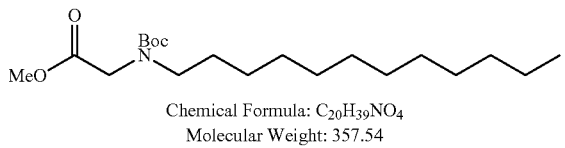 [SMILES: CCCCCCCCCCCCN(CC(=O)OC)C(=O)OC(C)(C)C]

Chemical Formula: C₂₀H₃₉NO₄
Molecular Weight: 357.54

A 0° C. solution of N-(tert-butoxycarbonyl)glycine methyl ester (7.7 g, 40.7 mmol) in DMF (100 mL) was treated with NaH (60%, 1.71 g, 42.7 mmol) and the mixture was allowed to stir for 30 minutes. The solution was allowed to return to room temperature before 1-bromododecane (15.2 g, 61.0 mmol) was added and the reaction was allowed to stir overnight. The reaction was quenched with water and extracted with EtOAc. The organics were washed with brine, dried over anhydrous Na₂SO₄, filtered, and concentrated in vacuo. Purification by ISCO silica flash chromatography (0-20% EtOAc/hexanes) provided methyl N-(tert-butoxycarbonyl)-N-dodecylglycinate (4.03 g, 28%).

¹H-NMR (300 MHz, CDCl₃) δ: ppm 4.01-3.84 (br. m, 2H); 3.75 (s, 3H); 3.27 (br. m, 2H); 1.67-1.39 (br. m, 11H); 1.28 (br, 18H); 0.90 (t, 3H).

Methyl Dodecylglycinate

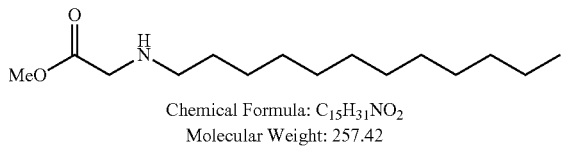 [SMILES: CCCCCCCCCCCCNCC(=O)OC]

Chemical Formula: C₁₅H₃₁NO₂
Molecular Weight: 257.42

To a 0° C. solution of methyl N-(tert-butoxycarbonyl)-N-dodecylglycinate (4.03 g, 11.3 mmol) in DCM (17 mL) was added dropwise TFA (17 mL, 226 mmol). The reaction was allowed to return to room temperature and stir for 6 hours. The reaction mixture was concentrated in vacuo and the crude material was dissolved in DCM. The solution was washed with 10% NaOH, brine, dried over anhydrous Na₂SO₄, filtered, and concentrated in vacuo to provide methyl dodecylglycinate (2.84 g, 98%).

¹H-NMR (300 MHz, CDCl₃) δ: ppm 3.75 (s, 3H); 3.44 (s, 2H); 2.62 (t, 2H); 1.70 (br, 1H); 1.51 (m, 2H); 1.29 (br, 18H); 0.90 (t, 3H).

2-(Didodecylamino)ethan-1-ol

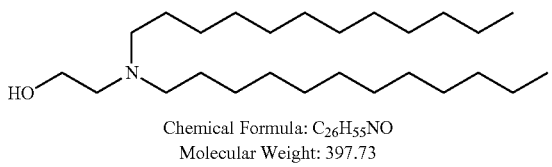 [SMILES: CCCCCCCCCCCCN(CCO)CCCCCCCCCCCC]

Chemical Formula: C₂₆H₅₅NO
Molecular Weight: 397.73

To a solution of 1-bromododecane (10 g, 40.1 mmol) in MeCN (84 mL) was added ethanolamine (1.10 mL, 18.2 mmol), K₂CO₃ (11.1 g, 80.1 mmol), and KI (302 mg, 1.82 mmol). The reaction was allowed to stir at 82° C. for 48 hours. The reaction mixture was cooled to room temperature, filtered, and the solids were washed with hexanes. The filtrate was extracted with hexanes, and the combined extracts were concentrated in vacuo. Purification by ISCO silica flash chromatography (0-20% MeOH/DCM) provided 2-(didodecylamino)ethan-1-ol (3.87 g, 53%).

UPLC/ELSD: RT=2.69 min. MS (ES): m/z (MH⁺) 398.56 for C₂₆H₅₅NO

¹H-NMR (300 MHz, CDCl₃) δ: ppm 3.57 (t, 2H); 2.63 (t, 2H); 2.49 (br. m, 4H); 1.48 (br. m, 4H); 1.29 (br, 36H); 0.91 (t, 6H).

N-(2-Chloroethyl)-N-dodecyldodecan-1-amine

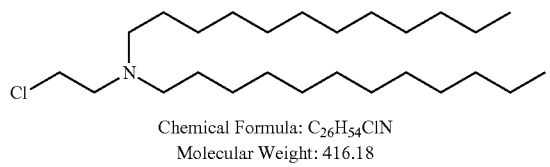 [SMILES: CCCCCCCCCCCCN(CCCl)CCCCCCCCCCCC]

Chemical Formula: C₂₆H₅₄ClN
Molecular Weight: 416.18

To a 0° C. solution of 2-(didodecylamino)ethan-1-ol (3.87 g, 9.73 mmol) and triethylamine (1.76 mL, 12.6 mmol) in DCM (50 mL) was added dropwise a solution of methanesulfonyl chloride (0.941 mL, 12.2 mmol) in DCM (5 mL). The reaction was allowed to return to room temperature and stir for 16 hours. The mixture was quenched by the addition of water and extracted with DCM. The organic layer was washed with saturated NaHCO₃, brine, dried over anhydrous Na₂SO₄, filtered, and concentrated in vacuo. Purification by ISCO silica flash chromatography (0-10% EtOAc/hexanes) provided N-(2-chloroethyl)-N-dodecyldodecan-1-amine (1.92 g, 47%).

¹H-NMR (300 MHz, CDCl₃) δ: ppm 3.51 (t, 2H); 2.78 (t, 2H); 2.47 (br. m, 4H); 1.44 (br. m, 4H); 1.28 (br, 36H); 0.90 (t, 6H).

Methyl N-(2-(didodecylamino)ethyl)-N-dodecylglycinate

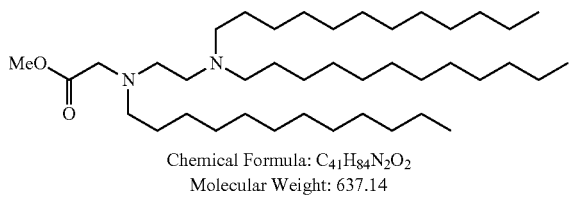 [SMILES: CCCCCCCCCCCCN(CCCCCCCCCCCC)CCN(CCCCCCCCCCCC)CC(=O)OC]

Chemical Formula: $C_{41}H_{84}N_2O_2$
Molecular Weight: 637.14

To a solution of methyl dodecylglycinate (425 mg, 1.65 mmol) in MeCN (10 mL) was added N-(2-chloroethyl)-N-dodecyldodecan-1-amine (825 mg, 1.98 mmol), $K_2CO_3$ (457 mg, 3.30 mmol), and KI (27 mg, 0.165 mmol). The reaction was allowed to stir at 82° C. for 72 hours. The reaction mixture was filtered and the solids were washed with hexanes. The filtrate was concentrated in vacuo to provide the crude product. Purification by ISCO silica flash chromatography (0-20% MeOH/DCM) provided methyl N-(2-(didodecylamino)ethyl)-N-dodecylglycinate (652 mg, 62%).

UPLC/ELSD: RT=3.77 min. MS (ES): m/z (MH$^+$) 638.18 for $C_{41}H_{84}N_2O_2$ $^1$H-NMR (300 MHz, CDCl$_3$) δ: ppm 3.72 (s, 3H); 3.41 (s, 2H); 2.90-2.20 (br. m, 10H); 1.60-1.00 (br. m, 60H); 0.90 (t, 9H).

N-(2-(Didodecylamino)ethyl)-N-dodecylglycine

Compound 393

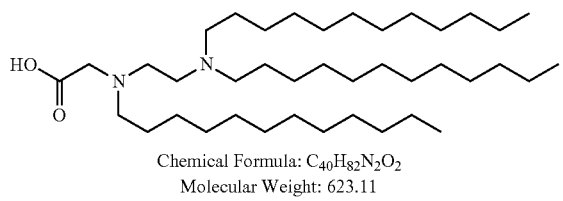 [SMILES: CCCCCCCCCCCCN(CCCCCCCCCCCC)CCN(CCCCCCCCCCCC)CC(=O)O]

Chemical Formula: $C_{40}H_{82}N_2O_2$
Molecular Weight: 623.11

A solution of methyl N-(2-(didodecylamino)ethyl)-N-dodecylglycinate (652 mg, 1.02 mmol) in THF (6 mL) and 1M LiOH (5 mL, 5 mmol) was allowed to stir at 65° C. for 16 hours. The reaction was cooled to room temperature and acidified with 10% HCl. The mixture was extracted with chloroform, and the organics were washed with brine, dried over anhydrous Na$_2$SO$_4$, filtered, and concentrated in vacuo. Purification by ISCO silica flash chromatography (0-20% MeOH/DCM) provided N-(2-(didodecylamino)ethyl)-N-dodecylglycine (153 mg, 24%).

UPLC/ELSD: RT=3.60 min. MS (ES): m/z (MH$^+$) 624.07 for $C_{40}H_{82}N_2O_2$ $^1$H-NMR (300 MHz, CDCl$_3$) δ: ppm 4.02-3.40 (br. m, 6H); 3.16 (br, 6H); 1.78 (br, 6H); 1.46-1.01 (br. m, 54H); 0.90 (t, 9H).

Compound 125: 3-((8-(Heptadecan-9-yloxy)-8-oxooctyl)(8-(nonyloxy)-8-oxooctyl)amino)propanoic Acid

Heptadecan-9-yl 8-bromooctanoate

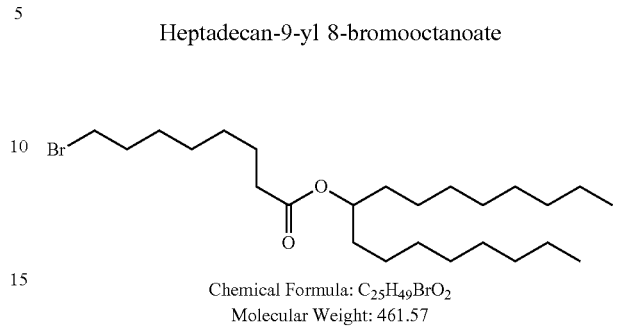

Chemical Formula: $C_{25}H_{49}BrO_2$
Molecular Weight: 461.57

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at rt for 18 h. The reaction was diluted with dichloromethane and washed with saturated sodium bicarbonate. The organic layer was separated and washed with brine, and dried over MgSO$_4$. The organic layer was filtered and evaporated in vacuo. The residue was purified by silica gel chromatography (0-10% ethyl acetate in hexanes) to obtain heptadecan-9-yl 8-bromooctanoate (875 mg, 1.9 mmol, 41%).

$^1$H NMR (300 MHz, CDCl$_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Nonyl 8-bromooctanoate

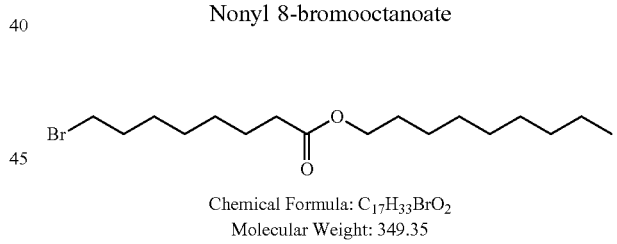

Chemical Formula: $C_{17}H_{33}BrO_2$
Molecular Weight: 349.35

To a solution of 8-bromooctanoic acid (5 g, 22 mmol) and nonan-1-ol (6.46 g, 45 mmol) in dichloromethane (100 mL) were added N-(3-Dimethylaminopropyl)-N'-ethylcarbodiimide hydrochloride (4.3 g, 22 mmol) and DMAP (547 mg, 4.5 mmol). The reaction was allowed to stir at rt for 18 h. The reaction was diluted with dichloromethane and washed with saturated sodium bicarbonate. The organic layer was separated and washed with brine, dried over MgSO$_4$. The organic layer was filtered and evaporated under vacuum. The residue was purified by silica gel chromatography (0-10% ethyl acetate in hexanes) to obtain nonyl 8-bromooctanoate (6.1 g, 17 mmol, 77%).

$^1$H NMR (300 MHz, CDCl$_3$) δ: ppm 4.06 (t, 2H); 3.40 (t, 2H); 2.29 (t, 2H); 1.85 (m, 2H); 1.72-0.97 (m, 22H); 0.88 (m, 3H).

Heptadecan-9-yl 8-((3-hydroxypropyl)amino)octanoate

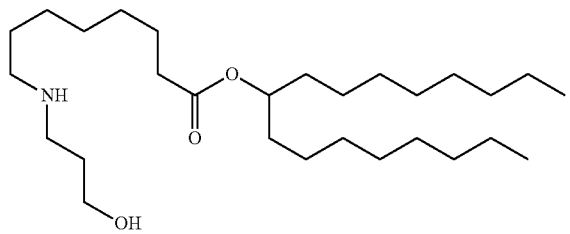

Chemical Formula: C$_{28}$H$_{57}$NO$_3$
Molecular Weight: 455.77

A solution of 8.87 g (19.2 mmol) heptadecan-9-yl 8-bromooctanoate and 29 mL (384 mmol) 3-aminopropanol in 250 mL ethanol was heated to 50° C. and stirred for 20 hours, after which no starting bromide remained by LC/MS. The solution was allowed to cool to room temp., conc., and the residue dissolved in DCM. The solution was washed twice with a 5% aqueous sodium bicarbonate solution, dried (Na$_2$SO$_4$), filtered and the filtrate conc. to a colorless oil. This was chromatographed on silica with 100% DCM going to 10% DCM/90% 80:20:1 DCM/MeOH/NH$_4$OH to give heptadecan-9-yl 8-((3-hydroxypropyl)amino)octanoate (7.98 g, 17.5 mmol, 91%) as a colorless oil.

UPLC/ELSD: RT=2.52 min. MS (ES): m/z (MH$^+$) 456.8 for C$_{28}$H$_{57}$NO$_3$.

$^1$H NMR (300 MHz, CDCl$_3$) δ: ppm 4.86 (quint., 1H, J=6 Hz); 3.81 (t, 2H, J=7.5 Hz); 2.88 (t, 2H, J=7.5 Hz); 2.60 (t, 2H, J=7.5 Hz); 2.44 (br. s, 1H); 2.27 (t, 2H, J=7.5 Hz); 1.70 (m, 2H); 1.61 (m, 2H); 1.49 (m, 6H); 1.25 (br. m, 31H); 0.88 (t, 6H, J=7.5 Hz).

Heptadecan-9-yl 8-((3-hydroxypropyl)(8-(nonyloxy)-8-oxooctyl)amino) octanoate

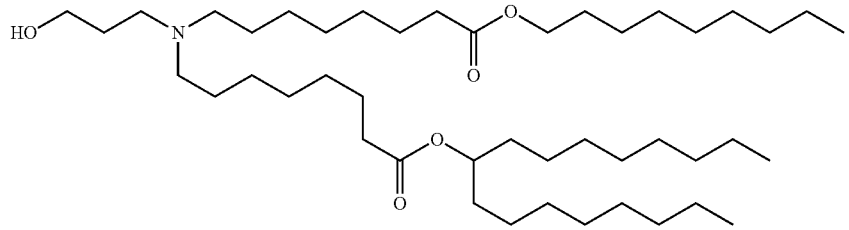

Chemical Formula: C$_{45}$H$_{89}$NO$_5$
Molecular Weight: 724.21

To a mixture of 7.98 g (17.5 mmol) heptadecan-9-yl 8-((3-hydroxypropyl)amino)octanoate and 6.12 g (17.5 mmol) nonyl 8-bromooctanoate in 100 mL dry acetonitrile under dry nitrogen was added 3.2 g (19.3 mmol) potassium iodide followed by 9.7 g (70 mmol) potassium carbonate and the mixture diluted with 25 mL dry cyclopentyl methyl ether. The resulting white mixture was heated to 90° C. and stirred for 28 hours, then allowed to cool to room temp., filtered, the filter solids washed with DCM and the filtrate conc. The residue was partitioned between a 5% aqueous sodium bicarbonate solution and DCM, the phases separated and the aqueous extracted twice with DCM. The organics were combined, dried (MgSO$_4$), filtered and the filtrate conc. to a yellow oil. This was chromatographed on silica with 100% DCM going to 50% DCM/50% 80:20:1 DCM:MeOH:NH$_4$OH to give heptadecan-9-yl 8-((3-hydroxypropyl)(8-(nonyloxy)-8-oxooctyl)amino)octanoate (10.14 g, 14 mmol, 80%) as a pale yellow oil.

$^1$H NMR (300 MHz, CDCl$_3$) δ: ppm 4.86 (p, 1H); 4.05 (t, 2H); 3.80 (m, 2H); 2.92-2.36 (br. m, 5H); 2.29 (m, 4H); 1.89-1.42 (br. m, 16H); 1.42-1.02 (br. m, 50H); 0.88 (m, 9H).

UPLC/ELSD: RT=4.51 min. MS (ES): m/z (MH$^+$) 725.19 for C$_{45}$H$_{89}$NO$_5$.

Heptadecan-9-yl 8-((8-(nonyloxy)-8-oxooctyl)amino)octanoate

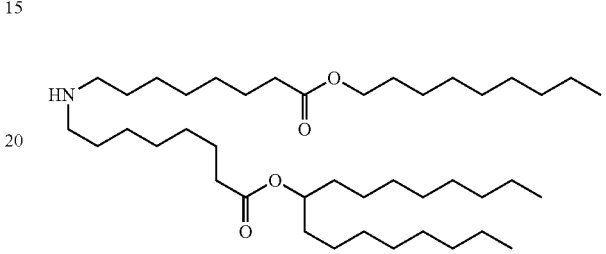

Chemical Formula: C$_{42}$H$_{83}$NO$_4$
Molecular Weight: 666.13

At −78° C., to a solution of oxalyl chloride (0.25 mL, 3.0 mmol) in 3 mL dichloromethane was added dropwise a solution of DMSO (0.43 mL, 6.0 mmol) in 2 mL dichloromethane, and then a solution of heptadecan-9-yl 8-((3-hydroxypropyl)(8-(nonyloxy)-8-oxooctyl)amino)octanoate (1.45 g, 2.0 mmol) in dichloromethane (10 mL) was added immediately. After it was stirred for 30 min at this temperature, triethylamine (1.45 mL, 10.4 mmol) was added and the reaction mixture was warmed up to room temperature. TLC and MS showed complete reaction (M+1: 722.7), and the reaction mixture was diluted with water and extracted with hexanes (2×). The combined organic layer was washed with brine. After drying over sodium sulfate, the filtrate was concentrated and the residue was purified by ISCO (SiO$_2$: EtOAc/Hexanes/0.5% Et$_3$N 0 to 50%) to afford the product as a brown oil (810 mg, 61%).

$^1$H NMR (300 MHz, CDCl$_3$) δ: ppm 4.85 (p, 1H, J=6.0 Hz); 4.05 (t, 2H, J=6.9 Hz); 2.56 (t, 4H, J=7.1 Hz); 2.31-2.24 (m, 4H); 1.67-1.19 (m, 63H); 0.87 (m, 9H).

MS (APCI): m/z (MH$^+$) 666.7.

Heptadecan-9-yl 8-((3-(benzyloxy)-3-oxopropyl)(8-(nonyloxy)-8-oxooctyl)amino)octanoate

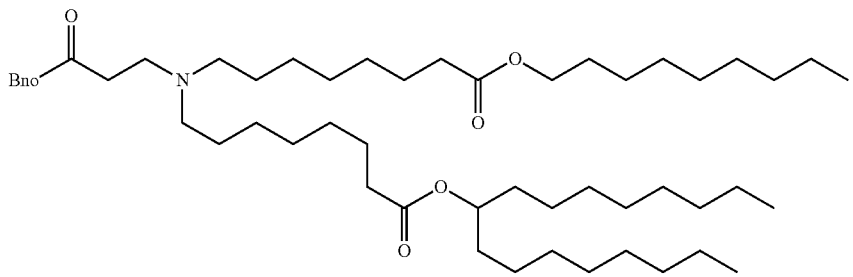

Chemical Formula: C₅₂H₉₃NO₆
Molecular Weight: 828.32

A solution of heptadecan-9-yl 8-((8-(nonyloxy)-8-oxooctyl)amino)octanoate (798 mg, 1.2 mmol) and benzyl acrylate (293 mg, 1.8 mmol) in dichloromethane (20 mL) was stirred at room temperature for 16 h. TLC and MS showed almost no reaction, 10 mL MeOH was added and the reaction mixture was stirred at room temperature for 16 h. MS showed the product with a small amount of methyl ester (M+1: 829.8, 752.7). The reaction mixture was concentrated to dryness and purified by ISCO (SiO$_2$: EtOAc/hexanes 0 to 35%) to afford the product as a colorless oil (280 mg, 28%).

$^1$H NMR (300 MHz, CDCl$_3$) δ: ppm 7.36-7.32 (m, 5H); 5.10 (s, 2H); 4.85 (p, 1H, J=6.0 Hz); 4.04 (t, 2H, J=6.9 Hz); 2.78 (t, 2H, J=6.9 Hz); 2.46 (t, 2H, J=7.0 Hz); 2.36 (t, 4H, J=6.9 Hz); 2.30-2.24 (m, 4H); 1.67-1.19 (m, 62H); 0.87 (m, 9H).

MS (APCI): m/z (MH$^+$) 829.8.

3-((8-(Heptadecan-9-yloxy)-8-oxooctyl)(8-(nonyloxy)-8-oxooctyl)amino)propanoic Acid Compound 125

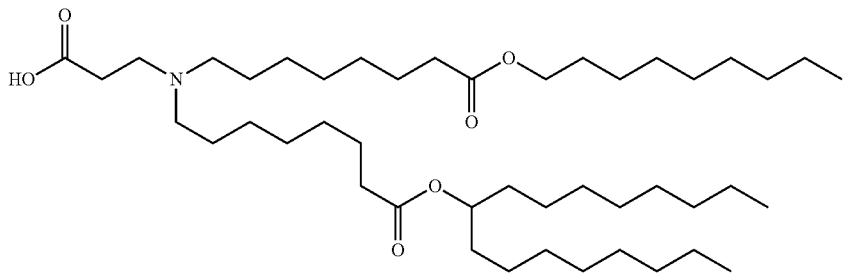

Chemical Formula: C₄₅H₈₇NO₆
Molecular Weight: 738.19

A mixture of heptadecan-9-yl 8-((3-(benzyloxy)-3-oxopropyl)(8-(nonyloxy)-8-oxooctyl)amino)octanoate (280 mg, 0.34 mmol) and Pd/C (10%, 28 mg) in 20 mL EtOAc was stirred under hydrogen balloon for 1 h. MS showed complete reaction. The reaction mixture was filtered and the filtrate was concentrated. The residue was purified by ISCO (SiO$_2$: MeOH/CH$_2$Cl$_2$ 0 to 10%) to afford the product as a colorless oil (230 mg, 91%).

$^1$H NMR (300 MHz, CDCl$_3$) δ: ppm 4.85 (p, 1H, J=6.0 Hz); 4.04 (t, 2H, J=6.6 Hz); 2.85 (t, 2H, J=6.0 Hz); 2.65 (t, 4H, J=7.7 Hz); 2.48 (t, 2H, J=6.0 Hz); 2.32-2.24 (m, 4H); 1.67-1.17 (m, 63H); 0.87 (m, 9H).

LC/UV (214 nm): RT=12.38 min.
MS (APCI): m/z (MH$^+$) 838.7.

Compound 154 3-(((2-Cyanoethoxy)(diisopropylamino)phosphino)oxy)propane-1,2-diyl dipalmitate 4-((Benzyloxy)methyl)-2,2-dimethyl-1,3-dioxolane
(Ref: EP1916255 A2, Pg 29)

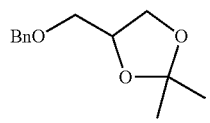

Chemical Formula: C₁₃H₁₈O₃
Molecular Weight: 222.28

At 0° C., to a mixture of NaH (60%, 4.4 g, 0.11 mole) in THF/DMF (25 mL/120 mL), a solution of (2,2-dimethyl-1,3-dioxolan-4-yl)methanol (13.2 g, 0.1 mole) in THF/DMF (25 mL/25 mL) was added dropwise. After addition, the mixture was stirred for 1 h, and then benzyl chloride (12.6 mL, 0.11 mole) was added. The mixture was warmed up to room temperature and stirred for 16 h. After confirmed the completion by TLC, the reaction was quenched with saturated ammonium chloride (300 mL) and extracted with ether (2×300 mL). The combined organic layer was washed with brine and dried over sodium sulfate. After filtration and concentration by vacuum, 4-((benzyloxy)methyl)-2,2-dimethyl-1,3-dioxolane was obtained as brown oil (23.3 g, quant.) which was used for the next step without further purification.

$^1$H NMR (300 MHz, CDCl$_3$) δ 7.25-7.41 (m, 5H), 4.52-4.61 (m, 2H), 4.25-4.34 (m, 1H), 4.02-4.08 (m, 1H), 3.71-3.78 (m, 1H), 3.43-3.58 (m, 2H), 1.41 (s, 3H), 1.35 (s, 3H).

3-(Benzyloxy)propane-1,2-diol (Ref: EP1916255 A2, Pg 30)

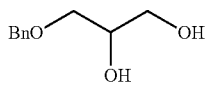

Chemical Formula: C₁₀H₁₄O₃
Molecular Weight: 182.22

To a solution of 4-((benzyloxy)methyl)-2,2-dimethyl-1,3-dioxolane (23.3 g, 0.1 mole) in 150 mL MeOH, 1 N HCl (40 mL) was added, and the mixture was stirred at room temperature for 16 h. After confirmed the completion by TLC, the reaction mixture was neutralized by saturated sodium bicarbonate to pH=7, and extracted with dichloromethane (4×300 mL). The combined organic layer was washed with brine and dried with sodium sulfate. After filtration and concentration by vacuum, the crude was purified with ISCO (330 g SiO₂: EtOAc/Hexanes 0 to 100%) to get 3-(benzyloxy)propane-1,2-diol as light yellow oil (13.39 g, 73%).
¹H NMR (300 MHz, CDCl₃) δ 7.25-7.38 (m, 5H), 4.55 (s, 2H), 3.54-3.75 (m, 4H), 3.85-3.95 (m, 1H), 2.62 (t, 1H, J=4.7 Hz), 2.12 (m, 1H).

3-(Benzyloxy)propane-1,2-diyl dipalmitate (Ref: EP1916255 A2, Pg 30)

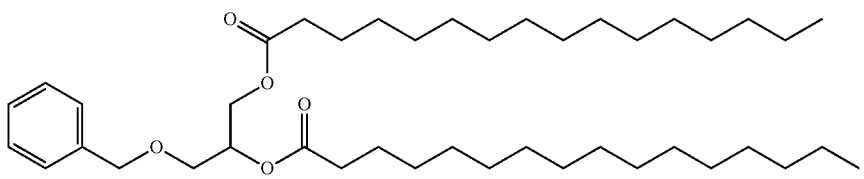

Chemical Formula: C₄₂H₇₄NO₅
Molecular Weight: 659.05

A mixture of 3-(benzyloxy)propane-1,2-diol (7.57 g, 41.5 mmol), palmitic acid (21.3 g, 83 mmol), EDCI (17.5 g, 91.4 mmol) and DMAP (1.02 g, 8.3 mmol) in 150 mL dichloromethane was stirred at room temperature for 48 h. The reaction mixture was diluted with water, extracted with dichloromethane (2×500 mL), and the combined organic layer was washed with brine and dried over sodium sulfate. After filtration and concentration under vacuum, the crude was purified by dissolving in hexanes and filtering through a pad of silica gel, and then eluted with EtOAc/Hexanes 0 to 20% to give 3-(benzyloxy)propane-1,2-diyl dipalmitate as colorless oil (21.0 g, 76%).

¹H NMR (300 MHz, CDCl₃) δ 7.27-7.33 (m, 5H), 5.31-5.36 (m, 1H), 5.29 (s, 2H), 5.21-5.26 (m, 1H), 4.53 (dd, 2H, J=12.3 Hz, 15.8 Hz), 4.33 (dd, 1H, J=11.8 Hz, 3.8 Hz), 4.18 (dt, 1H, J=12.0 Hz, 6.4 Hz), 3.58 (d, 2H, J=5.2 Hz), 2.24-2.33 (m, 4H), 1.95-2.02 (m, 2H), 1.55-1.63 (m, 3H), 1.24 (bs, 44H), 0.87 (t, 6H, J=6.8 Hz).

3-Hydroxypropane-1,2-diyldipalmitate

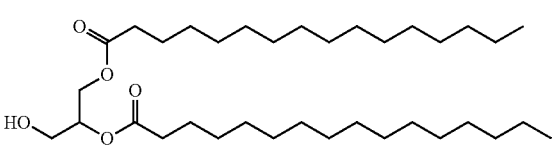

Chemical Formula: C₃₅H₆₈O₅
Molecular Weight: 568.92

A mixture of 3-(benzyloxy)propane-1,2-diyl dipalmitate (5.14 g, 7.8 mmol) and Pd/C (5%, Degaussa E10002U/W, Aldrich 330124, 514 mg) in 100 mL EtOAc was purged with nitrogen and hydrogen 3 times, respectively, and then the reaction was stirred at room temperature with balloon for 16 h. The suspension was filtered through Celite, washed with dichloromethane (300 mL). After concentration under vacuum, the residue was purified with ISCO (80 g SiO₂: EtOAc/Hexanes 0 to 40% to give 3-hydroxypropane-1,2-diyl dipalmitate as white solid (3.17 g, 71%).

¹H NMR (300 MHz, CDCl₃) δ 5.07 (pent, 1H, J=5.2 Hz), 4.27 (ddd, 2H, J=4.4 Hz, 11.9 Hz, 24.9 Hz), 3.72 (t, 2H, J=4.9 Hz), 2.33 (q, 4H, J=7.1 Hz), 1.99 (t, 1H, J=6.6 Hz), 1.56-1.66 (m, 4H), 1.24 (bs, 48H), 0.87 (t, 6H, J=6.8 Hz).

Step 5: 3-(((2-Cyanoethoxy)(diisopropylamino)phosphino)oxy)propane-1,2-diyldipalmitate

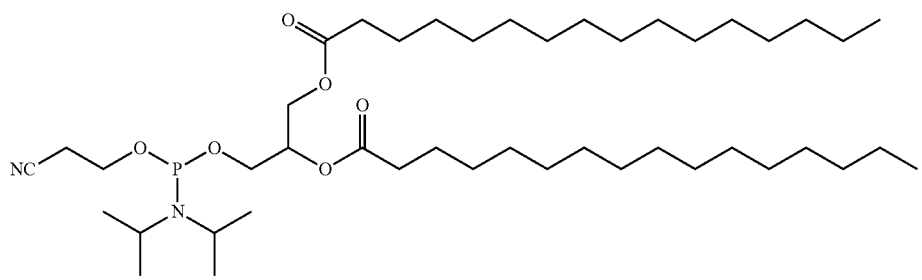

Chemical Formula: C₄₄H₈₅N₂O₆P
Molecular Weight: 769.15

To a solution of 3-hydroxypropane-1,2-diyl dipalmitate (2.70 g, 4.75 mmol) and tetrazole (0.45 M in MeCN, 21 mL, 9.490 mmol) in 80 mL dichloromethane, a solution of 3-((chloro(diisopropylamino)phosphino)oxy)propanenitrile (3.0 mL, 9.49 mmol) in 20 mL dichloromethane was added dropwise and the reaction mixture was stirred at room temperature for 1 h. The mixture was concentrated and purified by ISCO (80 g SiO$_2$: EtOAc/Hexanes (1% Et$_3$N) 0 to 10%) to give 3-(((2-cyanoethoxy)(diisopropylamino)phosphino)oxy)propane-1,2-diyl dipalmitate as white solid (3.22 g, 88%). The yield can be improved by pre-eluting the column with excess hexanes/1% Et$_3$N.

$^1$H NMR (300 MHz, CDCl$_3$) δ 5.14-5.21 (m, 1H), 4.33 (dt, 1H, J=11.2 Hz, 3.8 Hz), 4.11-4.20 (m, 1H), 3.56-3.87 (m, 5H), 2.62 (t, 2H, J=6.6 Hz), 2.29 (t, 4H, J=7.9 Hz), 1.55-1.64 (m, 3H), 1.24 (bs, 50H), 1.17 (d, 6H, J=6.8 Hz), 1.16 (d, 6H, J=6.8 Hz), 0.87 (t, 6H, J=6.3 Hz).

3-Hydroxy-N,N,N-trimethylpropan-1-aminium tosylate (Ref: *Eur. J. Med. Chem.* 2013, 66, 46)

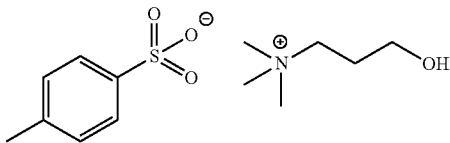

Chemical Formula: C$_{13}$H$_{23}$NO$_4$S
Molecular Weight: 289.39

A solution of 3-(dimethylamino)propan-1-ol (2.27 g, 22 mmol) and methyl tosylate (3.0 mL, 20 mmol) in 20 mL MeCN was heated to reflux for 4 h. The reaction mixture was concentrated under vacuum and precipitated in acetone to give 3-hydroxy-N,N,N-trimethylpropan-1-aminium tosylate as white solid (5.50 g, 86%).

$^1$H NMR (300 MHz, DMSO-d$_6$) δ 7.47 (d, 2H, J=7.9 Hz), 7.11 (d, 2H, J=7.9 Hz), 4.80 (t, 1H, J=4.9 Hz), 3.47 (q, 2H, J=5.8 Hz), 3.34 (m, 2H), 3.04 (s, 9H), 2.28 (s, 3H), 1.79-1.85 (m, 2H).

3-(((2,3-Bis(palmitoyloxy)propoxy)(2-cyanoethoxy)phosphoryl)oxy)-N,N,N-trimethylpropan-1-aminium chloride

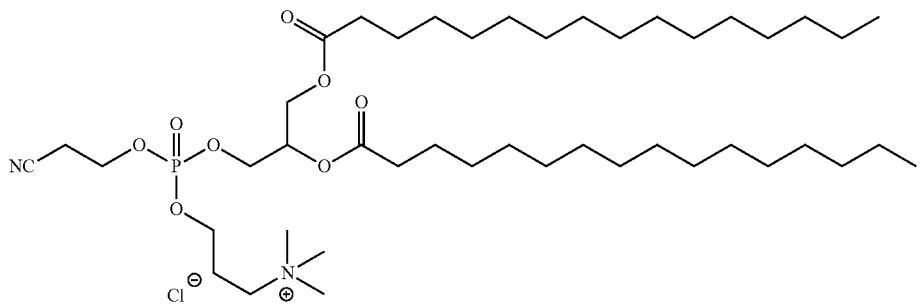

Chemical Formula: C$_{44}$H$_{86}$ClN$_2$O$_8$P
Molecular Weight: 837.60

To a solution of 3-(((2-cyanoethoxy)(diisopropylamino)phosphino)oxy)propane-1,2-diyl dipalmitate (769 mg, 1.0 mmol) and 3-hydroxy-N,N,N-trimethylpropan-1-aminium tosylate (289 mg, 1.0 mmol) in 10 mL dichloromethane, a solution of tetrazole in MeCN (0.45 M, 2.2 mL, 1.0 mmol) was added slowly, and then the reaction was stirred at room temperature for 16 h. After confirmed the disappearance of 3-(((2-cyanoethoxy)(diisopropylamino)phosphino)oxy)propane-1,2-diyl dipalmitate, $^t$BuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g SiO$_2$: MeOH/dichloromethane 0 to 10%) to give 3-(((2,3-bis(palmitoyloxy)propoxy)(2-cyanoethoxy) phosphoryl)oxy)-N,N,N-trimethylpropan-1-aminium chloride as white solid (407 mg, 48%).

$^1$H NMR (300 MHz, CDCl$_3$) δ 5.20-5.28 (m, 1H), 4.15-4.35 (m, 4H), 3.71-3.82 (m, 2H), 3.31 (s, 9H), 2.83 (m, 2H), 2.20-2.36 (m, 7H), 1.98 (s, 3H), 1.53-1.65 (m, 4H), 1.24 (bs, 48H), 0.87 (t, 6H, J=6.6 Hz).

2,3-Bis(palmitoyloxy)propyl (3-(trimethylammonio)propyl) phosphate

Compound 154

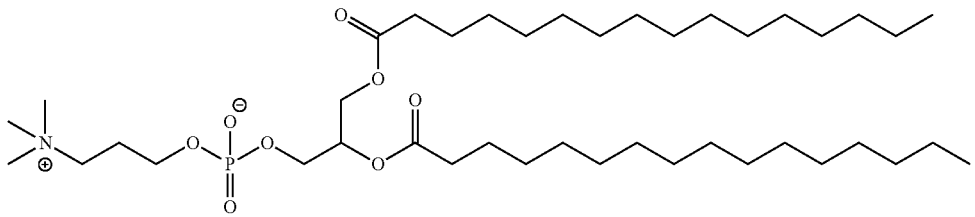

Chemical Formula: $C_{41}H_{82}NO_8P$

Molecular Weight: 748.08

A solution of 3-(((2,3-bis(palmitoyloxy)propoxy)(2-cyanoethoxy)phosphoryl)oxy)-N,N,N-trimethylpropan-1-aminium chloride (407 mg, 0.48 mmol) and diisopropylethylamine (0.62 mL, 3.5 mmol) in 20 mL MeCN was heated to 60° C. for 16 h. The reaction mixture was concentrated under vacuum and purified by ISCO (gold 24 g $SiO_2$: MeOH/dichloromethane 0 to 60%) to provide the desired product, 2,3-bis(palmitoyloxy)propyl (3-(trimethylammonio)propyl) phosphate as white solid (280 mg, 78%).

$^1$H NMR (300 MHz, $CDCl_3$) δ 5.20 (m, 1H), 4.40 (dd, 1H, J=12.2 Hz, 2.7 Hz), 4.13 (dd, 1H, J=11.7 Hz, 7.1 Hz), 3.93-4.03 (m, 4H), 3.82-3.88 (m, 2H), 3.28 (s, 9H), 2.23-2.30 (m, 4H), 2.13 (m, 2H), 1.56 (m, 4H), 1.24 (bs, 48H), 0.87 (t, 6H, J=6.6 Hz).

Compound 155: 2,3-Bis(palmitoyloxy)propyl (2-(4-methylmorpholino-4-ium)ethyl) phosphate S4-(2-Hydroxyethyl)-4-methylmorpholin-4-ium 4-methylbenzenesulfonate (Ref: *Eur. J. Med. Chem.* 2009, 44, 4970)

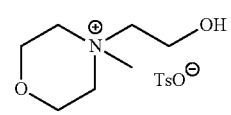

Chemical Formula: $C_{14}H_{23}NO_5S$
Molecular Weight: 317.40

A solution of 2-morpholinoethan-1-ol (2.7 mL, 22 mmol) and methyl tosylate (3.0 mL, 20 mmol) in 20 mL MeCN was heated to reflux for 4 h. The reaction mixture was concentrated under vacuum and precipitated in acetone to give 3-hydroxy-4-methylmorpholin-4-ium 4-methylbenzenesulfonate as brownish solid (5.57 g, 87%).

$^1$H NMR (300 MHz, DMSO-$d_6$) δ 7.47 (d, 2H, J=8.0 Hz), 7.11 (d, 2H, J=8.0 Hz), 5.32 (t, 1H, J=4.8 Hz), 3.86-3.96 (m, 6H), 3.38-3.58 (m, 6H), 3.19 (s, 3H), 2.28 (s, 3H).

4-(2-(((2,3-Bis(palmitoyloxy)propoxy)(2-cyanoethoxy)phosphoryl)oxy)ethyl)-4-methylmorpholin-4-ium chloride

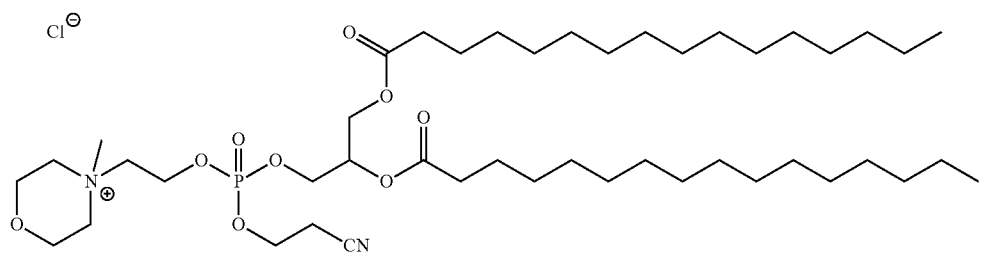

Chemical Formula: $C_{45}H_{86}ClN_2O_9P$
Molecular Weight: 865.61

To a solution of 3-(((2-cyanoethoxy)(diisopropylamino)phosphino)oxy)propane-1,2-diyl dipalmitate (769 mg, 1.0 mmol) 3-hydroxy-4-methylmorpholin-4-ium 4-methylbenzenesulfonate (317 mg, 1.0 mmol) in 10 mL dichloromethane, a solution of tetrazole in MeCN (0.45 M, 2.2 mL, 1.0 mmol) was added slowly, and then the reaction was stirred at room temperature for 48 h. After confirmed the disappearance of 3-(((2-cyanoethoxy)(diisopropylamino)phosphino)oxy)propane-1,2-diyl dipalmitate, $^t$BuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to give 4-(2-(((2,3-bis(palmitoyloxy)propoxy)(2-cyanoethoxy)phosphoryl)oxy)ethyl)-4-methylmorpholin-4-ium chloride as white solid (713 mg, 86%).

$^1$H NMR (300 MHz, $CDCl_3$) δ 5.24 (m, 1H), 4.73 (m, 2H), 4.11-4.38 (m, 7H), 4.02 (m, 3H), 3.67 (m, 3H), 3.48 (m, 2H), 2.58-2.83 (m, 5H), 2.27-2.34 (m, 5H), 1.58 (m, 4H), 1.19-1.34 (bs, 48H), 0.87 (t, 6H, J=6.6 Hz).

2,3-Bis(palmitoyloxy)propyl (2-(4-methylmorpholino-4-ium)ethyl) phosphate Compound 155

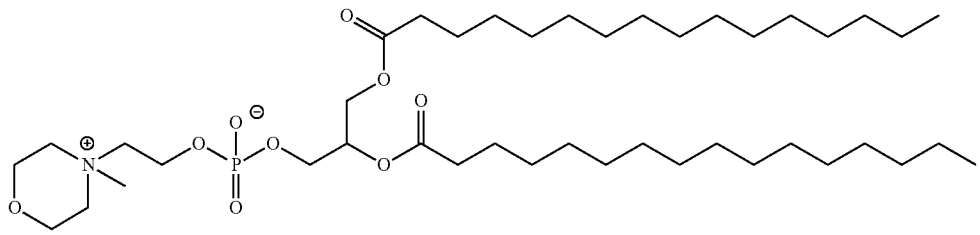

Chemical Formula: C₄₂H₈₂NO₉P
Molecular Weight: 776.09

A solution of 4-(2-(((2,3-bis(palmitoyloxy)propoxy)(2-cyanoethoxy)phosphoryl)oxy)ethyl)-4-methylmorpholin-4-ium chloride (713 mg, 0.86 mmol) and diisopropylethylamine (1.05 mL, 6.0 mmol) in 20 mL MeCN was heated to 60° C. for 16 h. The reaction mixture was concentrated under vacuum and purified by ISCO (gold 24 g SiO₂: MeOH/dichloromethane 0 to 60%) to provide the desired product, 2,3-bis(palmitoyloxy)propyl (2-(4-methylmorpholino-4-ium)ethyl) phosphate as white solid (446 mg, 67%).

¹H NMR (300 MHz, CDCl₃) δ 5.20 (m, 1H), 4.36-4.42 (m, 3H), 4.10 (dd, 1H, J=12.1 Hz, 7.4 Hz), 3.90-4.02 (m, 6H), 3.69 (m, 4H), 3.50 (m, 1H), 2.28 (q, 8H, J=6.8 Hz), 1.52-1.61 (m, 4H), 1.24 (bs, 48H), 0.87 (t, 6H, J=7.1 Hz).

Compound 156: 2,3-Bis(palmitoyloxy)propyl (4-(trimethylammonio)butyl) phosphate

4-Hydroxy-N,N,N-trimethylbutan-1-aminium 4-methylbenzenesulfonate (Ref: *Eur. J. Med. Chem.* 2013, 66, 46)

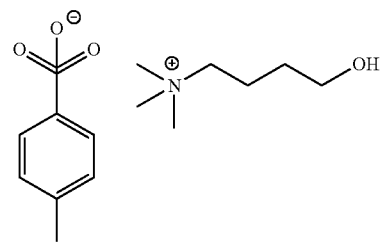

Chemical Formula: C₁₄H₂₅NO₄S
Molecular Weight: 303.42

A solution of 4-(dimethylamino)butan-1-ol (2.58 g, 22 mmol) and methyl tosylate (3.0 mL, 20 mmol) in 20 mL MeCN was heated to reflux for 16 h. The reaction mixture was concentrated under vacuum and precipitated in acetone to give 4-Hydroxy-N,N,N-trimethylbutan-1-aminium 4-methylbenzenesulfonate as white solid (5.13 g, 84%).

¹H NMR (300 MHz, DMSO-d₆) δ 7.46 (d, 2H, J=8.0 Hz), 7.11 (d, 2H, J=8.0 Hz), 4.58 (t, 1H, J=4.9 Hz), 3.43 (q, 2H, J=5.2 Hz), 3.24-3.30 (m, 2H), 3.02 (s, 9H), 2.28 (s, 3H), 1.64-1.73 (m, 2H), 1.36-1.45 (m, 2H).

4-(((2,3-Bis(palmitoyloxy)propoxy)(2-cyanoethoxy)phosphoryl)oxy)-N,N,N-trimethylbutan-1-aminium chloride

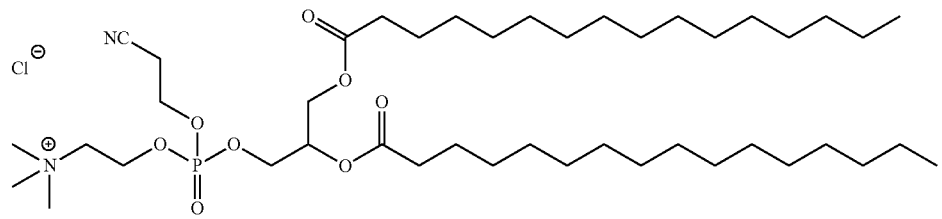

Chemical Formula: C₄₅H₈₈ClN₂O₈P
Molecular Weight: 851.63

To a solution of 3-(((2-cyanoethoxy)(diisopropylamino)phosphino)oxy)propane-1,2-diyl dipalmitate (769 mg, 1.0 mmol) 34-Hydroxy-N,N,N-trimethylbutan-1-aminium 4-methylbenzenesulfonate (303 mg, 1.0 mmol) in 10 mL dichloromethane, a solution of tetrazole in MeCN (0.45 M, 2.2 mL, 1.0 mmol) was added slowly, and then the reaction was stirred at room temperature for 16 h. After confirmed the disappearance of 3-(((2-cyanoethoxy)(diisopropylamino)phosphino)oxy)propane-1,2-diyl dipalmitate, ᵗBuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to give 4-(((2,3-bis(palmitoyloxy)propoxy)(2-cyanoethoxy)phosphoryl)oxy)-N,N,N-trimethylbutan-1-aminium chloride as white solid (531 mg, 65%).

$^1$H NMR (300 MHz, $CDCl_3$) δ 5.22-5.26 (m, 1H), 4.11-4.35 (m, 8H), 3.62-3.68 (m, 2H), 3.31 (s, 9H), 2.78-2.84 (m, 2H), 2.32 (q, 4H, J=7.6 Hz), 1.52-2.01 (m, 8H), 1.15-1.32 (m, 48H), 0.87 (t, 6H, J=7.1 Hz).

2,3-Bis(palmitoyloxy)propyl (4-(trimethylammonio)butyl) phosphate Compound 156

Chemical Formula: $C_{42}H_{84}NO_8P$

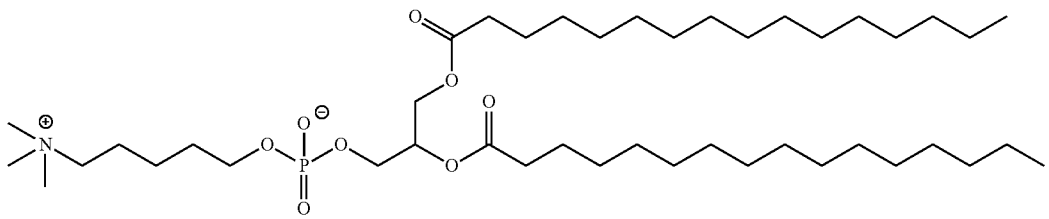

Molecular Weight: 762.11

A solution of 4-(((2,3-bis(palmitoyloxy)propoxy)(2-cyanoethoxy)phosphoryl)oxy)-N,N,N-trimethylbutan-1-aminium chloride (531 mg, 0.65 mmol) and diisopropylethylamine (0.79 mL, 4.56 mmol) in 20 mL MeCN was heated to 60° C. for 16 h. The reaction mixture was concentrated under vacuum and purified by ISCO (gold 24 g $SiO_2$: MeOH/dichloromethane 0 to 60%) to provide the desired product, 2,3-bis(palmitoyloxy)propyl (4-(trimethylammonio)butyl) phosphate as a white solid (383 mg, 77%).

$^1$H NMR (300 MHz, $CDCl_3$) δ 5.20 (m, 1H), 4.40 (dd, 1H, J=11.9 Hz, 2.7 Hz), 4.15 (dd, 1H, J=11.9 Hz, 6.8 Hz), 3.89-3.98 (m, 4H), 3.65-3.72 (m, 2H), 3.29 (s, 9H), 2.22-2.34 (m, 6H), 1.94-2.02 (m, 2H), 1.69-1.73 (m, 2H), 1.15-1.61 (m, 2H), 1.24 (bs, 48H), 0.87 (t, 6H, J=7.1 Hz).

Compound 150: 2,3-Bis(palmitoyloxy)propyl (2-(triethylammonio)ethyl) phosphate 2-(((2,3-Bis(palmitoyloxy)propoxy)(2-cyanoethoxy)phosphanyl)oxy)-N,N,N-triethylethan-1-aminium chloride

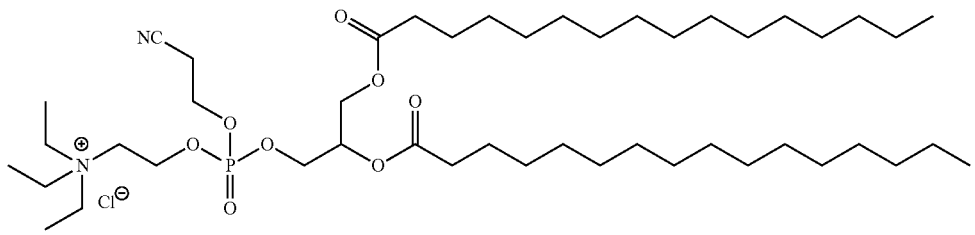

Chemical Formula: $C_{46}H_{90}ClN_2O_8P$
Molecular Weight: 865.66

To a solution of 3-(((2-cyanoethoxy)(diisopropylamino)phosphino)oxy)propane-1,2-diyl dipalmitate (769 mg, 1.0 mmol) and N,N,N-triethyl-2-hydroxyethanaminium iodide (126 mg, 0.46 mmol) in 10 mL dichloromethane, a solution of tetrazole in MeCN (0.45 M, 1.03 mL, 0.46 mmol) was added slowly, and then the reaction was stirred at room temperature for 16 h. After confirmed the disappearance of of 3-(((2-cyanoethoxy)(diisopropylamino)phosphino)oxy)propane-1,2-diyl dipalmitate, $^t$BuOOH (0.37 mL, 1.84 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (12 g SiO$_2$: MeOH/dichloromethane 0 to 50%) to provide 2-(((2,3-bis(palmitoyloxy)propoxy)(2-cyanoethoxy)phosphanyl)oxy)-N,N,N-triethylethan-1-aminium chloride as yellow foam (180 mg, 45%).

$^1$H NMR (300 MHz, CDCl$_3$) δ 5.26 (m, 1H), 4.70 (m, 2H), 4.05-4.45 (m, 6H), 3.56 (q, 6H, J=7.1 Hz), 2.87 (m, 2H), 2.28-2.36 (m, 4H), 1.70 (m, 2H), 1.58 (m, 4H), 1.41 (t, 9H, J=7.1 Hz), 1.24 (bs, 48H), 0.87 (t, 6H, J=7.1 Hz).

2,3-Bis(palmitoyloxy)propyl (2-(triethylammonio)ethyl) phosphate Compound 150

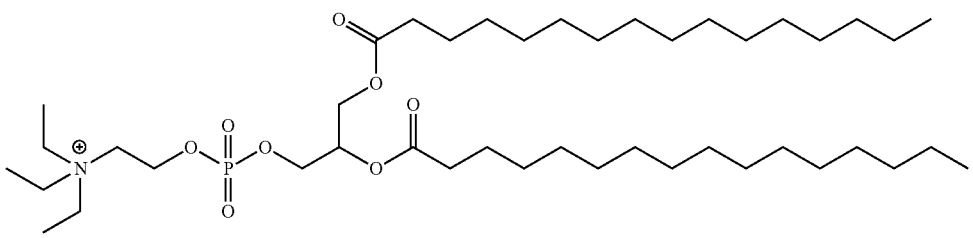

Chemical Formula: C$_{43}$H$_{86}$NO$_8$P
Molecular Weight: 776.13

A solution of 2-(((2,3-bis(palmitoyloxy)propoxy)(2-cyanoethoxy)phosphanyl)oxy)-N,N,N-triethylethan-1-aminium chloride (180 mg, 0.21 mmol) and diisopropylethylamine (0.27 mL, 1.53 mmol) in 5 mL MeCN was heated to 60° C. for 16 h. The reaction mixture was concentrated under vacuum and purified by ISCO (gold 12 g SiO$_2$: MeOH/dichloromethane 0 to 60%) to afford the desired product, 2,3-bis(palmitoyloxy)propyl (2-(triethylammonio)ethyl) phosphate as white solid (114 mg, 70%).

$^1$H NMR (300 MHz, CDCl$_3$) δ 5.21 (m, 1H), 4.41 (dd, 1H, J=11.9 Hz, 2.7 Hz), 4.31 (m, 2H), 4.15 (dd, 1H, J=11.9 Hz, 6.8 Hz), 4.01 (t, 2H, J=6.6 Hz), 3.51 (q, 8H, J=7.4 Hz), 2.28 (q, 4H, J=6.3 Hz), 1.71 (m, 4H), 1.37 (t, 9H, J=7.4 Hz), 1.24 (bs, 48H), 0.87 (t, 6H, J=7.1 Hz).

Compound 151: 2,3-Bis(palmitoyloxy)propyl (2-(tripropylammonio)ethyl) phosphate

N-(2-Hydroxyethyl)-N,N-dipropylpropan-1-aminium bromide (Ref: *Dalton Trans.* 2015, 44, 16680)

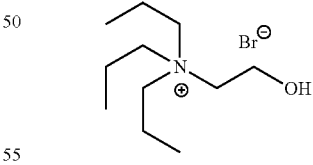

Chemical Formula: C$_{11}$H$_{26}$BrNO
Molecular Weight: 268.24

A solution of tripropylamine (3.8 mL, 20 mmol) and 2-bromoethanol (1.42 mL, 20 mmol) in 20 mL MeCN was heated to reflux for 16 h. The reaction mixture was concentrated and the residue was precipitated in hexanes/EtOAc mixture to get N-(2-hydroxyethyl)-N,N-dipropylpropan-1-aminium bromide as white solid (3.81 g, 71%).

$^1$H NMR (300 MHz, DMSO-d$_6$) δ 5.25 (t, 1H, J=5.2 Hz), 3.77 (m, 2H), 3.33 (t, 2H, J=7.1 Hz), 3.17-3.23 (m, 6H), 1.56-1.68 (m, 6H), 0.88 (t, 9H, J=7.1 Hz).

N-(2-(((2,3-Bis(palmitoyloxy)propoxy)(2-cyanoethoxy)phosphanyl)oxy)ethyl)-N,N-dipropylpropan-1-aminium chloride

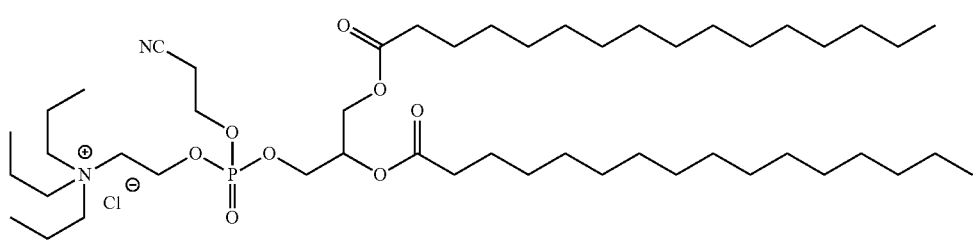

Chemical Formula: $C_{49}H_{96}ClN_2O_8P$
Molecular Weight: 907.74

To a solution of 3-(((2-cyanoethoxy)(diisopropylamino)phosphino)oxy)propane-1,2-diyl dipalmitate (769 mg, 1.0 mmol) and N-(2-hydroxyethyl)-N,N-dipropylpropan-1-aminium bromide (268 mg, 1.0 mmol) in 10 mL dichloromethane, a solution of tetrazole in MeCN (0.45 M, 2.2 mL, 1.0 mmol) was added slowly, and then the reaction was stirred at room temperature for 16 h. After confirmed the disappearance of 3-(((2-cyanoethoxy)(diisopropylamino)phosphino)oxy)propane-1,2-diyl dipalmitate, $^t$BuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 50%) to provide N-(2-(((2,3-bis(palmitoyloxy)propoxy)(2-cyanoethoxy)phosphanyl)oxy)ethyl)-N,N-dipropylpropan-1-aminium chloride as white foam (520 mg, 60%).

$^1$H NMR (300 MHz, $CDCl_3$) δ 5.26 (m, 1H), 4.64 (m, 2H), 4.10-4.42 (m, 6H), 3.97 (m, 2H), 3.31 (m, 6H), 2.87 (m, 2H), 2.32 (q, 4H, J=7.7 Hz), 1.54-2.00 (m, 10H), 1.24 (m, 48H), 1.03 (t, 9H, J=7.1 Hz), 0.87 (t, 6H, J=7.1 Hz).

2,3-Bis(palmitoyloxy)propyl (2-(tripropylammonio)ethyl) phosphate

Compound 151

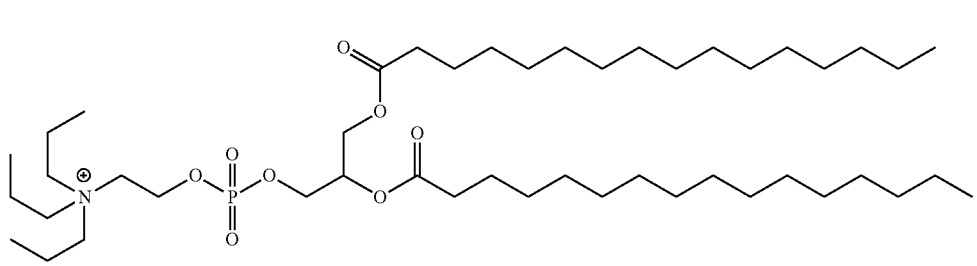

Chemical Formula: $C_{46}H_{92}NO_8P$
Molecular Weight: 818.21

A solution of N-(2-(((2,3-bis(palmitoyloxy)propoxy)(2-cyanoethoxy)phosphanyl)oxy)ethyl)-N,N-dipropylpropan-1-aminium chloride (520 mg, 0.60 mmol) and diisopropylethylamine (0.75 mL, 4.29 mmol) in 20 mL MeCN was heated to 60° C. for 16 h. The reaction mixture was concentrated under vacuum and purified by ISCO (gold 24 g $SiO_2$: MeOH/dichloromethane 0 to 60%) to afford the desired product, 2,3-bis(palmitoyloxy)propyl (2-(tripropylammonio)ethyl) phosphate as white solid (360 mg, 73%).

$^1$H NMR (300 MHz, $CDCl_3$) δ 5.20 (m, 1H), 4.41 (dd, 1H, J=11.9 Hz, 2.7 Hz), 4.28 (m, 2H), 4.13 (dd, 1H, J=11.9 Hz, 6.8 Hz), 4.00 (t, 2H, J=6.6 Hz), 3.62 (m, 2H), 3.31-3.38 (m, 6H), 2.27 (dd, 4H, J=7.0 Hz), 1.66-1.80 (m, 6H), 1.52-1.61 (m, 4H), 1.24 (bs, 48H), 1.04 (t, 9H, J=7.4 Hz), 0.87 (t, 6H, J=7.1 Hz).

Compound 152: 2,3-Bis(palmitoyloxy)propyl (2-(1-methylpiperidin-1-ium-1-yl)ethyl) phosphate

4-(2-Hydroxyethyl)-4-methylmorpholin-4-ium 4-methylbenzenesulfonate (Ref: *Eur. J. Med. Chem.* 2009, 44, 4970)

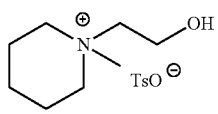

Chemical Formula: $C_{15}H_{25}NO_4S$
Molecular Weight: 315.43

A solution of 2-morpholinoethan-1-ol (2.7 mL, 22 mmol) and methyl tosylate (3.0 mL, 20 mmol) in 20 mL acetonitrile was heated to reflux for 4 h. The reaction mixture was concentrated under vacuum and precipitated in acetone to give 3-hydroxy-4-methylmorpholin-4-ium 4-methylbenzenesulfonate as brownish solid (5.57 g, 87%).

$^1$H NMR (300 MHz, DMSO-d$_6$) δ 7.47 (d, 2H, J=8.0 Hz), 7.11 (d, 2H, J=8.0 Hz), 5.27 (t, 1H, J=4.8 Hz), 3.79-3.86 (m, 2H), 3.36-3.46 (m, 6H), 3.06 (s, 3H), 2.28 (s, 3H), 1.72-1.83 (m, 4H), 1.46-1.55 (m, 2H).

1-(2-(((2,3-Bis(palmitoyloxy)propoxy)(2-cyanoethoxy)phosphanyl)oxy)ethyl)-1-methylpiperidin-1-ium chloride

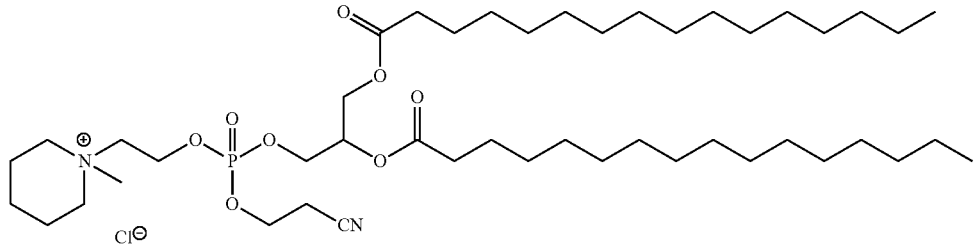

Chemical Formula: C$_{46}$H$_{88}$ClN$_2$O$_8$P
Molecular Weight: 863.64

To a solution of 3-(((2-cyanoethoxy)(diisopropylamino)phosphanyl)oxy)propane-1,2-diyl dipalmitate (769 mg, 1.0 mmol) and 1-(2-hydroxyethyl)-1-methylpiperidin-1-ium 4-methylbenzenesulfonate (315 mg, 1.0 mmol) in 10 mL dichloromethane, a solution of tetrazole in MeCN (0.45 M, 2.2 mL, 1.0 mmol) was added slowly, and then the reaction was stirred at room temperature for 16 h. After confirmed the disappearance of of 3-(((2-cyanoethoxy)(diisopropylamino)phosphanyl)oxy)propane-1,2-diyldipalmitate, $^t$BuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g SiO$_2$: MeOH/dichloromethane 0 to 50%) to provide 1-(2-(((2,3-bis(palmitoyloxy)propoxy)(2-cyanoethoxy)phosphanyl)oxy)ethyl)-1-methylpiperidin-1-ium chloride as white foam (690 mg, 84%).

$^1$H NMR (300 MHz, CDCl$_3$) δ 5.25 (m, 1H), 4.66 (m, 2H), 4.05-4.32 (m, 7H), 3.48 (s, 2H), 3.52-3.70 (m, 3H), 3.32 (s, 3H), 2.84 (m, 2H), 2.32 (q, 4H, J=8.0 Hz), 1.92 (m, 4H), 1.77 (m, 2H), 1.59 (m, 4H), 1.19-1.34 (bs, 48H), 0.87 (t, 6H, J=6.8 Hz).

2,3-Bis(palmitoyloxy)propyl (2-(1-methylpiperidin-1-ium-1-yl)ethyl) phosphate

Compound 152

A solution of 1-(2-(((2,3-bis(palmitoyloxy)propoxy)(2-cyanoethoxy)phosphanyl)oxy)ethyl)-1-methylpiperidin-1-ium chloride (690 mg, 0.83 mmol) and diisopropylethylamine (1.02 mL, 5.83 mmol) in 20 mL MeCN was heated to 60° C. for 16 h. The reaction mixture was concentrated under vacuum and purified by ISCO (gold 24 g SiO$_2$: MeOH/dichloromethane 0 to 60%) to afford the desired product, 2,3-bis(palmitoyloxy)propyl (2-(1-methylpiperidin-1-ium-1-yl)ethyl) phosphate as white solid (495 mg, 77%).

$^1$H NMR (300 MHz, CDCl$_3$) δ 5.18-5.20 (m, 1H), 4.30-4.42 (m, 3H), 4.12 (dd, 1H, J=11.9 Hz, 7.1 Hz), 3.98 (t, 2H, J=5.7 Hz), 3.82 (m, 2H), 3.60-3.71 (m, 2H), 3.46-3.55 (m, 2H), 3.33 (s, 3H), 2.27 (q, 4H, J=7.4 Hz), 2.10 (m, 2H), 1.84-1.96 (m, 4H), 1.66-1.76 (m, 2H), 1.50-1.63 (m, 2H), 1.24 (bs, 48H), 0.87 (t, 6H, J=6.6 Hz).

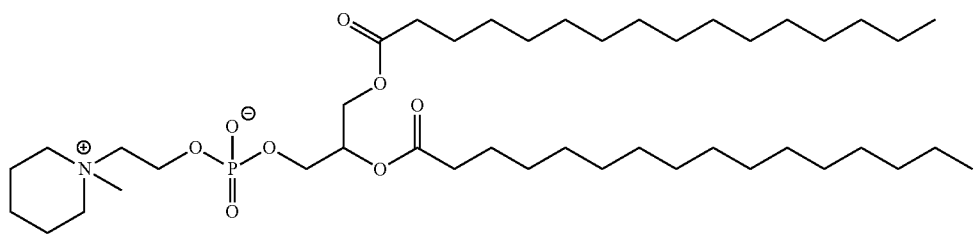

Chemical Formula: C$_{43}$H$_{84}$NO$_8$P
Molecular Weight: 774.12

Compound 153: 2,3-Bis(palmitoyloxy)propyl (2-(4-methylmorpholino-4-ium)ethyl) phosphate 1-(2-Hydroxyethyl)quinuclidin-1-ium bromide (Ref: Org. Bioorg. Chem. 2010, 425)

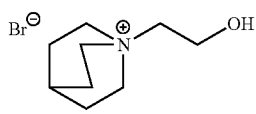

Chemical Formula: $C_9H_{18}BrNO$
Molecular Weight: 236.15

A solution of quinuclidine (2.22 g, 20 mmol) and 2-bromoethanol (1.42 mL, 20 mmol) in 20 mL THF was heated to 50° C. for 5 h. After cooled to room temperature, the solid was filtered and washed with ether to give 1-(2-hydroxyethyl)quinuclidin-1-ium bromide as white solid (4.61 g, 97%).

$^1$H NMR (300 MHz, DMSO-$d_6$) δ 5.24 (t, 1H, J=4.6 Hz), 3.76-3.83 (m, 2H), 3.46 (t, 6H, J=7.6 Hz), 3.21 (t, 2H, J=5.5 Hz), 2.01-2.08 (m, 1H), 1.81-1.88 (m, 6H).

1-(2-(((2,3-Bis(palmitoyloxy)propoxy)(2-cyanoethoxy)phosphanyl)oxy)ethyl)quinuclidin-1-ium chloride

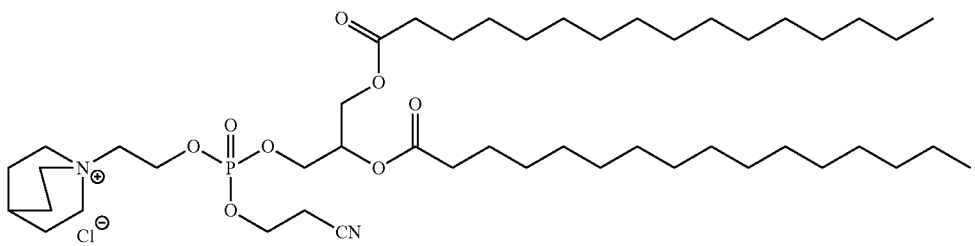

Chemical Formula: $C_{47}H_{88}ClN_2O_8P$
Molecular Weight: 875.65

To a solution of 3-(((2-cyanoethoxy)(diisopropylamino)phosphanyl)oxy)propane-1,2-diyl dipalmitate (769 mg, 1.0 mmol) and 1-(2-hydroxyethyl)quinuclidin-1-ium bromide (236 mg, 1.0 mmol) in 10 mL dichloromethane, a solution of tetrazole in MeCN (0.45 M, 2.2 mL, 1.0 mmol) was added slowly, and then the reaction was stirred at room temperature for 16 h. After confirmed the disappearance of 3-(((2-cyanoethoxy)(diisopropylamino)phosphanyl)oxy)propane-1,2-diyldipalmitate, $^t$BuOOH (0.80 mL, 4.0 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide 1-(2-(((2,3-bis(palmitoyloxy)propoxy)(2-cyanoethoxy)phosphanyl)oxy)ethyl)quinuclidin-1-ium chloride as white solid (646 mg, 76%).

$^1$H NMR (300 MHz, $CDCl_3$) δ 5.25 (m, 1H), 4.63 (m, 2H), 4.13-4.44 (m, 6H), 3.85 (m, 2H), 3.65 (m, 6H), 3.27 (m, 4H), 2.87 (m, 2H), 2.32 (q, 4H, J=7.6 Hz), 2.19 (m, 1H), 2.04 (m, 4H), 1.59 (m, 2H), 1.18-1.42 (m, 48H), 0.87 (t, 6H, J=7.0 Hz).

2,3-Bis(palmitoyloxy)propyl (2-(4-methylmorpholino-4-ium)ethyl) phosphate

Compound 153

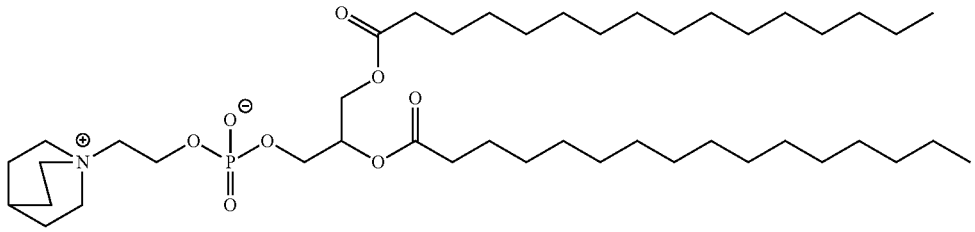

Chemical Formula: $C_{44}H_{84}NO_8P$
Molecular Weight: 786.13

A solution of 1-(2-(((2,3-bis(palmitoyloxy)propoxy)(2-cyanoethoxy)phosphanyl)oxy)ethyl)quinuclidin-1-ium chloride (646 mg, 0.76 mmol) and diisopropylethylamine (0.94 mL, 5.38 mmol) in 20 mL MeCN was heated to 60° C. for 16 h. The reaction mixture was concentrated under vacuum and purified by ISCO (gold 24 g $SiO_2$: MeOH/dichloromethane 0 to 60%) to get the desired product, 2,3-bis(palmitoyloxy)propyl (2-(4-methylmorpholino-4-ium)ethyl) phosphate as white solid (444 mg, 74%).

$^1$H NMR (300 MHz, $CDCl_3$) δ 5.22 (m, 1H), 4.40 (dd, 1H, J=11.6 Hz, 2.8 Hz), 4.30 (m, 2H), 4.12 (dd, 1H, J=11.8 Hz, 7.0 Hz), 3.98 (m, 2H), 3.63-3.73 (m, 8H), 2.15-2.34 (m, 8H), 2.00 (m, 5H), 1.50-1.62 (m, 2H), 1.18-1.42 (m, 48H), 0.87 (t, 6H, J=7.0 Hz).

Compound 160: 2,3-Bis(stearoyloxy)propyl (2-(triethylammonio)ethyl) phosphate 3-(Benzyloxy)propane-1,2-diyl distearate (Ref: EP1916255 A2, Pg 30)

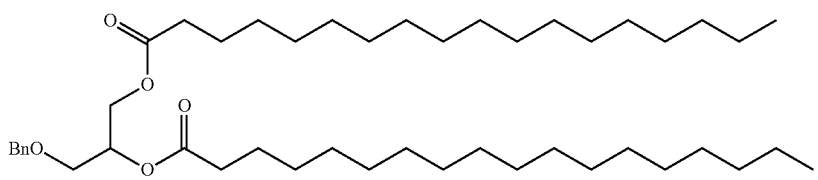

Chemical Formula: $C_{46}H_{82}O_5$
Molecular Weight: 715.16

A mixture of 3-(benzyloxy)propane-1,2-diol (13.39 g, 73.5 mmol), stearic acid (41.8 g, 0.147 mole), EDCI (31.0 g, 0.161 mole) and DMAP (1.80 g, 14.7 mmol) in 300 mL dichloromethane was stirred at room temperature for 40 h. The reaction mixture was diluted with water, extracted with dichloromethane (2×500 mL), and the combined organic layer was washed with brine and dried over sodium sulfate. After filtration and concentration under vacuum, the crude was purified by dissolving in hexanes and filtering through a pad of silica gel, and then eluted with EtOAc/Hexanes 0 to 30% to provide 3-(benzyloxy)propane-1,2-diyl distearate as white solid (48.2 g, 91%).

$^1$H NMR (300 MHz, $CDCl_3$) δ 7.27-7.34 (m, 5H), 5.21-5.25 (m, 1H), 4.53 (m, 2H), 4.34 (dd, 1H, J=3.8 Hz, 11.8 Hz), 4.18 (dd, 1H, J=6.6 Hz, 11.8 Hz), 3.58 (d, 2H, J=6.0 Hz), 2.24-2.34 (m, 4H), 1.54-1.63 (m, 4H), 1.24 (s, 56H), 0.87 (t, 6H, J=6.3 Hz).

3-Hydroxypropane-1,2-diyl distearate

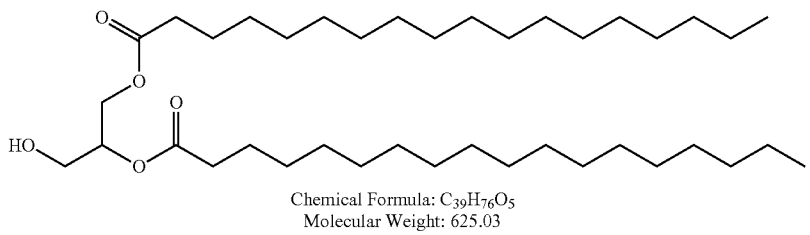 [SMILES: CCCCCCCCCCCCCCCCCC(=O)OCC(CO)OC(=O)CCCCCCCCCCCCCCCCC]

Chemical Formula: $C_{39}H_{76}O_5$
Molecular Weight: 625.03

A mixture of 3-(benzyloxy)propane-1,2-diyl distearate (48.2 g, 67.4 mmol) and Pd/C (5%, Degaussa E10002U/W, Aldrich 330124, 4.8 g) in 1 L EtOAc was purged with nitrogen and hydrogen 3 times, respectively, and then the reaction was stirred at room temperature with balloon for 16 h. The suspension was filtered through Celite, washed with dichloromethane (3 L). After concentration under vacuum, the solid was precipitated in dichloromethane to provide 3-hydroxypropane-1,2-diyl distearate as white solid (40.67 g, 96%).

$^1$H NMR (300 MHz, CDCl$_3$) δ 5.05-5.11 (m, 1H), 4.31 (dd, 1H, J=4.6 Hz, 11.9 Hz), 4.23 (dd, 1H, J=5.7 Hz, 11.9 Hz), 3.70-3.74 (m, 2H), 2.33 (q, 4H, J=7.1 Hz), 2.00 (t, 1H, J=6.3 Hz), 1.57-1.62 (m, 4H), 1.24 (s, 56H), 0.87 (t, 6H, J=7.1 Hz).

3-(((2-Cyanoethoxy)(diisopropylamino)phosphanyl)oxy)propane-1,2-diyl distearate

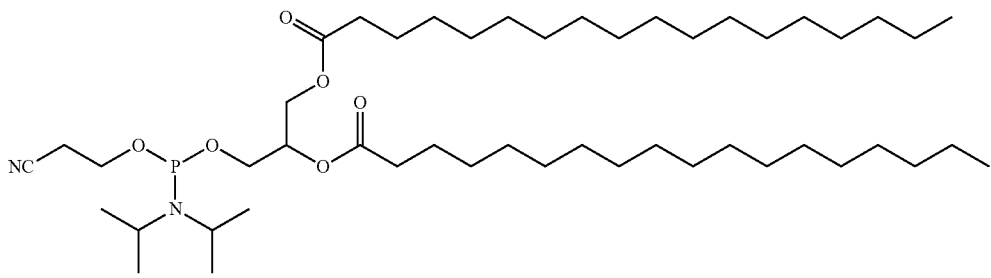

Chemical Formula: $C_{48}H_{93}N_2O_6P$
Molecular Weight: 825.25

To a solution of 3-hydroxypropane-1,2-diyl distearate (5.00 g, 8.0 mmol) and tetrazole (0.45 M in MeCN, 35.6 mL, 16.0 mmol) in 150 mL dichloromethane, a solution of 3-((chloro(diisopropylamino)phosphino)oxy)propanenitrile (5.1 mL, 16.0 mmol) in 100 mL dichloromethane was added dropwise and the reaction mixture was stirred at room temperature for 4 h. The mixture was concentrated and purified by ISCO (120 g SiO$_2$:EtOAc/Hexanes (1% Et$_3$N) 0 to 10%) to give 3-(((2-cyanoethoxy)(diisopropylamino)phosphanyl)oxy)propane-1,2-diyl distearate as white solid (3.73 g, 56%). The yield can be improved by pre-eluting the column with excess hexanes/1% Et$_3$N.

$^1$H NMR (300 MHz, CDCl$_3$) δ 5.16-5.20 (m, 1H), 4.28-4.37 (m, 1H), 4.11-4.17 (m, 1H), 2.62 (t, 2H, J=6.3 Hz), 2.26-2.32 (m, 8H), 1.57-1.64 (m, 6H), 1.24 (s, 56H), 1.14-1.19 (m, 12H), 0.87 (t, 6H, J=6.3 Hz).

2-(((2,3-Bis(stearoyloxy)propoxy)(2-cyanoethoxy)phosphoryl)oxy)-N,N,N-triethylethanaminium Chloride

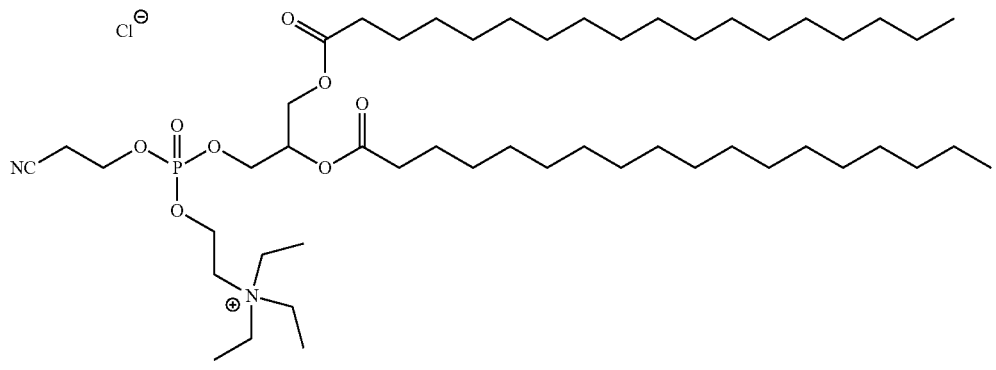

Chemical Formula: $C_{50}H_{98}ClN_2O_8P$
Molecular Weight: 921.76

To a solution of 3-(((2-cyanoethoxy)(diisopropylamino)phosphanyl)oxy)propane-1,2-diyl distearate (700 mg, 0.848 mmol) and N,N,N-triethyl-2-hydroxyethanaminium iodide (232 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide 2-(((2,3-bis(stearoyloxy)propoxy)(2-cyanoethoxy) phosphoryl)oxy)-N,N,N-triethylethanaminium chloride as yellowish foam (332 mg, 43%).

$^1$H NMR (300 MHz, $CDCl_3$) δ 5.29 (m, 1H), 4.67 (m, 1H), 4.14-4.44 (m, 7H), 3.98 (m, 1H), 3.51 (q, 6H, J=7.2 Hz), 2.87 (m, 2H), 2.28-2.37 (m, 4H), 1.60 (m, 5H), 1.41 (t, 9H, J=7.1 Hz), 1.24 (s, 56H), 0.87 (t, 6H, J=7.2 Hz).

2,3-Bis(stearoyloxy)propyl (2-(triethylammonio)ethyl) phosphate Compound 160

Chemical Formula: $C_{47}H_{94}NO_8P$
Molecular Weight: 832.24

A solution of 2-(((2,3-bis(stearoyloxy)propoxy)(2-cyanoethoxy) phosphoryl)oxy)-N,N,N-triethylethanaminium chloride (332 mg, 0.374 mmol) and diisopropylethylamine (0.46 mL, 2.62 mmol) in 10 mL MeCN was heated to 60° C. for 16 h. The reaction mixture was concentrated under vacuum and purified by ISCO (gold 24 g $SiO_2$: MeOH/dichloromethane 0 to 60%) to provide the desired product, 2,3-bis(stearoyloxy)propyl (2-(triethylammonio)ethyl) phosphate as white solid (200 mg, 64%).

$^1$H NMR (300 MHz, $CDCl_3$) δ 5.18-5.25 (m, 1H), 4.41 (dd, 1H, J=2.7 Hz, 11.8 Hz), 4.29 (m, 2H), 4.13 (dd, 1H, J=7.0 Hz, 11.8 Hz), 4.00 (t, 2H, J=6.6 Hz), 3.57-3.62 (m, 2H), 3.52 (q, 6H, J=7.4 Hz), 2.27 (q, 4H, J=6.6 Hz), 1.52-1.62 (m, 4H), 1.37 (t, 9H, J=7.1 Hz), 1.24 (s, 56H), 0.87 (t, 6H, J=7.1 Hz).

Compound 161: 2,3-Bis(stearoyloxy)propyl (2-(1-methylpiperidin-1-ium-1-yl)ethyl) phosphate 1-(2-(((2,3-Bis(stearoyloxy)propoxy)(2-cyanoethoxy)phosphoryl)oxy)ethyl)-1-methylpiperidin-1-ium chloride

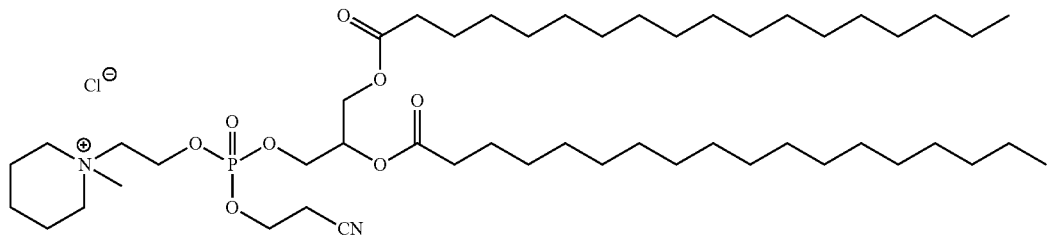

Chemical Formula: C$_{50}$H$_{96}$ClN$_2$O$_8$P
Molecular Weight: 919.75

To a solution of 3-(((2-cyanoethoxy)(diisopropylamino)phosphanyl)oxy)propane-1,2-diyl distearate (700 mg, 0.848 mmol) and 1-(2-hydroxyethyl)-1-methylpiperidin-1-ium 4-methylbenzenesulfonate (267 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g SiO$_2$: MeOH/dichloromethane 0 to 10%) to provide 1-(2-(((2,3-bis(stearoyloxy)propoxy)(2-cyanoethoxy)phosphoryl)oxy)ethyl)-1-methylpiperidin-1-ium chloride as white solid (470 mg, 62%).

$^1$H NMR (300 MHz, CDCl$_3$) δ 5.25 (m, 1H), 4.67 (m, 2H), 4.12-4.42 (m, 7H), 3.48 (s, 2H), 3.55-3.70 (m, 3H), 3.32 (s, 3H), 2.77-2.85 (m, 2H), 2.32 (q, 4H, J=8.0 Hz), 1.93 (m, 4H), 1.70-1.78 (m, 2H), 1.59 (m, 4H), 1.19-1.34 (bs, 56H), 0.87 (t, 6H, J=6.8 Hz).

2,3-Bis(stearoyloxy)propyl (2-(1-methylpiperidin-1-ium-1-yl)ethyl) phosphate Compound 161

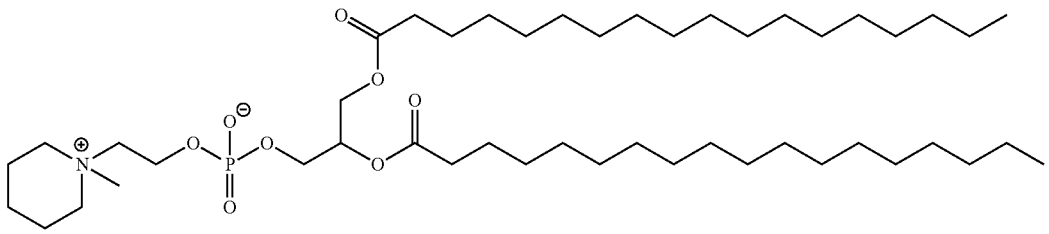

Chemical Formula: C$_{47}$H$_{92}$NO$_8$P
Molecular Weight: 830.23

A solution of 1-(2-(((2,3-bis(stearoyloxy)propoxy)(2-cyanoethoxy)phosphoryl)oxy)ethyl)-1-methylpiperidin-1-ium chloride (470 mg, 0.53 mmol) and diisopropylethylamine (0.65 mL, 3.72 mmol) in 15 mL MeCN was heated to 60° C. for 16 h. The reaction mixture was concentrated under vacuum and purified by ISCO (gold 24 g SiO$_2$: MeOH/dichloromethane 0 to 60%) to get the desired product, 2,3-bis(stearoyloxy)propyl (2-(1-methylpiperidin-1-ium-1-yl)ethyl) phosphate as white solid (269 mg, 61%).

$^1$H NMR (300 MHz, CDCl$_3$) δ 5.18-5.24 (m, 1H), 4.40 (dd, 1H, J=12.1 Hz, 3.0 Hz), 4.34 (m, 2H), 4.12 (dd, 1H, J=11.9 Hz, 7.1 Hz), 3.99 (t, 2H, J=5.7 Hz), 3.82 (m, 2H), 3.62-3.71 (m, 2H), 3.46-3.55 (m, 2H), 3.34 (s, 3H), 2.27 (q, 4H, J=7.4 Hz), 1.84-1.96 (m, 4H), 1.68-1.76 (m, 2H), 1.52-1.63 (m, 4H), 1.24 (bs, 56H), 0.87 (t, 6H, J=6.6 Hz).

Compound 162: 2,3-Bis(stearoyloxy)propyl (3-(trimethylammonio)propyl) phosphate 3-(((2,3-Bis(stearoyloxy)propoxy)(2-cyanoethoxy)phosphoryl)oxy)-N,N,N-trimethylpropan-1-aminium chloride

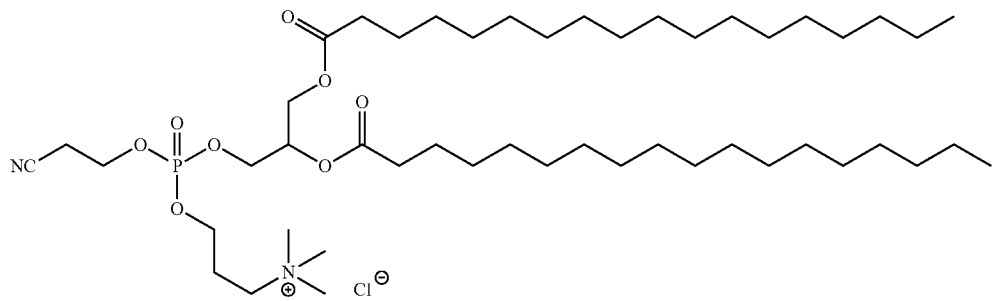

Chemical Formula: $C_{48}H_{94}ClN_2O_8P$
Molecular Weight: 893.71

To a solution of 3-(((2-cyanoethoxy)(diisopropylamino)phosphanyl)oxy)propane-1,2-diyl distearate (700 mg, 0.848 mmol) and 3-hydroxy-N,N,N-trimethylpropan-1-aminium tosylate (245 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide 3-(((2,3-bis(stearoyloxy)propoxy)(2-cyanoethoxy) phosphoryl)oxy)-N,N,N-trimethylpropan-1-aminium chloride as white foam (502 mg, 68%).

$^1$H NMR (300 MHz, $CDCl_3$) δ 5.25 (m, 1H), 4.15-4.35 (m, 7H), 3.78 (m, 2H), 3.31 (s, 9H), 2.83 (m, 2H), 2.27-2.35 (m, 10H), 1.98 (m, 3H), 1.59 (m, 4H), 1.24 (s, 50H), 0.87 (t, 6H, J=6.0 Hz).

2,3-Bis(stearoyloxy)propyl (3-(trimethylammonio)propyl) phosphate
Compound 162

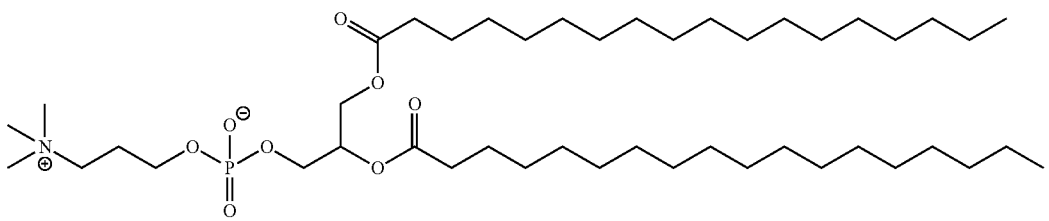

Chemical Formula: $C_{45}H_{90}NO_8P$
Molecular Weight: 804.19

A solution of 3-(((2,3-bis(stearoyloxy)propoxy)(2-cyanoethoxy) phosphoryl)oxy)-N,N,N-trimethylpropan-1-aminium chloride (502 mg, 0.58 mmol) and diisopropylethylamine (0.71 mL, 4.1 mmol) in 15 mL MeCN was heated to 60° C. for 16 h. The reaction mixture was concentrated under vacuum and purified by ISCO (gold 24 g $SiO_2$: MeOH/dichloromethane 0 to 60%) to get the desired product, 2,3-bis(stearoyloxy)propyl (3-(trimethylammonio)propyl) phosphate as white solid (385 mg, 82%).

$^1$H NMR (300 MHz, $CDCl_3$) δ 5.02 (m, 1H), 4.40 (dd, 1H, J=3.0 Hz, 11.8 Hz), 4.13 (dd, 1H, J=7.2 Hz, 11.8 Hz), 3.91-4.00 (m, 4H), 3.77-3.83 (m, 2H), 3.28 (s, 9H), 2.07-2.32 (m, 10H), 1.24 (s, 56H), 0.87 (t, 6H, J=6.0 Hz).

Compound 163: 2,3-Bis(stearoyloxy)propyl (3-(trimethylammonio)butyl) phosphate 4-(((2,3-Bis(stearoyloxy)propoxy)(2-cyanoethoxy)phosphoryl)oxy)-N,N,N-trimethylbutan-1-aminium chloride

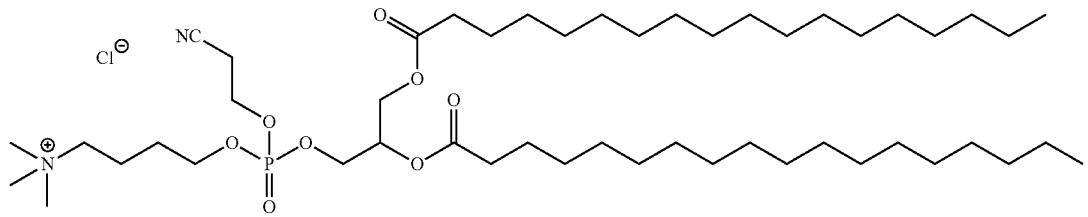

Chemical Formula: $C_{49}H_{96}ClN_2O_8P$
Molecular Weight: 907.74

To a solution of 3-(((2-cyanoethoxy)(diisopropylamino)phosphanyl)oxy)propane-1,2-diyl distearate (700 mg, 0.848 mmol) and 3-hydroxy-N,N,N-trimethylbutan-1-aminium 4-methylbenzenesulfonate (257 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide 3-(((2,3-bis(stearoyloxy)propoxy)(2-cyanoethoxy) phosphoryl)oxy)-N,N,N-trimethylbutan-1-aminim chloride as white solid (648 mg, 87%).

$^1$H NMR (300 MHz, CDCl$_3$) δ 5.19-5.27 (m, 1H), 4.11-4.34 (m, 8H), 3.60-3.68 (m, 2H), 3.32 (s, 9H), 2.77-2.85 (m, 2H), 2.31 (q, 4H, J=6.8 Hz), 1.90-2.00 (m, 2H), 1.78-1.86 (m, 2H), 1.54-1.64 (m, 4H), 1.19-1.35 (m, 56H), 0.86 (t, 6H, J=6.8 Hz).

2,3-Bis(stearoyloxy)propyl (3-(trimethylammonio)butyl) phosphate Compound 163

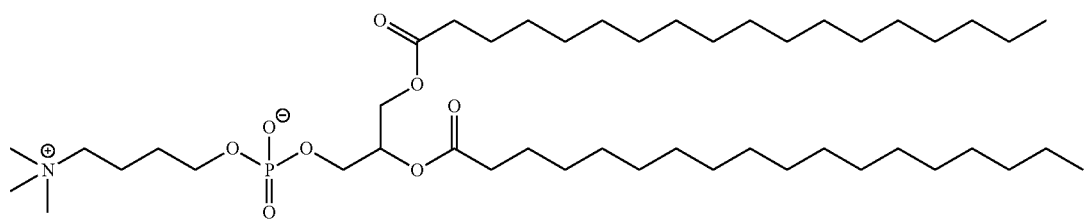

Chemical Formula: $C_{46}H_{92}NO_8P$
Molecular Weight: 818.21

A solution of 3-(((2,3-bis(stearoyloxy)propoxy)(2-cyanoethoxy) phosphoryl)oxy)-N,N,N-trimethylbutan-1-aminium chloride (648 mg, 0.74 mmol) and diisopropylethylamine (0.91 mL, 5.2 mmol) in 20 mL MeCN was heated to 60° C. for 16 h. The reaction mixture was concentrated under vacuum and purified by ISCO (gold 24 g $SiO_2$: MeOH/dichloromethane 0 to 60%) to get the desired product, 2,3-bis(stearoyloxy)propyl (3-(trimethylammonio)butyl) phosphate as white solid (330 mg, 54%).

$^1$H NMR (300 MHz, CDCl$_3$) δ 5.18-5.24 (m, 1H), 4.40 (dd, 1H, J=12.0 Hz, 3.0 Hz), 4.15 (dd, 1H, J=11.9 Hz, 6.8 Hz), 3.90-3.98 (m, 4H), 3.94-3.98 (m, 2H), 3.28 (s, 9H), 1.94-2.32 (m, 6H), 1.68-1.73 (m, 2H), 1.52-1.62 (m, 4H), 1.24 (bs, 56H), 0.87 (t, 6H, J=6.6 Hz).

Compound 164: 2,3-Bis(stearoyloxy)propyl (2-(quinuclidin-1-ium-1-yl)ethyl) phosphate 1-(2-(((2,3-Bis(stearoyloxy)propoxy)(2-cyanoethoxy)phosphoryl)oxy)ethyl)quinuclidin-1-ium chloride

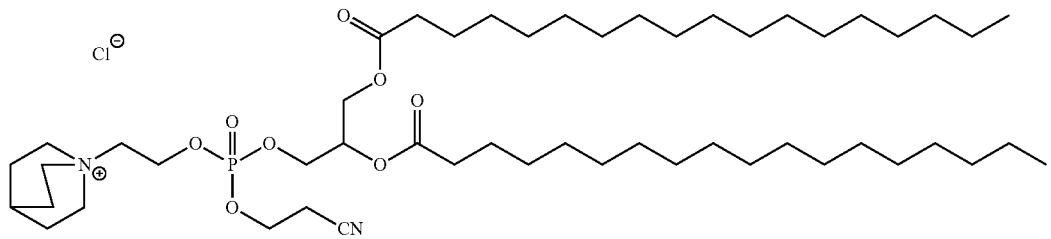

Chemical Formula: $C_{51}H_{96}ClN_2O_8P$
Molecular Weight: 931.76

To a solution of 3-(((2-cyanoethoxy)(diisopropylamino)phosphanyl)oxy)propane-1,2-diyl distearate (700 mg, 0.848 mmol) and 1-(2-hydroxyethyl)quinuclidin-1-ium bromide (200 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide 1-(2-(((2,3-bis(stearoyloxy)propoxy)(2-cyanoethoxy)phosphoryl)oxy)ethyl)quinuclidin-1-ium chloride as white solid (572 mg, 75%).

$^1$H NMR (300 MHz, $CDCl_3$) δ 5.26 (m, 1H), 4.62 (m, 2H), 4.16-4.42 (m, 6H), 3.85 (m, 2H), 3.63-3.73 (m, 6H), 2.84-2.92 (m, 2H), 2.32 (q, 4H, J=8.0 Hz), 2.20 (m, 1H), 2.04 (m, 6H), 1.52-1.84 (m, 10H), 1.18-1.33 (m, 50H), 0.87 (t, 6H, J=6.8 Hz).

2,3-Bis(stearoyloxy)propyl (2-(quinuclidin-1-ium-1-yl)ethyl) phosphate Compound 164

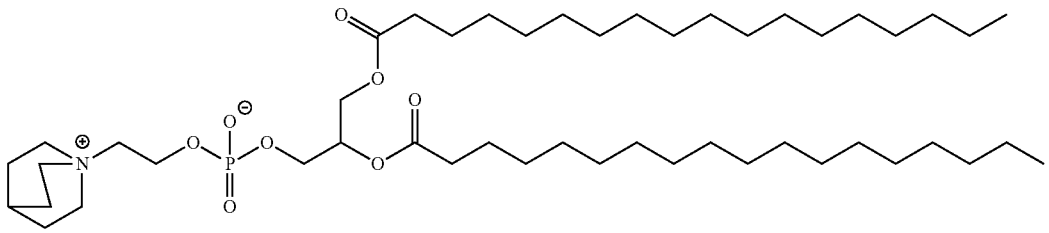

Chemical Formula: $C_{48}H_{92}NO_8P$
Molecular Weight: 842.24

A solution of 1-(2-(((2,3-bis(stearoyloxy)propoxy)(2-cyanoethoxy)phosphoryl)oxy)ethyl)quinuclidin-1-ium chloride (572 mg, 0.64 mmol) and diisopropylethylamine (0.78 mL, 4.47 mmol) in 15 mL MeCN was heated to 60° C. for 16 h. The reaction mixture was concentrated under vacuum and purified by ISCO (gold 24 g $SiO_2$: MeOH/dichloromethane 0 to 60%) to provide the desired product, 2,3-bis(stearoyloxy)propyl (2-(quinuclidin-1-ium-1-yl)ethyl) phosphate as white solid (387 mg, 72%).

$^1$H NMR (300 MHz, $CDCl_3$) δ 5.17-5.23 (m, 1H), 4.40 (dd, 1H, J=11.9 Hz, 2.6 Hz), 4.32 (m, 2H), 4.12 (dd, 1H, J=11.9 Hz, 7.1 Hz), 3.99 (t, 2H, J=6.4 Hz), 3.64-3.73 (m, 9H), 2.52 (m, 4H), 2.28 (q, 4H, J=7.7 Hz), 2.14-2.21 (m, 1H), 2.01 (m, 3H), 1.52-1.60 (m, 4H), 1.36-1.46 (m, 4H), 1.19-1.32 (bs, 50H), 0.87 (t, 6H, J=6.6 Hz).

Compound 165: 2,3-Bis(stearoyloxy)propyl (2-(tripropylammonio)ethyl) phosphate

N-(2-(((2,3-Bis(stearoyloxy)propoxy)(2-cyanoethoxy)phosphoryl)oxy)ethyl)-N,N-dipropylpropan-1-aminium chloride

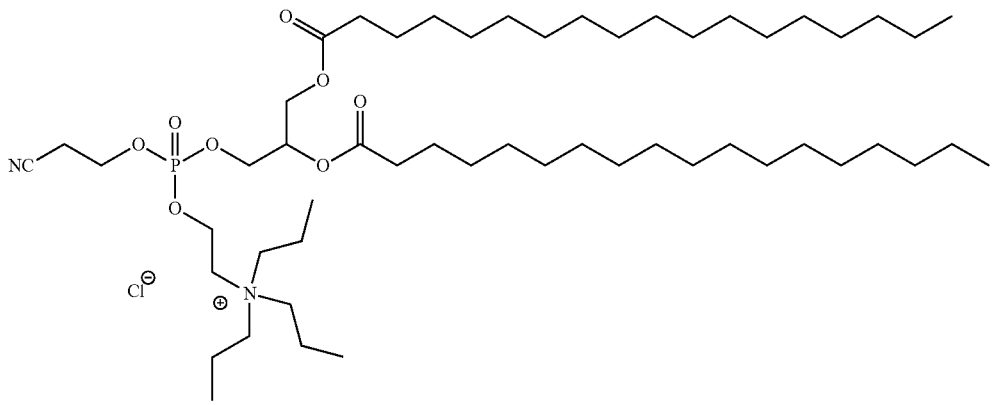

Chemical Formula: $C_{53}H_{104}ClN_2O_8P$
Molecular Weight: 963.84

To a solution of 3-(((2-cyanoethoxy)(diisopropylamino)phosphanyl)oxy)propane-1,2-diyl distearate (700 mg, 0.848 mmol) and N-(2-hydroxyethyl)-N,N-dipropylpropan-1-aminium bromide (227 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g $SiO_2$: MeOH/dichloromethane 0 to 10%) to provide N-(2-(((2,3-bis(stearoyloxy)propoxy)(2-cyanoethoxy)phosphoryl)oxy)ethyl)-N,N-dipropylpropan-1-aminium chloride as yellowish foam (535 mg, 68%).

$^1$H NMR (300 MHz, $CDCl_3$) δ 8.82 (bs, 1H), 5.18-5.27 (m, 1H), 4.64 (m, 1H), 4.12-4.42 (m, 4H), 3.98 (m, 1H), 3.27-3.34 (m, 4H), 2.84-2.91 (m, 1H), 2.27-2.35 (m, 3H), 1.69-1.82 (m, 4H), 1.52-1.64 (m, 5H), 1.39 (d, 12H, J=6.3 Hz), 1.19-1.33 (bs, 56H), 0.99-1.06 (m, 5H), 0.87 (t, 6H, J=6.8 Hz).

2,3-Bis(stearoyloxy)propyl (2-(tripropylammonio)ethyl) phosphate Compound 1665

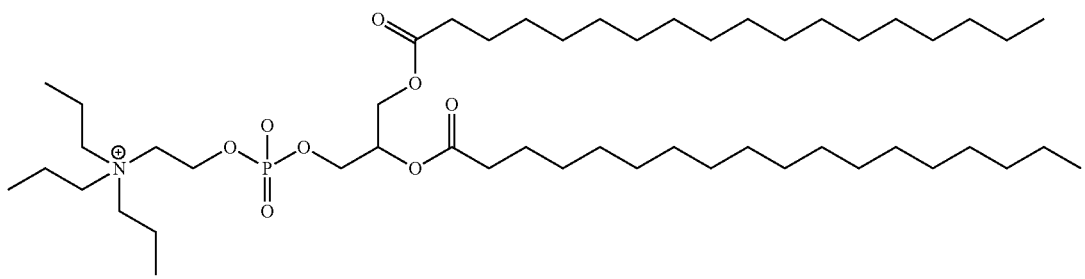

Chemical Formula: $C_{50}H_{100}NO_8P$
Molecular Weight: 874.32

A solution of 2-(((2,3-bis(stearoyloxy)propoxy)(2-cyanoethoxy) phosphoryl)oxy)-N,N,N-tripropylethanaminium chloride (535 mg, 0.57 mmol) and diisopropylethylamine (0.70 mL, 4.03 mmol) in 20 mL MeCN was heated to 60° C. for 16 h. The reaction mixture was concentrated under vacuum and purified by ISCO (gold 24 g SiO$_2$: MeOH/dichloromethane 0 to 60%) to provide the desired product, 2,3-bis(stearoyloxy)propyl (2-(tripropylammonio)ethyl) phosphate as white solid (472 mg, 94%).

$^1$H NMR (300 MHz, CDCl$_3$) δ 5.16-5.23 (m, 1H), 4.41 (dd, 1H, J=11.9 Hz, 3.3 Hz), 4.26 (m, 2H), 4.13 (dd, 1H, J=11.9 Hz, 7.1 Hz), 4.02 (t, 2H, J=6.3 Hz), 3.60 (m, 2H), 3.228-3.37 (m, 6H), 2.22-2.31 (m, 4H), 1.33-1.96 (m, 15H), 1.24 (bs, 51H), 1.04 (t, 9H, J=7.1 Hz), 0.87 (t, 6H, J=6.6 Hz).

Compound 166: 2,3-Bis(stearoyloxy)propyl (2-(4-methylmorpholino-4-ium)ethyl) phosphate 4-(2-(((2,3-Bis(stearoyloxy)propoxy)(2-cyanoethoxy)phosphoryl)oxy)ethyl)-4-methylmorpholin-4-ium chloride

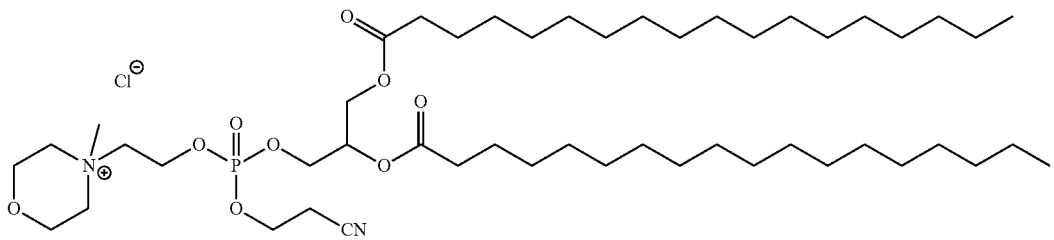

Chemical Formula: C$_{49}$H$_{94}$ClN$_2$O$_9$P
Molecular Weight: 921.72

To a solution of 3-(((2-cyanoethoxy)(diisopropylamino)phosphanyl)oxy)propane-1,2-diyl distearate (700 mg, 0.848 mmol) and 3-hydroxy-4-methylmorpholin-4-ium 4-methylbenzenesulfonate (269 mg, 0.848 mmol) in 10 mL dichloromethane, a solution of tetrazole in MeCN (0.45 M, 1.9 mL, 0.848 mmol) was added slowly, and then the reaction was stirred at room temperature for 16 h. After confirmed the disappearance of 3-(((2-cyanoethoxy)(diisopropylamino)phosphanyl)oxy)propane-1,2-diyl distearate, $^t$BuOOH (0.68 mL, 3.39 mmol) was added and the mixture was stirred for 4 h. The reaction mixture was diluted with dichloromethane, washed with 10% sodium bisulfate and brine, and then dried over sodium sulfate. After filtration and concentration under vacuum, the yellow foam residue was purified by ISCO (24 g SiO$_2$: MeOH/dichloromethane 0 to 10%) to provide 4-(2-(((2,3-bis(stearoyloxy)propoxy)(2-cyanoethoxy)phosphoryl)oxy)ethyl)-4-methylmorpholin-4-ium chloride as yellowish foam (456 mg, 60%).

$^1$H NMR (300 MHz, CDCl$_3$) δ 5.26 (m, 1H), 4.72 (m, 2H), 4.12-4.40 (m, 8H), 3.96-4.08 (m, 4H), 3.72 (m, 4H), 3.52 (s, 3H), 2.84 (m, 2H), 2.32 (q, 6H, J=7.9 Hz), 1.59 (m, 4H), 1.14-1.31 (m, 54H), 0.87 (t, 6H, J=6.6 Hz).

2,3-Bis(stearoyloxy)propyl (2-(4-methylmorpholino-4-ium)ethyl) phosphate Compound 166

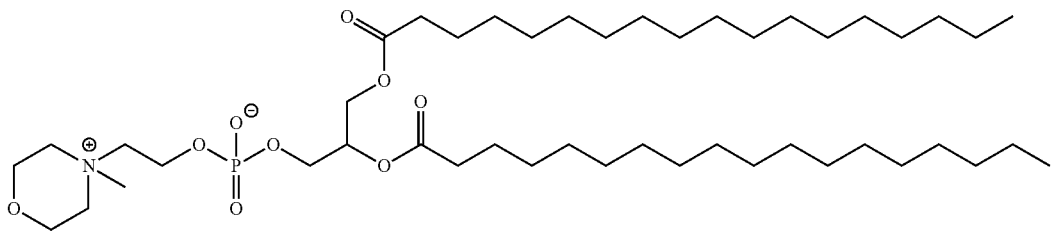

Chemical Formula: C$_{46}$H$_{90}$ClNO$_9$P
Molecular Weight: 832.20

A solution of 4-(2-(((2,3-bis(stearoyloxy)propoxy)(2-cyanoethoxy)phosphoryl)oxy)ethyl)-4-methylmorpholin-4-ium chloride (456 mg, 0.51 mmol) and diisopropylethylamine (0.63 mL, 4.03 mmol) in 15 mL MeCN was heated to 60° C. for 16 h. The reaction mixture was concentrated under vacuum and purified by ISCO (gold 24 g $SiO_2$: MeOH/dichloromethane 0 to 60%) to provide the desired product, 2,3-bis(stearoyloxy)propyl (2-(4-methylmorpholino-4-ium) ethyl) phosphate as white solid (360 mg, 84%).

$^1$H NMR (300 MHz, $CDCl_3$) δ 5.21 (m, 1H), 4.36-4.42 (m, 3H), 4.10 (dd, 1H, J=12.1 Hz, 7.4 Hz), 3.93-4.06 (m, 8H), 3.66-3.72 (m, 4H), 3.52 (s, 3H), 2.27 (q, 4H, J=7.1 Hz), 1.92-2.06 (m, 2H), 1.52-1.62 (m, 4H), 1.24 (m, 54H), 0.87 (t, 6H, J=6.6 Hz).

N-((2-Aminoethyl)sulfonyl)oleamide trifluoroacetate tert-Butyl (2-sulfamoylethyl)carbamate (Ref: WO2007/041634)

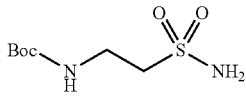

Chemical Formula: $C_7H_{16}N_2O_4S$
Molecular Weight: 224.28

A mixture of 2-aminoethane-1-sulfonamide (3.37 g, 21 mmol), di-tert-butyl dicarbonate (6.87 g, 31.5 mmol), triethylamine (11.7 mL, 84 mmol) and N,N-dimethylpyridin-4-amine (260 mg, 2.1 mmol) in 120 mL dichloromethane was stirred at room temperature for 16 h. The reaction mixture was diluted with water and extracted with dichloromethane. The combined organic layer was washed with brine and dried over sodium sulfate. After filtration and concentration, the residue was purified by ISCO (80 g $SiO_2$: EtOAc/hexanes 0 to 100%) to provide tert-butyl (2-sulfamoylethyl)carbamate as white solid (1.40 g, 30%).

$^1$H NMR (300 MHz, $CDCl_3$) δ 5.08 (bs, 1H), 4.87 (bs, 1H), 3.67 (q, 2H, J=6.0 Hz), 3.28 (t, 2H, J=6.0 Hz), 1.44 (s, 9H).

tert-Butyl (2-(N-oleoylsulfamoyl)ethyl)carbamate (Ref: WO2008/087190)

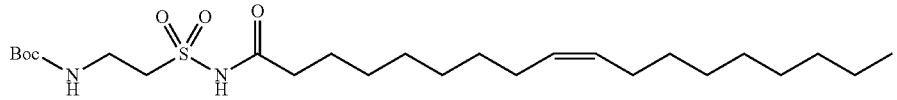

Chemical Formula: $C_{25}H_{48}N_2O_5S$
Molecular Weight: 488.73

A mixture of tert-butyl (2-sulfamoylethyl)carbamate (1.40 g, 6.24 mmol), oleic acid (2.0 mL, 6.24 mmol), 1,1'-carbonyldiimidazole (1.01 g, 6.24 mmol) and 1,8-diazabicyclo[5.4.0]undec-7-ene (2.0 mL, 13.7 mmol) in 60 mL N,N-dimethylformamide was stirred at room temperature for 16 h. TLC showed the formation of the product. The reaction mixture was acidified with 4N HCl solution to pH=2, and then extracted with ether. After dried over sodium sulfate, the solution was filtered and concentrated. The residue was purified by ISCO (80 g $SiO_2$: EtOAc/hexanes, 0 to 10%) to provide tert-butyl (2-(N-oleoylsulfamoyl)ethyl) carbamate (2.34 g, 76%).

$^1$H NMR (300 MHz, $CDCl_3$) δ 5.29-5.34 (m, 2H), 5.07 (bs, 1H), 3.60 (bs, 4H), 2.33 (t, 2H, J=7.5 Hz), 1.97-2.03 (m, 4H), 1.62-1.68 (m, 3H), 1.43 (s, 9H), 1.23-1.30 (m, 20H), 0.87 (t, 3H, J=5.8 Hz).

N-((2-Aminoethyl)sulfonyl)oleamide trifluoroacetate

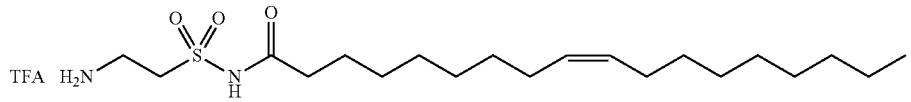

Chemical Formula: $C_{22}H_{41}F_3N_2O_4S$
Molecular Weight: 486.64

To a solution of tert-butyl (2-(N-oleoylsulfamoyl)ethyl) carbamate (378 mmol, 0.77 mmol) in 10 mL dichloromethane, trifluoroacetic acid (2 mL) was added slowly, and stirred at room temperature for 4 h. TLC showed the disappearance of tert-butyl (2-(N-oleoylsulfamoyl)ethyl) carbamate. The reaction mixture was concentrated to dryness and triturated with hexanes to provide N-((2-aminoethyl)sulfonyl)oleamide trifluoroacetate as white solid (344 mg, 88%).

$^1$H NMR (300 MHz, CDCl$_3$) δ 7.85 (bs, 2H), 5.28-5.36 (m, 2H), 3.84 (bs, 2H), 3.48 (bs, 2H), 2.30-2.40 (m, 2H), 1.94-2.04 (m, 4H), 1.18-1.36 (m, 20H), 0.87 (t, 6H, J=6.8 Hz).

MS (APCI): m/z (MH$^+$) 389.3, 371.3.

N-((2-(Dimethylamino)ethyl)sulfonyl)oleamide

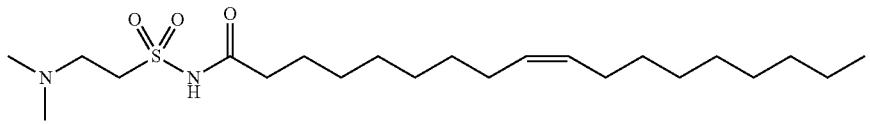

Chemical Formula: C$_{22}$H$_{44}$N$_2$O$_3$S
Molecular Weight: 416.67

(Ref: WO2008/087190) To a solution of 2-(dimethylamino)ethane-1-sulfonamide (500 mg, 3.28 mmol), triethylamine (0.92 mL, 6.57 mmol) and N,N-dimethylpyridin-4-amine (40 mg, 0.33 mmol) in 30 mL dichloromethane, oleoyl chloride (1.3 mL, 3.94 mmol) was added dropwise and the reaction mixture was warmed up to room temperature. MS showed complete reaction. The reaction mixture was diluted with water and extracted with dichloromethane. The combined organic layer was washed with brine and dried over sodium sulfate. After filtration and concentration, the residue was purified by ISCO (24 g SiO$_2$: MeOH/dichloromethane 0 to 10%) to provide N-((2-(dimethylamino)ethyl)sulfonyl)oleamide as white solid (437 mg, 32%).

$^1$H NMR (300 MHz, CDCl$_3$) δ 5.28-5.34 (m, 2H), 3.44 (t, 2H, J=6.3 Hz), 3.03 (t, 2H, J=6.3 Hz), 2.48 (s, 6H), 2.32 (t, 2H, J=7.6 Hz), 1.95-2.02 (m, 4H), 1.56-1.64 (m, 2H), 1.20-1.38 (m, 20H), 0.87 (t, 3H, J=6.6 Hz).

MS (APCI): m/z (MH$^+$) 417.3.

N,N,N-Trimethyl-2-(N-oleoylsulfamoyl)ethan-1-aminium iodide

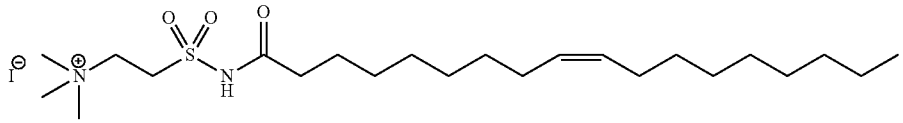

Chemical Formula: C$_{23}$H$_{47}$IN$_2$O$_3$S
Molecular Weight: 558.60

A solution of N-((2-(dimethylamino)ethyl)sulfonyl)oleamide (172 mg, 0.41 mmol) and iodomethane (3 mL) in 15 mL dimethoxyethane was stirred at room temperature for 16 h. TLC showed complete reaction. After concentration, the crude was purified by Gold ISCO (24 g SiO$_2$: MeOH/dichloromethane 0 to 20%) to get N,N,N-trimethyl-2-(N-oleoylsulfamoyl)ethan-1-aminium iodide as light yellow foam (217 mg, 94%).

$^1$H NMR (300 MHz, CDCl$_3$) δ 5.28-5.38 (m, 2H), 4.24 (bs, 4H), 3.45 (s, 9H), 2.54-2.64 (m, 2H), 1.94-2.06 (m, 4H), 1.56-1.68 (m, 2H), 1.20-1.38 (m, 20H), 0.87 (t, 3H, J=6.6 Hz).

MS (APCI): m/z (MH$^+$) 417.3, 391.3.

N-((3-(Dimethylamino)propyl)sulfonyl)oleamide

3-Chloro-N,N-bis(4-methoxybenzyl)propane-1-sulfonamide

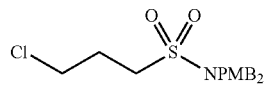

Chemical Formula: C$_{19}$H$_{24}$ClNO$_4$S
Molecular Weight: 397.91

At 0° C., to a solution of 3-chloropropane-1-sulfonyl chloride (2.68 mL, 22 mmol) and triethylamine (7.8 mL, 56 mmol) in 80 mL dichloromethane, a solution of bis(4-methoxybenzyl)amine (5.15 g, 20 mmol) in 20 mL dichloromethane was added slowly, and then the reaction was warmed up to room temperature for 16 h. The reaction mixture was diluted with water and extracted with dichloromethane. The combined organic layer was washed with brine and dried over sodium sulfate. The solution was filtered through a pad of silica gel and eluted with 30% EtOAc in hexanes. After concentration, the crude was purified with ISCO (120 g SiO$_2$: EtOAc/Hexanes 0 to 30%) to provide 3-chloro-N,N-bis(4-methoxybenzyl)propane-1-sulfonamide as brown oil (4.95, 62%).

$^1$H NMR (300 MHz, CDCl$_3$) δ 7.20-7.25 (m, 4H), 6.85-6.90 (m, 4H), 4.27 (s, 4H), 3.81 (s, 6H), 3.60 (t, 2H, J=6.8 Hz), 2.99 (t, 2H, J=7.1 Hz), 2.19-2.28 (m, 2H).

3-(Dimethylamino)-N,N-bis(4-methoxybenzyl)propane-1-sulfonamide

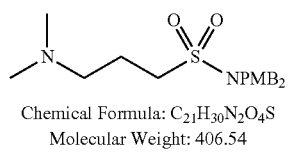

Chemical Formula: C$_{21}$H$_{30}$N$_2$O$_4$S
Molecular Weight: 406.54

In a seal tube, a mixture 3-chloro-N,N-bis(4-methoxybenzyl)propane-1-sulfonamide (4.95 g, 12.4 mmol) in dimethylamine solution in THF (2.0 M, 30 mL, 60 mmol) was heated to 70° C. for 16 h. MS showed the product. After cooled to room temperature, the reaction mixture was filtered and washed with dichloromethane. The filtrate was concentrated and the crude was purified with ISCO (120 g SiO$_2$: MeOH/dichloromethane 0 to 7%) to provide 3-(dimethylamino)-N,N-bis(4-methoxybenzyl)propane-1-sulfonamide as a brown oil (4.04, 80%).

$^1$H NMR (300 MHz, CDCl$_3$) δ 7.15-7.25 (m, 4H), 6.82-6.89 (m, 4H), 4.25 (s, 4H), 3.80 (s, 6H), 2.85-2.95 (m, 2H), 2.28 (t, 2H, J=6.6 Hz), 2.17 (s, 6H), 1.87-1.96 (m, 2H).

3-(Dimethylamino)propane-1-sulfonamide (Ref: WO2015/112441)

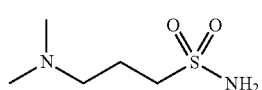

Chemical Formula: C$_5$H$_{14}$N$_2$O$_2$S
Molecular Weight: 166.24

To a solution of 3-(dimethylamino)-N,N-bis(4-methoxybenzyl)propane-1-sulfonamide (1.22 g, 3.0 mmol) and anisole (3.3 mL) in 15 mL dichloromethane, 22 mL trifluoroacetic acid was added dropwise, and then stirred at room temperature for 16 h. MS showed the product. The reaction mixture was concentrated to dryness to give 3-(dimethylamino)propane-1-sulfonamide as semi-solid (1.00 g, quant.), which was used for the next step without further purification.

$^1$H NMR (300 MHz, CD$_3$OD) δ 3.28-3.34 (m, 2H), 3.18 (t, 2H, J=6.6 Hz), 2.90 (s, 6H), 2.17-2.29 (m, 2H).

MS (APCI): m/z (MH$^+$) 167.1.

N-((3-(Dimethylamino)propyl)sulfonyl)oleamide

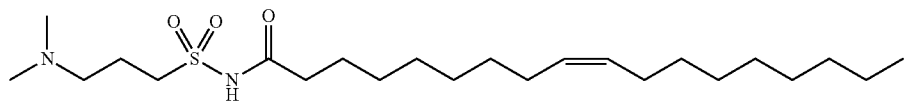

Chemical Formula: C$_{23}$H$_{46}$N$_2$O$_3$S
Molecular Weight: 430.69

To a solution of 3-(dimethylamino)propane-1-sulfonamide (1.00 g, 3.0 mmol), triethylamine (1.26 mL, 9.0 mmol) and N,N-dimethylpyridin-4-amine (37 mg, 0.3 mmol) in 60 mL dichloromethane, a solution of oleoyl chloride (1.2 mL, 3.6 mmol) was added dropwise, and then stirred at room temperature for 16 h. MS showed the product. The reaction mixture was diluted with water and extracted with dichloromethane. The combined organic layer was washed with brine and dried over sodium sulfate. After filtration and concentration, the residue was purified by ISCO (40 g SiO$_2$:

MeOH/dichloromethane 0 to 10%) to provide N-((3-(dimethylamino)propyl)sulfonyl)oleamide as white solid (255 mg, 20%).

$^1$H NMR (300 MHz, CDCl$_3$) δ 5.31-5.36 (m, 2H), 3.37 (t, 2H, J=7.1 Hz), 2.99 (t, 2H, J=7.0 Hz), 2.82 (bs, 1H), 2.68 (s, 6H), 2.37 (t, 2H, J=7.6 Hz), 2.21-2.29 (m, 2H), 1.96-2.02 (m, 4H), 1.57-1.66 (m, 2H), 1.20-1.36 (m, 20H), 0.87 (t, 3H, J=6.6 Hz).

MS (APCI): m/z (MH$^+$) 431.3.

N,N,N-Trimethyl-3-(N-oleoylsulfamoyl)propan-1-aminium iodide

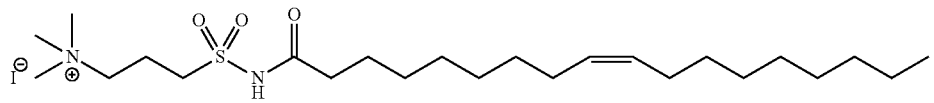

Chemical Formula: C$_{24}$H$_{49}$IN$_2$O$_3$S
Molecular Weight: 572.63

To a solution of N-((3-(dimethylamino)propyl)sulfonyl) oleamide (389 mg, 0.90 mmol) in 20 mL dimethoxyethane, iodomethane (5 mL) was added and the reaction mixture was stirred at room for 16 h. Either more iodomethane or longer time was not improving the yield. The reaction mixture was concentrated and purified with gold ISCO (24 g SiO$_2$: MeOH/dichloromethane 0 to 30%) to provide N,N,N-trimethyl-3-(N-oleoylsulfamoyl)propan-1-aminium iodide as yellow foam (237 mg, 46%).

$^1$H NMR (300 MHz, CD$_3$OD) δ 5.32-5.36 (m, 2H), 3.48-3.57 (m, 4H), 3.17 (s, 9H), 2.28-2.37 (m, 4H), 1.99-2.06 (m, 4H), 1.57-1.66 (m, 2H), 1.24-1.37 (m, 20H), 0.87 (t, 3H, J=6.6 Hz).

2-Octadecylicosanoic acid

Diethyl 2,2-dioctadecylmalonate (Ref: WO2014/195432)

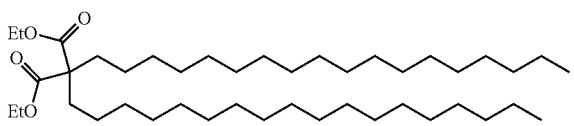

Chemical Formula: C$_{43}$H$_{84}$O$_4$
Molecular Weight: 665.14

At 0° C., NaH (1.20 g, 30 mmol) was added into a solution of diethyl malonate (1.52 mL, 10 mmol) in 60 mL N,N-dimethylformamide. After stirring for 30 min, a solution of 1-bromooctadecane (8.33 g, 25 mmol) in 60 mL THF was added slowly, and the reaction mixture was warmed up to room temperature and then heated to 50° C. for 6 h. After the reaction was cooled to room temperature, MeOH, acetic acid and ice-cold water (5 mL each) were added to quench the reaction. After extracted with dichloromethane, the combined organic layer was washed with brine (hard to separate). After drying over sodium sulfate, the solution was filtered and concentrated, and the crude was purified with ISCO (220 SiO$_2$: ether/hexanes 0 to 5%) to provide diethyl 2,2-dioctadecylmalonate as white solid (5.96 g, 85%).

$^1$H NMR (300 MHz, CDCl$_3$) δ 4.16 (q, 4H, J=7.1 Hz), 1.81-1.87 (m, 4H), 1.06-1.33 (m, 70H), 0.87 (t, 6H, J=7.1 Hz).

2,2-Dioctadecylmalonic acid

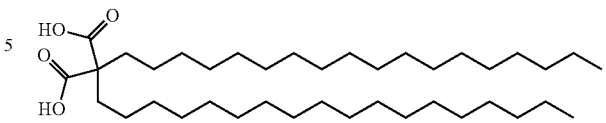

Chemical Formula: C$_{39}$H$_{76}$O$_4$
Molecular Weight: 609.03

To a solution of diethyl 2,2-dioctadecylmalonate (3.39 g, 5.1 mmol) in 60 mL $^i$PrOH, a solution of potassium hydroxide (11.0 g) in 60 mL water was added, and the mixture was heated to reflux for 48 h. TLC showed the disappearance of starting material with small amount of mono-ester. The reaction mixture was cooled to room temperature and diluted with water. 47% sulfuric acid was added to adjust pH=2, and precipitate was observed. The suspension was filtered and washed with water and dichloromethane. The solid was dissolved in ether and dried over sodium sulfate. After filtration and concentration, 2,2-dioctadecylmalonic acid was obtained as white solid (2.13 g, 68%).

$^1$H NMR (300 MHz, CDCl$_3$) δ 1.89-1.94 (m, 4H), 1.09-1.32 (m, 66H), 0.88 (t, 6H, J=7.1 Hz).

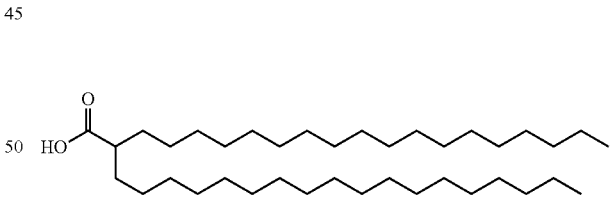

Chemical Formula: C$_{38}$H$_{76}$O$_2$
Molecular Weight: 565.02

A mixture of 2,2-dioctadecylmalonic acid (2.13 g, 3.5 mmol) in 60 mL n-decane was heated to reflux for 16 h. After removing the volatile under vacuum, the crude was precipitated in chloroform to give 2-octadecylicosanoic acid as white solid (1.76 g, 89%).

$^1$H NMR (300 MHz, CDCl$_3$) δ 2.28-2.36 (m, 1H), 1.40-1.56 (m, 4H), 1.08-1.33 (m, 64H), 0.87 (t, 6H, J=7.1 Hz).

N-(Methylsulfonyl)-2-octadecylicosanamide

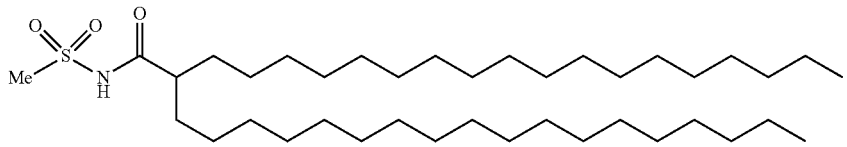

Chemical Formula: C$_{39}$H$_{79}$NO$_3$S
Molecular Weight: 642.13

At 0° C., oxalyl chloride (85 μL, 1 mmol) was slowly added into a suspension of 2-octadecylicosanoic acid (565 mg, 1 mmol) in 20 mL dichloromethane and followed with 5 drops of N,N-dimethylformamide, and then the reaction mixture was warmed up to room temperature for 1 h until turned into clear solution. Triethylamine (0.56 mL, 4 mmol), methanesulfonamide (95 mg, 1 mmol) and N,N-dimethylpyridin-4-amine (12 mg, 0.1 mmol) were added, and the mixture was stirred at room temperature for 48 h. The reaction mixture was diluted with water and extracted with dichloromethane. The combined organic layer was washed with brine and dried over sodium sulfate. After filtration and concentration, the crude was precipitated in dichloromethane to provide N-(methylsulfonyl)-2-octadecylicosanamide as white solid (502 mg, 78%).

$^1$H NMR (300 MHz, CDCl$_3$) δ 3.30 (s, 3H), 2.10-2.16 (m, 1H), 1.40-1.62 (m, 4H), 1.24 (m, 64H), 0.87 (t, 6H, J=7.1 Hz).

N-(Methylsulfonyl) stearamide

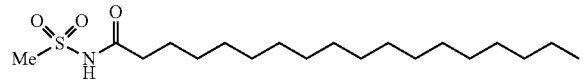

Chemical Formula: C$_{19}$H$_{39}$NO$_3$S
Molecular Weight: 361.59

(Ref: WO2008/087190) To a solution of methanesulfonamide (380 mg, 4.0 mmol), triethylamine (1.1 mL, 8.0 mmol) and N,N-dimethylpyridin-4-amine (49 mg, 0.4 mmol) in 30 mL dichloromethane, a solution of stearoyl chloride (1.21 g, 4 mmol) was added dropwise, and then stirred at room temperature for 16 h. MS showed the product. The reaction mixture was diluted with water and extracted with dichloromethane. The combined organic layer was washed with brine and dried over sodium sulfate. After filtration and concentration, the crude was precipitated in dichloromethane to provide N-(methylsulfonyl)stearamide as a white solid (580 mg, 40%).

$^1$H NMR (300 MHz, CDCl$_3$) δ 3.30 (s, 3H), 2.32 (t, 2H, J=7.4 Hz), 1.60-1.69 (m, 2H), 1.24 (m, 28H), 0.87 (t, 3H, J=6.8 Hz).

(Z)-2-((Z)-Octadec-9-en-1-yl)icos-11-enoic acid

(Z)-1-Bromooctadec-9-ene

Chemical Formula: C$_{18}$H$_{35}$Br
Molecular Weight: 331.38

A mixture of (Z)-octadec-9-en-1-yl methanesulfonate (3.40 g, 9.81 mmol) and LiBr (4.00 g, 45 mmol) in 40 mL acetone was stirred at room temperature for 16 h, and then heated to reflux for 4 h. TLC showed complete reaction. After filtration, the filtrate was diluted with water and dichloromethane. The organic layer was separated and washed with brine. After dried over sodium sulfate and filtration, the filtrate was concentrated to give (Z)-1-bromooctadec-9-ene (3.74 g, quant.).

$^1$H NMR (300 MHz, CDCl$_3$) δ 5.32-5.36 (m, 2H), 3.40 (t, 2H, J=6.8 Hz), 1.97-2.02 (m, 4H), 1.82-1.88 (m, 2H), 1.10-1.44 (m, 22H), 0.87 (t, 3H, J=7.1 Hz).

Diethyl 2,2-di((Z)-octadec-9-en-1-yl)malonate

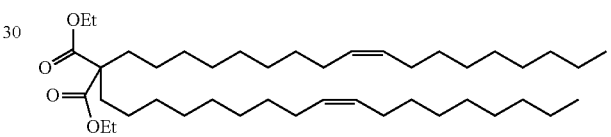

Chemical Formula: C$_{43}$H$_{80}$O$_4$
Molecular Weight: 661.11

To a solution of diethyl malonate (0.6 mL, 3.92 mmol) in 40 mL N,N-dimethylformamide, NaH (470 mg, 11.76 mmol) was added at 0° C. After 45 min, a solution of (Z)-1-bromooctadec-9-ene (3.74 g, 9.8 mmol) was added slowly, and then warmed up to room temperature for 16 h. TLC showed desired product with mono-substituted product. The reaction was quenched with MeOH/AcOH/water (5 mL each), and then extracted with dichloromethane. The combined organic layer was washed with brine and dried over sodium sulfate. After the filtration and concentration, the crude was purified by ISCO (80 g SiO$_2$: ether/hexanes 0 to 100%) to provide diethyl 2,2-di((Z)-octadec-9-en-1-yl)malonate (1.68 g, 64%) and diethyl (Z)-2-(octadec-9-en-1-yl)malonate (0.91 g).

$^1$H NMR (300 MHz, CDCl$_3$) δ 5.28-5.35 (m, 4H), 4.16 (q, 4H, J=7.1 Hz), 1.94-2.04 (m, 8H), 1.80-1.87 (m, 4H), 1.06-1.36 (m, 54H), 0.87 (t, 6H, J=7.1 Hz).

2,2-Di((Z)-octadec-9-en-1-yl)malonic acid

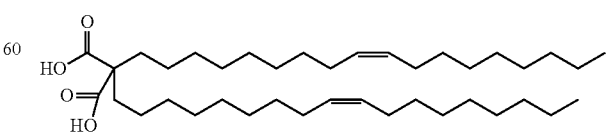

Chemical Formula: C$_{39}$H$_{72}$O$_4$
Molecular Weight: 605.00

To a solution of diethyl 2,2-di((Z)-octadec-9-en-1-yl)malonate (1.68 g, 2.54 mmol) in 40 mL $^i$PrOH, a solution of potassium hydroxide (6 g) in 40 mL water was added and the mixture was heated to reflux for 48 h. The reaction mixture was cooled to room temperature and diluted with water, acidified with 47% sulfuric acid to pH=2, no solid formed. The mixture was extracted with ether, and the combined organic layer was washed with brine and dried over sodium sulfate. After filtration and concentration, the residue was purified with ISCO (40 g SiO$_2$: EtOAc/Hexanes 0 to 35%) to provide 2,2-di((Z)-octadec-9-en-1-yl)malonic acid as colorless oil (1.36 g, 88%).

$^1$H NMR (300 MHz, CDCl$_3$) δ 5.30-5.34 (m, 4H), 1.88-2.02 (m, 12H), 1.13-1.32 (m, 48H), 0.87 (t, 6H, J=7.1 Hz).

(Z)-2-((Z)-Octadec-9-en-1-yl)icos-11-enoic acid

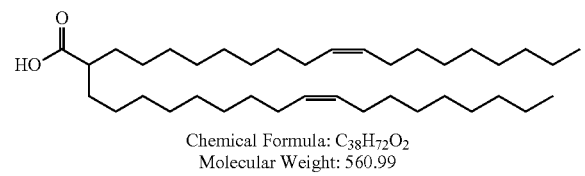 [SMILES: CCCCCCCC/C=C\CCCCCCCCC(CCCCCCCC/C=C\CCCCCCCC)C(=O)O]

Chemical Formula: C$_{38}$H$_{72}$O$_2$
Molecular Weight: 560.99

A solution of 2,2-di((Z)-octadec-9-en-1-yl)malonic acid (1.36 g, 2.24 mmol) in 40 mL n-decane was heated to reflux for 16 h. TLC showed complete reaction. After concentration, the crude was purified by ISCO (40 g SiO$_2$: EtOAc/Hexanes 0 to 20%) to give (Z)-2-((Z)-octadec-9-en-1-yl)icos-11-enoic acid as colorless oil (0.96 g, 76%).

$^1$H NMR (300 MHz, CDCl$_3$) δ 5.30-5.34 (m, 4H), 2.28-2.36 (m, 1H), 1.97-2.02 (m, 8H), 1.40-1.65 (m, 4H), 1.26 (m, 48H), 0.87 (t, 6H, J=7.1 Hz).

MS (APCI): m/z (MH$^+$) 561.6.

(Z)—N-(Methylsulfonyl)-2-((Z)-octadec-9-en-1-yl)icos-11-enamide

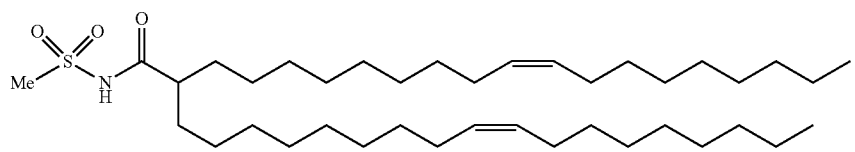

Chemical Formula: C$_{39}$H$_{75}$NO$_3$S
Molecular Weight: 638.09

At 0° C., oxalyl chloride (70 µL, 0.82 mmol) was added dropwise into a solution of (Z)-2-((Z)-octadec-9-en-1-yl)icos-11-enoic acid 462 mg, 0.82 mmol) in 20 mL dichloromethane and followed with 5 drops of N,N-dimethylformamide, and then warmed up to room temperature for 1.5 h. Methanesulfonamide (78 mg, 0.82 mmol), triethylamine (0.46 mL, 3.29 mmol) and N,N-dimethylpyridin-4-amine (20 mg, 0.16 mmol) were added and the mixture was stirred at room temperature for 16 h. TLC showed complete reaction. The reaction mixture was diluted with water and extracted with dichloromethane, and the combined organic layer was washed with brine and dried over sodium sulfate. After filtration and concentration, the crude was purified by ISCO (24 g SiO$_2$: EtOAc/Hexanes 0 to 60%) to provide (Z)—N-(methylsulfonyl)-2-((Z)-octadec-9-en-1-yl)icos-11-enamide as white foam.

$^1$H NMR (300 MHz, CDCl$_3$) δ 5.30-5.34 (m, 4H), 3.30 (s, 3H), 2.08-2.15 (m, 1H), 1.97-2.02 (m, 8H), 1.40-1.62 (m, 4H), 1.26 (m, 48H), 0.87 (t, 6H, J=6.6 Hz).

MS (APCI): m/z (MH$^+$) 638.5.

Lithium ditetradecylglycinate

Methyl ditetradecylglycinate

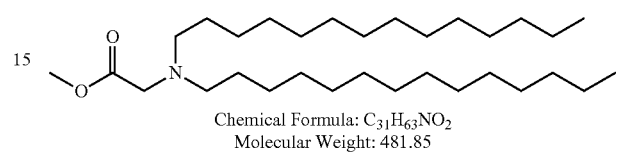

Chemical Formula: C$_{31}$H$_{63}$NO$_2$
Molecular Weight: 481.85

A solution of glycine methyl ester hydrochloride (564 mg, 4.49 mmol) and triethylamine (0.93 mL, 6.74 mmol) in DCE (11 mL) was allowed to stir at room temperature. After 15 minutes, tetradecanal (2.1 g, 9.89 mmol) in DCE (11 mL) was added and the mixture was cooled to 0° C. before the addition of sodium triacetoxyborohydride (2.1 g, 9.89 mmol) and acetic acid (0.6 mL, 9.89 mmol). The reaction was allowed to return to room temperature and stir for 16 hours. The reaction was quenched by slow addition of saturated sodium bicarbonate, and then extracted with DCM. The combined extracts were washed with brine, dried over anhydrous sodium sulfate, filtered, and concentrated in vacuo. Purification by ISCO silica flash chromatography (0-30% EtOAc/hexanes) afforded methyl ditetradecylglycinate (1.93 g, 89%).

$^1$H-NMR (300 MHz, CDCl$_3$) δ: ppm 3.72 (s, 3H); 3.34 (s, 2H); 1.56 (t, 4H); 1.60-1.03 (br. m, 48H); 0.91 (t, 6H).

Lithium ditetradecylglycinate

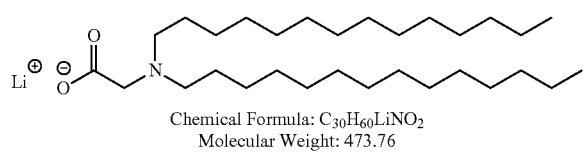 [SMILES: [Li+] ; CCCCCCCCCCCCCCN(CCCCCCCCCCCCCC)CC(=O)[O-]]

Chemical Formula: C$_{30}$H$_{60}$LiNO$_2$
Molecular Weight: 473.76

To a solution of methyl ditetradecylglycinate (1.93 g, 4.0 mmol) in THF (100 mL) was added 1M LiOH (90 mL, 90 mmol), and the reaction was allowed to stir at 65° C. for 16 hours. After cooling to room temperature, the reaction was concentrated in vacuo to a white powder. The powder was suspended in water, filtered, washed with water and diethyl ether, and dried under vacuum to afford lithium ditetradecylglycinate (1.81 g, 97%).

¹H-NMR (300 MHz, CDCl₃) δ: ppm 3.17 (s, 2H); 2.64 (t, 4H); 1.52 (br. m, 4H); 1.31 (br. m, 44H); 0.93 (t, 6H).

Compound: 9-(Nonan-2-yloxy)-9-oxononanoic Acid

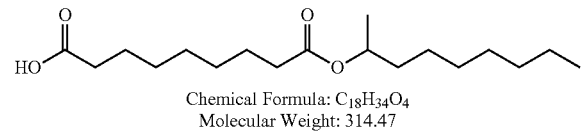 [SMILES: CCCCCCCC(C)OC(=O)CCCCCCCC(=O)O]

Chemical Formula: C₁₈H₃₄O₄
Molecular Weight: 314.47

A solution of nonanedioic acid (500 mg, 2.66 mmol), nonan-2-ol (556 µL, 3.19 mmol) and DMAP (65 mg, 0.53 mmol) in DCM (13 mL) was treated with EDC HCl (509 mg, 2.66 mmol). The reaction was allowed to stir at room temperature under nitrogen for 20 hours. Quenched reaction with H₂O and extracted three times with DCM. Washed organic layers with saturated aqueous NaHCO₃ followed by 10% citric acid and brine. Dried organic layers over Na₂SO₄, filtered and concentrated in vacuo. The residue was purified by silica gel chromatography (0-20% MeOH in DCM) to afford 9-(nonan-2-yloxy)-9-oxononanoic acid (350 mg, 1.11 mmol, 42%).

UPLC/ELSD: RT=2.21 min. MS (ES): m/z (MH⁻) 313.0 for C₁₈H₃₄O₄

¹H NMR (300 MHz, CDCl₃) δ: ppm 6.27 (br. s, 1H); 4.87 (m, 1H); 2.27 (m, 4H); 1.60-1.39 (br. m, 6H); 1.31-1.25 (br. m, 16H); 1.17 (d, 3H); 0.86 (m, 3H).

9-(Octyloxy)-9-oxononanoic Acid

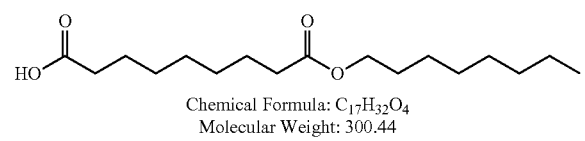 [SMILES: CCCCCCCCOC(=O)CCCCCCCC(=O)O]

Chemical Formula: C₁₇H₃₂O₄
Molecular Weight: 300.44

A solution of nonanedioic acid (500 mg, 2.66 mmol), octan-1-ol (418 µL, 3.19 mmol) and DMAP (65 mg, 0.53 mmol) in DCM (13 mL) was treated with EDC HCl (509 mg, 2.66 mmol). The reaction was allowed to stir at room temperature under nitrogen for 20 hours. Quenched reaction with H₂O and extracted three times with DCM. Washed organic layers with saturated aqueous NaHCO₃ followed by 10% citric acid and brine. Dried organic layers over Na₂SO₄, filtered and concentrated in vacuo. The residue was purified by silica gel chromatography (0-20% MeOH in DCM) to afford 9-(octyloxy)-9-oxononanoic acid (350 mg, 1.16 mmol, 44%).

UPLC/ELSD: RT=2.05 min. MS (ES): m/z (MH⁻) 299.0 for C₁₇H₃₂O₄

¹H NMR (300 MHz, CDCl₃) δ: ppm 7.88 (br. s, 1H); 3.99 (t, 2H); 2.24 (m, 4H); 1.57-1.53 (br. m, 6H); 1.26-1.21 (br. m, 16H); 0.86 (m, 3H).

Compound: N-(Methylsulfonyl)oleamide

Oleoyl chloride

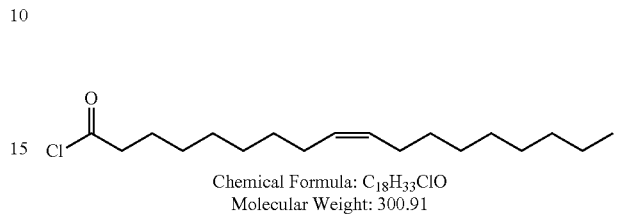

Chemical Formula: C₁₈H₃₃ClO
Molecular Weight: 300.91

To a solution of oleic acid (5 g, 17.70 mmol) in DCM (60 mL) at 0° C. was added oxalyl chloride (1.65 mL, 19.47 mmol) followed by DMF (13.8 µL, 0.177 mmol). The reaction mixture was allowed to warm to room temperature and stir for 20 hours at room temperature. Reaction mixture was concentrated in vacuo and carried on without further purification to afford oleoyl chloride (5.5 g, 18.28 mmol, > 99%).

¹H NMR (300 MHz, CDCl₃) δ: ppm 5.37 (m, 2H); 2.90 (t, 2H); 2.04 (m, 4H); 1.73 (m, 2H); 1.34-1.29 (br. m, 20H); 0.91 (m, 3H).

N-(methylsulfonyl)oleamide

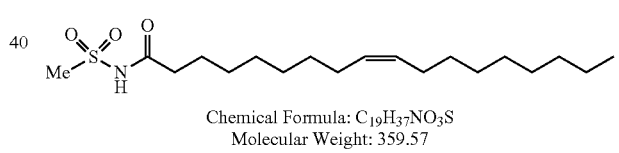

Chemical Formula: C₁₉H₃₇NO₃S
Molecular Weight: 359.57

To a solution of oleoyl chloride (500 mg, 1.66 mmol) in DCM (8.3 mL) was added DMAP (305 mg, 2.49 mmol) and methansulfonamide (237 mg, 2.49 mmol). The reaction mixture was allowed to stir at room temperature for 24 hours under nitrogen. The reaction mixture was quenched with 1N HCl and extracted with EtOAc. The organic layers were washed with saturated aqueous NaHCO₃, followed by brine. The organic layers were dried over Na₂SO₄, filtered and concentrated in vacuo. Triturated with EtOAc and concentrated filtrate in vacuo to afford N-(methylsulfonyl)oleamide (75 mg, 0.209 mmol, 13%).

UPLC/ELSD: RT=2.67 min. MS (ES): m/z (M+Na) 382.0 for C₁₉H₃₇NO₃S

¹H NMR (300 MHz, CDCl₃) δ: ppm 7.70 (br s, 1H); 5.37 (m, 2H); 3.33 (s, 3H); 2.35 (t, 2H); 2.04 (m, 4H); 1.69 (m, 2H); 1.34-1.29 (br. m, 20H); 0.90 (m, 3H).

N-(Cyclopropylsulfonyl)oleamide

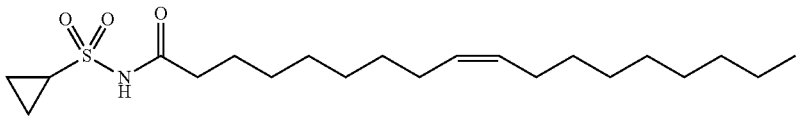

Chemical Formula: C₂₁H₃₉NO₃S
Molecular Weight: 385.61

A mixture of oleoyl chloride (500 mg, 1.66 mmol), DIPEA (868 µL, 4.99 mmol), cyclopropanesulfonamide (242 mg, 1.99 mmol) and DMAP (102 mg, 0.83 mmol) were dissolved in DCM (8.3 mL) and allowed to stir at room temperature for 24 hours under nitrogen.

The reaction mixture was quenched with 1N HCl and extracted with EtOAc. The organic layers were washed with saturated aqueous NaHCO₃, followed by brine. The organic layers were dried over Na₂SO₄, filtered and concentrated in vacuo. The residue was purified by silica gel chromatography (0-100% EtOAc in hexanes) to afford N-(cyclopropylsulfonyl)oleamide (315 mg, 0.82 mmol, 42%).

UPLC/ELSD: RT=2.83 min. MS (ES): m/z (MH⁻) 384.0 for C₂₁H₃₉NO₃S

¹H NMR (300 MHz, CDCl₃) δ: ppm 8.66 (br s, 1H); 5.35 (m, 2H); 2.98 (m, 1H); 2.34 (t, 2H); 2.02 (m, 4H); 1.66 (m, 2H); 1.37-1.28 (br. m, 22H); 1.13 (m, 2H); 0.89 (m, 3H).

9-(Heptadecan-9-yloxy)-9-oxononanoic acid

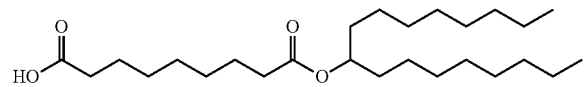

Chemical Formula: C₂₆H₅₀O₄
Molecular Weight: 426.68

A solution of nonanedioic acid (500 mg, 2.66 mmol), heptadecan-9-ol (681 mg, 2.66 mmol) and DMAP (65 mg, 0.53 mmol) in DCM (13 mL) was treated with EDC HCl (509 mg, 2.66 mmol). The reaction was allowed to stir at room temperature under nitrogen for 20 hours. Quenched reaction with H₂O and extracted three times with DCM. Washed organic layers with saturated aqueous NaHCO₃ followed by 10% citric acid and brine. Dried organic layers over Na₂SO₄, filtered and concentrated in vacuo. The residue was purified by silica gel chromatography (0-20% MeOH in DCM) to afford 9-(heptadecan-9-yloxy)-9-oxononanoic acid (350 mg, 1.05 mmol, 40%).

UPLC/ELSD: RT=3.49 min. MS (ES): m/z (MH⁻) 425.0 for C₂₆H₅₀O₄

¹H NMR (300 MHz, CDCl₃) δ: ppm 11.02 (br. s, 1H); 4.89 (m, 1H); 2.33 (m, 4H); 1.66-1.64 (br. m, 4H); 1.53-1.51 (br. m, 4H); 1.35-1.28 (br. m, 30H); 0.90 (m, 6H).

Dioctadecylglycine

Methyl dioctadecylglycinate

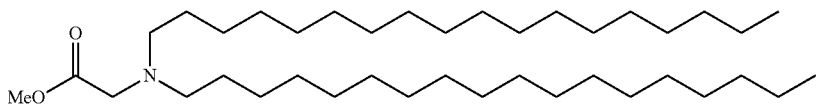

Chemical Formula: C₃₉H₇₉NO₂
Molecular Weight: 594.07

To a solution of methyl glycinate (1 g, 11.22 mmol) and 1-bromooctadecane (9.36 g, 28.06 mmol) in 1:1 CPME (10 mL):MeCN (10 mL) added K₂CO₃ (9.31 g, 67.35 mmol) and KI (4.66 g, 28.06 mmol). The reaction mixture was allowed to stir at 81° C. for 72 hours. The crude reaction mixture was allowed to cool to room temperature, filtered and concentrated in vacuo. The residue was dissolved in EtOAc and washed with water. Extracted aqueous layer three times with EtOAc. Dried organic layers over Na₂SO₄, filtered and concentrated in vacuo. The residue was purified by silica gel chromatography (0-40% (mixture of 1% NH₄OH, 20% MeOH in dichloromethane) in dichloromethane) to afford methyl dioctadecylglycinate (1.80 g, 3.03 mmol, 27%).

¹H NMR (300 MHz, CDCl₃) δ: ppm 3.72 (s, 3H); 3.35 (s, 2H); 2.57 (m, 4H); 1.48-1.44 (br. m, 4H); 1.30-1.26 (br. m, 60H); 0.90 (m, 6H).

Dioctadecylglycine

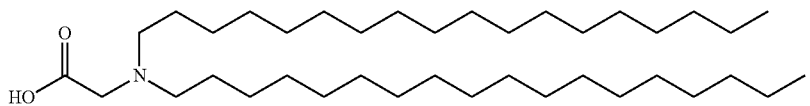

Chemical Formula: $C_{38}H_{77}NO_2$
Molecular Weight: 580.04

Dissolved methyl dioctadecylglycinate (1.8 g, 3.03 mmol) in EtOH (7.6 mL) and added 7.6 mL 2M NaOH to reaction mixture and allowed reaction to stir at 80° C. for 2 hours. Allowed the reaction mixture to cool to room temperature and concentrated in vacuo. Acidified the reaction mixture to pH 1 with 10% HCl. The residue was extracted three times with hexanes and concentrated in vacuo to afford dioctadecylglycine (305 mg, 0.526 mmol, 17%).

UPLC/ELSD: RT=3.81 min. MS (ES): m/z (MH+) 581.0.0 for $C_{38}H_{77}NO_2$ $^1$H NMR (300 MHz, CDCl$_3$) δ: ppm 3.95 (s, 2H); 3.28 (m, 4H); 1.81 (m, 4H); 1.34-1.28 (br. m, 60H); 0.90 (m, 6H).

3-(Dioctadecylamino)propanoic acid

Methyl 3-(dioctadecylamino)propanoate

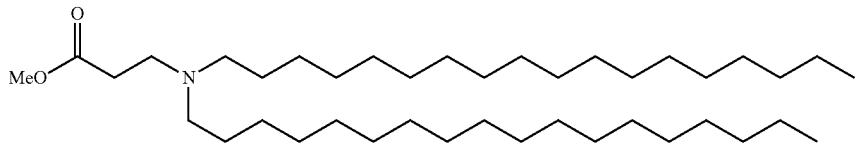

Chemical Formula: $C_{40}H_{81}NO_2$
Molecular Weight: 608.09

To a solution of methyl 3-aminopropanoate hydrochloride (1 g, 7.16 mmol) and 1-bromooctadecane (5.97 g, 17.91 mmol) in 1:1 CPME (10 mL):MeCN (10 mL) added K$_2$CO$_3$ (5.94 g, 42.99 mmol) and KI (2.97 g, 17.91 mmol). The reaction mixture was allowed to stir at 81° C. for 18 hours. The crude reaction mixture was allowed to cool to room temperature, filtered and concentrated in vacuo. The residue was dissolved in EtOAc and washed with water. Extracted aqueous layer three times with EtOAc. Dried organic layers over Na$_2$SO$_4$, filtered and concentrated in vacuo. The residue was purified by silica gel chromatography (0-20% (mixture of 1% NH$_4$OH, 20% MeOH in dichloromethane) in dichloromethane) to afford methyl 3-(dioctadecylamino) propanoate (5.01 g, 8.24 mmol, >99%).

$^1$H NMR (300 MHz, CDCl$_3$) δ: ppm 3.69 (s, 3H); 2.80 (t, 2H); 2.49-2.38 (br. m, 6H); 1.46-1.41 (br. m, 4H); 1.32-1.28 (br. m, 60H); 0.90 (m, 6H).

3-(Dioctadecylamino)propanoic acid

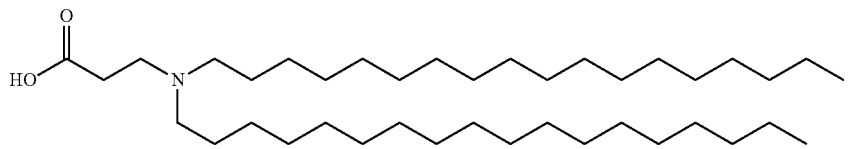

Chemical Formula: $C_{39}H_{79}NO_2$
Molecular Weight: 594.07

Dissolved methyl 3-(dioctadecylamino)propanoate (5.01 g, 8.24 mmol) in EtOH (20.6 mL) and added 20.6 mL 2M NaOH to reaction mixture and allowed reaction to stir at 80° C. for 2 hours. Allowed the reaction mixture to cool to room temperature and concentrated in vacuo. Acidified the reaction mixture to pH 1 with 10% HCl. The residue was extracted three times with hexanes and concentrated in vacuo to afford 3-(dioctadecylamino)propanoic acid (305 mg, 0.513 mmol, 6%).

UPLC/ELSD: RT=3.75 min. MS (ES): m/z (MH$^+$) 595.0 for $C_{39}H_{79}NO_2$ $^1$H NMR (300 MHz, CDCl$_3$) δ: ppm 11.48 (br s, 1H); 3.34 (m, 2H); 3.07 (m, 6H); 1.80 (m, 4H); 1.35-1.28 (br. m, 60H); 0.90 (m, 6H).

3-(Bis(8-(2-octylcyclopropyl)octyl)amino)propanoic acid 8-(2-Octylcyclopropyl)octan-1-ol

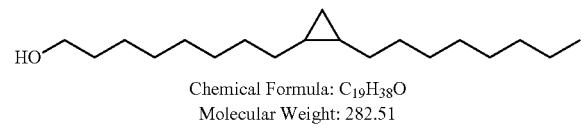 [SMILES: CCCCCCCCC1CC1CCCCCCCCO]

Chemical Formula: $C_{19}H_{38}O$
Molecular Weight: 282.51

To a solution of diethyl zinc (20 mL, 20 mmol, 1M in hexanes) in dichloromethane (20 mL), allowed reaction mixture to cool to −40° C. for 5 min. A solution of diiodomethane (3.22 mL, 40 mmol) in dichloromethane (10 mL) was added dropwise. The reaction mixture was allowed to stir for 1 hour at −40° C. and a solution of trichloro acetic acid (0.327 mg, 2 mmol) and DME (1 mL, 9.6 mmol) in dichloromethane (10 mL) was added. The reaction mixture was allowed to warm to −15° C. and allowed to stir at −15° C. temperature for 1 hour. A solution of (Z)-octadec-9-en-1-ol (2.68, 10 mmol) in dichloromethane (10 mL) was added at −15° C. The reaction mixture was allowed to slowly warm to room temperature and allowed to stir for 18 hours. The reaction mixture was washed with saturated aqueous NH$_4$Cl (200 mL) and extracted with dichloromethane three times. The organic layers were washed with brine, dried over Na$_2$SO$_4$, filtered and concentrated in vacuo. The residue was purified by silica gel chromatography (0-20% ethyl acetate in hexanes). The solvents were concentrated in vacuo and the residue was repurified by C18 silica gel chromatography (50-100% [MeCN with 0.1% TFA]/[water with 0.1% TFA]) to afford 8-(2-octylcyclopropyl)octan-1-ol (1.6 g, 5.7 mmol, 57%).

$^1$H NMR (300 MHz, CDCl$_3$) δ: ppm 3.67 (t, 2H); 1.60 (m, 2H); 1.50-1.06 (m, 27H); 0.90 (m, 3H); 0.63 (m, 3H); −0.31 (m, 1H).

1-(8-Bromooctyl)-2-octylcyclopropane

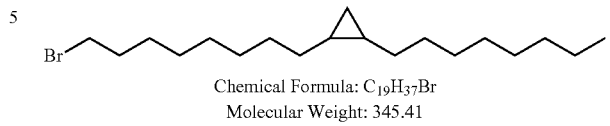

Chemical Formula: $C_{19}H_{37}Br$
Molecular Weight: 345.41

To a solution of PPh$_3$ (1.33 g, 5.1 mmol) and 8-(2-octylcyclopropyl)octan-1-ol (1.35 g, 4.7 mmol) in DCM (15 mL) at 0° C. NBS (0.986 g, 5.5 mmol) was added in one portion. The reaction was allowed to stir at 0° C. for 1 hour and then warmed to room temperature and allowed to stir for 1 hour. 300 mL of hexanes was added to the reaction mixture, filtered through a silica gel plug and concentrated in vacuo. 200 mL of hexanes was added to the reaction mixture, filtered through a silica gel plug and concentrated in vacuo to afford 1-(8-bromooctyl)-2-octylcyclopropane (1.44 g, 4.2 mmol, 89%).

$^1$H NMR (300 MHz, CDCl$_3$) δ: ppm 3.43 (t, 2H); 1.88 (m, 2H); 1.57-1.06 (m, 26H); 0.91 (m, 3H); 0.66 (m, 3H); −0.30 (m, 1H).

Methyl 3-((8-(2-octylcyclopropyl)octyl)amino)propanoate

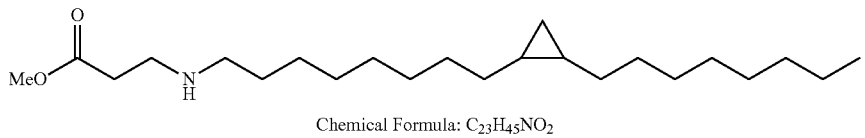

Chemical Formula: $C_{23}H_{45}NO_2$
Molecular Weight: 367.62

To a solution of methyl 3-aminopropanoate hydrochloride (200 mg, 1.45 mmol) and 1-(8-bromooctyl)-2-octylcyclopropane (1.26 g, 3.63 mmol) in 1:1 CPME (2 mL):MeCN (2 mL) added K$_2$CO$_3$ (1.21 g, 8.72 mmol) and KI (603.35 mg, 17.91 mmol). The reaction mixture was allowed to stir at 81° C. for 6 hours. The crude reaction mixture was allowed to cool to room temperature, filtered and concentrated in vacuo. The residue was dissolved in EtOAc and washed with water. Extracted aqueous layer three times with EtOAc. Dried organic layers over Na$_2$SO$_4$, filtered and concentrated in vacuo. The residue was purified by silica gel chromatography (0-20% DCM in MeOH) to afford methyl 3-((8-(2-octylcyclopropyl)octyl)amino)propanoate (700 mg, 1.11 mmol, 76%).

$^1$H NMR (300 MHz, CDCl$_3$) δ: ppm 3.71 (s, 3H); 2.92 (t, 2H); 2.64 (t, 2H); 2.57 (t, 2H); 1.98 (br. s, 1H); 1.53-1.14 (br. m, 28H); 0.90 (m, 3H); 0.68-0.54 (br. m, 3H); −0.32 (m, 1H).

Methyl 3-(bis(8-(2-octylcyclopropyl)octyl)amino)propanoate

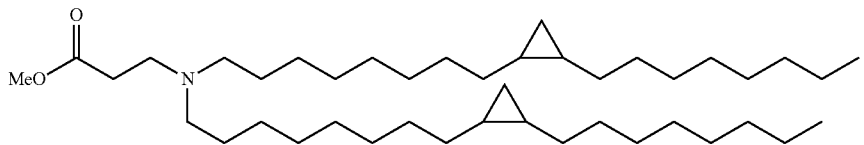

Chemical Formula: C$_{42}$H$_{81}$NO$_2$
Molecular Weight: 632.12

To a solution of methyl 3-((8-(2-octylcyclopropyl)octyl)amino)propanoate (700 mg, 1.9 mmol) and 1-(8-bromooctyl)-2-octylcyclopropane (280 mg, 0.82 mmol) in 1:1 CPME (7 mL):MeCN (7 mL) added K$_2$CO$_3$ (0.23 mg, 1.63 mmol) and KI (135.47 mg, 0.82 mmol). The reaction mixture was allowed to stir at 81° C. for 6 hours. The crude reaction mixture was allowed to cool to room temperature, filtered and concentrated in vacuo. The residue was dissolved in EtOAc and washed with water. Extracted aqueous layer three times with EtOAc. Dried organic layers over Na$_2$SO$_4$, filtered and concentrated in vacuo. The residue was purified by silica gel chromatography (0-20% DCM in MeOH) to afford methyl 3-(bis(8-(2-octylcyclopropyl)octyl)amino)propanoate (145 mg, 0.23 mmol, 28%).

$^1$H NMR (300 MHz, CDCl$_3$) δ: ppm 3.70 (s, 3H); 2.91 (m, 2H); 2.67-2.52 (br. m, 6H); 1.51-1.14 (br. m, 56H); 0.91 (m, 6H); 0.68-0.55 (br. m, 6H); −0.32 (m, 2H).

3-(Bis(8-(2-octylcyclopropyl)octyl)amino)propanoic acid

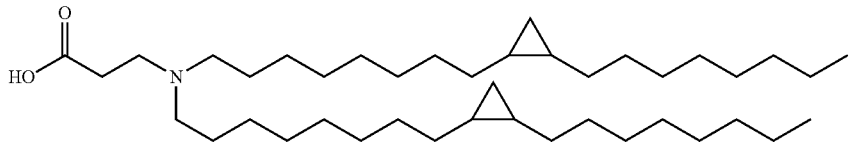

Chemical Formula: C$_{41}$H$_{79}$NO$_2$
Molecular Weight: 618.09

Dissolved methyl 3-(dioctadecylamino)propanoate (145 mg, 0.23 mmol) in EtOH (0.6 mL) and added 2M NaOH (0.6 mL) to reaction mixture and allowed reaction to stir at 40° C. for 2 hours. Allowed the reaction mixture to cool to room temperature and concentrated in vacuo. Acidified the reaction mixture to pH 1 with 2N HCl. The residue was extracted three times with hexanes and concentrated in vacuo to afford 3-(bis(8-(2-octylcyclopropyl)octyl)amino)propanoic acid (140 mg, 0.23 mmol, 98%).

UPLC/ELSD: RT=3.67 min. MS (ES): m/z (MH$^+$) 619.0 for C$_{41}$H$_{79}$NO$_2$ $^1$H NMR (300 MHz, CDCl$_3$) δ: ppm 11.10 (br s, 1H); 3.37 (m, 2H); 3.04 (br. m, 6H); 1.79 (br. m, 4H); 1.38-1.13 (br. m, 52H); 0.90 (m, 6H) 0.66-0.55 (br. m, 6H), −0.32 (m, 2H).

Methyl 3(di((Z)-octadec-9-en-1-yl)amino)propanoate (Z)-1-Bromooctadec-9-ene

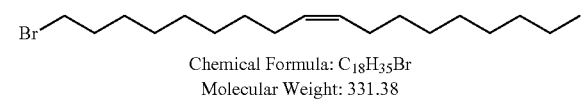 [SMILES: CCCCCCCC/C=C\CCCCCCCCBr]

Chemical Formula: C$_{18}$H$_{35}$Br
Molecular Weight: 331.38

To a solution of (Z)-octadec-9-en-1-ol (5 g, 18.62 mmol) and PPh$_3$ (5.18 g, 19.74 mmol) in DCM (60 mL) at 0° C., was added NBS (3.85 g, 21.60 mmol) in one portion. The reaction mixture was allowed to stir at 0° C. for 1 hour and then allowed to slowly warm to room temperature and allowed to stir for 1 hour. 240 mL of hexanes was added to the reaction mixture, filtered through a silica gel plug and concentrated in vacuo. 200 mL of hexanes was added to the reaction mixture, filtered through a silica gel plug and concentrated in vacuo to afford (Z)-1-bromooctadec-9-ene (4.70 g, 14.18 mmol, 76%).

$^1$H NMR (300 MHz, CDCl$_3$) δ: ppm 5.37 (m, 2H); 3.43 (t, 2H); 2.04 (m, 4H); 1.87 (m, 2H); 1.47-1.30 (br. m, 22H); 0.91 (m, 3H).

Methyl 3-(di((Z)-octadec-9-en-yl)amino)propanoate

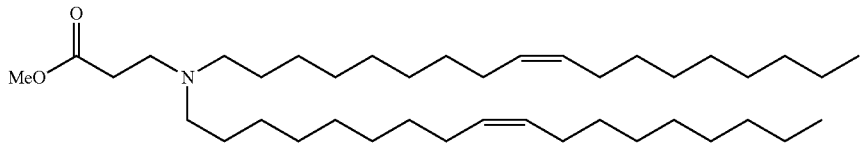

Chemical Formula: C₄₀H₇₇NO₂
Molecular Weight: 604.06

To a solution of methyl 3-aminopropanoate hydrochloride (100 mg, 0.72 mmol) and (Z)-1-bromooctadec-9-ene (594 mg, 1.79 mmol) in 1:1 CPME (2 mL):MeCN (2 mL) added K₂CO₃ (598 mg, 4.30 mmol) and KI (297 mg, 1.79 mmol). The reaction mixture was allowed to stir at 81° C. for 18 hours. The crude reaction mixture was allowed to cool to room temperature, filtered and concentrated in vacuo. The residue was dissolved in EtOAc and washed with water. Extracted aqueous layer three times with EtOAc. Dried organic layers over Na₂SO₄, filtered and concentrated in vacuo. The residue was purified by silica gel chromatography (0-20% (mixture of 1% NH₄OH, 20% MeOH in dichloromethane) in dichloromethane) to afford methyl 3-(di((Z)-octadec-9-en-yl)amino)propanoate (56 mg, 0.09 mmol, 13%).

¹H NMR (300 MHz, CDCl₃) δ: ppm 5.37 (m, 4H); 3.69 (s, 3H); 2.80 (t, 2H); 2.48-2.38 (br. m, 6H); 2.06-2.00 (br. m, 8H); 1.48-1.29 (br. m, 48H); 0.90 (m, 6H).

3-(Di((Z)-octadec-9-en-yl)amino)propanoic acid

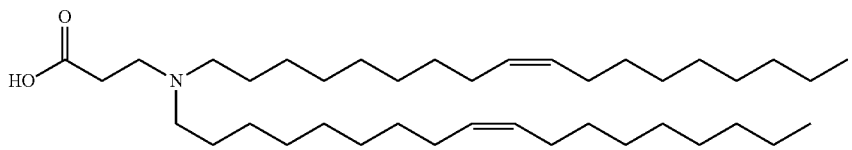

Chemical Formula: C₃₉H₇₅NO₂
Molecular Weight: 590.03

Dissolved methyl 3-(di((Z)-octadec-9-en-yl)amino)propanoate (56 mg, 0.09 mmol) in EtOH (0.23 mL) and added 2M NaOH (0.23 mL) to reaction mixture and allowed reaction mixture to stir at 30° C. for 30 min. Allowed the reaction mixture to cool to room temperature and concentrated in vacuo. Acidified the reaction mixture to pH 1 with 2N HCl. The residue was extracted three times with hexanes and concentrated in vacuo to afford 3-(di((Z)-octadec-9-en-yl)amino)propanoic acid (54 mg, 0.09 mmol, >99%).

UPLC/ELSD: RT=3.55 min. MS (ES): m/z (MH⁺) 591.0 for C₃₉H₇₅NO₂

¹H NMR (300 MHz, CDCl₃) δ: ppm 5.28 (m, 4H); 2.83 (m, 2H); 2.64 (m, 4H); 2.43 (m, 2H); 1.95-1.91 (br. m, 8H); 1.50 (m, 4H); 1.28-1.20 (br. m, 44H); 0.90 (m, 6H).

(Z)-3-(Octadec-9-en-1-ylamino)propanoic acid

Methyl (Z)-3-(octadec-9-en-1-ylamino)propanoate

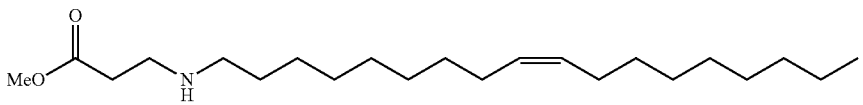

Chemical Formula: C₂₂H₄₃NO₂
Molecular Weight: 353.59

To a solution of methyl 3-aminopropanoate hydrochloride (100 mg, 0.72 mmol) and (Z)-1-bromooctadec-9-ene (594 mg, 1.79 mmol) in 1:1 CPME (2 mL):MeCN (2 mL) added K₂CO₃ (598 mg, 4.30 mmol) and KI (297 mg, 1.79 mmol). The reaction mixture was allowed to stir at 81° C. for 18 hours. The crude reaction mixture was allowed to cool to room temperature, filtered and concentrated in vacuo. The residue was dissolved in EtOAc and washed with water. Extracted aqueous layer three times with EtOAc. Dried organic layers over Na₂SO₄, filtered and concentrated in vacuo. The residue was purified by silica gel chromatography (0-20% MeOH in dichloromethane) to afford methyl (Z)-3-(octadec-9-en-1-ylamino)propanoate (64 mg, 0.18 mmol, 25%).

¹H NMR (300 MHz, CDCl₃) δ: ppm 5.36 (m, 2H); 3.70 (s, 3H); 2.90 (t, 2H); 2.62 (t, 2H); 2.54 (t, 2H); 2.18 (br. s, 1H); 2.05-1.98 (br. m, 4H); 1.52-1.45 (br. m, 2H); 1.36-1.28 (br. m, 22H); 0.89 (m, 3H).

(Z)-3-(Octadec-9-en-1-ylamino)propanoic acid

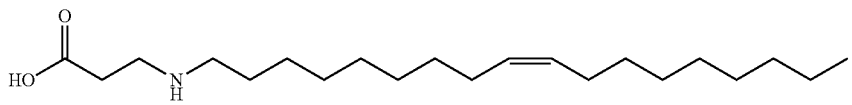

Chemical Formula: $C_{21}H_{41}NO_2$
Molecular Weight: 339.56

Dissolved methyl (Z)-3-(octadec-9-en-1-ylamino)propanoate (64 mg, 0.18 mmol) in EtOH (0.91 mL) and added 2M NaOH (0.91 mL) to reaction mixture and allowed reaction mixture to stir at room temperature for 1 hour. Allowed the reaction mixture to cool to room temperature and concentrated in vacuo. Acidified the reaction mixture to pH 1 with 2N HCl. The residue was extracted three times with hexanes and concentrated in vacuo to afford (Z)-3-(octadec-9-en-1-ylamino)propanoic acid (60 mg, 0.18 mmol, 98%).

UPLC/ELSD: RT=1.85 min. MS (ES): m/z (MH$^+$) 340.3 for $C_{21}H_{41}NO_2$ $^1$H NMR (300 MHz, CDCl$_3$) δ: ppm 8.59 (br. s, 1H); 5.27 (m, 2H); 4.88 (br. s, 1H); 3.18 (m, 2H); 2.98-2.92 (br. m, 4H); 1.97-1.90 (br. m, 4H); 1.78 (m, 2H); 1.26-1.19 (br. m, 22H); 0.81 (m, 3H).

3-(Di((9Z,12Z)-octadeca-9, 12-dien-1-yl)amino)propanoic acid (6Z,9Z)-18-Bromooctadeca-6,9-diene To a solution of (9Z,12Z)-octadeca-9,12-dien-1-ol (5 g, 18.76 mmol) and PPh$_3$ (5.22 g, 19.89 mmol) in DCM (60 mL) at 0° C., was added NBS (3.87 g, 21.77 mmol) in one portion. The reaction mixture was allowed to stir at 0° C. for 1 hour and then allowed to slowly warm to room temperature and allowed to stir for 1 hour. 240 mL of hexanes was added to the reaction mixture, filtered through a silica gel plug and concentrated in vacuo. 200 mL of hexanes was added to the reaction mixture, filtered through a silica gel plug and concentrated in vacuo to afford (6Z,9Z)-18-bromooctadeca-6,9-diene (4.06 g, 12.33 mmol, 66%).

$^1$H NMR (300 MHz, CDCl$_3$) δ: ppm 5.45-5.31 (br. m, 4H); 3.43 (t, 2H); 2.80 (m, 2H); 2.11-2.04 (br. m, 4H); 1.88 (m, 2H); 1.47-1.33 (br. m, 16H); 0.92 (m, 3H).

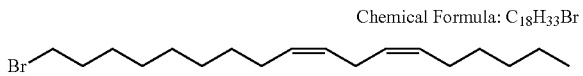

Chemical Formula: $C_{18}H_{33}Br$
Molecular Weight: 329.37

Methyl 3-(di((9Z,12Z)-octadeca-9, 12-dien-1-yl)amino)propanoate

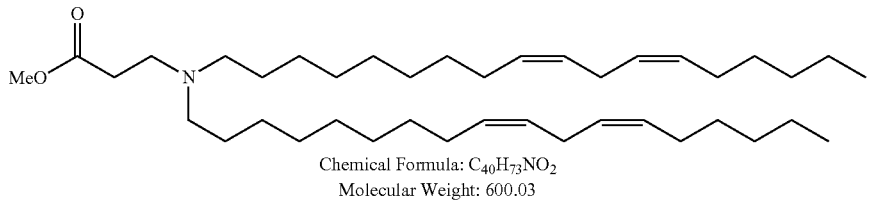 [SMILES: CCCCC/C=C\C/C=C\CCCCCCCCN(CCCCCCCC/C=C\C/C=C\CCCCC)CCC(=O)OC]

Chemical Formula: $C_{40}H_{73}NO_2$
Molecular Weight: 600.03

To a solution of methyl 3-aminopropanoate hydrochloride (100 mg, 0.72 mmol) and (6Z,9Z)-18-bromooctadeca-6,9-diene (590 mg, 1.79 mmol) in 1:1 CPME (2 mL):MeCN (2 mL) added K$_2$CO$_3$ (600 mg, 4.30 mmol) and KI (300 mg, 1.79 mmol). The reaction mixture was allowed to stir at 50° C. for 18 hours followed by 60° C. for 24 hours. The crude reaction mixture was allowed to cool to room temperature, filtered and concentrated in vacuo. The residue was dissolved in EtOAc and washed with water. Extracted aqueous layer three times with EtOAc. Dried organic layers over Na$_2$SO$_4$, filtered and concentrated in vacuo. The residue was purified by silica gel chromatography (0-15% MeOH in dichloromethane) to afford methyl 3-(di((9Z,12Z)-octadeca-9, 12-dien-1-yl)amino)propanoate (56 mg, 0.09 mmol, 13%).

$^1$H NMR (300 MHz, CDCl$_3$) δ: ppm 5.38 (m, 8H); 3.69 (s, 3H); 2.83-2.77 (br. m, 6H); 2.50-2.39 (br. m, 6H); 2.11-2.04 (br. m, 8H); 1.46-1.30 (br. m, 36H); 0.91 (m, 6H).

3-(Di((9Z,12Z)-octadeca-9, 12-dien-1-yl)amino)propanoic acid

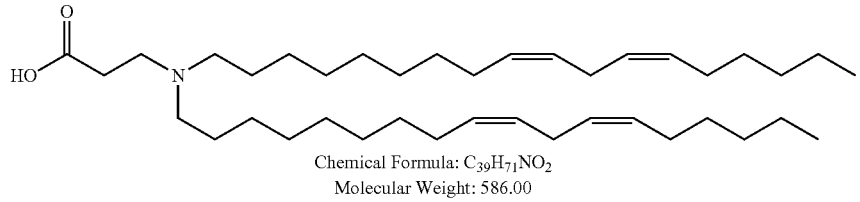 [SMILES: CCCCC/C=C\C/C=C\CCCCCCCCN(CCCCCCCC/C=C\C/C=C\CCCCC)CCC(=O)O]

Chemical Formula: C$_{39}$H$_{71}$NO$_2$
Molecular Weight: 586.00

Dissolved methyl 3-(di((9Z,12Z)-octadeca-9, 12-dien-1-yl)amino)propanoate (113 mg, 0.19 mmol) in EtOH (0.94 mL) and added 2M NaOH (0.94 mL) to reaction mixture and allowed reaction mixture to stir at room temperature for 1 hour and concentrated in vacuo. Acidified the reaction mixture to pH 1 with 1N HCl. The residue was extracted three times with hexanes and concentrated in vacuo to afford 3-(di((9Z,12Z)-octadeca-9, 12-dien-1-yl)amino)propanoic acid (106 mg, 0.18 mmol, 95%).

UPLC/ELSD: RT=3.32 min. MS (ES): m/z (MH$^+$) 586.8 for C$_{39}$H$_{71}$NO$_2$ $^1$H NMR (300 MHz, CDCl$_3$) δ: ppm 5.38 (m, 8H); 2.88-2.77 (br. m, 6H); 2.65 (m, 4H); 2.47 (m, 2H); 2.11-2.04 (br. m, 8H); 1.58-1.52 (br. m, 4H); 1.43-1.28 (br. m, 32H); 0.91 (m, 6H).

N-Methyloleamide

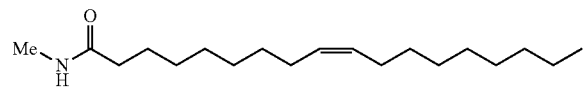

Chemical Formula: C$_{19}$H$_{37}$NO
Molecular Weight: 295.51

To a solution of oleic acid (500 mg, 1.77 mmol) in THF (8 mL) was added methylamine (885 μL, 1.77 mmol) HATU (673 mg, 1.77 mmol) and DIPEA (617 μL, 3.54 mmol). The reaction was allowed to stir at room temperature for 3 hours. Quenched reaction with 1N citric acid and extracted three times with diethyl ether. The organic layers were washed with water and brine. Dried organic layers over Na$_2$SO$_4$, filtered and concentrated in vacuo. The residue was purified by silica gel chromatography (10-100% EtOAc in hexanes) to afford N-methyloleamide (495 mg, 1.67 mmol, 95%).

UPLC/ELSD: RT=2.67 min. MS (ES): m/z (MH$^+$) 295.9 for C$_{19}$H$_{37}$NO $^1$H NMR (300 MHz, CDCl$_3$) δ: ppm 5.36 (m, 2H); 3.26 (br. s, 1H); 2.83 (d, 3H); 2.18 (t, 2H); 2.05-2.00 (br. m, 4H); 1.66-1.62 (br. m, 4H); 1.37-1.29 (br. m, 18H); 0.90 (m, 3H).

3-Ammonio-4-(2,3-bis(stearoyloxy)propoxy)-4-oxobutanoate

4-Benzyl 1-(2,3-bis(stearoyloxy)propyl) (tert-butoxycarbonyl)aspartate

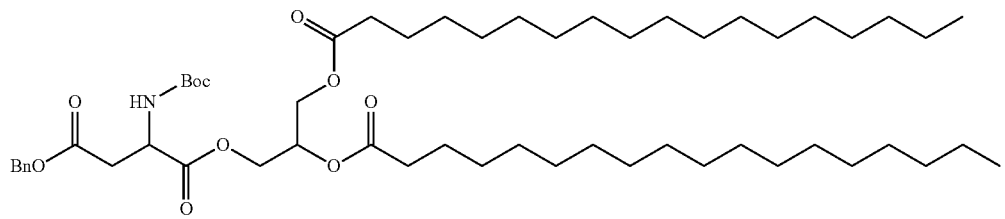

Chemical Formula: C$_{55}$H$_{95}$NO$_{10}$
Molecular Weight: 930.36

A mixture of 3-hydroxypropane-1,2-diyl distearate (625 mg, 1.0 mmol), 4-(benzyloxy)-2-((tert-butoxycarbonyl)amino)-4-oxobutanoic acid (647 mg, 2.0 mmol), EDCI (384 mg, 2.0 mmol) and DMAP (12 mg, 0.1 mmol) in 40 mL dichloromethane was stirred at room temperature for 16 h. TLC showed complete reaction. The reaction mixture was diluted with water and extracted with dichloromethane, and the combined organic layer was washed with brine and dried over sodium sulfate. After filtration and concentration, the crude was purified by ISCO (24 g SiO$_2$: EtOAc/Hexanes 0 to 40%) to provide 4-benzyl 1-(2,3-bis(stearoyloxy)propyl) (tert-butoxycarbonyl)aspartate as white solid (918 mg, 98%).

$^1$H NMR (300 MHz, CDCl$_3$) δ 7.31-7.36 (m, 5H), 5.48 (m, 1H), 5.21 (m, 1H), 5.17 (s, 2H), 4.58-4.63 (m, 1H), 4.19-4.26 (m, 2H), 4.05-4.13 (m, 2H), 2.95-3.08 (m, 1H), 2.78-2.87 (m, 1H), 2.29 (dt, 4H, J=7.4 Hz, 1.9 Hz), 1.55-1.64 (m, 6H), 1.42 (s, 9H), 1.24 (bs, 54H), 0.87 (t, 6H, J=6.8 Hz).

MS (APCI): m/z (MH$^+$) 830.6.

4-(2,3-Bis(stearoyloxy)propoxy)-3-((tert-butoxycarbonyl)amino)-4-oxobutanoic acid

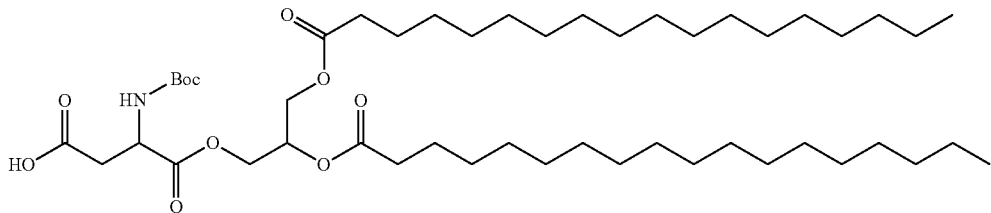

Chemical Formula: C$_{48}$H$_{89}$NO$_{10}$
Molecular Weight: 840.24

A mixture of 4-benzyl 1-(2,3-bis(stearoyloxy)propyl) (tert-butoxycarbonyl)aspartate (918 mg, 0.98 mmol) and Pd/C (5%, 300 mg) in 80 mL EtOAc was stirred for 16 h under hydrogen balloon. TLC showed complete reaction. The reaction mixture was filtered through Celite and washed with dichloromethane. The filtrate was concentrated to provide 4-(2,3-bis(stearoyloxy)propoxy)-3-((tert-butoxycarbonyl)amino)-4-oxobutanoic acid as white solid (805 mg, quant.), which was used for the next step without purification.

$^1$H NMR (300 MHz, CDCl$_3$) δ 5.46-5.52 (m, 1H), 5.26 (m, 1H), 4.58 (m, 1H), 4.07-4.44 (m, 4H), 2.76-3.06 (m, 2H), 2.30 (t, 4H, J=7.4 Hz), 1.54-1.64 (m, 4H), 1.44 (s, 9H), 1.24 (bs, 56H), 0.87 (t, 6H, J=6.8 Hz).

MS (APCI): m/z (MH$^+$) 740.6.

3-Ammonio-4-(2,3-bis(stearoyloxy)propoxy)-4-oxobutanoate

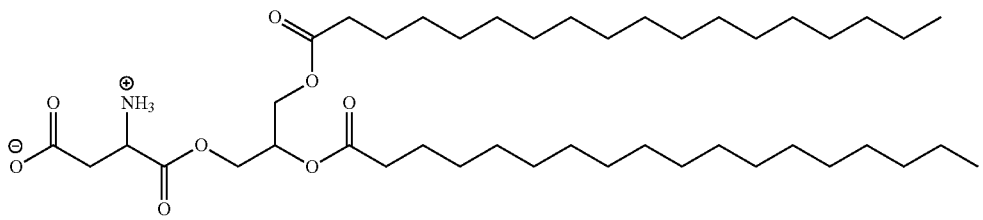

Chemical Formula: C$_{43}$H$_{81}$NO$_8$
Molecular Weight: 740.12

4-(2,3-Bis(stearoyloxy)propoxy)-3-((tert-butoxycarbonyl)amino)-4-oxobutanoic acid (800 mg, 0.98 mmol) was dissolved in 4M HCl in dioxane (5 mL), and the mixture was stirred at room temperature for 2 h. TLC showed the disappearance of starting material. Hexanes was added into the reaction mixture and triturated to provide the desired product, 3-ammonio-4-(2,3-bis(stearoyloxy)propoxy)-4-oxobutanoate as a white solid (701 mg, 92%).

$^1$H NMR (300 MHz, CDCl$_3$) δ 8.23 (bs, 2H), 5.31 (m, 1H), 4.08-4.54 (m, 5H), 3.14-3.36 (m, 2H), 2.31 (q, 4H, J=7.4 Hz), 1.58 (m, 4H), 1.24 (bs, 56H), 0.87 (t, 6H, J=7.1 Hz).

MS (APCI): m/z (MH$^+$) 740.6.

1-(2,3-Bis(stearoyloxy)propoxy)-4-carboxy-1-oxobutan-2-aminium chloride

5-Benzyl 1-(2,3-bis(stearoyloxy)propyl)(tert-butoxycarbonyl)glutamate

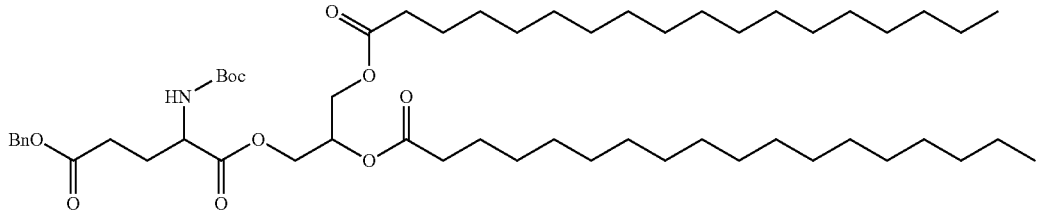

Chemical Formula: $C_{56}H_{97}NO_{10}$
Molecular Weight: 944.39

A mixture of 3-hydroxypropane-1,2-diyl distearate (625 mg, 1.0 mmol), 5-(benzyloxy)-2-((tert-butoxycarbonyl)amino)-5-oxopentanoic acid (674 mg, 2.0 mmol), EDCI (384 mg, 2.0 mmol) and DMAP (12 mg, 0.1 mmol) in 40 mL dichloromethane was stirred at room temperature for 16 h. TLC showed complete reaction. The reaction mixture was diluted with water and extracted with dichloromethane, and the combined organic layer was washed with brine and dried over sodium sulfate. After filtration and concentration, the crude was purified by ISCO (24 g $SiO_2$: EtOAc/Hexanes 0 to 40%) to provide 5-benzyl 1-(2,3-bis(stearoyloxy)propyl)(tert-butoxycarbonyl)glutamate as white solid (950 mg, Quant.).

$^1$H NMR (300 MHz, $CDCl_3$) δ 7.34 (m, 5H), 5.25 (m, 1H), 5.04-5.11 (m, 3H), 4.09-4.37 (m, 6H), 2.43-2.49 (m, 2H), 2.26-2.32 (m, 4H), 2.14-2.20 (m, 2H), 1.88-2.02 (m, 2H), 1.58 (m, 3H), 1.42 (s, 9H), 1.24 (bs, 54H), 0.87 (t, 6H, J=7.1 Hz).

MS (APCI): m/z (MH$^+$) 844.6.

5-(2,3-Bis(stearoyloxy)propoxy)-4-((tert-butoxycarbonyl)amino)-5-oxopentanoic acid

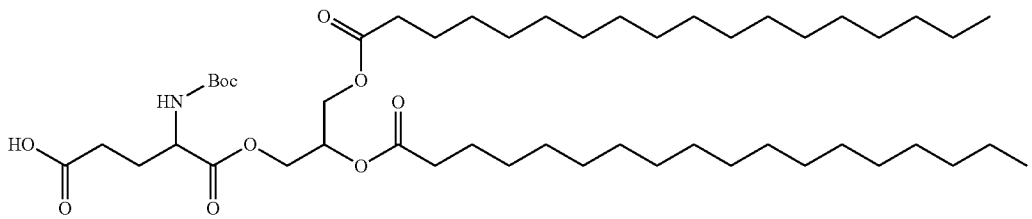

Chemical Formula: $C_{49}H_{91}NO_{10}$
Molecular Weight: 854.26

A mixture of 5-benzyl 1-(2,3-bis(stearoyloxy)propyl)(tert-butoxycarbonyl)glutamate (950 mg, 1.0 mmol) and Pd/C (5%, 300 mg) in 80 mL EtOAc was stirred for 16 h under hydrogen balloon. TLC showed complete reaction. The reaction mixture was filtered through Celite and washed with dichloromethane. The filtrate was concentrated to provide 5-(2,3-bis(stearoyloxy)propoxy)-4-((tert-butoxycarbonyl)amino)-5-oxopentanoic acid as white solid (848 mg, 99%), which was used for the next step without purification.

$^1$H NMR (300 MHz, $CDCl_3$) δ 6.39 (m, 0.5H), 6.25 (m, 0.5H), 5.10-5.29 (m, 2H), 4.06-4.34 (m, 3H), 3.74 (m, 1H), 3.25 (m, 1H), 2.44-2.52 (m, 2H), 2.31 (q, 2H, J=6.8 Hz), 2.00-2.21 (m, 5H), 1.54-1.66 (m, 4H), 1.44 (s, 9H), 1.24 (bs, 54H), 0.87 (t, 6H, J=6.8 Hz).

MS (APCI): m/z (MH$^+$) 754.6.

1-(2,3-Bis(stearoyloxy)propoxy)-4-carboxy-1-oxobutan-2-aminium chloride

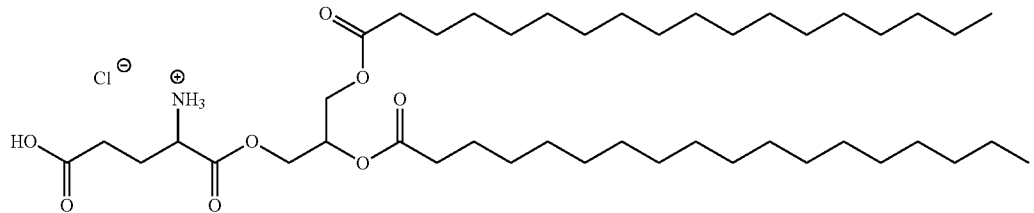

Chemical Formula: C$_{44}$H$_{84}$ClNO$_8$
Molecular Weight: 790.61

4-(2,3-Bis(stearoyloxy)propoxy)-3-((tert-butoxycarbonyl)amino)-4-oxobutanoic acid (848 mg, 0.99 mmol) was dissolved in 4M HCl in dioxane (20 mL), and the mixture was stirred at room temperature for 16 h. TLC showed the disappearance of starting material. Hexanes was added into the reaction mixture and triturated to provide the desired product, 1-(2,3-bis(stearoyloxy)propoxy)-4-carboxy-1-oxobutan-2-aminium chloride as white solid (740 mg, 94%).

$^1$H NMR (300 MHz, CDCl$_3$) δ 5.32 (m, 2H), 4.17-4.44 (m, 6H), 2.72 (m, 2H), 2.28-2.36 (m, 5H), 1.55-1.64 (m, 4H), 1.20-1.37 (bs, 58H), 0.88 (t, 6H, J=6.8 Hz).

MS (APCI): m/z (MH$^+$) 754.6.

3-(2,3-Bis(stearoyloxy)propoxy)-1-carboxy-3-oxopropan-1-aminium chloride

1-Benzyl 4-(2,3-bis(stearoyloxy)propyl) (tert-butoxycarbonyl)aspartate

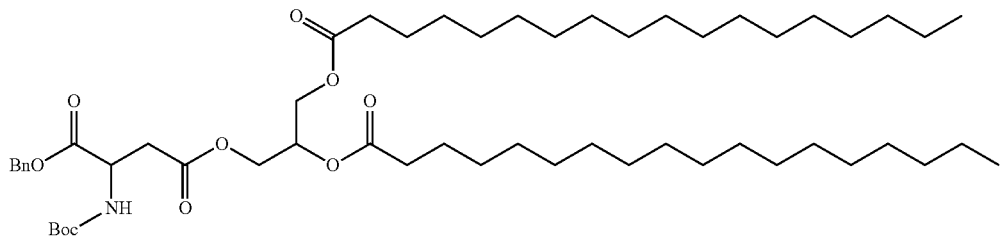

Chemical Formula: C$_{55}$H$_{95}$NO$_{10}$
Molecular Weight: 930.36

A mixture of 3-hydroxypropane-1,2-diyl distearate (625 mg, 1.0 mmol), 4-(benzyloxy)-3-((tert-butoxycarbonyl)amino)-4-oxobutanoic acid (647 mg, 2.0 mmol), EDCI (384 mg, 2.0 mmol) and DMAP (12 mg, 0.1 mmol) in 40 mL dichloromethane was stirred at room temperature for 16 h. TLC showed complete reaction. The reaction mixture was diluted with water and extracted with dichloromethane, and the combined organic layer was washed with brine and dried over sodium sulfate. After filtration and concentration, the crude was purified by ISCO (40 g SiO$_2$: EtOAc/Hexanes 0 to 20%) to provide 1-benzyl 4-(2,3-bis(stearoyloxy)propyl) (tert-butoxycarbonyl)aspartate as white solid (942 mg, Quant.)

$^1$H NMR (300 MHz, CDCl$_3$) δ 7.28-7.37 (m, 5H), 5.46-5.53 (m, 1H), 5.21 (m, 1H), 5.17 (s, 2H), 4.56-4.64 (m, 1H), 4.20-4.25 (m, 2H), 4.05-4.12 (m, 2H), 2.94-3.04 (m, 1H), 2.78-2.87 (m, 1H), 2.29 (dt, 4H, J=7.6 Hz, 1.9 Hz), 1.56-1.64 (m, 4H), 1.42 (s, 9H), 1.24 (bs, 56H), 0.87 (t, 6H, J=6.8 Hz).

MS (APCI): m/z (MH$^+$) 830.6.

4-(2,3-Bis(stearoyloxy)propoxy)-2-((tert-butoxycarbonyl)amino)-4-oxobutanoic acid

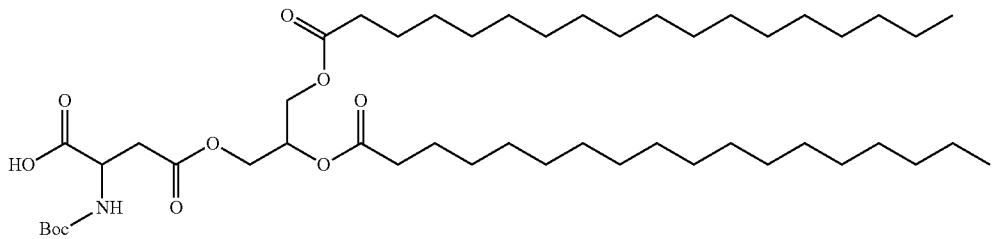

Chemical Formula: C_{48}H_{89}NO_{10}
Molecular Weight: 840.24

A mixture of 1-benzyl 4-(2,3-bis(stearoyloxy)propyl) (tert-butoxycarbonyl)aspartate (942 mg, 1.0 mmol) and Pd/C (5%, 300 mg) in 80 mL EtOAc was stirred for 16 h under hydrogen balloon. TLC showed complete reaction. The reaction mixture was filtered through Celite and washed with dichloromethane. The filtrate was concentrated to provide 4-(2,3-bis(stearoyloxy)propoxy)-2-((tert-butoxycarbonyl)amino)-4-oxobutanoic acid as white solid (800 mg, 95%), which was used for the next step without purification.

$^1$H NMR (300 MHz, CDCl$_3$) δ 5.56 (m, 1H), 5.23-5.28 (m, 1H), 4.56 (m, 1H), 4.12-4.32 (m, 5H), 2.98-3.07 (m, 2H), 2.81-2.89 (m, 2H), 2.28-2.35 (m, 4H), 1.60 (m, 4H), 1.45 (s, 9H), 1.24 (bs, 54H), 0.87 (t, 6H, J=7.1 Hz).

MS (APCI): m/z (MH$^+$) 740.6.

3-(2,3-Bis(stearoyloxy)propoxy)-1-carboxy-3-oxopropan-1-aminium chloride

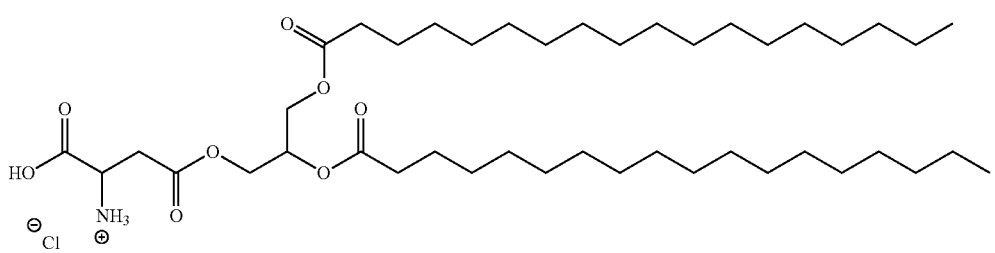

Chemical Formula: C_{43}H_{82}ClNO_{8}
Molecular Weight: 776.58

4-(2,3-Bis(stearoyloxy)propoxy)-2-((tert-butoxycarbonyl)amino)-4-oxobutanoic acid (800 mg, 0.95 mmol) was dissolved in 4M HCl in dioxane (20 mL), and the mixture was stirred at room temperature for 16 h. TLC showed the disappearance of starting material. Hexanes was added into the reaction mixture and triturated to provide the desired product, 3-(2,3-bis(stearoyloxy)propoxy)-1-carboxy-3-oxopropan-1-aminium chloride as white solid (718 mg, 97%).

$^1$H NMR (300 MHz, CDCl$_3$) δ 5.29 (m, 1H), 4.53 (m, 1H), 4.12-4.38 (m, 5H), 3.28 (m, 2H), 2.32 (q, 4H, J=7.7 Hz), 1.60 (m, 4H), 1.24 (bs, 59H), 0.88 (t, 6H, J=6.6 Hz).

MS (APCI): m/z (MH$^+$) 740.6.

1-((2,3-Bis(stearoyloxy)propyl)amino)-4-carboxy-1-oxobutan-2-aminium chloride 3-((Methylsulfonyl)oxy)propane-1,2-diyl distearate

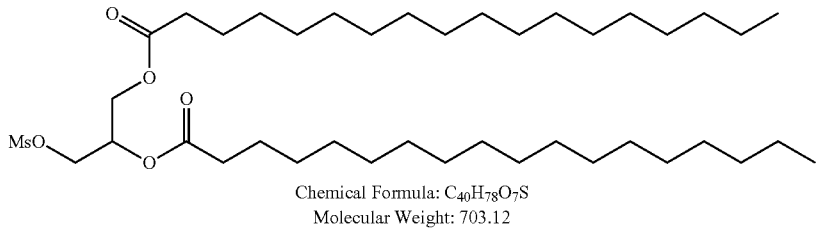 [SMILES: CCCCCCCCCCCCCCCCCC(=O)OCC(COS(C)(=O)=O)OC(=O)CCCCCCCCCCCCCCCCC]

Chemical Formula: $C_{40}H_{78}O_7S$
Molecular Weight: 703.12

To a solution of 3-hydroxypropane-1,2-diyl distearate (6.25 g, 10 mmol) and triethylamine (1.81 mL, 12.5 mmol) in 100 mL dichloromethane, methanesulfonyl chloride (0.97 mL, 12.5 mmol) was added dropwise at 0° C., and then the reaction was stirred at room temperature for 48 h. TLC showed complete reaction, and the reaction mixture was diluted with water and extracted with dichloromethane. The combined organic layer was washed with saturated sodium bicarbonate solution and brine. After dried over sodium sulfate, the filtrate was concentrated to provide 3-((methylsulfonyl)oxy)propane-1,2-diyl distearate as white solid (7.07 g, quant.), NMR showed mixture of mesylate and chloride, which was used for the next step without further purification.

$^1$H NMR (300 MHz, CDCl$_3$) δ 5.23-5.30 (m, 1H), 4.29-4.41 (m, 3H), 4.17 (dd, 1H, J=11.9 Hz, 5.7 Hz), 2.43 (q, 4H, J=7.6 Hz), 1.61 (m, 3H), 1.24 (bs, 60H), 0.87 (t, 6H, J=6.8 Hz).

3-Azidopropane-1,2-diyl distearate

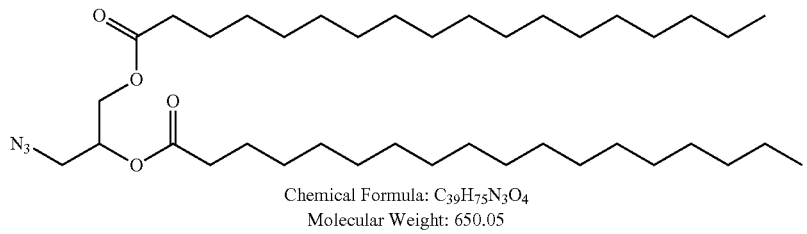 [SMILES: CCCCCCCCCCCCCCCCCC(=O)OCC(CN=[N+]=[N-])OC(=O)CCCCCCCCCCCCCCCCC]

Chemical Formula: $C_{39}H_{75}N_3O_4$
Molecular Weight: 650.05

In a sealed tube, a mixture of 3-((methylsulfonyl)oxy)propane-1,2-diyl distearate (7.07 g, 10 mmol) and sodium azide (3.26 g, 50 mmol) in 40 mL DMF was heated to 100° C. for 16 h. After cooled to room temperature, the reaction mixture was diluted with water and extracted with hexanes/ether mixture. The organic layer was washed with water and brine. After dried over sodium sulfate, the filtrate was concentrated and purified by ISCO (120 g SiO$_2$: EtOAc/hexanes 0 to 50%) to provide 3-azidopropane-1,2-diyl distearate as white solid (5.40 g, 83%).

$^1$H NMR (300 MHz, CDCl$_3$) δ 5.17 (pent, 1H, J=4.9 Hz), 4.29 (dd, 1H, J=11.9 Hz, 4.6 Hz), 4.14 (dd, 1H, J=11.9 Hz, 5.5 Hz), 3.45 (t, 2H, J=3.3 Hz), 2.34 (dt, 4H, J=10.2 Hz, 7.4 Hz), 1.57-1.65 (m, 4H), 1.24 (bs, 56H), 0.87 (t, 6H, J=7.1 Hz).

3-Aminopropane-1,2-diyl distearate

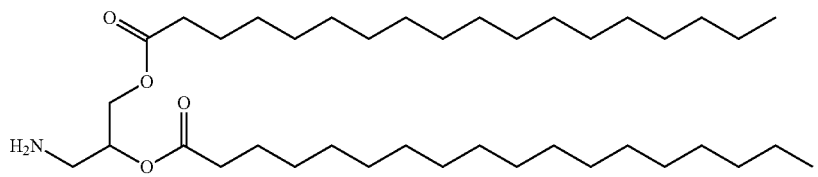

Chemical Formula: $C_{39}H_{77}NO_4$
Molecular Weight: 624.05

A mixture of 3-azidopropane-1,2-diyl distearate (3.71 g, 5.7 mmol) and Pd/C (5%, Degaussa E10002U/W, Aldrich 330124, 370 mg) in 100 mL EtOAc was purged with nitrogen and hydrogen 3 times, respectively, and then the reaction was stirred at room temperature with balloon for 16 h. TLC showed complete reaction. The reaction mixture was filtered through Celite and washed with hot dichloromethane to provide 3-aminopropane-1,2-diyl distearate as white solid (2.20 g, 62%). This compound has low solubility in most of the solvents at room temperature.

$^1$H NMR (300 MHz, CDCl$_3$) δ 5.90 (m, 0.5H), 5.74 (m, 0.5H), 3.91-4.20 (m, 2H), 3.12-3.70 (m, 2H), 2.30-2.36 (m, 3H), 2.18-2.25 (m, 1H), 1.53-1.66 (m, 6H), 1.24 (bs, 56H), 0.87 (t, 6H, J=7.1 Hz).

MS (APCI): m/z (MH$^+$) 624.6.

3-(5-(Benzyloxy)-2-((tert-butoxycarbonyl)amino)-5-oxopentanamido)propane-1,2-diyl distearate

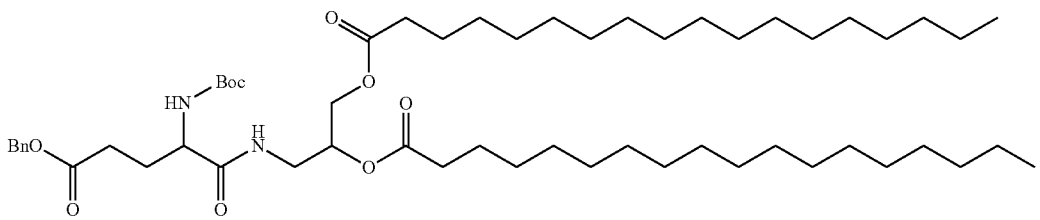

Chemical Formula: C$_{56}$H$_{98}$N$_2$O$_9$
Molecular Weight: 943.41

A mixture of 3-aminopropane-1,2-diyl distearate (624 mg, 1.0 mmol), 5-(benzyloxy)-2-((tert-butoxycarbonyl)amino)-5-oxopentanoic acid (674 mg, 2.0 mmol), EDCI (384 mg, 2.0 mmol) and DMAP (12 mg, 0.1 mmol) in 70 mL/70 mL dichloromethane/THF was heated to 45° C. for 16 h. TLC showed complete reaction. The reaction mixture was diluted with water and extracted with dichloromethane, and the combined organic layer was washed with brine and dried over sodium sulfate. After filtration and concentration, the crude was purified by ISCO (40 g SiO$_2$: EtOAc/Hexanes 0 to 20%) to provide 3-(5-(benzyloxy)-2-((tert-butoxycarbonyl)amino)-5-oxopentanamido)propane-1,2-diyl distearate as white solid (840 mg, 89%).

$^1$H NMR (300 MHz, CDCl$_3$) δ 7.31-7.39 (m, 5H), 6.25 (m, 1H), 5.39-5.44 (m, 1H), 5.12-5.22 (m, 3H), 4.08-4.53 (m, 4H), 2.44-2.49 (m, 4H), 2.20-2.38 (m, 2H), 2.30 (m, 4H), 2.16 (m, 1H), 1.95 (m, 1H), 1.55-1.64 (m, 1H), 1.43 (s, 9H), 1.24 (bs, 56H), 0.87 (t, 6H, J=6.8 Hz).

MS (APCI): m/z (MH$^+$) 943.7, 843.7.

5-((2,3-Bis(stearoyloxy)propyl)amino)-4-((tert-butoxycarbonyl)amino)-5-oxopentanoic acid

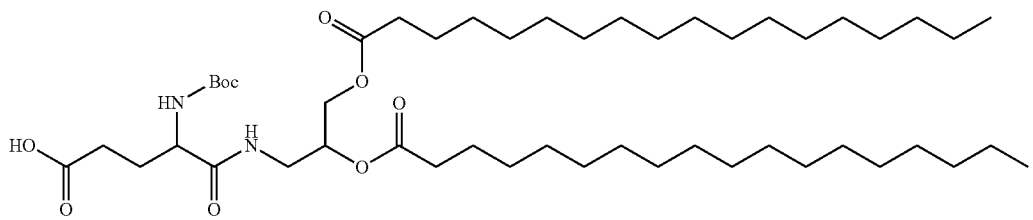

Chemical Formula: C$_{49}$H$_{92}$N$_2$O$_9$
Molecular Weight: 853.28

A mixture of 3-(5-(benzyloxy)-2-((tert-butoxycarbonyl)amino)-5-oxopentanamido)propane-1,2-diyl distearate (840 mg, 0.89 mmol) and Pd/C (5%, 250 mg) in 80 mL EtOAc was stirred for 16 h under hydrogen balloon. TLC showed complete reaction. The reaction mixture was filtered through Celite and washed with dichloromethane. The filtrate was concentrated to provide 5-((2,3-bis(stearoyloxy)propyl)amino)-4-((tert-butoxycarbonyl)amino)-5-oxopentanoic acid as a white solid (722 mg, 84%), which was used for the next step without purification.

$^1$H NMR (300 MHz, CDCl$_3$) δ 5.23-5.29 (m, 1H), 5.12-5.16 (m, 1H), 4.08-4.42 (m, 6H), 2.44-2.49 (m, 4H), 2.20-2.38 (m, 2H), 2.30 (t, 4H, J=7.6 Hz), 2.16 (m, 1H), 1.95 (m, 1H), 1.55-1.64 (m, 2H), 1.43 (s, 9H), 1.24 (bs, 54H), 0.87 (t, 6H, J=6.8 Hz).

MS (APCI): m/z (MH$^+$) 853.7, 753.6.

1-((2,3-Bis(stearoyloxy)propyl)amino)-4-carboxy-1-oxobutan-2-aminium chloride

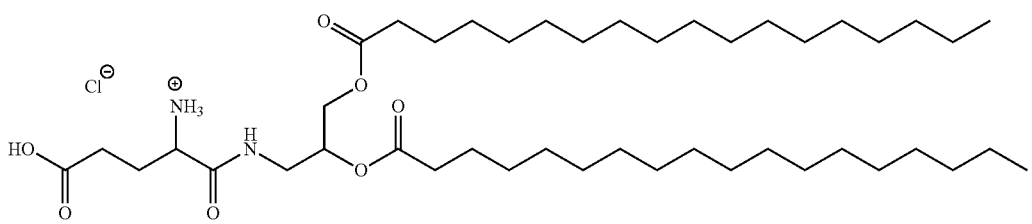

Chemical Formula: C$_{44}$H$_{85}$ClN$_2$O$_7$
Molecular Weight: 789.62

5-((2,3-Bis(stearoyloxy)propyl)amino)-4-((tert-butoxycarbonyl)amino)-5-oxopentanoic acid (722 mg, 0.84 mmol) was dissolved in 4M HCl in dioxane (20 mL), and the mixture was stirred at room temperature for 16 h. TLC showed the disappearance of starting material, and the reaction mixture is clear solution. After concentration, the crude was purified by Gold ISCO (24 g SiO$_2$: MeOH/dichloromethane 0 to 50%) to provide the desired product, 1-((2,3-bis(stearoyloxy)propyl)amino)-4-carboxy-1-oxobutan-2-aminium chloride as white solid (610 mg, 91%).

$^1$H NMR (300 MHz, CDCl$_3$) δ 8.43 (bs, 2H), 5.21 (m, 1H), 4.18-4.38 (m, 3H), 3.36-3.75 (m, 3H), 2.68 (m, 2H), 2.20-2.35 (m, 6H), 1.57 (m, 4H), 1.24 (bs, 56H), 0.87 (t, 6H, J=6.8 Hz).

MS (APCI): m/z (MH$^+$) 753.6.

3-((2,3-Bis(stearoyloxy)propyl)amino)-1-carboxy-3-oxopropan-1-aminium chloride 3-(4-(tert-Butoxy)-3-((tert-butoxycarbonyl)amino)-4-oxobutanamido)propane-1,2-diyl distearate

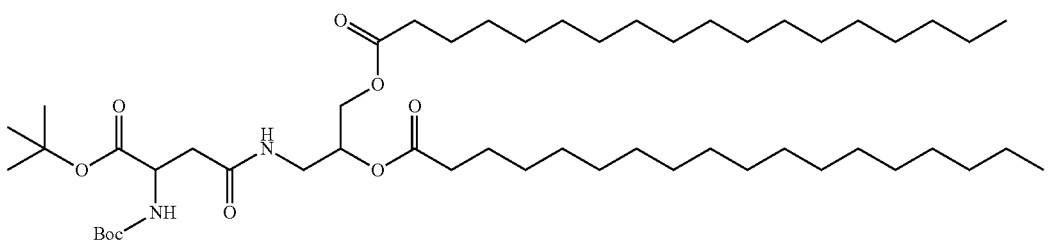

Chemical Formula: C$_{52}$H$_{98}$N$_2$O$_9$
Molecular Weight: 895.36

A mixture of 3-aminopropane-1,2-diyl distearate (500 mg, 0.80 mmol), 4-(tert-butoxy)-3-((tert-butoxycarbonyl)amino)-4-oxobutanoic acid (463 mg, 1.60 mmol), EDCI (307 mg, 1.60 mmol) and DMAP (10 mg, 0.08 mmol) in 70 mL/70 mL dichloromethane/THF was heated to 45° C. for 16 h. TLC showed complete reaction. The reaction mixture was diluted with water and extracted with dichloromethane, and the combined organic layer was washed with brine and dried over sodium sulfate. After filtration and concentration, the crude was purified by ISCO (24 g SiO$_2$: EtOAc/Hexanes 0 to 40%) to provide 3-(4-(tert-butoxy)-3-((tert-butoxycarbonyl)amino)-4-oxobutanamido)propane-1,2-diyl distearate as a white solid (685 mg, 76%).

$^1$H NMR (300 MHz, CDCl$_3$) δ 6.48 (m, 0.5H), 6.20 (m, 0.5H), 5.38 (m, 1H), 5.08-5.14 (m, 1H), 4.42-4.54 (m, 1H), 4.06-4.28 (m, 2H), 3.60-3.68 (m, 0.5H), 3.46-3.53 (m, 1H), 3.26-3.34 (m, 0.5H), 2.74-2.92 (m, 2H), 2.31 (dt, 2H, J=7.5 Hz, 1.9 Hz), 2.19 (t, 2H, J=7.7 Hz), 1.56-1.66 (m, 2H), 1.47 (s, 9H), 1.41-1.45 (m, 9H), 1.24 (bs, 58H), 0.87 (t, 6H, J=6.8 Hz).

MS (APCI): m/z (MH$^+$) 895.7, 795.6.

3-((2,3-Bis(stearoyloxy)propyl)amino)-1-carboxy-3-oxopropan-1-aminium chloride

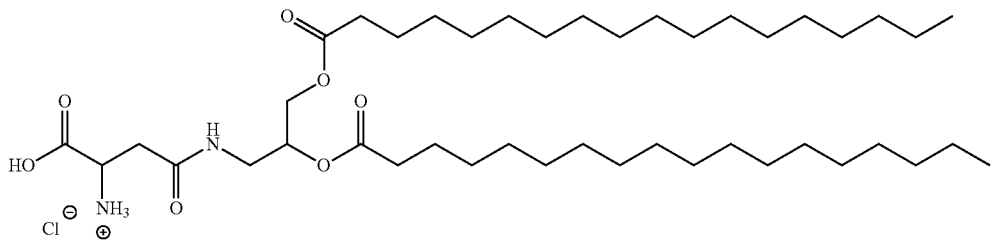

Chemical Formula: C$_{43}$H$_{83}$ClN$_2$O$_7$
Molecular Weight: 775.59

3-(4-(tert-Butoxy)-3-((tert-butoxycarbonyl)amino)-4-oxobutanamido)propane-1,2-diyl distearate (685 mg, 0.76 mmol) was dissolved in 4M HCl in dioxane (10 mL), and the mixture was stirred at room temperature for 16 h. TLC showed the disappearance of starting material. Hexanes was added into the reaction mixture and triturated to provide the desired product, 3-((2,3-bis(stearoyloxy)propyl)amino)-1-carboxy-3-oxopropan-1-aminium chloride as white solid (520 mg, 88%).

$^1$H NMR (300 MHz, CDCl$_3$) δ 8.26 (bs, 2H), 5.15 (m, 1H), 4.50 (m, 1H), 4.22 (m, 2H), 3.16-3.54 (m, 4H), 2.20-2.38 (m, 4H), 1.58 (m, 4H), 1.24 (bs, 56H), 0.87 (t, 6H, J=6.8 Hz).

MS (APCI): m/z (MH$^+$) 739.6

1-((2,3-Bis(stearoyloxy)propyl)amino)-3-carboxy-1-oxopropan-2-aminium chloride

3-(4-(Benzyloxy)-2-((tert-butoxycarbonyl)amino)-4-oxobutanamido)propane-1,2-diyl distearate

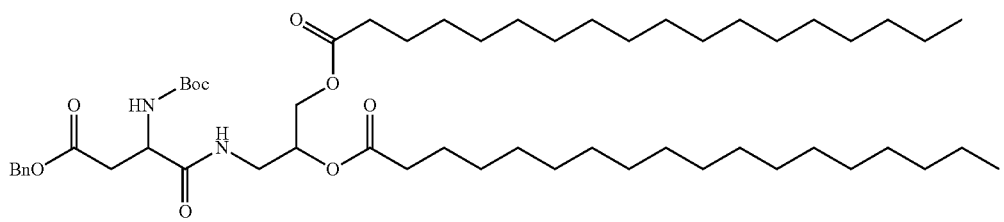

Chemical Formula: C$_{55}$H$_{96}$N$_2$O$_9$
Molecular Weight: 929.38

A mixture of 3-aminopropane-1,2-diyl distearate (320 mg, 0.51 mmol), 4-(benzyloxy)-2-((tert-butoxycarbonyl)amino)-4-oxobutanoic acid (332 mg, 1.02 mmol), EDCI (197 mg, 1.02 mmol) and DMAP (6 mg, 0.05 mmol) in 30 mL/30 mL dichloromethane/THF was heated to 50° C. for 16 h. TLC showed the product. The reaction mixture was diluted with water and extracted with dichloromethane, and the combined organic layer was washed with brine and dried over sodium sulfate. After filtration and concentration, the crude was purified by ISCO (24 g SiO$_2$: EtOAc/Hexanes 0 to 40%) to provide 3-(4-(benzyloxy)-2-((tert-butoxycarbonyl)amino)-4-oxobutanamido)propane-1,2-diyl distearate as a white solid (310 mg, 64%).

$^1$H NMR (300 MHz, CDCl$_3$) δ 7.31-7.39 (m, 5H), 6.24 (m, 1H), 5.39-5.43 (m, 1H), 5.11-5.22 (m, 3H), 4.53 (m, 1H), 4.06-4.22 (m, 2H), 3.72-3.80 (m, 1H), 2.88-3.10 (m, 2H), 2.26-2.32 (m, 2H), 2.12-2.17 (m, 2H), 1.53-1.64 (m, 9H), 1.44 (s, 9H), 1.24 (bs, 50H), 0.87 (t, 6H, J=6.8 Hz).

MS (APCI): m/z (MH$^+$) 929.7, 829.6.

4-((2,3-Bis(stearoyloxy)propyl)amino)-3-((tert-butoxycarbonyl)amino)-4-oxobutanoic Acid

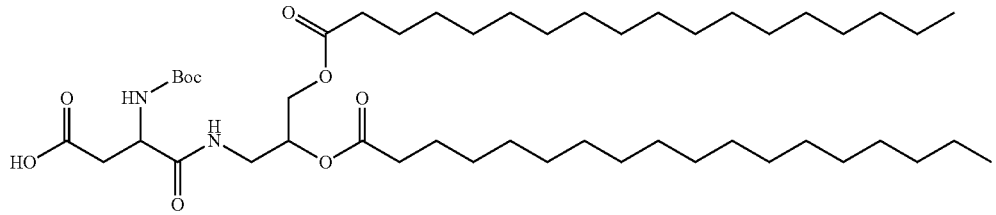

Chemical Formula: C$_{48}$H$_{90}$N$_2$O$_9$
Molecular Weight: 839.25

A mixture of 3-(4-(benzyloxy)-2-((tert-butoxycarbonyl)amino)-4-oxobutanamido)propane-1,2-diyl distearate (310 mg, 0.33 mmol) and Pd/C (5%, 100 mg) in 45 mL EtOAc was stirred for 16 h under hydrogen balloon. TLC showed complete reaction. The reaction mixture was filtered through Celite and washed with dichloromethane. The filtrate was concentrated to provide 4-((2,3-bis(stearoyloxy)propyl)amino)-3-((tert-butoxycarbonyl)amino)-4-oxobutanoic acid as a white solid (248 mg, 88%), which was used for the next step without purification.

$^1$H NMR (300 MHz, CDCl$_3$) δ 6.29 (m, 1H), 5.54 (m, 1H), 5.17 (m, 1H), 4.52 (m, 1H), 4.128-4.26 (m, 1H), 4.11 (q, 2H, J=6.8 Hz), 3.72 (m, 1H), 3.25 (m, 1H), 2.85-3.08 (m, 2H), 2.26-2.34 (m, 2H), 2.12-2.20 (m, 2H), 2.04 (s, 2H), 1.59 (m, 4H), 1.44 (s, 9H), 1.24 (bs, 52H), 0.87 (t, 6H, J=6.6 Hz).

MS (APCI): m/z (MH$^+$) 839.7, 739.6.

1-((2,3-Bis(stearoyloxy)propyl)amino)-3-carboxy-1-oxopropan-2-aminium chloride

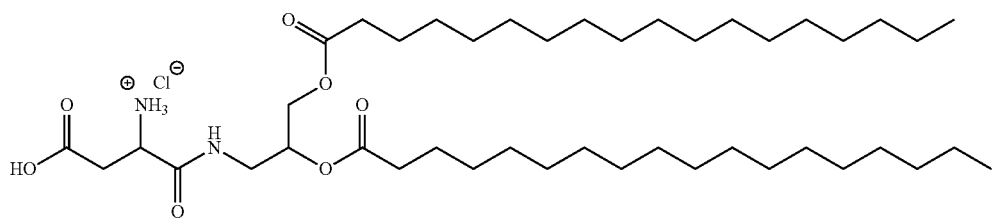

Chemical Formula: C$_{43}$H$_{83}$ClN$_2$O$_7$
Molecular Weight: 775.59

4-((2,3-bis(stearoyloxy)propyl)amino)-3-((tert-butoxy-carbonyl)amino)-4-oxobutanoic acid (248 mg, 0.29 mmol) was dissolved in 4M HCl in dioxane (20 mL), and the mixture was stirred at room temperature for 16 h. TLC showed the disappearance of starting material. Hexanes was added into the reaction mixture and triturated to provide the desired product, 1-((2,3-bis(stearoyloxy)propyl)amino)-3-carboxy-1-oxopropan-2-aminium chloride as white solid (170 mg, 78%).

$^1$H NMR (300 MHz, CDCl$_3$) δ 8.32 (bs, 2H), 5.19 (m, 1H), 4.24 (m, 2H), 3.14-3.65 (m, 4H), 2.20-2.38 (m, 4H), 1.58 (m, 4H), 1.44 (s, 9H), 1.24 (bs, 50H), 0.87 (t, 6H, J=6.8 Hz).

MS (APCI): m/z (MH$^+$) 739.6.

Representative Procedure 1:

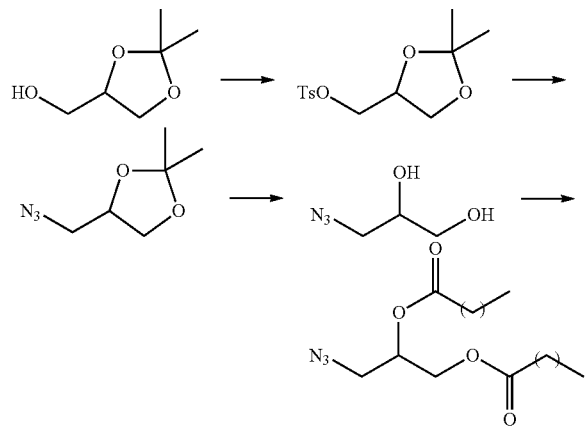

(2,2-Dimethyl-1,3-dioxolan-4-yl)methyl 4-methylbenzenesulfonate

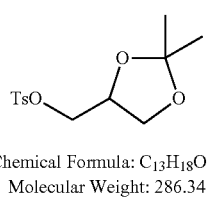

Chemical Formula: C$_{13}$H$_{18}$O$_5$S
Molecular Weight: 286.34

To a 0° C. solution of Solketal (2.0 g, 15.1 mmol) in pyridine (30 mL) was added tosyl chloride (3.2 g, 16.6 mmol), and the reaction was allowed to return to RT and stir for 12 hours. The mixture was concentrated, and azeotroped twice with toluene. The crude material was taken up in DCM and washed with water, saturated ammonium chloride, brine, dried over anhydrous Na$_2$SO$_4$, filtered, and concentrated in vacuo. Purification by ISCO silica flash chromatography (0-30% EtOAc/hexanes) provided (2,2-dimethyl-1,3-dioxolan-4-yl)methyl 4-methylbenzenesulfonate (4.18 g, 96%).

$^1$H-NMR (300 MHz, CDCl$_3$) δ: ppm 7.82 (d, 2H); 7.38 (d, 2H); 4.30 (m, 1H); 4.03 (m, 3H); 3.78 (m, 1H); 2.489 (s, 3H); 1.35 (m, 6H).

4-(Azidomethyl)-2,2-dimethyl-1,3-dioxolane

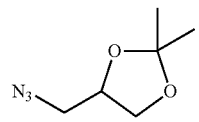

Chemical Formula: C$_6$H$_{11}$N$_3$O$_2$
Molecular Weight: 157.17

To a solution of (2,2-dimethyl-1,3-dioxolan-4-yl)methyl 4-methylbenzenesulfonate (4.18 g, 14.6 mmol) in DMF (36 mL) was added sodium azide (2.37 g, 36.5 mmol) and the reaction was allowed to stir at 80° C. for 12 hours. After cooling to RT, the reaction was quenched with saturated sodium bicarbonate and the suspension was filtered. The solution was extracted×3 with ether, and the combined ether extracts were washed with brine, dried over anhydrous MgSO$_4$, filtered, and concentrated in vacuo in the absence of external heat to provide 4-(azidomethyl)-2,2-dimethyl-1,3-dioxolane with residual DMF (3.37 g, 146%).

$^1$H-NMR (300 MHz, CDCl$_3$) δ: ppm 4.29 (m, 1H); 4.08 (m, 1H); 3.79 (m, 1H); 3.50-3.26 (br. m, 2H); 1.49 (s, 3H); 1.38 (s, 3H).

3-Azidopropane-1,2-diol

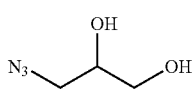

Chemical Formula: C$_3$H$_7$N$_3$O$_2$
Molecular Weight: 117.11

To a solution of 4-(azidomethyl)-2,2-dimethyl-1,3-dioxolane (2.29 g, 14.6 mmol) in MeOH (75 mL) was added tosylic acid monohydrate (1.39 g, 7.3 mmol) and the reaction was allowed to stir at RT. After 4 hours, solid sodium carbonate (3 g) was added and the mixture was allowed to stir for 20 minutes. The suspension was filtered and concentrated in vacuo in the absence of external heat. Purification by ISCO silica flash chromatography (50-100% EtOAc/hexanes) provided 3-azidopropane-1,2-diol (1.35 g, 79%).

$^1$H-NMR (300 MHz, CDCl$_3$) δ: ppm 3.90 (m, 1H); 3.80-3.57 (br. m, 2H); 3.44 (m, 2H); 2.42 (br, 2H).

409

3-Azidopropane-1,2-diylbis(decanoate)

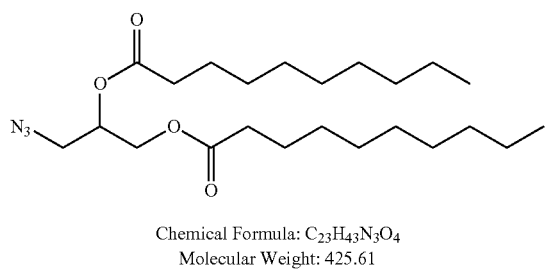 [SMILES: CCCCCCCCCC(=O)OCC(CN=[N+]=[N-])OC(=O)CCCCCCCCC]

Chemical Formula: $C_{23}H_{43}N_3O_4$
Molecular Weight: 425.61

To a solution of 3-azidopropane-1,2-diol (100 mg, 0.854 mmol) and decanoic acid (368 mg, 2.13 mmol) in DCM (4 mL) was added DCC (440 mg, 2.13 mmol) and DMAP (260 mg, 2.13 mmol), and the reaction was allowed to stir at RT for 48 hours. The mixture was filtered, and the solids rinsed with DCM. The filtrate was washed with 10% citric acid, saturated sodium bicarbonate, brine, dried over anhydrous sodium sulfate, filtered, and concentrated in vacuo. Purification by ISCO silica flash chromatography (0-30% EtOAc/hexanes) provided 3-azidopropane-1,2-diylbis(decanoate) (318 mg, 88%).

410

$^1$H-NMR (300 MHz, CDCl$_3$) δ: ppm 5.20 (quint, 1H); 4.37-4.12 (br. m, 2H); 3.49 (m, 2H); 2.35 (m, 4H); 1.65 (m, 4H); 1.42-1.10 (br. m, 24H); 0.90 (t, 6H).

3-Azidopropane-1,2-diyl ditetradecanoate

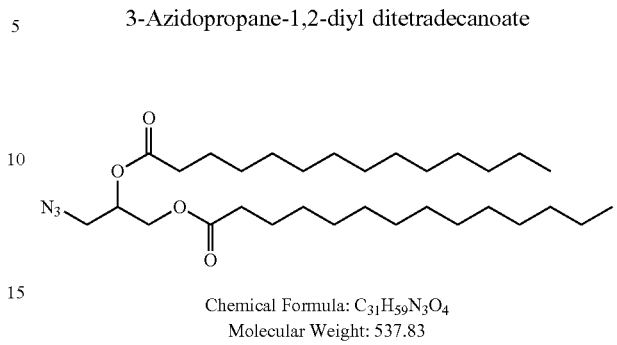

Chemical Formula: $C_{31}H_{59}N_3O_4$
Molecular Weight: 537.83

In the same manner as 3-azidopropane-1,2-diyl bis(decanoate), 3-azidopropane-1,2-diyl ditetradecanoate was synthesized from 3-azidopropane-1,2-diol (300 mg, 2.56 mmol), myristic acid (1.46 g, 6.40 mmol), DCC (1.32 g, 6.40 mmol), and DMAP (782 mg, 6.40 mmol) in DCM (12 mL). Yield (1.21 g, 88%).

$^1$H-NMR (300 MHz, CDCl$_3$) δ: ppm 5.20 (quint, 1H); 4.37-4.12 (br. m, 2H); 3.49 (m, 2H); 2.35 (m, 4H); 1.65 (m, 4H); 1.42-1.10 (br. m, 40H); 0.90 (t, 6H).

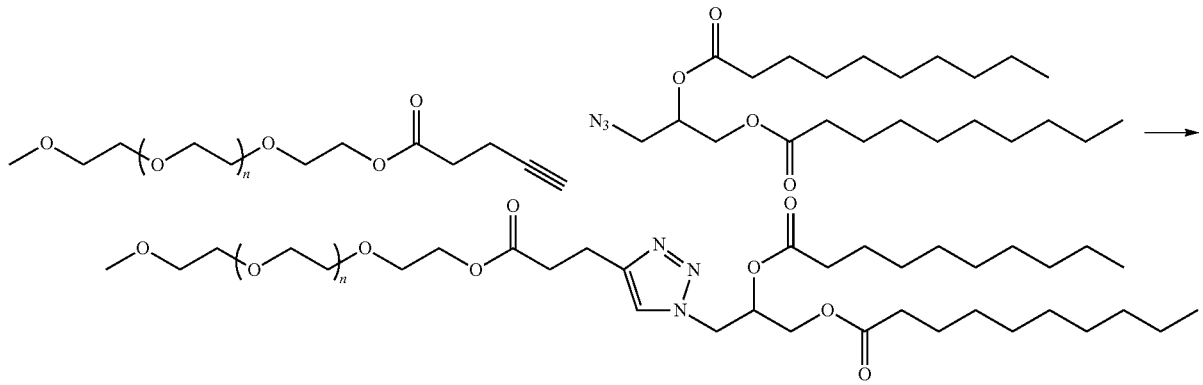

Compound Methoxy-PEG$_{2000}$-ester-click-glycerol C10

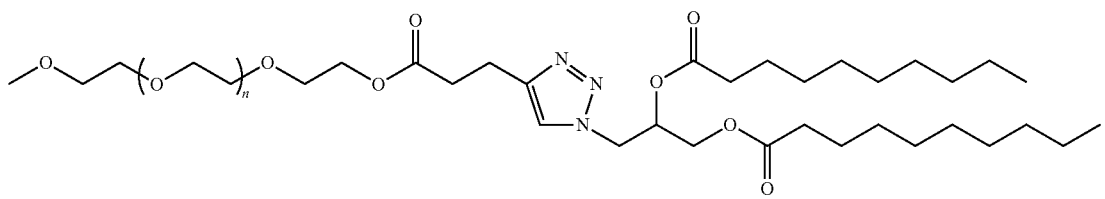

To a solution of O-(2-Azidoethyl)-O'-methylpolyethylene glycol 2000 (587 mg, 0.29 mmol) and 3-azidopropane-1,2-diyl bis(decanoate) (150 mg, 0.35 mmol) in t-butanol (1.5 mL) and water (1.5 mL) was added CuSO$_4$ (12 mg, 0.07 mmol) and sodium ascorbate (29 mg, 0.15 mmol). The reaction was allowed to stir at RT for 24 hours and then concentrated in vacuo. Purification by ISCO silica flash chromatography (0-20% MeOH/DCM) provided the desired product (205 mg, 29%).

¹H-NMR (300 MHz, CDCl₃) δ: ppm 7.46 (s, 1H); 5.39 (quint, 1H); 4.58 (m, 2H); 4.38-4.20 (br. m, 4H); 4.09 (m, 2H); 3.89 (m, 2H); 3.67 (br. m, 170-200H); 3.40 (s, 3H); 3.07 (m, 2H); 2.77 (m, 2H); 2.33 (m, 4H); 1.86 (br, 4.6H, water); 1.60 (m, 4H); 1.29 (br. m, 24H); 0.90 (t, 6H).

Compound Methoxy-PEG$_{2000}$-ester-click-glycerol C8

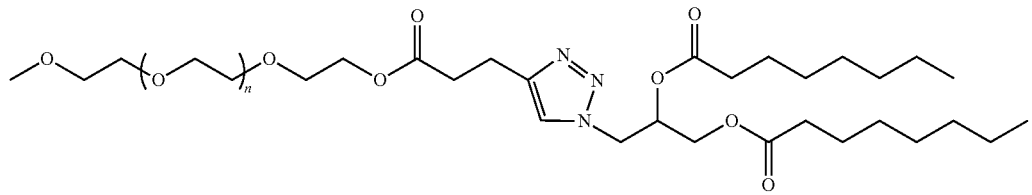

In the same manner as C10, C8 was synthesized from O-(2-Azidoethyl)-O'-methylpolyethylene glycol 2000 (250 mg, 0.125 mmol), 3-azidopropane-1,2-diyl dioctanoate (56 mg, 0.15 mmol), CuSO₄ (5 mg, 0.03 mmol) and sodium ascorbate (13 mg, 0.06 mmol) in t-butanol (1.5 mL) and water (1.5 mL). Yield (73 mg, 25%).

¹H-NMR (300 MHz, CDCl₃) δ: ppm 7.44 (s, 1H); 5.39 (quint, 1H); 4.58 (m, 2H); 4.38-4.20 (br. m, 4H); 4.09 (m, 2H); 3.89 (m, 2H); 3.67 (br. m, 170-200H); 3.40 (s, 3H); 3.07 (m, 2H); 2.77 (m, 2H); 2.33 (m, 4H); 1.86 (br, 3H, water); 1.60 (m, 4H); 1.29 (br. m, 16H); 0.90 (t, 6H).

Compound Methoxy-PEG$_{2000}$-ester-click-glycerol C14

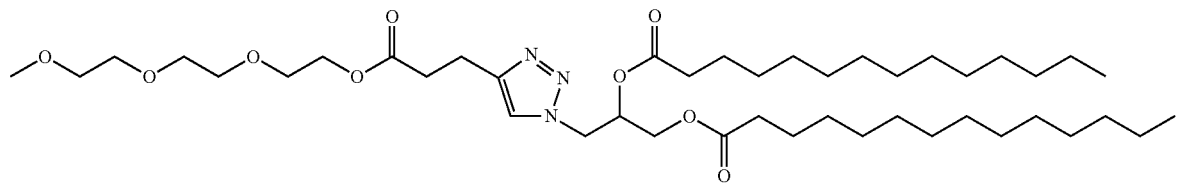 [SMILES: CCCCCCCCCCCCCC(=O)OCC(Cn1cc(CCC(=O)OCCOCCOCCOC)nn1)OC(=O)CCCCCCCCCCCCC]

In the same manner as C10, C14 was synthesized from 3-azidopropane-1,2-diyl ditetradecanoate.

¹H-NMR (300 MHz, CDCl₃) δ: ppm 7.57 (s, 1H); 5.39 (quint, 1H); 4.62 (m, 2H); 4.42-3.85 (br. m, 8H); 3.77-3.49 (br. m, 170-200H); 3.40 (s, 3H); 3.11 (m, 2H); 2.80 (m, 2H); 2.33 (m, 4H); 1.87-1.45 (br. m, 4H+20H water); 1.42-1.16 (br. m, 40H); 0.90 (t, 6H).

Compound Methoxy-PEG$_{2000}$-ester-click-glycerol C13/C14

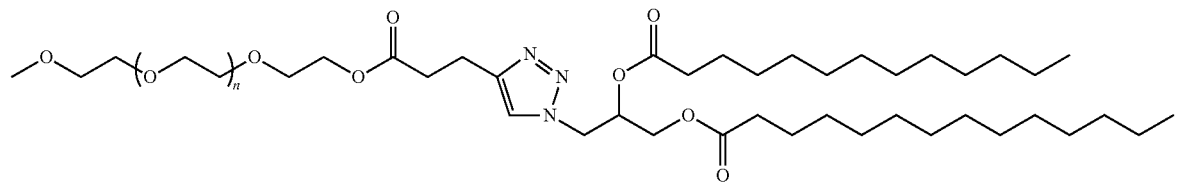

In the same manner as C10, C13/14 was synthesized from 1-azido-3-(tridecanoyloxy)propan-2-yl tetradecanoate.

¹H-NMR (300 MHz, CDCl₃) δ: ppm 7.55 (s, 1H); 5.39 (quint, 1H); 4.61 (m, 2H); 4.39-3.81 (br. m, 8H); 3.79-3.49 (br. m, 170-200H); 3.40 (s, 3H); 3.10 (m, 2H); 2.80 (m, 2H); 2.33 (m, 4H); 1.75-1.47 (m, 4H); 1.42-1.16 (br. m, 38H); 0.90 (t, 6H).

Compound Methoxy-PEG$_{2000}$-ester-click-glycerol C13

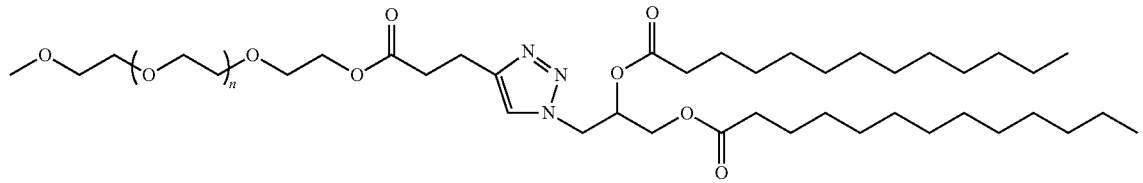

In the same manner as C10, C13 was synthesized from 3-azidopropane-1,2-diyl ditridecanoate.

$^1$H-NMR (300 MHz, CDCl$_3$) δ: ppm 7.68 (s, 1H); 5.33 (quint, 1H); 4.65 (m, 2H); 4.36-3.85 (br. m, 8H); 3.78-3.55 (br. m, 170-200H); 3.40 (s, 3H); 3.15 (m, 2H); 2.80 (m, 2H); 2.33 (m, 4H); 1.78-1.38 (m, 4H+24H water); 1.38-1.20 (br. m, 36H); 0.90 (t, 6H).

Compound Methoxy-PEG$_{2000}$-ester-click-glycerol C12

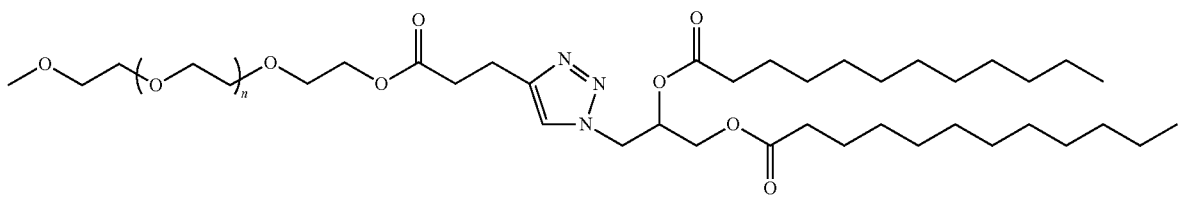

In the same manner as C10, C12 was synthesized from 3-azidopropane-1,2-diyl didodecanoate.

$^1$H-NMR (300 MHz, CDCl$_3$) δ: ppm 7.59 (s, 1H); 5.40 (quint, 1H); 4.62 (m, 2H); 4.37-3.83 (br. m, 8H); 3.78-3.48 (br. m, 170-200H); 3.40 (s, 3H); 3.12 (m, 2H); 2.82 (m, 2H); 2.33 (m, 4H); 2.09-1.82 (br. m, 7H water); 1.60 (m, 4H); 1.39-1.17 (br. m, 32H); 0.90 (t, 6H)

Compound: 3-((1H-Imidazole-1-carbonyl)oxy)propane-1,2-diylditetradecanoate

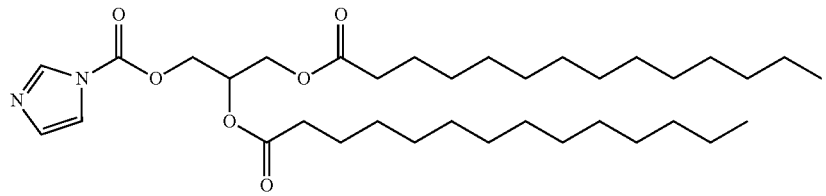

Chemical Formula: C$_{35}$H$_{62}$N$_2$O$_6$
Molecular Weight: 606.89

A solution of 3-hydroxypropane-1,2-diyl ditetradecanoate (0.10 g, 0.2 mmol), CDI (65 mg, 0.40 mmol) and Et$_3$N in DCM (1 mL) was allowed to stir at RT for 2 h. After this time the reaction was quenched with 10% citric acid and the layers were separated. The organics were washed with brine, dried over MgSO4, filtered and concentrated to afford 3-((1H-imidazole-1-carbonyl)oxy)propane-1,2-diylditetradecanoate (97 mg, 80%) which was carried on with no purification.

Methoxy-PEG$_{2000}$-carbamate-glycerol C14

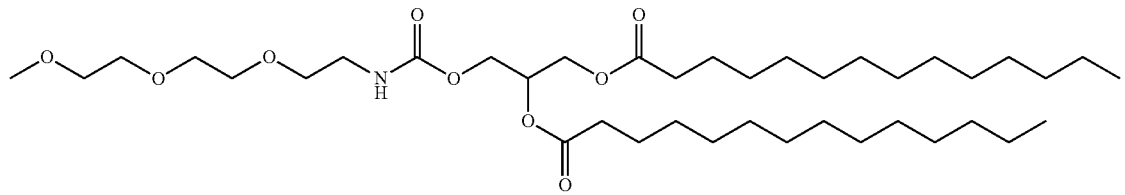 [SMILES: CCCCCCCCCCCCCC(=O)OCC(COC(=O)NCCOCCOCCOC)OC(=O)CCCCCCCCCCCCC]

3-((1H-Imidazole-1-carbonyl)oxy)propane-1,2-diyl ditetradecanoate (97 mg, 0.16 mmol) MeO-PEG$_{2K}$-NH$_2$ (100 mg, 0.053 mmol), DMAP (2 mg, 0.011 mmol) and Hunig's base (0.055 mL, 0.32 mmol) were combined in THF and allowed to stir at 65° C. for 6 h and then RT for 48 h. Reaction was concentrated and dissolved in DCM for purification. The crude material was purified by silica gel chromatography (0-20% MeOH in DCM with 1% NH$_4$OH) to provide 107 mg of the desired product.

$^1$H-NMR (300 MHz, CDCl$_3$) δ: ppm 5.26 (m, 1H); 4.36-4.06 (br. m, 4H); 3.93-3.42 (br. m, 170-200H); 3.39 (s, 3H); 3.30 (m, 2H); 2.32 (t, 4H); 1.78 (m, 4H); 1.61 (br. m, 5H water); 1.42-1.20 (br. m, 40H); 0.89 (t, 6H).

Representative Procedure 2

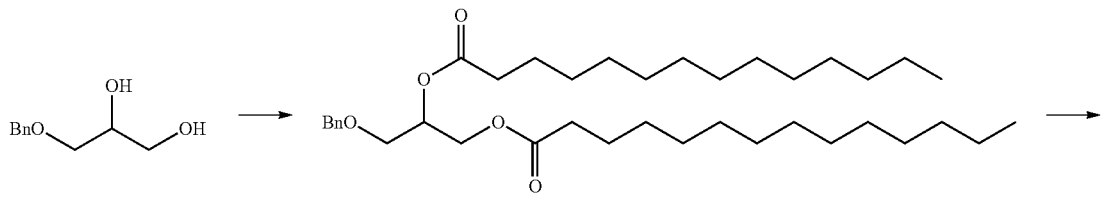

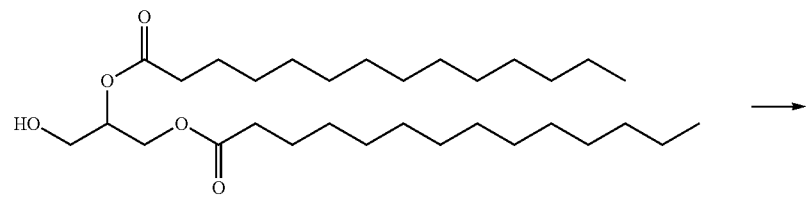

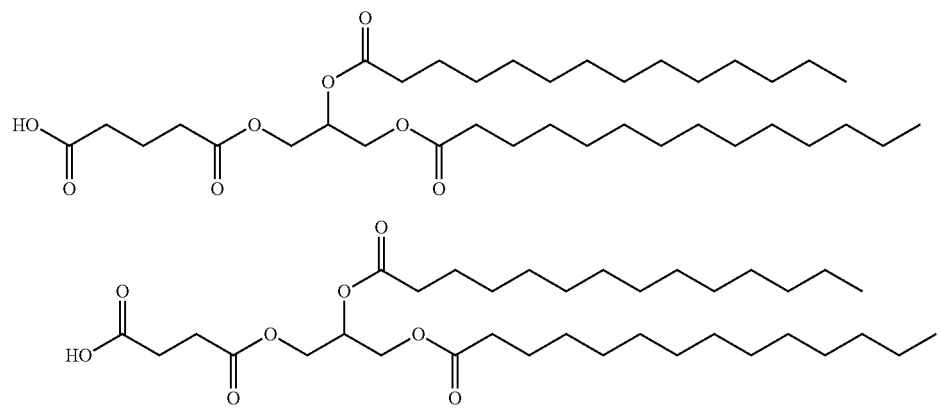

417
3-(Benzyloxy)propane-1,2-diylditetradecanoate

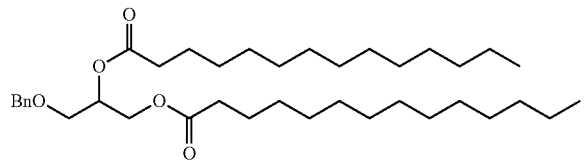

Chemical Formula: $C_{38}H_{66}O_5$
Molecular Weight: 602.94

To a solution of 3-(benzyloxy)propane-1,2-diol (1.0 g, 5.5 mmol) and myristic acid (3.1 g, 13.7 mmol) in DCM (26 mL) was added DCC (2.8 g, 13.7 mmol) and DMAP (1.7 g, 13.7 mmol), and the reaction was allowed to stir at RT for 72 hours. The mixture was filtered, and the solids were rinsed with DCM. The filtrate was washed with 10% citric acid, saturated sodium bicarbonate, brine, dried over anhydrous sodium sulfate, filtered, and concentrated in vacuo. Purification by ISCO silica flash chromatography (0-30% EtOAc/hexanes) provided 3-(benzyloxy)propane-1,2-diyl ditetradecanoate (2.78 g, 84%).

$^1$H-NMR (300 MHz, CDCl$_3$) δ: ppm 7.34 (br. m, 5H); 5.27 (quint, 1H); 4.56 (m, 2H); 4.44-4.14 (br. m, 2H); 3.61 (m, 2H); 2.32 (m, 4H); 1.62 (m, 4H); 1.40-1.06 (br. m, 40H); 0.90 (t, 6H).

418
3-Hydroxypropane-1,2-diylditetradecanoate

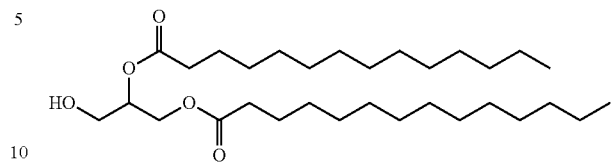

Chemical Formula: $C_{31}H_{60}O_5$
Molecular Weight: 512.82

To a nitrogen filled flask containing palladium on carbon (10 wt. %, 490 mg, 0.461 mmol) was added 3-(benzyloxy)propane-1,2-diyl ditetradecanoate (2.78 g, 4.61 mmol) and EtOH (22 mL). The flask was evacuated and backfilled with H$_2$ three times, and allowed to stir at RT and 1 atm H$_2$ for 12 hours. The mixture was filtered through celite, rinsing with EtOAc, and the filtrate was concentrated in vacuo to provide 3-hydroxypropane-1,2-diyl ditetradecanoate (1.50 g, 64%).

$^1$H-NMR (300 MHz, CDCl$_3$) δ: ppm 5.11 (quint, 1H); 4.30 (m, 2H); 3.75 (m, 2H); 2.36 (m, 4H); 1.72-1.10 (br. m, 44H); 0.91 (t, 6H).

5-(2,3-Bis(tetradecanoyloxy)propoxy)-5-oxopentanoic acid

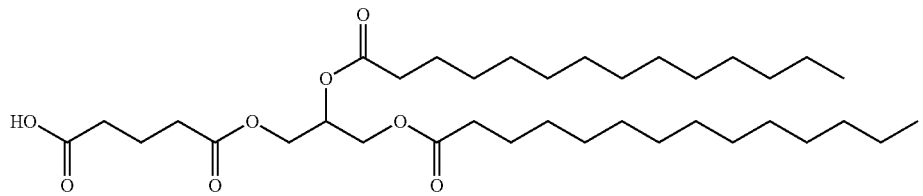

Chemical Formula: $C_{36}H_{66}O_8$
Molecular Weight: 626.92

To a solution of 3-hydroxypropane-1,2-diyl ditetradecanoate (300 mg, 0.585 mmol) and glutaric acid (77 mg, 0.585 mmol) in DCM (4 mL) was added DCC (121 mg, 0.585 mmol) and DMAP (71 mg, 0.585 mmol), and the reaction was allowed to stir at RT for 12 hours. The mixture was filtered and the solids were rinsed with DCM. The filtrate was washed with 10% citric acid, brine, dried over anhydrous sodium sulfate, filtered, and concentrated in vacuo. Purification by ISCO silica flash chromatography (0-20% MeOH/DCM) provided 5-(2,3-bis(tetradecanoyloxy)propoxy)-5-oxopentanoic acid (93 mg, 25%).

$^1$H-NMR (300 MHz, CDCl$_3$) δ: ppm 5.29 (quint, 1H); 4.41-4.11 (br. m, 4H); 2.46 (m, 4H); 2.34 (m, 4H); 1.99 (m, 2H); 1.63 (m, 4H); 1.40-1.10 (br. m, 40H); 0.90 (t, 6H).

4-(2,3-Bis(tetradecanoyloxy)propoxy)-4-oxobutanoic acid

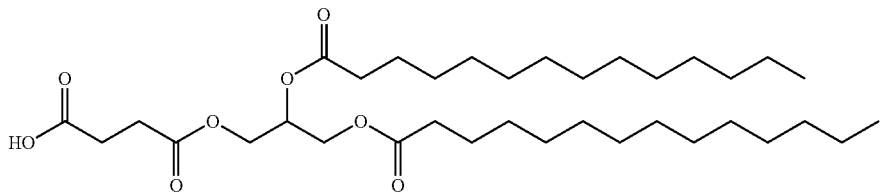

Chemical Formula: $C_{35}H_{64}O_8$
Molecular Weight: 612.89

In the same manner as 5-(2,3-bis(tetradecanoyloxy)propoxy)-5-oxopentanoic acid, 4-(2,3-bis(tetradecanoyloxy)propoxy)-4-oxobutanoic acid was synthesized from 3-hydroxypropane-1,2-diyl ditetradecanoate (300 mg, 0.585 mmol), glutaric acid (69 mg, 0.585 mmol), DCC (121 mg, 0.585 mmol) and DMAP (71 mg, 0.585 mmol) in DCM (4 mL). Yield (267 mg, 75%).

$^1$H-NMR (300 MHz, CDCl$_3$) δ: ppm 5.29 (quint, 1H); 4.41-4.11 (br. m, 4H); 2.69 (m, 4H); 2.34 (m, 4H); 1.63 (m, 4H); 1.46-1.10 (br. m, 10H); 0.90 (t, 6H).

Compound Methoxy-PEG$_{2000}$-ester-propyl-ester-glycerol C14

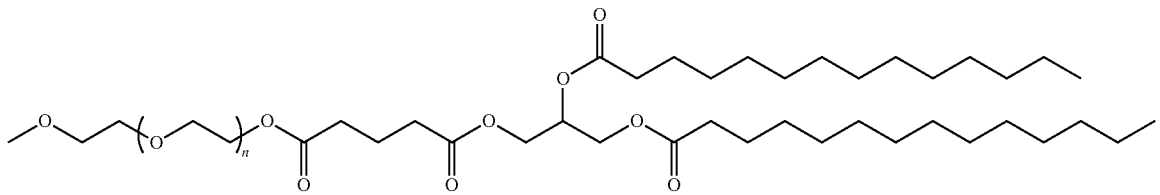

To a solution of methoxy-PEG$_{2000}$ (247 mg, 0.124 mmol) and 5-(2,3-bis(tetradecanoyloxy)propoxy)-5-oxopentanoic acid (93 mg, 0.148 mmol) in DCM (2 mL) was added DCC (31 mg, 0.148 mmol) and DMAP (19 mg, 0.148 mmol) and the reaction was allowed to stir at 40° C. for 12 hours. The mixture was allowed to cool to RT and concentrated in vacuo. Purification by ISCO C18 flash chromatography (50-100% [MeCN 0.1% TFA]/[water 0.1% TFA]) provided the desired product (75 mg, 23%).

$^1$H-NMR (300 MHz, CDCl$_3$) δ: ppm 5.28 (quint, 1H); 4.38-4.07 (br. m, 6H); 3.90 (m, 2H); 3.79-3.48 (br. m, 170-200H); 3.40 (s, 3H); 2.48-1.89 (br. m, 10H); 1.64 (br. m, 4H+7.25H water); 1.41-1.08 (br. m, 40H); 0.90 (t, 6H).

Compound: Methoxy-PEG$_{2000}$-ester-ethyl-ester-glycerol C14

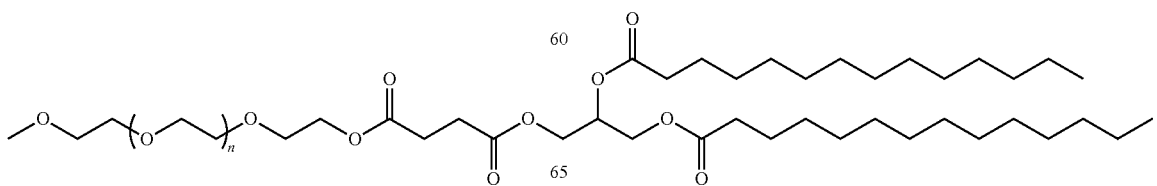

In the same manner as in representative procedure 2, the compound was synthesized from methoxy-PEG$_{2000}$ (272 mg, 0.136 mmol), 4-(2,3-bis(tetradecanoyloxy)propoxy)-4-oxobutanoic acid (100 mg, 0.163 mmol), DCC (34 mg, 0.163 mmol), and DMAP (20 mg, 0.163 mmol) in DCM (2 mL). Yield (134 mg, 38%).

$^1$H-NMR (300 MHz, CDCl$_3$) δ: ppm 5.28 (m, 1H); 4.39-4.10 (br. m, 6H); 3.89 (m, 2H); 3.79-3.48 (br. m, 170-200H); 3.40 (s, 3H); 2.67 (m, 4H); 2.33 (m, 4H); 1.63 (m, 4H+7.25H water); 1.42-1.16 (br. m, 40H); 0.90 (t, 6H).

Compound Methoxy-PEG$_{2000}$-ester-C18

Representative Procedure 3

Methoxy-PEG$_{2000}$-ester-C18

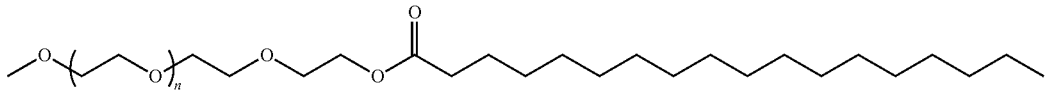

To a solution of methoxy-PEG$_{2000}$ (1.0 g, 0.50 mmol) and stearic acid (171 mg, 0.60 mmol) in DCM (10 mL) was added DCC (124 mg, 0.60 mmol) and DMAP (73 mg, 0.60 mmol) and the reaction was allowed to stir at RT for 48 hours. The reaction was concentrated in vacuo, and purification by ISCO silica flash chromatography (0-20% MeOH/DCM) provided the desired product (620 mg, 55%).

$^1$H-NMR (300 MHz, CDCl$_3$) δ: ppm 4.24 (t, 2H); 3.94-3.52 (br. m, 170-200H); 3.40 (s, 3H); 2.34 (t, 2H); 1.65 (m, 4H); 1.28 (br. m, 2H+2H water); 0.90 (t, 3H).

Compound: Methoxy-PEG$_{2000}$-ester-C18:1 (9)

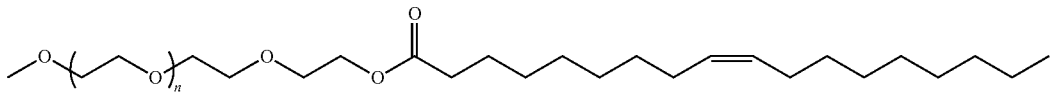

In the same manner as representative procedure 3, the compound was synthesized from methoxy-PEG$_{2000}$ (1.0 g, 0.50 mmol), oleic acid (169 mg, 0.60 mmol), DCC (124 mg, 0.60 mmol), and DMAP (73 mg, 0.60 mmol) in DCM (10 mL). Yield (298 mg, 26%).

$^1$H-NMR (300 MHz, CDCl$_3$) δ: ppm 5.37 (m, 2H); 4.24 (t, 2H); 3.94-3.46 (br. m, 170-200H); 3.40 (s, 3H); 2.34 (t, 2H); 2.04 (m, 4H); 1.68 (m, 2H+3H water); 1.46-1.18 (br. m, 20H); 0.90 (t, 3H).

Compound Methoxy-PEG$_{2000}$-ester-C18:2 (9,12)

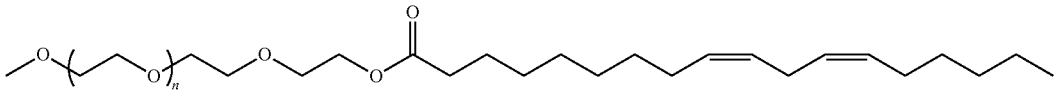

In the same manner as representative procedure 3, the compound was synthesized from methoxy-PEG$_{2000}$ (1.0 g, 0.50 mmol), linoleic acid (168 mg, 0.60 mmol), DCC (124 mg, 0.60 mmol), and DMAP (73 mg, 0.60 mmol) in DCM (10 mL). Yield (451 mg, 40%).

$^1$H-NMR (300 MHz, CDCl$_3$) δ: ppm 5.38 (br. m, 4H); 4.24 (t, 2H); 3.94-3.50 (br. m, 170-200H); 3.40 (s, 3H); 2.79 (t, 2H); 2.34 (t, 2H); 2.06 (m, 4H); 1.67 (br. m, 2H+2H water); 1.47-1.21 (br. m, 14H); 0.91 (t, 3H).

Compound: Methoxy-PEG$_{2000}$-ester-C20

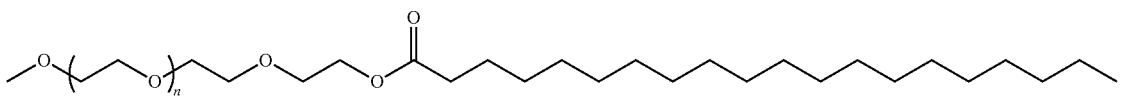

In the same manner as representative procedure 3, the compound was synthesized from methoxy-PEG$_{2000}$ (1.0 g, 0.50 mmol), arachidic acid (188 mg, 0.60 mmol), DCC (124 mg, 0.60 mmol), and DMAP (73 mg, 0.60 mmol) in DCM (10 mL). Yield (739 mg, 64%).

$^1$H-NMR (300 MHz, CDCl$_3$) δ: ppm 4.24 (t, 2H); 3.96-3.50 (br. m, 170-200H); 3.40 (s, 3H); 2.34 (t, 2H); 1.63 (br. m, 2H+1H water); 1.44-1.10 (32H); 0.90 (t, 3H).

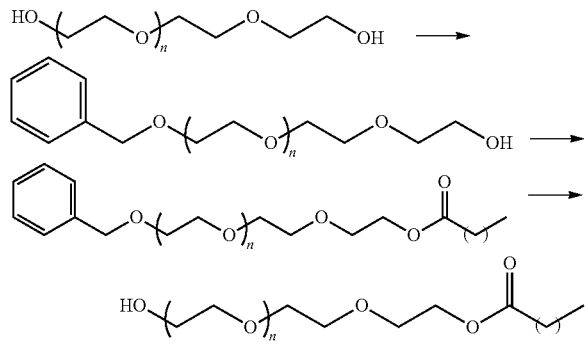

Benzyl-PEG$_{2000}$-OH

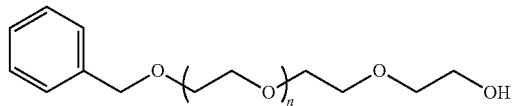

To a solution of PEG$_{2000}$ (6.0 g, 3.0 mmol) in THF (30 mL) was added potassium tert-butoxide (168 mg, 1.50 mmol) and the solution was allowed to stir for 30 minutes before the addition of benzyl bromide (180 µL, 1.50 mmol) in THF (6 mL) over 12 hours (0.125 mmol/hr). After the addition was complete, the reaction was allowed to continue to stir at RT for 4 hours and then concentrated in vacuo. Purification by ISCO C18 flash chromatography (0-100% [MeCN 0.1% TFA]/[water 0.1% TFA]) provided the desired product (1.80 g, 29%).

$^1$H-NMR (300 MHz, CDCl$_3$) δ: ppm 7.35 (br. m, 5H); 4.59 (s, 2H); 3.94-3.37 (br. m, 170-200H); 2.07-1.78 (br, 3.5H water).

Compound: Benzyl-PEG$_{2000}$-ester-C18

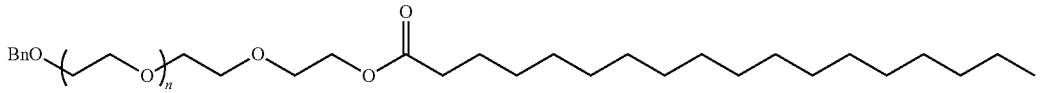

In the same manner as representative procedure 3, the compound was synthesized from Benzyl-PEG$_{2000}$-OH (218 mg, 0.104 mmol), stearic acid (36 mg, 0.125 mmol), DCC (26 mg, 0.125 mmol), and DMAP (16 mg, 0.125 mmol) in DCM (2 mL). Yield (150 mg, 61%).

$^1$H-NMR (300 MHz, CDCl$_3$) δ: ppm 7.35 (br. m, 5H); 4.59 (s, 2H); 4.24 (m, 2H); 3.95-3.31 (br. m, 170-200H); 2.34 (t, 2H); 1.64 (br. m, 2H+2H water); 1.41-1.15 (br. m, 28H); 0.90 (t, 3H).

Compound: Benzyl-PEG$_{2000}$-ester-C18:2 (9,12)

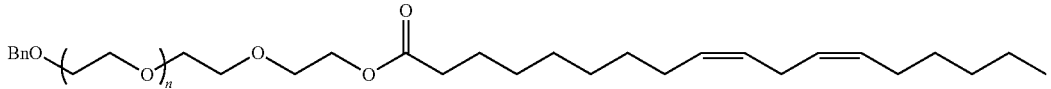

In the same manner as representative procedure 3, the compound was synthesized from Benzyl-PEG$_{2000}$-OH (200 mg, 0.095 mmol), linoleic acid (32 mg, 0.114 mmol), DCC (24 mg, 0.114 mmol), and DMAP (14 mg, 0.114 mmol) in DCM (2 mL). Yield (110 mg, 49%).

$^1$H-NMR (300 MHz, CDCl$_3$) δ: ppm 7.36 (br. m, 5H); 5.46-5.26 (br. m, 4H); 4.59 (s, 2H); 4.24 (t, 2H); 3.94-3.39 (br. m, 170-200H); 2.79 (t, 2H); 2.34 (t, 2H); 2.06 (m, 4H); 1.68 (br. m, 2H+5H water); 1.48-1.23 (br. m, 14H); 0.91 (t, 3H).

Compound: Benzyl-PEG$_{2000}$-ester-C18:1 (9)

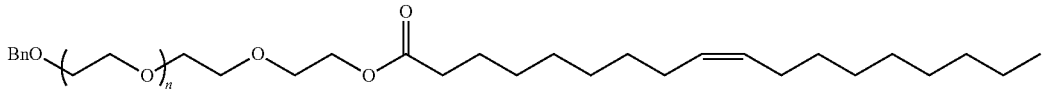

In the same manner as representative procedure 3, the compound was synthesized from Benzyl-PEG$_{2000}$-OH (200 mg, 0.095 mmol), oleic acid (32 mg, 0.114 mmol), DCC (24 mg, 0.114 mmol), and DMAP (14 mg, 0.114 mmol) in DCM (2 mL). Yield (94 mg, 42%).

$^1$H-NMR (300 MHz, CDCl$_3$) δ: ppm 7.36 (br. m, 5H); 5.36 (m, 2H); 4.59 (s, 2H); 4.24 (t, 2H); 3.95-3.35 (br. m, 170-200H); 2.35 (t, 2H); 2.03 (m, 4H); 1.64 (m, 2H); 1.48-1.16 (br. m, 20H); 0.90 (t, 3H).

Compound: Benzyl-PEG$_{2000}$-ester-C20

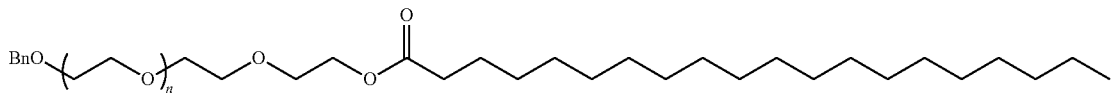

In the same manner as representative procedure 3, the compound was synthesized from Benzyl-PEG$_{2000}$-OH (200 mg, 0.095 mmol), arachidic acid (36 mg, 0.114 mmol), DCC (24 mg, 0.114 mmol), and DMAP (14 mg, 0.114 mmol) in DCM (2 mL). Yield (101 mg, 44%).

$^1$H-NMR (300 MHz, CDCl$_3$) δ: ppm 7.36 (br. m, 5H); 4.59 (s, 2H); 4.24 (t, 2H); 3.95-3.35 (br. m, 170-200H); 2.34 (t, 2H); 1.78 (br, 3H water); 1.63 (m, 2H); 1.40-1.17 (br. m, 34H); 0.90 (t, 3H).

Compound: HO-PEG$_{2000}$-ester-C18

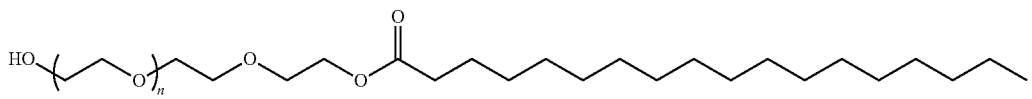

To a nitrogen filled flask containing palladium on carbon (10 wt. %, 74 mg, 0.070 mmol) was added Benzyl-PEG$_{2000}$-ester-C18 (822 mg, 0.35 mmol) and MeOH (20 mL). The flask was evacuated nad backfilled with H$_2$ three times, and allowed to stir at RT and 1 atm H$_2$ for 12 hours. The mixture was filtered through celite, rinsing with DCM, and the filtrate was concentrated in vacuo to provide the desired product (692 mg, 88%).

$^1$H-NMR (300 MHz, CDCl$_3$) δ: ppm 4.24 (t, 2H); 3.95-3.34 (br. m, 170-200H); 2.34 (t, 2H); 1.63 (m, 2H); 1.40-1.17 (br. m, 28H); 0.90 (t, 3H).

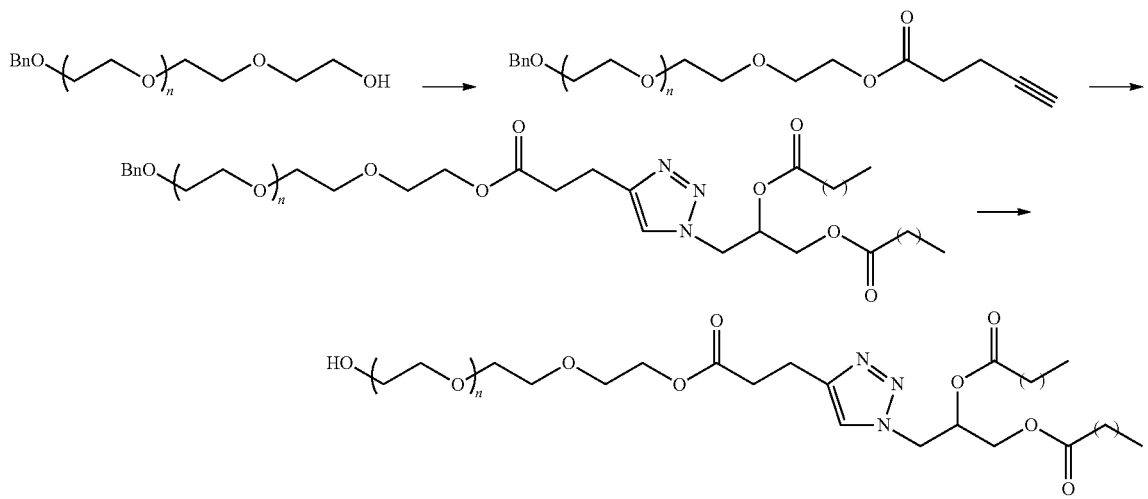

Compound: Benzyl-PEG$_{2000}$-ester-ethyl-alkyne

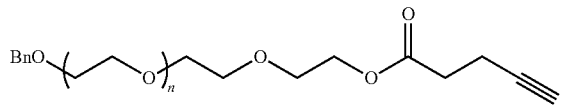

To a solution of Benzyl-PEG$_{2000}$-OH (1.0 g, 0.48 mmol) and 4-pentynoic acid (70 mg, 0.71 mmol) in DCM (10 mL) was added DCC (147 mg, 0.71 mmol) and DMAP (87 mg, 0.71 mmol), and the reaction was allowed to stir at RT for 12 hours. The mixture was filtered, the solids rinsed with DCM, and concentrated in vacuo. Purification by ISCO silica flash chromatography (0-100% DCM/[DCM 20% MeOH 1% NH$_4$OH]) provided the desired product (436 mg, 42%).

$^1$H-NMR (300 MHz, CDCl$_3$) δ: ppm 7.36 (br. m, 5H); 4.59 (s, 2H); 4.29 (t, 2H); 3.95-3.35 (br. m, 170-200H); 2.67-2.47 (br. m, 4H); 2.01 (m, 1H); 1.67 (br, 3H water).

Compound: Benzyl-PEG$_{2000}$-ester-click-glycerol C10

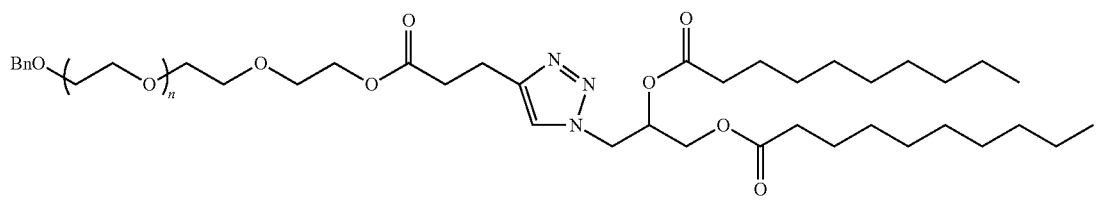

To a solution of Benzyl-PEG$_{2000}$-ester-ethyl-alkyne (175 mg, 0.080 mmol) and 3-azidopropane-1,2-diyl bis(decanoate) (51 mg, 0.119 mmol) in tert-butanol (2 mL) and water (2 mL) was added CuSO$_4$ (7 mg, 0.040 mmol) and sodium ascorbate (16 mg, 0.080 mmol) and the reaction was allowed to stir at RT for 12 hours. The mixture was concentrated in vacuo. Purification by ISCO silica flash chromatography (0-100% DCM/[DCM 20% MeOH 1% NH$_4$OH]) provided the desired product (161 mg, 77%).

$^1$H-NMR (300 MHz, CDCl$_3$) δ: ppm 8.08 (m, 1H); 7.53-7.30 (br. m, 5H); 5.39 (m, 1H); 4.59 (s, 2H); 4.54-3.98 (br. m, 4H); 3.94-3.36 (br. m, 170-200H); 3.06 (t, 2H); 2.78 (t, 2H); 2.34 (m, 4H); 2.01-1.75 (br, 2H water); 1.62 (m, 4H); 1.45-1.12 (br. m, 24H); 0.90 (t, 6H).

Benzyl-PEG$_{2000}$-ester-click-glycerol C10

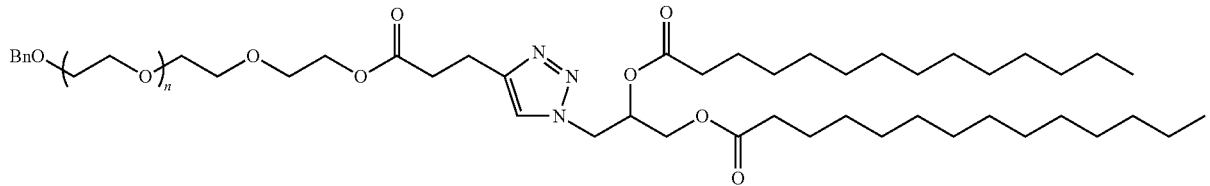

In the same manner as Benzyl-PEG$_{2000}$-ester-click-glycerol C10, Benzyl-PEG$_{2000}$-ester-click-glycerol C10 was synthesized from Benzyl-PEG$_{2000}$-ester-ethyl-alkyne (175 mg, 0.080 mmol), 3-azidopropane-1,2-diyl ditetradecanoate (64 mg, 0.119 mmol), CuSO$_4$ (7 mg, 0.040 mmol) and sodium ascorbate (16 mg, 0.080 mmol) in in tert-butanol (2 mL) and water (2 mL). Yield (156 mg, 72%).

$^1$H-NMR (300 MHz, CDCl$_3$) δ: ppm 8.07 (s, 1H); 7.57-7.30 (br. m, 5H); 5.39 (m, 1H); 4.59 (s, 2H); 4.54-4.00 (br. m, 4H); 3.97-3.38 (br. m, 170-200H); 3.08 (t, 2H); 2.78 (t, 2H); 2.33 (m, 4H); 1.97-1.44 (br. m, 4H+8H water); 1.44-1.16 (br. m, 40H); 0.90 (t, 6H).

HO-PEG₂₀₀₀-ester-click-glycerol-C10

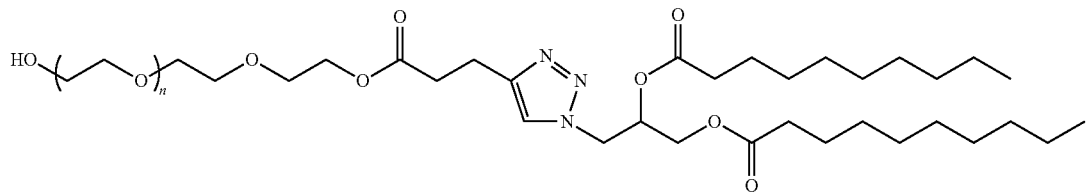

In the same manner as HO-PEG₂₀₀₀-ester-C18, HO-PEG₂₀₀₀-ester-click-glycerol-C10 was synthesized from Benzyl-PEG₂₀₀₀-ester-click-glycerol C10 (161 mg, 0.061 mmol) and palladium on carbon (10 wt. %, 7 mg, 0.061 mmol) under 1 atm H₂ in MeOH (2 mL). Yield (58 mg, 37%).

¹H-NMR (300 MHz, CDCl₃) δ: ppm 7.45 (s, 1H); 5.39 (m, 1H); 4.59 (m, 2H); 4.39-4.03 (br. m, 4H); 3.95-3.37 (br. m, 170-200H); 3.06 (t, 2H); 2.78 (t, 2H); 2.33 (m, 4H); 2.04 (br, 4H water); 1.61 (m, 4H); 1.44-1.19 (br. m, 24H); 0.90 (t, 6H).

HO-PEG₂₀₀₀-ester-click-glycerol-C14

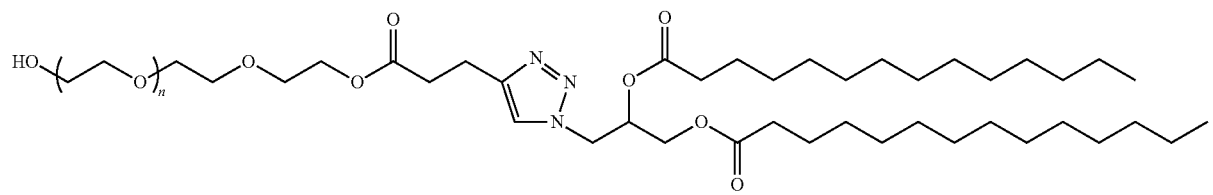

In the same manner as HO-PEG₂₀₀₀-ester-C18, HO-PEG₂₀₀₀-ester-click-glycerol-C14 was synthesized from Benzyl-PEG₂₀₀₀-ester-click-glycerol C14 (156 mg, 0.057 mmol) and palladium on carbon (10 wt. %, 6 mg, 0.057 mmol) under 1 atm H₂ in MeOH (2 mL). Yield (42 mg, 28%).

¹H-NMR (300 MHz, CDCl₃) δ: ppm 7.45 (s, 1H); 5.39 (m, 1H); 4.59 (m, 2H); 4.39-4.03 (br. m, 4H); 3.95-3.37 (br. m, 170-200H); 3.06 (t, 2H); 2.78 (t, 2H); 2.33 (m, 4H); 2.04 (br, 4H water); 1.61 (m, 4H); 1.44-1.19 (br. m, 40H); 0.90 (t, 6H).

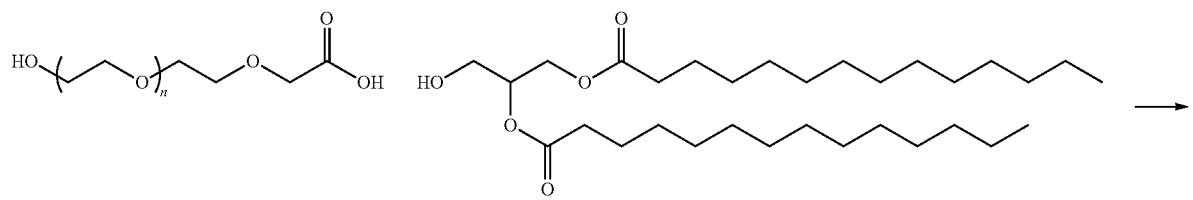

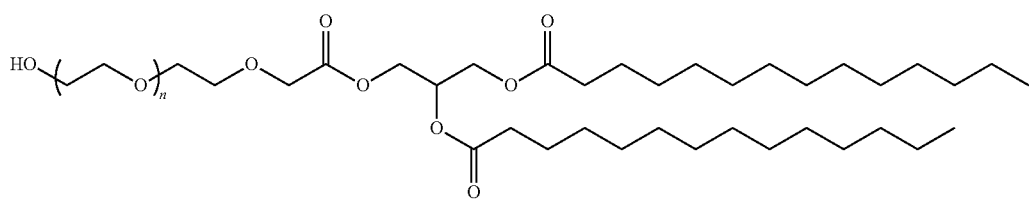

O-PEG$_{2000}$-ester-click-glycerol-C14

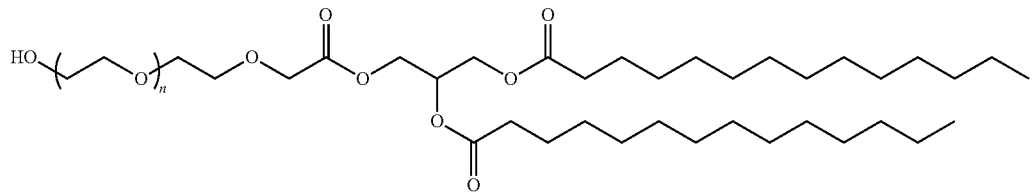

To a solution of 3-hydroxypropane-1,2-diyl ditetradecanoate (78 mg, 0.15 mmol), DCC (31 mg, 0.15 mmol), and DMAP (19 mg, 0.15 mmol) in DCM (4 mL) was added HO-PEG$_{2000}$-COOH in DCM (2 mL) at a rate of 50 mg/hr for 5 hours. After the addition was complete, the reaction was allowed to continue to stir at RT for 12 hours. The reaction was filtered, rinsing the solids with DCM, and the filtrate was concentrated in vacuo. Purification by ISCO silica flash chromatography (0-100% [MeCN 0.1% TFA]/[water 0.1% TFA]).

$^1$H-NMR (300 MHz, CDCl$_3$) δ: ppm 5.30 (m, 1H); 4.45-4.10 (br. m, 6H); 3.95-3.34 (br. m, 170-200H); 2.33 (t, 4H); 1.81 (br, 4H water); 1.63 (m, 4H); 1.39-1.16 (br. m, 40H); 0.90 (t, 6H).

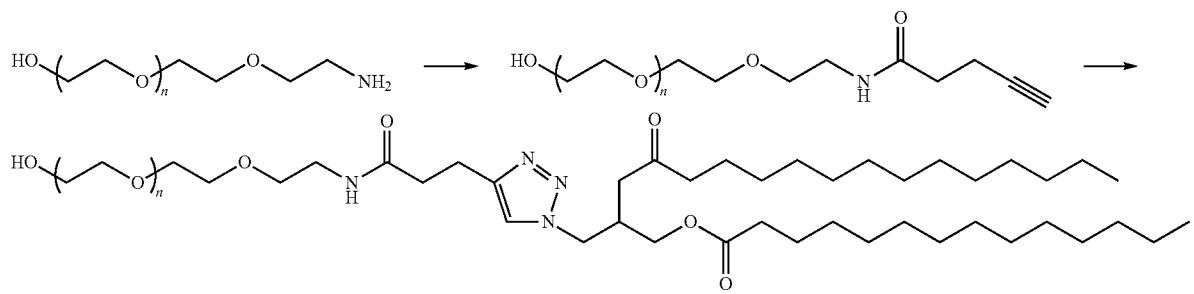

Benzyl-PEG$_{2000}$-ester-ethyl-alkyne

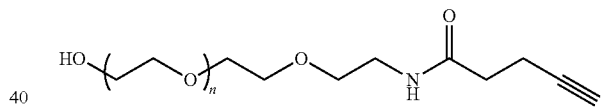

To a solution of HO-PEG$_{2000}$-NH$_2$ (250 mg, 0.125 mmol) and 4-pentynoic acid (12 mg, 0.125 mmol) in THF (4 mL) was added (benzotriazol-1-yloxy)tripyrrolidinophosphonium hexafluorophosphate (228 mg, 0.438 mmol) and triethylamine (61 µL, 0.438 mmol) and the reaction was allowed to stir at RT for 12 hours. The mixture was concentrated in vacuo. The crude product was purified by ISCO C18 flash chromatography (0-100% [MeCN 0.1% TFA]/[water 0.1% TFA]). The product was taken up in DCM and washed with 5% sodium carbonate, brine, dried over anhydrous sodium sulfate, filtered, and concentrated in vacuo. Yield (91 mg, 35%).

$^1$H-NMR (300 MHz, CDCl$_3$) δ: ppm 3.98-3.30 (br. m, 170-200H); 2.55 (m, 2H); 2.44 (m, 2H); 2.06-1.73 (br. m, 3H+5H water).

HO-PEG$_{2000}$-ester-click-glycerol-C14

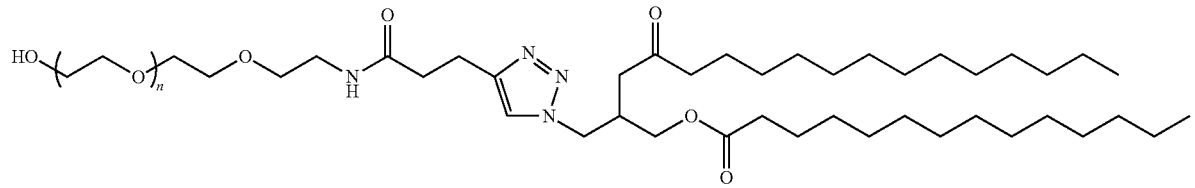

To a solution of benzyl-PEG$_{2000}$-ester-ethyl-alkyne (91 mg, 0.043 mmol) and 3-azidopropane-1,2-diyl ditetradecanoate (28 mg, 0.052 mmol) in tert-butanol (1.5 mL) and water (1.5 mL) was added CuSO$_4$ (4 mg, 0.022 mmol) and sodium ascorbate (9 mg, 0.043 mmol). The reaction was allowed to stir at RT overnight. The mixture was concentrated in vacuo. The crude product was purified by ISCO C18 flash chromatography (0-100% [MeCN 0.1% TFA]/[water 0.1% TFA]). The product was taken up in DCM and washed with 5% sodium carbonate, brine, dried over anhydrous sodium sulfate, filtered, and concentrated in vacuo. Yield (34 mg, 30%).

$^1$H-NMR (300 MHz, CDCl$_3$) δ: ppm 7.52 (s, 1H); 5.38 (m, 1H); 4.65-3.98 (br. m, 6H); 3.95-3.30 (br. m, 170-200H); 3.09 (t, 2H); 2.63 (t, 2H); 1.76 (m, 4H); 1.82-1.52 (br. m, 4H+2H water); 1.41-1.16 (br. m, 40H); 0.90 (t, 6H).

Examples of Embodiments

Examples of embodiments described herein include, but are not limited to:

A1. A method for reducing accelerated blood clearance (ABC) in a subject being treated with a therapeutic regimen involving repeat dosing of lipid nanoparticles (LNPs), the method comprising:
administering LNPs to the subject, wherein the LNPs do not activate B1a cells and/or do not induce production of natural IgM molecules capable of binding to the LNPs, such that ABC is reduced upon repeat administration of the LNPs to the subject.

A1.1 A method for reducing accelerated blood clearance (ABC) in a subject being treated with a therapeutic regimen involving multiple dosing of lipid nanoparticles (LNPs), the method comprising:
administering a dose of LNPs to the subject, wherein the LNPs do not activate B1a cells and/or do not induce production of natural IgM molecules capable of binding to the LNPs, such that ABC is reduced upon administration of one or more subsequent doses of the LNPs to the subject.

A1.2 A method for reducing accelerated blood clearance (ABC) of lipid nanoparticles (LNPs) in a subject being treated with a multi-dose or repeat dosing therapeutic regimen, the method comprising:
administering LNPs to the subject, wherein the LNPs do not activate B1a cells and/or do not induce production of natural IgM molecules capable of binding to the LNPs, such that ABC is reduced upon subsequent or repeat dosing of LNPs in the subject.

A1.3 A method for decelerating blood clearance of LNPs, the method comprising:
administering LNPs to a subject, wherein the LNPs do not activate B1a cells and/or do not induce production of natural IgM molecules capable of binding to the LNPs, such that upon administration of a subsequent dose of the LNPs to the subject blood clearance of the LNPs is decelerated.

A1.4. A method for delivering lipid nanoparticles (LNPs) to a subject without promoting accelerated blood clearance (ABC), the method comprising:
administering LNPs to the subject, wherein the LNPs do not promote ABC.

A1.5 The method of paragraph A1, wherein the LNPs do not induce production of natural IgM molecules capable of binding to the LNPs.

A2. The method of any one of paragraphs A1-A1.5, wherein the LNPs do not activate B1a cells.

A2.1 The method of any one of preceding paragraphs, wherein the LNPs do not activate CD36 or B1a cells.

A3. The method of paragraph A2 or A2.1, wherein the LNPs are free of an epitope that activates B1a cells.

A4. The method of any one of paragraphs A1 to A3, wherein the LNPs comprise a helper lipid, which comprises a polar moiety and a lipidic moiety, linked by a core moiety, and wherein the helper lipid does not activate B1a cells.

A5. The method of any one of paragraphs A1 to A4, wherein the LNPs are free of phosphatidyl choline (PC).

A6. The method of paragraph A4 or A5, wherein the helper lipid is a phosphatidyl choline analog.

A7. The method of paragraph A6, wherein the phosphatidyl choline analog comprises a modified PC head group, a modified PC core group, and/or a modified PC lipid tail.

A8 The method of any one of paragraphs A4 to A7, wherein the helper lipid competitively inhibits phosphocholine from binding to CD36.

A9. The method of any one of paragraphs A4 to A7, wherein the helper lipid does not bind or has low binding activity to CD36.

A10. The method of any one of paragraphs A1 to A9, wherein the LNPs comprise oleic acid or an oleic acid analog.

A11. The method of any one of paragraphs A1 to A10, wherein the LNPs are free of PEG or a PEGylated lipid.

A12. The method of any one of paragraphs A1-A10, wherein the LNPs further comprise a PEGylated lipid.

A13. The method of paragraph A12, wherein the PEGylated lipid is an alkyl-PEGylated lipid.

A14. The method of paragraph A12, wherein the PEGylated lipid is a methoxy-PEGylated lipid.

A15. The method of paragraph A12, wherein the PEGylated lipid is DMG-PEG.

A16. The method of paragraph A12, wherein the PEGylated lipid is a hydroxy-PEGylated lipid.

A17. The method of any one of paragraphs A12-A17, wherein the PEGylated lipid is less than 0.5% (w/w).

A18. The method of paragraph A17, wherein the PEGylated lipid is less than 0.25% (w/w).

A19. The method of any one of paragraphs A1 to A18, wherein the LNPs further comprise a cationic lipid.

A20. The method of paragraph A19, wherein the cationic lipid is MC3 or DLin-MC3-DMA.

A21. The method of any one or paragraphs A1 to A20, wherein the LNPs further comprise a sterol.

A22. The method of paragraph A21, wherein the sterol is cholesterol.

A23. The method of any one of paragraphs A1-A22, wherein the LNPs encapsulate a therapeutic agent.

A24. The method of paragraph A23, wherein the therapeutic agent is a protein or a nucleic acid.

A25. The method of paragraph A24, wherein the therapeutic agent is a mRNA coding for a therapeutic protein.

A26. The method of any one or paragraphs A1-A25, wherein the LNPs are administered to the subject at multiple doses.

A27. The method of paragraph A26, wherein the interval of two consecutive doses is less than 2 weeks.

A28. The method of paragraph A27, wherein the interval of two consecutive doses is less than 1 week.

B1. A method for reducing accelerated blood clearance (ABC) in a subject being treated with a therapeutic regimen involving repeat dosing of lipid nanoparticles (LNPs), the method comprising:
administering to the subject LNPs and an agent that inhibits B1a cell-mediated immune responses induced by the LNPs, such that ABC is reduced upon repeat administration of the LNPs to the subject.

B1.1. A method for reducing accelerated blood clearance (ABC) in a subject being treated with a therapeutic regimen involving multiple dosing of lipid nanoparticles (LNPs), the method comprising:

administering to the subject LNPs and an agent that inhibits B1a cell-mediated immune responses induced by the LNPs, such that ABC is reduced upon administration of one or more subsequent doses of the LNPs to the subject.

B1.2 A method for reducing accelerated blood clearance (ABC) of lipid nanoparticles (LNPs) in a subject being treated with a multi-dose or repeat dosing therapeutic regimen, the method comprising:

administering to the subject LNPs and an agent that inhibits B1a cell-mediated immune responses induced by the LNPs, such that ABC is reduced upon subsequent or repeat dosing of LNPs in the subject.

B1.3 A method for decelerating blood clearance of LNPs, the method comprising:

administering to a subject LNPs and an agent that inhibits B1a cell-mediated immune responses induced by the LNPs, such that upon administration of a subsequent dose of the LNPs to the subject blood clearance of the LNPs is decelerated.

B1.4. A method for reducing or inhibiting accelerated blood clearance (ABC) of lipid nanoparticles (LNPs) in a subject, the method comprising:

administering to the subject LNPs and an agent that inhibits immune responses induced by the LNPs, such that ABC of the LNPs is reduced or inhibited.

B2. The method of any one of paragraphs B1-B1.4, wherein the agent inhibits production of or neutralizes natural IgM capable of binding to the LNPs.

B3. The method of any one of paragraphs B1 to B2, wherein the immune response induced by the LNPs is activation of B1a cells.

B3.1 The method of any one of paragraphs B1 to B1.4, wherein the immune response induced by the LNPs is binding of natural IgM to the LNPs.

B4. The method of paragraph C3, wherein the agent binds and/or inhibits CD36 on B1a cells.

B5. The method of any one of paragraphs B1 to B4, wherein the agent is administered to the subject prior to, after, or concurrently with the administration of the LNPs.

B6. The method of any one of paragraphs B1 to B5, wherein the LNPs encapsulate a therapeutic agent.

B7. The method of paragraph B6, wherein the therapeutic agent is a protein or a nucleic acid.

B8. The method of paragraph B7, wherein the therapeutic agent is a mRNA coding for a therapeutic protein.

B9. The method of any one or paragraphs B1 to B8, wherein the subject is administered with the LNPs at multiple doses.

B10. The method of paragraph B9, wherein the interval between two consecutive doses is less than 2 weeks.

B11. The method of paragraph B10, wherein the interval between two consecutive doses is less than 1 week.

C1. A method for reducing dose-limiting toxicity (DLT) in a subject being treated with therapeutic regimen involving lipid nanoparticle (LNP)-mediated drug delivery, the method comprising:

administering LNPs to the subject, wherein the LNPs do not promote platelet activation, such that DLT is reduced in the subject being treated with therapeutic regimen.

C1.1 A method for reducing toxicity associated with delivery of therapeutic doses of lipid nanoparticle (LNP)-encapsulated drug to a subject, the method comprising:

administering LNPs to the subject, wherein the LNPs do not promote platelet activation, such that the toxicity is reduced.

C1.2. A method for delivering lipid nanoparticles (LNPs) to a subject without promoting toxicity associated with LNPs, the method comprising:

administering LNPs to the subject, wherein the LNPs do not promote LNP-related toxicity.

C1.3. The method of any one of paragraphs C1 to C1.2, wherein the LNP-related toxicity comprises coagulopathy, disseminated intravascular coagulation (DIC), vascular thrombosis, complement activation-related pseudoallergy (CARPA) or a combination thereof.

C2. The method of any one of paragraphs C1 to C1.3, wherein the LNPs do not promote a classical pathway (CP).

C3. The method of any one of paragraphs C1 to C1.3, wherein the LNPs do not promote an alternative pathway (AP).

C4. The method of any one of paragraphs C1 to C1.3, wherein the LNPs do not promote platelet activation or aggregation.

C5. The method of any one of paragraphs C1 to C4, wherein the LNPs do not activate CD36.

C6. The method of paragraph C5, wherein the LNPs are free of an epitope that activates CD36.

C7. The method of any one of paragraphs C1 to C6, wherein the LNPs comprise a helper lipid, which comprises at least one fatty acid chain of at least 8C and at least one polar moiety, and wherein the helper lipid does not activate B1a cells.

C8. The method of any one of paragraphs C1 to C7, wherein the LNPs are free of phosphatidyl choline (PC).

C9. The method of paragraph C7 or C8, wherein the helper lipid is a phosphatidyl choline analog.

C10. The method of paragraph C9, wherein the phosphatidyl choline analog comprises a modified PC head group, a modified PC core group, and/or a modified PC lipid tail.

C11 The method of any one of paragraphs C7 to C10, wherein the helper lipid competitively inhibits phosphocholine from binding to CD36.

C12. The method of any one of paragraphs C7 to C10, wherein the helper lipid does not bind or has low binding activity to CD36.

C13. The method of any one of paragraphs C1 to C12, wherein the LNPs comprise oleic acid or an oleic acid analog.

C14. The method of any one of paragraphs C1 to C13, wherein the LNPs are free of PEG or a PEGylated lipid.

C15. The method of any one of paragraphs C1 to C14, wherein the LNPs further comprise a PEGylated lipid.

C16. The method of paragraph C15, wherein the PEGylated lipid is an alkyl-PEGylated lipid.

C17. The method of paragraph C15, wherein the PEGylated lipid is a methoxy-PEGylated lipid.

C18. The method of paragraph C15, wherein the PEGylated lipid is DMG-PEG.

C19. The method of paragraph C15, wherein the PEGylated lipid is a hydroxy-PEGylated lipid.

C20. The method of any one of paragraphs C15 to C19, wherein the PEGylated lipid is less than 0.5% (w/w).

C21. The method of paragraph C20, wherein the PEGylated lipid is less than 0.25% (w/w).

C22. The method of any one of paragraphs C1 to C21, wherein the LNPs further comprise a cationic lipid.

C23. The method of paragraph C22, wherein the cationic lipid is MC3 or DLin-MC3-DMA.

C24. The method of any one or paragraphs C1 to C23, wherein the LNPs further comprise a sterol.

C25. The method of paragraph C24, wherein the sterol is cholesterol.

C26. The method of any one of paragraphs C1 to C25, wherein the LNPs encapsulate a therapeutic agent.

C27. The method of paragraph C26, wherein the therapeutic agent is a protein or a nucleic acid.

C28. The method of paragraph C27, wherein the therapeutic agent is a mRNA coding for a therapeutic protein.

D1. A method for reducing dose-limiting toxicity (DLT) in a subject being treated with therapeutic regimen involving lipid nanoparticle (LNP)-mediated drug delivery, the method comprising:

administering to the subject LNPs and an agent that inhibits platelet activation, such that DLT is reduced in the subject being treated with therapeutic regimen.

D1.1 A method for reducing toxicity associated with delivery of therapeutic doses of lipid nanoparticle (LNP)-encapsulated drug to a subject, the method comprising:

administering to the subject LNPs and an agent that inhibits platelet activation, such that the toxicity is reduced.

D1.2. A method for lessening lipid nanoparticle (LNP)-related toxicity in a subject, the method comprising:

administering to the subject LNPs and an agent that inhibits the LNP-related toxicity or alleviate at least one symptom thereof.

D2. The method of any one of paragraphs D1 to D1.2, wherein the LNP-related toxicity comprises coagulopathy, disseminated intravascular coagulation (DIC), vascular thrombosis, activation-related pseudoallergy (CARPA), or a combination thereof.

D3. The method of paragraph D1 or D2, wherein the agent is administered to the subject prior to, after, or currently with the administration of the LNPs.

D4. The method of any one of paragraphs D1 to D4, wherein the LNPs encapsulate a therapeutic agent.

D5. The method of paragraph D4, wherein the therapeutic agent is a protein or a nucleic acid.

D6. The method of paragraph D5, wherein the therapeutic agent is a mRNA coding for a therapeutic protein.

D7. The method of any one of paragraphs D1 to D6, wherein the agent alleviates at least one symptom associated with the LNP-related toxicity.

D8. The method of paragraph D7, wherein the agent is a nonsteroidal anti-inflammatory drug (NSAID) or an antihistamine agent, wherein the anti-histamine is a histamine receptor blocker, such as an H1 antagonist or an H1 inverse agonist.

D9. The method of paragraph D8, wherein the NSAID is a COX-2 and/or 5-LOX inhibitor.

D10. The method of paragraph D8, wherein the antihistamine is a histamine receptor blocker.

D11. The method of paragraph D10, wherein the histamine receptor blocker is an H1 antagonist or an H1 inverse agonist.

D12. The method of paragraph D11, wherein the H1 antagonist is diphenhydramine (Benadryl), fexofenadine (Allegra) or loratadine (Claritin), and the H1 inverse agonist is cetirizine.

D12. The method of any one of paragraphs D1 to D6, wherein the agent inhibits CARPA.

D13. The method of any one of paragraphs D12, wherein the agent inhibits a classical pathway (CP).

D14. The method of any one of paragraphs D12, wherein the agent inhibits an alternative pathway.

D15. The method of any one of paragraphs D1 to D6, and D12 to D14, wherein the agent inhibits platelet activation.

D16. The method of paragraph D15, wherein the agent is a platelet aggregation inhibitor.

D17. The method of paragraph D16, wherein the platelet aggregation inhibitor is an ADP receptor antagonist.

D18. The method of paragraph D17, wherein the platelet aggregation inhibitor is aspirin or clopidrogrel (Plavix®).

D19. The method of paragraph D17, wherein the platelet aggregation inhibitor is selected from aspirin/pravastatin, cilostazol, prasugrel, aspirin/dipyridamole, ticagrelor, cangrelor, elinogrel, dipyridamole, and ticlopidine.

D20. The method of any one of paragraphs D1 to D6 and D12 to D15, wherein the agent inhibits CD36.

D21. The method of any one of paragraphs D1 to D6 and D12 to D15, wherein the agent inhibits a TLR receptor, CD62P, properdin, a component of the complement system, C-reactive protein or other proteins of the acute phase response.

E1. A method for delivering a therapeutic level of a protein of interest to a subject, the method comprising:

administering to the subject lipid nanoparticles (LNPs), which encapsulate an mRNA coding for the protein of interest, wherein the LNPs do not induce drug responses associated with LNPs.

E2. The method of paragraph E1, wherein the drug response associated with LNPs is accelerated blood clearance.

E3. The method of paragraph E2, wherein the LNPs do not induce production of natural IgM molecules capable of binding to the LNPs.

E4. The method of paragraph E2, wherein the LNPs do not activate B1a cells.

E5. The method of paragraph E4, wherein the LNPs is free of an epitope that activates B1a cells.

E6. The method of any one of paragraphs E2 to E5, wherein the LNPs are administered to the subject at multiple doses.

E7. The method of paragraph E6, wherein the interval of two consecutive doses is less than 2 weeks.

E8. The method of paragraph E7, wherein the interval of two consecutive doses is less than 1 week.

E9. The method of paragraph E1, wherein the drug response associated with LNPs is an adverse reaction induced by the LNPs.

E10. The method of paragraph E9, wherein the adverse reaction comprises coagulopathy, disseminated intravascular coagulation (DIC), vascular thrombosis, activation-related pseudoallergy (CARPA), or a combination thereof.

E11. The method of paragraph E10, wherein the LNPs do not promote CARPA.

E11.1 The method of paragraph E11, wherein the LNPs do not promote a classical pathway (CP).

E12. The method of paragraph E11, wherein the LNPs do not promote an alternative pathway (AP).

E13. The method of paragraph E10, wherein the LNPs do not promote platelet activation or aggregation.

E14. The method of paragraph E1, wherein the LNPs do not activate CD36.

E15. The method of any one of paragraphs E1 to E14, wherein the LNPs comprise a helper lipid, which comprises at least one fatty acid chain of at least 8C and at least one polar moiety, and wherein the helper lipid does not induce production of natural IgM capable of binding to the LNPs, do not activate B1a cells, do not activate CD36, and/or do not activate platelet.

E16. The method of any one of paragraphs E1 to E15, wherein the LNPs are free of phosphatidyl choline (PC).

E17. The method of paragraph E15 or E16, wherein the helper lipid is a phosphatidyl choline analog.

E18. The method of paragraph E17, wherein the phosphatidyl choline analog comprises a modified PC head group, a modified PC core group, and/or a modified PC lipid tail.

E19 The method of any one of paragraphs E15 to E18, wherein the helper lipid competitively inhibits phosphocholine from binding to CD36.

E20. The method of any one of paragraphs E15 to E18, wherein the helper lipid does not bind or has low binding activity to CD36.

E21. The method of any one of paragraphs E1 to E20, wherein the LNPs comprise oleic acid or an oleic acid analog.

E22. The method of any one of paragraphs E1 to E21, wherein the LNPs are free of PEG or a PEGylated lipid.

E23. The method of any one of paragraphs E1 to E22, wherein the LNPs further comprise a PEGylated lipid.

E24. The method of paragraph E23, wherein the PEGylated lipid is an alkyl-PEGylated lipid.

E25. The method of paragraph E23, wherein the PEGylated lipid is a methoxy-PEGylated lipid.

E26. The method of paragraph E23, wherein the PEGylated lipid is DMG-PEG.

E27. The method of paragraph E23, wherein the PEGylated lipid is a hydroxy-PEGylated lipid.

E28. The method of any one of paragraphs E23 to E27, wherein the PEGylated lipid is less than 0.5% (w/w).

E29. The method of paragraph E28, wherein the PEGylated lipid is less than 0.25% (w/w).

E30. The method of any one of paragraphs E1 to E29, wherein the LNPs further comprise a cationic lipid.

E31. The method of paragraph E30, wherein the cationic lipid is MC3 or DLin-MC3-DMA.

E32. The method of any one or paragraphs E1 to E31, wherein the LNPs further comprise a sterol.

E33. The method of paragraph E32, wherein the sterol is cholesterol.

E34. The method of any one of paragraphs E1 to E33, wherein the mRNA encodes a therapeutic protein.

F1. A method for delivering a therapeutic level of a protein of interest to a subject, the method comprising:
 administering to the subject lipid nanoparticles (LNPs), which encapsulate an mRNA coding for the protein of interest, and an agent in amount effective to inhibit a drug response induced by the LNPs or alleviate at least one symptom thereof.

F2. The method of paragraph F1, wherein the drug response is accelerated blood clearance.

F3. The method of paragraph F2, wherein the agent inhibits production of or neutralizes natural IgM capable of binding to the LNPs.

F3.1 The method of paragraph F2, wherein the agent inhibits binding of natural IgM to a target.

F3.2 The method of paragraph F2, wherein the agent removes B1a cells.

F4. The method of paragraph F2, wherein the agent inhibits activation of B1a cells.

F5. The method of paragraph F4, wherein the agent binds and/or inhibits CD36 on B1a cells.

F6. The method of any one of paragraphs F2 to F5, wherein the agent is administered to the subject prior to, or currently with the administration of the LNPs.

F7. The method of any one or paragraphs F2 to F6, wherein an LNP is administered to the subject at multiple doses.

F8. The method of paragraph F7, wherein the interval between two consecutive doses is less than 2 weeks.

F9. The method of paragraph F8, wherein the interval between two consecutive doses is less than 1 week.

F10. The method of paragraph F1, wherein the drug response is LNP-related toxicity.

F11. The method of paragraph F10, wherein the LNP-related toxicity comprises coagulopathy, disseminated intravascular coagulation (DIC), vascular thrombosis, activation-related pseudoallergy (CARPA), or a combination thereof.

F12. The method of paragraph F10 or F11, wherein the agent is administered to the subject prior to, after, or currently with the administration of the LNPs.

F13. The method of any one of paragraphs F10 to F12, wherein the agent alleviates at least one symptom associated the LNP-related toxicity.

F14. The method of paragraph F13, wherein the agent is a nonsteroidal anti-inflammatory drug (NSAID) or an antihistamine agent.

F15. The method of paragraph F14, wherein the NSAID is a COX-2 and/or 5-LOX inhibitor.

F16. The method of paragraph F14, wherein the antihistamine is a histamine receptor blocker.

F17. The method of paragraph F16, wherein the histamine receptor blocker is an H1 antagonist or an H1 inverse agonist.

F18. The method of paragraph F17, wherein the H1 antagonist is diphenhydramine (Benadryl), fexofenadine (Allegra) or loratadine (Claritin), and the H1 inverse agonist is cetirizine.

F19. The method of any one of paragraphs F10 to F12, wherein the agent inhibits CARPA.

F20. The method of any one of paragraphs F19, wherein the agent inhibits a classical pathway (CP).

F21. The method of any one of paragraphs F19, wherein the agent inhibits an alternative pathway.

F22. The method of any one of paragraphs F1 to F12 and F19 to F21, wherein the agent inhibits platelet activation.

F23. The method of paragraph F22, wherein the agent is a platelet aggregation inhibitor.

F24. The method of paragraph F23, wherein the platelet aggregation inhibitor is an ADP receptor antagonist.

F25. The method of paragraph F24, wherein the platelet aggregation inhibitor is aspirin or clopidrogrel (Plavix®).

F26. The method of paragraph F25, wherein the platelet aggregation inhibitor is selected from aspirin/pravastatin, cilostazol, prasugrel, aspirin/dipyridamole, ticagrelor, cangrelor, elinogrel, dipyridamole, and ticlopidine.

F27. The method of any one of paragraphs F1 to F12 and F19 to F21, wherein the agent inhibits CD36.

G1. A method for reducing dose-limiting toxicity (DLT) and/or accelerated blood clearance (ABC) in a subject being treated with a therapeutic regimen involving lipid nanoparticle (LNP)-mediated drug delivery, the method comprising:
 administering to the subject LNPs encapsulating the therapeutic agent, wherein the LNPs do not activate immune cell CD36, such that ABC is reduced upon repeat administration of the LNPs to the subject.

G1.1 The method of paragraph G1, wherein the immune cells are platelets and/or B cells, I particular, B1a cells.

G1.2. A method for delivering a therapeutically effective amount of a therapeutic agent via lipid nanoparticles to a subject, the method comprising:

administering to the subject LNPs encapsulating the therapeutic agent, wherein the LNPs do not activate CD36.

G2. The method of any one of paragraphs G1 to G1.2, wherein the LNPs are free of an epitope that activates CD36.

G3. The method of paragraph G2, wherein the LNPs are free of phosphodityl choline (PC).

G4. The method of any one of paragraphs G1 to G3, wherein the LNPs comprise a helper lipid that does not bind or has low binding activity to CD36, or competitively inhibits phosphocholine from binding to CD36.

G5. The method of paragraph G4, wherein the helper lipid comprises at least one fatty acid chain of at least 8C and at least one polar moiety.

G6. The method of paragraph G4 or G5, wherein the helper lipid is a phosphatidyl choline analog.

G7. The method of paragraph G6, wherein the phosphatidyl choline analog comprises a modified PC head group, a modified PC core group, and/or a modified PC lipid tail.

G8. The method of any one of paragraphs G1 to G7, wherein the LNPs comprise oleic acid or an oleic acid analog.

G9. The method of any one of paragraphs G1 to G8, wherein the LNPs are free of PEG or a PEGylated lipid.

G10. The method of any one of paragraphs G1 to G9, wherein the LNPs further comprise a PEGylated lipid.

G11. The method of paragraph G10, wherein the PEGylated lipid is an alkyl-PEGylated lipid.

G12. The method of paragraph G10, wherein the PEGylated lipid is a methoxy-PEGylated lipid.

G13. The method of paragraph G10, wherein the PEGylated lipid is DMG-PEG.

G14. The method of paragraph G10, wherein the PEGylated lipid is a hydroxy-PEGylated lipid.

G15. The method of any one of paragraphs G10 to G14, wherein the PEGylated lipid is less than 0.5% (w/w).

G16. The method of paragraph G15, wherein the PEGylated lipid is less than 0.25% (w/w).

G17. The method of any one of paragraphs G1 to G16, wherein the LNPs further comprise a cationic lipid.

G18. The method of paragraph G17, wherein the cationic lipid is MC3 or DLin-MC3-DMA.

G19. The method of any one or paragraphs G1 to G18, wherein the LNPs further comprise a sterol.

G20. The method of paragraph G19, wherein the sterol is cholesterol.

G21. The method of any one of paragraphs G1 to G20, wherein the LNPs encapsulate a therapeutic agent.

G22. The method of paragraph G21, wherein the therapeutic agent is a protein or a nucleic acid.

G23. The method of paragraph G22, wherein the therapeutic agent is a mRNA coding for a therapeutic protein.

G23. The method of any one or paragraphs G1 to G25, wherein the LNPs are administered to the subject at multiple doses.

G24. The method of paragraph G23, wherein the interval of two consecutive doses is less than 2 weeks.

G25. The method of paragraph G24, wherein the interval of two consecutive doses is less than 1 week.

J1. An accelerated blood clearance (ABC) insensitive lipid nanoparticle (LNP), comprising an cationic lipid, a PEG-lipid, a sterol, and a helper lipid, wherein the helper lipid does not comprise a phosphatidyl choline (PC).

J2. The ABC insensitive LNP of paragraph J1, wherein the helper lipid comprises a phosphatidyl choline (PC) analog.

J3. The ABC insensitive LNP of paragraph J1, wherein the LNP is not subject to accelerated blood clearance (ABC) when administered at least twice to a subject in a time period of 10 days or less.

J4. The ABC insensitive LNP of paragraph J2, wherein the PC analog comprises a modified PC head group, a modified PC core group, and/or a modified PC lipid tail.

J5. The ABC insensitive LNP of any one of the preceding paragraphs, wherein the LNP has no or reduced B1a stimulating activity compared to an LNP comprising phosphatidyl choline.

J6. The ABC insensitive LNP of any one of the preceding paragraphs, wherein the LNP has no or reduced binding to CD36 relative to an LNP comprising phosphatidyl choline.

J7. The ABC insensitive LNP of any one of the preceding paragraphs, wherein the PC analog has no or reduced binding to CD36 relative to phosphatidyl choline (PC).

J8. The ABC insensitive LNP of any one of the preceding paragraphs, wherein the PC analog has no or reduced CD36 binding relative to phosphatidyl choline (PC).

J9. The ABC insensitive LNP of any one of the preceding paragraphs, wherein the helper lipid comprises oleic acid or an oleic acid analog.

J10. The ABC insensitive LNP of any one of the preceding paragraphs, wherein the LNP comprises less than 0.5% (w/w) of a PEGylated lipid.

J11. The ABC insensitive LNP of paragraph J10, comprising less than 0.25% of the PEGylated lipid.

J12. The ABC insensitive LNP of paragraph J10, wherein the PEGylated lipid is an alkyl-PEGylated lipid.

J13. The ABC insensitive LNP of paragraph J10, wherein the PEGylated lipid is a methoxy-PEGylated lipid.

J14. The ABC insensitive LNP of paragraph J10, wherein the PEGylated lipid is DMG-PEG.

J15. The ABC insensitive LNP of any one of paragraphs J1-J9, further comprising a lipid conjugated to hydroxy-PEG (hydroxy-PEGylated lipid).

J16. The ABC insensitive LNP of any one of paragraphs J1-J12, wherein the LNP has reduced platelet aggregation activity compared to an LNP comprising a methoxy-PEGylated lipid.

J17. The ABC insensitive LNP of paragraph J1, wherein the cationic lipid is MC3 (or DLin-MC3-DMA).

J18. A lipid nanoparticle (LNP) comprising
a cationic lipid,
a non-cationic, non-PC lipid,
less than 0.5% (w/w) of a PEGylated lipid, and
a sterol, and
wherein the LNP is insensitive to accelerated blood clearance upon repeated administration in vivo within 10 days.

J19. The LNP of paragraph J18, further comprising a protein or a nucleic acid.

J20. The LNP of paragraph J19, wherein the nucleic acid is DNA.

J21. The LNP of paragraph J19, wherein the nucleic acid is RNA.

J22. The LNP of paragraph J19, wherein the nucleic acid is mRNA.

K1. A method of delivering an agent to a subject, comprising:
administering to a subject an agent formulated in a lipid nanoparticle (LNP), wherein the subject is administered a platelet inhibitor.

K2. The method of paragraph K1, wherein the platelet inhibitor is administered to the subject at the same time as the agent formulated in a LNP.

K3. The method of paragraph K1, wherein the platelet inhibitor is administered to the subject 1 minute to 24 hours prior to the agent formulated in a LNP.

K4. The method of paragraph K1, wherein the platelet inhibitor is administered to the subject 24-48 hours prior to the agent formulated in a LNP.

K5. The method of any one of paragraphs K1-K4, further comprising administering to the subject a histamine receptor blocker.

K6. The method of any one of paragraphs K1-K5, further comprising administering to the subject a non-specific inhibitor of COX enzyme.

K7. The method of any one of paragraphs K1-K8, wherein the agent is a nucleic acid.

K8. The method of paragraph K7, wherein the nucleic acid is a RNA.

K9. The method of paragraph K8, wherein the RNA is siRNA or mRNA.

K10. The method of any one of paragraphs K1-K9, wherein the LNP comprises a cationic lipid, a PEG-lipid, cholesterol and a helper lipid.

K11. The method of any one of paragraphs K1-K10, wherein the subject is not administered a corticosteroid.

K12. The method of paragraph K1, wherein the platelet inhibitor is an inhibitor of P2Y12 subtype receptor.

K13. The method of paragraph K1, wherein the platelet inhibitor is clopidogrel.

K14. The method of paragraph K1, wherein the platelet inhibitor is ticagrelor.

K15. The method of paragraph K1, wherein the platelet inhibitor is prasugrel, ticlopidine, cangrelor, or elinogrel.

K16. The method of paragraph K5, wherein the histamine receptor blocker is an antihistamine.

K17. The method of paragraph K16, wherein the antihistamine is Benadryl.

K18. The method of paragraph K6, wherein the non-specific inhibitor of COX enzyme is aspirin.

K19. The method of paragraph K6, wherein the non-specific inhibitor of COX enzyme is a COX-2 inhibitor.

K20. The method of paragraph K6, wherein the non-specific inhibitor of COX enzyme is a COX-2 and 5-lipoxygenase (5-LOX) inhibitor.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment of the present invention.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for delivering a therapeutic level of a protein of interest to a subject, the method comprising:
   administering to the subject at least two doses of lipid nanoparticles (LNPs) comprising an mRNA coding for the protein of interest, wherein the LNPs comprise an ionizable lipid, a helper lipid, a structural lipid, and a PEG-lipid,
   wherein the PEG-lipid is a compound of Formula (V—OH):

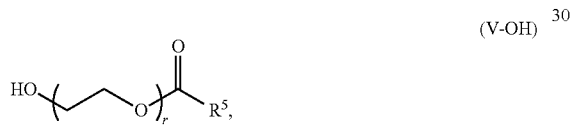

(V-OH)

or a pharmaceutically acceptable salt thereof, wherein:
   r is an integer between 1 and 100, inclusive; and
   $R^5$ is optionally substituted $C_{10-40}$ alkyl; and
   wherein said LNPs result in a reduced anti-PEG IgM response in the subject as compared to LNPs lacking a PEG-lipid of Formula (V—OH).

2. The method of claim 1, wherein the compound of Formula (V—OH) is Cmpd452:

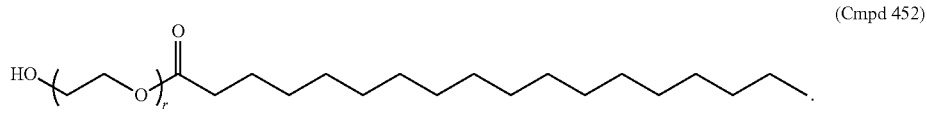

(Cmpd 452)

3. The method of claim 2, wherein the PEG-lipid comprises a PEG molecule of an average molecular weight of 2,000 Da or less.

4. The method of claim 3, wherein the PEG-lipid is HO-PEG2000-ester-C18 (Cmpd403).

5. The method of claim 1, wherein the ionizable lipid is a compound of Formula (XI):

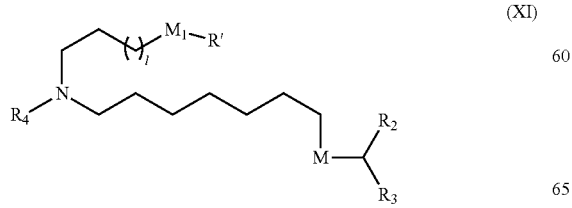

(XI)

or a pharmaceutically acceptable salt thereof, wherein:

l is selected from 1, 2, 3, 4, and 5;

M and M' are independently selected from C(O)O, and OC(O);

$M_1$ is M';

$R_2$ and $R_3$ are both $C_{1-14}$ alkyl, or $C_{2-14}$ alkenyl;

$R_4$ is $(CH_2)_nQ$, in which Q is OH, and n is selected from 2, 3, or 4; and

R' is a $C_1$-$C_{18}$ linear alkyl.

6. The method of claim 5, wherein R' is $C_9$ alkyl.

7. The method of claim 5, wherein n is 2.

8. The method of claim 5, wherein the compound of Formula (XI) has the structure of Cmpd18:

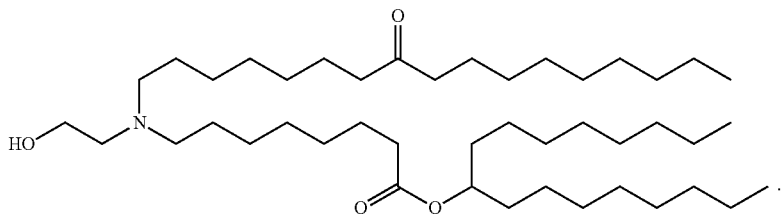
(Cmpd 18)

9. The method of claim 1, wherein the helper lipid comprises at least one fatty acid chain of at least 8 carbons in length and at least one polar headgroup moiety, and wherein the helper lipid does not comprise a phosphatidyl choline (PC) and is a zwitterionic non-cationic helper lipid, a DSPC analog, oleic acid, an oleic acid analog, DSPC, or a 1,2-distearoyl-sn-glycero-3-phosphocholine (DSPC) substitute.

10. The method of claim 9, wherein the helper lipid is DSPC.

11. The method of claim 1, wherein the helper lipid is oleic acid or an oleic acid analog.

12. The method of claim 1, wherein the LNPs comprise a molar ratio of about 45-65% ionizable lipid: 5-25% helper lipid: 15-45% structural lipid; and 0.15-15% PEG-lipid.

13. The method of claim 12, wherein the PEG-lipid is present in the LNPs in an amount of less than 0.5% (w/w).

14. The method of claim 1, wherein said administering results in a reduced IgG response in the subject.

15. The method of claim 1, wherein said administering results in a reduced anti-DSPC IgM response in the subject.

16. The method of claim 1, wherein said administering results in reduced B1a cell activation in the subject.

17. The method of claim 1, wherein said administering results in reduced CD36 positive cell activation in the subject.

18. The method of claim 1, wherein said at least two doses of LNPs is more than two doses of LNPs.

19. The method of claim 1, wherein the interval between the doses is about 21 days or less.

20. The method of claim 1, wherein the mRNA is chemically-modified.

21. The method of claim 1, wherein the mRNA comprises at least one miR binding site.

22. The method of claim 21, wherein the miR binding site is selected from miR 122, 126, miR 155, and miR 142.3p.

23. The method of claim 1, further comprising administering to the subject an additional agent that inhibits immune responses.

24. The method of claim 1, comprising:
administering to the subject a first dose of lipid nanoparticles (LNPs) comprising an mRNA coding for the protein of interest, wherein the LNPs comprise an ionizable lipid, a helper lipid, a structural lipid, and a PEG-lipid, wherein:

the PEG-lipid

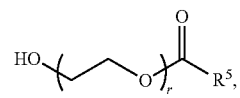

is Cmpd452:

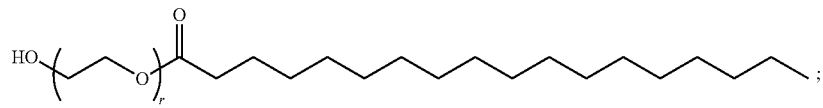
(Cmpd 452)

the ionizable lipid is a compound of Formula (XI):

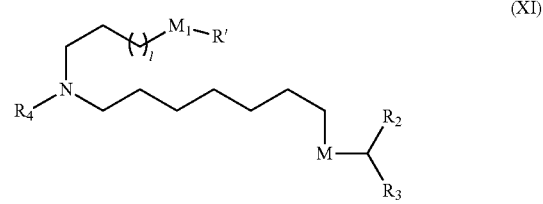
(XI)

or a pharmaceutically acceptable salt thereof, wherein:
l is selected from 1, 2, 3, 4, and 5;
M and M' are independently selected from C(O)O, and OC(O);
$M_1$ is M';
$R_2$ and $R_3$ are both $C_{1-14}$ alkyl, or $C_{2-14}$ alkenyl;
$R_4$ is $(CH_2)_nQ$, in which Q is OH, and n is selected from 2, 3, or 4; and
R' is a $C_1$-$C_{18}$ linear alkyl;
the helper lipid comprises at least one fatty acid chain of at least 8 carbons in length and at least one polar headgroup moiety, and wherein the helper lipid does not comprise a phosphatidyl choline (PC) and is a zwitterionic non-cationic helper lipid, a DSPC analog, oleic acid, an oleic acid analog, DSPC, or a 1,2-distearoyl-sn-glycero-3-phosphocholine (DSPC) substitute; and
the structural lipid is a steroid; and
administering a second dose of said LNPs;
wherein said LNPs result in a reduced anti-PEG IgM response in the subject as compared to LNPs lacking a PEG-lipid of Formula (V—OH).

25. The method of claim 24, wherein the PEG-lipid is HO-PEG2000-ester-C18(Cmpd403).

26. The method of claim 24, wherein the compound of Formula (XI) has the structure of Cmpd18:
(Cmpd 18)
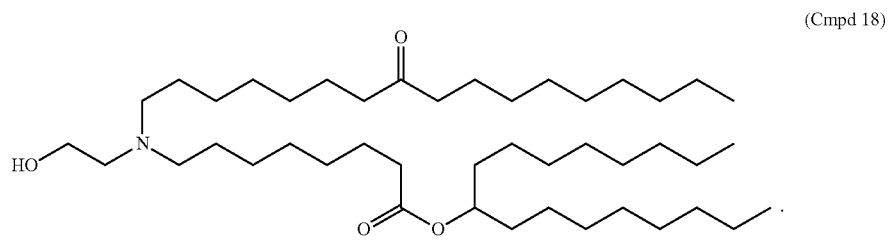 [SMILES: CCCCCCCCCC(=O)CCCCCCCN(CCO)CCCCCCCC(=O)OC(CCCCCCCC)CCCCCCCC]
27. The method of claim 24, wherein the helper lipid is DSPC.
28. The method of claim 24, wherein the structural lipid is cholesterol.
* * * * *